(12) United States Patent
Glunz et al.

(10) Patent No.: US 10,123,993 B2
(45) Date of Patent: Nov. 13, 2018

(54) CYCLIC UREAS AS INHIBITORS OF ROCK

(71) Applicant: BRISTOL-MYERS SQUIBB COMPANY, Princeton, NJ (US)

(72) Inventors: Peter W. Glunz, Yardley, PA (US); Doree F. Sitkoff, Dresher, PA (US); Navnath Dnyanoba Yadav, Bangalore (IN); Mandar Shrikrishna Bodas, Bangalore (IN); Rajeev S. Bhide, Princeton Junction, NJ (US); Sharanabasappa Patil, Raichur (IN); Kumaresan Chinnakotti, Sankarankovil (IN); Prasanna Savanor Maddu Rao, Shimoga (IN); Jeevan Prakash Shetty, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/541,725

(22) PCT Filed: Jan. 8, 2016

(86) PCT No.: PCT/US2016/012560
§ 371 (c)(1),
(2) Date: Jul. 6, 2017

(87) PCT Pub. No.: WO2016/112236
PCT Pub. Date: Jul. 14, 2016

(65) Prior Publication Data
US 2018/0000788 A1 Jan. 4, 2018

Related U.S. Application Data

(60) Provisional application No. 62/101,434, filed on Jan. 9, 2015.

(51) Int. Cl.
| | | |
|---|---|---|
| *A61K 31/4178* | (2006.01) | |
| *A61K 31/422* | (2006.01) | |
| *A61K 31/498* | (2006.01) | |
| *C07D 401/14* | (2006.01) | |
| *C07D 401/10* | (2006.01) | |
| *C07D 403/10* | (2006.01) | |
| *C07D 413/10* | (2006.01) | |
| *C07D 471/04* | (2006.01) | |
| *C07D 487/04* | (2006.01) | |

(52) U.S. Cl.
CPC ........ *A61K 31/4178* (2013.01); *A61K 31/422* (2013.01); *A61K 31/498* (2013.01); *C07D 401/10* (2013.01); *C07D 401/14* (2013.01); *C07D 403/10* (2013.01); *C07D 413/10* (2013.01); *C07D 471/04* (2013.01); *C07D 487/04* (2013.01); *H05K 999/99* (2013.01)

(58) Field of Classification Search
CPC ... C07D 401/14; C07D 413/00; C07D 487/00
See application file for complete search history.

(56) References Cited

U.S. PATENT DOCUMENTS

2015/0175576 A1 6/2015 Labile et al.

FOREIGN PATENT DOCUMENTS

| WO | WO 2009/078992 | * | 6/2009 | ........... C07D 401/04 |
|---|---|---|---|---|
| WO | WO2014/113620 A2 | | 7/2014 | |
| WO | WO2014/134388 A1 | | 9/2014 | |
| WO | WO2014/134391 A1 | | 9/2014 | |
| WO | WO2014/145022 A1 | | 9/2014 | |
| WO | WO2015/002915 A1 | | 1/2015 | |
| WO | WO2015/002926 A1 | | 1/2015 | |
| WO | WO2015/014944 A1 | | 2/2015 | |
| WO | WO2015/089634 A1 | | 6/2015 | |
| WO | WO2015/107053 A1 | | 7/2015 | |
| WO | WO2016/010950 A1 | | 1/2016 | |
| WO | WO2016/028971 A1 | | 2/2016 | |
| WO | WO2016/112236 A1 | | 7/2016 | |
| WO | WO2016/144936 A1 | | 9/2016 | |
| WO | WO2017/123860 A1 | | 7/2017 | |

* cited by examiner

*Primary Examiner* — Erich A Leeser
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

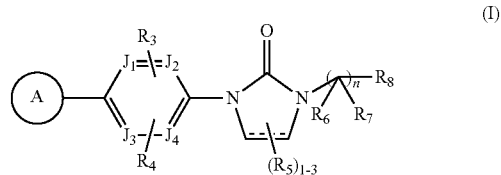

(I)

18 Claims, No Drawings

CYCLIC UREAS AS INHIBITORS OF ROCK

CROSS REFERENCE TO RELATED APPLICATIONS

This application is a 371 application of PCT/US2016/012560, filed Jan. 8, 2016, which is entitled to priority pursuant to 35 U.S.C. § 119(e) to U.S. provisional patent application No. 62/101,434, filed on Jan. 9, 2015, each of which is fully incorporated herein in its entirety.

FIELD OF THE INVENTION

The present invention relates to novel cyclic urea derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., nt. *J. Mol. Sci.*, 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel cyclic urea derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

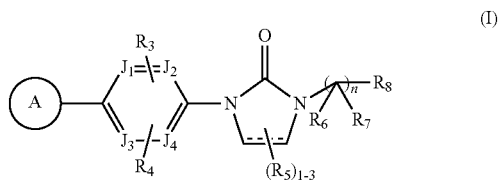

or stereoisomers, enantiomers, diastereoisomers, tautomers, pharmaceutically acceptable salts, solvates, or prodrugs thereof, wherein --- is an optional bond;

Ring A is independently selected from

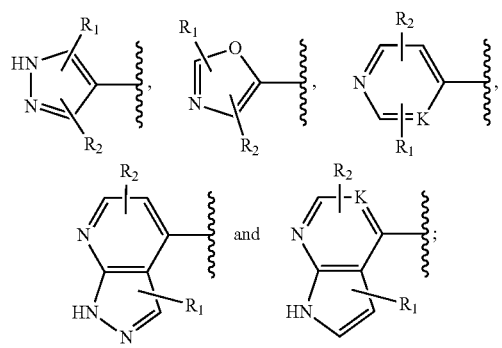

$J_1$, $J_2$, $J_3$, and $J_4$ are independently selected from N and $CR_3$; provided one of $J_1$, $J_2$, $J_3$, and $J_4$ is N and no more than two of $J_1$, $J_2$, $J_3$, and $J_4$ are N;

K is independently selected from N and $CR_1$;

R₁ is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R₂ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R₃ is independently selected from H, F, Cl, Br, CN, C$_{1-4}$ alkyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R₄ is independently selected from H, F, Cl, Br, OH, CN, OC$_{1-4}$ alkyl substituted with 0-3 R$_e$, NR$_a$R$_a$, and C$_{1-4}$ alkyl substituted with 0-3 R$_e$;

R₅ is independently selected from H, =O, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R₆ and R₇ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R₈ is independently selected from C$_{3-6}$ cycloalkyl, heterocyclyl, aryl and heteroaryl, each substituted with 0-5 R$_9$;

R₉ is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$ S(O)$_p$R$_f$ C(=O)NR$_f$R$_f$ NR$_f$C(=O)R$_d$, S(O)$_p$NR$_f$R$_f$ NR$_f$S(O)$_p$R$_d$, NR$_f$C(=O)OR$_d$, OC(=O)NR$_f$R$_f$ and —(CH$_2$)$_r$NR$_f$R$_f$;

R$_f$ at each occurrence, is independently selected from H, F, Cl, Br, CN, OH, C$_{1-5}$alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1, 2, and 3;

p, at each occurrence, is independently selected from zero, 1, and 2; and r, at each occurrence, is independently selected from zero, 1, 2, 3, and 4; provided when A is

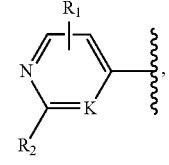

R₂ is not —C(=O)NR$_a$R$_a$, —NR$_a$C(=O)R$_b$, and —NR$_a$C(=O)NR$_a$R$_a$.

In another aspect, the present invention provides compounds of Formula (I) or stereoisomers, enantiomers, diastereoisomers, tautomers, pharmaceutically acceptable salts, solvates, or prodrugs thereof, wherein --- is an optional bond;

Ring A is independently selected from

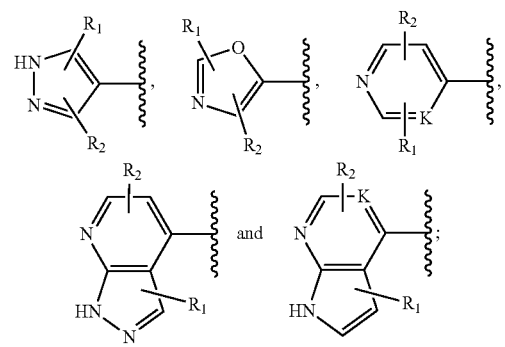

J₁, J₂, J₃, and J₄ are independently selected from N and CH; provided no more than two of J₁, J₂, J₃, and J₄ are N;

K is independently selected from N and CH;

R₁ is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R₂ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_3$ is independently selected from H, F, Cl, Br, CN, C$_{1-4}$ alkyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H, F, Cl, Br, OH, CN, OC$_{1-4}$ alkyl substituted with 0-3 R$_e$, NR$_a$R$_a$, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_8$ is independently selected from aryl and heteroaryl, each substituted with 0-5 R$_9$;

R$_9$ is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, —(CH$_2$)$_r$-aryl, —(CH$_2$)$_r$-heteroaryl, F, Cl, Br, CN, NO$_2$, =O, CO$_2$H, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$ and —(CH$_2$)$_r$NR$_f$R$_f$;

R$_f$, at each occurrence, is independently selected from H, F, Cl, Br, CN, OH, C$_{1-5}$alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1, 2, and 3;

p, at each occurrence, is independently selected from zero, 1, and 2; and r, at each occurrence, is independently selected from zero, 1, 2, 3, and 4; and provided (1) R$_9$ is not a substituted piperazine;

(2) when n is 3, R$_8$ is not

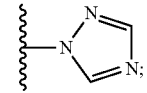

and (3) when A is

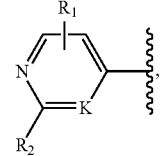

R$_2$ is not —C(=O)NR$_a$R$_a$, —NR$_a$C(=O)R$_b$, and —NR$_a$C(=O)NR$_a$R$_a$.

In another aspect, the present invention provides compounds of Formula (I) or stereoisomers, enantiomers, diastereoisomers, tautomers, pharmaceutically acceptable salts, solvates, or prodrugs thereof, wherein R$_1$ is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R$_2$ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

R$_3$ is independently selected from H, F, Cl, Br, CN, C$_{1-4}$ alkyl substituted with 0-3 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—C$_{3-6}$ carbocyclyl substituted with 0-3 R$_e$, and —(CH$_2$)$_r$-heterocyclyl substituted with 0-3 R$_e$;

$R_4$ is independently selected from H, F, Cl, Br, OH, CN, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rC(=O)OR_b$, $(CH_2)_r-C_{3-6}$ carbocyclyl substituted with 0-3 $R_e$, and $-(CH_2)_r$-heterocyclyl substituted with 0-3 $R_e$;

$R_8$ is independently selected from

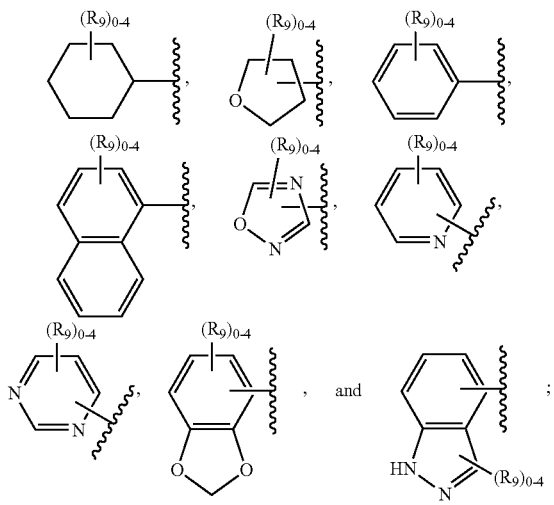

$R_9$ is independently selected from F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$, and other variables are as defined in Formula (I) above.

In another aspect, the present invention provides compounds of Formula (I) or stereoisomers, tautomers, pharmaceutically acceptable salts, solvates, or prodrugs thereof, wherein $R_1$ is independently selected from H, F, Cl, Br, OH, CN, $NR_aR_a$, $-OC_{1-4}$ alkyl substituted with 0-3 $R_e$, and $C_{1-4}$ alkyl substituted with 0-3 $R_e$;

$R_2$ is independently selected from H, $-(CH_2)_rOR_b$, $(CH_2)_rS(O)_pR_c$, $-(CH_2)_rC(=O)R_b$, $-(CH_2)_rNR_aR_a$, $-(CH_2)_rCN$, $-(CH_2)_rNR_aC(=O)OR_b$, $-(CH_2)_rOC(=O)NR_aR_a$, $-(CH_2)_rC(=O)OR_b$, $-(CH_2)_rNR_aS(O)_pNR_aR_a$, and $-(CH_2)_rNR_aS(O)_pR_c$;

$R_3$ is independently selected from H, F, Cl, Br, CN, $C_{1-4}$ alkyl substituted with 0-3 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_r-C_{3-6}$ carbocyclyl substituted with 0-3 $R_e$, and $-(CH_2)_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r-C_{3-6}$ carbocyclyl substituted with 0-3 $R_e$, and $-(CH_2)_r$-heterocyclyl substituted with 0-3 $R_e$;

$R_8$ is independently selected from

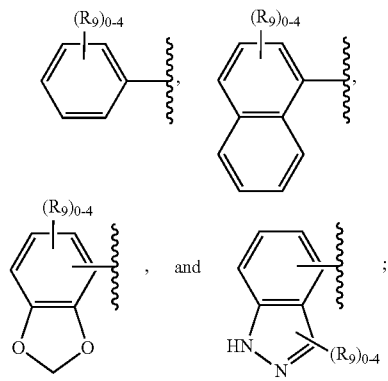

$R_9$ is independently selected from F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$; and other variables are as defined in Formula (I) above.

In another aspect, the present invention provides compounds of Formula (II):

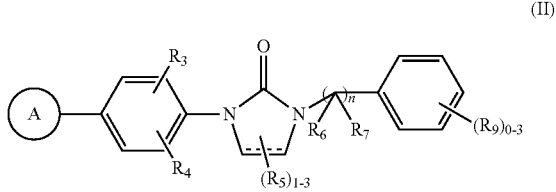

(II)

or stereoisomers, enantiomers, diastereoisomers, tautomers, pharmaceutically acceptable salts, solvates, or prodrugs thereof, wherein --- is an optional bond;

Ring A is independently selected from

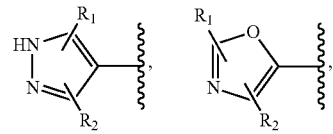

-continued

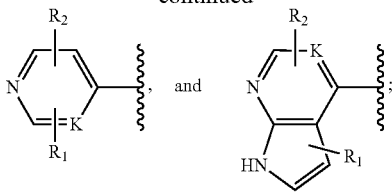

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rC(=O)OR_b$, $(CH_2)_r$—$C_{3-6}$ carbocyclyl substituted with 0-3 $R_e$, and —$(CH_2)_r$-heterocyclyl substituted with 0-3 $R_e$;

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rC_{4-6}$ heterocyclyl, F, Cl, Br, CN, $NO_2$, =O, $CO_2H$, —$(CH_2)_rOR_f$, $S(O)_pR_f$, $S(O)_pNR_fR_f$ and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

In another aspect, the present invention provides compounds of Formula (II) or stereoisomers, enantiomers, diastereoisomers, tautomers, pharmaceutically acceptable salts, solvates, or prodrugs thereof, wherein --- is an optional bond;

Ring A is independently selected from

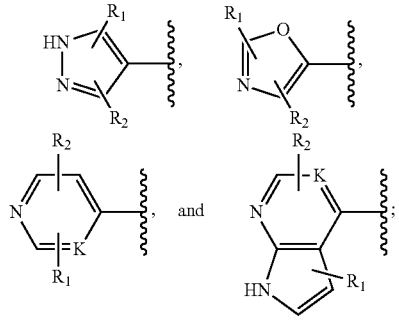

K is independently selected from N and CH;

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, and —$(CH_2)_rOR_b$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aC(=O)R_b$, —$(CH_2)_rC(=O)OR_b$, $(CH_2)_r$—$C_{3-6}$ carbocyclyl substituted with 0-3 $R_e$, and —$(CH_2)_r$-heterocyclyl substituted with 0-3 $R_e$;

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2;

r, at each occurrence, is independently selected from zero, 1, 2, 3, and 4; and other variables are as defined in Formula (II) above.

In another aspect, the present invention provides compounds of Formula (II) or stereoisomers, tautomers, pharmaceutically acceptable salts, solvates, or prodrugs thereof, wherein $R_3$ is independently selected from F, Cl, Br, CN, $C_{1-4}$ alkyl substituted with 0-3 $R_e$, —(CH$_2$)$_r$OR$_b$, —(CH$_2$)$_r$S(O)$_p$R$_c$, —(CH$_2$)$_r$NR$_a$R$_a$, —(CH$_2$)$_r$C(=O)NR$_a$R$_a$, —(CH$_2$)$_r$OC(=O)NR$_a$R$_a$, —(CH$_2$)$_r$NR$_a$C(=O)NR$_a$R$_a$, —(CH$_2$)$_r$C(=O)R$_b$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—$C_{3-6}$ carbocyclyl substituted with 0-3 $R_e$, and —(CH$_2$)$_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_6$ and $R_7$ are independently selected from H, CN, $C_{1-4}$alkyl substituted with 0-4 $R_e$, $C_{2-4}$ alkenyl substituted with 0-3 $R_e$, —(CH$_2$)$_r$OR$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$NR$_a$C(=O)OR$_b$, —(CH$_2$)$_r$C(=O)OR$_b$, —(CH$_2$)$_r$NR$_a$S(O)$_p$R$_c$, —(CH$_2$)$_r$—$C_{3-6}$ carbocyclyl substituted with 0-3 $R_e$, and —(CH$_2$)$_r$-heterocyclyl substituted with 0-3 $R_e$;

alternatively, $R_6$ and $R_7$ together with the carbon atom to which they are both attached form a cycloalkyl substituted with 0-5 $R_e$; alternatively, when n is 2 or 3, two adjacent $R_6$ groups may form a cycloalkyl substituted with 0-5 $R_e$ and two $R_7$ groups are both hydrogen;

$R_9$ is independently selected from F, Cl, Br, CN, $C_{1-4}$ alkyl, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$C(=O)OR$_b$, —(CHR$_d$)$_r$C(=O)R$_b$, —(CHR$_d$)$_r$OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, F, Cl, NH$_2$, OH, OC$_{1-5}$alkyl, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2;

r, at each occurrence, is independently selected from zero, 1, 2, 3, and 4; and other variables are as defined in Formula (II) above.

In another aspect, the present invention provides compounds of Formula (IIa):

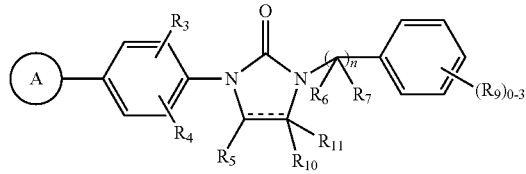

(IIa)

or stereoisomers, enantiomers, diastereoisomers, tautomers, pharmaceutically acceptable salts, solvates, or prodrugs thereof, wherein --- is an optional bond;

Ring A is independently selected from

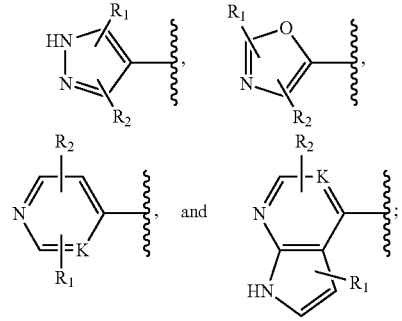

$R_1$ is independently selected from H, F, Cl, Br, CN, NR$_a$R$_a$, and $C_{1-4}$alkyl substituted with 0-4 $R_e$;

$R_2$ is independently selected from H, F, Cl, Br, OH, CN, NR$_a$R$_a$, and $C_{1-4}$alkyl substituted with 0-4 $R_e$;

$R_3$ is independently selected from H, F, Cl, Br, CN, $C_{1-4}$ alkyl substituted with 0-3 $R_e$, —(CH$_2$)$_r$OR$_b$, and —$C_{3-6}$ cycloalkyl;

$R_4$ is independently selected from H, F, Cl, Br, OH, CN, OC$_{1-4}$ alkyl substituted with 0-3 $R_e$, and $C_{1-4}$ alkyl substituted with 0-3 $R_e$;

$R_5$, $R_{10}$, and $R_{11}$ are independently selected from H, =O, and $C_{1-4}$alkyl substituted with 0-4 $R_e$; provided $R_5$, $R_{10}$, and $R_{11}$ are not all H;

$R_6$ and $R_7$ are independently selected from H, $C_{1-4}$alkyl substituted with 0-4 $R_e$, —$(CH_2)_r OR_b$, —$(CH_2)_r C(=O)R_b$, —$(CH_2)_r NR_a R_a$, —$(CH_2)_r C(=O)NR_a R_a$, —$(CH_2)_r NR_a C(=O)R_b$, —$(CH_2)_r C(=O)OR_b$, $(CH_2)_r$—$C_{3-6}$ carbocyclyl substituted with 0-3 $R_e$, and —$(CH_2)_r$-heterocyclyl substituted with 0-3 $R_e$;

$R_9$ is independently selected from F, Cl, Br, $C_{1-4}$ alkyl, nitro, —$(CH_2)_r S(O)_p R_c$, —$(CH_2)_r S(O)_p NR_a R_a$, —$(CH_2)_r NR_a S(O)_p R_c$, —$(CH_2)_r OR_b$, —$(CH_2)_r CN$, —$(CH_2)_r NR_a R_a$, —$(CH_2)_r NR_a C(=O)R_b$, —$(CH_2)_r NR_a C(=O)NR_a R_a$, —$(CH_2)_r C(=O)OR_b$, —$(CH_2)_r C(=O)R_b$, —$(CH_2)_r OC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$; $R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4; and provided (1) $R_9$ is not a substituted piperazine;

(2) when n is 3, $R_8$ is not

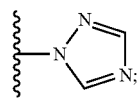

and (3) when A is

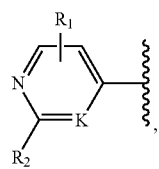

$R_2$ is not —$C(=O)NR_a R_a$, —$NR_a C(=O)R_b$, and —$NR_a C(=O)NR_a R_a$.

In another aspect, the present invention provides compounds of Formula (III):

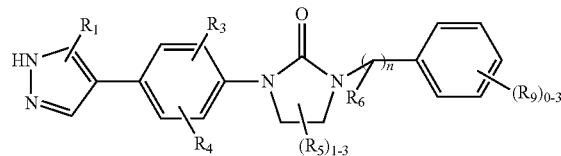

(III)

or stereoisomers, tautomers, pharmaceutically acceptable salts, solvates, or prodrugs thereof, wherein --- is an optional bond;

$R_1$ is independently selected from H, F, Cl, Br, CN, $NR_a R_a$, and $C_{1-4}$alkyl substituted with 0-4 $R_e$;

$R_3$ is independently selected from H, F, Cl, Br, CN, $C_{1-4}$ alkyl substituted with 0-3 $R_e$, and —$(CH_2)_r OR_b$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_r OR_b$, $C(=O)R_b$, and —$C(=O)OR_b$;

$R_6$ is independently selected from H, $C_{1-4}$alkyl substituted with 0-4 $R_e$, —$(CH_2)_r OR_b$, —$(CH_2)_r C(=O)R_b$, —$(CH_2)_r NR_a C(=O)R_b$, —$(CH_2)_r C(=O)OR_b$, and heterocyclyl substituted with 0-3 $R_e$;

$R_9$ is independently selected from F, Cl, Br, $C_{1-4}$ alkyl, nitro, —$(CH_2)_r S(O)_p R_c$, —$(CH_2)_r S(O)_p NR_a R_a$, —$(CH_2)_r NR_a S(O)_p R_c$, —$(CH_2)_r OR_b$, —$(CH_2)_r CN$, —$(CH_2)_r NR_a R_a$, —$(CH_2)_r NR_a C(=O)R_b$, —$(CH_2)_r NR_a C(=O)NR_a R_a$, —$(CH_2)_r C(=O)OR_b$, —$(CH_2)_r C(=O)R_b$, —$(CH_2)_r OC(=O)R_b$, —$(CH_2)_r C(=O)NR_a R_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (III) or stereoisomers, tautomers, pharmaceutically acceptable salts, solvates, or prodrugs thereof, wherein $R_1$ is independently selected from H;

$R_3$ is independently selected from H, F, Cl, $C_{1-4}$ alkyl, and —$OC_{1-3}$ alkyl;

$R_5$ is independently selected from H, =O, $C_{1-4}$alkyl substituted with 0-4 $R_e$, —$OR_b$, $C(=O)R_b$, and —$C(=O)OR_b$;

$R_6$ is independently selected from H, $C_{1-4}$alkyl substituted with 0-3 $R_e$, —$(CH_2)_rOR_b$, and —$(CH_2)_rC(=O)OR_b$;

$R_9$ is independently selected from F, Cl, $C_{1-4}$ alkyl substituted with 0-3 $R_e$, —$OR_b$, and heterocyclyl substituted with 0-3 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

n is independently selected from 1 and 2;

r, at each occurrence, is independently selected from zero, 1, 2, and 3; and other variables are as defined in Formula (III) above.

In another aspect, the present invention provides compounds of Formula (IIIa)

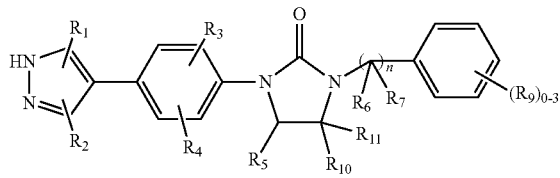

(IIIa)

or stereoisomers, enantiomers, diastereoisomers, tautomers, pharmaceutically acceptable salts, solvates, or prodrugs thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$, $R_{10}$, and $R_{11}$ are independently selected from H, =O, and $C_{1-4}$alkyl substituted with 0-4 $R_e$; provided $R_5$, $R_{10}$, and $R_{11}$ are not all H;

$R_6$ is independently selected from H, $C_{1-4}$alkyl substituted with 0-4 $R_e$, —$CH_2OR_b$, —$C(=O)R_b$, $NR_aC(=O)R_b$, —$CH_2NR_aR_a$, —$C(=O)NR_aR_a$, —$_rC(=O)OR_b$, and heterocyclyl substituted with 0-3 $R_e$;

$R_7$ is independently selected from H and $C_{1-4}$alkyl;

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (IIIb):

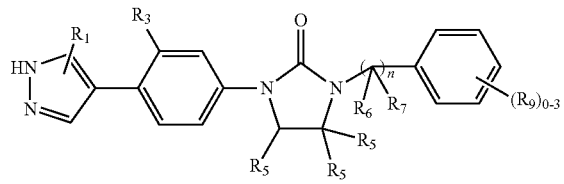

(IIIb)

or stereoisomers, enantiomers, diastereoisomers, tautomers, pharmaceutically acceptable salts, solvates, or prodrugs thereof, wherein $R_1$ is independently selected from F, Cl, Br, CN, $NR_aR_a$, and $C_{1-4}$alkyl substituted with 0-4 $R_e$;

$R_3$ is independently selected from H, CN, $C_{1-4}$ alkyl, —$OC_{1-3}$ alkyl, and $C_{3-6}$ cycloalkyl;

$R_5$ is independently selected from H, =O, $C_{1-4}$alkyl substituted with 0-4 $R_e$, —$CH_2OR_b$, $C(=O)R_b$, and —$C(=O)OR_b$;

$R_6$ is independently selected from H, $C_{1-4}$alkyl substituted with 0-3 $R_e$, —$(CH_2)_rOR_b$, —$CH_2NR_aR_a$, —$C(=O)NR_aR_a$ and —$(CH_2)_rC(=O)OR_b$;

$R_7$ is independently selected from H and $C_{1-4}$alkyl;

$R_9$ is independently selected from F, Cl, $C_{1-4}$ alkyl substituted with 0-3 $R_e$, —$OR_b$, and heterocyclyl substituted with 0-3 $R_e$;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

n is independently selected from 1 and 2; and r, at each occurrence, is independently selected from zero, 1, 2, and 3.

In another aspect, the present invention provides compounds of Formula (IV):

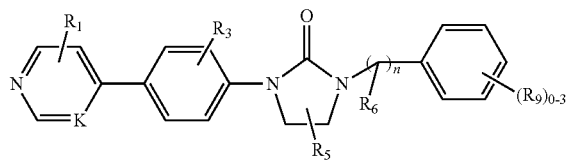

(IV)

or stereoisomers, tautomers, pharmaceutically acceptable salts, solvates, or prodrugs thereof, wherein K is independently selected from N and CH;

$R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and —$OR_b$; $R_5$ is independently selected from H, =O, $C_{1-4}$alkyl substituted with 0-4 $R_e$, —$(CH_2)_rOR_b$, $C(=O)R_b$, and —$C(=O)OR_b$;

$R_6$ is independently selected from H, $C_{1-4}$alkyl substituted with 0-4 $R_e$, —$(CH_2)_rOR_b$, —$(CH_2)_rC(=O)R_b$, —$(CH_2)_rNR_aC(=O)R_b$, —$(CH_2)_rC(=O)OR_b$, and heterocyclyl substituted with 0-3 $R_e$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_rC_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (IVa):

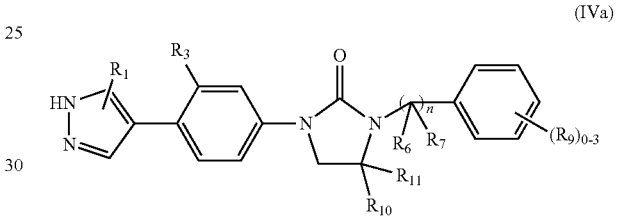

(IVa)

or stereoisomers, enantiomers, diastereoisomers, tautomers, pharmaceutically acceptable salts, solvates, or prodrugs thereof, wherein $R_1$ is independently selected from H and $CF_3$;

$R_3$ is independently selected from H, CN, $C_{1-4}$ alkyl, —$OC_{1-3}$ alkyl, and —$C_{3-6}$ cycloalkyl;

$R_5$ is independently selected from H, =O, $C_{1-4}$alkyl substituted with 0-4 $R_e$, —$CH_2OR_b$, $C(=O)R_b$, and —$C(=O)OR_b$;

$R_6$ is independently selected from H, $C_{1-4}$alkyl substituted with 0-3 $R_e$, —$(CH_2)_rOR_b$, —$CH_2NR_aR_a$, —$C(=O)NR_aR_a$ and —$(CH_2)_rC(=O)OR_b$;

$R_7$ is independently selected from H and $C_{1-4}$alkyl;

$R_9$ is independently selected from F, Cl, $C_{1-4}$ alkyl substituted with 0-3 $R_e$, —$OR_b$, and heterocyclyl substituted with 0-3 $R_e$;

$R_{10}$, and $R_{11}$ are independently selected from H, $C_{1-4}$alkyl substituted with 0-4 $R_e$; provided $R_{10}$ and $R_{11}$ are not all H;

$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

n is independently selected from 1 and 2; and r, at each occurrence, is independently selected from zero, 1, 2, and 3.

In another aspect, the present invention provides compounds of Formula (V):

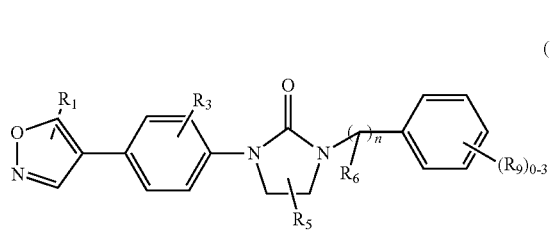

(V)

or stereoisomers, tautomers, pharmaceutically acceptable salts, solvates, or prodrugs thereof, wherein $R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and —$OR_b$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_6$ is independently selected from H, $C_{1-4}$alkyl substituted with 0-4 $R_e$, —$(CH_2)_rOR_b$, —$(CH_2)_rC(=O)R_b$, —$(CH_2)_rNR_aC(=O)R_b$, —$(CH_2)_rC(=O)OR_b$, and heterocyclyl substituted with 0-3 $R_e$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$ at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (Va):

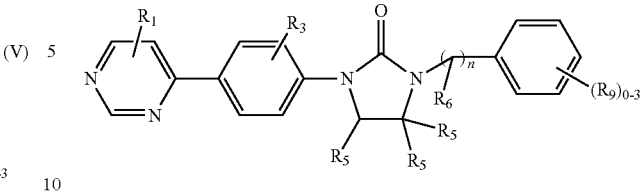

(Va)

or stereoisomers, tautomers, pharmaceutically acceptable salts, solvates, or prodrugs thereof, wherein $R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and —$OR_b$;

$R_5$ is independently selected from H, =O, $C_{1-4}$alkyl substituted with 0-4 $R_e$, —$(CH_2)_rOR_b$, $C(=O)R_b$, and —$C(=O)OR_b$;

$R_6$ is independently selected from H, $C_{1-4}$alkyl substituted with 0-4 $R_e$, —$(CH_2)_rOR_b$, —$(CH_2)_rC(=O)R_b$, —$(CH_2)_rNR_aC(=O)R_b$, —$(CH_2)_rC(=O)OR_b$, and heterocyclyl substituted with 0-3 $R_e$;

$R_9$ is independently selected from F, Cl, Br, $C_{1-4}$ alkyl, nitro, —$S(O)_pR_c$, —$S(O)_pNR_aR_a$, —$OR_b$, —$NR_aR_a$, —$C(=O)OR_b$, —$(CH_2)_rC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$ at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (VI):

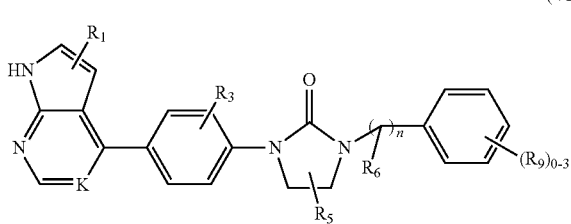

(VI)

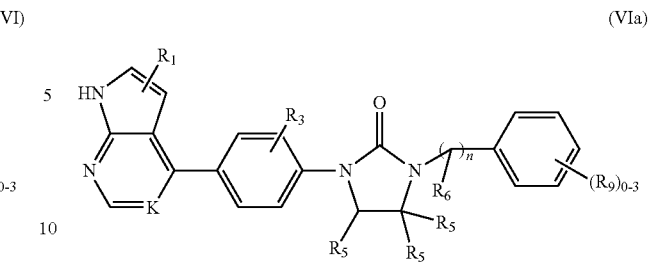

(VIa)

or stereoisomers, tautomers, pharmaceutically acceptable salts, solvates, or prodrugs thereof, wherein K is independently selected from N and CH;

$R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and $-OR_b$;

$R_5$ is independently selected from H, $=O$, $C_{1-4}$alkyl substituted with 0-4 $R_e$, $-(CH_2)_rOR_b$, $C(=O)R_b$, and $-C(=O)OR_b$;

$R_6$ is independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, and heterocyclyl substituted with 0-3 $R_e$;

$R_9$ is independently selected from F, Cl, Br, $C_{1-4}$ alkyl, nitro, $-S(O)_pR_c$, $-S(O)_pNR_aR_a$, $-OR_b$, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (VIa):

or stereoisomers, enantiomers, diastereoisomers, tautomers, pharmaceutically acceptable salts, solvates, or prodrugs thereof, wherein K is independently selected from N and CH;

$R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and $-OR_b$;

$R_5$ is independently selected from H, $=O$, $C_{1-4}$alkyl substituted with 0-4 $R_e$, $-(CH_2)_rOR_b$, $C(=O)R_b$, and $-C(=O)OR_b$;

$R_6$ is independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, and heterocyclyl substituted with 0-3 $R_e$;

$R_9$ is independently selected from F, Cl, Br, $C_{1-4}$ alkyl, nitro, $-S(O)_pR_c$, $-S(O)_pNR_aR_a$, $-OR_b$, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (VII):

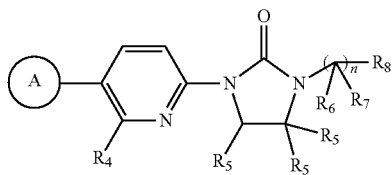

(VII)

or stereoisomers, enantiomers, diastereoisomers, tautomers, pharmaceutically acceptable salts, solvates, or prodrugs thereof, wherein Ring A is independently selected from

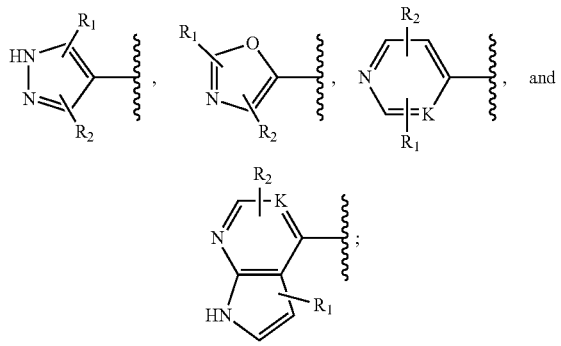

K is independently selected from N and $CR_1$;

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r-C_{3-6}$ carbocyclyl substituted with 0-3 $R_e$, and $-(CH_2)_r$-heterocyclyl substituted with 0-3 $R_e$;

$R_8$ is independently selected from

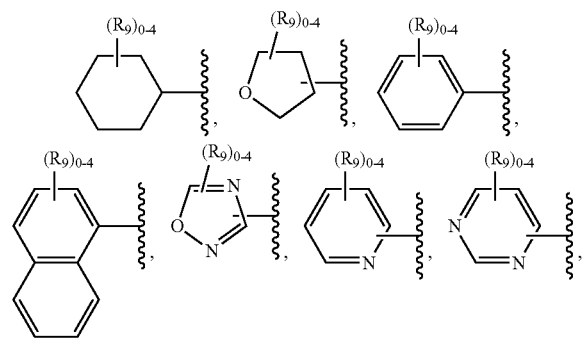

$R_9$ is independently selected from F, Cl, Br, $C_{1-4}$ alkyl, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-(CH_2)_rOC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, =O, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

In another aspect, the present invention provides compounds of Formula (VIII):

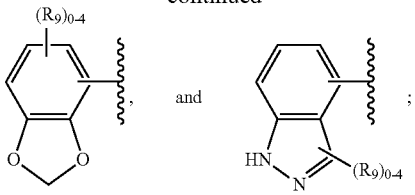

(VIII)

or stereoisomers, enantiomers, diastereoisomers, tautomers, pharmaceutically acceptable salts, solvates, or prodrugs thereof, wherein

27

Ring A is independently selected from

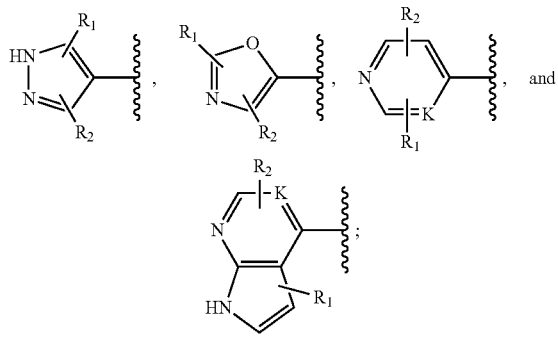

K is independently selected from N and CR$_1$;
R$_1$ is independently selected from H, F, Cl, Br, CN, NR$_a$R$_a$, and C$_{1-4}$alkyl substituted with 0-4 R$_e$;
R$_2$ is independently selected from H, F, Cl, Br, OH, CN, NR$_a$R$_a$, and C$_{1-4}$alkyl substituted with 0-4 R$_e$;
R$_4$ is independently selected from H, F, Cl, Br, OH, CN, OC$_{1-4}$ alkyl substituted with 0-3 R$_e$, and C$_{1-4}$ alkyl substituted with 0-3 R$_e$;
R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;
R$_6$ and R$_7$ are independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$C(=O)R$_b$, —(CH$_2$)$_r$C(=O)OR$_b$, (CH$_2$)$_r$—C$_{3-6}$ carbocyclyl substituted with 0-3 R$_e$, and —(CH$_2$)$_r$-heterocyclyl substituted with 0-3 R$_e$;
R$_8$ is independently selected from

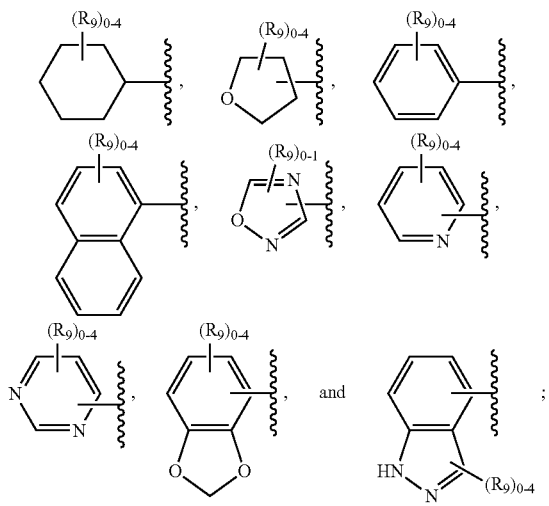

R$_9$ is independently selected from F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;
R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;
R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;
R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;
n is independently selected from 1, 2, and 3;
p, at each occurrence, is independently selected from zero, 1, and 2; and
r, at each occurrence, is independently selected from zero, 1, 2, 3, and 4.

In another aspect, the present invention provides compounds of Formula (IX):

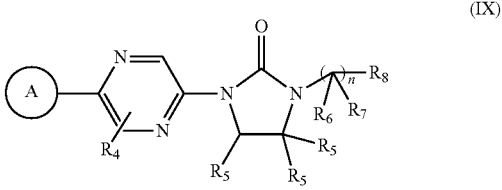

(IX)

or stereoisomers, enantiomers, diastereoisomers, tautomers, pharmaceutically acceptable salts, solvates, or prodrugs thereof, wherein
Ring A is independently selected from

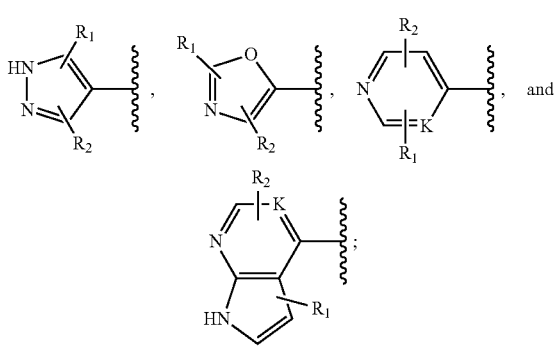

K is independently selected from N and CR$_1$;
R$_1$ is independently selected from H, F, Cl, Br, CN, NR$_a$R$_a$, and C$_{1-4}$alkyl substituted with 0-4 R$_e$;

$R_2$ is independently selected from H, F, Cl, Br, OH, CN, $NR_aR_a$, and $C_{1-4}$alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r$—$C_{3-6}$ carbocyclyl substituted with 0-3 $R_e$, and $-(CH_2)_r$-heterocyclyl substituted with 0-3 $R_e$;

$R_8$ is independently selected from

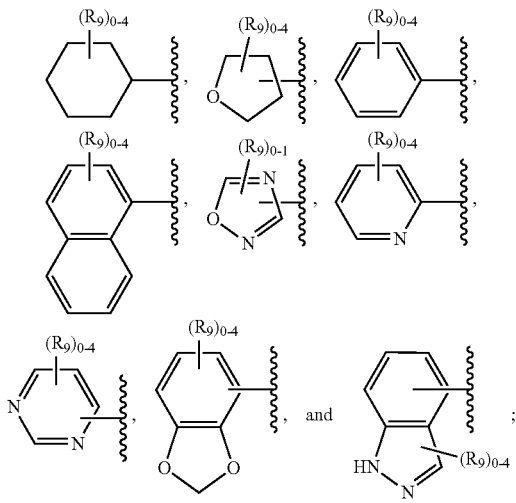

$R_9$ is independently selected from F, Cl, Br, $C_{1-4}$ alkyl, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-(CH_2)_rOC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$—$C_{3-10}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$—$C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r$—$C_{3-6}$ cycloalkyl, $-(CH_2)_r$—$C_{4-6}$ heterocyclyl, F, Cl, Br, CN, $NO_2$, =O, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

In another aspect, the present invention provides compounds of Formula (X):

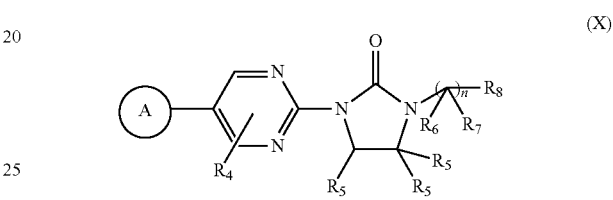

(X)

or stereoisomers, enantiomers, diastereoisomers, tautomers, pharmaceutically acceptable salts, solvates, or prodrugs thereof, wherein Ring A is independently selected from

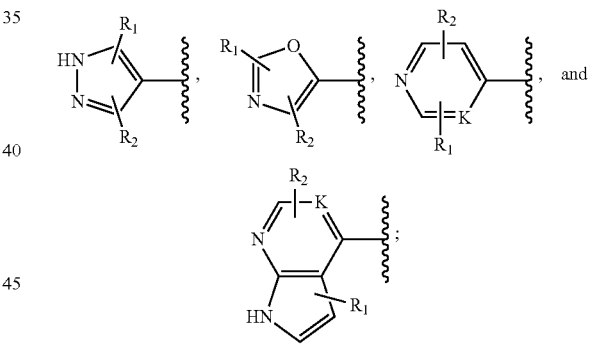

K is independently selected from N and $CR_1$;

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $C(=O)R_b$, and $-C(=O)OR_b$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r$—$C_{3-6}$ carbocyclyl substituted with 0-3 $R_e$, and $-(CH_2)_r$-heterocyclyl substituted with 0-3 $R_e$;

$R_8$ is independently selected from

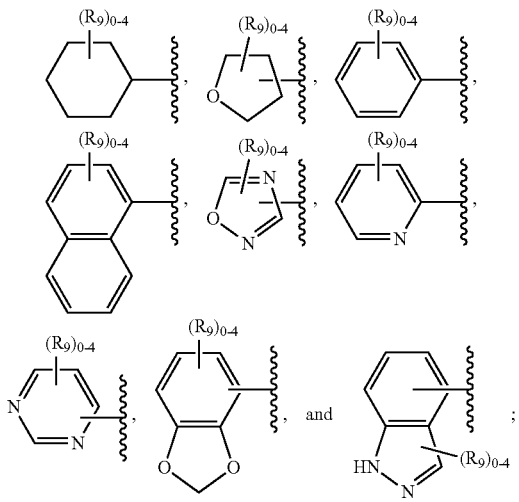

$R_9$ is independently selected from F, Cl, Br, $C_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$ and —(CH$_2$)$_r$NR$_f$R$_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;
p, at each occurrence, is independently selected from zero, 1, and 2; and
r, at each occurrence, is independently selected from zero, 1, 2, 3, and 4.

In another aspect, the present invention provides compounds of Formula (XI):

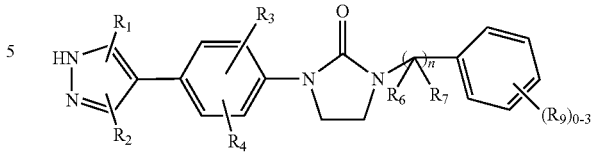

(XI)

or stereoisomers, enantiomers, diastereoisomers, tautomers, pharmaceutically acceptable salts, solvates, or prodrugs thereof, wherein $R_1$ is independently selected from H, F, Cl, Br, CN, NR$_a$R$_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —(CH$_2$)$_r$OR$_b$, and —$C_{3-6}$ cycloalkyl;

$R_3$ is independently selected from H, F, Cl, Br, CN, $C_{1-4}$ alkyl substituted with 0-3 $R_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—$C_{3-6}$ carbocyclyl substituted with 0-3 $R_e$, and —(CH$_2$)$_r$-heterocyclyl substituted with 0-3 $R_e$;

$R_4$ is independently selected from H, F, Cl, Br, OH, CN, OC$_{1-4}$ alkyl substituted with 0-3 $R_e$, and $C_{1-4}$ alkyl substituted with 0-3 $R_e$;

$R_6$ is independently selected from H, $C_{1-4}$alkyl substituted with OH, —CH$_2$OR$_b$, —C(=O)R$_b$, NR$_a$C(=O)R$_b$, —CH$_2$NR$_a$R$_a$, —C(=O)NR$_a$R$_a$, —,C(=O)OR$_b$, and heterocyclyl substituted with 0-3 $R_e$;

$R_7$ is independently selected from H and $C_{1-4}$alkyl; provided $R_6$ and $R_7$ are not both H; when $R_7$ is $C_{1-4}$alkyl, $R_6$ is not H;

$R_9$ is independently selected from F, Cl, Br, $C_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —(CH$_2$)$_r$OC(=O)R$_b$, —(CH$_2$)$_r$C(=O)NR$_a$R$_a$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$—$C_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (XII):

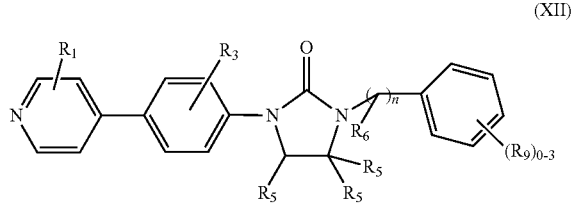

(XII)

or stereoisomers, enantiomers, diastereoisomers, tautomers, pharmaceutically acceptable salts, solvates, or prodrugs thereof, wherein R$_1$ is independently selected from F, Cl, Br, CN, NR$_a$R$_a$, and C$_{1-4}$alkyl substituted with 0-4 R$_e$;

R$_3$ is independently selected from H, CN, C$_{1-4}$ alkyl substituted with 0-3 R$_e$, and —OR$_b$;

R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_6$ is independently selected from H, C$_{1-4}$alkyl substituted with 0-4 R$_e$, —(CH$_2$)$_r$OR$_b$, —(CH$_2$)$_r$C(=O)R$_b$, —(CH$_2$)$_r$NR$_a$C(=O)R$_b$, —(CH$_2$)$_r$C(=O)OR$_b$, and heterocyclyl substituted with 0-3 R$_e$;

R$_9$ is independently selected from F, Cl, Br, C$_{1-4}$ alkyl, nitro, —S(O)$_p$R$_c$, —S(O)$_p$NR$_a$R$_a$, —OR$_b$, —NR$_a$R$_a$, —C(=O)OR$_b$, —(CH$_2$)$_r$C(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, —(CH$_2$)$_r$—C$_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$—C$_{4-6}$ heterocyclyl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (XIII):

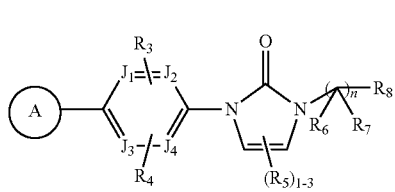

(XIII)

or stereoisomers, enantiomers, diastereoisomers, tautomers, pharmaceutically acceptable salts, solvates, or prodrugs thereof, wherein Ring A is independently selected from

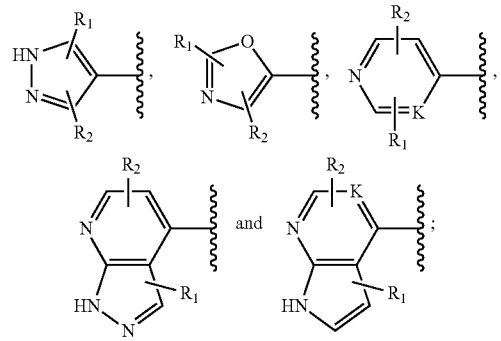

J$_1$, J$_2$, J$_3$, and J$_4$ are independently selected from N and CR$_3$;

K is independently selected from N and CR$_1$;

R$_1$ is independently selected from H, F, Cl, Br, OH, CN, NR$_a$R$_a$, —OC$_{1-4}$ alkyl substituted with 0-3 R$_e$, and C$_{1-4}$ alkyl substituted with 0-3 R$_e$;

R$_2$ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

R$_3$ is independently selected from H, F, Cl, Br, CN, C$_{1-4}$ alkyl substituted with 0-3 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from H, =O, $C_{1-4}$alkyl substituted with 0-4 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rCN$, $-(CH_2)_rC(=O)NR_aR_a$, $-(CH_2)_rNR_aC(=O)R_b$, $-(CH_2)_rNR_aC(=O)NR_aR_a$, $-(CH_2)_rNR_aC(=O)OR_b$, $-(CH_2)_rOC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_6$ and $R_7$ are independently selected from H, $C_{1-4}$alkyl substituted with 0-4 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_8$ is independently selected from $C_{3-6}$ cycloalkyl, heterocyclyl, aryl and heteroaryl, each substituted with 0-5 $R_9$;

$R_9$ is independently selected from F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, $-(CH_2)_r$-aryl, $-(CH_2)_r$-heteroaryl, F, Cl, Br, CN, $NO_2$, =O, $CO_2H$, $-(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$, and $-(CH_2)_rNR_fR_f$;

$R_f$, at each occurrence, is independently selected from H, F, Cl, Br, CN, OH, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4; and provided $R_9$ is not a substituted piperazine.

In another aspect, the present invention provides a compound selected from any subset list of compounds exemplified in the present application.

In another embodiment, the compounds of the present invention have ROCK $IC_{50}$ values ≤10 μM.

In another embodiment, the compounds of the present invention have ROCK $IC_{50}$ values ≤1 μM.

In another embodiment, the compounds of the present invention have ROCK $IC_{50}$ values ≤0.1 μM.

In another embodiment, the compounds of the present invention have ROCK $IC_{50}$ values ≤0.05 μM.

In another embodiment, the compounds of the present invention have ROCK $IC_{50}$ values ≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene PyBOP benzotriazol-1-yl-oxytripyrrolidinophosphonium hexafluorophosphate
SEM-Cl 2-(trimethysilyl)ethoxymethyl chloride
2nd generation XPhos precatalyst Chloro(2-dicyclohexylphosphino-2',4',6'-triisopropyl-1,1' biphenyl)[2-(2'-amino-1,1'-biphenyl)]palladium(II), THF adduct
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P® propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl$_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK2 assay described above and found having ROCK inhibitory activity. Table A below lists the ROCK2 IC$_{50}$ value ranges measured for the examples: A=0-2 nM; B=2.1-20 nM; C=20.1-200 nM; D=200.1-2000 nM.

TABLE A

| Example No. | ROCK2 IC$_{50}$ |
|---|---|
| 1 | B |
| 2 | B |
| 3 | B |
| 4 | B |
| 5 | C |
| 6 | B |
| 7 | B |
| 8 | D |
| 9 | C |
| 10 | B |
| 11 | C |
| 12 | D |
| 13 | A |
| 14 | C |
| 15 | C |
| 16 | C |
| 17 | C |
| 18 | C |
| 19 | C |
| 20 | D |
| 21 | B |
| 22 | D |
| 23 | B |
| 24 | B |
| 25 | C |
| 26 | C |
| 27 | D |
| 28 | B |
| 29 | C |
| 30 | C |
| 31 | C |
| 32 | D |
| 33 | D |
| 34 | C |
| 35 | C |
| 36 | B |
| 37 | A |
| 38 | B |
| 39 | B |
| 40 | A |
| 41 | B |
| 42 | A |
| 43 | A |
| 44 | A |
| 45 | A |
| 46 | A |
| 47 | C |
| 48 | B |
| 49 | C |
| 50 | C |
| 51 | D |
| 52 | C |
| 53 | D |
| 54 | C |
| 55 | C |
| 56 | C |
| 57 | D |
| 58 | D |
| 59 | C |
| 60 | C |
| 61 | D |
| 62 | C |
| 63 | C |
| 64 | D |
| 65 | B |
| 66 | D |
| 67 | C |
| 68 | C |
| 69 | C |
| 70 | B |
| 71 | C |
| 72 | B |
| 73 | C |
| 74 | B |
| 75 | A |
| 76 | C |
| 77 | B |
| 78 | C |
| 79 | C |
| 80 | C |
| 81 | D |
| 82 | C |
| 83 | D |
| 84 | C |
| 85 | D |
| 86 | D |
| 87 | D |
| 88 | D |
| 89 | D |
| 90 | C |
| 91 | D |
| 92 | D |
| 93 | C |
| 94 | C |
| 95 | C |
| 96 | D |

TABLE A-continued

| Example No. | ROCK2 IC$_{50}$ |
|---|---|
| 97 | D |
| 98 | C |
| 99 | C |
| 100 | C |
| 101 | B |
| 102 | C |
| 103 | C |
| 104 | C |
| 105 | B |
| 106 | C |
| 107 | B |
| 108 | D |
| 109 | D |
| 110 | C |
| 111 | B |
| 112 | A |
| 113 | C |
| 114 | C |
| 115 | C |
| 116 | C |
| 117 | D |
| 118 | A |
| 119 | C |
| 120 | C |
| 121 | D |
| 122 | A |
| 123 | A |
| 124 | A |
| 125 | A |
| 126 | C |
| 127 | A |
| 128 | B |
| 129 | A |
| 130 | B |
| 131 | B |
| 132 | B |
| 133 | C |
| 134 | D |
| 135 | D |
| 137 | A |
| 138 | B |
| 139 | D |
| 140 | B |
| 141 | B |
| 142 | C |
| 143 | C |
| 144 | B |
| 145 | B |
| 146 | C |
| 147 | B |
| 148 | B |
| 151 | B |
| 152 | B |
| 153 | D |
| 154 | C |
| 155 | A |
| 156 | B |
| 157 | D |
| 158 | C |
| 159 | A |
| 160 | C |
| 161 | B |
| 162 | D |
| 163 | B |
| 164 | D |
| 165 | B |
| 166 | B |
| 167 | A |
| 168 | A |
| 169 | C |
| 170 | B |
| 171 | C |
| 172 | B |
| 173 | A |
| 174 | D |
| 175 | A |
| 176 | A |
| 177 | C |
| 178 | B |
| 179 | B |
| 180 | A |
| 181 | B |
| 182 | D |
| 183 | A |
| 184 | D |
| 185 | B |
| 186 | C |
| 187 | B |
| 188 | A |
| 189 | C |
| 190 | D |
| 191 | D |
| 192 | D |
| 193 | B |
| 194 | D |
| 195 | D |
| 196 | B |
| 197 | A |
| 198 | D |
| 199 | C |
| 200 | B |
| 201 | D |
| 202 | B |
| 202 | B |
| 204 | C |
| 205 | D |
| 206 | A |
| 207 | D |
| 208 | D |
| 209 | B |
| 210 | C |
| 211 | D |
| 212 | B |
| 213 | D |
| 214 | A |
| 218 | B |
| 219 | A |
| 220 | C |
| 221 | A |
| 222 | B |
| 223 | B |
| 224 | B |
| 225 | B |
| 226 | A |
| 227 | B |
| 228 | A |
| 229 | B |
| 230 | A |
| 231 | C |
| 233 | B |
| 234 | C |
| 235 | D |
| 236 | D |
| 236 | B |
| 237 | C |
| 238 | D |
| 239 | C |
| 240 | D |
| 241 | D |
| 242 | D |
| 243 | D |
| 244 | B |
| 245 | C |
| 246 | B |
| 247 | A |
| 248 | A |
| 249 | C |
| 250 | B |
| 251 | C |
| 252 | B |
| 253 | B |
| 254 | C |
| 255 | D |
| 256 | B |
| 257 | B |
| 258 | C |

TABLE A-continued

| Example No. | ROCK2 IC$_{50}$ |
|---|---|
| 259 | D |
| 260 | A |
| 261 | C |
| 262 | C |
| 263 | B |
| 264 | C |
| 265 | C |
| 266 | B |
| 267 | D |
| 268 | A |
| 269 | C |
| 270 | B |
| 271 | D |
| 272 | B |
| 273 | B |
| 274 | A |
| 275 | C |
| 276 | C |
| 277 | D |
| 278 | C |
| 279 | D |
| 280 | B |
| 281 | B |
| 282 | B |
| 283 | D |
| 284 | C |
| 285 | D |
| 286 | C |
| 287 | C |
| 288 | D |
| 289 | B |
| 290 | C |
| 291 | C |
| 292 | B |
| 293 | D |
| 294 | B |
| 295 | C |
| 296 | C |
| 297 | D |
| 299 | C |
| 300 | C |
| 301 | B |
| 303 | C |
| 304 | D |
| 306 | C |
| 309 | C |
| 310 | B |
| 311 | C |
| 312 | B |
| 313 | C |
| 314 | B |
| 316 | B |
| 318 | C |
| 319 | B |
| 320 | B |
| 321 | B |
| 322 | B |
| 323 | D |
| 324 | A |
| 325 | C |
| 326 | B |
| 327 | D |
| 330 | C |
| 331 | B |
| 332 | C |
| 333 | B |
| 334 | A |
| 335 | C |
| 336 | B |
| 337 | C |
| 338 | C |
| 339 | A |
| 340 | C |
| 342 | A |
| 343 | B |
| 344 | B |
| 345 | B |
| 346 | C |

TABLE A-continued

| Example No. | ROCK2 IC$_{50}$ |
|---|---|
| 347 | C |
| 348 | C |
| 351 | D |
| 352 | D |
| 353 | B |
| 354 | C |
| 355 | A |
| 356 | D |
| 357 | C |
| 358 | D |
| 359 | C |
| 360 | D |
| 361 | B |
| 362 | A |
| 363 | D |
| 364 | C |
| 365 | D |
| 366 | A |
| 367 | C |
| 368 | D |
| 369 | B |
| 370 | B |
| 371 | C |
| 372 | C |
| 373 | A |
| 374 | B |
| 375 | B |
| 376 | A |
| 377 | B |
| 378 | A |
| 380 | A |
| 381 | B |
| 382 | B |
| 383 | C |
| 387 | C |
| 388 | B |
| 389 | A |
| 390 | C |
| 391 | B |
| 392 | D |
| 393 | B |
| 394 | C |
| 395 | B |
| 396 | C |
| 397 | A |
| 398 | B |
| 399 | B |
| 400 | A |
| 401 | B |
| 402 | B |
| 403 | C |
| 404 | C |
| 405 | C |
| 406 | C |
| 407 | C |
| 408 | C |
| 409 | C |
| 410 | C |
| 412 | D |
| 413 | A |
| 414 | C |
| 415 | B |
| 416 | B |
| 417 | B |
| 418 | C |
| 419 | A |
| 420 | C |
| 423 | B |
| 424 | B |
| 425 | A |
| 426 | B |
| 427 | C |
| 428 | B |
| 429 | B |
| 430 | B |
| 431 | C |
| 432 | C |
| 433 | C |

TABLE A-continued

| Example No. | ROCK2 IC$_{50}$ |
|---|---|
| 434 | B |
| 437 | C |
| 438 | C |
| 439 | B |
| 440 | C |
| 441 | D |
| 442 | D |
| 443 | B |
| 444 | C |
| 446 | B |
| 447 | C |
| 448 | C |
| 449 | C |
| 450 | B |
| 451 | A |
| 452 | B |
| 453 | C |
| 454 | C |
| 455 | D |
| 456 | C |
| 458 | B |
| 459 | C |
| 460 | A |
| 461 | A |
| 462 | C |
| 463 | B |
| 464 | C |
| 465 | C |
| 466 | A |
| 467 | A |
| 468 | C |
| 469 | C |
| 470 | C |
| 471 | C |
| 472 | B |
| 473 | C |
| 474 | B |
| 475 | A |
| 476 | B |
| 477 | A |
| 478 | A |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, Fourth Edition, Wiley-Interscience (2006)).

Scheme 1

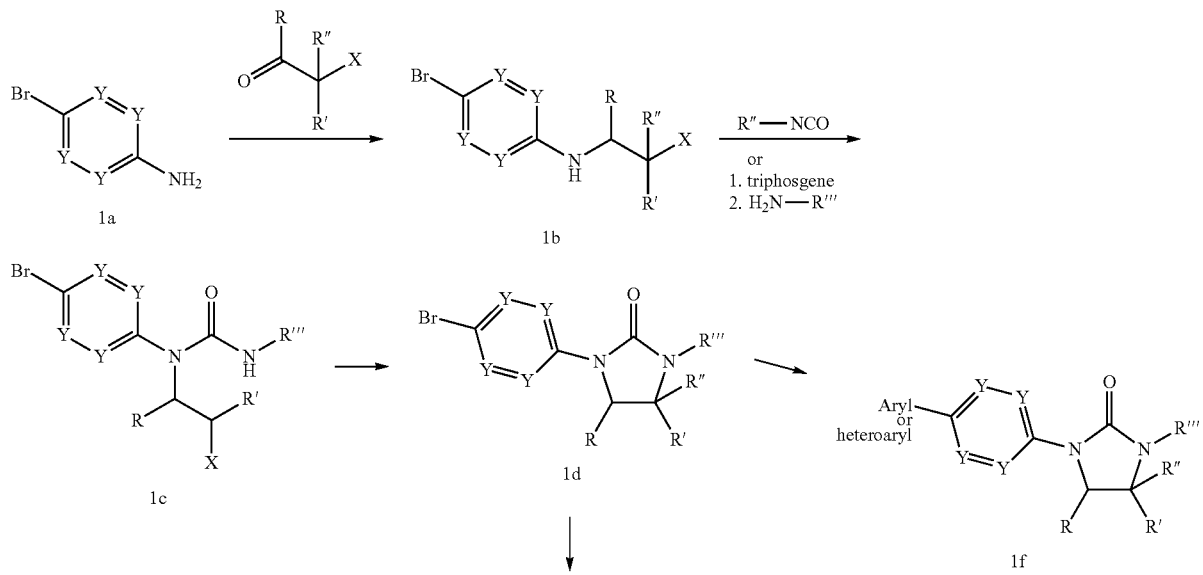

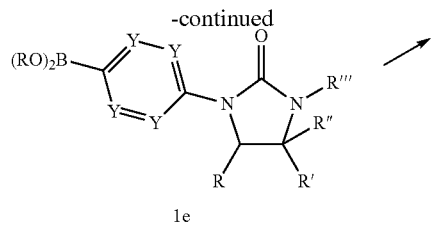

1e

Y = N, CR¹
X = Cl, Br

Scheme 1 shows the synthesis of compound 1f from amine 1a. Reductive amination with an appropriate haloaldehyde or haloketone affords amine 1b. Urea formation to afford 1c is accomplished by reaction with an isocyanate or treatment with triphosgene, followed by an amine. Cyclization of 1c with a base such as NaH affords the cyclic urea 1d. This intermediate can be directly coupled with an aryl or heteroaryl boronic acid using Pd-catalysis to afford 1f. Alternatively, 1d can be converted to the boronic acid/ester 1e via a Suzuki/Miyaura coupling and subsequently to the compound 1f via coupling with the appropriate aryl or heteroaryl halide using Pd-catalysis.

Scheme 2 shows the preparation of compounds of the generic structure 2d. Compound 1a is alkylated with a dihaloester to afford 2a, which can be treated with an isocyanate or triphosgene, followed by an amine (H₂NR'), to afford a urea, which either spontaneously cyclizes or cyclizes with heat or optional treatment with base such as NaH or K₂CO₃, to afford 2b. 2b is optionally further functionalized by deprotonation with a base such as LiHMDS or LDA, followed by treatment with an electrophile R"X to afford 2c. The ester moiety is optionally further functionalized by reduction with a base such as LiBH₄, alkylation by treatment with an alkylmetal species such as a Grignard reagent, or by hydrolysis and amide formation with the resultant acid to afford 2c. Suzuki coupling affords 2d.

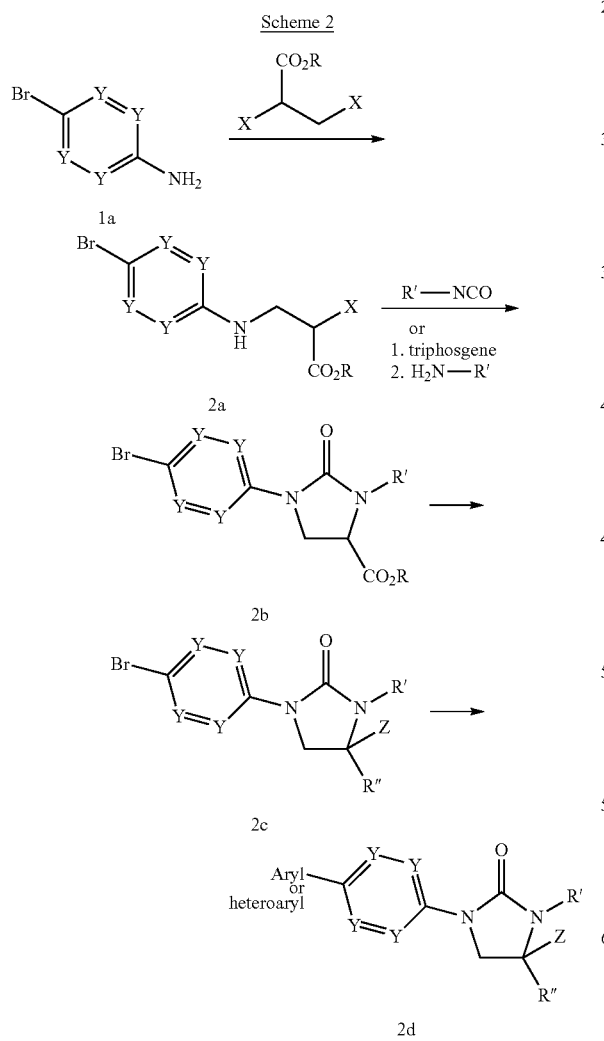

Z = CO₂R¹, CH₂OH, C(R''')OH, CONR¹R², etc. R" = H, optionally substituted alkyl

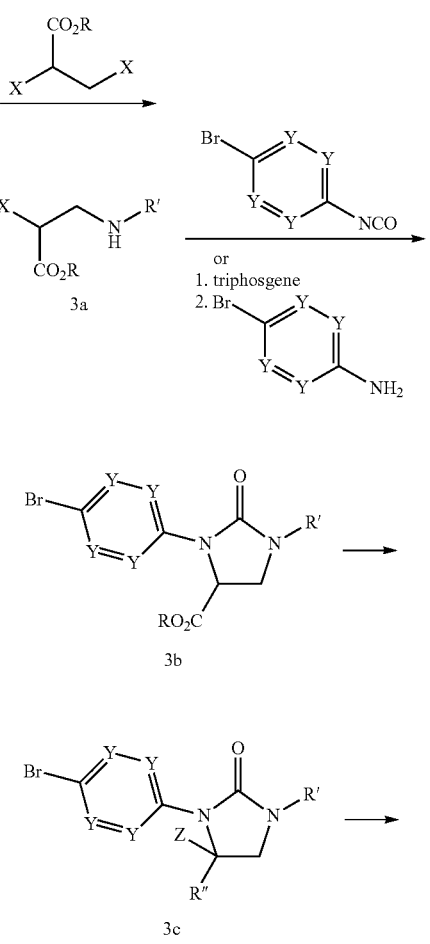

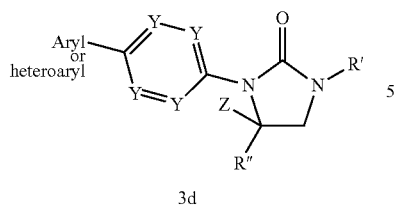

3d

Z = CO$_2$R$^1$, CH$_2$OH, C(R''')OH, CONR$^1$R$^2$, etc. R'' = H, optionally substituted alkyl Scheme 3 shows the synthesis of compounds of the generic structure 3d. Reaction of R'NH$_2$ with a dihaloester affords 3a. Reaction of 3a with an isocyanate (related to 1a), or triphosgene, followed by treatment with amine 1a affords a urea, which either cyclizes spontaneously or with heat or optional treatment with base such as NaH or K$_2$CO$_3$, to afford 3b. 3b is optionally further functionalized by deprotonation with a base such as LiHMDS or LDA, followed by treatment with an electrophile R''X to afford 3c. The ester moiety is optionally further functionalized by reduction with a base such as LiBH$_4$, alkylation by treatment with an alkylmetal species such as a Grignard reagent, or by hydrolysis and amide formation with the resultant acid to afford 3c. Suzuki coupling affords 3d.

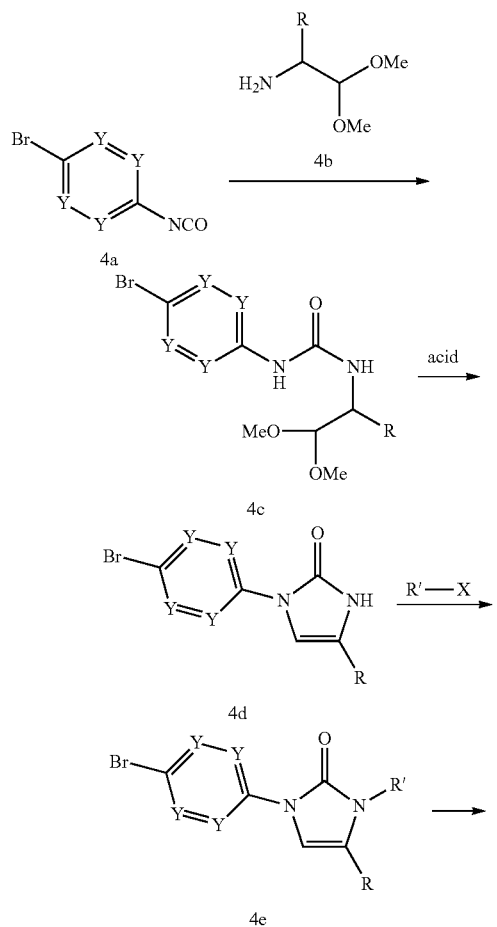

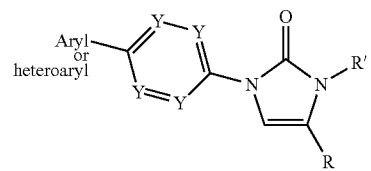

4f

Scheme 4 shows the synthesis of imidazolone 4f, beginning from isocyanate 4a, which is either commercially available or can be prepared from the amine precursor via treatment with phosgene and base, such as TEA. Treatment of 4a with amine 4b affords urea 4c. Cyclization is accomplished by treatment with acid such as HCl to afford 4d. Alkylation of 4d by treatment with a base such as NaH or K$_2$CO$_3$ and an electrophile affords 4e. Suzuki coupling affords 4f.

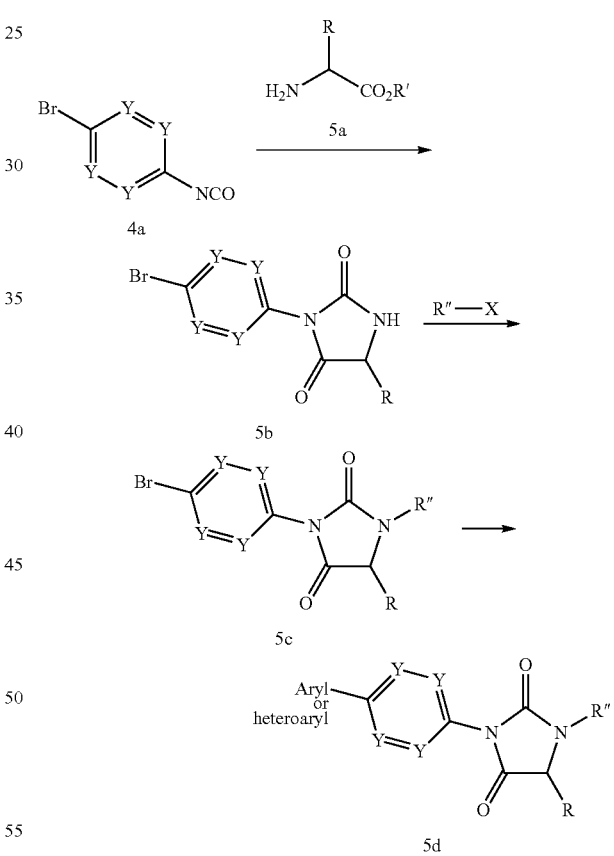

Scheme 5 shows the synthesis of imidazodinedione 5d, beginning from isocyanate 4a, which is either commercially available or can be prepared from the amine precursor via treatment with phosgene and base, such as TEA. Treatment of 4a with aminoester 5a affords a urea, which either cyclizes spontaneously or with heat or optional treatment with base such as NaH or K$_2$CO$_3$, to afford imidazolidinonedione 5b. Alkylation by treatment with a base such as NaH or K$_2$CO$_3$ and an electrophile affords 5c. Suzuki coupling affords 5d.

Scheme 6

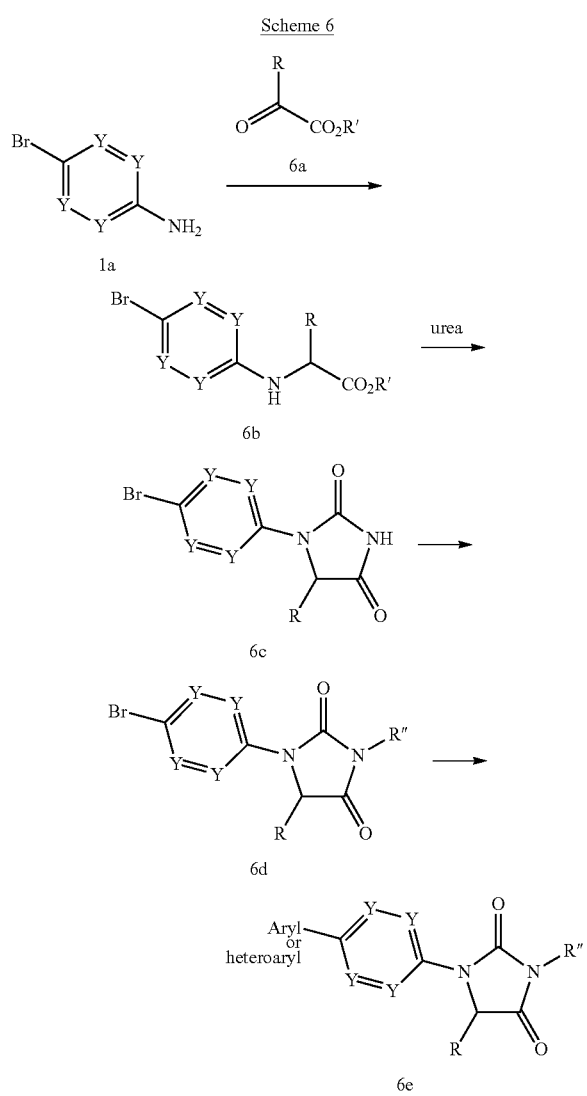

Scheme 6 shows the synthesis of imidazolidinedione 6e, beginning with amine 1a, which is subjected to reductive amination with 6a using a reducing agent such as Na(OAc)$_3$BH. Treatment of 6b with urea in a base such as pyridine with heating affords 6c. Alkylation by treatment with a base such as NaH or K$_2$CO$_3$ and an electrophile affords 6d. Suzuki coupling affords 6e.

Scheme 7

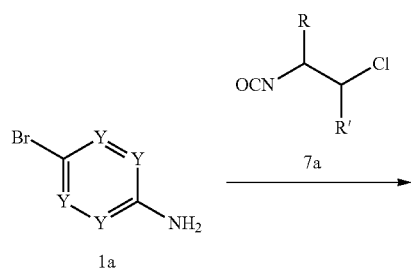

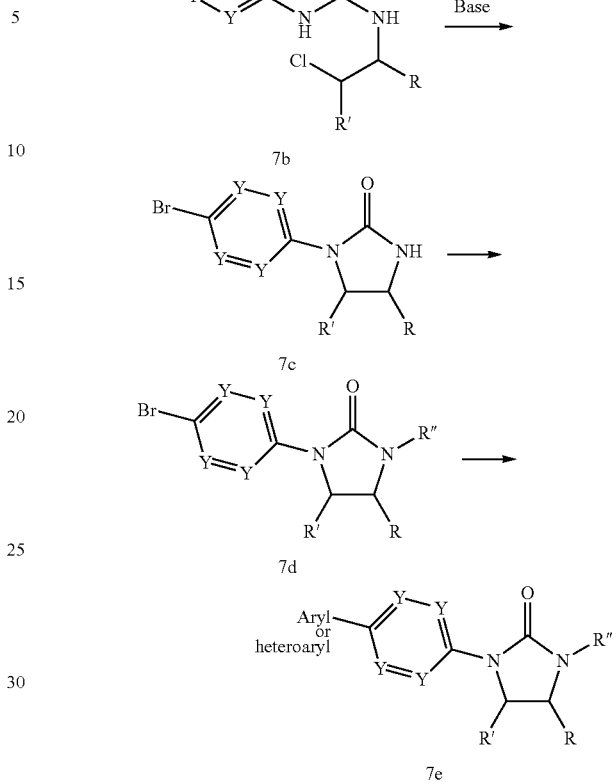

Scheme 7 shows the synthesis of generic compound 7e, beginning from amine 1a. Treatment with isocyanate 7a, which is either commercially available or can be prepared from the amine precursor via treatment with phosgene and base, such as TEA, affords urea 7b. Treatment with a base such as NaH or K$_2$CO$_3$ affords the cyclized product 7c. Alkylation by treatment with a base such as NaH or K$_2$CO$_3$ and an electrophile affords 7d. Suzuki coupling affords 7e.

Purification of intermediates and final products was carried out via either normal or reverse phase chromatography. Normal phase chromatography was carried out using prepacked SiO$_2$ cartridges eluting with either gradients of hexanes and EtOAc or DCM and MeOH unless otherwise indicated. Reverse phase preparative HPLC was carried out using C18 columns eluting with gradients of Solvent A (90% H$_2$O, 10% MeOH, 0.1% TFA) and Solvent B (10% H$_2$O, 90% MeOH, 0.1% TFA, UV 220 nm) or with gradients of Solvent A (90% H$_2$O, 10% ACN, 0.1% TFA) and Solvent B (10% H$_2$O, 90% ACN, 0.1% TFA, UV 220 nm) or with gradients of Solvent A (98% H$_2$O, 2% ACN, 0.05% TFA) and Solvent B (98% ACN, 2% H$_2$O, 0.05% TFA, UV 220 nm) (or) SunFire Prep C18 OBD 5μ 30×100 mm, 25 min gradient from 0-100% B. A=H$_2$O/ACN/TFA 90:10:0.1. B=ACN/H$_2$O/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A: SunFire C18 column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method B: XBridge Phenyl column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method C: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 4 minutes, then a 1-minute hold at 100% B; Flow: 1.1 mL/min.

Method D: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min.

Method E: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method F: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

Method G: SunFire C18 column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method H: XBridge Phenyl column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method I: SunFire C18 column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J: XBridge Phenyl column (3.5 m, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method K: SunFire C18 column (3.5 m, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L: XBridge Phenyl column (3.5 m, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method M: SunFire C18 column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method N: XBridge Phenyl column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

SFC and Chiral Purity Methods

Method I: CHIRALPAK® AD-H, 250×4.6 mm, 5.0-μm particles; $CO_2$: 60%, Co-solvent: 40% {0.2% DEA in IPA:ACN (1:1)}, Total Flow: 4.0 g/min, Back Pressure: 100 bars, Temperature: 25° C., UV: 218 nm.

Method II: CHIRALPAK® OD-H, 250×4.6 mm, 5.0-μm particles; $CO_2$: 60%, Co-solvent: 40% {0.2% DEA in IPA:ACN (1:1)}, Total Flow: 4.0 g/min, Back Pressure: 104 bars, Temperature: 24.9° C., UV: 287 nm.

Method III: CHIRALPAK® OJ-H, 250×4.6 mm, 5.0-μm particles; $CO_2$: 60%, Co-solvent: 30% (0.3% DEA in methanol), Total Flow: 4.0 g/min, Back Pressure: 101 bars, Temperature: 23.6° C., UV: 272 nm.

Method IV: CHIRALPAK® AS-H, 250×4.6 mm, 5.0-μm particles; $CO_2$: 60%, Co-solvent: 40% (0.3% DEA in methanol), Total Flow: 4.0 g/min, Back Pressure: 102 bars, Temperature: 25.4° C., UV: 272 nm.

Method V: CHIRALCEL® OJ-H, 250×4.6 mm, 5.0-μm particles; $CO_2$: 60%, Co-solvent: 40% (0.2% DEA in methanol), Total Flow: 4.0 g/min, Back Pressure: 102 bars, Temperature: 24.6° C., UV: 272 nm.

Method VI: Lux Cellulose-2, 250×4.6 mm, 5.0-μm particles; $CO_2$: 60%, Co-solvent: 35% (0.2% DEA in methanol), Total Flow: 3.0 g/min, Back Pressure: 101 bars, Temperature: 23.6° C., UV: 260 nm.

Method VII: CHIRALCEL® AS-H, 250×4.6 mm, 5.0-μm particles; $CO_2$: 60%, Co-solvent: 40% (0.2% DEA in methanol), Total Flow: 4.0 g/min, Back Pressure: 101 bars, Temperature: 24.4° C., UV: 270 nm.

Method VIII: CHIRALPAK® IC, 250×4.6 mm, 5.0-μm particles; $CO_2$: 60%, Co-solvent: 40% (0.2% DEA in methanol), Total Flow: 4.0 g/min, Back Pressure: 101 bars, Temperature: 24.4° C., UV: 270 nm.

Method IX: Column: CHIRALPAK® IF (250×4.6 mm), 5μ, Mobile Phase: 0.2% DEA in ethanol, Flow: 1.0 ml/min.

Method X: Column: Lux Amylose 2 (250×4.6 mm), 5μ, Mobile Phase: 0.2% DEA in n-hexane:ethanol: 5:95, Flow: 1.0 ml/min.

Method XI: Column: CHIRALCEL® OD-H (250×4.6 mm), 5μ, Mobile Phase: 0.2% DEA in n-hexane:ethanol: 70:30, Flow: 1.0 ml/min.

Method XII: Column: CHIRALPAK® ID (250×4.6 mm), 5μ, Mobile Phase: 0.1% DEA in methanol, Flow: 1.0 ml/min.

Intermediate 1

4-Bromo-N-(2-chloroethyl)aniline

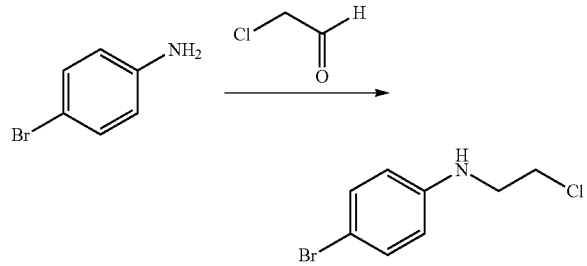

To a solution of 4-bromoaniline (3.00 g, 17.4 mmol) and 2-chloroacetaldehyde (2.69 mL, 20.9 mmol) in MeOH (25 mL), was added sodium cyanoborohydride (2.74 g, 43.6 mmol), followed by acetic acid (1.00 mL, 17.0 mmol). The mixture was stirred at rt overnight. Additional sodium cyanoborohydride (2.74 g, 43.6 mmol) was added and the mixture was stirred for 1 day. MeOH was evaporated and the mixture was basified with aq. NaHCO$_3$ and extracted with ethyl acetate (3×50 ml). The organic layer was dried (Na$_2$SO$_4$) and evaporated. The product was purified by flash chromatography (0-15% EtOAc/Hex gradient) to obtain 3.25 g (79% yield) of Intermediate 1 as a colorless oil. MS(ESI) m/z: 233.9 (M+H)$^+$; $^1$H NMR (400 MHz, CD$_3$OD) δ ppm 7.21 (d, J=8.80 Hz, 2H), 6.57 (d, J=8.80 Hz, 2H), 3.65 (t, J=6.40 Hz, 2H), 3.43 (t, J=6.40 Hz, 2H).

Intermediate 2

4-Bromo-N-(2-chloroethyl)-3-methoxyaniline

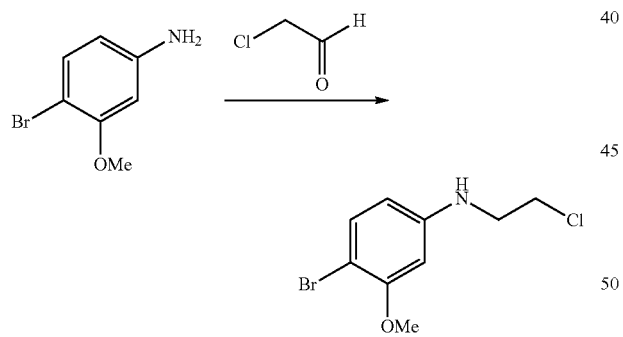

To a solution of 4-bromo-3-methoxyaniline (4.00 g, 19.8 mmol) and 2-chloroacetaldehyde (3.05 mL, 23.8 mmol) in MeOH (25 mL), was added sodium cyanoborohydride (3.11 g, 49.5 mmol), followed by acetic acid (1.13 mL, 19.8 mmol). The mixture was stirred at rt overnight. MeOH was evaporated and the mixture was basified with NaHCO$_3$ and extracted with ethyl acetate (3×40 ml). The organic layer was dried (Na$_2$SO$_4$) and evaporated. The product was purified by flash chromatography (0-15% EtOAc/hexanes gradient) to obtained 3.20 g (61% yield) of Intermediate 2 as a colorless oil. MS(ESI) m/z: 263.9 (M+H)$^+$; $^1$H NMR (300 MHz, CDCl$_3$) δ ppm 7.26-7.34 (m, 1H), 6.23 (d, J=2.41 Hz, 1H), 6.16 (dd, J=8.50, 2.50 Hz, 1H), 4.12 (brs, 1H), 3.87 (s, 3H), 3.69-3.77 (m, 2H), 3.51 (q, J=5.45 Hz, 2H).

Intermediate 3

4-Bromo-N-(2-chloroethyl)-2-methoxyaniline

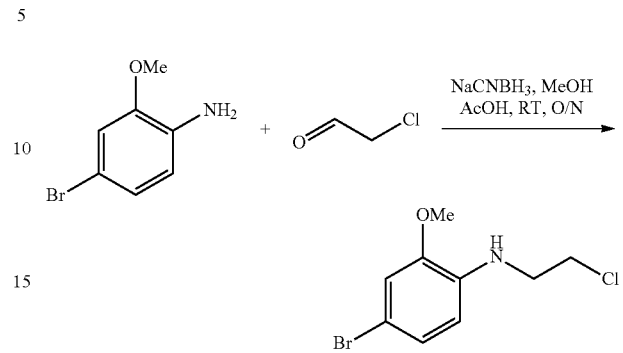

To the solution of 4-bromo-2-methoxyaniline (2.00 g, 9.90 mmol) and 2-chloroacetaldehyde (1.87 g, 11.9 mmol) in methanol (20 mL), was added sodium cyanoborohydride (1.56 g, 24.7 mmol) and acetic acid (0.567 mL, 9.90 mmol). The mixture was stirred at rt overnight, then was concentrated. The product was purified by flash chromatography (0-50% EtOAc/hexanes gradient) to obtained 2.20 g (59% yield) of Intermediate 3 as a yellow oil. MS(ESI) m/z: 264.3 (M+H)$^+$; $^1$H NMR (300 MHz, CDCl$_3$) δ ppm 6.99 (dd, J=8.40, 2.12 Hz, 1H) 6.89 (d, J=2.12 Hz, 1H) 6.47 (d, J=8.45 Hz, 1H) 4.60 (s, 1H) 3.87 (s, 3H) 3.69-3.75 (m, 2H) 3.51 (q, J=6.06 Hz, 2H).

Intermediate 4

Ethyl 2-bromo-3-((4-bromophenyl)amino)propanoate

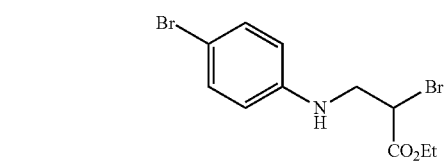 [SMILES: CCOC(=O)C(Br)CNc1ccc(Br)cc1]

Preparation of ethyl 2-bromo-3-((4-bromophenyl)amino)propanoate

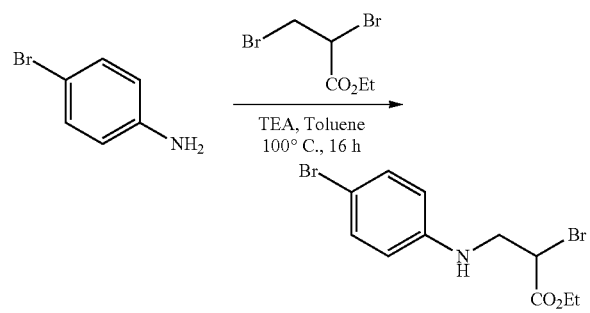

To a suspension of 4-bromoaniline (20 g, 116 mmol) in toluene (100 mL) was added TEA (48.6 mL, 349 mmol) and the mixture was heated to 50° C., then an ethyl 2,3-dibromopropanoate (16.90 mL, 116 mmol) in toluene (50 mL) was added dropwise and reaction mixture was heated at 100° C. for 20 h. The reaction mixture was cooled to rt and diluted with DCM (100 mL) and hexanes and filtered. The filtrate was concentrated to afford ethyl 2-bromo-3-((4-bromophenyl)amino)propanoate (5.8 g, 11.8% yield) as a brown solid. MS(ESI) m/z: 352.4 (M+H)+. 1H NMR (400 MHz, DMSO-d6) δ ppm 7.23 (d, J=9.0 Hz, 2H), 6.62 (d, J=9.0 Hz, 2H), 4.48 (dd, J=8.5, 6.0 Hz, 1H), 4.20-4.12 (m, 2H), 3.72 (dd, J=14.3, 8.3 Hz, 1H), 3.49 (dd, J=14.3, 6.3 Hz, 1H), 1.22-1.16 (m, 3H).

Intermediate 5

1-(4-Bromophenyl)-3-(1-hydroxy-2-methylpropan-2-yl)urea

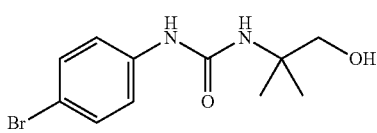 [SMILES: CC(C)(CO)NC(=O)Nc1ccc(Br)cc1]

Preparation of 1-(4-bromophenyl)-3-(1-hydroxy-2-methylpropan-2-yl)urea

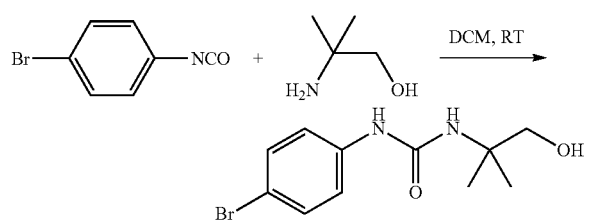

To a solution of 1-bromo-4-isocyanatobenzene (500 mg, 2.53 mmol) in DCM (25 mL) was added dropwise 2-amino-2-methylpropan-1-ol (270 mg, 3.03 mmol) and the reaction mixture was stirred at rt for 16 h. DCM was concentrated to dryness and residue was diluted with hexanes, solid formed was filtered and washed with hexane and dried under vacuum to afford the Intermediate 5 (1-(4-bromophenyl)-3-(1-hydroxy-2-methylpropan-2-yl)urea (0.7 g, 97% yield) as a white solid. MS(ESI) m/z: 289.0 (M+H)+. 1H NMR (400 MHz, DMSO-d6) δ ppm 8.62 (s, 1H), 7.39-7.25 (m, 4H), 5.94 (s, 1H), 5.00-4.91 (m, 1H), 3.36 (d, J=5.5 Hz, 2H), 1.22 (s, 6H).

Intermediate-6

Preparation of ethyl 1-(3-methoxybenzyl)aziridine-2-carboxylate

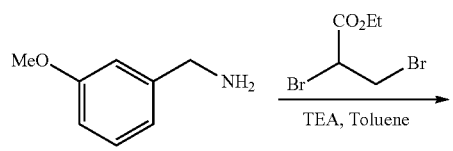

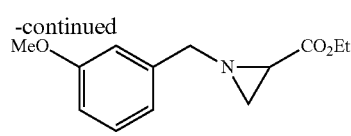

To a solution of (3-methoxyphenyl)methanamine (2.0 g, 14.58 mmol) in toluene (30 mL) was added TEA (8.13 mL, 58.3 mmol) and ethyl 2,3-dibromopropanoate (3.79 g, 14.58 mmol) in toluene (10 mL) at rt and the reaction mixture was stirred at 85° C. for 16 h. Reaction mixture was cooled to rt, solid formed was filtered and dried under vacuum to afford the Intermediate 6 (ethyl 1-(3-methoxybenzyl)aziridine-2-carboxylate) (4.2 g, 76% yield) as a yellow solid. MS(ESI) m/z: 236.4 (M+H)+. 1H NMR (300 MHz, chloroform-d) δ ppm 7.29-7.22 (m, 1H), 6.97-6.90 (m, 2H), 6.83 (dd, J=8.1, 2.1 Hz, 1H), 4.26-4.17 (m, 2H), 3.82 (s, 3H), 3.63-3.47 (m, 2H), 2.28 (dd, J=3.0, 1.1 Hz, 1H), 2.20 (dd, J=6.4, 3.0 Hz, 1H), 1.77 (dd, J=6.4, 0.8 Hz, 1H), 1.29 (t, J=7.0 Hz, 3H)

Intermediate 7

Preparation of ethyl 2-chloro-3-((3-methoxybenzyl)amino)propanoate

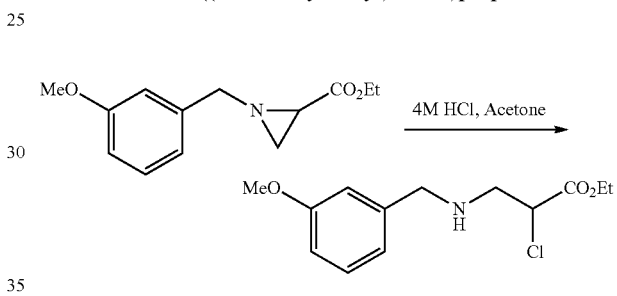

To a solution of ethyl 1-(3-methoxybenzyl)aziridine-2-carboxylate (4.2 g, 17.85 mmol) in acetone (45 mL) was 4 M HCl in dioxane (13.39 mL, 53.6 mmol) at 0° C., reaction mixture was slowly stirred at rt for 16 h. Reaction was carefully quenched with NaHCO3 (100 mL) and extracted with EtOAc (2×100 mL). Combined organic layer was washed with water, brine solution, dried over Na2SO4, filtered and concentrated. The crude product was purified by CombiFlash chromatography (40 g REDISEP® SiO2 column, gradient elution; 100% Hex for 5 min; 0-60% EtOAc/Hex for 30 min) to afford the Intermediate 7, ethyl 2-chloro-3-((3-methoxybenzyl)amino)propanoate (0.39 g, 4.7% yield) as a yellow liquid. MS(ESI) m/z: 272.1 (M+H)+.

Intermediate 8

Preparation of 1-(4-bromophenyl)-3-(2-chloroethyl)urea

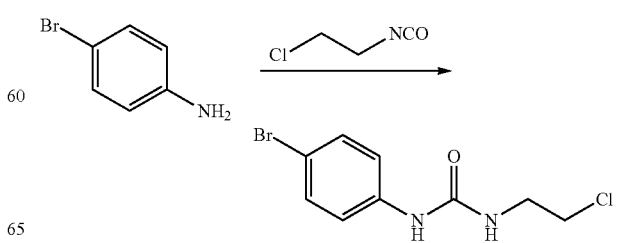

To a mixture of 4-bromoaniline (5.00 g, 29.1 mmol) in dichloromethane (80 mL) at 0° C., was slowly added 1-chloro-2-isocyanatoethane (2.98 mL, 34.9 mmol). The mixture was stirred at rt for 16 h. The mixture was concentrated. The crude product mixture was purified by trituration with pet. ether to afford 6.00 g of Intermediate 8 (74% yield) as an off-white solid. MS(ESI) m/z: 277.2 (M+H)+; 1H NMR (400 MHz, DMSO-d6) δ 8.79 (s, 1H), 7.43-7.33 (m, 4H), 6.44 (t, J=5.8 Hz, 1H), 3.65 (t, J=6.0 Hz, 2H), 3.41 (q, J=6.0 Hz, 2H).

Intermediate 9

1-(4-Bromophenyl)imidazolidin-2-one

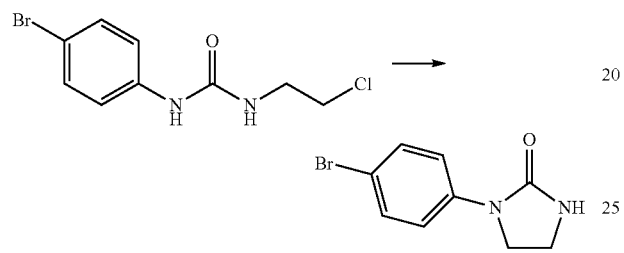

To an ice cold mixture of Intermediate 6 (8.00 g, 28.8 mmol) in THF (100 mL) was added sodium hydride (2.08 g, 860 mmol) in portions over 30 min. The mixture was stirred at rt for 16 h, then was quenched with ice and diluted in ethyl acetate. The organic layer was separated and washed with water and brine, dried (Na2SO4) and concentrated. This crude product was purified by triturating with hexanes to afford Intermediate 9 (5.00 g, 72% yield) as an off-white solid. MS(ESI) m/z: 241.3 (M+H)+; 1H NMR (300 MHz, DMSO-d6) δ 7.61-7.35 (m, 1H), 7.05 (s, 1H), 3.82 (dd, J=9.1, 6.8 Hz, 2H), 3.44-3.35 (m, 2H).

Intermediate 10

1-(5-Bromo-6-methoxypyridin-2-yl)-3-(2-chloroethyl)urea

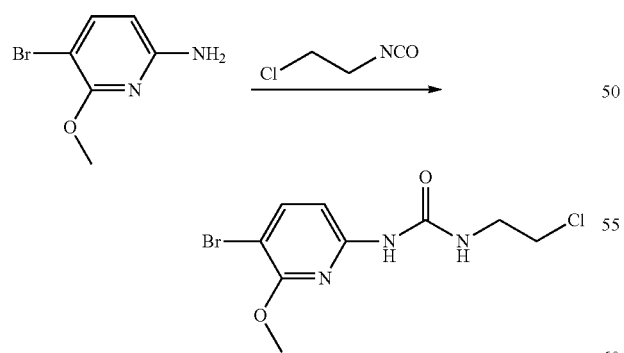

5-Bromo-6-methoxypyridin-2-amine (1 g, 4.93 mmol) was taken in dichloromethane (30 mL) under nitrogen atmosphere. Cooled to 0° C. and added 2-chloroethyl isocyanate (2.079 g, 19.70 mmol) dropwise and the reaction mixture was stirred at RT for 20 h. Solvent was removed under reduced pressure and the residue obtained was washed with hexanes and dried under suction to give 1-(5-bromo-6-methoxypyridin-2-yl)-3-(2-chloroethyl)urea (1.12 g, 3.60 mmol, 73% yield) as an off-white solid. MS(ESI) m/z: 308.0 (M+H)+. 1H NMR (400 MHz, DMSO-d6) δ ppm 9.31 (s, 1H), 7.85 (d, J=8.5 Hz, 1H), 7.56 (t, J=5.8 Hz, 1H), 7.12 (d, J=8.5 Hz, 1H), 3.90 (s, 3H), 3.72-3.66 (m, 2H), 3.54-3.47 (m, 2H).

Intermediate 11

1-(5-Bromo-6-methoxypyridin-2-yl)imidazolidin-2-one

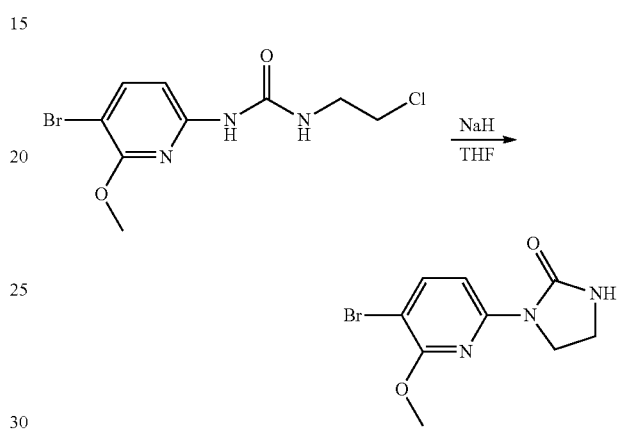

1-(5-Bromo-6-methoxypyridin-2-yl)-3-(2-chloroethyl)urea (1.1 g, 3.56 mmol) was taken in THF (30 mL) under nitrogen atmosphere. Cooled to 0° C. and added sodium hydride (60% suspension in mineral oil) (0.428 g, 10.69 mmol) and the reaction mixture was stirred at RT for 6 h. Added MeOH (10 mL) and the solvent was removed under reduced pressure. The solid obtained was washed with water and dried under suction to give Intermediate 11: 1-(5-bromo-6-methoxypyridin-2-yl)imidazolidin-2-one (0.84 g, 3.04 mmol, 85% yield) as an off-white solid. MS(ESI) m/z: 272.0 (M+H)+. 1H NMR (400 MHz, DMSO-d6) δ ppm 7.85 (d, J=8.5 Hz, 1H), 7.66 (d, J=8.5 Hz, 1H), 7.27 (s, 1H), 4.05-3.98 (m, 2H), 3.90 (s, 3H), 3.45-3.37 (m, 2H).

Intermediate 12

1-(4-Bromophenyl)-3-(2,2-dimethoxyethyl)urea

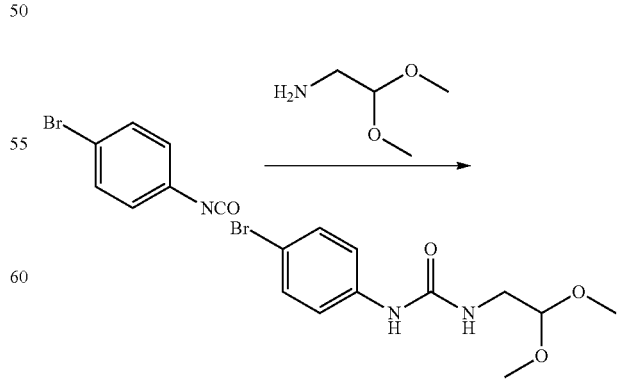

To an ice cold mixture of 2,2-dimethoxyethanamine (3.01 mL, 27.8 mmol) in dichloromethane (100 mL) was added 1-bromo-4-isocyanatobenzene (5.5 g, 27.8 mmol) dropwise and the mixture was stirred well at ambient temperature for 16 h. The reaction mixture was concentrated in vacuo to get the crude, which was triturated with hexanes to afford 1-(4-bromophenyl)-3-(2,2-dimethoxyethyl)urea (8 g, 22.17 mmol, 80% yield) as an off-white solid. MS(ESI) m/z: 302.9 (M−H)$^+$. $^1$H NMR (300 MHz, DMSO-d$_6$) δ=8.71 (s, 1H), 7.50-7.31 (m, 5H), 6.18 (t, J=5.9 Hz, 1H), 4.38 (t, J=5.3 Hz, 1H), 3.29 (s, 6H), 3.20 (t, J=5.5 Hz, 2H).

Intermediate 13

1-(4-Bromophenyl)-1H-imidazol-2(3H)-one

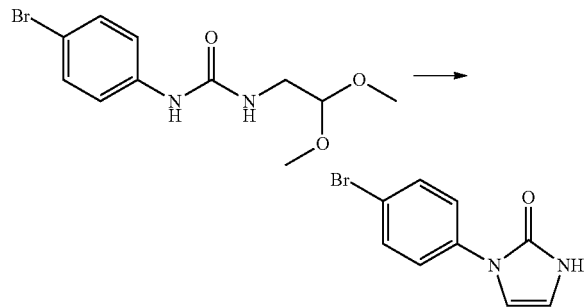

To 1.5 M HCl in water (88 ml, 132 mmol) was added 1-(4-bromophenyl)-3-(2,2-dimethoxyethyl)urea (8 g, 26.4 mmol) and the mixture was stirred well at ambient temperature for 20 h. Then the reaction mixture was basified by using saturated aq. NaHCO$_3$ solution and the product was extracted with DCM. The combined extracts were washed in water followed by brine, dried over anhydrous sodium sulfate and concentrated in vacuo to afford 1-(4-bromophenyl)-1H-imidazol-2(3H)-one (5 g, 18.61 mmol, 70.5% yield) as an off-white solid. MS(ESI) m/z: 238.9 (M+H)$^+$. $^1$H NMR (300 MHz, DMSO-d$_6$) δ=10.37 (br. s., 1H), 7.78-7.70 (m, 2H), 7.64-7.57 (m, 2H), 7.00 (dd, J=3.2, 2.1 Hz, 1H), 6.62 (dd, J=3.0, 2.3 Hz, 1H).

Intermediate 14

Phenyl (5-bromopyridin-2-yl)carbamate

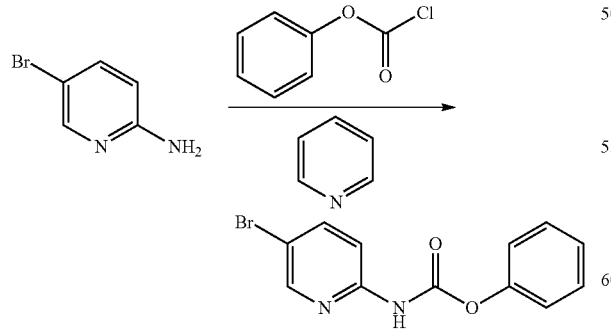

To an ice cold mixture of 5-bromopyridin-2-amine (5 g, 28.9 mmol) and pyridine (2.80 mL, 34.7 mmol) in acetonitrile (100 mL) was added phenyl carbonochloridate (4.36 mL, 34.7 mmol) and stirred well at ambient temperature for 1 h. The solid formed in the reaction mixture was filtered, washed with water and dried to afford phenyl (5-bromopyridin-2-yl)carbamate (8.5 g, 20.42 mmol, 70.6% yield) as an off-white solid. MS(ESI) m/z: 294.9; $^1$H NMR (400 MHz, DMSO-d$_6$) δ=10.92 (s, 1H), 8.45 (d, J=2.5 Hz, 1H), 8.03 (dd, J=8.8, 2.8 Hz, 1H), 7.82-7.78 (m, 1H), 7.47-7.40 (m, 2H), 7.31-7.20 (m, 3H).

Intermediate 15

1-(5-Bromopyridin-2-yl)-3-(2,2-dimethoxyethyl)urea

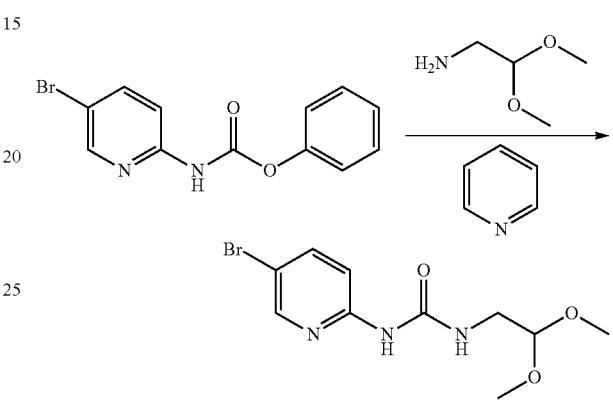

To the mixture of phenyl (5-bromopyridin-2-yl)carbamate (8.5 g, 29.0 mmol) and pyridine (2.81 mL, 34.8 mmol) in THF (150 mL) was added 2,2-dimethoxyethanamine (3.77 mL, 34.8 mmol) and heated at 70° C. for 16 h. The reaction mixture was quenched with ice and diluted with diethylether. The precipitated solid was filtered, washed with water and dried to afford 1-(5-bromopyridin-2-yl)-3-(2,2-dimethoxyethyl)urea (7 g, 22.27 mmol, 77% yield) as an off-white solid. MS(ESI) m/z: 304.0; $^1$H NMR (400 MHz, DMSO-d$_6$) δ=9.33 (s, 1H), 8.29 (d, J=2.5 Hz, 1H), 7.88 (dd, J=8.8, 2.8 Hz, 1H), 7.62-7.50 (m, 2H), 4.43-4.33 (m, 1H), 3.35-3.29 (m, 6H), 3.26 (t, J=5.8 Hz, 2H).

Intermediate 16

1-(5-Bromopyridin-2-yl)-1H-imidazol-2(3H)-one

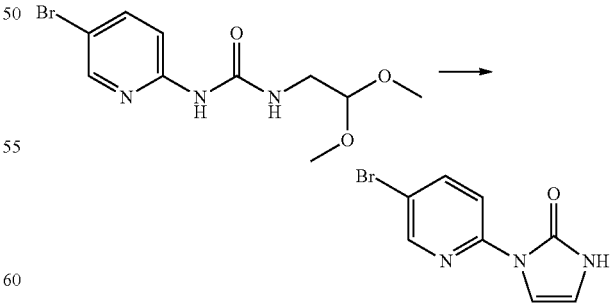

The solution of 1-(5-bromopyridin-2-yl)-3-(2,2-dimethoxyethyl)urea (7 g, 23.02 mmol) in 2N aq. HCl (200 ml, 400 mmol) was heated at 60° C. for 16 h. The reaction mixture was cooled to 0° C. and basified to pH-8 using 10% aq. NaOH solution and extracted with chloroform. The combined extracts were washed with water followed by brine, dried over anhydrous sodium sulfate and concentrated in vacuo to afford 1-(5-bromopyridin-2-yl)-1H-imidazol-2 (3H)-one (4.6 g, 18.31 mmol, 80% yield) as an off-white solid. MS(ESI) m/z: 241.1; $^1$H NMR (400 MHz, DMSO-$d_6$) δ=10.51 (br. s., 1H), 8.56-8.51 (m, 1H), 8.40-8.34 (m, 1H), 8.12 (dd, J=8.8, 2.8 Hz, 1H), 7.20 (d, J=3.5 Hz, 1H), 6.66 (d, J=3.5 Hz, 1H).

Intermediate 17

Preparation of 1-(5-bromo-4-methylpyridin-2-yl)-3-(2-chloroethyl)urea

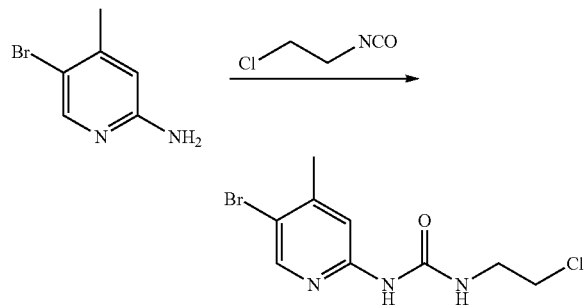

To a mixture of 5-bromo-4-methylpyridin-2-amine (2 g, 10.69 mmol) in dichloromethane (50 mL) at 0° C., was slowly added 1-chloro-2-isocyanatoethane (1.095 mL, 12.83 mmol). After stirring the mixture at rt for 16 h, it was concentrated. The crude product mixture was purified by trituration with hexanes to afford 1-(5-bromo-4-methylpyridin-2-yl)-3-(2-chloroethyl)urea (2.10 g, 77% yield) as an off-white solid. MS(ESI) m/z: 294.2 (M+H)$^+$; $^1$H NMR (400 MHz, DMSO-$d_6$) δ 9.34 (s, 1H), 8.25 (s, 1H), 7.87 (t, J=5.8 Hz, 1H), 7.50 (s, 1H), 3.68 (t, J=6.0 Hz, 2H), 3.49 (q, J=6.0 Hz, 2H), 2.30 (s, 3H).

Intermediate 18

Preparation of 1-(5-bromo-4-fluoropyridin-2-yl)-3-(2-chloroethyl)urea

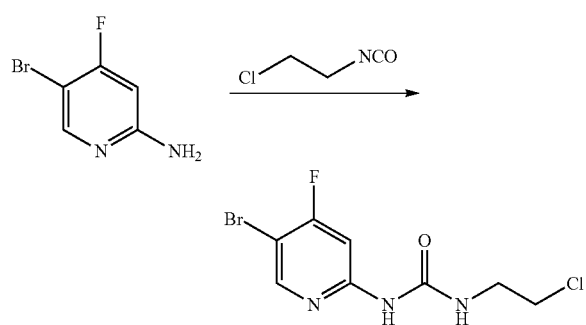

To a mixture of 5-bromo-4-fluoropyridin-2-amine (1.6 g, 8.38 mmol) in dichloromethane (30 mL) at 0° C. was slowly added 1-chloro-2-isocyanatoethane (0.884 g, 8.38 mmol). After stirring the mixture at rt for 16 h, it was concentrated. The crude product mixture was purified by trituration with hexanes to afford of 1-(5-bromo-4-fluoropyridin-2-yl)-3-(2-chloroethyl)urea (1.50 g, 60.4% yield) as an off-white solid. MS(ESI) m/z: 298.1 (M+H)$^+$; $^1$H NMR (400 MHz, DMSO-$d_6$) δ 9.60 (s, 1H), 8.40-8.44 (m, 1H), 7.60-7.65 (m, 1H), 7.48 (s, 1H), 3.67 (t, J=6.0 Hz, 2H), 3.47 (q, J=6.0 Hz, 2H).

Intermediate 19

1-(5-Bromo-4-fluoropyridin-2-yl)imidazolidin-2-one

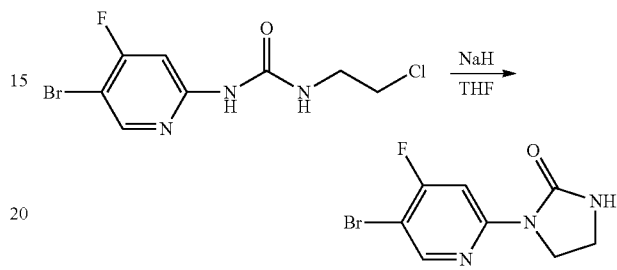

1-(5-Bromo-4-fluoropyridin-2-yl)-3-(2-chloroethyl)urea (1.5 g, 5.06 mmol) was taken in THF (30 mL) under nitrogen atmosphere. Cooled to 0° C. and added sodium hydride (60% suspension in mineral oil) (0.121 g, 5.06 mmol) and the reaction mixture was stirred at RT for 6 h. MeOH (10 mL) was added and the volatiles were removed under reduced pressure. The solid obtained was washed with water and dried under suction to give 1-(5-bromo-4-fluoropyridin-2-yl)imidazolidin-2-one (0.8 g, 3.08 mmol, 60.8% yield) as an off-white solid. MS(ESI) m/z: 262.1 (M+H)$^+$. $^1$H NMR (400 MHz, DMSO-$d_6$) δ ppm 8.50 (d, J=8.5 Hz, 1H), 8.14 (d, J=8.5 Hz, 1H), 7.48 (s, 1H), 3.99-3.95 (m, 2H), 3.43-3.37 (m, 2H).

Intermediate 20

3-Cyclopropylaniline

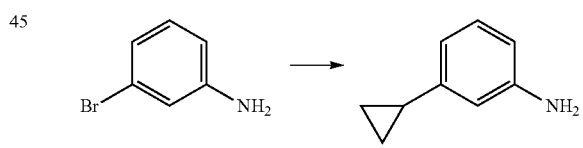

To a degassed solution of 3-bromoaniline (4 g, 23.25 mmol) in toluene (20 mL), were added cyclopropylboronic acid (3.99 g, 46.5 mmol), tricyclohexyl-phosphine (1.304 g, 4.65 mmol), potassium phosphate, dibasic (8.10 g, 46.5 mmol) and palladium (II) acetate (0.522 g, 2.325 mmol), at rt. The reaction was stirred under argon at 90° C. for 6 h. The reaction mixture was allowed to cool to rt, diluted with the DCM, washed with water, dried over sodium sulfate and concentrated to get the crude compound. The crude compound was purified by the CombiFlash (silica gel 60-120, hexanes-ethyl acetate as mobile phase 0-80%) to afford 3-cyclopropylaniline (2.0 g, 45%). MS(ESI) m/z: 135.1; $^1$H NMR (400 MHz, DMSO-$d_6$) δ 6.87 (t, J=7.72 Hz, 1H) 6.32 (ddd, J=7.91, 2.23, 0.97 Hz, 1H) 6.25-6.28 (m, 1H) 6.21-6.25 (m, 1H) 4.88 (s, 2H) 1.68-1.77 (m, 1H) 0.81-0.88 (m, 2H) 0.52-0.58 (m, 2H).

Intermediate 21 tert-Butyl (3-cyclopropylphenyl)carbamate

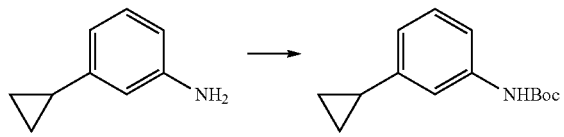 [SMILES: Nc1cccc(C2CC2)c1 ; CC(C)(C)OC(=O)Nc1cccc(C2CC2)c1]

To a solution of 3-cyclopropylaniline (2.0 g, 15.02 mmol) in DCM (20 mL) was added TEA (5.23 mL, 37.5 mmol) and BOC$_2$O (4.18 mL, 18 mmol). After stirring the reaction mixture for 4.5 h, it was diluted with DCM, washed with the water dried over sodium sulfate and concentrated to get the crude compound. The crude compound was purified by the CombiFlash (silica gel 60-120, hexanes-ethyl acetate as mobile phase 0-80%). Desired fractions were concentrated in vacuo to afford tert-butyl (3-cyclopropylphenyl)carbamate (1.8 g). $^1$H NMR (400 MHz, DMSO-d$_6$) δ 7.17-7.23 (m, 2H) 7.07-7.13 (m, 1H) 6.64-6.70 (m, 1H) 1.78-1.89 (m, 1H) 1.40-1.50 (s, 9H) 0.89-0.95 (m, 2H) 0.57-0.62 (m, 2H).

Intermediate 22 tert-Butyl (4-bromo-3-cyclopropylphenyl)carbamate

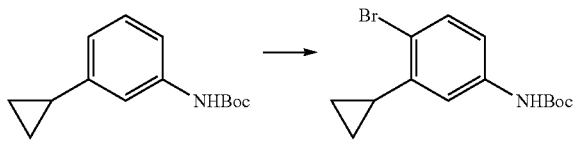 [SMILES: CC(C)(C)OC(=O)Nc1cccc(C2CC2)c1 ; CC(C)(C)OC(=O)Nc1ccc(Br)c(C2CC2)c1]

To a solution of tert-butyl (3-cyclopropylphenyl)carbamate (1.8 g, 7.72 mmol) in DM F (20 mL) was added 1-bromopyrrolidine-2,5-dione (1.373 g, 7.72 mmol) and the reaction mixture was stirred for 3 h. The reaction mixture was diluted with DCM, washed with the water dried over sodium sulfate and concentrated to get the crude compound. The crude compound was purified by the CombiFlash (silica gel 60-120, pet ether-ethyl acetate as mobile phase 0-80%). Collected fractions were concentrated in vacuo to afford tert-butyl (4-bromo-3-cyclopropylphenyl)carbamate (1.8 g). MS(ESI) m/z: 312.0; $^1$H NMR (400 MHz, DMSO-d$_6$) δ 9.34 (s, 1H) 7.42 (d, J=8.59 Hz, 1H) 7.23 (m, 1H) 7.12 (m, 1H) 1.46 (s, 9H) 0.99 (d, J=8.26 Hz, 2H) 0.57 (d, J=5.05 Hz, 2H).

Intermediate 23

4-Bromo-3-cyclopropylaniline

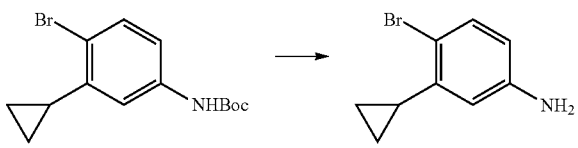 [SMILES: CC(C)(C)OC(=O)Nc1ccc(Br)c(C2CC2)c1 ; Nc1ccc(Br)c(C2CC2)c1]

To a solution of tert-butyl (4-bromo-3-cyclopropylphenyl)carbamate (1.8 g, 7.72 mmol) in dioxane (20 mL) was added 3 M HCl solution (5 mL) and the reaction mixture was stirred overnight, concentrated in vacuo and partitioned between DCM and water. The organic layer was separated washed with the water dried over sodium sulfate and concentrated to get the crude compound. The crude compound was purified by the CombiFlash (silica gel 60-120, hexanes-ethyl acetate as mobile phase 0-100%). Desired fractions were concentrated in vacuo to 4-bromo-3-cyclopropylaniline (1.0 g). MS(ESI) m/z: 212.2; $^1$H NMR (400 MHz, DMSO-d$_6$) δ 7.13 (d, J=8.47 Hz, 1H) 6.31 (dd, J=8.50, 2.73 Hz, 1H) 6.20 (d, J=2.70 Hz, 1H) 5.12 (br. s., 2H) 1.90-2.01 (m, 1H) 0.89-0.95 (m, 2H) 0.52-0.57 (m, 2H).

Example 1

1-(4-(1H-Pyrazol-4-yl)phenyl)-3-phenethylimidazolidin-2-one

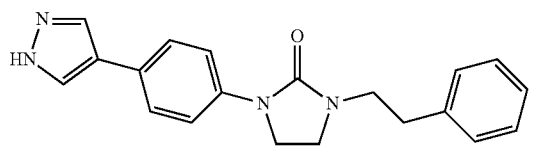 [SMILES: O=C1N(CCc2ccccc2)CCN1c1ccc(-c2cn[nH]c2)cc1]

Example 1A: 1-(4-Bromophenyl)-1-(2-chloroethyl)-3-phenethylurea

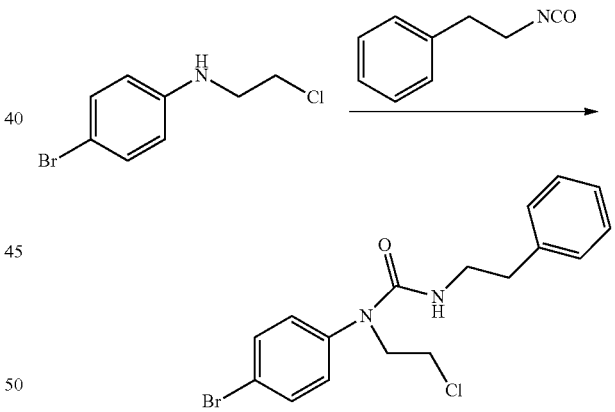

To a solution of Intermediate 1 (0.200 g, 0.850 mmol) in benzene (2 mL), was added (2-isocyanatoethyl)benzene (0.142 mL, 1.02 mmol). The mixture was stirred at 70° C. overnight. Benzene was evaporated and reaction mixture was diluted with water (10 mL) and extracted with ethyl acetate (3×10 mL). The organic layer washed with brine (20 mL) and dried over Na$_2$SO$_4$ and evaporated. The product was purified by flash chromatography (0-30% EtOAc/Hex gradient) to obtained 0.24 g (74% yield) of Example 1A as a colorless oil. MS(ESI) m/z: 381.0 (M+H)$^+$; $^1$H NMR (400 MHz, DMSO-d$_6$) δ ppm 7.54-7.61 (m, 2H), 7.24-7.32 (m, 2H), 7.12-7.22 (m, 5H), 5.90 (t, J=5.65 Hz, 1H), 3.81 (t, J=6.80 Hz, 2H), 3.60 (t, J=6.80 Hz, 2H), 3.16-3.24 (m, 2H), 2.67 (t, J=7.40 Hz, 2H).

Example 1B: 1-(4-Bromophenyl)-3-phenethylimidazolidin-2-one

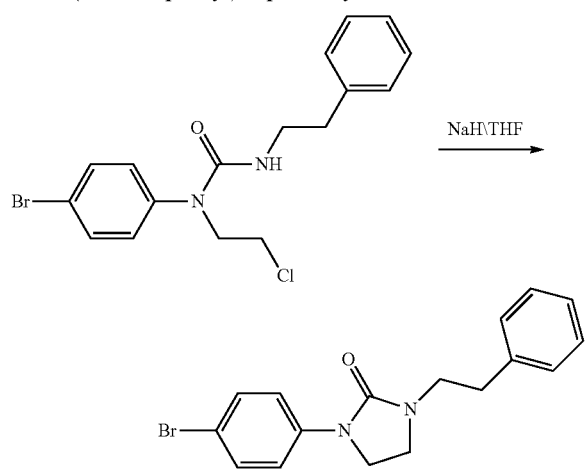

To a solution of Example 1A (0.220 g, 0.576 mmol) in THF (5 mL), was added 95% NaH (0.029 g, 1.15 mmol) at 0° C. and reaction mixture was stirred at rt 1.5 h. The reaction mixture was cooled to 0° C. and diluted with water. The resultant precipitate was collected by filtration, then was washed with diethyl ether and dried under vacuum to obtain 0.18 g (90% yield) of Example 1B as a white solid. MS(ESI) m/z: 344.9 (M+H)$^+$; $^1$H NMR (300 MHz, DMSO-d$_6$) δ ppm 7.43-7.57 (m, 4H), 7.16-7.35 (m, 5H), 3.68-3.81 (m, 2H), 3.36-3.51 (m, 4H), 2.82 (t, J=7.46 Hz, 2H).

Example 1

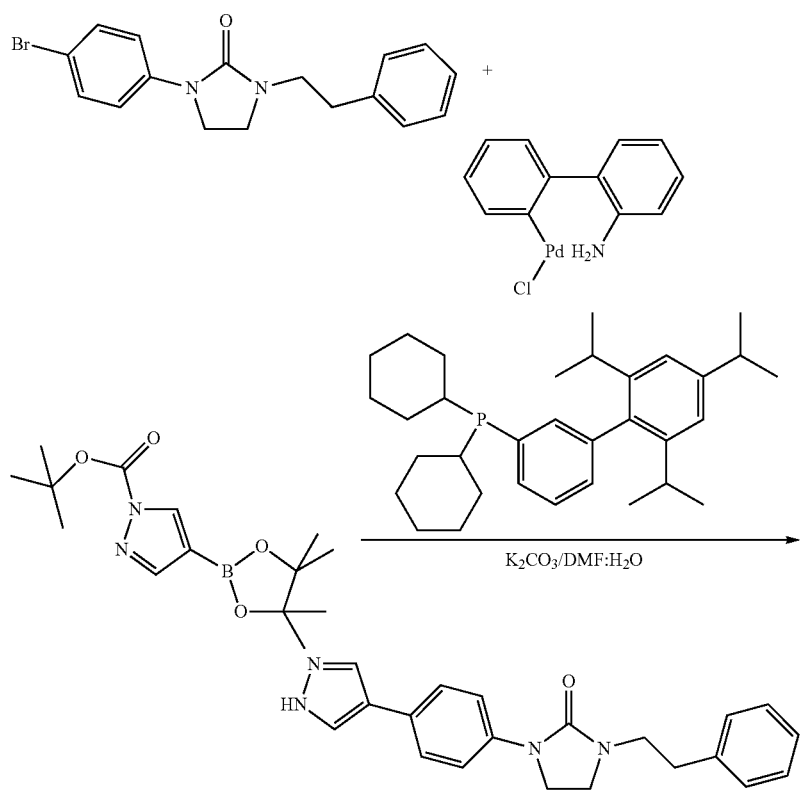

To a solution of Example 1B (0.100 g, 0.290 mmol), tert-butyl 4-(4,4,5,5-tetramethyl-1,3,2-dioxaborolan-2-yl)-1H-pyrazole-1-carboxylate (0.128 g, 0.434 mmol) in DMF (3 mL) and water (0.3 mL), was added K$_2$CO$_3$ (0.120 g, 0.869 mmol). The resulting reaction mixture was degassed using N$_2$ gas for 5 min. 2nd generation XPhos precatalyst (0.046 g, 0.058 mmol) was added to the reaction, which was degassed again. The mixture was then heated to 90° C. for 2 h. Reaction mixture was cooled and filtered, and the filtrate was concentrated. The product was purified by preparative HPLC to afford 15 mg (15% yield) of Example 1. MS(ESI) m/z: 333.2 (M+H)$^+$; $^1$H NMR (400 MHz, DMSO-d$_6$) δ ppm 12.85 (br s, 1H), 7.98 (br s, 2H), 7.54 (s, 4H), 7.26-7.36 (m, 4H), 7.17-7.26 (m, 1H), 3.78 (dd, J=9.38, 6.62 Hz, 2H), 3.40-3.50 (m, 4H), 2.84 (t, J=7.44 Hz, 2H); HPLC RT=9.24 min (Method A), 8.73 min (Method B).

The following Examples in Table 1 were made by using the same procedure as shown in Example 1. (2-Isocyanatoethyl)benzene is substituted with the appropriate isocyanate.

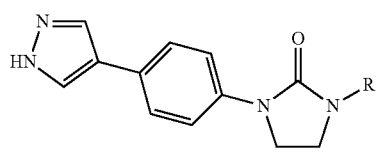

TABLE 1

| Ex. | R | Name | LCMS (M + H)+ | HPLC Method, RT (min.) | NMR |
|---|---|---|---|---|---|
| 2 | 3-methoxybenzyl | 1-(4-(1H-pyrazol-4-yl)phenyl)-3-(3-methoxybenzyl)imidazolidin-2-one | 349.2 | A: 9.04 B: 8.62 | $^1$H NMR (400 MHz, DMSO-$d_6$) δ ppm 12.45 (br s, 1H), 8.00 (s, 2 H), 7.54-7.61 (m, 4 H), 7.26-7.32 (m, 1 H), 6.84-6.92 (m, 3H), 4.37 (s, 2 H), 3.83 (dd, J = 9.04, 6.96 Hz, 2 H), 3.76 (s, 3H), 3.31-3.38 (m, 2 H) |
| 3 | benzyl | 1-(4-(1H-pyrazol-4-yl)phenyl)-3-benzylimidazolidin-2-one | 319.2 | A: 9.10 B: 8.64 | $^1$H NMR (400 MHz, DMSO-$d_6$) δ ppm 12.86 (br. s., 1 H), 8.12 (br. s., 1 H), 7.88 (br. s., 1 H), 7.54-7.61 (m, 4 H), 7.35 - 7.41 (m, 2 H), 7.30-7.34 (m, 3 H), 4.41 (s, 2 H), 3.83 (dd, J = 9.00, 7.00 Hz, 2 H), 3.34-3.40 (m, 2 H) |
| 4 | 3-fluorobenzyl | 1-(4-(1H-pyrazol-4-yl)phenyl)-3-(3-fluorobenzyl)imidazolidin-2-one | 337.2 | A: 9.27 B: 8.84 | $^1$H NMR (400 MHz, DMSO-$d_6$) δ ppm 12.81 (br s, 1 H), 8.00 (s, 2 H), 7.58 (m, 4H), 7.39-7.46 (m, 1 H), 7.10-7.19 (m, 3 H), 4.43 (s, 2 H), 3.85 (dd, J = 9.04, 6.96 Hz, 2 H), 3.37-3.43 (m, 2 H); $^{19}$F NMR: (400 MHz, DMSO-$d_6$): −113.40 |
| 5 | 4-fluorobenzyl | 1-(4-(1H-pyrazol-4-yl)phenyl)-3-(4-fluorobenzyl)imidazolidin-2-one | 337.3 | A: 9.11 B: 8.84 | $^1$H NMR (400 MHz, DMSO-$d_6$) δ ppm 12.69 (brs, 1 H), 8.00 (s, 2 H), 7.56-7.59 (m, 4 H), 7.35-7.39 (m, 2 H), 7.18-7.23 (m, 2 H), 4.39 (s, 2 H), 3.83 (dd, J = 9.07, 7.00 Hz, 2 H), 3.33-3.39 (m, 2 H); $^{19}$F NMR: (400 MHz, DMSO-$d_6$): −115.492 |

Example 6

1-(3-Fluorobenzyl)-3-(3-methoxy-4-(1H-pyrazol-4-yl)phenyl)imidazolidin-2-one

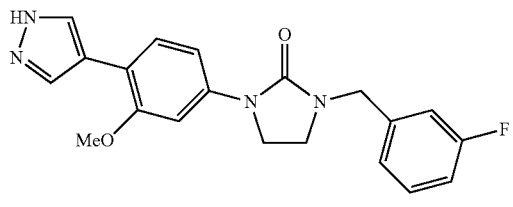 [SMILES: COc1cc(N2CCN(Cc3cccc(F)c3)C2=O)ccc1-c1cn[nH]c1]

Example 6A: 1-(4-Bromo-3-methoxyphenyl)-1-(2-chloroethyl)-3-(3-fluorobenzyl)urea

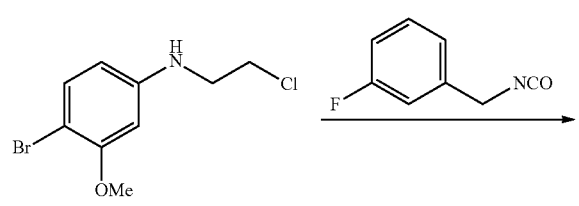

To a solution of Intermediate 2 (0.300 g, 1.13 mmol) in benzene (3 mL), was added 1-fluoro-3-(isocyanatomethyl)benzene (0.189 mL, 1.36 mmol). The mixture was stirred at 75° C. overnight. Benzene was evaporated, then the reaction mixture was diluted with water (10 mL) and extracted with ethyl acetate (3×10 mL). The organic layer was washed with brine (20 mL), dried over Na$_2$SO$_4$ and evaporated. The oil was washed with 10% diethyl ether in n-hexane to obtained 0.370 g (78%) of Example 6A as a yellow oil. MS(ESI) m/z: 414.9 (M+H)+.

Example 6B

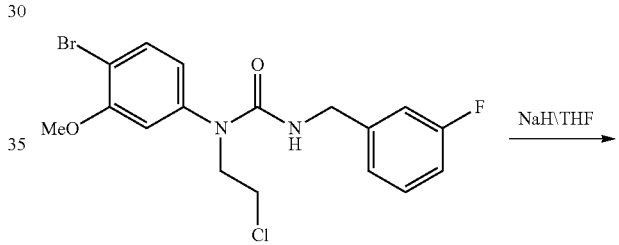

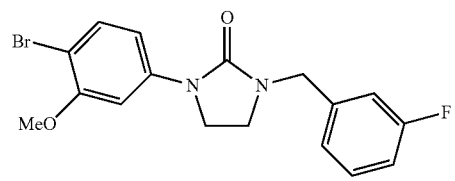

To a solution of Example 6A (0.350 g, 0.842 mmol) in THF (5 mL) at 0° C., was added NaH (0.043 g, 1.68 mmol). The reaction mixture was stirred at rt for 1.5 h. The reaction mixture was cooled to 0° C. and diluted with water. The resultant solid mass was collected by filtration, washed with diethyl ether and dried to obtain 0.285 g (89% yield) as a white solid. MS(ESI) m/z: 378.9 (M+H)+; $^1$H NMR (400 MHz, DMSO-$d_6$) δ ppm 7.59 (d, J=2.45 Hz, 1H), 7.50 (s, 1H), 7.39-7.46 (m, 1H), 7.12-7.20 (m, 3H), 7.00 (dd, J=8.72, 2.51 Hz, 1H), 4.43 (s, 2H), 3.82-3.89 (m, 5H), 3.38-3.45 (m, 2H); $^{19}$F NMR: (400 MHz, DMSO-$d_6$): −113.122.

Example 6

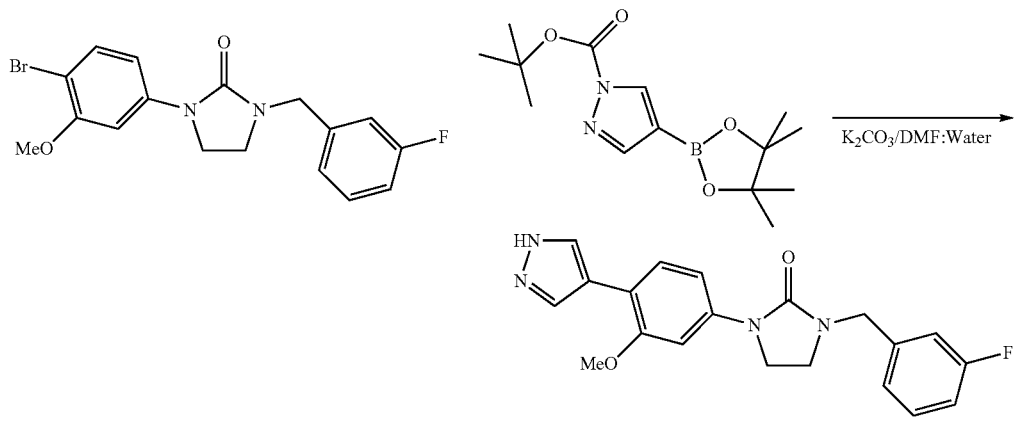

To a solution of Example 6B (0.070 g, 0.185 mmol), tert-butyl 4-(4,4,5,5-tetramethyl-1,3,2-dioxaborolan-2-yl)-1H-pyrazole-1-carboxylate (0.081 g, 0.280 mmol) in DMF (3 mL) and water (0.3 mL), was added $K_2CO_3$ (0.077 g, 0.55 mmol). The resulting reaction mixture was degassed using $N_2$ for 5 min. 2nd generation XPhos precatalyst (0.029 g, 0.037 mmol) was added to the reaction, which was degassed again. The mixture was then heated to 90° C. for 8 h. The reaction mixture was cooled to rt, then was filtered through CELITE®, rinsing with EtOAc. The filtrate was concentrated, and the resultant solid was washed with $Et_2O$, EtOAc and methanol to afford 43 mg (62% yield) of Example 6 as an off-white solid. MS(ESI) m/z: 367.2 $(M+H)^+$; $^1$H NMR (400 MHz, DMSO-$d_6$) δ ppm 12.54 (br s, 1H), 7.98 (s, 2H), 7.56 (d, J=5.58 Hz, 1H), 7.55 (s, 1H), 7.39-7.47 (m, 1H), 7.12-7.20 (m, 3H), 7.02 (dd, J=8.53, 2.07 Hz, 1H), 4.43 (s, 2H), 3.86 (m, 5H), 3.37-3.44 (m, 2H); $^{19}$F NMR: (400 MHz, DMSO-$d_6$): −113.144; HPLC RT=9.18 min (Method A), 8.73 min (Method B).

Example 7

1-(3-Methoxy-4-(1H-pyrazol-4-yl)phenyl)-3-(3-methoxybenzyl)imidazolidin-2-one

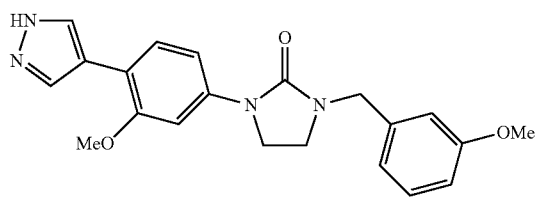 [SMILES: COc1cccc(CN2CCN(c3ccc(-c4cn[nH]c4)c(OC)c3)C2=O)c1]

According to the procedure for the preparation of Example 6, substituting 1-(isocyanatomethyl)-3-methoxybenzene for 1-fluoro-3-(isocyanatomethyl)benzene afforded Example 7. MS(ESI) m/z: 379.2 $(M+H)^+$; $^1$H NMR (400 MHz, DMSO-$d_6$) δ ppm 12.71 (br s, 1H), 7.98 (s, 2H), 7.56 (d, J=5.27 Hz, 1H), 7.54 (s, 1H), 7.26-7.33 (m, 1H), 7.02 (dd, J=8.53, 2.07 Hz, 1H), 6.85-6.91 (m, 3H), 4.38 (s, 2H), 3.82-3.89 (m, 5H), 3.76 (s, 3H), 3.35-3.41 (m, 2H); HPLC RT=8.98 min (Method A), 8.56 min (Method B).

Example 8

1-(4-Fluorophenethyl)-3-(3-methoxy-4-(1H-pyrazol-4-yl)phenyl)imidazolidin-2-one

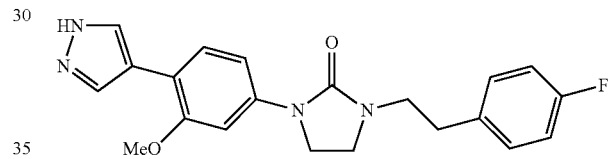

According to the procedure for the preparation of Example 6, substituting 1-fluoro-4-(2-isocyanatoethyl)benzene for 1-fluoro-3-(isocyanatomethyl)benzene afforded Example 7. MS(ESI) m/z: 381.2 $(M+H)^+$; $^1$H NMR (400 MHz, DMSO-$d_6$) δ ppm 12.29 (br s, 1H), 7.97 (s, 2H), 7.52 (d, J=8.41 Hz, 1H), 7.50 (d, J=2.13 Hz, 1H), 7.30-7.34 (m, 2H), 7.10-7.16 (m, 2H), 6.96 (dd, J=8.50, 2.16 Hz, 1H), 3.84 (s, 3H), 3.80 (dd, J=9.35, 6.65 Hz, 2H), 3.40-3.49 (m, 4H), 2.82 (t, J=7.20 Hz, 2H); $^{19}$F NMR: (400 MHz, DMSO-$d_6$): −117.059; HPLC RT=9.39 min (Method A), 8.90 min (Method B).

Example 9

1-(3-Fluorobenzyl)-3-(2-methoxy-4-(1H-pyrazol-4-yl)phenyl)imidazolidin-2-one

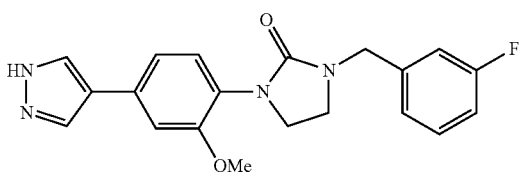 [SMILES: COc1cc(-c2cn[nH]c2)ccc1N1CCN(Cc2cccc(F)c2)C1=O]

85

Example 9A: 1-(4-Bromo-2-methoxyphenyl)-1-(2-chloroethyl)-3-(3-fluorobenzyl)urea

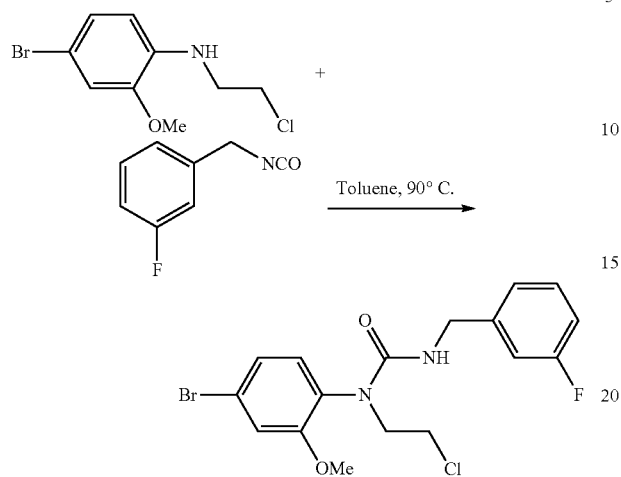

To the solution of Intermediate 3 (200 mg, 0.756 mmol) in toluene (4 mL), was added 1-fluoro-3-(isocyanatomethyl)benzene (171 mg, 1.13 mmol). The mixture was heated at 90° C. overnight. The toluene was concentrated. The solid was washed with petroleum ether and was dried to give Example 9A as a brown, gummy solid (400 mg), which was used in the following step without further purification. MS(ESI) m/z: 415.4 (M+H)+.

Example 9B: 1-(4-Bromo-2-methoxyphenyl)-3-(3-fluorobenzyl)imidazolidin-2-one

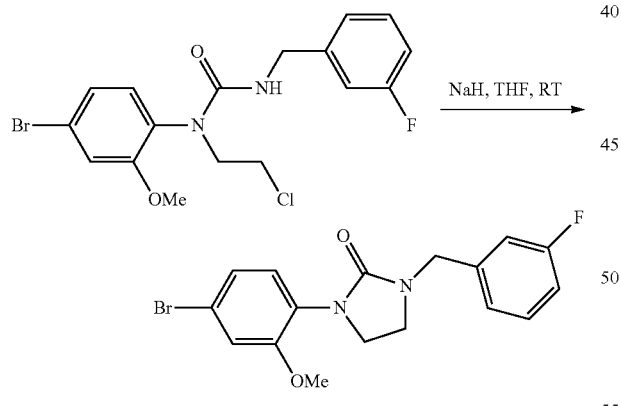

To the solution of Example 9A (400 mg, 0.962 mmol) in THF (10 mL), was added NaH (77 mg, 1.9 mmol). The mixture was stirred at rt overnight. Additional NaH (77 mg, 1.9 mmol) was added, and the mixture was stirred for another 5 h. The reaction was quenched with cold water and was extracted with ethyl acetate. The combined ethyl acetate layers were washed with brine, dried (Na$_2$SO$_4$) and concentrated. The residue was washed with 10% diethyl ether in petroleum ether (3×5 mL), then dried to afford 220 mg of Example 9B as a gummy solid that was used in the following step without purification. MS(ESI) m/z: 381.4 (M+H)+.

86

Example 9: 1-(2-Methoxy-4-(1H-pyrazol-4-yl)phenyl)-3-(3-methoxybenzyl)imidazolidin-2-one

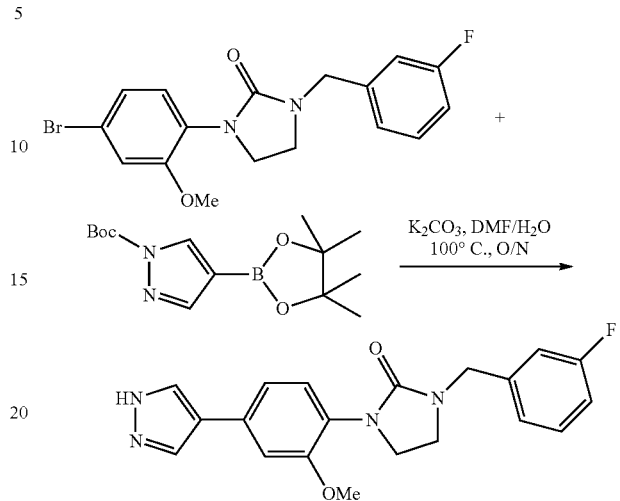

To a solution of Example 9B (100 mg, 0.264 mmol) in DMF (2 mL), was added tert-butyl 4-(4,4,5,5-tetramethyl-1,3,2-dioxaborolan-2-yl)-1H-pyrazole-1-carboxylate (155 mg, 0.527 mmol), K$_2$CO$_3$ (109 mg, 0.791 mmol) and water (0.5 mL). The mixture was purged with nitrogen for 5 min, and then 2nd generation XPhos precatalyst (12.5 mg, 0.016 mmol) was added. The mixture was heated at 100° C. overnight. The reaction was cooled to rt, diluted with DMF, filtered and purified by preparative HPLC to afford 30 mg (30% yield) of Example 9. MS(ESI) m/z: 367.0 (M+H)+; $^1$H NMR (400 MHz, DMSO-d$_6$) δ ppm 12.93 (s, 1H) 8.22 (s, 1H) 7.95 (s, 1H) 7.40-7.47 (m, 1H) 7.28 (d, J=1.69 Hz, 1H) 7.10-7.25 (m, 5H) 4.37 (s, 2H) 3.86 (s, 3H) 3.66 (dd, J=9.13, 6.75 Hz, 2H) 3.34-3.38 (m, 2H); $^{19}$F NMR (400 MHz, DMSO-d$_6$) δ ppm −113.203; HPLC RT=2.22 min (Method C), 2.14 min (Method D).

Example 10

1-(2-Methoxy-4-(1H-pyrazol-4-yl)phenyl)-3-(3-methoxybenzyl)imidazolidin-2-one

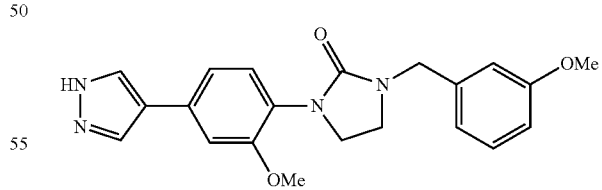

According to the procedure for the preparation of Example 9, substituting 1-(isocyanatomethyl)-3-methoxybenzene for 1-fluoro-3-(isocyanatomethyl)benzene afforded Example 10. MS(ESI) m/z: 379.2 (M+H)+; $^1$H NMR (400 MHz, DMSO-d$_6$) δ ppm 12.93 (s, 1H) 8.22 (s, 1H) 7.95 (s, 1H) 7.26-7.33 (m, 2H) 7.16-7.24 (m, 2H) 6.85-6.90 (m, 3H) 4.32 (s, 2H) 3.86 (s, 3H) 3.76 (s, 3H) 3.61-3.68 (m, 2H) 3.31-3.34 (m, 2H); HPLC RT=2.19 min (Method C), 2.12 min (Method D).

Example 11

1-(2-Fluorophenethyl)-3-(2-methoxy-4-(1H-pyrazol-4-yl)phenyl)imidazolidin-2-one

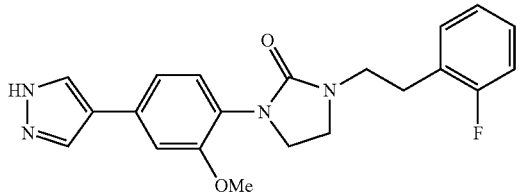 [SMILES: COc1cc(-c2cn[nH]c2)ccc1N1CCN(CCc2ccccc2F)C1=O]

According to the procedure for the preparation of Example 9, substituting 1-(isocyanatomethyl)-3-methoxybenzene for 1-fluoro-3-(isocyanatomethyl)benzene afforded Example 11. MS(ESI) m/z: 381.2 (M+H)+; $^1$H NMR (400 MHz, DMSO-$d_6$) δ ppm 12.92 (s, 1H) 8.20 (s, 1H) 7.94 (s, 1H) 7.38 (td, J=7.70, 1.60 Hz, 1H) 7.23-7.32 (m, 2H) 7.09-7.20 (m, 4H) 3.83 (s, 3H) 3.59-3.65 (m, 2H) 3.35-3.47 (m, 4H) 2.85 (t, J=7.37 Hz, 2H). $^{19}$F NMR (400 MHz, DMSO-$d_6$) δ ppm −118.905; HPLC RT=2.39 min (Method C), 2.33 min (Method D).

Example 12

1-Benzyl-3-(2-methoxy-4-(1H-pyrazol-4-yl)phenyl)imidazolidin-2-one

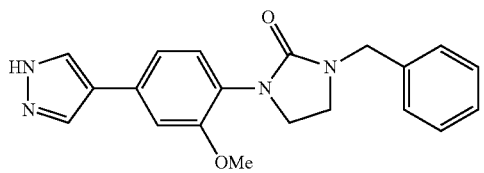 [SMILES: COc1cc(-c2cn[nH]c2)ccc1N1CCN(Cc2ccccc2)C1=O]

According to the procedure for the preparation of Example 9, substituting (isocyanatomethyl)benzene for 1-fluoro-3-(isocyanatomethyl)benzene afforded Example 12. MS(ESI) m/z: 349.2 (M+H)+; $^1$H NMR (400 MHz, DMSO-$d_6$) δ ppm 12.93 (s, 1H) 8.22 (s, 1H) 7.95 (s, 1H) 7.35-7.42 (m, 1H) 7.26-7.33 (m, 4H) 7.15-7.24 (m, 2H) 6.85-6.90 (m, 1H) 4.35 (s, 2H) 3.86 (s, 3H) 3.64 (dd, J=9.22, 6.65 Hz, 2H) 3.32-3.35 (m, 1H) 3.26-3.30 (m, 1H); HPLC RT=1.36 min (Method E), 1.40 min (Method F).

Example 13

(R)-1-(3-Methoxy-4-(1H-pyrazol-4-yl)phenyl)-3-(1-(3-methoxyphenyl)ethyl)imidazolidin-2-one

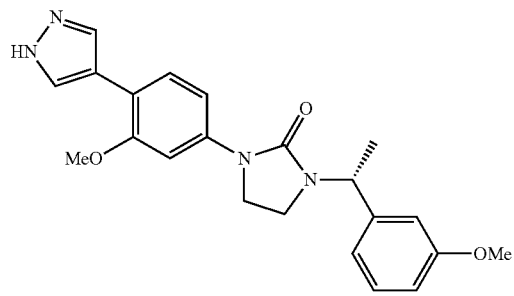 [SMILES: COc1cccc([C@@H](C)N2CCN(c3ccc(-c4cn[nH]c4)c(OC)c3)C2=O)c1]

Example 13A: (R)-1-(4-Bromo-3-methoxyphenyl)-1-(2-chloroethyl)-3-(1-(3-methoxyphenyl)ethyl)urea

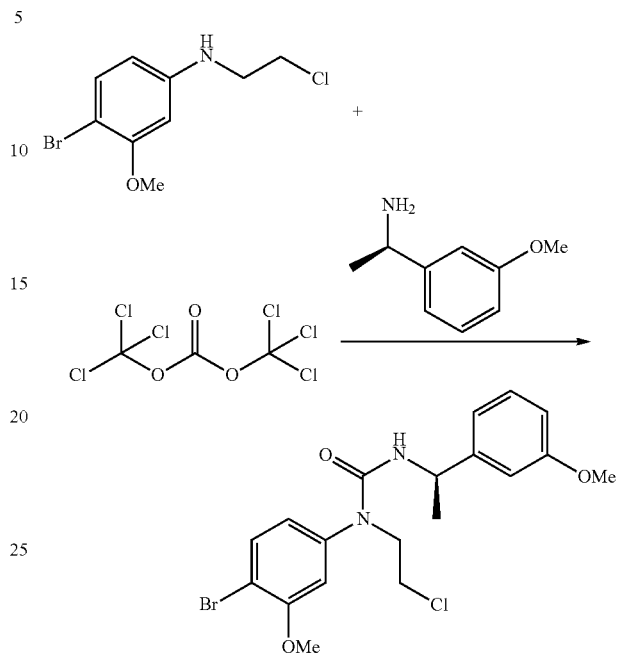

To a solution of Intermediate 2 (0.200 g, 0.756 mmol) in CHCl$_3$ (5 mL) at 0° C., was added TEA (0.316 mL, 2.27 mmol), followed by bis(trichloromethyl)carbonate (0.269 g, 0.907 mmol), and the mixture was stirred at the same temperature for 2 h. (R)-1-(3-methoxyphenyl)ethanamine (0.114 g, 0.756 mmol) was added, and the reaction mixture was stirred overnight. The reaction mixture was diluted with water, acidified by 5% HCl, and extracted by DCM. The organic phase was dried over Na$_2$SO$_4$ and concentrated. The residue was washed with 10% diethyl ether in hexane to obtained 0.45 g (79%) of Example 13A as a yellow oil. MS(ESI) m/z: 441.5 (M+H)+.

Example 13B: (R)-1-(4-Bromo-3-methoxyphenyl)-3-(1-(3-methoxyphenyl)ethyl) imidazolidin-2-one

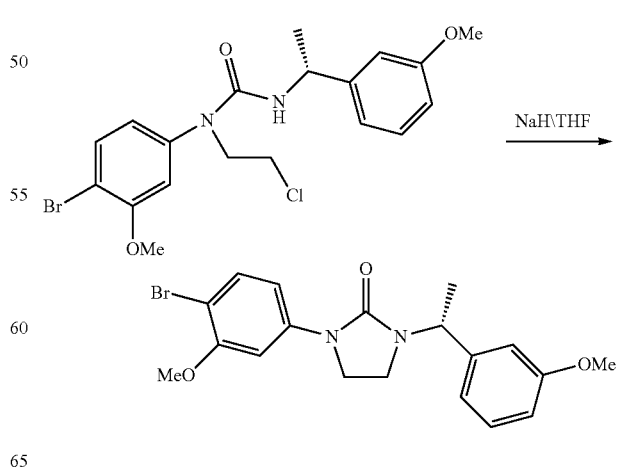

To a solution of Example 13A (0.330 g, 0.747 mmol) in THF (5 mL) at 0° C., was added NaH (0.038 g, 1.49 mmol), and the reaction mixture was stirred at rt for 2 h. The reaction mixture was cooled to 0° C., diluted with water, and extracted with ethyl acetate. The organic layer was washed with brine, dried over $Na_2SO_4$ and concentrated to obtain 0.285 g (94%) of Example 13B as a burgundy oil. MS(ESI) m/z: 405.4 (M+H)+; $^1$H NMR (400 MHz, DMSO-$d_6$) δ ppm 7.57 (d, J=2.45 Hz, 1H), 7.47 (d, J=8.72 Hz, 1H), 7.26-7.32 (m, 1H), 6.91-6.98 (m, 2H), 6.82-6.90 (m, 2H), 5.12 (q, J=7.09 Hz, 1H), 3.78-3.84 (m, 4H), 3.75-3.55 (m, 4H), 3.51-3.55 (m, 1H), 3.09-3.18 (m, 1H), 1.51 (d, J=7.15 Hz, 3H).

Example 13

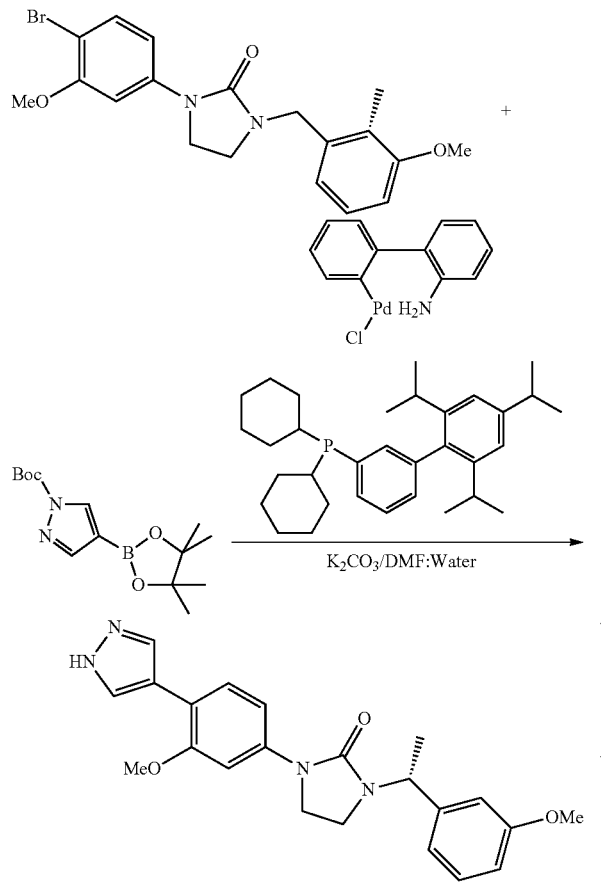

To a solution of Example 13B (0.070 g, 0.17 mmol), tert-butyl 4-(4,4,5,5-tetramethyl-1,3,2-dioxaborolan-2-yl)-1H-pyrazole-1-carboxylate (0.076 g, 0.26 mmol) in DMF (3 mL) and water (0.3 mL), was added $K_2CO_3$ (0.072 g, 0.52 mmol). The reaction mixture was degassed using $N_2$ for 5 min. 2nd generation XPhos precatalyst (0.027 g, 0.035 mmol) was added, then the reaction mixture was degassed again. The mixture was heated to 90° C. for 4 h. The reaction mixture was filtered through CELITE®, rinsing with MeOH. The filtrate was evaporated. The resultant solid was washed with water, then was purified by preparative HPLC to afford 14 mg (21%) of Example 13 as a pale yellow solid. MS(ESI) m/z: 393.2 (M+H)+; $^1$H NMR (400 MHz, DMSO-$d_6$) δ ppm 12.79 (br s, 1H), 7.96 (br s, 2H), 7.51-7.56 (m, 2H), 7.29 (t, J=7.84 Hz, 1H), 6.99 (dd, J=8.53, 2.13 Hz, 1H), 6.94 (d, J=7.72 Hz, 1H), 6.83-6.91 (m, 2H), 5.13 (q, J=7.11 Hz, 1H), 3.85 (s, 3H), 3.82 (t, J=8.16 Hz, 2H), 3.76 (s, 3H), 3.47-3.56 (m, 1H), 3.08-3.18 (m, 1H), 1.51 (d, J=7.15 Hz, 3H); HPLC RT=2.41 min (Method C), 2.44 min (Method D).

Example 14

(R)-1-(2-Methoxy-4-(1H-pyrazol-4-yl)phenyl)-3-(1-(3-methoxyphenyl)ethyl)imidazolidin-2-one

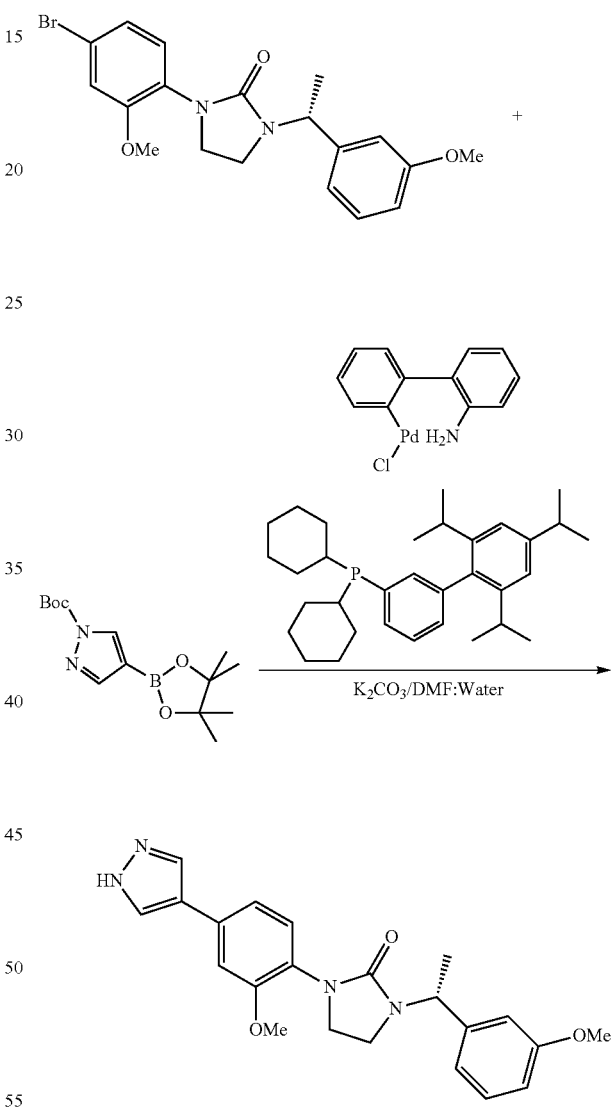

According to the procedure for the preparation of Example 13, substituting Intermediate 3 for Intermediate 2 afforded Example 14. MS(ESI) m/z: 393.2 (M+H)+; $^1$H NMR (400 MHz, DMSO-$d_6$) δ ppm 12.91 (br s, 1H), 8.08 (br s, 2H), 7.31 (t, J=7.97 Hz, 1H), 7.27 (d, J=1.63 Hz, 1H), 7.20-7.23 (m, 1H), 7.15-7.19 (m, 1H), 6.93-6.97 (m, 1H), 6.86-6.91 (m, 2H), 5.08 (q, J=7.11 Hz, 1H), 3.85 (s, 3H), 3.78 (s, 3H), 3.58-3.67 (m, 2H), 3.43-3.50 (m, 1H), 3.07 (dd, J=16.00, 8.80 Hz, 1H), 1.51 (d, J=7.15 Hz, 3H); HPLC RT=2.36 min (Method C), 2.43 min (Method D).

Example 15

1-(2-Fluoro-5-methoxybenzyl)-3-(3-methoxy-4-(1H-pyrazol-4-yl)phenyl)imidazolidin-2-one

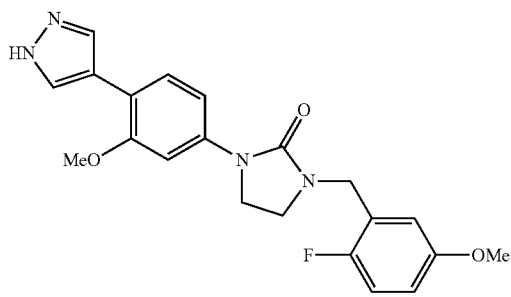 [SMILES: COc1ccc(F)c(CN2CCN(c3ccc(-c4cn[nH]c4)c(OC)c3)C2=O)c1]

Example 15A: Trichloromethyl (4-bromo-3-methoxyphenyl)(2-chloroethyl)carbamate

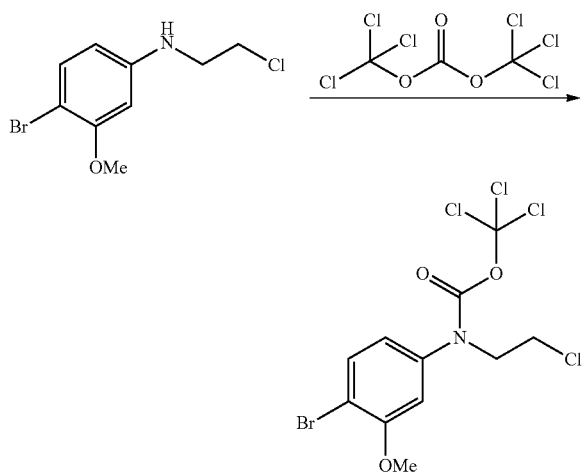

To a solution of 4-bromo-N-(2-chloroethyl)-3-methoxyaniline (0.600 g, 2.27 mmol) in CHCl₃ (3 mL) at 0° C., was added TEA (0.948 mL, 6.80 mmol), followed by bis(trichloromethyl)carbonate (0.808 g, 2.72 mmol). The mixture was stirred at 0° C. for 2 h, then was concentrated to afford 0.900 g of Example 15A, which was used without purification.

Example 15B: 1-(4-Bromo-3-methoxyphenyl)-1-(2-chloroethyl)-3-(2-fluoro-5-methoxybenzyl)urea

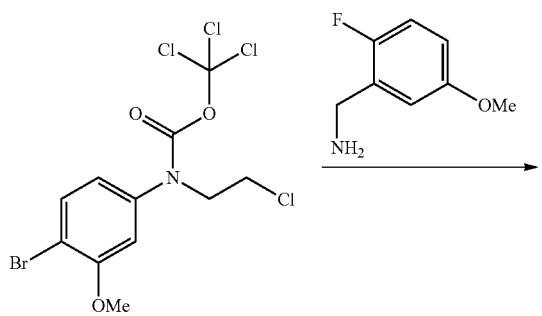

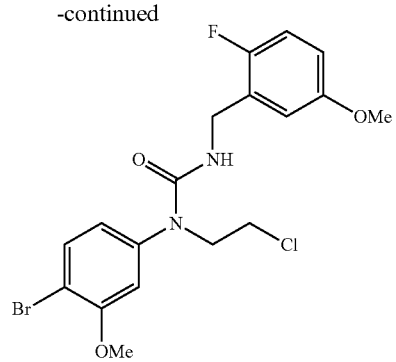

To a solution of (2-fluoro-5-methoxyphenyl)methanamine (0.066 g, 0.42 mmol) and TEA (0.118 mL, 0.845 mmol) in CHCl₃ (3 mL) at 0° C., was added a solution of Example 15A (0.120 g, 0.282 mmol) in 1 ml CHCl₃. The mixture was stirred at rt overnight. The reaction mixture was diluted with water and acidified with 5% HCl, then was extracted by DCM. The organic layer was dried over Na₂SO₄ and evaporated to obtain a residue. The residue was extracted with diethyl ether (10 mL), which was concentrated to afford 0.130 g of Example 15B as a yellow oil, which was used without further purification. MS(ESI) m/z: 445.5 (M+H)⁺.

Example 15C: 1-(4-Bromo-3-methoxyphenyl)-3-(2-fluoro-5-methoxybenzyl) imidazolidin-2-one

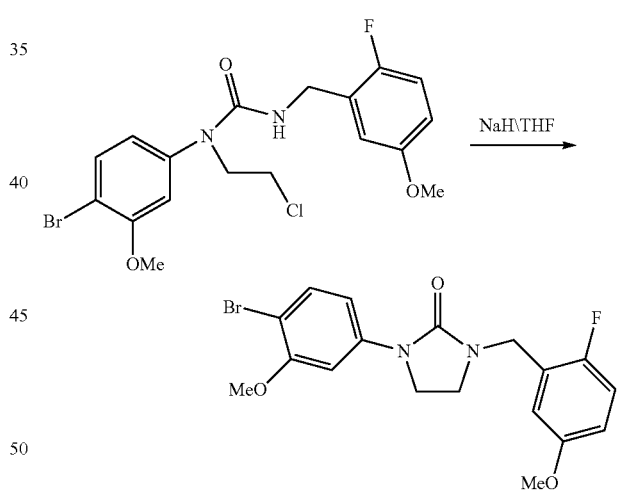

To a solution of Example 15B (0.110 g, 0.247 mmol) in THF (5 mL) at 0° C., was added NaH (0.012 g, 0.49 mmol). The reaction mixture was stirred at rt for 8 h. The reaction mixture was cooled to 0° C., diluted with water, and extracted with ethyl acetate. The organic layer was washed with brine, dried over Na₂SO₄ and concentrated. The residue was purified by flash chromatography (gradient elution 0-20% EtOAc/Hex) to afford 0.11 g (98% yield) of Example 15C as a pale yellow solid. MS(ESI) m/z: 409.4 (M+H)⁺; $^{1}$H NMR (300 MHz, DMSO-$d_6$) δ ppm 7.57 (d, J=2.36 Hz, 1H) 7.48 (d, J=8.69 Hz, 1H) 7.16 (t, J=9.49 Hz, 1H) 6.98 (dd, J=8.78, 2.55 Hz, 1H) 6.87-6.94 (m, 2H) 4.42 (s, 2H) 3.79-3.89 (m, 5H) 3.41 (dd, J=9.06, 6.89 Hz, 2H) 3.33 (s, 3H); $^{19}$F NMR (400 MHz, DMSO-$d_6$) δ ppm −119.893.

Example 15: 1-(2-Fluoro-5-methoxybenzyl)-3-(3-methoxy-4-(1H-pyrazol-4-yl)phenyl) imidazolidin-2-one

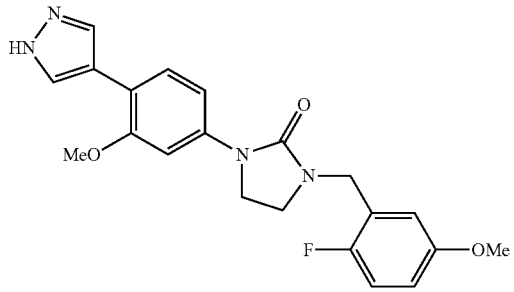 [SMILES: COc1ccc(F)c(CN2CCN(c3ccc(-c4cn[nH]c4)c(OC)c3)C2=O)c1]

To a solution of Example 15C (0.100 g, 0.24 mmol) and tert-butyl 4-(4,4,5,5-tetramethyl-1,3,2-dioxaborolan-2-yl)-1H-pyrazole-1-carboxylate (0.108 g, 0.367 mmol) in DMF (3 mL) and water (0.3 mL), was added $K_2CO_3$ (0.101 g, 0.733 mmol). The resulting reaction mixture was degassed with $N_2$ for 5 min, then 2nd generation XPhos precatalyst (0.038 g, 0.049 mmol) was added. The reaction was degassed again, then was heated to 90° C. for 6 h. The reaction mixture was filtered through CELITE®, rinsing with MeOH. The filtrate was concentrated, and the resultant solid was washed with water. The residue was purified by preparative HPLC to afford 7 mg (7% yield) of Example 15. MS(ESI) m/z: 397.2 $(M+H)^+$; $^1$H NMR (400 MHz, DMSO-$d_6$) δ ppm 12.79 (br s, 1H), 8.02 (br s, 1H), 7.94 (br s, 1H), 7.56 (d, J=8.47 Hz, 1H), 7.53 (d, J=2.13 Hz, 1H), 7.13-7.20 (m, 1H), 7.02 (dd, J=8.53, 2.20 Hz, 1H), 6.89-6.94 (m, 2H), 4.43 (s, 2H), 3.83-3.89 (m, 5H), 3.75 (s, 3H), 3.41 (t, J=8.00 Hz, 2H); $^{19}$F NMR (400 MHz, DMSO-$d_6$) δ ppm −129.868; HPLC RT=1.45 min (Method E), 1.53 min (Method F).

Example 16

1-(2,6-Difluorobenzyl)-3-(3-methoxy-4-(1H-pyrazol-4-yl)phenyl)imidazolidin-2-one

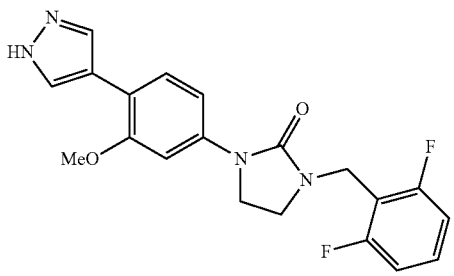 [SMILES: COc1cc(N2CCN(Cc3c(F)cccc3F)C2=O)ccc1-c1cn[nH]c1]

According to the procedure for the preparation of Example 15, substituting (2,6-difluorophenyl)methanamine for (2-fluoro-5-methoxyphenyl)methanamine afforded Example 16. MS(ESI) m/z: 385.2 $(M+H)^+$; $^1$H NMR (400 MHz, DMSO-$d_6$) δ ppm 12.79 (br s, 1H), 8.04 (br s, 1H), 7.91 (br s, 1H), 7.54 (d, J=8.47 Hz, 1H), 7.52 (d, J=2.13 Hz, 1H), 7.42-7.51 (m, 1H), 7.12-7.20 (m, 2H), 6.98-7.02 (m, 1H), 4.51 (s, 2H), 3.86 (s, 3H), 3.81 (dd, J=9.04, 6.96 Hz, 2H), 3.38 (t, J=8.00 Hz, 2H); $^{19}$F NMR (400 MHz, DMSO-$d_6$) δ ppm −114.791; HPLC RT=1.43 min (Method E), 1.50 min (Method F).

Example 17

1-(2-Fluorobenzyl)-3-(3-methoxy-4-(1H-pyrazol-4-yl)phenyl)imidazolidin-2-one

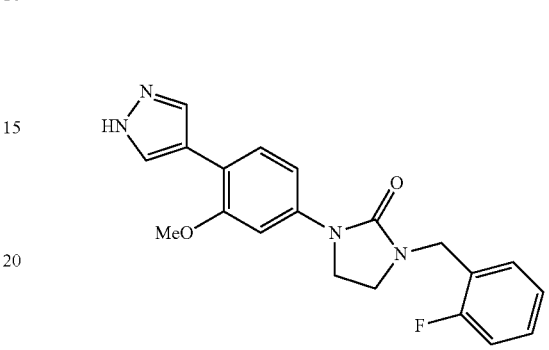

According to the procedure for the preparation of Example 15, substituting (2-fluorophenyl)methanamine for (2-fluoro-5-methoxyphenyl)methanamine afforded Example 17. MS(ESI) m/z: 367.2 $(M+H)^+$; $^1$H NMR (400 MHz, DMSO-$d_6$) δ ppm 12.77 (br s, 1H), 8.00 (br s, 1H), 7.94 (br s, 1H), 7.53-7.58 (m, 2H), 7.35-7.44 (m, 2H), 7.20-7.27 (m, 2H), 7.02 (dd, J=8.47, 2.20 Hz, 1H), 4.47 (s, 2H), 3.83-3.89 (m, 5H), 3.40 (t, J=8.40 Hz, 2H); $^{19}$F NMR (400 MHz, DMSO-$d_6$) δ ppm −118.993; HPLC RT=1.43 min (Method E), 1.50 min (Method F).

Example 18

1-Benzyl-3-(3-methoxy-4-(1H-pyrazol-4-yl)phenyl)imidazolidin-2-one

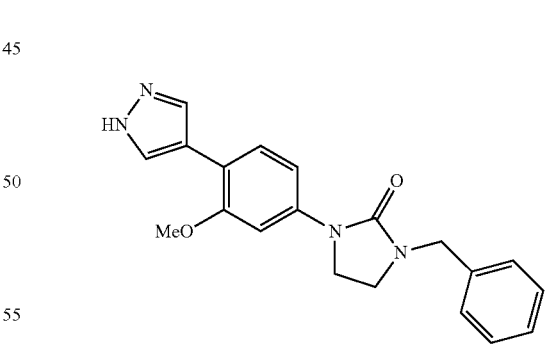

According to the procedure for the preparation of Example 15, substituting benzylamine for (2-fluoro-5-methoxyphenyl)methanamine afforded Example 18. MS(ESI) m/z: 349.2 $(M+H)^+$; $^1$H NMR (400 MHz, DMSO-$d_6$) δ ppm 12.77 (br s, 1H), 7.97 (s, 2H), 7.53-7.57 (m, 2H), 7.35-7.40 (m, 2H), 7.28-7.33 (m, 3H), 7.01 (dd, J=8.53, 2.13 Hz, 1H), 4.40 (s, 2H), 3.86 (s, 3H), 3.82-3.85 (m, 2H), 3.37 (dd, J=8.00, 6.40 Hz, 2H); HPLC RT=1.41 min (Method E), 1.47 min (Method F).

Example 19

3-(3-(3-Methoxy-4-(1H-pyrazol-4-yl)phenyl)-2-oxoimidazolidin-1-yl)-3-(3-methoxyphenyl)propanoic Acid, TFA

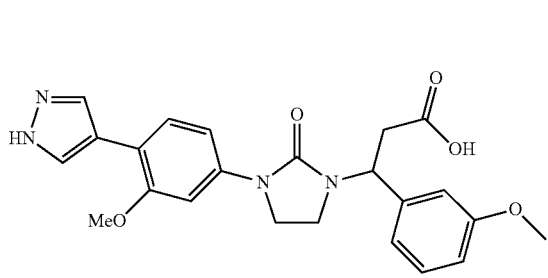 [SMILES: COc1cccc(C(CC(=O)O)N2CCN(c3ccc(-c4cn[nH]c4)c(OC)c3)C2=O)c1]

According to the procedure for the preparation of Example 15, substituting methyl 3-amino-3-(3-methoxyphenyl)propanoate, HCl for (2-fluoro-5-methoxyphenyl) methanamine afforded Example 19. MS(ESI) m/z: 437.3 (M+H)+; 1H NMR (400 MHz, DMSO-d6) δ ppm 7.98 (s, 2H) 7.53 (d, J=8.47 Hz, 1H) 7.51 (d, J=2.13 Hz, 1H) 7.30 (t, J=7.91 Hz, 1H) 6.86-6.99 (m, 4H) 5.38 (t, J=7.87 Hz, 1H) 3.89 (s, 3H) 3.76-3.82 (m, 2H) 3.75 (s, 3H) 3.49-3.56 (m, 1H) 3.09-3.16 (m, 2H) 2.92-3.07 (m, 2H); HPLC RT=1.21 min (Method E), 0.88 min (Method F).

Example 20

Methyl 3-(3-(3-methoxy-4-(1H-pyrazol-4-yl)phenyl)-2-oxoimidazolidin-1-yl)-3-(3-methoxyphenyl)propanoate

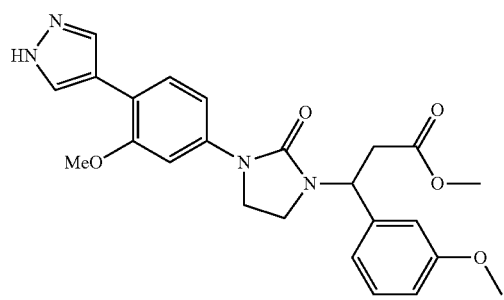 [SMILES: COC(=O)CC(c1cccc(OC)c1)N1CCN(c2ccc(-c3cn[nH]c3)c(OC)c2)C1=O]

Example 20A: Methyl 3-(3-(4-bromo-3-methoxyphenyl)-3-(2-chloroethyl)ureido)-3-(3-methoxyphenyl)propanoate

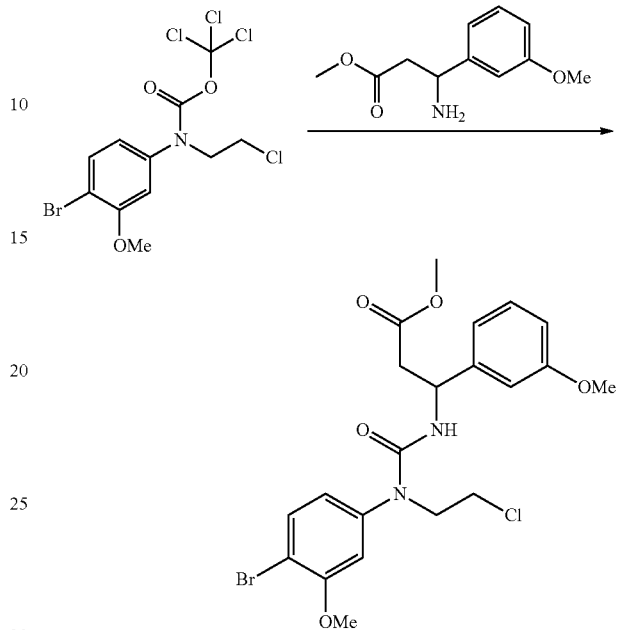

To a solution of methyl 3-amino-3-(3-methoxyphenyl) propanoate, HCl (0.606 g, 2.46 mmol) and TEA (1.15 mL, 8.22 mmol) in CHCl3 (3 mL) at 0° C., was added a solution of Example 15A (0.700 g, 1.64 mmol) in 1 mL CHCl3. The mixture was stirred for 6 h, then was diluted with water, acidified with 5% HCl, and extracted with DCM. The organic layer was dried over Na2SO4 and concentrated to obtain 1.80 g of Example 20A as a yellow oil that was used without further purification. MS(ESI) m/z: 499.5 (M+H)+.

Example 20B: Methyl 3-(3-(4-bromo-3-methoxyphenyl)-2-oxoimidazolidin-1-yl)-3-(3-methoxyphenyl)propanoate

Example 20C: 3-(3-(4-Bromo-3-methoxyphenyl)-2-oxoimidazolidin-1-yl)-3-(3-methoxyphenyl)propanoic Acid

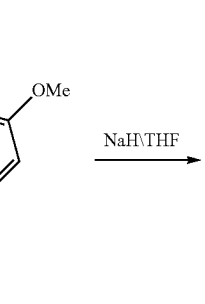

NaH\THF

-continued

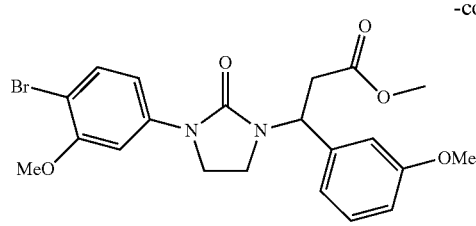
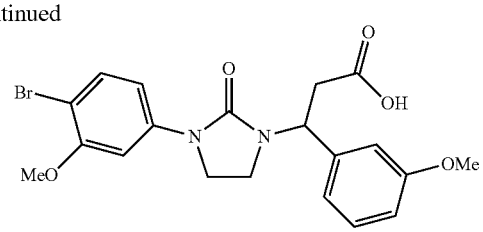

To a solution of Example 20A (1.40 g, 2.80 mmol) in THF (5 mL) at 0° C., was added NaH (0.142 g, 5.60 mmol). The reaction mixture was stirred at rt for 2 h. The reaction mixture was cooled to 0° C., then was diluted with water and extracted with ethyl acetate. The organic layer was washed with brine, dried over $Na_2SO_4$ and concentrated. The residue was purified by flash chromatography (0-20% EtOAc/Hex) to afford 0.30 g of Example 20B as a colorless oil. MS(ESI) m/z: 463.5 $(M+H)^+$; $^1H$ NMR (300 MHz, DMSO-$d_6$) δ ppm 7.53 (d, J=2.46 Hz, 1H) 7.46 (d, J=8.73 Hz, 1H) 7.26-7.33 (m, 1H) 6.86-6.97 (m, 4H) 5.38 (t, J=7.91 Hz, 1H) 3.82 (s, 3H) 3.73-3.80 (m, 4H) 3.58 (s, 3H) 3.47-3.55 (m, 1H) 3.07-3.19 (m, 4H). The aqueous phase was acidified with 5% HCl, then was extracted with EtOAc. The organic phase was washed with brine, dried ($Na_2SO_4$) and concentrated to afford 0.15 g of Example 20C as a burgundy oil. MS(ESI) m/z: 449.1 $(M+H)^+$.

Example 20D: tert-Butyl 4-(2-methoxy-4-(3-(3-methoxy-1-(3-methoxyphenyl)-3-oxopropyl)-2-oxoimidazolidin-1-yl)phenyl)-1H-pyrazole-1-carboxylate

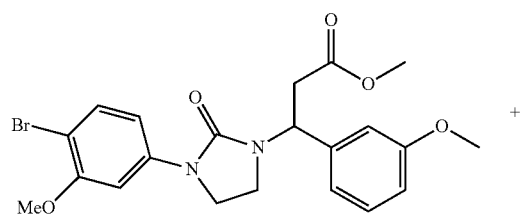

-continued

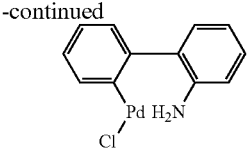

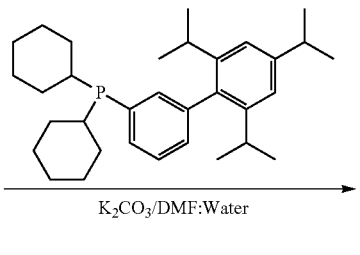

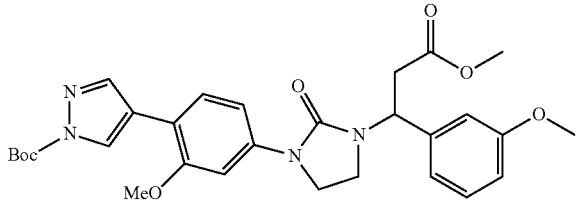

To a solution of Example 20B (0.030 g, 0.065 mmol) and tert-butyl 4-(4,4,5,5-tetramethyl-1,3,2-dioxaborolan-2-yl)-1H-pyrazole-1-carboxylate (0.029 g, 0.097 mmol) in dioxane (3 mL) and water (0.3 mL), was added $K_2CO_3$ (0.027 g, 0.19 mmol). The reaction mixture was degassed with $N_2$ for 5 min, then 2nd generation XPhos precatalyst (10.2 mg, 0.013 mmol) was added. The reaction was degassed again, then was then heated to 90° C. for 6 h. The reaction mixture was filtered through CELITE®, rinsing with MeOH. The filtrate was evaporated. The resultant solid was washed with water to afford 0.040 g of Example 20D, which was used as is in the following step. MS(ESI) m/z: 551.7 $(M+H)^+$.

Example 20

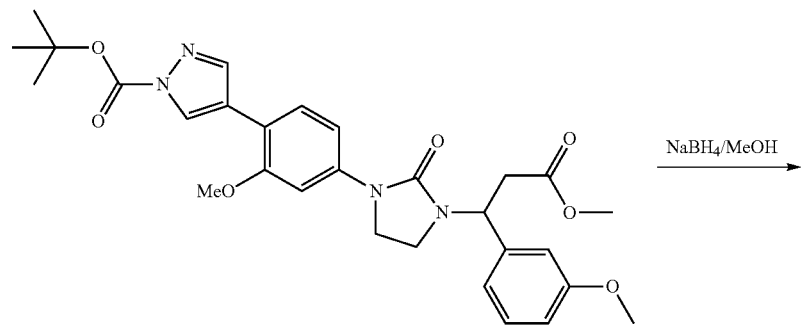

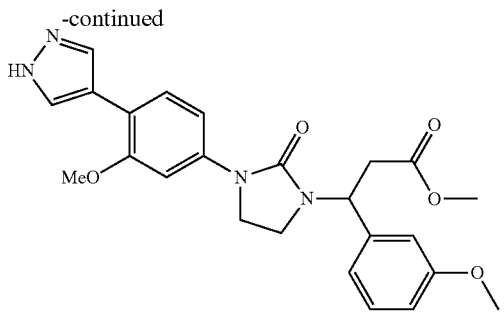

To a solution of Example 20D (0.030 g, 0.054 mmol) in MeOH, was added NaBH$_4$ (0.021 g, 0.545 mmol). The reaction mixture was stirred at rt overnight. The methanol was evaporated, and the mixture was partitioned between ethyl acetate and water. The organic layer was dried over Na$_2$SO$_4$ and concentrated. The residue was purified by preparative HPLC to afford 5 mg (20% yield) of Example 20. MS(ESI) m/z: 451.3 (M+H)$^+$; $^1$H NMR (400 MHz, DMSO-d$_6$) δ ppm 12.78 (br s, 1H) 8.04 (br s, 1H) 7.89 (br s, 1H) 7.54 (d, J=8.47 Hz, 1H) 7.50 (d, J=2.13 Hz, 1H) 7.31 (t, J=7.91 Hz, 1H) 6.88-7.00 (m, 4H) 5.41 (t, J=7.87 Hz, 1H) 3.86 (s, 3H) 3.75-3.83 (m, 5H) 3.60 (s, 3H) 3.48-3.55 (m, 1H) 3.10-3.15 (m, 3H); HPLC RT=1.41 min (Method E), 1.44 min (Method F).

Example 21

1-(3-Hydroxy-1-(3-methoxyphenyl)propyl)-3-(3-methoxy-4-(1H-pyrazol-4-yl)phenyl)imidazolidin-2-one

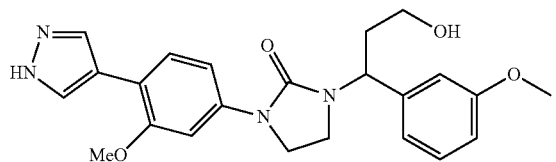 [SMILES: COc1cccc(C(CCO)N2CCN(c3ccc(-c4cn[nH]c4)c(OC)c3)C2=O)c1]

Example 21A: 1-(4-Bromo-3-methoxyphenyl)-3-(3-hydroxy-1-(3-methoxyphenyl)propyl) imidazolidin-2-one

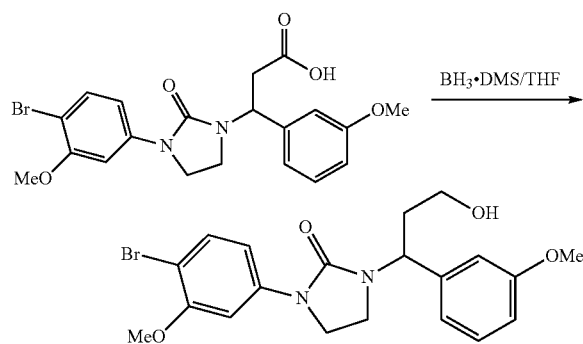

To a solution of Example 20C (0.140 g, 0.312 mmol) in THF (2 mL) at 0° C., was added borane-methyl sulfide complex (0.311 mL, 3.12 mmol), dropwise. The reaction mixture was stirred at 50° C. for 1.5 h, then was concentrated. The residue was treated with 6 N HCl in MeOH (2 mL) at rt for 30 min. The mixture was diluted with water and was extracted with methylene chloride (3×40 mL). The combined extracts were dried over sodium sulfate, filtered and concentrated. The product was purified by flash chromatography to afford 0.030 g (22% yield) of Example 21A as a white solid. MS(ESI) m/z: 435.6 (M+H)$^+$.

Example 21

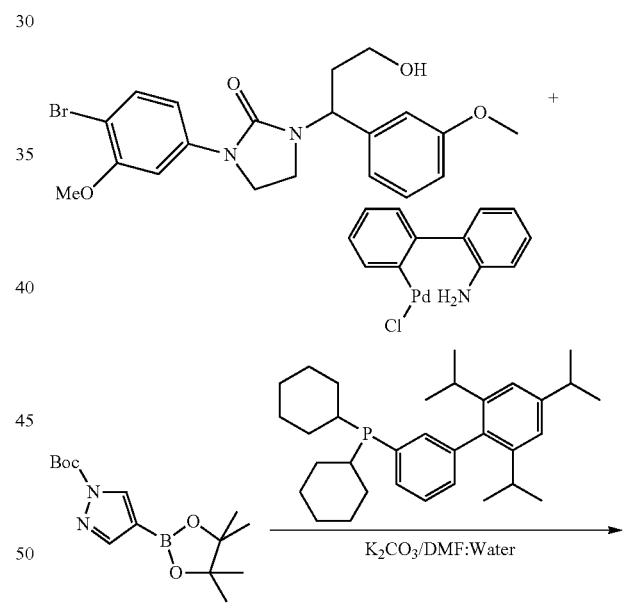

To a solution of Example 21A (0.030 g, 0.069 mmol) and tert-butyl 4-(4,4,5,5-tetramethyl-1,3,2-dioxaborolan-2-yl)-1H-pyrazole-1-carboxylate (0.030 g, 0.103 mmol) in DMF (2 mL) and water (0.3 mL), was added K$_2$CO$_3$ (0.029 g, 0.207 mmol). The reaction mixture was degassed with N$_2$ for 5 min, then 2nd generation XPhos precatalyst (10.8 mg, 0.014 mmol) was added to the reaction. The reaction mixture was degassed again, then was heated to 90° C. for 6 h. The reaction mixture was filtered through CELITE®, rinsing with MeOH. The filtrate was evaporated. The resultant solid was purified by preparative HPLC to afford 5 mg (17% yield) of Example 21. MS(ESI) m/z: 423.3 (M+H)+; 1H NMR (400 MHz, DMSO-d6) δ ppm 12.94 (br s, 1H) 8.04 (br s, 1H) 7.90 (br s, 1H) 7.51-7.56 (m, 2H) 7.30 (t, J=7.87 Hz, 1H) 6.94-7.00 (m, 2H) 6.86-6.92 (m, 2H) 5.13 (dd, J=9.07, 6.68 Hz, 1H) 4.53 (t, J=5.02 Hz, 1H) 3.86 (s, 3H) 3.78-3.84 (m, 2H) 3.77 (s, 3H) 3.49-3.56 (m, 1H) 3.40-3.48 (m, 2H) 3.10-3.19 (m, 1H) 2.03-2.18 (m, 2H); HPLC RT=1.29 min (Method E), 1.30 min (Method F).

Example 22

1-(3-Hydroxy-1-(3-methoxyphenyl)-3-methylbutyl)-3-(3-methoxy-4-(1H-pyrazol-4-yl)phenyl)imidazolidin-2-one

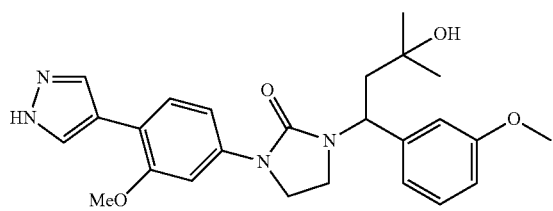 [SMILES: COc1cccc(C(CC(C)(C)O)N2CCN(c3ccc(-c4cn[nH]c4)c(OC)c3)C2=O)c1]

Example 22A: 1-(4-Bromo-3-methoxyphenyl)-3-(3-hydroxy-1-(3-methoxyphenyl)-3-methylbutyl)imidazolidin-2-one

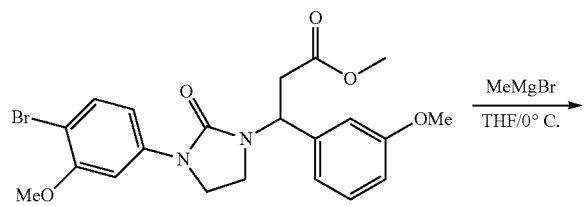

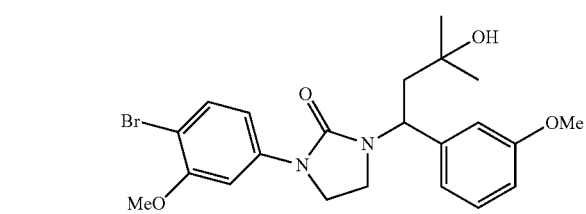

To a solution of Example 20B (0.070 g, 0.151 mmol) in THF (2 mL) at 0° C., was added 3M methylmagnesium bromide (0.201 mL, 0.604 mmol), dropwise. The reaction mixture was stirred at rt for 2 h. The mixture was diluted with water, then was extracted with ethyl acetate (3×20 mL). The combined extracts were dried over sodium sulfate and concentrated to afford 0.080 g of Example 22A, which was used in the following step without further purification. MS(ESI) m/z: 463.2 (M+H)+.

Example 22

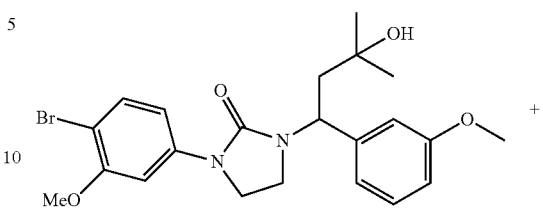

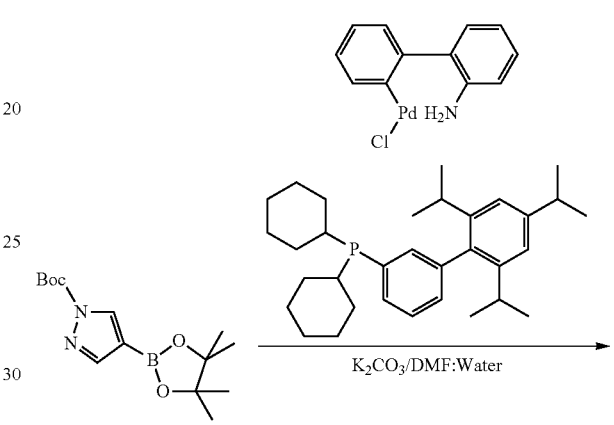

To a solution of Example 22A (0.070 g, 0.15 mmol) and tert-butyl 4-(4,4,5,5-tetramethyl-1,3,2-dioxaborolan-2-yl)-1H-pyrazole-1-carboxylate (0.067 g, 0.23 mmol) in DMF (2 mL) and water (0.3 mL), was added $K_2CO_3$ (0.063 g, 0.45 mmol). The reaction mixture was degassed with $N_2$ for 5 min, then 2nd generation XPhos precatalyst (0.024 g, 0.030 mmol) was added. The reaction mixture was degassed again, then was heated at 90° C. for 6 h. The reaction mixture was filtered through CELITE®, rinsing with MeOH. The filtrate was evaporated. The resultant solid was purified by preparative HPLC to afford 4 mg (6% yield) of Example 22. MS(ESI) m/z: 451.3 (M+H)+; 1H NMR (400 MHz, DMSO-d6) δ ppm 7.97 (s, 2H) 7.49-7.55 (m, 2H) 7.29 (t, J=7.91 Hz, 1H) 6.92-7.00 (m, 2H) 6.83-6.91 (m, 2H) 5.27 (dd, J=9.04, 4.14 Hz, 1H) 4.31 (br s, 1H) 3.84 (s, 3H) 3.74-3.78 (m, 4H) 3.59-3.67 (m, 2H) 3.07-3.17 (m, 2H) 2.17-2.26 (m, 1H) 1.94 (dd, J=14.40, 4.42 Hz, 1H) 1.14 (s, 3H) 1.12 (s, 3H); HPLC RT=1.43 min (Method E), 1.45 min (Method F).

Example 23

1-(3-Ethyl-4-(1H-pyrazol-4-yl)phenyl)-3-(3-methoxybenzyl)imidazolidin-2-one

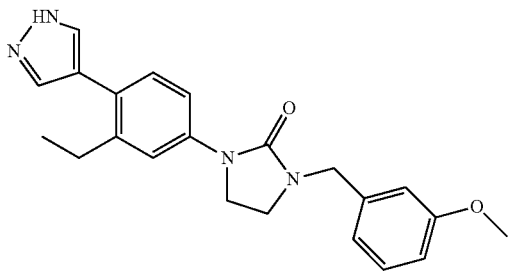 [SMILES: CCc1cc(N2CCN(Cc3cccc(OC)c3)C2=O)ccc1-c1cn[nH]c1]

Example 23A: 4-Bromo-N-(2-chloroethyl)-3-ethylaniline

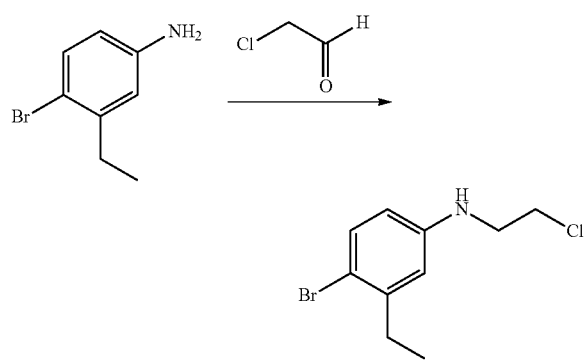

To a solution of 4-bromo-3-ethylaniline (5.00 g, 25.0 mmol) and 2-chloroacetaldehyde (4.82 mL, 37.5 mmol) in MeOH (25 mL), was added sodium cyanoborohydride (3.93 g, 62.5 mmol), followed by acetic acid (1.43 mL, 25.0 mmol). The mixture was stirred at rt overnight, then was concentrated. The mixture was basified with aq. NaHCO$_3$, then was extracted with ethyl acetate (3×40 mL). The organic layer was dried (Na$_2$SO$_4$) and concentrated. The residue was purified by flash chromatography (gradient elution: 0-15% EtOAc/Hex) to afford 4.50 g of Example 23A as a yellow oil. MS(ESI) m/z: 451.3 (M+H)$^+$; $^1$H NMR (300 MHz, CDCl$_3$) δ ppm 7.32 (d, J=8.59 Hz, 1H) 6.54 (d, J=2.88 Hz, 1H) 6.38 (dd, J=8.57, 2.90 Hz, 1H) 4.04 (br. s., 1H) 3.69-3.75 (m, 2H) 3.46-3.53 (m, 2H) 2.70 (q, J=7.50 Hz, 2H) 1.22 (t, J=7.50 Hz, 3H).

Example 23B: 1-(4-Bromo-3-ethylphenyl)-1-(2-chloroethyl)-3-(3-methoxybenzyl)urea

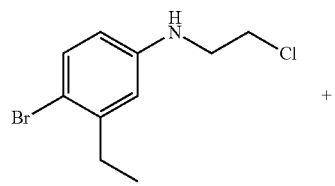

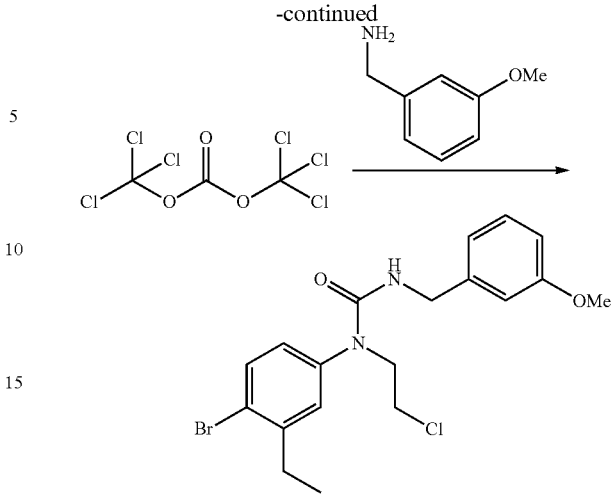

To a solution of Example 23A (0.300 g, 1.14 mmol) in CHCl$_3$ (5 mL) at 0° C., was added TEA (0.478 mL, 3.43 mmol) followed by bis(trichloromethyl)carbonate (0.407 g, 1.37 mmol). The mixture was stirred at 0° C. for 2 h, then (3-methoxyphenyl) methanamine (0.188 g, 1.37 mmol) was added and reaction mixture was stirred at rt overnight. The reaction mixture was diluted with water, acidified with 5% HCl, and extracted by DCM. The organic layer was dried over Na$_2$SO$_4$ and evaporated. The crude product was washed with 10% diethyl ether in n-hexane (30 mL), to obtain 0.55 g of Example 23B as a yellow oil, which was used as is without further purification. MS(ESI) m/z: 425.0 (M+H)$^+$.

Example 23C: 1-(4-Bromo-3-ethylphenyl)-3-(3-methoxybenzyl)imidazolidin-2-one

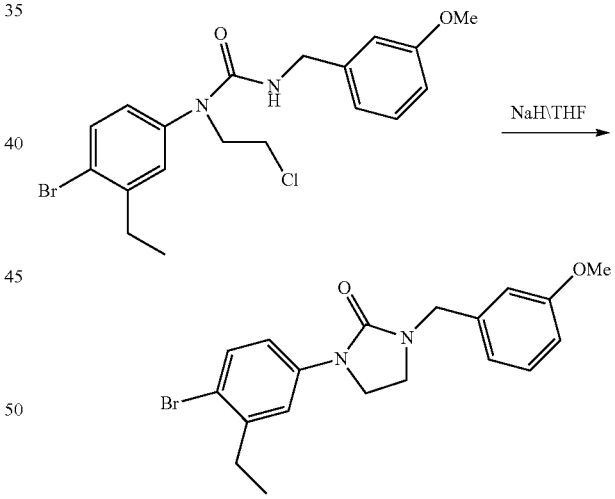

To a solution of Example 23B (0.400 g, 0.507 mmol) in THF (5 mL) at 0° C., was added NaH (0.026 g, 1.02 mmol). The reaction mixture was stirred at rt for 2 h, then was cooled to 0° C. and diluted with water. The mixture was extracted with ethyl acetate (3×30 mL). The organic layer was washed with brine, dried over Na$_2$SO$_4$ and concentrated to an oil, which was washed with 10% diethyl ether in n-hexane to afford 0.230 g of Example 23C as a yellow oil, which was used as is without further purification. MS(ESI) m/z: 389.1 (M+H)$^+$; $^1$H NMR (300 MHz, DMSO-d$_6$) δ ppm 7.58 (d, J=2.69 Hz, 1H) 7.47-7.53 (m, 1H) 7.37-7.44 (m, 1H) 7.24-7.33 (m, 1H) 6.84-6.90 (m, 3H) 4.36 (s, 2H) 3.82-3.74 (m, 2H) 3.73 (s, 3H) 3.35-3.40 (m, 2H) 2.68 (q, J=7.51 Hz, 2H) 1.18 (t, J=7.51 Hz, 3H).

Example 23

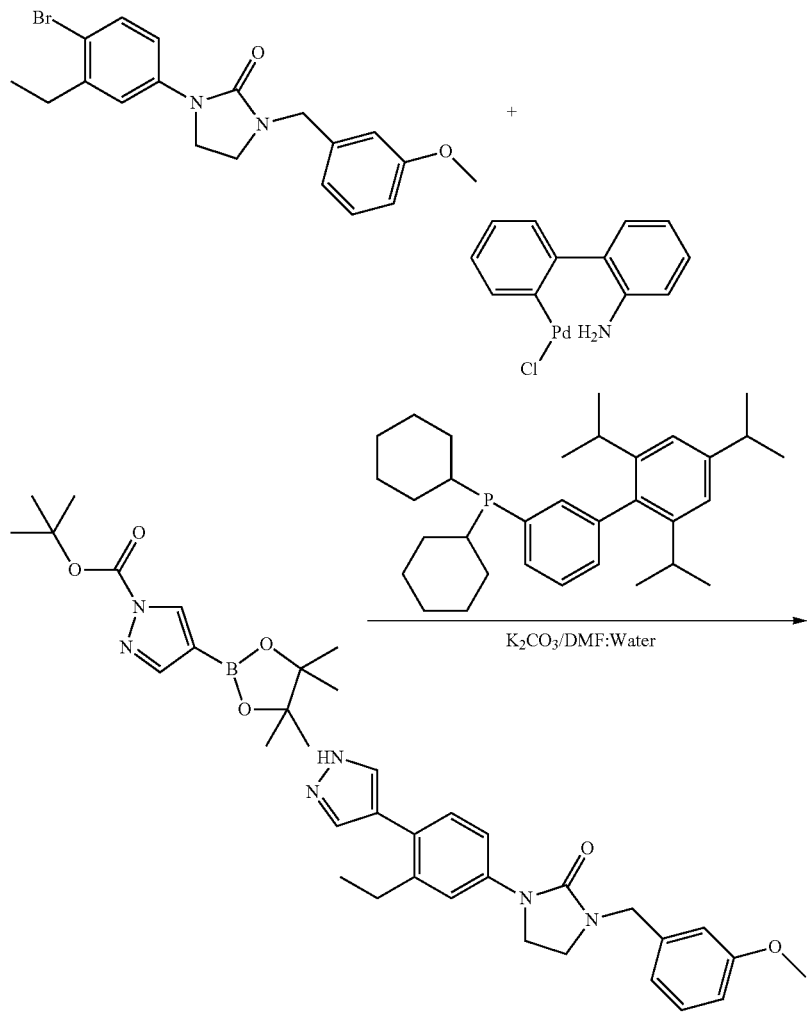

To a solution of Example 23 (0.070 g, 0.15 mmol) in DMF (2 mL) and water (0.3 mL), was added K$_2$CO$_3$ (0.062 g, 0.45 mmol). The reaction mixture was degassed with N$_2$ for 5 min, then 2nd generation XPhos precatalyst (0.023 g, 0.030 mmol) was added. The reaction mixture was degassed again, then was heated to 90° C. overnight. The reaction mixture was filtered through CELITE®, rinsing with MeOH. The filtrate was concentrated, and the residue was purified by preparative HPLC to afford 25 mg (32% yield) of Example 23. MS(ESI) m/z: 377.3 (M+H)$^+$; $^1$H NMR (400 MHz, DMSO-d$_6$) δ ppm 7.72 (br. s., 2H) 7.52 (d, J=2.07 Hz, 1H) 7.39-7.45 (m, 1H) 7.23-7.33 (m, 2H) 6.83-6.91 (m, 3H) 4.36 (s., 2H) 3.83 (t, J=7.84 Hz, 2H) 3.72 (s., 3H) 3.36 (t, J=7.84 Hz, 2H) 2.63-2.73 (m, 2H) 1.12 (t, J=7.60 Hz, 3H); $^{19}$F NMR (400 MHz, DMSO-d$_6$) δ ppm −74.22; HPLC RT=1.53 min (Method E), 1.57 min (Method F).

Example 24

1-(3-Ethyl-4-(1H-pyrazol-4-yl)phenyl)-3-(3-fluorobenzyl)imidazolidin-2-one

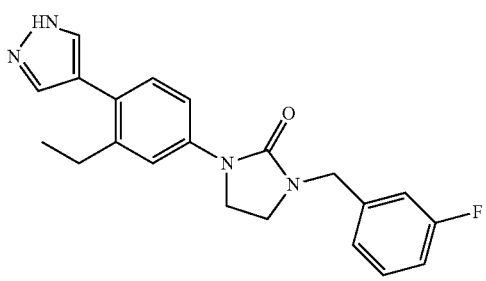 [SMILES: CCc1cc(N2CCN(Cc3cccc(F)c3)C2=O)ccc1-c1cn[nH]c1]

According to the procedure for the synthesis of Example 23, substituting (3-fluorophenyl)methanamine for (3-methoxyphenyl)methanamine afforded Example 24. MS(ESI) m/z: 365.3 (M+H)$^+$; $^1$H NMR (400 MHz, DMSO-d$_6$) δ ppm 7.72 (br. s., 2H) 7.52 (d, J=2.38 Hz, 1H) 7.38-7.45

(m, 2H) 7.26 (d, J=8.47 Hz, 1H) 7.08-7.18 (m, 3H) 4.42 (s, 2H) 3.84 (dd, J=9.00, 7.00 Hz, 2H) 3.36-3.42 (m, 2H) 2.68 (q, J=7.57 Hz, 2H) 1.12 (t, J=7.53 Hz, 3H); $^{19}$F NMR (400 MHz, DMSO-$d_6$) δ ppm −113.151; HPLC RT=1.56 min (Method E), 1.61 min (Method F).

Example 25

1-(3-Ethyl-4-(1H-pyrazol-4-yl)phenyl)-3-(2-fluorobenzyl)imidazolidin-2-one

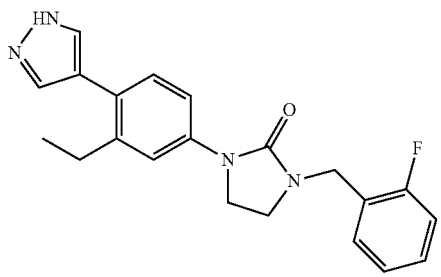 [SMILES: CCc1cc(N2CCN(Cc3ccccc3F)C2=O)ccc1-c1cn[nH]c1]

According to the procedure for the synthesis of Example 23, substituting (2-fluorophenyl)methanamine for (3-methoxyphenyl)methanamine afforded Example 25. MS(ESI) m/z: 365.3 (M+H)$^+$; $^1$H NMR (400 MHz, DMSO-$d_6$) δ ppm 7.72 (br. s., 2H) 7.51 (d, J=2.38 Hz, 1H) 7.33-7.43 (m, 3H) 7.19-7.27 (m, 3H) 4.46 (s, 2H) 3.83 (dd, J=9.04, 6.96 Hz, 2H) 3.38-3.43 (m, 2H) 2.63-2.72 (m, 2H) 1.12 (t, J=7.50 Hz, 3H); $^{19}$F NMR (400 MHz, DMSO-$d_6$) δ ppm −118.756; HPLC RT=1.56 min (Method E), 1.61 min (Method F).

Example 26

1-Benzyl-3-(3-ethyl-4-(1H-pyrazol-4-yl)phenyl)imidazolidin-2-one

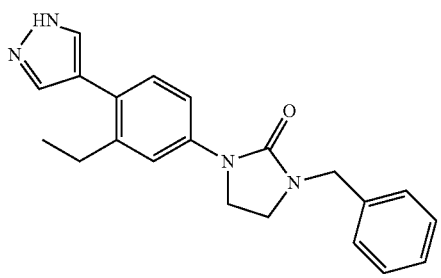 [SMILES: CCc1cc(N2CCN(Cc3ccccc3)C2=O)ccc1-c1cn[nH]c1]

According to the procedure for the synthesis of Example 23, substituting benzylamine for (3-methoxyphenyl)methanamine afforded Example 26. MS(ESI) m/z: 347.3 (M+H)$^+$; $^1$H NMR (400 MHz, DMSO-$d_6$) δ ppm 12.87 (br. s., 1H) 7.71 (br. s., 2H) 7.52 (d, J=2.38 Hz, 1H) 7.39-7.44 (m, 1H) 7.34-7.38 (m, 2H) 7.28-7.33 (m, 3H) 7.25 (d, J=8.47 Hz, 1H) 4.40 (s, 2H) 3.82 (dd, J=9.00, 7.00 Hz, 2H) 3.35-3.38 (m, 2H) 2.68 (q, J=7.53 Hz, 2H) 1.12 (t, J=7.53 Hz, 3H); HPLC RT=2.24 min (Method C), 2.28 min (Method D).

Example 27

1-(3-Ethyl-4-(1H-pyrazol-4-yl)phenyl)-3-(3-methoxyphenethyl)imidazolidin-2-one, TFA

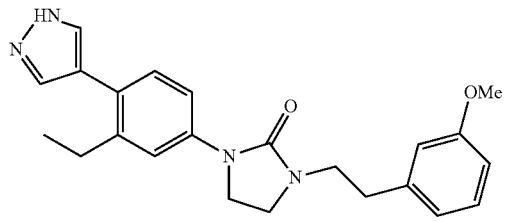 [SMILES: CCc1cc(N2CCN(CCc3cccc(OC)c3)C2=O)ccc1-c1cn[nH]c1]

According to the procedure for the synthesis of Example 23, substituting phenethylamine for (3-methoxyphenyl)methanamine afforded Example 27. MS(ESI) m/z: 391.3 (M+H)$^+$; $^1$H NMR (400 MHz, DMSO-$d_6$) δ ppm 7.71 (br. s., 2H) 7.48 (d, J=2.32 Hz, 1H) 7.36 (dd, J=8.50, 2.42 Hz, 1H) 7.20-7.25 (m, 2H) 6.82-6.87 (m, 2H) 6.78 (ddd, J=8.22, 2.38, 1.00 Hz, 1H) 3.77 (dd, J=9.26, 6.68 Hz, 2H) 3.74 (s, 3H) 3.40-3.48 (m, 4H) 2.80 (t, J=7.40 Hz, 2H) 2.66 (q, J=7.47 Hz, 2H) 1.11 (t, J=7.53 Hz, 3H); HPLC RT=2.29 min (Method C), 2.33 min (Method D).

Example 28

(R)-1-(3-Ethyl-4-(1H-pyrazol-4-yl)phenyl)-3-(1-(3-methoxyphenyl)ethyl)imidazolidin-2-one

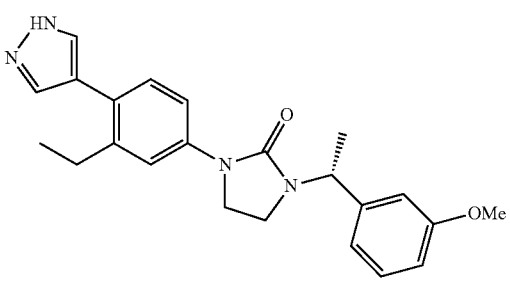 [SMILES: CCc1cc(N2CCN([C@H](C)c3cccc(OC)c3)C2=O)ccc1-c1cn[nH]c1]

According to the procedure for the synthesis of Example 23, substituting (R)-1-(3-methoxyphenyl)ethanamine for (3-methoxyphenyl)methanamine afforded Example 28. MS(ESI) m/z: 391.2 (M+H)$^+$; $^1$H NMR (400 MHz, DMSO-$d_6$) δ ppm 12.89 (br. s., 1H) 7.85 (br. s., 1H) 7.66 (br. s., 1H) 7.50 (d, J=2.38 Hz, 1H) 7.39 (dd, J=8.50, 2.42 Hz, 1H) 7.29 (t, J=7.87 Hz, 1H) 7.24 (d, J=8.47 Hz, 1H) 6.94 (dd, J=7.62, 0.72 Hz, 1H) 6.84-6.90 (m, 2H) 5.12 (q, J=7.15 Hz, 1H) 3.77-3.83 (m, 2H) 3.75 (s, 3H) 3.46-3.55 (m, 1H) 3.11 (q, J=8.51 Hz, 1H) 2.67 (q, J=7.47 Hz, 2H) 1.51 (d, J=7.22 Hz, 3H) 1.11 (t, J=7.50 Hz, 3H); HPLC RT=10.13 min (Method A), 9.67 min (Method B).

Example 29

Ethyl 3-(4-(1H-pyrazol-4-yl)phenyl)-1-benzyl-2-oxoimidazolidine-4-carboxylate

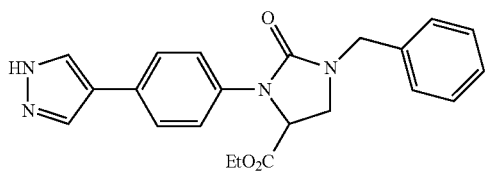 [SMILES: CCOC(=O)C1CN(Cc2ccccc2)C(=O)N1c1ccc(-c2cn[nH]c2)cc1]

Example 29A: Ethyl 3-(benzylamino)-2-chloropropanoate

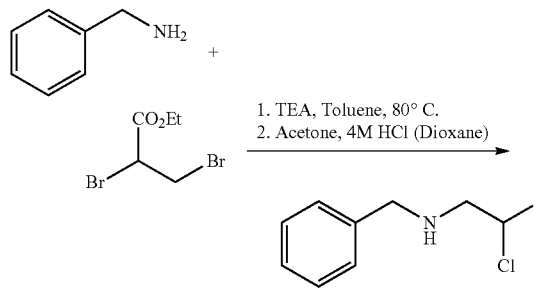

To the solution of benzylamine (1.00 g, 9.33 mmol) in toluene (15 mL), was added TEA (3.25 mL, 23.3 mmol) and ethyl 2,3-dibromopropanoate (1.36 mL, 9.33 mmol) in toluene (10 mL). The mixture was stirred at 80° C. overnight, then was concentrated. The residue was dissolved in DCM (10 mL), then was precipitated with petroleum ether. The mixture was filtered and filtrate was concentrated to give a yellow liquid. The oil was dissolved in acetone (10 mL) and cooled to 0° C., then was treated slowly with HCl (4 M in dioxane) (3.0 mL, 12 mmol) and warmed to rt and stirred at rt for 2.5 h. The reaction mixture was concentrated to give a yellow liquid, which was basified with 10% NaHCO$_3$ and extracted with ethyl acetate. The combined organic phase was washed with brine, dried over Na$_2$SO$_4$ and concentrated. The residue was purified by flash chromatography (0-60% EtOAc/Hex) to afford 600 mg of Example 29A as a yellow liquid. MS(ESI) m/z: 244.2 (M+H)$^+$.

Example 29B: Ethyl 1-benzyl-3-(4-bromophenyl)-2-oxoimidazolidine-4-carboxylate

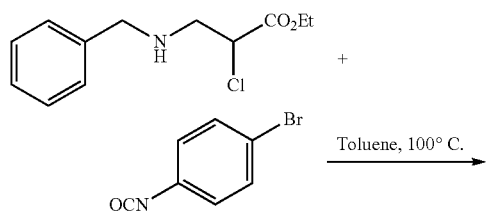

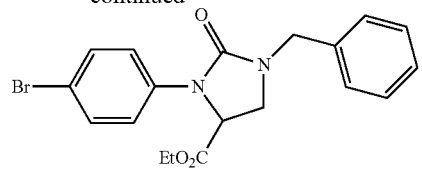

To the solution of Example 29A (600 mg, 2.48 mmol) in toluene (10 mL), was added 1-bromo-4-isocyanatobenzene (541 mg, 2.73 mmol). The mixture was heated at 100° C. overnight. The reaction mixture was concentrated, and the product was purified by flash chromatography (0-100% EtOAc/Hex) to afford 700 mg of Example 29B as a white solid. MS(ESI) m/z: 403.5 (M+H)$^+$; $^1$H NMR (400 MHz, DMSO-d$_6$) δ ppm 7.44-7.53 (m, 4H) 7.33-7.39 (m, 2H) 7.24-7.32 (m, 3H) 5.08 (dd, J=10.04, 3.26 Hz, 1H) 4.32-4.48 (m, 2H) 4.07-4.15 (m, 2H) 3.68 (t, J=9.73 Hz, 1H) 3.36 (dd, J=9.47, 3.26 Hz, 1H) 1.11 (t, J=10.8 Hz, 3H).

Example 29C: tert-Butyl 4-(4-(3-benzyl-5-(ethoxycarbonyl)-2-oxoimidazolidin-1-yl)phenyl)-1H-pyrazole-1-carboxylate

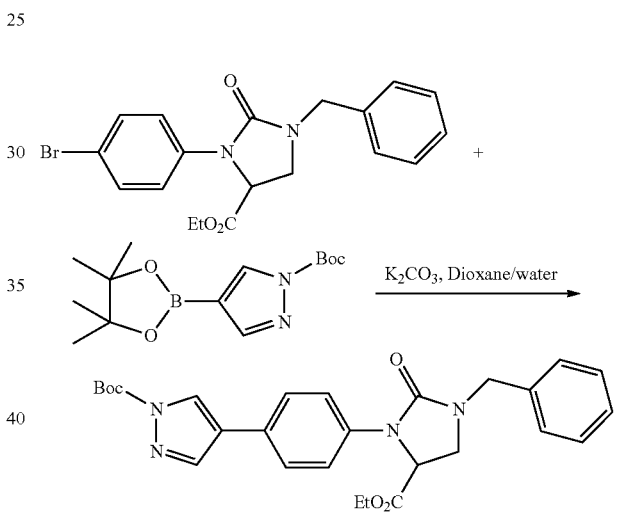

To the solution of Example 29B (50 mg, 0.124 mmol) and tert-butyl 4-(4,4,5,5-tetramethyl-1,3,2-dioxaborolan-2-yl)-1H-pyrazole-1-carboxylate (54.7 mg, 0.186 mmol) in dioxane (5 mL) and water (0.5 mL), was added K$_2$CO$_3$ (42.8 mg, 0.310 mmol). The mixture was degassed with nitrogen for 5 min, then 2nd generation XPhos precatalyst (5.9 mg, 7.4 μmol) was added. The mixture was heated at 85° C. for 1.5 h. The reaction was diluted with ethyl acetate, washed with water and brine, dried (Na$_2$SO$_4$), and concentrated to afford Example 29C. The product was used as in the following step without further purification. MS(ESI) m/z: 491.7 (M+H)$^+$.

Example 29

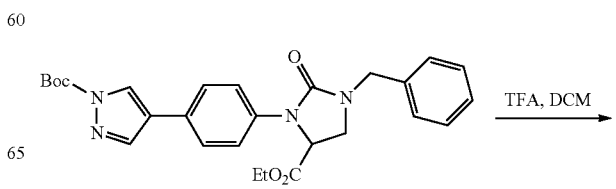

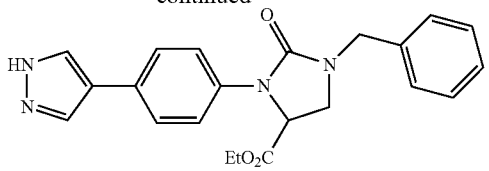

To the solution of Example 29C (85 mg, 0.173 mmol) in DCM (5 mL), was added TFA (0.25 mL, 3.24 mmol), and the mixture was stirred at rt for 3 h. The mixture was evaporated. The residue was purified by preparative HPLC to afford 14 mg (20% yield) of Example 29. MS(ESI) m/z: 391.3 (M+H)$^+$; $^1$H NMR (400 MHz, DMSO-d$_6$) δ ppm 12.98 (s, 1H) 7.57 (s, 2H) 7.52-7.58 (m, 2H) 7.44-7.50 (m, 2H) 7.33-7.40 (m, 2H) 7.24-7.32 (m, 3H) 5.07 (dd, J=10.04, 3.39 Hz, 1H) 4.42-4.50 (m, 1H) 4.31-4.39 (m, 1H) 4.12 (q, J=7.09 Hz, 2H) 3.68 (t, J=9.73 Hz, 1H) 3.34 (dd, J=9.41, 3.39 Hz, 1H) 1.12 (d, J=14.18 Hz, 3H); HPLC RT=1.48 min (Method E), 1.51 min (Method F).

Example 30

3-(4-(1H-Pyrazol-4-yl)phenyl)-1-benzyl-4-(hydroxymethyl)imidazolidin-2-one

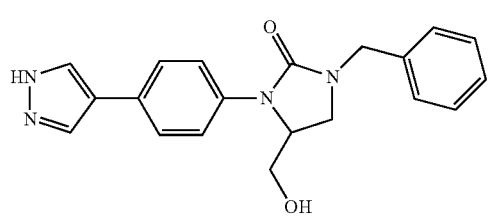 [SMILES: O=C1N(Cc2ccccc2)CC(CO)N1c1ccc(-c2cn[nH]c2)cc1]

Example 30A: 1-Benzyl-3-(4-bromophenyl)-4-(hydroxymethyl)imidazolidin-2-one

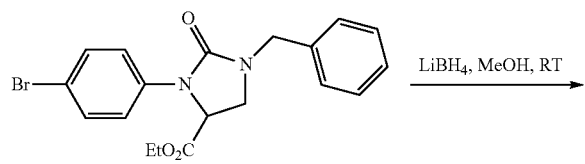

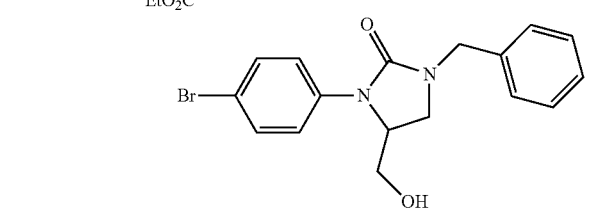

To the solution of Example 29B (100 mg, 0.248 mmol) in methanol (5 mL) at rt, was added LiBH$_4$ (13.5 mg, 0.620 mmol). The mixture was stirred at rt overnight, then the solvent was evaporated. The residue was diluted with water and extracted with EtOAc (2×). The combined organic phase was washed with brine, dried (Na$_2$SO$_4$), and concentrated. The residue was purified by flash chromatography (0-100% EtOAc/Hex) to afford Example 30A, which was used as is without further purification. MS(ESI) m/z: 361.5 (M+H)$^+$.

Example 30

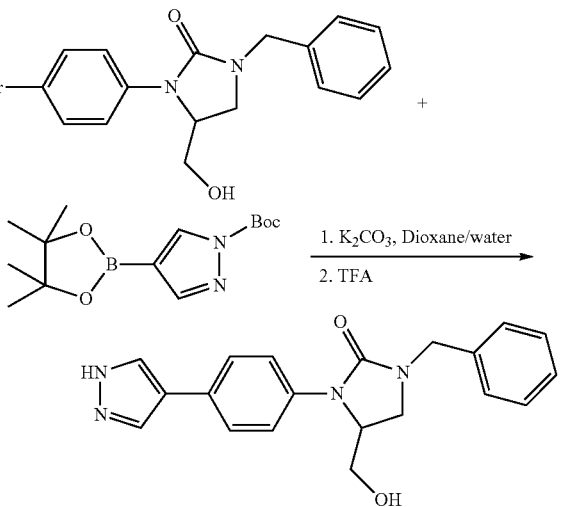

To the solution of Example 30A (100 mg, 0.277 mmol) and tert-butyl 4-(4,4,5,5-tetramethyl-1,3,2-dioxaborolan-2-yl)-1H-pyrazole-1-carboxylate (122 mg, 0.415 mmol) in DMF (3 mL) and water (0.5 mL), was added K$_2$CO$_3$ (96 mg, 0.692 mmol). The mixture was degassed, then 2nd generation XPhos precatalyst (13 mg, 0.017 mmol) was added. The mixture was heated at 85° C. for 2 h. The reaction was diluted with ethyl acetate, washed with water and brine, dried (Na$_2$SO$_4$), filtered and concentrated. The residue was dissolved in TFA and stirred for 3 h. The mixture was concentrated and the product was purified by preparative HPLC to afford 4 mg of Example 30. MS(ESI) m/z: 349.2 (M+H)$^+$; $^1$H NMR (400 MHz, DMSO-d$_6$) δ ppm 12.87 (s, 1H) 8.13 (s, 1H) 7.88 (s, 1H) 7.51-7.59 (m, 4H) 7.35-7.41 (m, 2H) 7.27-7.34 (m, 3H) 4.93 (t, J=5.40 Hz, 1H) 4.32-4.46 (m, 3H) 3.46-3.52 (m, 1H) 3.36-3.45 (m, 2H) 3.26-3.31 (m, 1H); HPLC RT=1.06 min (Method E), 1.10 min (Method F).

Example 31

1-(2-(1H-Pyrazol-4-yl)benzyl)-3-(3-methoxy-4-(1H-pyrazol-4-yl)phenyl)imidazolidin-2-one, TFA

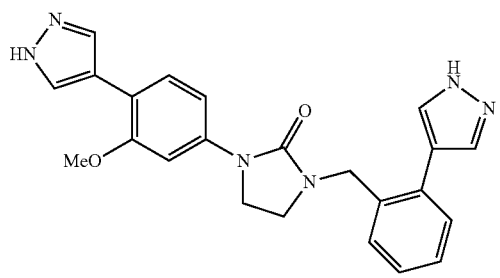 [SMILES: COc1cc(N2CCN(Cc3ccccc3-c3cn[nH]c3)C2=O)ccc1-c1cn[nH]c1]

According to the procedure for the preparation of Example 15, substituting (2-chlorophenyl)methanamine for (2-fluoro-5-methoxyphenyl)methanamine afforded Example 31. MS(ESI) m/z: 415.3 (M+H)⁺; ¹H NMR (400 MHz, DMSO-d₆) δ ppm 13.00 (br s, 1H), 12.80 (br s, 1H), 7.97 (br s, 3H), 7.72 (br s, 1H), 7.56 (d, J=8.47 Hz, 1H), 7.54 (d, J=2.13 Hz, 1H), 7.41-7.46 (m, 1H), 7.29-7.38 (m, 3H), 7.03 (dd, J=8.50, 2.16 Hz, 1H), 4.52 (s, 2H), 3.83-3.89 (m, 5H), 3.33-3.38 (m, 2H); HPLC RT=1.21 min (Method E), 1.29 min (Method F).

Example 32

1-(4-(1H-Pyrazol-4-yl)phenyl)-3-(3-fluorobenzyl)-2-oxoimidazolidine-4-carboxylic Acid

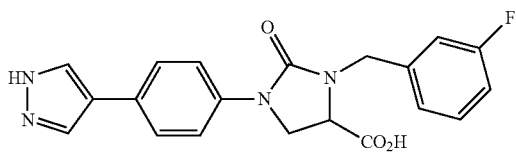

Example 32A: Ethyl 2-bromo-3-((4-bromophenyl)amino)propanoate

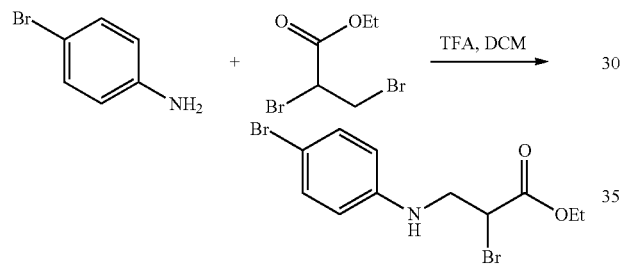

To a solution of 4-bromoaniline (1.0 g, 5.8 mmol) in toluene (15 mL), was added TEA (2.43 mL, 17.4 mmol). The mixture was heated to 50° C., then a solution of ethyl 2,3-dibromopropanoate (0.845 mL, 5.81 mmol) in toluene (4 mL) was added, dropwise. The mixture was heated 100° C. for 2 days. The mixture was concentrated and the product was purified by flash chromatography (0-4% EtOAc/Hex) to give 350 mg of Example 32A as a brown liquid. MS(ESI) m/z: 350.3 (M+H)⁺; ¹H NMR (300 MHz, chloroform-d) δ 7.30 (d, J=8.9 Hz, 2H), 6.60-6.50 (m, 2H), 4.40 (dd, J=8.1, 6.0 Hz, 1H), 4.26 (dtt, J=10.7, 7.1, 3.6 Hz, 2H), 3.90-3.77 (m, 1H), 3.69-3.58 (m, 1H), 1.31 (t, J=7.2 Hz, 3H).

Example 32B: Ethyl 1-(4-bromophenyl)-3-(3-fluorobenzyl)-2-oxoimidazolidine-4-carboxylate

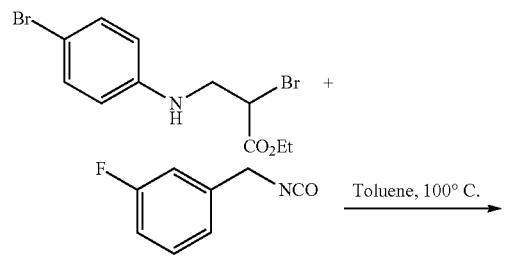

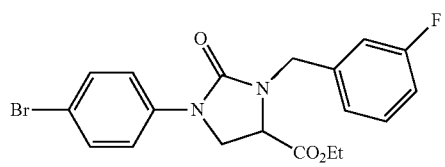

To a solution of Example 32A (350 mg, 0.997 mmol) in toluene (5 mL), was added 1-fluoro-3-(isocyanatomethyl)benzene (226 mg, 1.50 mmol). The mixture was heated at 100° C. overnight. The mixture was concentrated, and the residue was purified flash chromatography (0-40% EtOAc/Hex) to afford 200 mg of Example 32B as a yellow solid as a mixture of regioisomers. MS(ESI) m/z: 421.4 (M+H)⁺.

Example 32

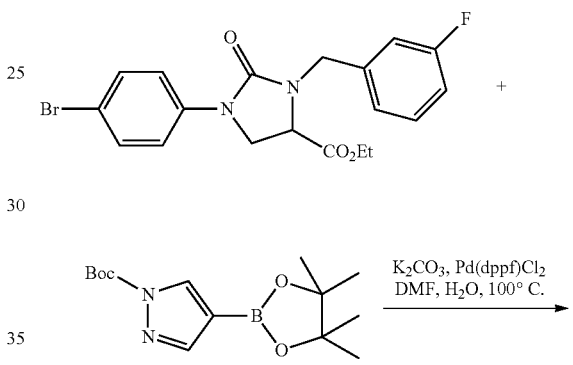

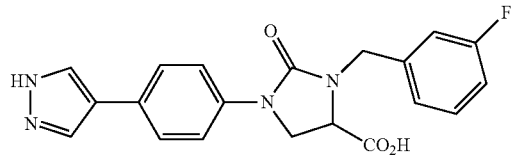

To a solution of Example 32B (200 mg, 0.475 mmol) and tert-butyl 4-(4,4,5,5-tetramethyl-1,3,2-dioxaborolan-2-yl)-1H-pyrazole-1-carboxylate (279 mg, 0.950 mmol) in DMF (5 mL) and water (0.5 mL), was added K₂CO₃ (197 mg, 1.42 mmol). The mixture was degassed, then was treated with 2nd generation XPhos precatalyst (22 mg, 0.028 mmol) and again degassed. The mixture was heated at 100° C. overnight. The reaction was diluted with ethyl acetate, filtered through CELITE®, rinsing with ethyl acetate. The filtrate was concentrated, and the residue was purified by preparative HPLC to afford 18 mg of Example 32 as a white solid. MS(ESI) m/z: 381.2 (M+H)⁺; ¹H NMR (400 MHz, DMSO-d₆) δ ppm 13.00 (br. s, 1H) 7.99 (s, 2H) 7.57 (s, 1H) 7.56 (s, 4H) 7.33-7.43 (m, 1H) 7.05-7.16 (m, 3H) 4.79 (d, J=15.86 Hz, 1H) 4.26 (d, J=15.58 Hz, 1H) 3.93-4.11 (m, 2H) 3.79 (dd, J=8.71, 4.32 Hz, 1H); ¹⁹F NMR (400 MHz, methanol-d₄) δ ppm −113.321; HPLC RT=7.98 min (Method A), 7.66 min (Method B).

Example 33

3-(4-(1H-Pyrazol-4-yl)phenyl)-1-(3-fluorobenzyl)-2-oxoimidazolidine-4-carboxylic Acid

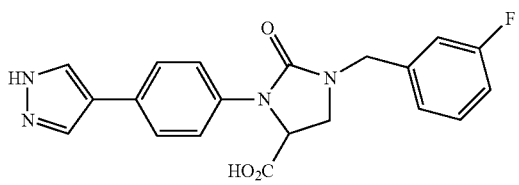 [SMILES: O=C(O)C1CN(Cc2cccc(F)c2)C(=O)N1c1ccc(-c2cn[nH]c2)cc1]

Example 33A: Ethyl 2-chloro-3-((3-fluorobenzyl)amino)propanoate

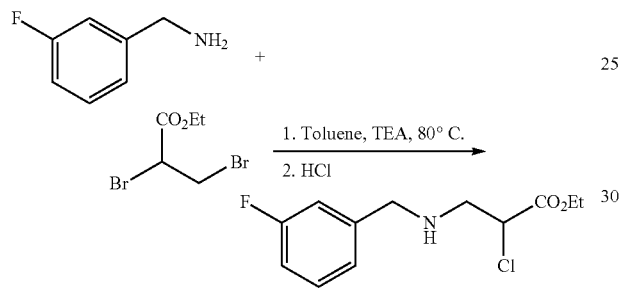

To the solution of (3-fluorophenyl)methanamine (1.00 g, 7.99 mmol) in toluene (15 mL), was added TEA (4.46 mL, 32.0 mmol) and ethyl 2,3-dibromopropanoate (2.08 g, 7.99 mmol) in toluene (10 mL). The mixture was stirred at 85° C. overnight. The reaction mixture was concentrated. The residue was dissolved in DCM (10 mL) and precipitated by adding petroleum ether. The solid was collected by filtration, then was dissolved in acetone (15 mL) and cooled to 0° C. To this solution, was added 4 M HCl in dioxane, then the mixture was allowed to warm to rt and stir for 16 h. The reaction mixture was concentrated to give a yellow liquid, which was basified with 10% NaHCO$_3$ and extracted with ethyl acetate. The combined ethyl acetate layers were washed with brine, dried (Na$_2$SO$_4$), and concentrated. The residue was purified by flash chromatography (0-60% EtOAc/Hex) to afford 850 mg of Example 33A as a yellow oil. MS(ESI) m/z: 260.5 (M+H)$^+$.

Example 33B: Ethyl 3-(3-(4-bromophenyl)-1-(3-fluorobenzyl)ureido)-2-chloropropanoate

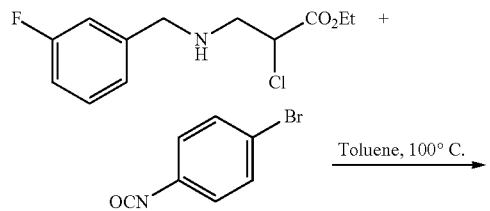

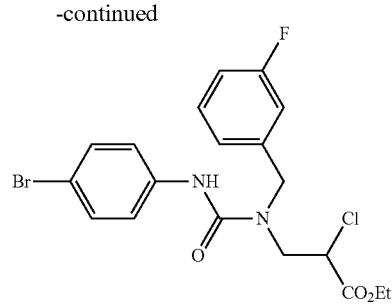

To the solution of ethyl 2-chloro-3-((3-fluorobenzyl)amino)propanoate (850 mg, 3.27 mmol) in toluene (10 mL), was added 1-bromo-4-isocyanatobenzene (713 mg, 3.60 mmol). The mixture was heated at 100° C. overnight. The mixture was concentrated to afford 1.80 g of a yellow solid, which was used as is in the following step. MS(ESI) m/z: 457.5 (M+H)$^+$.

Example 33C: Methyl 3-(4-bromophenyl)-1-(3-fluorobenzyl)-2-oxoimidazolidine-4-carboxylate

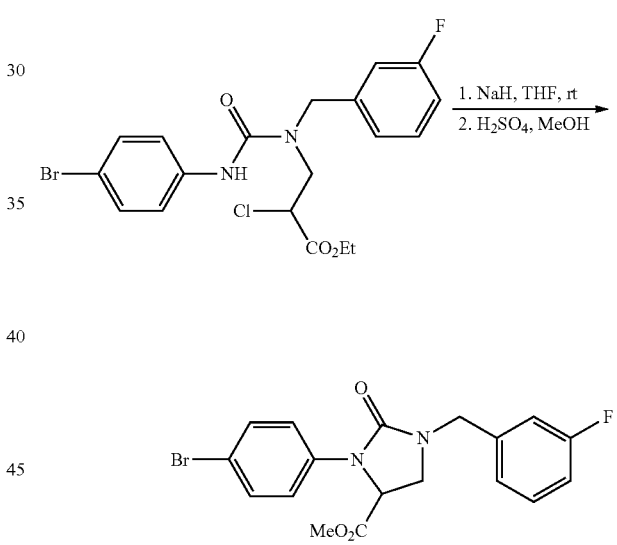

To the solution of Example 33B (1.80 g, 3.93 mmol) in THF (10 mL) at 0° C., was added NaH (0.199 g, 7.87 mmol). The mixture was stirred at rt for 4 h, then the reaction was quenched with ice water and concentrated to give a yellow gummy solid. The residue was dissolved in methanol (25 mL), then the solution was treated with H$_2$SO$_4$ (0.868 mL, 16.28 mmol) and was stirred at rt for 6 h. The methanol was evaporated, then the residue was basified with 10% NaHCO$_3$ (aqueous), then extracted with ethyl acetate. The combined ethyl acetate layers were washed with brine, dried (Na$_2$SO$_4$), and concentrated. The residue was purified by flash chromatography (0-100% EtOAc/Hex) to afford 1.00 g of Example 33C as an off-white solid. MS(ESI) m/z: 407.5 (M+H)$^+$; $^1$H NMR (400 MHz, DMSO-d$_6$) δ ppm 7.45-7.53 (m, 4H) 7.34-7.44 (m, 1H) 7.05-7.20 (m, 3H) 5.12 (dd, J=10.04, 3.26 Hz, 1H) 4.36-4.48 (m, 2H) 3.68-3.74 (m, 1H) 3.66 (s, 3H) 3.42 (dd, J=9.51, 3.29 Hz, 1H).

Example 33

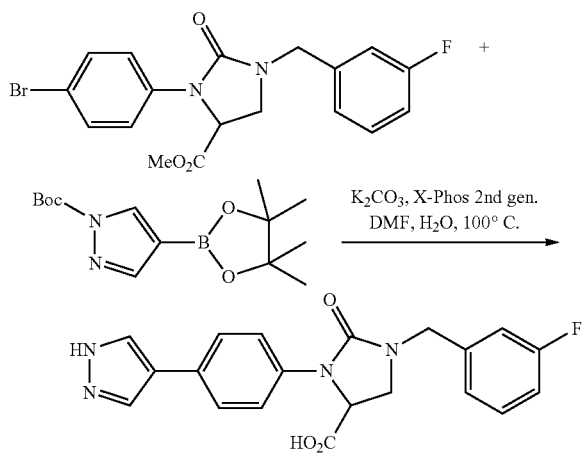

To the solution of Example 33C (75 mg, 0.184 mmol) and tert-butyl 4-(4,4,5,5-tetramethyl-1,3,2-dioxaborolan-2-yl)-1H-pyrazole-1-carboxylate (108 mg, 0.368 mmol) in DMF (3 mL) and water (0.5 mL), was added $K_2CO_3$ (76 mg, 0.55 mmol). The mixture was degassed, then 2nd generation XPhos precatalyst (8.7 mg, 0.011 mmol) was added. The mixture was heated at 85° C. for 3.5 h. The reaction was diluted with water (15 mL) and filtered through CELITE®. The filtrate was washed with ethyl acetate (2×20 mL). The aqueous was acidified to pH 3, and the resultant solid was collected by filtration. The solid was washed with water and petroleum ether to afford 44.0 mg of Example 33 as an off-white solid. MS(ESI) m/z: 381.2 (M+H)$^+$; $^1$H NMR (400 MHz, DMSO-$d_6$) δ ppm 13.08 (s, 2H) 8.00 (s, 2H) 7.51-7.58 (m, 2H) 7.47-7.52 (m, 2H) 7.38-7.45 (m, 1H) 7.08-7.17 (m, 3H) 4.96 (dd, J=10.04, 3.39 Hz, 1H) 4.34-4.53 (m, 2H) 3.72 (t, J=9.66 Hz, 1H) 3.39 (dd, J=9.35, 3.39 Hz, 1H); $^{19}$F NMR (400 MHz, DMSO-$d_6$) δ ppm −113.072; HPLC RT=7.93 min (Method A), 7.69 min (Method B).

Example 34

Methyl 3-(4-(1H-pyrazol-4-yl)phenyl)-1-(3-fluorobenzyl)-2-oxoimidazolidine-4-carboxylate

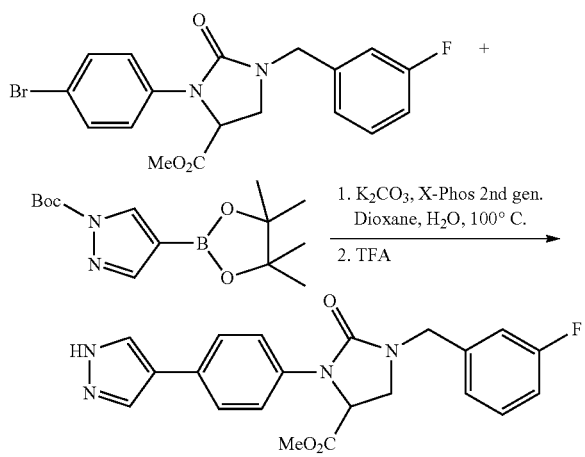

To the solution of Example 33A (200 mg, 0.491 mmol) and tert-butyl 4-(4,4,5,5-tetramethyl-1,3,2-dioxaborolan-2-yl)-1H-pyrazole-1-carboxylate (289 mg, 0.982 mmol) in dioxane (3 mL) and water (0.5 mL), was added $K_2CO_3$ (204 mg, 1.47 mmol). The mixture was degassed, then 2nd generation XPhos precatalyst (23 mg, 0.029 mmol) was added. The mixture was heated at 85° C. for 3.5 h. The reaction was diluted with water (15 mL) and filtered through CELITE®. The filtrate was washed with brine, dried ($Na_2SO_4$), and concentrated. The residue was dissolved in DCM (5 mL) and was treated with TFA (0.1 mL) and stirred at rt for 3 h. The mixture was concentrated and the residue was purified by preparative HPLC to afford 32 mg of Example 34. MS(ESI) m/z: 395.2 (M+H)$^+$; $^1$H NMR (400 MHz, DMSO-$d_6$) δ ppm 12.87 (br. s., 1H) 8.11 (s, 1H) 7.88 (s, 1H) 7.53-7.58 (m, 2H) 7.44-7.50 (m, 2H) 7.38-7.43 (m, 1H) 7.06-7.16 (m, 3H) 5.12 (dd, J=10.01, 3.42 Hz, 1H) 4.36-4.49 (m, 2H) 3.71 (t, J=9.73 Hz, 1H) 3.67 (s, 3H) 3.41 (dd, J=9.44, 3.42 Hz, 1H); $^{19}$F NMR (400 MHz, DMSO-$d_6$) δ ppm −113.080; HPLC RT=1.43 min (Method E), 1.43 min (Method F).

Example 35

3-(4-(1H-Pyrazol-4-yl)phenyl)-1-(3-methoxybenzyl)-2-oxoimidazolidine-4-carboxylic Acid

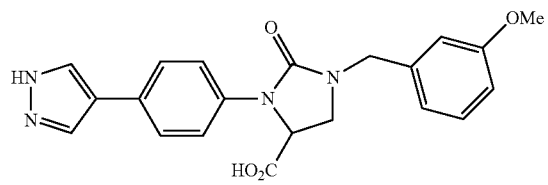 [SMILES: COc1cccc(CN2CC(C(=O)O)N(c3ccc(-c4cn[nH]c4)cc3)C2=O)c1]

According to the procedure for the preparation of Example 33, substituting (3-methoxyphenyl)methanamine for (3-fluorophenyl)methanamine afforded Example 35. MS(ESI) m/z: 393.6 (M+H)$^+$; $^1$H NMR (400 MHz, DMSO-$d_6$) δ ppm 13.06 (s, 1H) 12.96 (s, 1H) 7.98 (s, 2H) 7.52-7.57 (m, 2H) 7.46-7.52 (m, 2H) 7.24-7.30 (m, 1H) 6.82-6.87 (m, 3H) 4.94 (dd, J=9.98, 3.39 Hz, 1H) 4.42-4.49 (m, 1H) 4.26-4.33 (m, 1H) 3.74 (s, 3H) 3.67 (t, J=9.66 Hz, 1H) 3.32-3.37 (m, 1H); HPLC RT=7.78 min (Method A), 7.54 min (Method B).

Example 36

Ethyl 3-(4-(1H-pyrazol-4-yl)phenyl)-1-(3-methoxybenzyl)-2-oxoimidazolidine-4-carboxylate

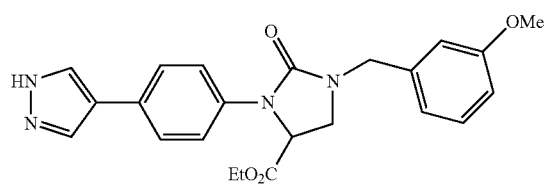 [SMILES: CCOC(=O)C1CN(Cc2cccc(OC)c2)C(=O)N1c1ccc(-c2cn[nH]c2)cc1]

According to the procedure for the preparation of Example 34, substituting (3-methoxyphenyl)methanamine for (3-fluorophenyl)methanamine afforded Example 36. MS(ESI) m/z: 421.3 (M+H)$^+$; $^1$H NMR (400 MHz, DMSO-d$_6$) δ ppm 12.85 (br. s., 1H) 7.99 (s, 2H) 7.53-7.58 (m, 2H) 7.45-7.49 (m, 2H) 7.25-7.31 (m, 1H) 6.82-6.88 (m, 3H) 5.07 (dd, J=10.04, 3.33 Hz, 1H) 4.41-4.48 (m, 1H) 4.28-4.34 (m, 1H) 4.12 (q, J=7.03 Hz, 2H) 3.74 (s, 3H) 3.68 (t, J=9.69 Hz, 1H) 3.34-3.37 (m, 1H) 1.12 (t, J=7.09 Hz, 3H); HPLC RT=1.52 min (Method E), 1.52 min (Method F).

Example 37

1-(4-(1H-Pyrazol-4-yl)phenyl)-4-(hydroxymethyl)-3-(3-methoxybenzyl)imidazolidin-2-one

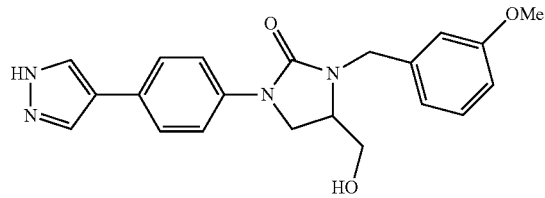 [SMILES: COc1cccc(CN2C(=O)N(c3ccc(-c4cn[nH]c4)cc3)CC2CO)c1]

Example 37A: Ethyl 2-bromo-3-((4-bromophenyl)amino)propanoate

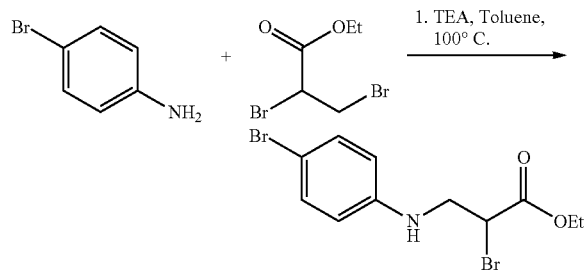

To a solution of 4-bromoaniline (4.00 g, 23.3 mmol) in toluene (25 mL), was added TEA (9.72 mL, 69.8 mmol). The mixture was heated to 50° C., then ethyl 2,3-dibromopropanoate (3.38 mL, 23.3 mmol) in toluene (25 mL) was added, dropwise. The reaction mixture was heated at 100° C. for 50 h, then was concentrated. The residue was dissolved in minimal DCM and precipitated by adding petroleum ether. The mixture was filtered, and the filtrate was concentrated. The residue was purified by flash chromatography (0-30% EtOAc/hexanes) to afford 700 mg of a brown gummy solid. MS(ESI) m/z: 350.3 (M+H)$^+$; $^1$H NMR (300 MHz, DMSO-d$_6$) δ ppm 7.18-7.25 (m, 2H) 6.58-6.64 (m, 2H) 4.47 (dd, J=8.38, 6.16 Hz, 1H) 4.11-4.19 (m, 2H) 3.66-3.78 (m, 1H) 3.48 (dd, J=14.31, 6.14 Hz, 1H) 1.19 (t, J=7.08 Hz, 3H).

Example 37B: tert-Butyl 4-(4-(4-(ethoxycarbonyl)-3-(3-methoxybenzyl)-2-oxoimidazolidin-1-yl)phenyl)-1H-pyrazole-1-carboxylate

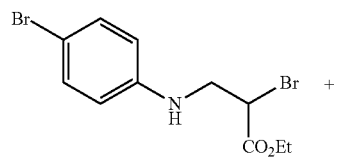

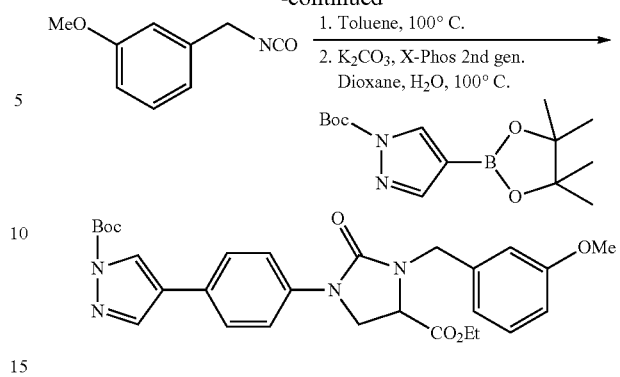

To a solution of Example 37A (300 mg, 0.855 mmol) in toluene (5 mL), was added 1-(isocyanatomethyl)-3-methoxybenzene (209 mg, 1.28 mmol) and heated at 100° C. for overnight. The mixture was concentrated, then was purified by flash chromatography (0-60% EtOAc/Hex) to afford 230 mg of ethyl 1-(4-bromophenyl)-3-(3-methoxybenzyl)-2-oxoimidazolidine-4-carboxylate as a gummy solid. To a solution of this product and tert-butyl 4-(4,4,5,5-tetramethyl-1,3,2-dioxaborolan-2-yl)-1H-pyrazole-1-carboxylate (312 mg, 1.06 mmol) in DMF (5 mL) and water (0.5 mL) was added K$_2$CO$_3$ (220 mg, 1.59 mmol). The mixture was degassed, then treated with 2nd generation XPhos precatalyst (25 mg, 0.032 mmol) and degassed again. The mixture was heated at 85° C. for 3.5 h. The reaction mixture was diluted with ethyl acetate, filtered through CELITE® bed, rinsing with ethyl acetate. The filtrate was washed with brine, dried (Na$_2$SO$_4$), and concentrated. The residue was purified by flash chromatography (0-100% EtOAc/Hex) to afford 150 mg of Example 37B. MS(ESI) m/z: 521.6 (M+H)$^+$.

Example 37

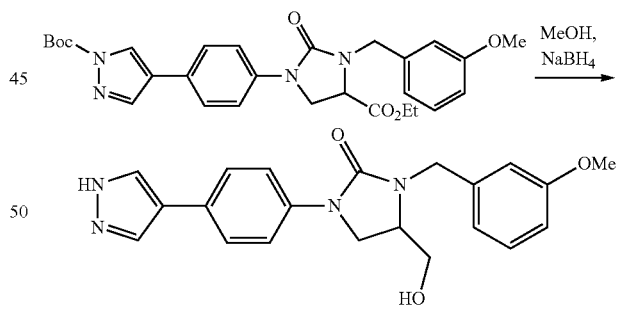

To the solution of Example 37B (150 mg, 0.288 mmol) in ethanol (5 mL), was added NaBH$_4$ (54.5 mg, 1.441 mmol). The mixture was stirred at rt for 3 h. The volatiles were removed, then the residue was partitioned between water and ethyl acetate. The aqueous was extracted with ethyl acetate. The combined organic phase was washed with brine, dried (Na$_2$SO$_4$), filtered and concentrated. The residue was purified by preparative HPLC to afford 15 mg of Example 37. MS(ESI) m/z: 379.3 (M+H)$^+$; $^1$H NMR (400 MHz, DMSO-d$_6$) δ ppm 12.85 (br. s., 1H) 8.11 (s, 1H) 7.87 (s, 1H) 7.53-7.61 (m, 4H) 7.23-7.29 (m, 1H) 6.82-6.91 (m, 3H) 4.98 (t, J=5.21 Hz, 1H) 4.68 (d, J=15.50 Hz, 1H) 4.19 (d, J=15.50

Hz, 1H) 3.86-3.94 (m, 1H) 3.74 (s, 3H) 3.54-3.65 (m, 3H) 3.47-3.54 (m, 1H); HPLC RT=1.15 min (Method E), 1.16 min (Method F).

Example 38

1-(4-(1H-Pyrazol-4-yl)phenyl)-3-benzyl-4-(hydroxymethyl)imidazolidin-2-one

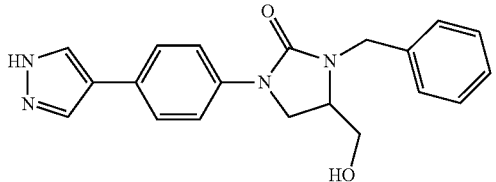 [SMILES: O=C1N(c2ccc(-c3cn[nH]c3)cc2)CC(CO)N1Cc1ccccc1]

According to the procedure for the preparation of Example 37, substituting (isocyanatomethyl)benzene for 1-(isocyanatomethyl)-3-methoxybenzene afforded Example 38. MS(ESI) m/z: 349.2 (M+H)+; 1H NMR (400 MHz, DMSO-$d_6$) δ ppm 12.85 (br. s., 1H) 8.01 (s, 1H) 7.95 (s, 1H) 7.52-7.61 (m, 4H) 7.25-7.38 (m, 5H) 4.98 (s, 1H) 4.72 (d, J=15.50 Hz, 1H) 4.22 (d, J=15.56 Hz, 1H) 3.87-3.93 (m, 1H) 3.54-3.64 (m, 3H) 3.46-3.53 (m, 1H); HPLC RT=1.14 min (Method E), 1.14 min (Method F).

Example 39

3-(4-(1H-Pyrazol-4-yl)phenyl)-1-(3-fluorobenzyl)-4-(hydroxymethyl)imidazolidin-2-one

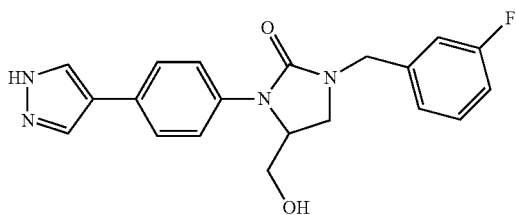 [SMILES: O=C1N(Cc2cccc(F)c2)CC(CO)N1c1ccc(-c2cn[nH]c2)cc1]

According to the route for the preparation of Example 30, substitution of 3-fluorobenzylamine for benzylamine affords Example 39. MS(ESI) m/z: 367.2 (M+H)+; 1H NMR (400 MHz, DMSO-$d_6$) δ ppm 12.88 (br. s., 1H) 8.13 (s, 1H) 7.88 (br. s., 1H) 7.50-7.58 (m, 4H) 7.41 (td, J=7.95, 5.99 Hz, 1H) 7.07-7.18 (m, 3H) 4.95 (t, J=5.40 Hz, 1H) 4.44-4.50 (m, 1H) 4.40 (dq, J=8.85, 4.50 Hz, 1H) 4.31-4.36 (m, 1H) 3.43-3.50 (m, 3H); 19F NMR (400 MHz, DMSO-$d_6$) δ ppm −113.407; HPLC RT=1.12 min (Method E), 1.11 min (Method F).

Example 40

4-(Hydroxymethyl)-1-(3-methoxy-4-(1H-pyrazol-4-yl)phenyl)-3-(3-methoxybenzyl)imidazolidin-2-one

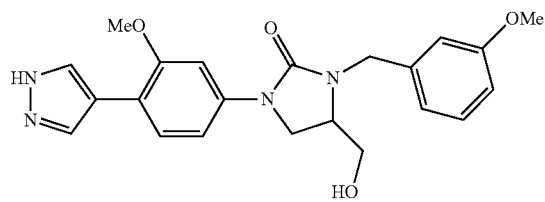 [SMILES: COc1cccc(CN2C(=O)N(c3ccc(-c4cn[nH]c4)c(OC)c3)CC2CO)c1]

According to the procedure for the preparation of Example 37, substituting 4-bromo-2-methoxyaniline for 4-bromoaniline afforded Example 40. MS(ESI) m/z: 409.3 (M+H)+; 1H NMR (400 MHz, DMSO-$d_6$) δ ppm 12.80 (br. s., 1H), 8.05 (s, 1H), 7.90 (s, 1H), 7.58-7.51 (m, 2H), 7.27 (t, J=8.1 Hz, 1H), 7.04 (dd, J=2.2, 8.5 Hz, 1H), 6.91-6.81 (m, 3H), 5.00 (t, J=5.3 Hz, 1H), 4.68 (d, J=15.5 Hz, 1H), 4.19 (d, J=15.6 Hz, 1H), 3.97-3.90 (m, 1H), 3.86 (s, 3H), 3.74 (s, 3H), 3.68-3.47 (m, 4H); HPLC RT=1.16 min (Method E), 1.22 min (Method F).

Example 41

3-Benzyl-4-(hydroxymethyl)-1-(3-methoxy-4-(1H-pyrazol-4-yl)phenyl)imidazolidin-2-one

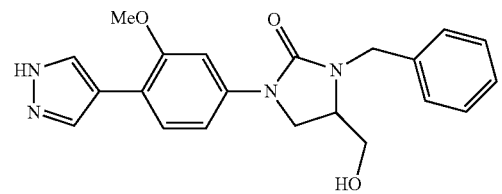 [SMILES: COc1cc(N2CC(CO)N(Cc3ccccc3)C2=O)ccc1-c1cn[nH]c1]

Example 41 was prepared according to the general route used to prepare Example 37. MS(ESI) m/z: 379.3 (M+H)+; 1H NMR (400 MHz, DMSO-$d_6$) δ ppm 12.79 (s, 1H) 8.05 (br. s., 1H) 7.90 (br. s., 1H) 7.52-7.57 (m, 2H) 7.25-7.39 (m, 5H) 7.04 (dd, J=8.53, 2.20 Hz, 1H) 5.00 (t, J=5.27 Hz, 1H) 4.72 (d, J=15.56 Hz, 1H) 4.22 (d, J=15.56 Hz, 1H) 3.93 (t, J=8.82 Hz, 1H) 3.86 (s, 3H) 3.55-3.67 (m, 3H) 3.47-3.54 (m, 1H); HPLC RT=1.14 min (Method E), 1.20 min (Method F).

Example 42

(+)-1-(4-(1H-Pyrazol-4-yl)phenyl)-4-(hydroxymethyl)-3-(3-methoxybenzyl)imidazolidin-2-one Example 43

(−)-1-(4-(1H-Pyrazol-4-yl)phenyl)-4-(hydroxymethyl)-3-(3-methoxybenzyl)imidazolidin-2-one

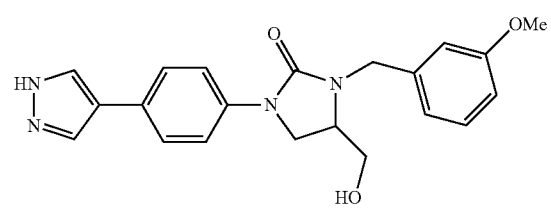 [SMILES: COc1cccc(CN2C(=O)N(c3ccc(-c4cn[nH]c4)cc3)CC2CO)c1]

Racemic Example 37 was separated into its enantiomers via Supercritical Fluid Chromatography [Column: CHIRALPAK® OJ-H (250×4.6 mm), 5 μm, Co-solvent is 4% (0.25% DEA in MeOH)] to afford Example 42 followed by Example 43.

Data for Example 42: MS(ESI) m/z: 379.0 (M+H)+; 1H NMR (400 MHz, DMSO-$d_6$) δ ppm 12.85 (s, 1H) 7.99 (s, 2H) 7.53-7.61 (m, 4H) 7.27 (t, J=8.00 Hz, 1H) 6.82-6.91 (m, 3H) 4.99 (br. s., 1H) 4.68 (d, J=15.50 Hz, 1H) 4.18 (d, J=15.56 Hz, 1H) 3.87-3.93 (m, 1H) 3.74 (s, 3H) 3.54-3.64 (m, 3H) 3.47-3.54 (m, 1H); HPLC RT=7.56 min (Method A), 7.46 min (Method B).

Data for Example 43: MS(ESI) m/z: 379.0 (M+H)+; 1H NMR (400 MHz, DMSO-d6) δ ppm 12.86 (s, 1H) 8.12 (s, 1H) 7.87 (br. s., 1H) 7.53-7.61 (m, 4H) 7.27 (t, J=7.94 Hz, 1H) 6.82-6.91 (m, 3H) 4.99 (t, J=5.15 Hz, 1H) 4.68 (d, J=15.50 Hz, 1H) 4.19 (d, J=15.50 Hz, 1H) 3.87-3.93 (m, 1H) 3.74 (s, 3H) 3.55-3.65 (m, 3H) 3.47-3.54 (m, 1H); HPLC RT=7.56 min (Method A), 7.34 min (Method B).

Example 44

(−)-1-(4-(1H-Pyrazol-4-yl)phenyl)-4-(2-hydroxypropan-2-yl)-3-(3-methoxybenzyl)imidazolidin-2-one Example 45

(+)-1-(4-(1H-Pyrazol-4-yl)phenyl)-4-(2-hydroxypropan-2-yl)-3-(3-methoxybenzyl)imidazolidin-2-one

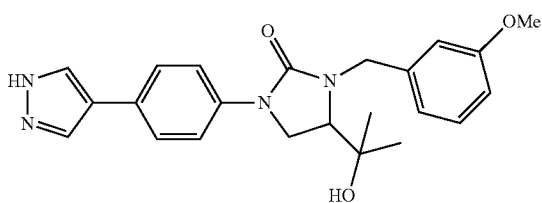 [SMILES: COc1cccc(CN2C(=O)N(c3ccc(-c4cn[nH]c4)cc3)CC2C(C)(C)O)c1]

Example 44A: 1-(4-Bromophenyl)-4-(2-hydroxypropan-2-yl)-3-(3-methoxybenzyl) imidazolidin-2-one

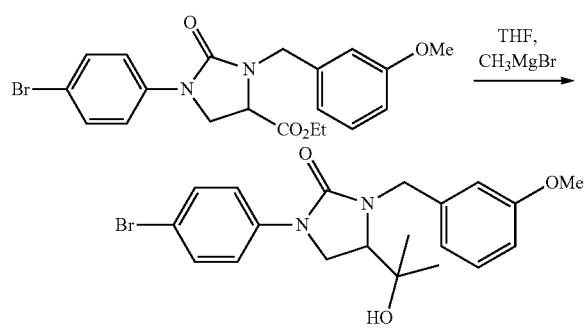

To a solution of ethyl 1-(4-bromophenyl)-3-(3-methoxybenzyl)-2-oxoimidazolidine-4-carboxylate (which is prepared as an intermediate in Example 37) (270 mg, 0.623 mmol) in THF (10 mL) at −20° C., was added methylmagnesium bromide (3 M in diethyl ether) (1.04 mL, 3.12 mmol). The mixture was allowed to slowly warm to 16° C. over 2 h. The reaction was quenched with sat. NH4Cl and extracted with ethyl acetate. The combined ethyl acetate layer was washed with brine, dried (Na2SO4), and concentrated to give 190 mg of Example 44A as viscous yellow oil, which was used without further purification. MS(ESI) m/z: 419.1 (M+H)+.

Examples 44 and 45

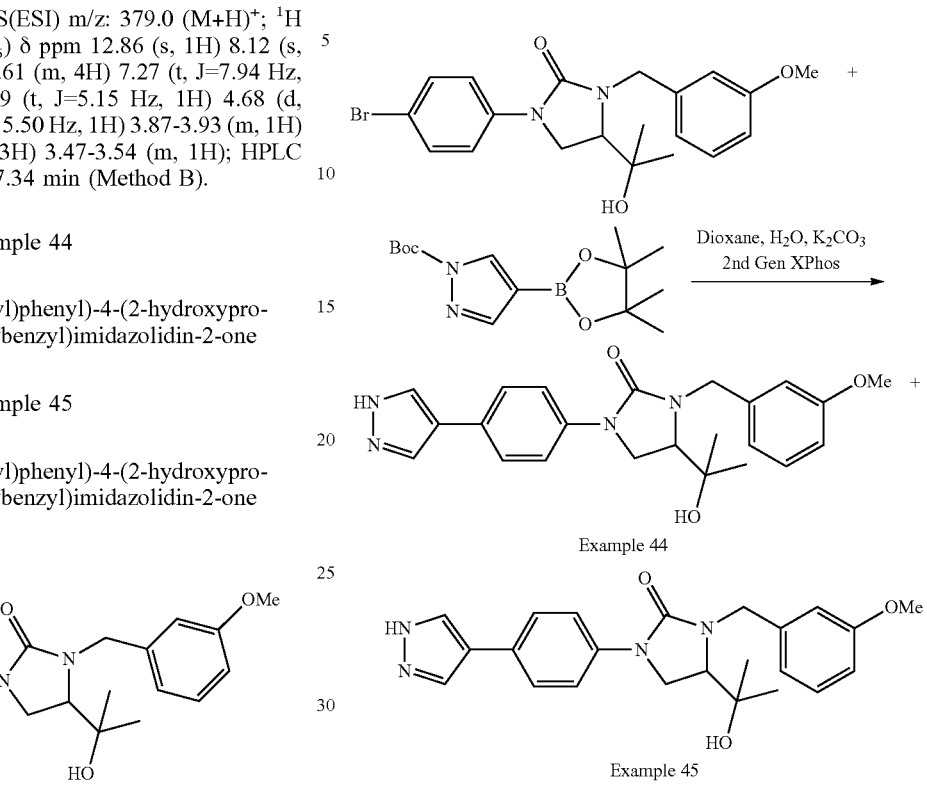

Example 44

Example 45

To a solution of Example 44A (190 mg, 0.453 mmol) in DMF (3 mL) and water (0.5 mL), was added tert-butyl 4-(4,4,5,5-tetramethyl-1,3,2-dioxaborolan-2-yl)-1H-pyrazole-1-carboxylate (200 mg, 0.680 mmol) and K2CO3 (188 mg, 1.36 mmol). The mixture was degassed, then charged with 2nd generation XPhos precatalyst (21 mg, 0.027 mmol). The mixture was degassed, then was heated at 90° C. overnight. The reaction mixture was filtered and the filtrate was diluted with water and extracted with EtOAc. The organic phase was washed with water and brine, dried (Na2SO4) and concentrated. The product was purified by preparative HPLC, then the enantiomers were separated by Supercritical Fluid Chromatography [Column: CHIRALPAK® IC (250×2.1 mm), 5 μm, Co-solvent is 40% MeOH] to afford Example 44 followed by Example 45.

Data for Example 44: MS(ESI) m/z: 407.2 (M+H)+; 1H NMR (300 MHz, DMSO-d6) δ ppm 12.84 (br. s., 1H) 7.99 (s, 2H) 7.52-7.63 (m, 4H) 7.25 (t, J=8.03 Hz, 1H) 6.80-6.89 (m, 3H) 4.79 (d, J=15.20 Hz, 2H) 4.48 (d, J=15.39 Hz, 1H) 3.81-3.91 (m, 1H) 3.73 (s, 3H) 3.50 (q, J=5.63 Hz, 2H) 1.11 (d, J=6.04 Hz, 6H); HPLC RT=8.17 min (Method A), 7.72 min (Method B).

Data for Example 45: MS(ESI) m/z: 407.2 (M+H)+; 1H NMR (300 MHz, DMSO-d6) δ ppm 12.74 (br. s., 1H) 7.99 (s, 2H) 7.52-7.63 (m, 4H) 7.25 (t, J=8.03 Hz, 1H) 6.80-6.89 (m, 3H) 4.79 (d, J=15.30 Hz, 2H) 4.48 (d, J=15.30 Hz, 1H) 3.81-3.90 (m, 1H) 3.73 (s, 3H) 3.46-3.54 (m, 2H) 1.11 (d, J=6.04 Hz, 6H); HPLC RT=8.17 min (Method A), 7.72 min (Method B).

Example 46

(R)-1-(4-(1H-Pyrazol-4-yl)phenyl)-3-(1-(3-methoxyphenyl)ethyl)imidazolidin-2-one

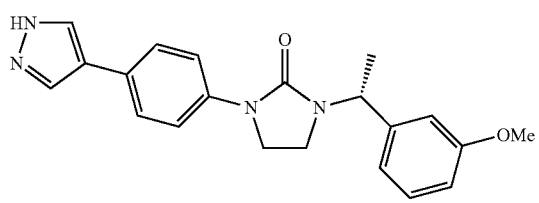 [SMILES: COc1cccc([C@@H](C)N2CCN(c3ccc(-c4cn[nH]c4)cc3)C2=O)c1]

Example 46A: (R)-1-(4-Bromophenyl)-1-(2-chloroethyl)-3-(1-(3-methoxyphenyl)ethyl) urea

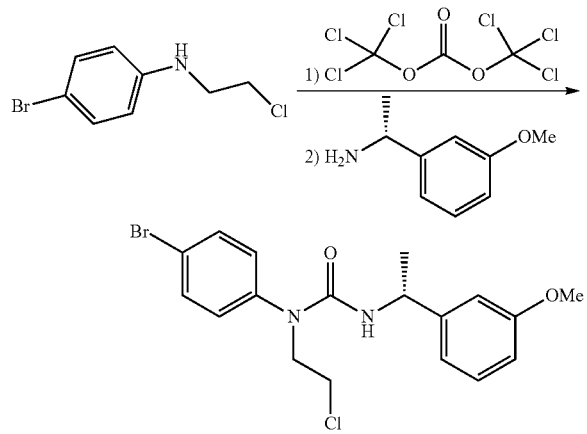

To a mixture of Intermediate 1 (0.35 g, 1.49 mmol) and triethylamine (0.624 mL, 4.48 mmol) in chloroform (10 mL) at 0° C., was added triphosgene (0.531 g, 1.79 mmol). The reaction mixture was stirred at rt for 2 h, then the reaction mixture was cooled to 0° C. and to this was added (R)-1-(3-methoxyphenyl)ethanamine (0.226 g, 1.492 mmol), dropwise. The reaction mixture was stirred at rt overnight. The reaction mixture was diluted with water, acidified with 0.5 N HCl and extracted with dichloromethane (2×50 mL). Combined organic extracts were washed with water and brine, dried over Na$_2$SO$_4$ and concentrated to afford Example 46A, which was used without further purification. MS(ESI) m/z: 411.1 (M+H)$^+$.

Example 46

According to the procedure for the preparation of Example 1, Example 46A was converted to Example 46. MS(ESI) m/z: 363.3 (M+H)$^+$; $^1$H NMR (400 MHz, DMSO-d$_6$) δ ppm 12.86 (br. s., 1H), 8.11 (br. s., 1H), 7.87 (br. s., 1H), 7.55 (s, 4H), 7.29 (t, J=7.9 Hz, 1H), 6.97-6.83 (m, 3H), 5.18-5.07 (m, 1H), 3.83-3.76 (m, 2H), 3.75 (s, 3H), 3.57-3.46 (m, 1H), 3.17-3.06 (m, 1H), 1.51 (d, J=7.2 Hz, 3H); HPLC RT=1.44 min (Method E), 1.47 min (Method F).

Example 47

(−)-3-(4-(1H-Pyrazol-4-yl)phenyl)-4-(hydroxymethyl)-1-(3-methoxybenzyl)imidazolidin-2-one

Example 48

(+)-3-(4-(1H-Pyrazol-4-yl)phenyl)-4-(hydroxymethyl)-1-(3-methoxybenzyl)imidazolidin-2-one

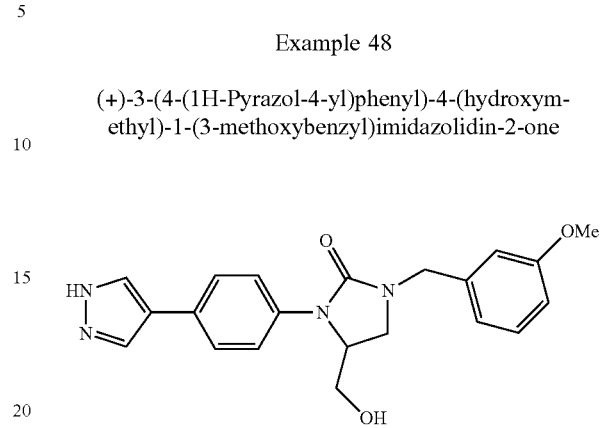

Example 47A: Ethyl 2-chloro-3-((3-methoxybenzyl)amino)propanoate

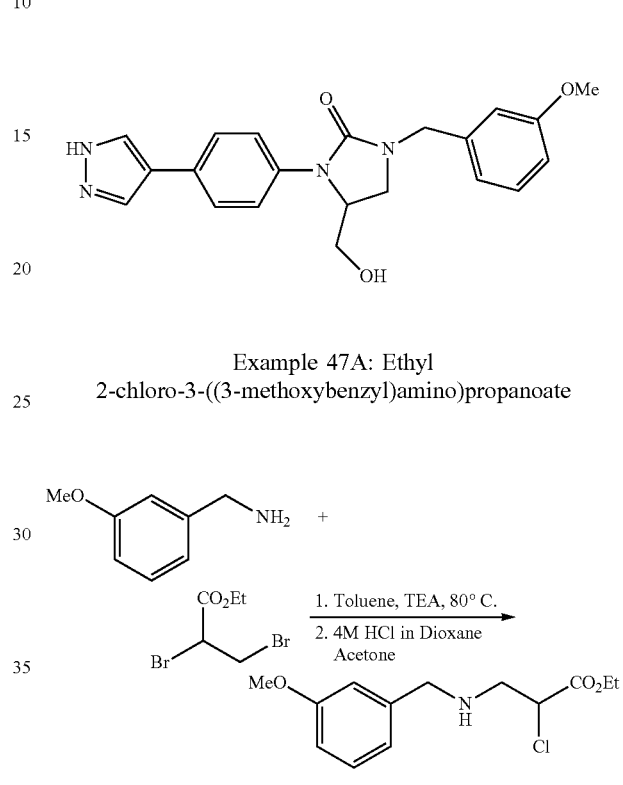

To a solution of (3-methoxyphenyl)methanamine (2.00 g, 14.6 mmol) in toluene (30 mL), was added TEA (8.13 mL, 58.3 mmol) and ethyl 2,3-dibromopropanoate (3.79 g, 14.6 mmol) in toluene (10 mL). The mixture was stirred at 85° C. overnight. The reaction mixture was cooled to rt, and the precipitated solid was filtered. The filterate was concentrated to give a yellow oil. The oil was dissolved in acetone (45 mL), cooled to 0° C. and treated with 4 M HCl in dioxane (13.4 mL, 53.6 mmol). The mixture was stirred at rt for 16 h. The reaction mixture was concentrated to give yellow liquid, which was basified with 10% NaHCO$_3$ and extracted with ethyl acetate. The combined ethyl acetate layers were washed with brine, dried (Na$_2$SO$_4$), and concentrated. The product was purified by flash chromatography (0-60% EtOAc/Hex) to afford 390 mg of Example 47A as a yellow liquid. MS(ESI) m/z: 272.1 (M+H)$^+$.

Example 47B: 3-(4-Bromophenyl)-1-(3-methoxybenzyl)-2-oxoimidazolidine-4-carboxylic Acid

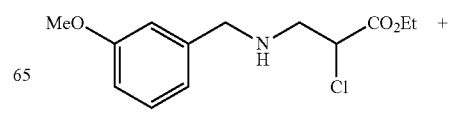

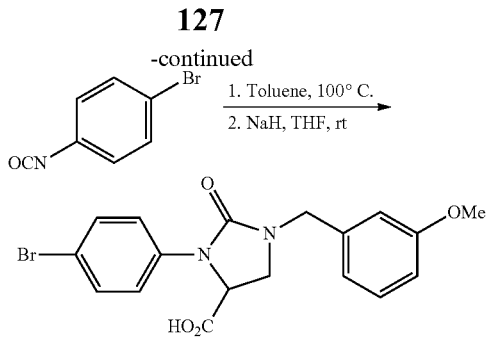

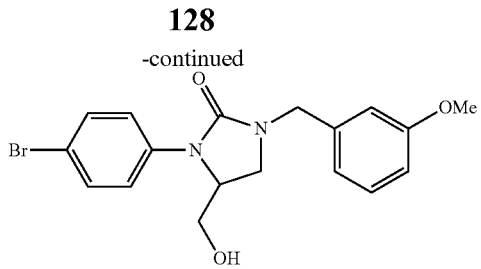

To the solution of Example 47A (390 mg, 1.44 mmol) in toluene (10 mL), was added 1-bromo-4-isocyanatobenzene (313 mg, 1.58 mmol). The mixture was heated at 100° C. for 16 h, then was concentrated. The residue was dissolved in THF (10 mL) and cooled to 0° C., then was treated with NaH (69.9 mg, 2.77 mmol). The mixture was stirred at rt overnight. The reaction was quenched with ice cold water and acidified with 1.5 N HCl to pH 2, then extracted with ethyl acetate. The combined organic phase was washed with brine, dried (Na$_2$SO$_4$), and concentrated to give 550 mg of Example 47B as a brown gummy solid, which was used in the following step without further purification. MS(ESI) m/z: 405.1 (M+H)$^+$.

Example 47C: Ethyl 3-(4-bromophenyl)-1-(3-methoxybenzyl)-2-oxoimidazolidine-4-carboxylate

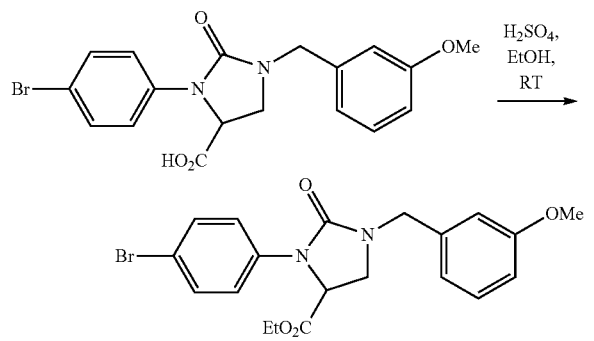

To the solution of Example 47B (550 mg, 1.36 mmol) in ethanol (15 mL), was added H$_2$SO$_4$ (0.289 mL, 5.43 mmol). The mixture was stirred at rt overnight, then was concentrated. The residue was basified with 10% aq. NaHCO$_3$, then was extracted with ethyl acetate. The combined ethyl acetate layer was washed with brine, dried (Na$_2$SO$_4$), and concentrated. The residue was purified by flash chromatography (0-100% EtOAc/Hex) to afford 180 mg of Example 47C as a gummy, yellow solid. MS(ESI) m/z: 435.1 (M+H)$^+$.

Example 47D: 3-(4-Bromophenyl)-4-(hydroxymethyl)-1-(3-methoxybenzyl)imidazolidin-2-one

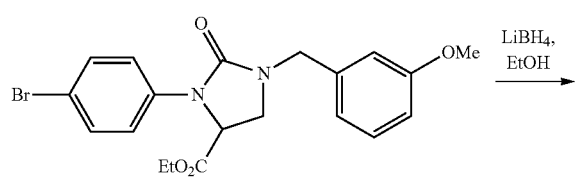

To a solution of Example 47C (180 mg, 0.415 mmol) in ethanol (10 mL) at 0° C., was added LiBH$_4$ (36.2 mg, 1.662 mmol). The mixture was stirred at rt overnight, then was concentrated. The product was partitioned between EtOAc and water. The aqueous phase was extracted with EtOAc. The combined organic phase was washed with brine, dried (Na$_2$SO$_4$), and concentrated to afford 140 mg of Example 47D as a yellow, gummy solid. MS(ESI) m/z: 391.1 (M+H)$^+$.

Examples 47 and 48

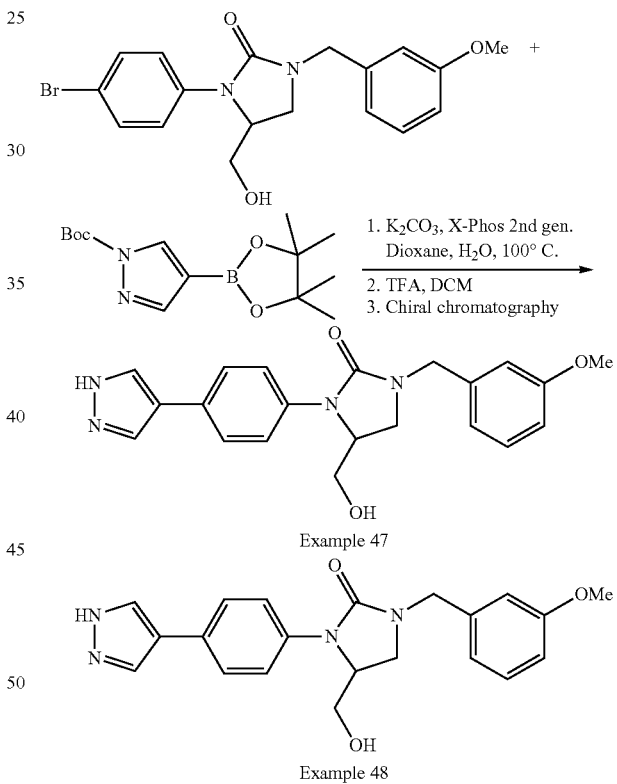

To the solution of Example 47D (140 mg, 0.358 mmol) and tert-butyl 4-(4,4,5,5-tetramethyl-1,3,2-dioxaborolan-2-yl)-1H-pyrazole-1-carboxylate (137 mg, 0.465 mmol) in DMF (3 mL) and water (0.5 mL), was added K$_2$CO$_3$ (148 mg, 1.07 mmol). The mixture was degassed, then charged with 2nd generation XPhos precatalyst (16.9 mg, 0.021 mmol), degassed, then heated at 95° C. overnight. The reaction was diluted with water and extracted with ethyl acetate. The combined organic phase was washed with brine, dried (Na$_2$SO$_4$), and concentrated. The residue was dissolved in DCM (5 mL), then was treated with TFA (0.20 mL). The mixture was stirred at rt for 3 h, then was concentrated. The product was purified by preparative HPLC, then the enantiomers were separated by Supercritical Fluid Chromatography [Column: CHIRALPAK® AS-H (250×4.6 mm), 5μ, Co-solvent is 45% (0.25% DEA in methanol)] to afford 19 mg of Example 47 and 18 mg of Example 48, both as white solids.

Data for Example 47: MS(ESI) m/z: 379.4 (M+H)+; 1H NMR (400 MHz, DMSO-d6) δ ppm 12.76 (s, 1H) 8.00 (s, 2H) 7.50-7.58 (m, 4H) 7.28 (t, J=7.97 Hz, 1H) 6.83-6.90 (m, 3H) 4.95 (br. s., 1H) 4.25-4.45 (m, 3H) 3.75 (s, 3H) 3.38-3.50 (m, 3H) 3.26-3.30 (m, 1H); HPLC RT=7.35 min (Method A), 7.35 min (Method B).

Data for Example 48: MS(ESI) m/z: 379.4 (M+H)+; 1H NMR (400 MHz, DMSO-d6) δ ppm 12.83 (s, 1H) 8.00 (s, 2H) 7.50-7.58 (m, 4H) 7.28 (t, J=7.97 Hz, 1H) 6.82-6.90 (m, 3H) 4.95 (br. s., 1H) 4.26-4.45 (m, 3H) 3.75 (s, 3H) 3.38-3.51 (m, 3H) 3.29 (d, J=4.27 Hz, 1H); HPLC RT=7.36 min (Method B).

The following Examples in Table 2 were prepared in a similar fashion as Example 1. The appropriate isocyanate and boronic acid is used for each Example.

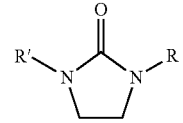

TABLE 2

| Ex. | R | R' | Name | LCMS (M + H)+ | HPLC Method, RT (min.) | NMR |
|---|---|---|---|---|---|---|
| 49 | 3-fluorobenzyl | 3-fluoropyridin-4-yl | 1-(3-fluorobenzyl)-3-(4-(3-fluoropyridin-4-yl)phenyl)imidazolidin-2-one | 366.2 | C: 2.16 D: 2.51 | 1H NMR (400 MHz, DMSO-d6) δ ppm 8.63 (d, J = 2.89 Hz, 1 H) 8.48 (dd, J = 4.99, 1.04 Hz, 1 H), 7.76-7.80 (m, 2 H), 7.68-7.73 (m, 2 H), 7.65 (dd, J = 7.12, 4.99 Hz, 1 H), 7.43 (td, J = 7.98, 5.80 Hz, 1 H), 7.10-7.20 (m, 3 H), 4.45 (s, 2 H), 3.87-3.94 (m, 2 H), 3.40-3.48 (m, 2 H); 19F NMR (376 MHz, DMSO-d6) δ -113.112, -133.645 |
| 50 | 3-methoxybenzyl | 3-fluoropyridin-4-yl | 1-(4-(3-fluoropyridin-4-yl)phenyl)-3-(3-methoxybenzyl)imidazolidin-2-one | 378.2 | C: 2.11 D: 2.47 | 1H NMR (400 MHz, DMSO-d6) δ ppm 8.63 (d, J = 2.95 Hz, 1 H), 8.48 (dd, J = 5.02, 1.00 Hz, 1 H), 7.75-7.81 (m, 2 H), 7.68-7.72 (m, 2 H), 7.65 (dd, J = 7.15, 5.02 Hz, 1 H), 7.27-7.33 (m, 1 H), 6.85-6.92 (m, 3 H), 4.40 (s, 2 H), 3.89 (dd, J = 9.00, 7.00 Hz, 2 H), 3.76 (s, 3 H), 3.41 (dd, J = 8.00, 6.00 Hz, 2 H); 19F NMR (376 MHz, DMSO-d6) δ -133.646 |
| 51 | 3-fluorobenzyl | 2-fluoropyridin-4-yl | 1-(3-fluorobenzyl)-3-(4-(2-fluoropyridin-4-yl)phenyl)imidazolidin-2-one | 366.2 | C: 2.67 D: 2.68 | 1H NMR (400 MHz, DMSO-d6) δ ppm 8.27 (d, J = 5.33 Hz, 1 H), 7.88-7.93 (m, 2 H), 7.77 (d, J = 9.04 Hz, 2 H), 7.71 (dt, J = 5.24, 1.90 Hz, 1 H), 7.53 (s, 1 H), 7.43 (td, J = 8.00, 6.02 Hz, 1 H), 7.11-7.20 (m, 3 H), 4.45 (s, 2 H), 3.91 (dd, J = 8.97, 6.96 Hz, 2 H), 3.44 (dd, J = 10.00, 8.00 Hz, 2 H); 19F NMR (376 MHz, DMSO-d6) δ -69.267, -133.358 |
| 52 | benzyl | 3-fluoropyridin-4-yl | 1-benzyl-3-(4-(3-fluoropyridin-4-yl)phenyl)imidazolidin-2-one | 348.2 | C: 2.09 D: 2.45 | 1H NMR (400 MHz, DMSO-d6) δ ppm 8.63 (d, J = 2.95 Hz, 1 H), 8.48 (dd, J = 4.96, 1.07 Hz, 1 H), 7.75-7.81 (m, 2 H), 7.68-7.73 (m, 2 H), 7.65 (dd, J = 7.15, 5.02 Hz, 1 H), 7.36-7.42 (m, 2 H), 7.29-7.35 (m, 3 H), 4.44 (s, 2 H), 3.89 (dd, J = 10.00, 8.40 Hz, 2 H), 3.41 (dd, J = 10.00, 8.00 Hz, 2 H); 19F NMR (376 MHz, DMSO-d6) δ -133.887 |

TABLE 2-continued

| Ex. | R | R' | Name | LCMS (M + H)+ | HPLC Method, RT (min.) | NMR |
|---|---|---|---|---|---|---|
| 53 | phenethyl | 3-fluoropyridin-4-yl on phenyl | 1-(4-(3-fluoropyridin-4-yl)phenyl)-3-phenethylimidazolidin-2-one | 362.2 | C: 2.21 D: 2.58 | $^{1}$H NMR (400 MHz, DMSO-$d_6$) d ppm 8.62 (d, J = 2.89 Hz, 1 H), 8.47 (dd, J = 4.96, 0.94 Hz, 1 H), 7.70-7.75 (m, 2 H), 7.61-7.69 (m, 3 H), 7.26-7.34 (m, 4 H), 7.19-7.25 (m, 1 H), 3.83 (dd, J = 9.10, 6.90 Hz, 2 H), 3.43-3.52 (m, 4 H), 2.85 (t, J = 7.44 Hz, 2 H); $^{19}$F NMR (376 MHz, DMSO-$d_6$) δ −133.667 |
| 54 | 3-methoxybenzyl | 2-fluoropyridin-4-yl on phenyl | 1-(4-(2-fluoropyridin-4-yl)phenyl)-3-(3-methoxybenzyl)imidazolidin-2-one | 378.2 | C: 2.57 D: 2.63 | $^{1}$H NMR (400 MHz, DMSO-$d_6$) δ ppm 8.26 (d, J = 5.33 Hz, 1 H), 7.87-7.93 (m, 2 H), 7.74-7.79 (m, 2 H), 7.71 (dt, J = 5.30, 1.87 Hz, 1 H), 7.52 (s, 1 H), 7.27-7.32 (m, 1 H), 6.84-6.92 (m, 3 H), 4.40 (s, 2 H), 3.89 (dd, J = 9.00, 7.00 Hz, 2 H), 3.75 (s, 3 H), 3.40 (dd, J = 9.60, 8.40 Hz, 2 H); $^{19}$F NMR: (400 MHz, DMSO-$d_6$) −69.003 |
| 55 | benzyl | pyridin-4-yl on phenyl | 1-benzyl-3-(4-(pyridin-4-yl)phenyl)imidazolidin-2-one, TFA | 330.2 | E: 1.08 F: 1.61 | $^{1}$H NMR (400 MHz, DMSO-$d_6$) δ ppm 8.80 (d, J = 6.46 Hz, 2 H) 8.17-8.22 (m, 2 H) 8.00-8.06 (m, 2 H) 7.80-7.85 (m, 2 H) 7.35-7.45 (m, 2 H) 7.20-7.32 (m, 3 H) 4.50 (s, 2 H) 3.92 (dd, J = 9.07, 7.00 Hz, 2 H) 3.42 (dd, J = 10.00, 8.00 Hz, 2 H); $^{19}$F NMR (376 MHz, DMSO-$d_6$) δ −74.290 |
| 56 | 3-fluorobenzyl | pyridin-4-yl on phenyl | 1-(3-fluorobenzyl)-3-(4-(pyridin-4-yl)phenyl)imidazolidin-2-one, TFA | 348.2 | E: 1.11 F: 1.65 | $^{1}$H NMR (400 MHz, DMSO-$d_6$) δ ppm 8.80 (d, J = 6.59 Hz, 2 H) 8.17-8.22 (m, 2 H) 8.00-8.07 (m, 2 H) 7.81-7.87 (m, 2 H) 7.44 (td, J = 7.98, 5.87 Hz, 1 H) 7.11-7.22 (m, 3 H) 4.46 (s, 2 H) 3.91-3.98 (m, 2 H) 3.45 (dd, J = 10.00, 8.00 Hz, 2 H); $^{19}$F NMR (376 MHz, DMSO-$d_6$) δ −74.296, −113.334 |
| 57 | 2-fluorobenzyl | pyridin-4-yl on phenyl | 1-(2-fluorobenzyl)-3-(4-(pyridin-4-yl)phenyl)imidazolidin-2-one, TFA | 348.2 | E: 1.11 F: 1.64 | $^{1}$H NMR (400 MHz, DMSO-$d_6$) δ ppm 8.80 (d, J = 6.46 Hz, 2 H) 8.17-8.22 (m, 2 H) 8.00-8.06 (m, 2 H) 7.80-7.85 (m, 2 H) 7.35-7.45 (m, 2 H) 7.20-7.28 (m, 2 H) 4.50 (s, 2 H) 3.92 (dd, J = 9.07, 7.00 Hz, 2 H) 3.45 (t, J = 8.00 Hz, 2 H); $^{19}$F NMR (376 MHz, DMSO-$d_6$) δ −74.294, −118.881 |
| 58 | 2-fluoro-5-methoxybenzyl | pyridin-4-yl on phenyl with OMe | 1-(2-fluoro-5-methoxybenzyl)-3-(3-methoxy-4-(pyridin-4-yl)phenyl)imidazolidin-2-one, TFA | 408.3 | E: 1.22 F: 1.72 | $^{1}$H NMR (400 MHz, DMSO-$d_6$) δ ppm 8.77 (br. s., 2 H) 8.05 (br. s., 2 H) 7.67 (d, J = 2.01 Hz, 1 H) 7.61 (d, J = 8.66 Hz, 1 H) 7.26 (dd, J = 8.66, 1.88 Hz, 1 H) 7.14-7.21 (m, 1 H) 6.90-6.95 (m, 2 H) 4.46 (s, 2 H) 3.93 (dd, J = 9.13, 6.87 Hz, 2 H) 3.88 (s, 3 H) 3.75 (s, 3 H) 3.46 (t, J = 8.0 Hz, 2 H); $^{19}$F NMR (376 MHz, DMSO-$d_6$) δ −74.217, −129.774 |

TABLE 2-continued

| Ex. | R | R' | Name | LCMS (M + H)+ | HPLC Method, RT (min.) | NMR |
|---|---|---|---|---|---|---|
| 59 | 3-fluorobenzyl | 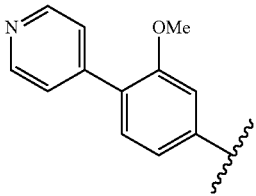 [SMILES: *c1ccc(-c2ccncc2)c(OC)c1] | 1-(3-fluorobenzyl)-3-(3-methoxy-4-(pyridin-4-yl)phenyl)imidazolidin-2-one, TFA | 378.2 | E: 1.18  F: 1.70 | 1H NMR (400 MHz, DMSO-d6) δ ppm 8.77 (d, J = 6.15 Hz, 2 H) 8.07 (d, J = 6.65 Hz, 2 H) 7.69 (d, J = 2.07 Hz, 1 H) 7.62 (d, J = 8.66 Hz, 1 H) 7.41-7.47 (m, 1 H) 7.26 (dd, J = 8.66, 2.07 Hz, 1 H) 7.12-7.20 (m, 3 H) 4.46 (s, 2 H) 3.95 (dd, J = 9.07, 7.00 Hz, 2 H) 3.87 (s, 3 H) 3.45 (dd, J = 10.00, 8.00 Hz, 2 H); 19F NMR (376 MHz, DMSO-d6) δ −74.237, −113.322 |
| 60 | benzyl | 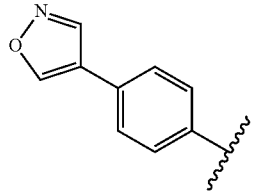 [SMILES: *c1ccc(-c2cnoc2)cc1] | 1-benzyl-3-(4-(isoxazol-4-yl)phenyl)imidazolidin-2-one | 320.2 | E: 1.09  F: 1.48 | 1H NMR (400 MHz, DMSO-d6) δ ppm 11.90 (br s, 1H) 7.94 (s, 1 H) 7.57-7.65 (m, 3H) 7.29-7.39 (m, 6 H) 4.39 (s, 2 H) 3.79-3.83 (m, 2 H) 3.26-3.38 (m, 2 H) |
| 61 | 3-fluorobenzyl | 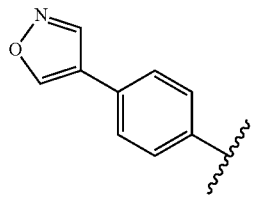 [SMILES: *c1ccc(-c2cnoc2)cc1] | 1-(3-fluorobenzyl)-3-(4-(isoxazol-4-yl)phenyl)imidazolidin-2-one | 338.2 | E: 1.51  F: 1.12 | 1H NMR (400 MHz, DMSO-d6) δ ppm 11.82 (br s, 1H) 7.93 (s, 1 H) 7.55-7.60 (m, 3 H) 7.35-7.45 (m, 2 H) 7.11-7.18 (m, 3 H) 4.41 (s, 2 H) 3.79-3.87 (m, 2 H) 3.36-3.42 (m, 2 H); 19F NMR (376 MHz, DMSO-d6) δ −113.144 |

Example 62

1-(4-(2-Aminopyridin-4-yl)phenyl)-3-(3-methoxy-benzyl)imidazolidin-2-one, TFA

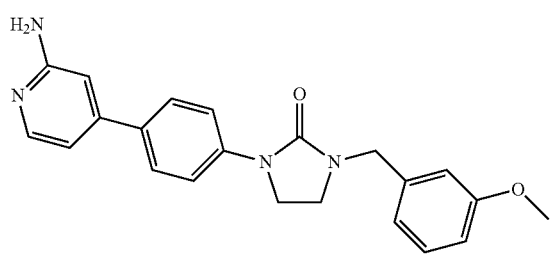 [SMILES: COc1cccc(CN2CCN(c3ccc(-c4ccnc(N)c4)cc3)C2=O)c1]

Example 62A: 1-(4-Bromophenyl)-3-(3-methoxy-benzyl)imidazolidin-2-one

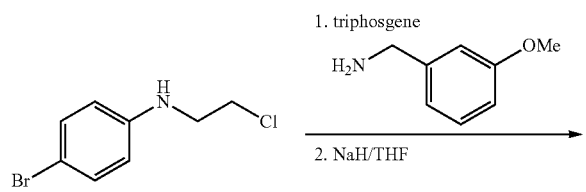

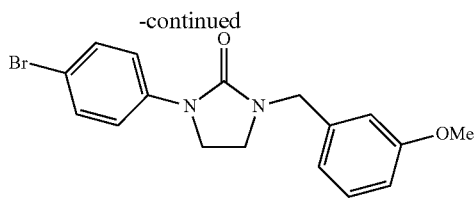

To a solution of Intermediate 1 (1.00 g, 4.26 mmol) in CHCl3 (10 mL) at 0° C., was added TEA (1.78 mL, 12.8 mmol), followed by bis(trichloromethyl)carbonate (1.52 g, 5.12 mmol). The mixture was stirred at 0° C. for 2 h, then (3-methoxyphenyl) methanamine (0.828 mL, 6.40 mmol) was added and the reaction mixture was stirred at rt overnight. The reaction mixture was diluted with water (10 mL) and acidified by 5% HCl. The mixture was extracted by DCM. The organic layer was dried (Na2SO4) and evaporated to obtain a yellow oil. The product was dissolved in THF (15 mL) and cooled to 0° C. and treated with NaH (0.203 g, 8.05 mmol). The reaction mixture was stirred at rt for 1.5 h, then was cooled to 0° C. and treated with water. The resultant precipitate was collected by filtration. MS(ESI) m/z: 361.0 (M+H)+.

Example 62B: 1-(3-Methoxybenzyl)-3-(4-(4,4,5,5-tetramethyl-1,3,2-dioxaborolan-2-yl)phenyl)imidazolidin-2-one

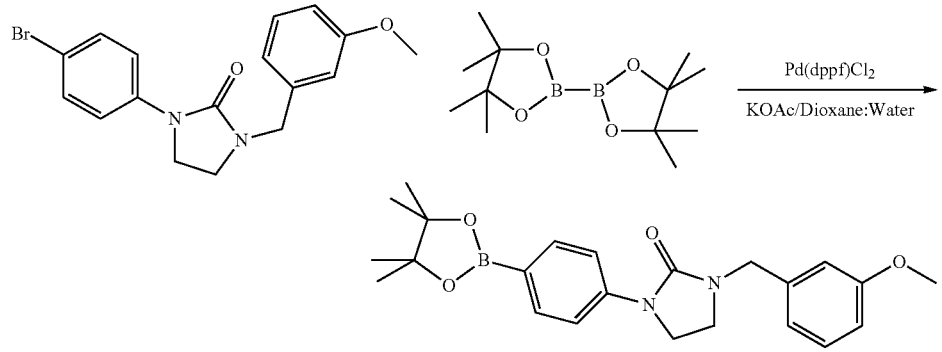

To a solution of Example 62B (0.800 g, 2.22 mmol) and 4,4,4',4',5,5,5',5'-octamethyl-2,2'-bi(1,3,2-dioxaborolane) (0.675 g, 2.66 mmol) in dioxane (10 mL), was added potassium acetate (0.652 g, 6.64 mmol), and the resulting reaction mixture was degassed. Pd(dppf)Cl$_2$CH$_2$Cl$_2$ complex (0.181 g, 0.221 mmol) was added, and the mixture was degassed again, then was heated to 90° C. for 6 h. The mixture was filtered through CELITE®, then the filtrate was concentrated. The residue was diluted with water and extracted with ethyl acetate (3×50 ml). The combined organic layer was dried (Na$_2$SO$_4$) and concentrated. The material was purified by flash chromatography (0-20% EtOAc/Hex) to obtain 0.850 g of Example 62B as a white solid. MS(ESI) m/z: 409.3 (M+H)$^+$; $^1$H NMR (400 MHz, DMSO-d$_6$) δ ppm 7.58-7.64 (m, 4H) 7.25-7.31 (m, 1H) 6.83-6.89 (m, 3H) 4.36 (s, 2H) 3.79-3.86 (m, 2H) 3.74 (s, 3H) 3.34-3.40 (m, 2H) 1.28 (s, 12H).

Example 62

To a solution of Example 62B (0.080 g, 0.196 mmol), 4-chloropyridin-2-amine (0.025 g, 0.196 mmol) in DMF (2 mL) and water (0.3 mL), was added K$_2$CO$_3$ (0.081 g, 0.588 mmol). The mixture was degassed using N$_2$, then was charged with 2nd generation XPhos precatalyst (0.031 g, 0.039 mmol), and the reaction was degassed again. The mixture was then heated at 90° C. overnight. The reaction mixture was filtered through CELITE®, rinsing with MeOH, and the filtrate was evaporated. The product was purified by preparative HPLC to afford 1 mg of Example 62. MS(ESI) m/z: 375.3 (M+H)$^+$; $^1$H NMR (400 MHz, DMSO-d$_6$) δ ppm 7.93 (d, J=9.60 Hz, 1H) 7.69-7.75 (m, 2H) 7.64-7.69 (m, 2H) 7.26-7.32 (m, 1H) 6.84-6.91 (m, 4H) 6.79 (s, 1H) 4.38 (s, 2H) 3.86 (dd, J=9.07, 7.00 Hz, 2H) 3.75 (s, 3H) 3.39-3.43 (m, 2H); HPLC RT=1.18 min (Method E), 1.50 min (Method F).

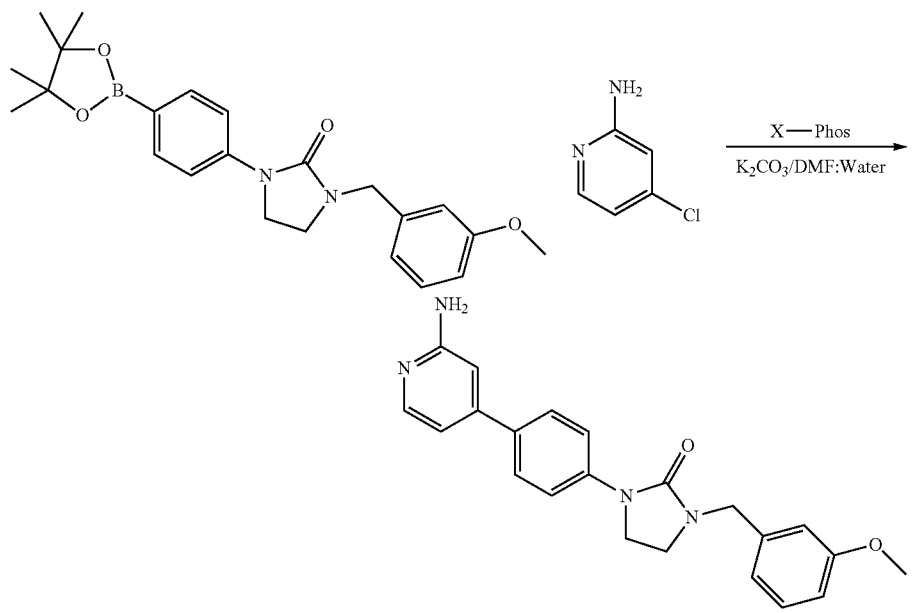

Example 63

1-(4-(2-Aminopyrimidin-4-yl)phenyl)-3-(3-methoxybenzyl)imidazolidin-2-one

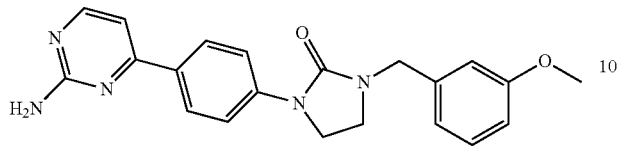

According to the procedure for the preparation of Example 62, Example 63 was prepared. MS(ESI) m/z: 376.3 (M+H)+; 1H NMR (400 MHz, DMSO-d6) δ ppm 8.25 (d, J=5.27 Hz, 1H) 8.04-8.09 (m, 2H) 7.72 (d, J=9.04 Hz, 2H) 7.26-7.31 (m, 1H) 7.09 (d, J=5.33 Hz, 1H) 6.84-6.90 (m, 3H) 6.58 (s, 2H) 4.39 (s, 2H) 3.88 (dd, J=9.07, 7.00 Hz, 2H) 3.75 (s, 3H) 3.36-3.43 (m, 2H); HPLC RT=1.14 min (Method E), 1.41 min (Method F).

Example 64

1-(4-(7H-Pyrrolo[2,3-d]pyrimidin-4-yl)phenyl)-3-(3-methoxybenzyl)imidazolidin-2-one

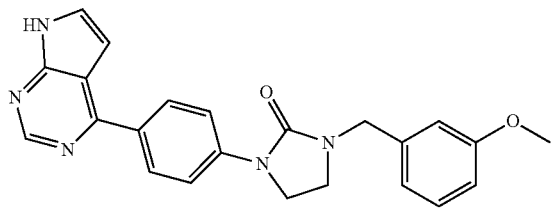 [SMILES: COc1cccc(CN2CCN(c3ccc(-c4ncnc5[nH]ccc45)cc3)C2=O)c1]

According to the procedure for the preparation of Example 62, Example 64 was prepared. MS(ESI) m/z: 400.3 (M+H)+; 1H NMR (400 MHz, DMSO-d6) δ ppm 12.54 (br. s., 1H) 8.88 (s, 1H) 8.19 (d, J=8.91 Hz, 2H) 7.86 (d, J=8.91 Hz, 2H) 7.73-7.77 (m, 1H) 7.26-7.32 (m, 1H) 7.01 (d, J=1.95 Hz, 1H) 6.85-6.93 (m, 3H) 4.41 (s, 2H) 3.93 (dd, J=9.16, 6.78 Hz, 2H) 3.76 (s, 3H) 3.39-3.46 (m, 2H); HPLC RT=1.14 min (Method E), 1.48 min (Method F).

Example 65

1-(4-(1H-Pyrrolo[2,3-b]pyridin-4-yl)phenyl)-3-(3-methoxybenzyl)imidazolidin-2-one

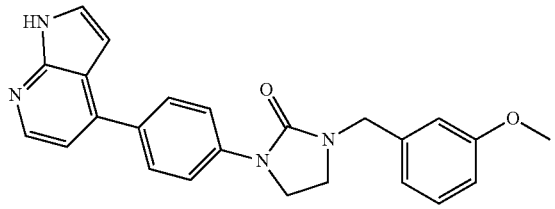 [SMILES: COc1cccc(CN2CCN(c3ccc(-c4ccnc5[nH]ccc45)cc3)C2=O)c1]

According to the procedure for the preparation of Example 62, Example 65 was prepared. MS(ESI) m/z: 399.3 (M+H)+; 1H NMR (400 MHz, DMSO-d6) δ ppm 11.91 (br. s., 1H) 8.30 (d, J=5.15 Hz, 1H) 7.80 (s, 4H) 7.55-7.60 (m, 1H) 7.23-7.34 (m, 2H) 6.84-6.92 (m, 3H) 6.70 (dd, J=3.45, 1.82 Hz, 1H) 4.40 (s, 2H) 3.90 (dd, J=9.07, 6.93 Hz, 2H) 3.76 (s, 3H) 3.38-3.45 (m, 2H); HPLC RT=1.69 min (Method E), 1.28 min (Method F).

Example 66

1-(4-(1H-Pyrazol-4-yl)phenyl)-3-(2-methoxyphenethyl)-1H-imidazol-2(3H)-one

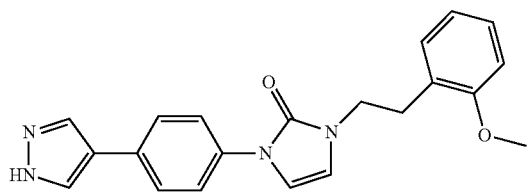 [SMILES: COc1ccccc1CCn1ccn(-c2ccc(-c3cn[nH]c3)cc2)c1=O]

Example 66A:
1-(4-Bromophenyl)-3-(2,2-dimethoxyethyl)urea

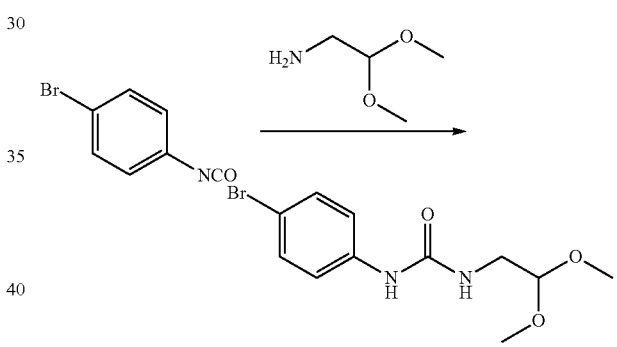

To a mixture of 2,2-dimethoxyethanamine (1.64 mL, 15.2 mmol) in dichloromethane (50 mL) at 0° C., was added 1-bromo-4-isocyanatobenzene (3.00 g, 15.2 mmol) dropwise. The mixture was stirred at ambient temperature for 16 h, then was concentrated in vacuo. The crude product was triturated with petroleum ether to afford Example 66A (4.50 g, 96% yield) as an off-white solid. MS(ESI) m/z: 271.0 (M-OMe)+; 1H NMR (300 MHz, DMSO-d6) δ 8.71 (s, 1H), 7.44-7.26 (m, 4H), 6.18 (t, J=5.9 Hz, 1H), 4.38 (t, J=5.3 Hz, 1H), 3.29 (s, 6H), 3.20 (t, J=5.5 Hz, 2H).

Example 66B:
1-(4-Bromophenyl)-1H-imidazol-2(3H)-one

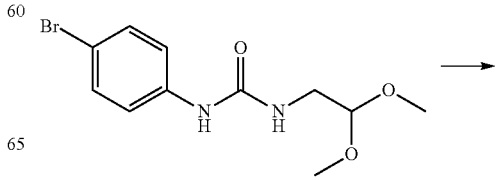

-continued

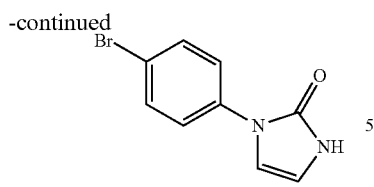

To 1.5 M HCl (49.5 ml, 74.2 mmol), was added 1-(4-bromophenyl)-3-(2,2-dimethoxyethyl)urea (4.50 g, 14.8 mmol). The mixture was stirred at ambient temperature for 20 h, then the reaction mixture was basified with saturated aq. NaHCO$_3$. The product was extracted with DCM and the combined extract was washed with water and brine, dried (Na$_2$SO$_4$) and concentrated to afford Example 66B (3.00 g, 79% yield) as an off-white solid. MS(ESI) m/z: 238.9 (M+H)$^+$; $^1$H NMR (300 MHz, DMSO-d$_6$) δ 10.37 (br. s., 1H), 7.79-7.70 (m, 2H), 7.65-7.54 (m, 2H), 7.00 (dd, J=3.0, 2.3 Hz, 1H), 6.66-6.57 (m, 1H).

Example 66C: 1-(4-Bromophenyl)-3-(2-methoxyphenethyl)-1H-imidazol-2(3H)-one

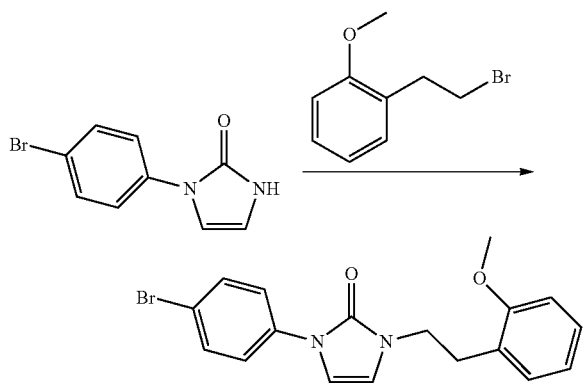

To a mixture of Example 66B (0.10 g, 0.42 mmol) and K$_2$CO$_3$ (0.116 g, 0.837 mmol) in acetonitrile (5 mL), was added 1-(2-bromoethyl)-2-methoxybenzene (0.135 g, 0.627 mmol). The mixture was stirred at ambient temperature for 16 h, then the reaction mixture was filtered through CELITE®, and the filtrate was concentrated. The residue was dissolved in ethyl acetate, washed with water and brine, dried (Na$_2$SO$_4$) and concentrated to afford Example 66C as a yellow oil, which was used in the following step without further purification. MS(ESI) m/z: 373.0 (M+H)$^+$.

Example 66

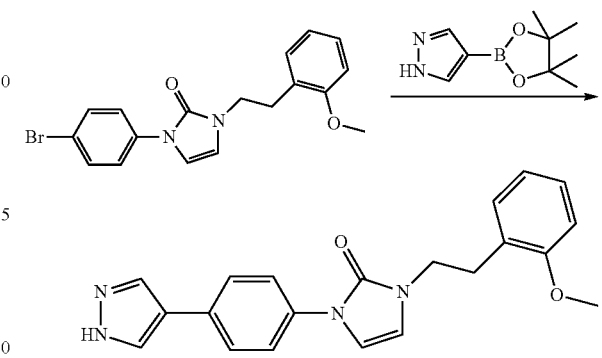

A mixture of Example 66C (0.45 g, 0.615 mmol), 4-(4,4,5,5-tetramethyl-1,3,2-dioxaborolan-2-yl)-1H-pyrazole (0.239 g, 1.23 mmol) and K$_2$CO$_3$ (0.255 g, 1.85 mmol) in DMF (3 mL) and water (1 mL) was degassed with N$_2$. 2nd generation XPhos precatalyst (0.073 g, 0.092 mmol) was added and the mixture was heated at 100° C. for 16 h. The reaction mixture was filtered through CELITE®. The filtrate was diluted with ethyl acetate and was washed with water and brine, then was concentrated. The product was purified by preparative HPLC to afford 5 mg of Example 66 as a pale yellow solid. MS(ESI) m/z: 361.2 (M+H)$^+$; $^1$H NMR (400 MHz, DMSO-d$_6$) δ 8.08 (s, 1H), 7.87 (s, 1H), 7.71-7.65 (m, 2H), 7.61-7.55 (m, 1H), 7.25-7.18 (m, 1H), 7.15-7.11 (m, 1H), 7.06 (dd, J=1.5, 7.5 Hz, 1H), 7.01-6.93 (m, 2H), 6.88-6.80 (m, 1H), 6.63-6.57 (m, 1H), 4.32-4.26 (m, 2H), 3.82-3.77 (m, 3H), 3.10 (t, J=7.5 Hz, 2H); HPLC RT=1.37 min (Method E), 1.40 min (Method F).

The Examples in Table 3 were prepared following the route used to prepare Example 66.

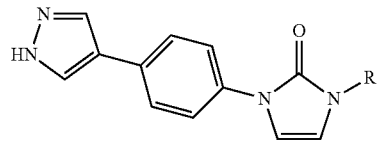

TABLE 3

| Ex. | R | Name | LCMS (M + H)$^+$ | HPLC Method, RT (min.) | NMR |
|---|---|---|---|---|---|
| 67 | 4-fluorobenzyl | 1-(4-(1H-pyrazol-4-yl)phenyl)-3-(4-fluorobenzyl)-1H-imidazol-2(3H)-one | 335.2 | E: 1.24 F: 1.28 | $^1$H NMR (400 MHz, DMSO-d$_6$) δ 12.95 (br. s, 1H), 8.28-7.82 (m, 2H), 7.73-7.64 (m, 4H), 7.41-7.34 (m, 2H), 7.24-7.15 (m, 2H), 7.08 (d, J = 3.5 Hz, 1H), 6.83-6.79 (m, 1H), 4.79 (s, 2H); $^{19}$F NMR (376 MHz, DMSO-d$_6$) δ −114.65 (s, 1F) |
| 68 | 2,6-difluorobenzyl | 1-(4-(1H-pyrazol-4-yl)phenyl)-3-(2,6-difluorobenzyl)-1H-imidazol-2(3H)-one | 353.2 | E: 1.24 F: 1.28 | $^1$H NMR (400 MHz, DMSO-d$_6$) δ 12.94 (br. s, 1H), 8.20 (br. s., 1H), 7.93 (br. s., 1H), 7.70-7.62 (m, 4H), 7.46 (quin, J = 7.5 Hz, 1H), 7.20-7.10 (m, 2H), 7.05 (d, J = 3.5 Hz, 1H), 6.65 (d, J = 3.0 Hz, 1H), 4.88 (s, 2H); $^{19}$F NMR (376 MHz, DMSO-d$_6$) δ −114.10 (s, 1F) |
| 69 | 2-fluorobenzyl | 1-(4-(1H-pyrazol-4-yl)phenyl)-3-(2-fluorobenzyl)-1H-imidazol-2(3H)-one | 335.2 | E: 1.25 F: 1.29 | $^1$H NMR (400 MHz, DMSO-d$_6$) δ 12.95 (br. s, 1H), 8.30-7.79 (m, 2H), 7.73-7.65 (m, 4H), 7.42-7.34 (m, 1H), 7.32-7.18 (m, 3H), 7.12-7.08 (m, 1H), 6.76 (d, J = 3.0 Hz, 1H), 4.87 (s, 2H); $^{19}$F NMR (376 MHz, DMSO-d$_6$) δ −118.36 (s, 1F) |

TABLE 3-continued

| Ex. | R | Name | LCMS (M + H)+ | HPLC Method, RT (min.) | NMR |
|---|---|---|---|---|---|
| 70 | 3-fluorobenzyl | 1-(4-(1H-pyrazol-4-yl)phenyl)-3-(3-fluorobenzyl)-1H-imidazol-2(3H)-one | 335.2 | A: 8.43 B: 8.14 | $^1$H NMR (400 MHz, DMSO-d$_6$) δ 12.95 (br. s., 1H), 8.20 (br. s., 1H), 7.95 (br. s., 1H), 7.74-7.64 (m, 4H), 7.46-7.37 (m, 1H), 7.17-7.07 (m, 4H), 6.85 (d, J = 3.0 Hz, 1H), 4.83 (s, 2H); $^{19}$F NMR (376 MHz, DMSO-d$_6$) δ −113.03 (s, 1F) |
| 71 | 2-fluorophenethyl | 1-(4-(1H-pyrazol-4-yl)phenyl)-3-(2-fluorophenethyl)-1H-imidazol-2(3H)-one | 349.2 | A: 8.69 B: 8.32 | $^1$H NMR (400 MHz, DMSO-d$_6$) δ 13.03-12.88 (m, 1H), 8.19 (br. s., 1H), 7.95 (br. s., 1H), 7.70-7.62 (m, 4H), 7.35-7.24 (m, 2H), 7.20-7.09 (m, 2H), 7.00 (d, J = 3.5 Hz, 1H), 6.68 (d, J = 3.0 Hz, 1H), 3.84 (t, J = 7.3 Hz, 2H), 3.00 (t, J = 7.0 Hz, 2H); $^{19}$F NMR (376 MHz, DMSO-d$_6$) δ −118.80 (s, 1F) |
| 72 | 1-phenylethyl | (+)-1-(4-(1H-pyrazol-4-yl)phenyl)-3-(1-phenylethyl)-1H-imidazol-2(3H)-one | 331.2 | A: 5.94 B: 8.47 | $^1$H NMR (400 MHz, DMSO-d$_6$) δ 12.90 (br. s., 1H), 8.07 (s, 2H), 7.73-7.61 (m, 4H), 7.40-7.24 (m, 5H), 7.11 (d, J = 3.0 Hz, 1H), 6.97 (d, J = 3.0 Hz, 1H), 5.36 (q, J = 7.4 Hz, 1H), 1.68 (d, J = 7.0 Hz, 3H) |
| 73 | 1-phenylethyl | (−)-1-(4-(1H-pyrazol-4-yl)phenyl)-3-(1-phenylethyl)-1H-imidazol-2(3H)-one | 331.2 | A: 5.93 B: 8.47 | $^1$H NMR (400 MHz, DMSO-d$_6$) δ 12.95 (br. s., 1H), 8.18 (br. s., 1H), 7.94 (br. s., 1H), 7.72-7.62 (m, 4H), 7.41-7.31 (m, 3H), 7.31-7.24 (m, 2H), 7.11 (d, J = 3.5 Hz, 1H), 6.97 (d, J = 3.0 Hz, 1H), 5.36 (q, J = 7.4 Hz, 1H), 1.68 (d, J = 7.0 Hz, 3H) |
| 74 | 3-(difluoromethoxy)benzyl | 1-(4-(1H-pyrazol-4-yl)phenyl)-3-(3-(difluoromethoxy)benzyl)-1H-imidazol-2(3H)-one | 383.2 | A: 8.86 B: 8.54 | $^1$H NMR (400 MHz, DMSO-d$_6$) δ 12.94 (br. s., 1H), 8.21 (br. s., 1H), 7.94 (br. s., 1H), 7.74-7.64 (m, 4H), 7.46-7.38 (m, 1H), 7.25-7.03 (m, 5H), 6.84 (d, J = 3.0 Hz, 1H), 4.83 (s, 2H); $^{19}$F NMR (376 MHz, DMSO-d$_6$) δ −81.82 (s, 2F) |
| 75 | 3-methoxybenzyl | 1-(4-(1H-pyrazol-4-yl)phenyl)-3-(3-methoxybenzyl)-1H-imidazol-2(3H)-one | 347.2 | A: 8.26 B: 7.99 | $^1$H NMR (400 MHz, DMSO-d$_6$) δ 12.94 (br. s., 1H), 8.21 (br. s., 1H), 7.94 (br. s., 1H), 7.69 (q, J = 8.5 Hz, 4H), 7.28 (t, J = 7.8 Hz, 1H), 7.08 (d, J = 3.0 Hz, 1H), 6.93-6.84 (m, 3H), 6.81 (d, J = 3.0 Hz, 1H), 4.77 (s, 2H), 3.74 (s, 3H) |
| 76 | phenethyl | 1-(4-(1H-pyrazol-4-yl)phenyl)-3-phenethyl-1H-imidazol-2(3H)-one | 331.2 | G: 13.12 H: 12.25 | $^1$H NMR (400 MHz, DMSO-d$_6$) δ 13.02 (s, 1H), 8.06 (br. s., 2H), 7.72-7.60 (m, 4H), 7.35-7.18 (m, 5H), 7.01 (d, J = 3.4 Hz, 1H), 6.71 (d, J = 3.0 Hz, 1H), 3.90-3.70 (m, 2H), 2.96 (t, J = 7.4 Hz, 2H) |
| 77 | 3-fluoro-5-methoxybenzyl | 1-(4-(1H-pyrazol-4-yl)phenyl)-3-(3-fluoro-5-methoxybenzyl)-1H-imidazol-2(3H)-one | 365.2 | A: 8.68 B: 8.38 | $^1$H NMR (400 MHz, DMSO-d$_6$) δ 12.95 (br. s., 1H), 8.21 (br. s., 1H), 7.94 (br. s., 1H), 7.75-7.62 (m, 4H), 7.09 (br. s., 1H), 6.84 (br. s., 1H), 6.80-6.65 (m, 3H), 4.77 (s, 2H), 3.76 (s, 3H); $^{19}$F NMR (376 MHz, DMSO-d$_6$) δ −111.35 (s, F) |
| 78 | 2-fluoro-3-methoxybenzyl | 1-(4-(1H-pyrazol-4-yl)phenyl)-3-(2-fluoro-3-methoxybenzyl)-1H-imidazol-2(3H)-one | 365.2 | G: 12.63 H: 11.81 | $^1$H NMR (400 MHz, DMSO-d$_6$) δ 12.94 (br. s., 1H), 8.21 (br. s., 1H), 7.94 (br. s., 1H), 7.77-7.60 (m, 4H), 7.18-7.05 (m, 3H), 6.84-6.77 (m, 1H), 6.75 (d, J = 3.0 Hz, 1H), 4.85 (s, 2H), 3.84 (s, 3H); $^{19}$F NMR (376 MHz, DMSO-d$_6$) δ −141.12 (s, F) |
| 79 | 2-fluoro-5-methoxybenzyl | 1-(4-(1H-pyrazol-4-yl)phenyl)-3-(2-fluoro-5-methoxybenzyl)-1H-imidazol-2(3H)-one | 365.2 | G: 13.19 H: 12.32 | $^1$H NMR (400 MHz, DMSO-d$_6$) δ 12.98 (br. s., 1H), 8.07 (br. s., 2H), 7.73-7.61 (m, 4H), 7.17 (t, J = 93 Hz, 1H), 7.09 (d, J = 3.0 Hz, 1H), 6.95-6.87 (m, 1H), 6.82 (dd, J = 3.0, 6.0 Hz, 1H), 6.76 (d, J = 3.0 Hz, 1H), 4.82 (s, 2H), 3.72 (s, 3H); $^{19}$F NMR (376 MHz, DMSO-d$_6$) δ −129.21 (s, F) |

Example 80

3-(4-(1H-Pyrazol-4-yl)phenyl)-1-(3-methoxybenzyl)imidazolidine-2,4-dione

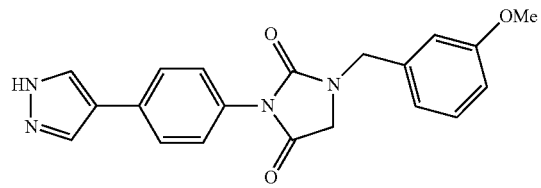 [SMILES: COc1cccc(CN2CC(=O)N(c3ccc(-c4cn[nH]c4)cc3)C2=O)c1]

Example 80A:
3-(4-Bromophenyl)imidazolidine-2,4-dione

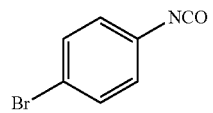

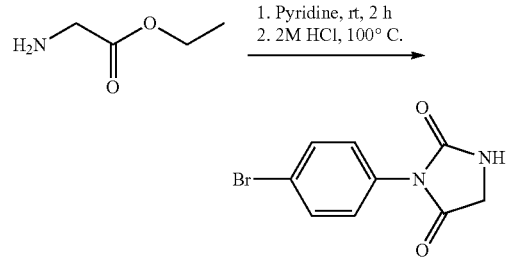

To a solution of 1-bromo-4-isocyanatobenzene (500 mg, 2.53 mmol) in pyridine (9 mL), was added ethyl 2-aminoacetate, HCl (352 mg, 2.53 mmol). The mixture was stirred at rt for 2 h, then was concentrated to a yellow gummy solid. The solid was heated at 100° C. in 2M aq. HCl (10 mL) overnight, then was cooled to rt. The mixture was diluted with water, then the resultant precipitate was collected by filtration, washed with water and petroleum ether, and dried to give 500 mg of Example 80A as a white solid, which was used without further purification. MS(ESI) m/z: 255.4 (M+H)$^+$.

Example 80B: 3-(4-Bromophenyl)-1-(3-methoxy-benzyl)imidazolidine-2,4-dione

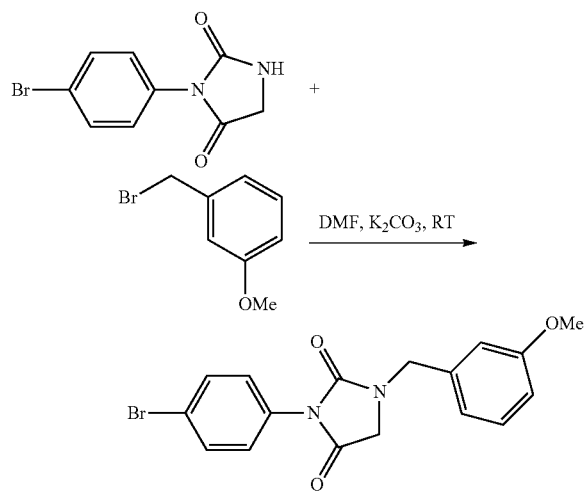

To a solution of Example 80A (150 mg, 0.588 mmol) in DMF (3 mL), were added $K_2CO_3$ (122 mg, 0.882 mmol) and 1-(bromomethyl)-3-methoxybenzene (118 mg, 0.588 mmol). The mixture was stirred at rt for 2 h. The mixture was diluted with water, then the resultant precipitate was collected by filtration. The solid was washed with water and petroleum ether, and dried to give 170 mg of Example 80B as an off-white solid, which was used without further purification. MS(ESI) m/z: 375.5 (M+H)$^+$; $^1$H NMR (400 MHz, DMSO-d$_6$) δ 7.70 (d, J=9.0 Hz, 2H), 7.42-7.36 (m, 2H), 7.34-7.26 (m, 1H), 6.96-6.85 (m, 3H), 4.54 (s, 2H), 4.04 (s, 2H), 3.76 (s, 3H).

Example 80

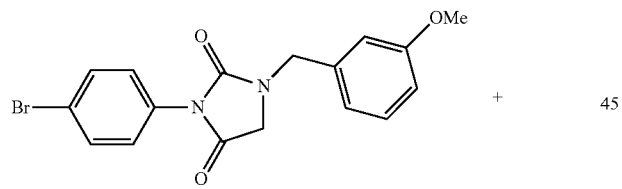

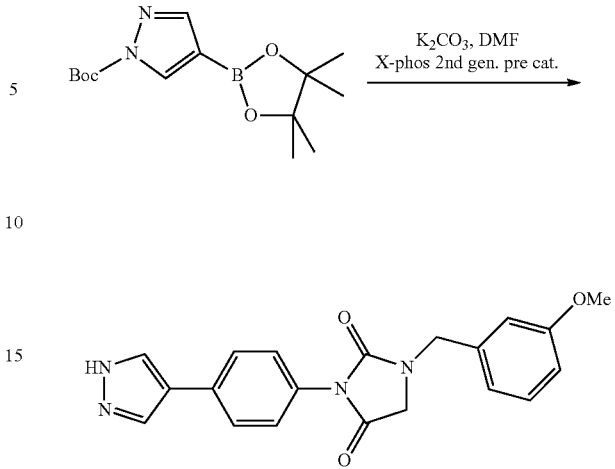

To a solution of Example 80B (100 mg, 0.267 mmol) in DMF (3 mL) and water (0.3 mL), were added tert-butyl 4-(4,4,5,5-tetramethyl-1,3,2-dioxaborolan-2-yl)-1H-pyrazole-1-carboxylate (118 mg, 0.400 mmol) and $K_2CO_3$ (111 mg, 0.800 mmol). The mixture was degassed with $N_2$, then 2nd generation XPhos precatalyst (12.6 mg, 0.016 mmol) was added, and the mixture was degassed again. The mixture was heated at 100° C. overnight, then was cooled to rt and filtered. The filtrate was purified by preparative HPLC to afford 18 mg of Example 80. MS(ESI) m/z: 363.2 (M+H)$^+$; $^1$H NMR (400 MHz, DMSO-d$_6$) δ ppm 13.00 (br. s., 1H) 8.23 (s, 1H) 7.98 (s, 1H) 7.69-7.75 (m, 2H) 7.35-7.41 (m, 2H) 7.28-7.34 (m, 1H) 6.92-6.97 (m, 2H) 6.87-6.91 (m, 1H) 4.56 (s, 2H) 4.06 (s, 2H) 3.78 (s, 3H); HPLC RT=1.22 min (Method E), 1.25 min (Method F).

The following Examples in Table 4 were prepared in a similar fashion to Example 80.

TABLE 4

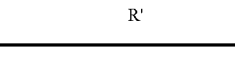

| Ex. | R | R' | Name | LCMS (M + H)$^+$ | HPLC Method, RT (min.) | NMR |
|---|---|---|---|---|---|---|
| 81 | 3-fluorobenzyl | HN-N pyrazol-4-yl-phenyl | 3-(4-(1H-pyrazol-4-yl)phenyl)-1-(3-fluoro-benzyl)imidazolidine-2,4-dione | 351.2 | E: 1.23 F: 1.26 | $^1$H NMR (400 MHz, DMSO-d$_6$) δ ppm 12.99 (br. s., 1 H) 8.24 (br. s., 1 H) 7.96 (br. s., 1 H) 7.68-7.74 (m, 2 H) 7.43 (td, J = 7.89, 6.12 Hz, 1 H) 7.37 (q, J = 4.20 Hz, 2 H) 7.19-7.27 (m, 2 H) 7.11-7.17 (m, 1 H) 4.60 (s, 2 H) 4.08 (s, 2 H); $^{19}$F NMR (376 MHz, DMSO-d$_6$) δ -112.99 |

TABLE 4-continued

| Ex. | R | R' | Name | LCMS (M + H)⁺ | HPLC Method, RT (min.) | NMR |
|---|---|---|---|---|---|---|
| 82 | 2-chlorobenzyl | 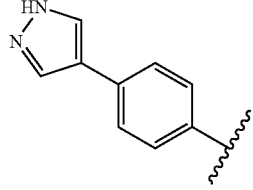 [SMILES: *c1ccc(-c2cn[nH]c2)cc1] | 3-(4-(1H-pyrazol-4-yl)phenyl)-1-(2-chloro-benzyl)imidazolidine-2,4-dione | 367.2 | E: 1.35 F: 1.38 | $^1$H NMR (400 MHz, DMSO-$d_6$) δ ppm 8.11 (br. s., 2 H) 7.70-7.75 (m, 2 H) 7.50-7.57 (m, 2 H) 7.35-7.43 (m, 4 H) 4.68 (s, 2 H) 4.12 (s, 2 H) |
| 83 | 2,5-difluorobenzyl | 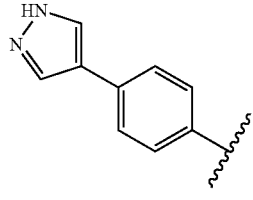 [SMILES: *c1ccc(-c2cn[nH]c2)cc1] | 3-(4-(1H-pyrazol-4-yl)phenyl)-1-(2,5-difluorobenzyl)imidazolidine-2,4-dione | 369.2 | E: 1.27 F: 1.29 | $^1$H NMR (400 MHz, DMSO-$d_6$) δ ppm 12.81 (s, 1 H) 8.10 (s, 2 H) 7.68-7.74 (m, 2 H) 7.34-7.43 (m, 3 H) 7.26-7.34 (m, 1 H) 7.18-7.25 (m, 1 H) 4.62 (s, 2 H) 4.11 (s, 2 H); $^{19}$F NMR (376 MHz, DMSO-$d_6$) δ −118.326, −124.026. |
| 84 | 3-fluoro-5-methoxybenzyl | 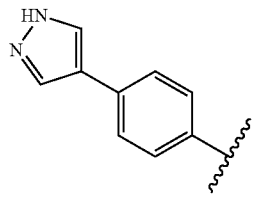 [SMILES: *c1ccc(-c2cn[nH]c2)cc1] | 3-(4-(1H-pyrazol-4-yl)phenyl)-1-(3-fluoro-5-methoxybenzyl)imidazolidine-2,4-dione | 381.2 | E: 1.31 F: 1.33 | $^1$H NMR (400 MHz, DMSO-$d_6$) δ ppm 12.98 (br. s., 1 H) 8.24 (br. s., 1 H) 7.96 (br. s., 1 H) 7.67-7.74 (m, 2 H) 7.34-7.40 (m, 2 H) 6.73-6.85 (m, 3 H) 4.55 (s, 2 H) 4.07 (s, 2 H) 3.79 (s, 3 H); $^{19}$F NMR (376 MHz, DMSO-$d_6$) δ −101.44 |
| 85 | phenethyl | 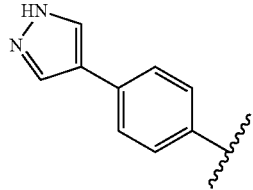 | 3-(4-(1H-pyrazol-4-yl)phenyl)-1-phenethyl-imidazolidine-2,4-dione | 347.2 | E: 1.26 F: 1.29 | $^1$H NMR (400 MHz, DMSO-$d_6$) δ ppm 12.99 (br. s., 1 H) 8.24 (s, 1 H) 7.97 (s, 1 H) 7.67-7.72 (m, 2 H) 7.21-7.37 (m, 7 H) 4.11 (s, 2 H) 3.61 (t, J = 7.47 Hz, 2 H) 2.90 (t, J = 7.44 Hz, 2 H) |
| 86 | 2-fluorobenzyl | 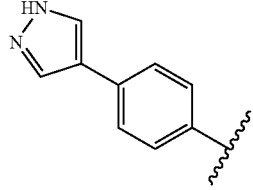 | 3-(4-(1H-pyrazol-4-yl)phenyl)-1-(2-fluoro-benzyl)imidazolidine-2,4-dione | 351.2 | E: 1.21 F: 1.24 | $^1$H NMR (400 MHz, DMSO-$d_6$) δ ppm 12.99 (s, 1 H) 8.24 (s, 1 H) 7.96 (s, 1 H) 7.68-7.73 (m, 2 H) 7.48 (td, J = 7.73, 1.66 Hz, 1 H) 7.33-7.43 (m, 3 H) 7.20-7.28 (m, 2 H) 4.64 (s, 2 H) 4.08 (s, 2 H).; $^{19}$F NMR (376 MHz, DMSO-$d_6$) δ −118.54 |
| 87 | benzyl | 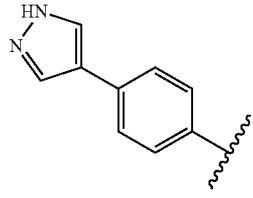 [SMILES: *c1ccc(-c2cn[nH]c2)cc1] | 3-(4-(1H-pyrazol-4-yl)phenyl)-1-benzyl-imidazolidine-2,4-dione | 333.2 | E: 1.19 F: 1.23 | $^1$H NMR (400 MHz, methanol-$d_4$) δ ppm 8.09 (s, 1 H) 7.96 (s, 1 H) 7.69-7.74 (m, 2 H) 7.39-7.45 (m, 5 H) 7.32-7.39 (m, 2 H) 4.67 (s, 2 H) 4.02 (s, 2 H) |
| 88 | benzyl | 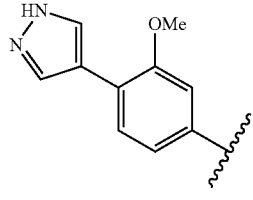 [SMILES: *c1ccc(-c2cn[nH]c2)c(OC)c1] | 1-benzyl-3-(3-methoxy-4-(1H-pyrazol-4-yl)phenyl)imidazolidine-2,4-dione | 363.2 | E: 1.23 F: 1.26 | $^1$H NMR (400 MHz, DMSO-$d_6$) δ ppm 8.08 (s, 2 H) 7.71 (d, J = 8.22 Hz, 1 H) 7.29-7.43 (m, 5 H) 7.10 (d, J = 1.88 Hz, 1 H) 6.99 (dd, J = 8.19, 1.91 Hz, 1 H) 4.58 (s, 2 H) 4.04 (s, 2 H) 3.86 (s, 3 H) |

TABLE 4-continued

| Ex. | R | R' | Name | LCMS (M + H)+ | HPLC Method, RT (min.) | NMR |
|---|---|---|---|---|---|---|
| 89 | 2-chlorobenzyl | pyrazole-phenyl-OMe | 1-(2-chlorobenzyl)-3-(3-methoxy-4-(1H-pyrazol-4-yl)phenyl)imidazolidine-2,4-dione | 397.2 | E: 1.38 F: 1.42 | $^1$H NMR (400 MHz, DMSO-$d_6$) δ ppm 8.09 (s, 2 H) 7.71 (d, J = 8.22 Hz, 1 H) 7.49-7.56 (m, 2 H) 7.34-7.41 (m, 2 H) 7.11 (d, J = 1.88 Hz, 1 H) 6.99 (dd, J = 8.22, 1.95 Hz, 1 H) 4.67 (s, 2 H) 4.12 (s, 2 H) 3.86 (s, 3 H) |
| 90 | 3-fluorobenzyl | pyrazole-phenyl-OMe | 1-(3-fluorobenzyl)-3-(3-methoxy-4-(1H-pyrazol-4-yl)phenyl)imidazolidine-2,4-dione | 381.2 | E: 1.27 F: 1.31 | $^1$H NMR (400 MHz, DMSO-$d_6$) δ ppm 8.08 (s, 2 H) 7.71 (d, J = 8.22 Hz, 1 H) 7.43 (td, J = 7.87, 6.09 Hz, 1 H) 7.20-7.29 (m, 2 H) 7.09-7.18 (m, 2 H) 6.99 (dd, J = 8.19, 1.91 Hz, 1 H) 4.60 (s, 2 H) 4.08 (s, 2 H) 3.86 (s, 3 H); $^{19}$F NMR (376 MHz, DMSO-$d_6$) δ −113.21 |
| 91 | 2-fluorobenzyl | pyrazole-phenyl-OMe | 1-(2-fluorobenzyl)-3-(3-methoxy-4-(1H-pyrazol-4-yl)phenyl)imidazolidine-2,4-dione, TFA | 381.2 | E: 1.25 F: 1.29 | $^1$H NMR (400 MHz, DMSO-$d_6$) δ ppm 8.08 (s, 2 H) 7.70 (d, J = 8.22 Hz, 1 H) 7.49 (td, J = 7.73, 1.54 Hz, 1 H) 7.35-7.43 (m, 1 H) 7.21-7.28 (m, 2 H) 7.09 (d, J = 1.95 Hz, 1 H) 6.97 (dd, J = 8.22, 1.94 Hz, 1 H) 4.64 (s, 2 H) 4.08 (s, 2 H) 3.86 (s, 3 H); $^{19}$F NMR (376 MHz, DMSO-$d_6$) δ −74.797, −118.487 |
| 92 | 2,5-difluorobenzyl | pyrazole-phenyl-OMe | 1-(2,5-difluorobenzyl)-3-(3-methoxy-4-(1H-pyrazol-4-yl)phenyl)imidazolidine-2,4-dione, TFA | 399.2 | E: 1.28 F: 1.32 | $^1$H NMR (400 MHz, DMSO-$d_6$) δ ppm 8.08 (s, 2 H) 7.71 (d, J = 8.22 Hz, 1 H) 7.41 (ddd, J = 8.94, 5.84, 3.17 Hz, 1 H) 7.26-7.34 (m, 1 H) 7.18-7.26 (m, 1 H) 7.10 (d, J = 1.94 Hz, 1 H) 6.99 (dd, J = 8.22, 1.95 Hz, 1 H) 4.63 (s, 2 H) 4.12 (s, 2 H) 3.86 (s, 3 H); $^{19}$F NMR (376 MHz, DMSO-$d_6$) δ −75.068, −118.543, −124.225. |
| 93 | 3-methoxybenzyl | pyrazole-phenyl-OMe | 3-(3-methoxy-4-(1H-pyrazol-4-yl)phenyl)-1-(3-methoxybenzyl)imidazolidine-2,4-dione, TFA | 393.2 | E: 1.25 F: 1.29 | $^1$H NMR (400 MHz, DMSO-$d_6$) δ ppm 8.08 (s, 2 H) 7.71 (d, J = 8.22 Hz, 1 H) 7.28-7.34 (m, 1 H) 7.10 (d, J = 1.88 Hz, 1 H) 6.98 (dd, J = 8.22, 1.94 Hz, 1 H) 6.91-6.96 (m, 2 H) 6.86-6.91 (m, 1 H) 4.55 (s, 2 H) 4.04 (s, 2 H) 3.86 (s, 3 H) 3.77 (s, 3 H) |
| 94 | 3-fluoro-5-methoxybenzyl | pyrazole-phenyl-OMe | 1-(3-fluoro-5-methoxybenzyl)-3-(3-methoxy-4-(1H-pyrazol-4-yl)phenyl)imidazolidine-2,4-dione, TFA | 399.2 | E: 1.34 F: 1.38 | $^1$H NMR (400 MHz, DMSO-$d_6$) δ ppm 8.08 (s, 2 H) 7.71 (d, J = 8.16 Hz, 1 H) 7.11 (d, J = 1.95 Hz, 1 H) 6.99 (dd, J = 8.19, 1.98 Hz, 1 H) 6.74-6.85 (m, 3 H) 4.55 (s, 2 H) 4.07 (s, 2 H) 3.86 (s, 3 H) 3.79 (s, 3 H); $^{19}$F NMR (376 MHz, DMSO-$d_6$) δ −74.886, −111.653 |
| 95 | 1-phenylethyl | pyrazole-phenyl | 3-(4-(1H-pyrazol-4-yl)phenyl)-1-(1-phenylethyl)imidazolidine-2,4-dione | 347.2 | E: 1.30 F: 1.32 | $^1$H NMR (400 MHz, DMSO-$d_6$) δ ppm 8.09 (s, 2 H) 7.66-7.72 (m, 2 H) 7.37-7.44 (m, 4 H) 7.27-7.36 (m, 3 H) 5.30 (q, J = 7.09 Hz, 1 H) 4.24 (d, J = 17.57 Hz, 1 H) 3.85 (d, J = 17.57 Hz, 1 H) 1.58 (d, J = 7.15 Hz, 3 H) |

TABLE 4-continued

| Ex. | R | R' | Name | LCMS (M + H)+ | HPLC Method, RT (min.) | NMR |
|---|---|---|---|---|---|---|
| 96 | 1-phenylethyl | (structure: HN-N pyrazole, OMe phenyl) | 3-(3-methoxy-4-(1H-pyrazol-4-yl)phenyl)-1-(1-phenylethyl)imidazolidine-2,4-dione | 377.2 | E: 1.35 F: 1.36 | $^1$H NMR (400 MHz, DMSO-$d_6$) δ ppm 8.09 (s, 2 H) 7.70 (d, J = 8.22 Hz, 1 H) 7.38-7.45 (m, 4 H) 7.30-7.35 (m, 1 H) 7.10 (d, J = 1.88 Hz, 1 H) 6.98 (dd, J = 8.22, 1.95 Hz, 1 H) 5.32 (q, J = 7.15 Hz, 1 H) 4.25 (d, J = 17.57 Hz, 1 H) 3.97 (s, 1 H) 3.88 (s, 1 H) 3.87 (s, 3 H) 1.60 (d, J = 7.15 Hz, 3 H) |
| 97 | phenylethyl | (structure: HN-N pyrazole, OMe phenyl) | 3-(3-methoxy-4-(1H-pyrazol-4-yl)phenyl)-1-phenethylimidazolidine-2,4-dione | 377.2 | E: 1.31 F: 1.30 | $^1$H NMR (400 MHz, DMSO-$d_6$) δ ppm 8.08 (s, 2 H) 7.69 (d, J = 8.16 Hz, 1 H) 7.29-7.38 (m, 3 H) 7.21-7.27 (m, 1 H) 7.11 (s, 1 H) 6.97-7.02 (m, 1 H) 6.91 (dd, J = 8.16, 1.95 Hz, 1 H) 4.12 (s, 2 H) 3.85 (s, 3 H) 3.61 (t, J = 7.47 Hz, 2 H) 2.91 (t, J = 7.47 Hz, 2 H). |

Example 98

3-Benzyl-1-(3-methoxy-4-(1H-pyrazol-4-yl)phenyl)imidazolidine-2,4-dione

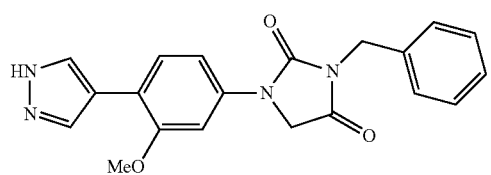 [SMILES: COc1cc(N2CC(=O)N(Cc3ccccc3)C2=O)ccc1-c1cn[nH]c1]

Example 98A: Ethyl 2-((4-bromo-3-methoxyphenyl)amino)acetate

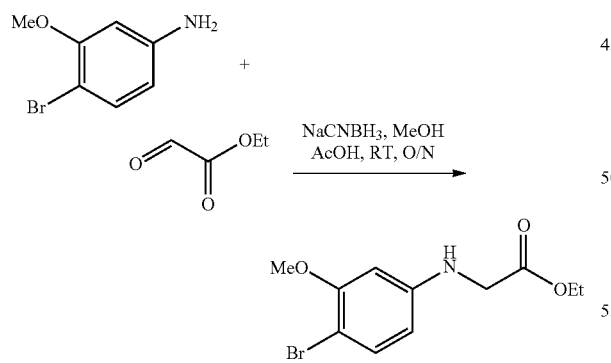

To a solution of 4-bromo-3-methoxyaniline (2.50 g, 12.4 mmol) and ethyl 2-oxoacetate (2.94 mL, 14.9 mmol) in methanol (30 mL), was added sodium cyanoborohydride (1.17 g, 18.6 mmol) and acetic acid (0.708 mL, 12.4 mmol). The mixture was stirred at rt overnight, then was concentrated to remove methanol. The product was neutralized with saturated aq. NaHCO₃, then the resultant precipitate was collected by filtration and washed with water and petroleum ether. The product was purified by flash chromatography (0-100% EtOAc/Hex) to afford 2.00 g of Example 98A as a white solid. MS(ESI) m/z: 288.4 (M+H)⁺; $^1$H NMR (400 MHz, DMSO-$d_6$) δ ppm 7.18 (d, J=11.5 Hz, 1H) 6.34 (d, J=3.6 Hz, 1H) 6.18-6.20 (m, 1H) 6.08 (dd, J=11.5, 3.6 Hz, 1H) 4.12 (q, J=9.5 Hz, 2H) 3.91 (d, J=8.4 Hz, 2H) 3.75 (s, 3H) 1.20 (t, J=9.5 Hz, 3H).

Example 98B: 1-(4-Bromo-3-methoxyphenyl)imidazolidine-2,4-dione

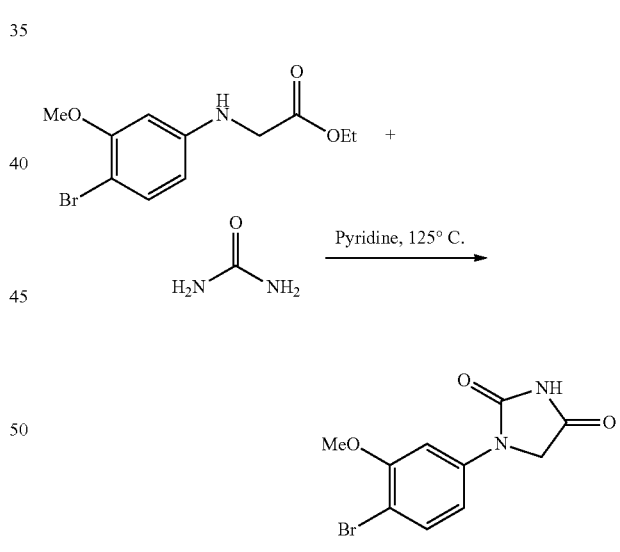

To a solution of Example 98A (2.00 g, 6.94 mmol) in pyridine (10 mL), was added urea (1.04 g, 17.4 mmol). The mixture was heated at 125° C. for 50 h, then was cooled to rt and treated with petroleum ether. The resultant precipitate was collected by filtration. The solid was redissolved in DCM and was treated with petroleum ether to give a precipitate that was collected by filtration to afford 1.90 g of Example 98B as a white solid. MS(ESI) m/z: 285.0 (M+H)⁺; $^1$H NMR (400 MHz, DMSO-$d_6$) δ 8.51 (s, 1H), 7.53 (d, J=9.0 Hz, 1H), 7.41 (d, J=2.5 Hz, 1H), 7.10 (dd, J=9.0, 2.5 Hz, 1H), 4.44 (s, 2H), 3.84 (s, 3H).

Example 98C: 3-Benzyl-1-(4-bromo-3-methoxyphenyl)imidazolidine-2,4-dione

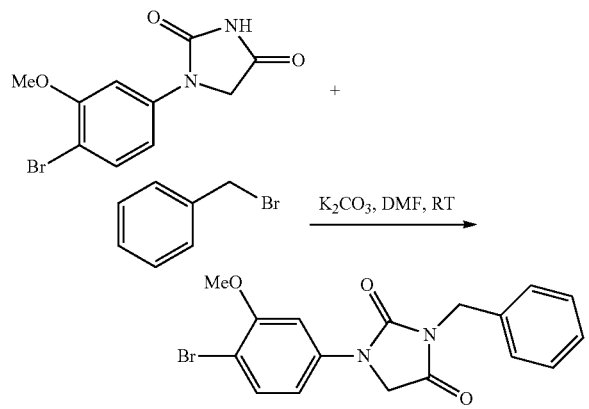

To the solution of Example 98B (200 mg, 0.702 mmol) in DMF (2 mL), was added K₂CO₃ (145 mg, 1.052 mmol) and benzyl bromide (120 mg, 0.702 mmol). The mixture was stirred at rt for 3 h, then was diluted with water to afford a precipitate, which was collected. The solid was washed with water and petroleum ether, and dried to afford 120 mg of Example 98C as a yellow solid. MS(ESI) m/z: 375.5 (M+H)⁺; ¹H NMR (400 MHz, DMSO-d₆) δ 7.57 (d, J=8.5 Hz, 1H), 7.48 (d, J=2.5 Hz, 1H), 7.37-7.32 (m, 5H), 7.12 (dd, J=9.0, 2.5 Hz, 1H), 4.65 (s, 2H), 4.61 (s, 2H), 3.85 (s, 3H).

Example 98

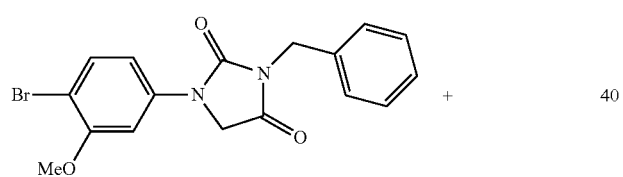

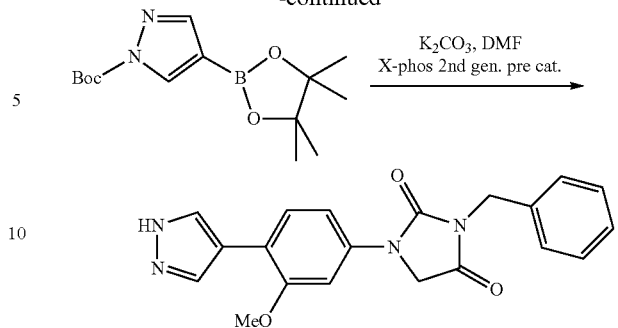

To a solution of Example 98A (120 mg, 0.32 mmol) in DMF (3 mL) and water (0.3 mL), were added tert-butyl 4-(4,4,5,5-tetramethyl-1,3,2-dioxaborolan-2-yl)-1H-pyrazole-1-carboxylate (113 mg, 0.384 mmol) and K₂CO₃ (133 mg, 0.959 mmol). The mixture was degassed with N₂, then 2nd generation XPhos precatalyst (15.1 mg, 0.019 mmol) was added. The mixture was degassed again, then was at 100° C. overnight. The reaction was diluted with water and extracted with ethyl acetate. The combined ethyl acetate phase was washed with water and brine solution, dried (Na₂SO₄), and concentrated. The residue was purified by preparative HPLC to afford 4 mg of Example 98. MS(ESI) m/z: 363.2 (M+H)⁺; ¹H NMR (400 MHz, DMSO-d₆) δ ppm 8.09 (br. s., 1H) 7.93 (br. s., 1H) 7.63 (d, J=8.41 Hz, 1H) 7.48 (d, J=2.20 Hz, 1H) 7.37 (d, J=4.45 Hz, 4H) 7.28-7.33 (m, 1H) 7.15 (dd, J=8.47, 2.26 Hz, 1H) 4.67 (s, 2H) 4.64 (s, 2H) 3.89 (s, 3H); HPLC RT=1.44 min (Method E), 1.45 min (Method F).

The following Examples in Table 5 were prepared in a similar fashion to Example 98.

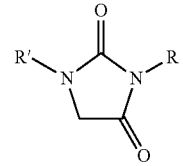

TABLE 5

| Ex. | R | R' | Name | LCMS (M + H)⁺ | HPLC Method, RT (min.) | NMR |
|---|---|---|---|---|---|---|
| 99 | 2-fluorobenzyl | ![structure with HN-N pyrazole, OMe, phenyl] | 3-(2-fluorobenzyl)-1-(3-methoxy-4-(1H-pyrazol-4-yl)phenyl)imidazolidine-2,4-dione | 381.2 | E: 1.45 F: 1.46 | ¹H NMR (400 MHz, DMSO-d₆) δ ppm 12.84 (br. s., 1 H) 8.10 (s, 1 H) 7.95 (s, 1 H) 7.64 (d, J = 8.47 Hz, 1 H) 7.47 (d, J = 2.13 Hz, 1 H) 7.34-7.44 (m, 2 H) 7.13-7.26 (m, 3 H) 4.72 (s, 2 H) 4.64 (s, 2 H) 3.89 (s, 3 H); ¹⁹F NMR (376 MHz, DMSO-d₆) δ −118.21 |
| 100 | 3-fluorobenzyl | ![structure with HN-N pyrazole, OMe, phenyl] | 3-(3-fluorobenzyl)-1-(3-methoxy-4-(1H-pyrazol-4-yl)phenyl)imidazolidine-2,4-dione | 381.2 | E: 1.49 F: 1.49 | ¹H NMR (400 MHz, DMSO-d₆) δ ppm 12.84 (br. s., 1 H) 8.10 (s, 1 H) 7.95 (s, 1 H) 7.64 (d, J = 8.47 Hz, 1 H) 7.48 (d, J = 2.20 Hz, 1 H) 7.36-7.45 (m, 1 H) 7.18-7.23 (m, 2 H) 7.10-7.17 (m, 2 H) 4.68 (s, 2 H) 4.63 (s, 2 H) 3.89 (s, 3 H); ¹⁹F NMR (376 MHz, DMSO-d₆) δ −113.16 |

TABLE 5-continued

| Ex. | R | R' | Name | LCMS (M + H)+ | HPLC Method, RT (min.) | NMR |
|---|---|---|---|---|---|---|
| 101 | 3-fluoro-5-methoxybenzyl | 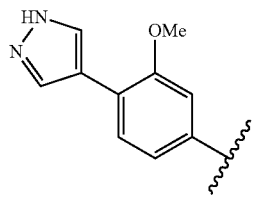 [SMILES: *c1ccc(-c2cn[nH]c2)c(OC)c1] | 3-(3-fluoro-5-methoxybenzyl)-1-(3-methoxy-4-(1H-pyrazol-4-yl)phenyl)imidazolidine-2,4-dione | 411.2 | E: 1.53 F: 1.54 | $^1$H NMR (400 MHz, DMSO-$d_6$) δ ppm 12.84 (br. s., 1 H) 8.11 (s, 1 H) 7.94 (s, 1 H) 7.64 (d, J = 8.47 Hz, 1 H) 7.48 (d, J = 2.20 Hz, 1 H) 7.15 (dd, J = 8.47, 2.20 Hz, 1 H) 6.74-6.79 (m, 3 H) 4.64 (s, 4 H) 3.89 (s, 3 H) 3.78 (s, 3 H); $^{19}$F NMR (376 MHz, DMSO-$d_6$) δ −111.53 |
| 102 | 2,6-difluorobenzyl | 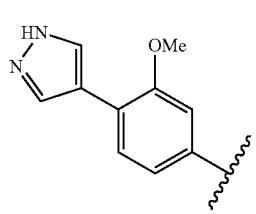 | 3-(2,6-difluorobenzyl)-1-(3-methoxy-4-(1H-pyrazol-4-yl)phenyl)imidazolidine-2,4-dione | 399.2 | E: 1.43 F: 1.44 | $^1$H NMR (400 MHz, DMSO-$d_6$) δ ppm 12.83 (br. s., 1 H) 8.10 (s, 1 H) 7.94 (s, 1 H) 7.62 (d, J = 8.47 Hz, 1 H) 7.39-7.46 (m, 2 H) 7.09-7.15 (m, 3 H) 4.74 (s, 2 H) 4.59 (s, 2 H) 3.88 (s, 3 H); $^{19}$F NMR (376 MHz, DMSO-$d_6$) δ −113.79 |
| 103 | phenethyl | 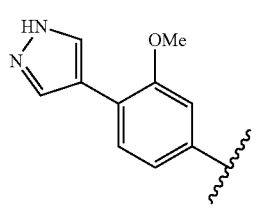 [SMILES: *c1ccc(-c2cn[nH]c2)c(OC)c1] | 1-(3-methoxy-4-(1H-pyrazol-4-yl)phenyl)-3-phenethylimidazolidine-2,4-dione | 377.2 | E: 1.51 F: 1.52 | $^1$H NMR (400 MHz, DMSO-$d_6$) δ ppm 12.84 (br. s., 1 H) 8.09 (s, 1 H) 7.93 (s, 1 H) 7.63 (d, J = 8.47 Hz, 1 H) 7.44 (d, J = 2.20 Hz, 1 H) 7.30-7.35 (m, 2 H) 7.23-7.28 (m, 3 H) 7.14 (dd, J = 8.47, 2.26 Hz, 1 H) 4.52 (s, 2 H) 3.89 (s, 3 H) 3.67-3.72 (m, 2 H) 2.89-2.94 (m, 2 H) |
| 104 | 2-chlorobenzyl | 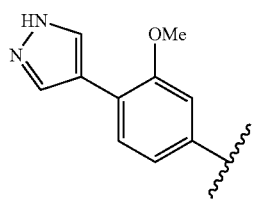 | 3-(2-chlorobenzyl)-1-(3-methoxy-4-(1H-pyrazol-4-yl)phenyl)imidazolidine-2,4-dione | 397.2 | E: 1.56 F: 1.58 | $^1$H NMR (400 MHz, DMSO-$d_6$) δ ppm 12.84 (s, 1 H) 8.11 (s, 1 H) 7.95 (s, 1 H) 7.65 (d, J = 8.47 Hz, 1 H) 7.47-7.53 (m, 2 H) 7.33-7.41 (m, 3 H) 7.17 (dd, J = 8.50, 2.23 Hz, 1 H) 4.74 (s, 2 H) 4.68 (s, 2 H) 3.89 (s, 3 H) |
| 105 | 3-methoxybenzyl | 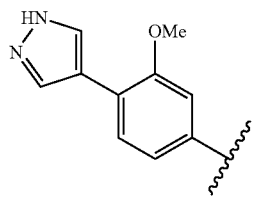 | 1-(3-methoxy-4-(1H-pyrazol-4-yl)phenyl)-3-(3-methoxybenzyl)imidazolidine-2,4-dione | 393.2 | E: 1.45 F: 1.46 | $^1$H NMR (400 MHz, DMSO-$d_6$) δ ppm 12.84 (br. s., 1 H) 8.10 (s, 1 H) 7.94 (s, 1 H) 7.64 (s, 1 H) 7.47 (s, 1 H) 7.25-7.31 (m, 1 H) 7.15 (dd, J = 8.47, 2.20 Hz, 1 H) 6.90-6.95 (m, 2 H) 6.85-6.89 (m, 1 H) 4.64 (s, 4 H) 3.87 (s, 3 H) 3.76 (s, 3 H) |
| 106 | 1-phenylethyl | 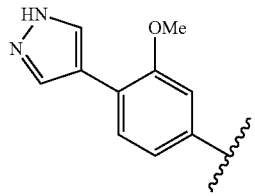 [SMILES: *c1ccc(-c2cn[nH]c2)c(OC)c1] | 1-(3-methoxy-4-(1H-pyrazol-4-yl)phenyl)-3-(1-phenylethyl)imidazolidine-2,4-dione | 377.2 | E: 1.56 F: 1.57 | $^1$H NMR (400 MHz, DMSO-$d_6$) δ ppm 12.85 (br. s., 1 H) 8.00 (s, 2 H) 7.62 (d, J = 8.47 Hz, 1 H) 7.42-7.48 (m, 3 H) 7.34-7.40 (m, 2 H) 7.26-7.32 (m, 1 H) 7.12 (dd, J = 8.50, 2.23 Hz, 1 H) 5.34 (q, J = 7.40 Hz, 1 H) 4.57 (s, 2 H) 3.88 (s, 3 H) 1.82 (d, J = 7.20 Hz, 3 H) |
| 107 | 3-fluoro-5-methoxybenzyl | 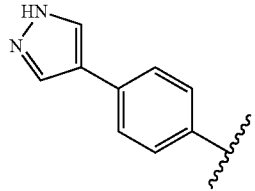 [SMILES: *c1ccc(-c2cn[nH]c2)cc1] | 1-(4-(1H-pyrazol-4-yl)phenyl)-3-(3-fluoro-5-methoxybenzyl)imidazolidine-2,4-dione | 381.2 | E: 1.37 F: 1.51 | $^1$H NMR (400 MHz, DMSO-$d_6$) δ ppm 12.92 (s, 1 H) 8.18 (s, 1 H) 7.92 (s, 1 H) 7.60-7.67 (m, 4 H) 6.73-6.79 (m, 3 H) 4.64 (s, 2 H) 4.61 (s, 2 H) 3.76-3.78 (m, 3 H); $^{19}$F NMR (376 MHz, DMSO-$d_6$) δ −111.54 |

TABLE 5-continued

| Ex. | R | R' | Name | LCMS (M + H)+ | HPLC Method, RT (min.) | NMR |
|---|---|---|---|---|---|---|
| 108 | 2,6-difluorobenzyl | pyrazol-4-yl-phenyl | 1-(4-(1H-pyrazol-4-yl)phenyl)-3-(2,6-difluorobenzyl)imidazolidine-2,4-dione | 369.2 | E: 1.26<br>F: 1.41 | $^1$H NMR (400 MHz, DMSO-d$_6$) δ ppm 12.92 (s, 1 H) 8.18 (s, 1 H) 7.91 (s, 1 H) 7.56-7.65 (m, 4 H) 7.43 (tt, J = 8.43, 6.60 Hz, 1 H) 7.07-7.15 (m, 2 H) 4.73 (s, 2 H) 4.55 (s, 2 H); $^{19}$F NMR (376 MHz, DMSO-d$_6$) δ −113.77 |
| 109 | 1-phenylethyl | pyrazol-4-yl-phenyl | 1-(4-(1H-pyrazol-4-yl)phenyl)-3-(1-phenylethyl)imidazolidine-2,4-dione | 347.2 | E: 1.40<br>F: 1.54 | $^1$H NMR (400 MHz, DMSO-d$_6$) δ ppm 12.91 (s, 1 H) 8.17 (s, 1 H) 7.91 (s, 1 H) 7.57-7.64 (m, 4 H) 7.41-7.45 (m, 2 H) 7.33-7.38 (m, 2 H) 7.25-7.30 (m, 1 H) 5.33 (q, J = 7.22 Hz, 1 H) 4.48-4.58 (m, 2 H) 1.80 (d, J = 7.34 Hz, 3 H). |
| 110 | benzyl | pyrazol-4-yl-phenyl | 1-(4-(1H-pyrazol-4-yl)phenyl)-3-benzyl-imidazolidine-2,4-dione | 333.2 | E: 1.27<br>F: 1.42 | $^1$H NMR (400 MHz, DMSO-d$_6$) δ ppm 12.91 (s, 1 H) 8.17 (s, 1 H) 7.91 (s, 1 H) 7.57-7.64 (m, 4 H) 7.41-7.45 (m, 2 H) 7.33-7.38 (m, 2 H) 7.25-7.30 (m, 1 H) 5.33 (q, J = 7.22 Hz, 1 H) 4.48-4.58 (m, 2 H) 1.80 (d, J = 7.34 Hz, 3 H) |
| 111 | 2-chlorobenzyl | pyrazol-4-yl-phenyl | 1-(4-(1H-pyrazol-4-yl)phenyl)-3-(2-chlorobenzyl)imidazolidine-2,4-dione | 367.1 | E: 1.46<br>F: 1.55 | $^1$H NMR (400 MHz, DMSO-d$_6$) δ ppm 8.05 (s, 2 H) 7.61-7.67 (m, 4 H) 7.48-7.51 (m, 1 H) 7.31-7.39 (m, 3 H) 4.72 (s, 2 H) 4.64 (s, 2 H) |
| 112 | 3-methoxybenzyl | pyrazol-4-yl-phenyl | 1-(4-(1H-pyrazol-4-yl)phenyl)-3-(3-methoxybenzyl)imidazolidine-2,4-dione | 363.2 | E: 1.32<br>F: 1.43 | $^1$H NMR (400 MHz, DMSO-d$_6$) δ ppm 8.04 (br. s., 2 H) 7.58-7.66 (m, 4 H) 7.22-7.31 (m, 1 H) 6.83-6.93 (m, 3 H) 4.62 (s, 2 H) 4.60 (s, 2 H) 3.74 (s, 3 H) |
| 113 | phenethyl | pyrazol-4-yl-phenyl | 1-(4-(1H-pyrazol-4-yl)phenyl)-3-phenethyl-imidazolidine-2,4-dione | 347.2 | E: 1.39<br>F: 1.49 | $^1$H NMR (400 MHz, DMSO-d$_6$) δ ppm 12.95 (br. s, 1 H) 8.22 (s, 2 H) 7.56-7.65 (m, 4 H) 7.27-7.34 (m, 2 H) 7.20-7.26 (m, 3 H) 4.48 (s, 2 H) 3.68 (dd, J = 8.38, 6.81 Hz, 2 H) 2.90 (t, J = 7.56 Hz, 2 H) |
| 114 | 3-fluorobenzyl | pyrazol-4-yl-phenyl | 1-(4-(1H-pyrazol-4-yl)phenyl)-3-(3-fluorobenzyl)imidazolidine-2,4-dione | 351.2 | E: 1.36<br>F: 1.46 | $^1$H NMR (400 MHz, DMSO-d$_6$) δ ppm 12.92 (s, 1 H) 8.04 (s, 2 H) 7.59-7.66 (m, 4 H) 7.36-7.43 (m, 1 H) 7.16-7.21 (m, 2 H) 7.08-7.15 (m, 1 H) 4.68 (s, 2 H) 4.60 (s, 2 H); $^{19}$F NMR (376 MHz, DMSO-d$_6$) δ −113.17 |

TABLE 5-continued

| Ex. | R | R' | Name | LCMS (M + H)+ | HPLC Method, RT (min.) | NMR |
|---|---|---|---|---|---|---|
| 115 | 2,5-difluorobenzyl | 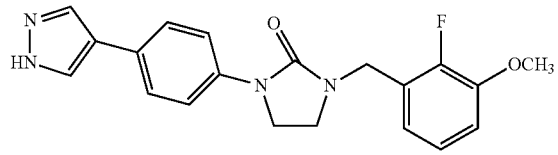 | 1-(4-(1H-pyrazol-4-yl)phenyl)-3-(2,5-difluorobenzyl)imidazolidine-2,4-dione | 369.2 | E: 1.36<br>F: 1.46 | $^1$H NMR (400 MHz, DMSO-d$_6$) δ ppm 12.93 (s, 1 H) 8.17 (s, 1 H) 7.92 (s, 1 H) 7.59-7.66 (m, 4 H) 7.24-7.32 (m, 2 H) 7.16-7.23 (m, 1 H) 4.69 (s, 2 H) 4.59 (s, 2 H); $^{19}$F NMR (376 MHz, DMSO-d$_6$) δ −118.54, −123.68 |

Example 116

1-(4-(1H-Pyrazol-4-yl)phenyl)-3-(2-fluoro-3-methoxybenzyl)imidazolidin-2-one

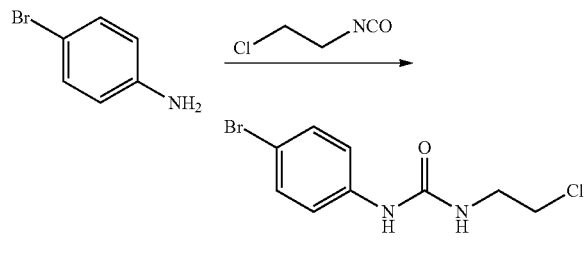

Example 116A:
1-(4-Bromophenyl)-3-(2-chloroethyl)urea

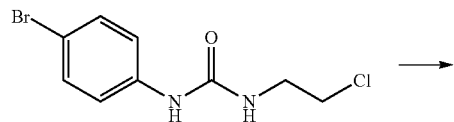

To a mixture of 4-bromoaniline (5.00 g, 29.1 mmol) in dichloromethane (80 mL) at 0° C., was slowly added 1-chloro-2-isocyanatoethane (2.98 mL, 34.9 mmol). The mixture was stirred at rt for 16 h. The mixture was concentrated. The crude product mixture was purified by trituration with petroleum ether to afford 6.00 g of Example 116A (74% yield) as an off-white solid. MS(ESI) m/z: 277.2 (M+H)$^+$; $^1$H NMR (400 MHz, DMSO-d$_6$) δ 8.79 (s, 1H), 7.43-7.33 (m, 4H), 6.44 (t, J=5.8 Hz, 1H), 3.65 (t, J=6.0 Hz, 2H), 3.41 (q, J=6.0 Hz, 2H).

Example 116B:
1-(4-Bromophenyl)imidazolidin-2-one

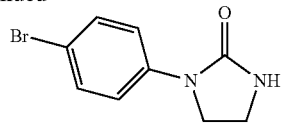

To an ice cold mixture of Example 116A (8.00 g, 28.8 mmol) in THF (100 mL), was added sodium hydride (2.08 g, 860 mmol) in portions over 30 min. The mixture was stirred at rt for 16 h, then was quenched with ice and diluted in ethyl acetate. The organic layer was separated and washed with water and brine, dried (Na$_2$SO$_4$) and concentrated. This crude product was purified by triturating with petroleum ether to afford Example 116B (5.00 g, 72% yield) as an off-white solid. MS(ESI) m/z: 241.3 (M+H)$^+$; $^1$H NMR (300 MHz, DMSO-d$_6$) δ 7.61-7.35 (m, 1H), 7.05 (s, 1H), 3.82 (dd, J=9.1, 6.8 Hz, 2H), 3.44-3.35 (m, 2H).

Example 116C: 1-(4-Bromophenyl)-3-(2-fluoro-3-methoxybenzyl)imidazolidin-2-one

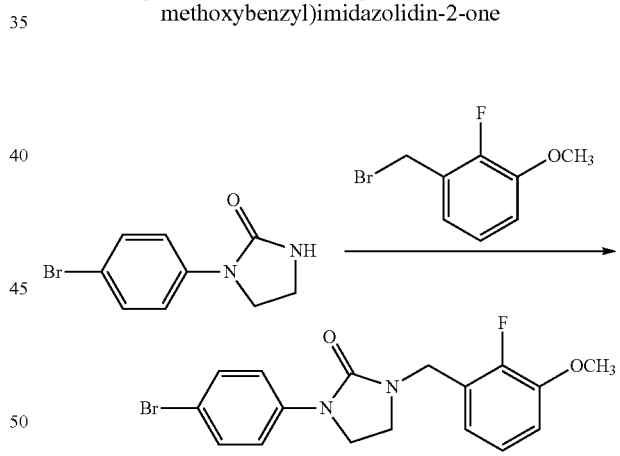

To mixture of Example 116B (0.200 g, 0.830 mmol) in THF (10 mL) at 0° C., was added sodium hydride (0.050 g, 2.07 mmol). The mixture was stirred at rt for 10 min, then was cooled to 0° C. and treated with 1-(bromomethyl)-2-fluoro-3-methoxybenzene (0.363 g, 1.66 mmol). The mixture was heated at 70° C. for 4 h. The reaction mixture was quenched with ice and diluted with ethyl acetate. The organic layer was separated and washed with water and brine, dried (Na$_2$SO$_4$) and concentrated. This crude product was purified by triturating with diethyl ether to afford 0.180 g (55% yield) of Example 116C as an off-white solid. MS(ESI) m/z: 379.2 (M+H)$^+$; $^1$H NMR (400 MHz, DMSO-d$_6$) δ 7.58-7.53 (m, 2H), 7.52-7.46 (m, 2H), 7.16-7.08 (m, 2H), 6.95-6.86 (m, 1H), 4.44 (s, 2H), 3.83 (s, 3H), 3.82-3.75 (m, 2H), 3.38 (dd, J=7.3, 8.8 Hz, 2H).

Example 116

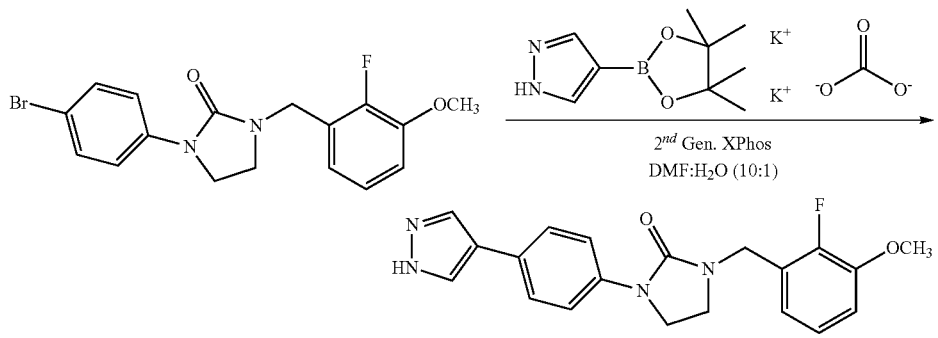

According to the procedure for the preparation of Example 98, Example 116C (100 mg, 0.264 mmol) afforded 20 mg (20% yield) of Example 116 as an off-white solid. MS(ESI) m/z: 367.0 (M+H)$^+$; $^1$H NMR (400 MHz, DMSO-d$_6$) δ=12.86 (br. s., 1H), 8.12 (br. s., 1H), 7.87 (br. s., 1H), 7.56 (s, 4H), 7.17-7.08 (m, 2H), 6.92 (dd, J=8.8, 4.8 Hz, 1H), 4.44 (s, 2H), 3.86-3.75 (m, 5H), 3.43-3.35 (m, 2H); $^{19}$F NMR (376 MHz, DMSO-d$_6$) δ −141.10 (s, 1F); HPLC RT=8.87 min (Method A), 8.64 min (Method B).

The following Examples in Table 6 were prepared in a similar fashion to Example 116.

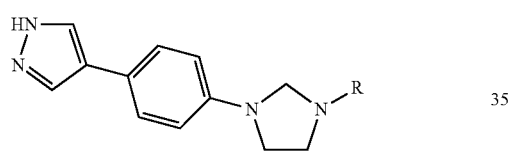

Example 121: 3-(4-(1H-Pyrazol-4-yl)phenyl)-5-(hydroxymethyl)-1-(3-methoxybenzyl)imidazolidine-2,4-dione

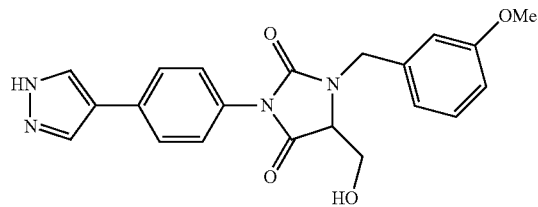 [SMILES: COc1cccc(CN2C(=O)N(c3ccc(-c4cn[nH]c4)cc3)C(=O)C2CO)c1]

TABLE 6

| Ex. | R | Name | LCMS (M + H)$^+$ | HPLC Method, RT (min.) | NMR |
|---|---|---|---|---|---|
| 117 | 3-fluoro-4-methoxybenzyl | 1-(4-(1H-pyrazol-4-yl)phenyl)-3-(3-fluoro-4-methoxybenzyl)imidazolidin-2-one | 367.0 | A: 8.80 B: 8.56 | $^1$H NMR (400 MHz, DMSO-d$_6$) δ 12.87 (br. s., 1H), 8.11 (br. s., 1H), 7.88 (br. s., 1H), 7.56 (s, 4H), 7.19-7.06 (m, 3H), 4.33 (s, 2H), 3.86-3.77 (m, 5H), 3.37 (s, 2H); $^{19}$F NMR (376 MHz, DMSO-d$_6$) δ −135.24 |
| 118 | 3-fluoro-5-methoxybenzyl | 1-(4-(1H-pyrazol-4-yl)phenyl)-3-(3-fluoro-5-methoxybenzyl)imidazolidin-2-one | 367.0 | A: 9.33 B: 9.00 | $^1$H NMR (400 MHz, DMSO-d$_6$) δ 12.86 (br. s., 1H), 8.12 (br. s., 1H), 7.87 (br. s., 1H), 7.61-7.53 (m, 4H), 6.79-6.67 (m, 3H), 4.37 (s, 2H), 3.88-3.81 (m, 2H), 3.77 (s, 3H), 3.40 (d, J = 8.0 Hz, 2H); $^{19}$F NMR (376 MHz, DMSO-d$_6$) δ −111.56 |
| 119 | 5-fluoro-2-methoxybenzyl | 1-(4-(1H-pyrazol-4-yl)phenyl)-3-(5-fluoro-2-methoxybenzyl)imidazolidin-2-one | 367.0 | A: 9.33 B: 9.04 | $^1$H NMR (400 MHz, DMSO-d$_6$) δ 12.86 (br. s., 1H), 8.12 (br. s., 1H), 7.87 (br. s., 1H), 7.61-7.53 (m, 4H), 6.79-6.67 (m, 3H), 4.37 (s, 2H), 3.88-3.81 (m, 2H), 3.77 (s, 3H), 3.40 (d, J = 8.0 Hz, 2H); $^{19}$F NMR (376 MHz, DMSO-d$_6$) δ −123.80 |
| 120 | 2-fluoro-5-methoxybenzyl | 1-(4-(1H-pyrazol-4-yl)phenyl)-3-(2-fluoro-5-methoxybenzyl)imidazolidin-2-one | 367.0 | A: 9.08 B: 8.76 | $^1$H NMR (400 MHz, DMSO-d$_6$) δ 12.87 (br. s., 1H), 8.12 (br. s., 1H), 7.87 (br. s., 1H), 7.56 (s, 4H), 7.20-7.10 (m, 1H), 6.94-6.86 (m, 2H), 4.41 (s, 2H), 3.83 (dd, J = 9.5, 6.5 Hz, 2H), 3.74 (s, 3H), 3.44-3.36 (m, 2H); $^{19}$F NMR (376 MHz, DMSO-d$_6$) δ −129.64 |

Example 121A: (S)-3-(4-Bromophenyl)-5-(hydroxymethyl)imidazolidine-2,4-dione

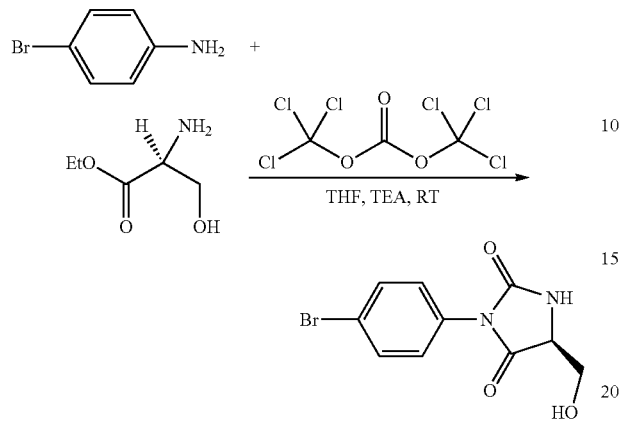

To the solution of 4-bromoaniline (500 mg, 2.91 mmol) in THF (10 mL) at 0° C., was added triphosgene (431 mg, 1.45 mmol), followed by dropwise addition of TEA (1.22 mL, 8.72 mmol). The mixture was stirred at rt for 30 min, then a suspension of(S)-ethyl 2-amino-3-hydroxypropanoate (387 mg, 2.91 mmol) and TEA (1.22 mL, 8.72 mmol) in THF (10 mL) was added. The mixture was stirred at rt for 2.5 h, then was concentrated. The residue was treated with water, and the resultant suspension was filtered. The filtrate was extracted with EtOAc. The organic phase was washed with brine, dried ($Na_2SO_4$) and concentrated to afford 300 mg (21% yield) of Example 121A as an off-white solid. MS(ESI) m/z: 285.0 (M+H)$^+$; $^1$H NMR (300 MHz, DMSO-$d_6$) δ 8.46 (s, 1H), 7.73-7.60 (m, 2H), 7.32 (d, J=8.7 Hz, 2H), 5.20 (t, J=5.3 Hz, 1H), 4.23 (t, J=2.8 Hz, 1H), 3.85-3.72 (m, 1H), 3.72-3.61 (m, 1H).

Example 121B: 3-(4-Bromophenyl)-5-(hydroxymethyl)-1-(3-methoxybenzyl) imidazolidine-2,4-dione

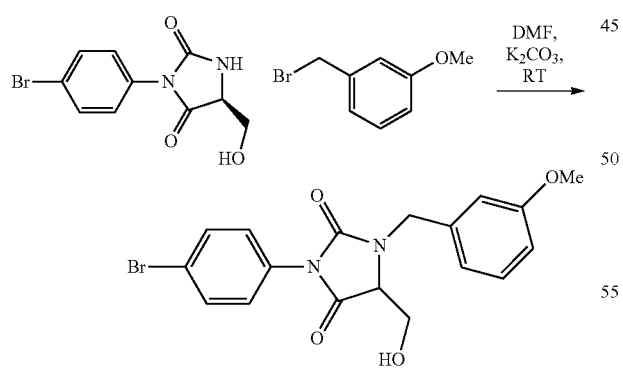

To the solution of Example 121A (200 mg, 0.702 mmol) in DMF (5 mL), was added $K_2CO_3$ (145 mg, 1.05 mmol) and 1-(bromomethyl)-3-methoxybenzene (141 mg, 0.702 mmol). The mixture was stirred at rt for 3 h. The mixture was diluted with water and extracted with ethyl acetate. The combined organic phase was washed with brine and concentrated. The product was purified by flash chromatography (0-100% EtOAc/Hex) to give 150 mg (46% yield) of Example 121B as a white solid. MS(ESI) m/z: 405.1 (M+H)$^+$; $^1$H NMR (300 MHz, DMSO-$d_6$) δ 7.70 (d, J=9.1 Hz, 2H), 7.37 (d, J=8.7 Hz, 2H), 7.28 (t, J=7.9 Hz, 1H), 6.96 (d, J=4.2 Hz, 2H), 6.87 (d, J=7.2 Hz, 1H), 5.28 (t, J=5.3 Hz, 1H), 4.88 (d, J=15.9 Hz, 1H), 4.31 (d, J=15.9 Hz, 1H), 4.10 (s, 1H), 3.90-3.77 (m, 2H), 3.76 (s, 3H).

Example 121

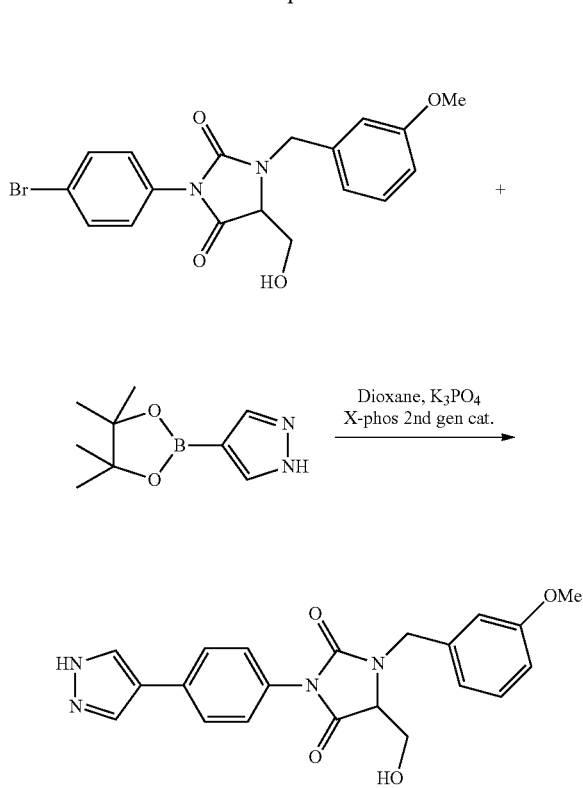

According to the procedure for the preparation of Example 98, Example 121B (150 mg, 0.370 mmol) afforded 25 mg (17% yield) of Example 121 as a yellow solid. MS(ESI) m/z: 367.0 (M+H)$^+$; $^1$H NMR (400 MHz, DMSO-$d_6$) δ ppm 12.92 (br. s., 1H) 8.25 (s, 1H) 7.97 (s, 1H) 7.69-7.74 (m, 2H) 7.34 (d, J=8.60 Hz, 2H) 7.29 (t, J=8.06 Hz, 1H) 6.94-6.98 (m, 2H) 6.85-6.89 (m, 1H) 5.29 (t, J=5.24 Hz, 1H) 4.89 (d, J=15.81 Hz, 1H) 4.31 (d, J=15.81 Hz, 1H) 4.09 (t, J=2.23 Hz, 1H) 3.79-3.89 (m, 2H) 3.76 (s, 3H); HPLC RT=7.46 min (Method A), 7.22 min (Method B).

Example 122

(R)-1-(4-(1H-Pyrazol-4-yl)phenyl)-3-(1-(3-methoxyphenyl)ethyl)imidazolidin-2-one

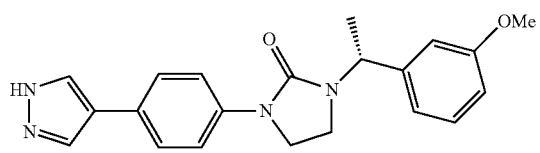 [SMILES: COc1cccc([C@@H](C)N2CCN(c3ccc(-c4cn[nH]c4)cc3)C2=O)c1]

Example 122A: Preparation of (R)-1-(4-bromophenyl)-1-(2-chloroethyl)-3-(1-(3-methoxyphenyl)ethyl) urea

Example 122B: Preparation of (R)-1-(4-bromophenyl)-3-(1-(3-methoxyphenyl)ethyl) imidazolidin-2-one

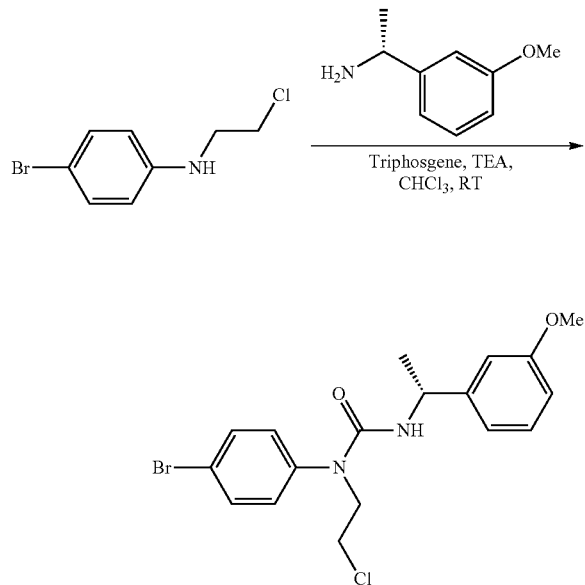

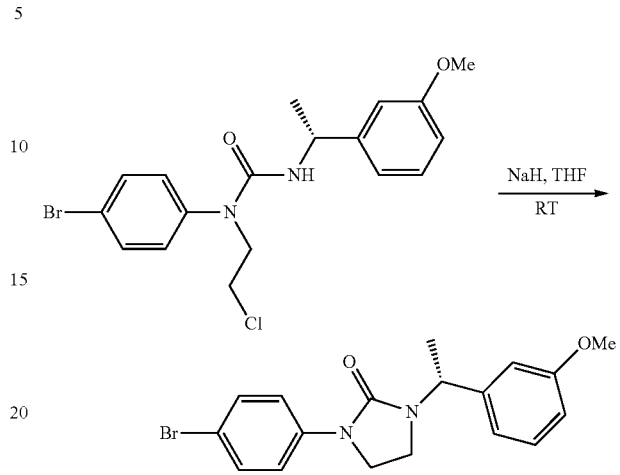

To a stirred solution of 4-bromo-N-(2-chloroethyl)aniline (3 g, 12.8 mmol) and TEA (5.35 mL, 38.4 mmol) in chloroform (100 mL) under nitrogen atmosphere, was added triphosgene (4.18 g, 14.1 mmol) at 0° C. and the reaction mixture was allowed to stirred at rt. After 2 h the reaction mixture was again cooled to 0° C. and was added (R)-1-(3-methoxyphenyl)ethanamine (1.93 g, 12.8 mmol) dropwise and the reaction mixture was stirred at rt for 16 h. Reaction mixture was diluted with DCM (100 mL), washed with 0.1M HCl (50 mL), sat NaHCO$_3$, brine solution. The organic layer was dried over Na$_2$SO$_4$, filtered and concentrated. The crude product was purified by CombiFlash chromatography (40 g REDISEP SiO$_2$ column, eluting with 20-30% EtOAc in hexane) to afford Example 122A (2.8 g, 55% yield) white solid. MS(ESI) m/z: 413.0 (M+H)$^+$. $^1$H NMR (300 MHz, chloroform-d) δ ppm 7.62-7.56 (m, 2H), 7.30-7.16 (m, 3H), 6.82-6.73 (m, 3H), 4.97 (quin, J=7.1 Hz, 1H), 4.44 (d, J=7.9 Hz, 1H), 4.01-3.85 (m, 2H), 3.81 (s, 3H), 3.66 (td, J=6.5, 2.1 Hz, 2H), 1.37 (d, J=6.8 Hz, 3H).

To a solution of Example 122A (2.8 g, 6.80 mmol) in THF (50 mL) was added NaH (0.544 g, 13.6 mmol, 60% in mineral oil) at 0° C., the reaction mixture was allowed to stir at rt for 16 h., was quenched with 10% NH$_4$Cl solution (100 mL) and extracted with EtOAc (2×50 mL). Combined the organic layers was washed with brine (1×50 mL), dried over Na$_2$SO$_4$, filtered and concentrated. The crude product was purified by flash chromatography (40 g REDISEP SiO$_2$ column, eluting with 30% EtOAc in hexane) to afford the Example 122B (2.4 g, 71.5% yield) as white solid. MS(ESI) m/z: 375.0 (M+H)$^+$. $^1$H NMR (300 MHz, chloroform-d) δ ppm 7.51-7.41 (m, 3H), 7.33-7.28 (m, 1H), 7.00-6.92 (m, 1H), 6.85 (dd, J=8.1, 1.7 Hz, 1H), 5.37 (q, J=7.4 Hz, 1H), 3.84-3.81 (m, 2H), 3.79-3.66 (m, 1H), 3.46 (td, J=9.2, 6.2 Hz, 1H), 3.14 (td, J=9.1, 6.4 Hz, 1H), 1.60 (s, 3H).

Preparation of (R)-1-(4-(1H-pyrazol-4-yl)phenyl)-3-(1-(3-methoxyphenyl)ethyl) imidazolidin-2-one

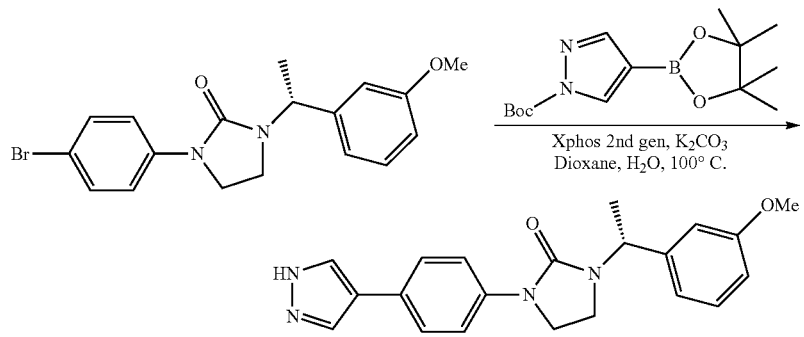

A solution of Example 122B (400 mg, 1.066 mmol), potassium phosphate, dibasic (464 mg, 2.66 mmol), and tert-butyl 4-(4,4,5,5-tetramethyl-1,3,2-dioxaborolan-2-yl)-1H-pyrazole-1-carboxylate (376 mg, 1.279 mmol) in a mixture of 1,4-dioxane (20 mL) and water (0.2 mL) was purged with nitrogen for 10 min and then charged with 2nd generation XPhos precatalyst (25.2 mg, 0.032 mmol) and heated to reflux at 90° C. for 2 h. Dioxane was concentrated, the residue was diluted with EtOAc (100 mL), washed with water, brine, dried over Na$_2$SO$_4$, filtered and concentrated. The crude product was purified by Preparative HPLC (Method info: Column: Gemini NX-C18 (100 mm×21.2 mm×5μ) Mobile Phase A: 10 mM ammonium acetate in water. Mobile Phase B: Acetonitrile Flow: 16 mL/min Time (min)/% B: 0/30, 10/65) to afford Example 122 (180 mg, 45.3% yield) as a white solid. MS(ESI) m/z: 363.2 (M+H)$^+$. 400 MHz, DMSO-d$_6$) δ ppm 12.86 (br. s., 1H) 8.11 (s, 1H) 7.89 (s, 1H) 7.55 (s, 4H) 7.27-7.37 (m, 1H) 7.63-7.69 (m, 1H) 6.85-6.89 (m, 2H) 5.10 (q, J=7.2 Hz, 1H) 3.76-3.79 (m, 5H) 3.48-3.54 (m, 1H) 3.08-3.14 (m, 1H) 1.50 (d, J=7.2 Hz, 3H). HPLC RT-14.82 purity 96.99% and 13.69 purity 98.6% and 97.6% ee with Chiral HPLC RT=15.64 min, [α]$^{24.7}_D$=174.00 (c 0.1, MeOH).

Examples 123 and 124 (Enantiomers 1 and 2)

1-(4-(1H-Pyrazol-4-yl)phenyl)-4-(2-hydroxypropan-2-yl)-3-(3-methoxybenzyl)imidazolidin-2-one

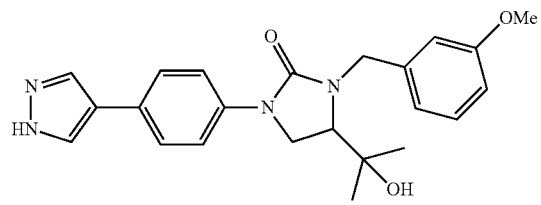 [SMILES: COc1cccc(CN2C(=O)N(c3ccc(-c4cn[nH]c4)cc3)CC2C(C)(C)O)c1]

To the solution of ethyl 1-(4-bromophenyl)-3-(3-methoxybenzyl)-2-oxoimidazolidine-4-carboxylate (270 mg, 0.623 mmol) in THF (10 mL) was added methyl magnesium bromide (3 M in diethyl ether) (1.039 mL, 3.12 mmol) at −20° C. and reaction mixture was stirred at same temperature for 2 h. Reaction was quenched with saturated NH$_4$Cl solution, extracted with EtOAc (2×25 mL). Combined organic extracts were washed with brine, dried over Na$_2$SO$_4$ and concentrated to afford the Example 123A (190 mg, 58% yield) as a viscous yellow liquid. MS(ESI) m/z: 419.1 (M+H)$^+$

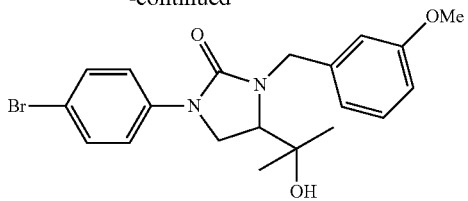

Example 123 and 124

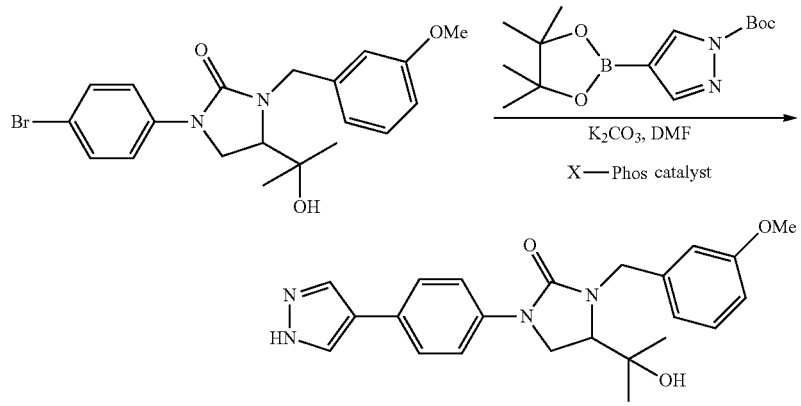

Example 123A: Preparation of 1-(4-bromophenyl)-4-(2-hydroxypropan-2-yl)-3-(3-methoxybenzyl)imidazolidin-2-one

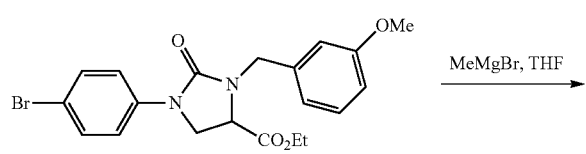

To the solution of Example 123A (190 mg, 0.453 mmol) in DMF (3 mL) were added K$_2$CO$_3$ (188 mg, 1.359 mmol) and water (0.5 mL), the reaction mixture was purged with nitrogen for 10 min and then charged with tert-butyl 4-(4,4,5,5-tetramethyl-1,3,2-dioxaborolan-2-yl)-1H-pyrazole-1-carboxylate (200 mg, 0.680 mmol) and 2nd generation XPhos precatalyst (21.39 mg, 0.027 mmol) and again purged with nitrogen for 10 min and heated at 90° C. for 16 h. The reaction mixture was cooled, diluted with water, extracted with EtOAc (2×25 mL), combined organic layer was washed with water, brine solution, dried over Na$_2$SO$_4$, filtered and concentrated. The crude product was purified by preparative HPLC (Column: SunFire C18 (150×19 mm, 5μ), Solvent A (90% water, 10% ACN, 0.1% HCOOH) and Solvent B (10% water, 90% ACN, 0.1% HCOOH, UV 220 nm). The crude was subjected to SFC purification to afford to separate the enantiomers. The fractions were concentrated to afford Example 123 (Enantiomer 1, 38 mg, 19.5% yield) as a white solid. MS(ESI) m/z: 407.2 (M+H)+; ¹H NMR (300 MHz, DMSO-d₆) δ ppm 12.84 (br. s., 1H) 7.99 (s, 2H) 7.52-7.63 (m, 4H) 7.25 (t, J=8.03 Hz, 1H) 6.80-6.89 (m, 3H) 4.79 (d, J=15.20 Hz, 2H) 4.48 (d, J=15.39 Hz, 1H) 3.81-3.91 (m, 1H) 3.73 (s, 3H) 3.50 (q, J=5.63 Hz, 2H) 1.11 (d, J=6.04 Hz, 6H). Example 124 (Enantiomer 2, 37 mg, 19.1% yield) as a white solid. MS(ESI) m/z: 407.2 (M+H)+; ¹H NMR (300 MHz, DMSO-d₆) δ ppm 12.74 (br. s., 1H) 7.99 (s, 2H) 7.52-7.63 (m, 4H) 7.25 (t, J=8.03 Hz, 1H) 6.80-6.89 (m, 3H) 4.79 (d, J=15.30 Hz, 2H) 4.48 (d, J=15.30 Hz, 1H) 3.81-3.90 (m, 1H) 3.73 (s, 3H) 3.46-3.54 (m, 2H) 1.11 (d, J=6.04 Hz, 6H).

Example 125

(R)-1-(4-(1H-Pyrazol-4-yl)phenyl)-4-(hydroxymethyl)-3-(3-methoxybenzyl)imidazolidin-2-one

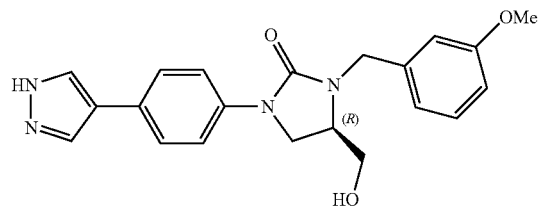

Example 125A: Preparation of (S)-ethyl 2-(3-(4-bromophenyl)ureido)-3-hydroxypropanoate

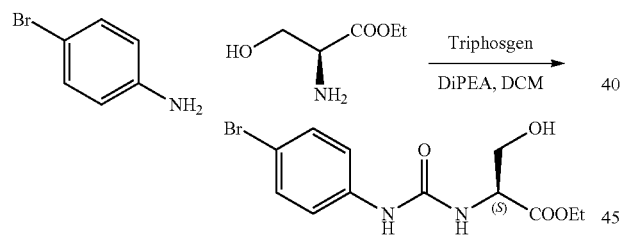

To a solution of triphosgene (3.19 g, 10.75 mmol) in DCM (100 mL) at rt, was added slowly a mixture of 4-bromoaniline (5.0 g, 29.1 mmol) and DIPEA (5.58 mL, 32.0 mmol) in DCM (50 mL) over a period of 10 min under nitrogen, then stirred at rt for 30 min. A solution of (S)-ethyl 2-amino-3-hydroxypropanoate, HCl (4.93 g, 29.1 mmol) and DIPEA (10.66 mL, 61.0 mmol) in DCM (75 mL) was added. The reaction mixture was stirred for 2.5 h. The reaction mixture was concentrated, and the residue was dissolved in EtOAc and washed with water, brine, dried over Na₂SO₄, and concentrated. The residue was dissolved in DCM and precipitated by adding hexane. The solid was filtered and washed with hexane and dried to afford (S)-ethyl 2-(3-(4-bromophenyl)ureido)-3-hydroxypropanoate (9.0 g, 94% yield) as a white solid. MS(ESI) m/z: 331.0 (M+H)+. ¹H NMR (400 MHz, DMSO-d₆) δ ppm 9.00 (s, 1H), 7.42-7.33 (m, 5H), 6.56 (d, J=8.5 Hz, 1H), 5.18 (t, J=5.3 Hz, 1H), 4.31-4.25 (m, 1H), 4.16-4.09 (m, 2H), 3.80 (ddd, J=10.8, 5.0, 3.8 Hz, 1H), 3.65 (ddd, J=10.8, 5.3, 4.0 Hz, 1H), 1.21 (t, J=7.0 Hz, 3H).

Example 125B: Preparation of (S)-ethyl 2-(3-(4-bromophenyl)ureido)-3-((tert-butyldimethylsilyl)oxy)propanoate

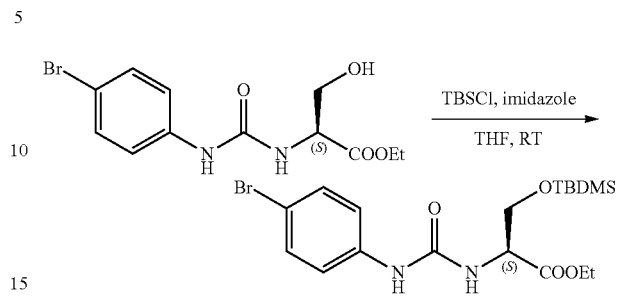

To the solution of (S)-ethyl 2-(3-(4-bromophenyl)ureido)-3-hydroxypropanoate (12 g, 36.2 mmol) in THF (250 mL) at 0° C., was added imidazole (4.93 g, 72.5 mmol), TBDMS-Cl (8.19 g, 54.4 mmol) and DMAP (1.328 g, 10.87 mmol). Reaction was slowly warmed to rt and stirred for 16 h. Reaction was diluted with EtOAc (100 mL), washed with water (2×100 mL), brine solution, dried over Na₂SO₄, and concentrate. The crude product was purified by flash chromatography (120 g REDISEP® SiO₂ column, eluting with 40% EtOAc in n-hexanes) to afford the (S)-ethyl 2-(3-(4-bromophenyl)ureido)-3-((tert-butyldimethylsilyl)oxy)propanoate (13.5 g, 84% yield) as a white solid. MS(ESI) m/z: 447.1 (M+H)+. ¹H NMR (300 MHz, DMSO-d₆) δ ppm 9.08 (s, 1H), 7.44-7.32 (m, 4H), 6.47 (d, J=8.7 Hz, 1H), 4.41 (dt, J=8.4, 3.4 Hz, 1H), 4.13 (q, J=7.2 Hz, 2H), 4.00 (dd, J=10.2, 3.4 Hz, 1H), 3.78 (dd, J=10.2, 3.8 Hz, 1H), 1.21 (t, J=7.2 Hz, 3H), 0.88-0.82 (m, 9H), 0.03 (d, J=3.4 Hz, 6H).

Example 125C: Preparation of (R)-1-(4-bromophenyl)-3-(1-((tert-butyldimethylsilyl) oxy)-3-hydroxypropan-2-yl)urea

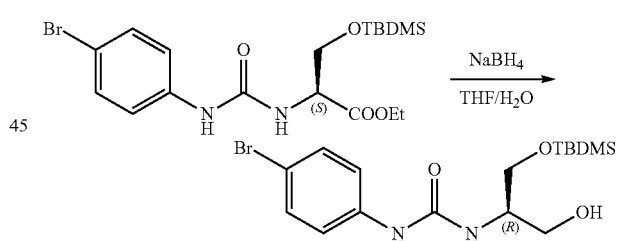

To a solution of (S)-ethyl 2-(3-(4-bromophenyl)ureido)-3-((tert-butyldimethylsilyl)oxy)propanoate (8.75 g, 19.64 mmol) in THF (100 mL) at 0° C., was added NaBH₄ (2.230 g, 58.9 mmol) and water (50 mL). The reaction mixture was warmed to rt and stirred for 16 h. The reaction was slowly quenched with water (100 mL), extracted with EtOAc (2×100 mL). The organic phase was washed with brine, dried over Na₂SO₄, and concentrate. The crude product was purified by flash chromatography (120 g REDISEP® SiO₂ column, eluting with 40% EtOAc in n-hexanes) to afford the (R)-1-(4-bromophenyl)-3-(1-((tert-butyldimethylsilyl)oxy)-3-hydroxypropan-2-yl)urea (6.0 g, 76% yield) as a white gummy solid. MS(ESI) m/z: 405.1 (M+H)+. ¹H NMR (300 MHz, DMSO-d₆) δ ppm 8.78 (s, 1H), 7.41-7.30 (m, 4H), 6.01 (d, J=7.9 Hz, 1H), 4.79 (t, J=4.9 Hz, 1H), 3.66-3.36 (m, 5H), 0.87 (s, 9H), 0.05 (s, 6H).

Example 125D: Preparation of (R)-1-(4-bromophenyl)-4-(((tert-butyldimethylsilyl)oxy) methyl)imidazolidin-2-one

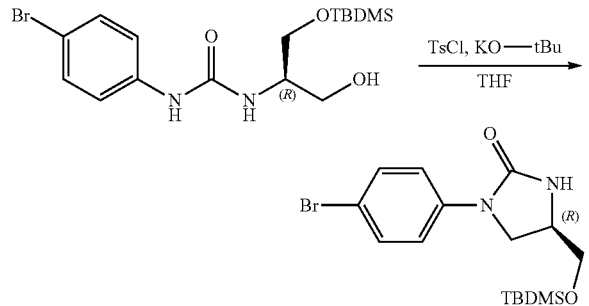

To a solution of (R)-1-(4-bromophenyl)-3-(1-((tert-butyldimethylsilyl)oxy)-3-hydroxypropan-2-yl)urea (1.0 g, 2.479 mmol) in THF (60 mL) at 0° C., was added potassium tert-butoxide (0.668 g, 5.95 mmol), followed by p-toluenesulfonyl chloride (0.567 g, 2.97 mmol). The mixture was stirred at 0° C. for 40 min. The reaction was warmed to rt and filtered through CELITE® pad, which was rinsed with THF. The filtrate was concentrated. The crude product was purified by flash chromatography (40 g REDISEP® $SiO_2$ column, eluting with 100% EtOAc in n-hexanes) to afford (R)-1-(4-bromophenyl)-4-(((tert-butyldimethylsilyl)oxy) methyl)imidazolidin-2-one (500 mg, 52.3% yield) as a white solid. MS(ESI) m/z: 385.6 (M+H)$^+$

Example 125E: Preparation of (R)-1-(4-bromophenyl)-4-(((tert-butyldimethylsilyl)oxy) methyl)-3-(3-methoxybenzyl)imidazolidin-2-one

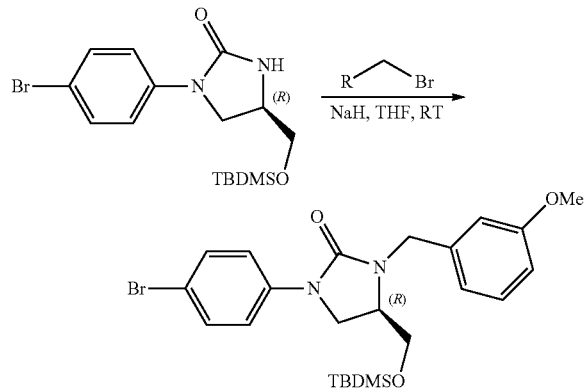

To the solution of Example 125D (520 mg, 1.349 mmol) in THF (20 mL) at 0° C., was added NaH (108 mg, 2.70 mmol, 60% in mineral oil) portionwise over 10 min. Then 1-(bromomethyl)-3-methoxybenzene (353 mg, 1.754 mmol) was added and the reaction mixture was stirred at rt for 2.5 h. The reaction mixture was quenched with methanol, concentrated under reduced pressure, The crude product was purified by flash chromatography (40 g REDISEP® $SiO_2$ column, eluting with 100% hexane for 3 min; 0-100% EtOAc/hexane for 30 min) to afford Example 125E (580 mg, 85% yield) as a white gummy solid. MS(ESI) m/z: 507.1 (M+H)$^+$. $^1$H NMR (400 MHz, methanol-$d_4$) δ ppm 7.56-7.51 (m, 2H), 7.49-7.45 (m, 2H), 7.30-7.25 (m, 1H), 6.94-6.90 (m, 2H), 6.88-6.85 (m, 1H), 4.75 (d, J=15.6 Hz, 1H), 4.29 (d, J=15.6 Hz, 1H), 3.99-3.94 (m, 1H), 3.84-3.81 (m, 1H), 3.80 (s, 3H), 3.78-3.72 (m, 1H), 3.70-3.63 (m, 2H), 3.36-3.35 (m, 1H), 0.85 (s, 9H), 0.05 (d, J=5.5 Hz, 6H).

Example 125F: Preparation of (R)-1-(4-bromophenyl)-4-(hydroxymethyl)-3-(3-methoxybenzyl)imidazolidin-2-one

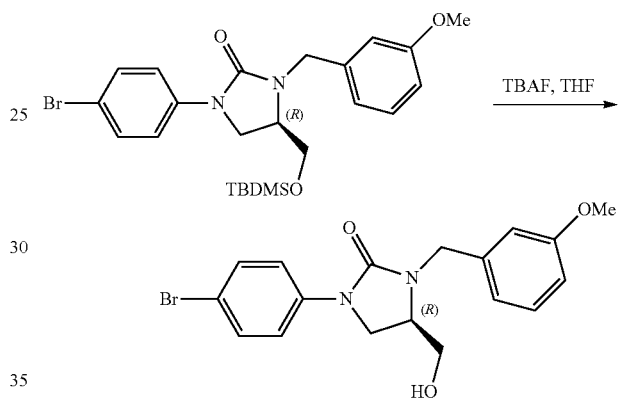

To a solution of Example 125E (580 mg, 1.147 mmol) in THF (15 mL) at rt, was added TBAF (1 M in THF) (1.61 mL, 1.61 mmol) and stirred for 3 h. The reaction mixture was diluted with EtOAc, washed with 10% NaHCO$_3$ solution and brine. The organic layer was dried over Na$_2$SO$_4$ and concentrated. The crude product was recrystallized with DCM/hexane to afford Example 125F (280 mg, 62.5% yield) as a white solid. MS(ESI) m/z: 393.2 (M+H)$^+$. $^1$H NMR (400 MHz, DMSO-$d_6$) δ ppm 7.61-7.56 (m, 2H), 7.52-7.48 (m, 2H), 7.29-7.24 (m, 1H), 6.90-6.83 (m, 3H), 4.99 (t, J=5.3 Hz, 1H), 4.68 (d, J=15.6 Hz, 1H), 4.19 (d, J=15.6 Hz, 1H), 3.92-3.84 (m, 1H), 3.62-3.54 (m, 3H), 3.52-3.46 (m, 1H).

Example 125

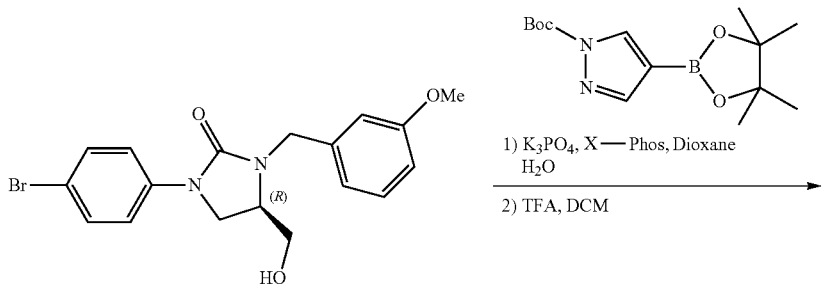

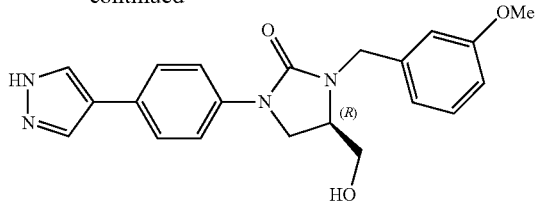

To the solution of Example 125F (100 mg, 0.256 mmol) in dioxane (8 mL), was added tert-butyl 4-(4,4,5,5-tetramethyl-1,3,2-dioxaborolan-2-yl)-1H-pyrazole-1-carboxylate (113 mg, 0.383 mmol), potassium phosphate tribasic (109 mg, 0.511 mmol) and water (1 mL). The reaction mixture was purged with nitrogen for 10 min and then 2nd generation XPhos precatalyst (12.07 mg, 0.015 mmol) was added and again purged with nitrogen for 10 min. The mixture was heated at 80° C. for 3 h. The reaction was cooled to rt and diluted with EtOAc, washed with water and brine, dried over $Na_2SO_4$, filtered and concentrated. The crude product was dissolved in DCM (8 mL) and TFA (0.3 mL, 3.89 mmol) was added. The mixture was stirred at rt for 4 h. The reaction mixture was concentrated to dryness, and purified by preparative HPLC purification, to afford Example 125 (26 mg, 27% yield) as a white solid. MS(ESI) m/z: 379.2 $(M+H)^+$. $^1$H NMR (400 MHz, DMSO-$d_6$) δ ppm 13.11 (br. s., 1H) 8.37 (s, 1H) 8.13 (s, 1H) 7.77-7.88 (m, 4H) 7.49-7.58 (m, 1H) 7.05-7.17 (m, 3H) 5.24 (t, J=5.26 Hz, 1H) 4.94 (d, J=15.65 Hz, 1H) 4.45 (d, J=15.65 Hz, 1H) 4.11-4.21 (m, 1H) 4.00 (s, 3H) 3.81-3.91 (m, 3H) 3.72-3.79 (m, 1H). HPLC RT=7.74 min, 99.89% (Method A), HPLC RT=7.42 min, 99.93% (Method B). 100% ee with Chiral HPLC RT=8.81 min. $[α]^{25.2}_D$=−128.00 (c 0.1, MeOH).

Examples 126 and 127

3-(4-(1H-Pyrazol-4-yl)phenyl)-4-(hydroxymethyl)-1-(3-methoxybenzyl)imidazolidin-2-one (Enantiomers 1 and 2)

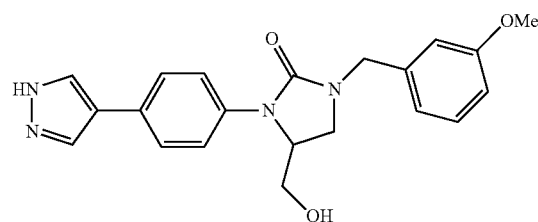 [SMILES: COc1cccc(CN2CC(CO)N(c3ccc(-c4cn[nH]c4)cc3)C2=O)c1]

Example 126A: Preparation of ethyl 3-(3-(4-bromophenyl)-1-(3-methoxybenzyl)ureido)-2-chloropropanoate

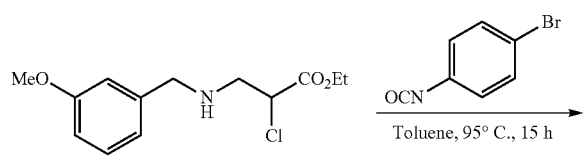

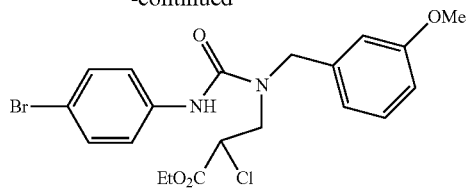

To a solution of ethyl 2-chloro-3-((3-methoxybenzyl)amino)propanoate (390 mg, 1.435 mmol) in Toluene (10 mL) was added 1-bromo-4-isocyanatobenzene (313 mg, 1.579 mmol). The reaction mixture was heated at 100° C. for 16 h. The mixture was concentrated to dryness to afford ethyl 3-(3-(4-bromophenyl)-1-(3-methoxybenzyl) ureido)-2-chloropropanoate (0.65 g, 13.5% yield) as a brown gummy solid. Crude product was used further without purification. MS(ESI) m/z: 471.2 $(M+H)^+$.

Example 126B: 3-(4-Bromophenyl)-1-(3-methoxybenzyl)-2-oxoimidazolidine-4-carboxylic Acid To a solution of ethyl 3-(3-(4-bromophenyl)-1-(3-methoxybenzyl)ureido)-2-chloropropanoate (650 mg, 1.384 mmol) in THF (10 mL) at 0° C., was added NaH (69.9 mg, 2.77 mmol, 60% in mineral oil). The mixture was stirred at rt for 16 h. The reaction mixture was slowly quenched with ice water (25 mL), then extracted with EtOAc (2×25 mL). The combined organic layer was washed with water and brine, dried over $Na_2SO_4$, and concentrated to afford 3-(4-bromophenyl)-1-(3-methoxybenzyl)-2-oxoimidazolidine-4-carboxylic acid (0.55 g, 34% yield) as a yellow gummy solid. MS(ESI) m/z: 405.1 $(M+H)^+$.

Example 126C: Preparation of ethyl 3-(4-bromophenyl)-1-(3-methoxybenzyl)-2-oxoimidazolidine-4-carboxylate

Example 126D: Preparation of 3-(4-bromophenyl)-4-(hydroxymethyl)-1-(3-methoxybenzyl)imidazolidin-2-one

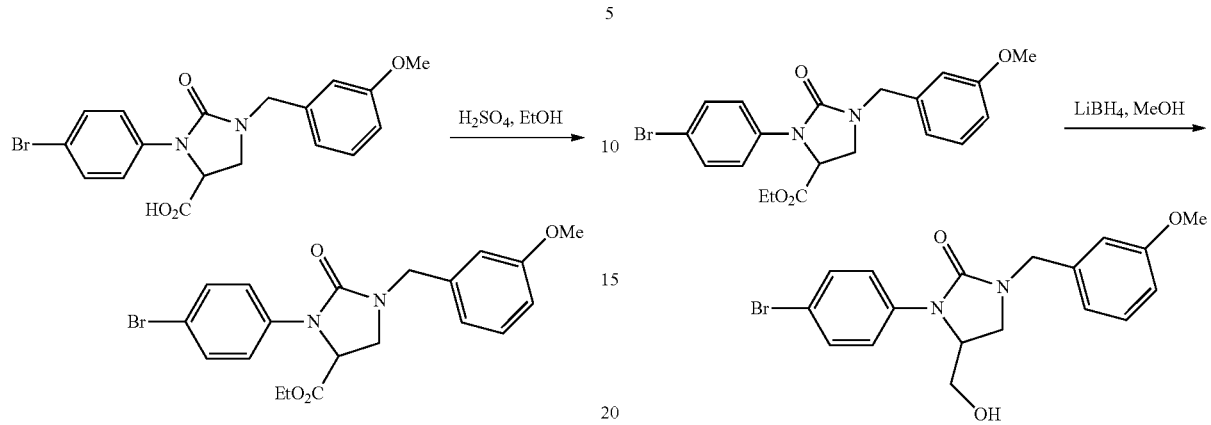

To a solution of 3-(4-bromophenyl)-1-(3-methoxybenzyl)-2-oxoimidazolidine-4-carboxylic acid (550 mg, 1.357 mmol) in ethanol (15 mL) was added H$_2$SO$_4$ (0.289 mL, 5.43 mmol). The reaction mixture was stirred at rt for 16 h. The reaction mixture was slowly quenched with NaHCO$_3$ (50 mL), then extracted with EtOAc (2×50 mL). The combined organic layer was washed with water and brine, dried over Na$_2$SO$_4$, and concentrated. The crude product was purified by flash chromatography (24 g REDISEP® SiO$_2$ gradient elution; 100% Hex for 5 min; 0-100% EtOAc/Hex for 30 min) to afford ethyl 3-(4-bromophenyl)-1-(3-methoxybenzyl)-2-oxoimidazolidine-4-carboxylate (0.18 g, 14.3% yield) as yellow gummy solid. MS(ESI) m/z: 435.1 (M+H)$^+$. $^1$H NMR (400 MHz, DMSO-d$_6$) δ ppm 7.53-7.41 (m, 4H), 7.30-7.25 (m, 1H), 6.91-6.80 (m, 3H), 5.09 (dd, J=10.0, 3.5 Hz, 1H), 4.47-4.26 (m, 2H), 4.14-4.08 (m, 2H), 3.68 (t, J=9.8 Hz, 1H), 3.36 (dd, J=9.5, 3.0 Hz, 1H), 1.11 (t, J=7.0 Hz, 3H).

To a solution of ethyl 3-(4-bromophenyl)-1-(3-methoxybenzyl)-2-oxoimidazolidine-4-carboxylate (180 mg, 0.415 mmol) in ethanol (10 mL) at 0° C., was added LiBH$_4$ (36.2 mg, 1.662 mmol). The mixture was allowed to stir at rt for 16 h. The ethanol was concentrated. The residue was diluted with water (50 mL), then extracted with EtOAc (2×50 mL). The combined organic layer was washed with water and brine solution, dried over Na$_2$SO$_4$, filtered and concentrated to afford 3-(4-bromophenyl)-4-(hydroxymethyl)-1-(3-methoxybenzyl)imidazolidin-2-one (140 mg, 52% yield) as a pale yellow gummy solid. Crude product was taken for next step without further purification. MS(ESI) m/z: 393.1 (M+H)$^+$. $^1$H NMR (300 MHz, DMSO-d$_6$) δ ppm 7.59-7.42 (m, 4H), 7.28 (t, J=7.9 Hz, 1H), 6.86 (br. s., 2H), 4.97 (t, J=5.3 Hz, 1H), 4.47-4.24 (m, 3H), 3.74 (s, 3H), 3.48-3.40 (m, 3H), 3.28 (d, J=3.4 Hz, 1H).

Example 126E: Preparation of tert-butyl 4-(4-(5-(hydroxymethyl)-3-(3-methoxybenzyl)-2-oxoimidazolidin-1-yl)phenyl)-1H-pyrazole-1-carboxylate

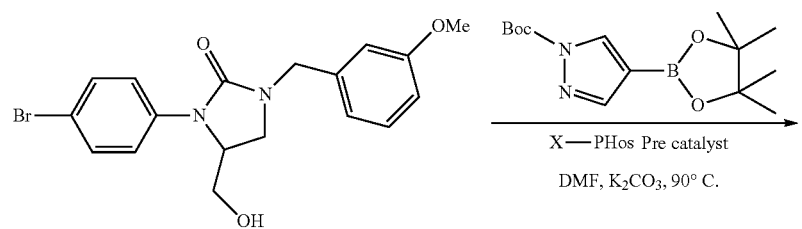

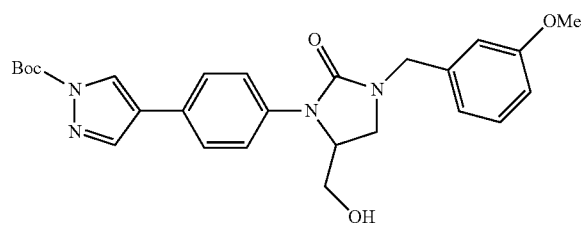

To a solution of 3-(4-bromophenyl)-4-(hydroxymethyl)-1-(3-methoxybenzyl) imidazolidin-2-one (140 mg, 0.358 mmol) and tert-butyl 4-(4,4,5,5-tetramethyl-1,3,2-dioxaborolan-2-yl)-1H-pyrazole-1-carboxylate (137 mg, 0.465 mmol) in DMF (3 mL), was added $K_2CO_3$ (148 mg, 1.073 mmol) and water (0.5 mL). The mixture was purged with nitrogen for 10 min and then 2nd generation XPhos precatalyst (16.89 mg, 0.021 mmol) was added and reaction mixture was heated at 95° C. for 16 h. Reaction mixture was diluted with water (25 mL), then extracted with EtOAc (2×25 mL). The combined organic layer was washed with water and brine, dried over $Na_2SO_4$, filtered and concentrated to afford 3-(4-bromophenyl)-4-(hydroxymethyl)-1-(3-methoxybenzyl) imidazolidin-2-one (250 mg, 51% yield) as a brown gummy solid. Crude product was taken for next step without further purification. MS(ESI) m/z: 479.3 (M+H)+.

Preparation of 3-(4-(1H-pyrazol-4-yl)phenyl)-4-(hydroxymethyl)-1-(3-methoxybenzyl)imidazolidin-2-one

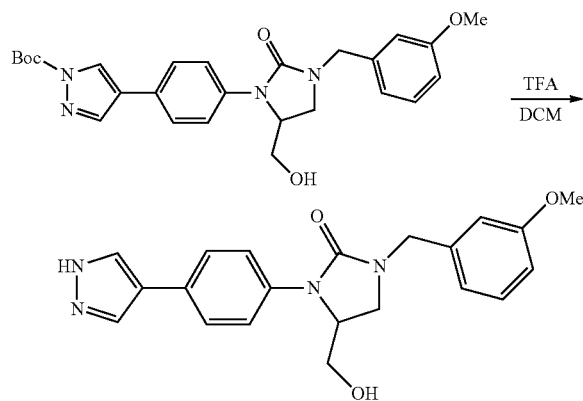

To a solution of tert-butyl 4-(4-(5-(hydroxymethyl)-3-(3-methoxybenzyl)-2-oxoimidazolidin-1-yl)phenyl)-1H-pyrazole-1-carboxylate (250 mg, 0.522 mmol) in DCM (5 mL) at rt, was added TFA (0.201 mL, 2.61 mmol). The reaction mixture was stirred for 3 h, then was concentrated. The residue was washed with hexane and diethyl ether, then the residue was purified by prep HPLC. The enantiomers were separated by Supercritical Fluid Chromatography [CHIRALPAK® AS-H (250×4.6) mm, 5 Co-solvent is 45% (0.25% DEA in methanol)] to give Example 126, Enantiomer 1 (19 mg, 9.4% yield) as a white solid. MS(ESI) m z: 379.4 (M+H)+; $^1$H NMR (400 MHz, DMSO-$d_6$) δ ppm 12.76 (s, 1H) 8.00 (s, 2H) 7.50-7.58 (m, 4H) 7.28 (t, J=7.97 Hz, 1H) 6.83-6.90 (m, 3H) 4.95 (br. s., 1H) 4.25-4.45 (m, 3H) 3.75 (s, 3H) 3.38-3.50 (m, 3H) 3.26-3.30 (m, 1H). 99.44% Chiral HPLC RT=2.4 min. $[α]^{24.9}_D$=−20 (c 0.1, MeOH). The slower eluting peak is Enantiomer 2, Example 127 (18 mg, 9.0% yield), a white solid. MS(ESI) m z: 379.4 (M+H)+. $^1$H NMR (400 MHz, DMSO-$d_6$) δ ppm 12.83 (s, 1H) 8.00 (s, 2H) 7.50-7.58 (m, 4H) 7.28 (t, J=7.97 Hz, 1H) 6.82-6.90 (m, 3H) 4.95 (br. s., 1H) 4.26-4.45 (m, 3H) 3.75 (s, 3H) 3.38-3.51 (m, 3H) 3.29 (d, J=4.27 Hz, 1H). 98.1% Chiral HPLC RT=3.25 min. (Method X); $[α]^{24.9}_D$=18.4 (c 0.1, MeOH).

The following Examples in Table 7 were made by using the same procedure as shown in Examples 122 to 127.

TABLE 7

| Ex. | R | Name | LCMS (M + H)+ | HPLC Method, RT (min.) and Purity | NMR |
|---|---|---|---|---|---|
| 128 | Chiral | (R)-1-(4-(1H-pyrazol-4-yl)phenyl)-3-(4-fluoro-3-methoxybenzyl)-4-(hydroxymethyl)imidazolidin-2-one (Enantiomer 1) | 397.2 | I: 8.13, 99.3% J: 780, 99.9% | $^1$H NMR (400 MHz, DMSO-$d_6$) d ppm 12.86 (br. s., 1H) 8.12 (s, 1H) 7.87 (s, 1H) 7.53-7.63 (m, 4H) 6.70-6.79 (m, 3H) 5.00 (t, J = 5.27 Hz, 1H) 4.63 (d, J = 16.06 Hz, 1H) 4.25 (d, J = 16.06 Hz, 1H) 3.89-3.99 (m, 1H) 3.75 (s, 3H) 3.56-3.67 (m, 3H) 3.47-3.55 (m, 1H). |
| 129 | Chiral | (S)-1-(4-(1H-pyrazol-4-yl)phenyl)-3-(3-fluoro-5-methoxybenzyl)-4-(hydroxymethyl)-imidazolidin-2-one | 397.2 | I: 8.12, 99.8% J: 7.82, 99.7% | $^1$H NMR (400 MHz, DMSO-$d_6$) d ppm 12.86 (br. s., 1H) 8.09 (br. s., 2H) 7.53-7.62 (m, 4H) 6.69-6.78 (m, 3H) 5.00 (t, J = 5.02 Hz, 1H) 4.63 (d, J = 16.06 Hz, 1H) 4.25 (d, J = 16.06 Hz, 1H) 3.87-3.98 (m, 1H) 3.77 (s, 3 H) 3.55-3.68 (m, 3H) 3.50-3.55 (m, 1H). |

TABLE 7-continued

| Ex. | R | Name | LCMS (M + H)+ | HPLC Method, RT (min.) and Purity | NMR |
|---|---|---|---|---|---|
| 130 | (structure) | (R)-1-(4-bromophenyl)-4-(hydroxymethyl)-3-(3-methoxybenzyl)-imidazolidin-2-one (Enantiomer 1) | 397.2 | I: 7.86, 99.5% J: 7.61, 99.5% | ¹H NMR (400 MHz, DMSO-d₆) d ppm 12.85 (br. s., 1H) 8.11 (br. s., 1H) 7.87 (br. s., 1H) 7.51-7.63 (m, 4H) 7.08-7.22 (m, 2H) 6.88 (ddd, J = 8.28, 4.27, 2.01 Hz, 1H) 4.99 (t, J = 5.27 Hz, 1H) 4.64 (d, J = 15.56 Hz, 1H) 4.23 (d, J = 15.06 Hz, 1H) 3.86-3.95 (m, 1H) 3.83 (s, 3H) 3.55-3.68 (m, 3H) 3.46-3.54 (m, 1H). |
| 131 | (structure) | (S)-1-(4-(1H-pyrazol-4-yl)phenyl)-3-(4-fluoro-3-methoxybenzyl)-4-(hydroxymethyl)-imidazolidin-2-one (Enantiomer 2) | 397.2 | I: 7.85, 99.5% J: 7.58, 99.6% | ¹H NMR (400 MHz, DMSO-d₆) d ppm 12.85 (br. s., 1H) 8.10 (br. s., 1H) 7.88 (br. s., 1H) 7.49-7.65 (m, 4H) 7.07-7.23 (m, 2H) 6.88 (ddd, J = 8.16, 4.39, 2.01 Hz, 1H) 4.95-5.04 (m, 1H) 4.64 (d, J = 15.56 Hz, 1H) 4.22 (d, J = 15.56 Hz, 1H) 3.86-3.96 (m, 1H) 3.78-3.85 (m, 3H) 3.55-3.66 (m, 3H) 3.45-3.54 (m, 1H). |
| 132 | (structure) | (4R)-1-(4-(1H-pyrazol-4-yl)phenyl)-4-(hydroxymethyl)-3-(1-(3-methoxyphenyl)ethyl)imidazolidin-2-one (Enantiomer 1) | 393.2 | E: 1.44, 100.0% F: 1.59, 100.0% | ¹H NMR (400 MHz, DMSO-d₆) d ppm 12.86 (br. s., 1H) 8.11 (br. s., 1H) 7.87 (br. s., 1H) 7.51-7.59 (m, 4H) 7.26 (t, J = 7.95 Hz, 1H) 6.95-7.03 (m, 2H) 6.84 (dd, J = 7.83, 2.45 Hz, 1H) 4.98 (q, J = 6.68 Hz, 1H) 4.85 (t, J = 5.26 Hz, 1H) 3.87-3.96 (m, 1H) 3.83 (br. s., 1H) 3.75 (s, 3H) 3.64 (dd, J = 8.93, 4.77 Hz, 1H) 3.18-3.25 (m, 1H) 3.12 (dt, J = 11.00, 5.75 Hz, 1H) 1.64 (d, J = 7.34 Hz, 3H). |
| 133 | (structure) | (4R)-1-(4-(1H-pyrazol-4-yl)phenyl)-4-(hydroxymethyl)-3-(1-(3-methoxyphenyl)ethyl)imidazolidin-2-one (Enantiomer 2) | 393.3 | I: 8.14, 99.7% J: 7.70, 99.9% | ¹H NMR (300 MHz, DMSO-d₆) d ppm 7.99 (s, 2H) 7.55 (s, 4H) 7.24-7.35 (m, 1H) 6.90-6.99 (m, 2H) 6.86 (dd, J = 7.93, 2.27 Hz, 1H) 5.04-5.16 (m, 1H) 3.78-3.88 (m, 1H) 3.75 (s, 3H) 3.39-3.65 (m, 4H) 1.58 (d, J = 7.18 Hz, 3H). |

TABLE 7-continued

| Ex. | R | Name | LCMS (M + H)+ | HPLC Method, RT (min.) and Purity | NMR |
|---|---|---|---|---|---|
| 134 | (structure) | 4-(hydroxymethyl)-1-(3-methoxy-4-(1H-pyrazol-4-yl)phenyl)-3-(3-methoxybenzyl)imidazolidin-2-one (Enantiomer 1) | 409.2 | I: 5.32 99.76% J: 6.37, 99.00% XIII: 10.53, 9.44% ee | 1H NMR (400 MHz, DMSO-d6) d ppm 12.78 (s, 1H) 8.09 (d, J = 2.01 Hz, 1H) 8.05 (s, 1H) 7.92 (s, 1H) 7.56 (d, J = 8.53 Hz, 1H) 7.21-7.27 (m, 1H) 7.12 (dd, J = 8.50, 2.10 Hz, 1H) 6.98-7.03 (m, 2H) 6.76-6.80 (m, 1H) 5.17 (t, J = 5.62 Hz, 1H) 4.69-4.76 (m, 1H) 4.48 (s, 2H) 4.08 (t, J = 8.66 Hz, 1H) 3.86 (s, 3H) 3.80-3.85 (m, 1H) 3.75 (s, 3H) 3.67-3.74 (m, 1H) 3.58-3.65 (m, 1H). |
| 135 | (structure) | 4-(hydroxymethyl)-1-(3-methoxy-4-(1H-pyrazol-4-yl)phenyl)-3-(3-methoxybenzyl)imidazolidin-2-one (Enantiomer 2) | 409.2 | I: 5.34, 98.21% J: 6.37, 96.80% XIII: 19.90 98.46% ee | 1H NMR (400 MHz, DMSO-d6) d ppm 12.80 (s, 1H) 8.09 (d, J = 2.00 Hz, 1H) 8.01 (s, 1H) 7.94 (s, 1H) 7.56 (d, J = 8.47 Hz, 1H) 7.21-7.27 (m, 1H) 7.12 (dd, J = 8.50, 2.16 Hz, 1H) 6.99-7.03 (m, 2H) 6.78 (dd, J = 7.44, 2.16 Hz, 1H) 5.17 (t, J = 5.62 Hz, 1H) 4.69-4.76 (m, 1H) 4.48 (s, 2H) 4.08 (t, J = 8.60 Hz, 1H) 3.86 (s, 3H) 3.83 (dd, J = 8.85, 6.84 Hz, 1H) 3.75 (s, 3H) 3.68-3.73 (m, 1H) 3.58-3.66 (m, 1H). |
| 136 | Chiral (structure) | (R)-1-(4-(3-fluoropyridin-4-yl)phenyl)-4-(hydroxymethyl)-3-(3-methoxybenzyl)imidazolidin-2-one | 408.2 | E: 1.57, 99.65% F: 1.80, 99.73% X: 25.55, 100% ee | 1H NMR (400 MHz, DMSO-d6) d ppm 8.62 (d, J = 2.93 Hz, 1H) 8.47 (d, J = 4.40 Hz, 1H) 7.73-7.84 (m, 2H) 7.59-7.71 (m, 3H) 7.27 (t, J = 7.95 Hz, 1H) 6.81-6.93 (m, 3H) 5.00 (t, J = 5.14 Hz, 1H) 4.71 (d, J = 15.65 Hz, 1H) 4.21 (d, J = 15.65 Hz, 1H) 3.91-4.01 (m, 1H) 3.74 (s, 3H) 3.57-3.70 (m, 3H) 3.46-3.55 (m, 1H). 19F NMR (400 MHz, methanol-d4) d ppm −133.649. [α]25.3D = −120 (c 0.05, DMSO). |

Example 137

1-(4-(1H-Pyrazol-4-yl)phenyl)-3-(3-methoxybenzyl)-4,4-dimethylimidazolidin-2-one

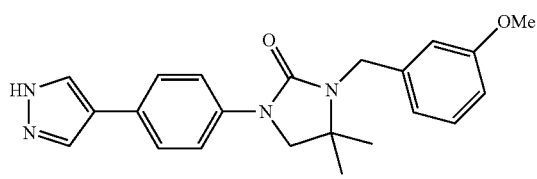 [SMILES: COc1cccc(CN2C(=O)N(c3ccc(-c4cn[nH]c4)cc3)CC2(C)C)c1]

Example 137A: Preparation of 1-(4-bromophenyl)-4,4-dimethylimidazolidin-2-one

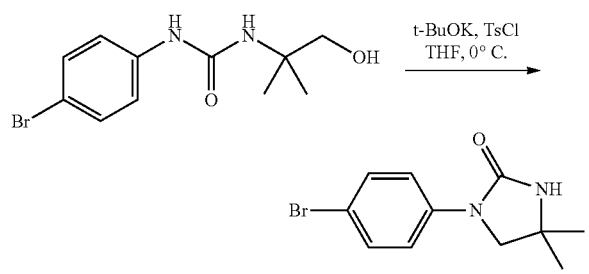

To a stirred suspension of 1-(4-bromophenyl)-3-(1-hydroxy-2-methylpropan-2-yl)urea (700 mg, 2.438 mmol) and potassium tert-butoxide (657 mg, 5.85 mmol) in THF at 0° C., was added dropwise a solution of p-toluenesulfonyl chloride (558 mg, 2.93 mmol) in THF (10 mL). The reaction mixture was stirred at the same temperature for 2 h. The reaction mixture was slowly quenched with water (25 mL), then extracted with EtOAc (2×25 mL). The combined organic layer was washed with brine, dried over $Na_2SO_4$, and concentrated. The crude product 1-(4-bromophenyl)-4,4-dimethylimidazolidin-2-one (0.4 g, 61% yield, white solid) was used without further purification. MS(ESI) m/z: 271.4 $(M+H)^+$. $^1H$ NMR (300 MHz, DMSO-$d_6$) δ ppm 7.53-7.43 (m, 4H), 3.55 (s, 2H), 1.27 (s, 6H).

Example 137B: Preparation of 1-(4-bromophenyl)-3-(3-methoxybenzyl)-4,4-dimethylimidazolidin-2-one

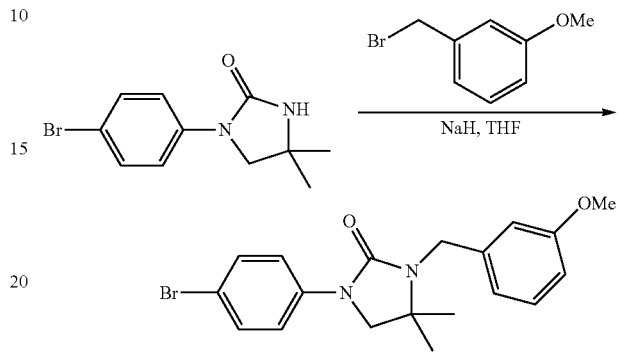

To a solution of 1-(4-bromophenyl)-4,4-dimethylimidazolidin-2-one (200 mg, 0.743 mmol) in THF (10 mL), was added NaH (59.4 mg, 1.486 mmol, 60% in mineral oil) and 1-(bromomethyl)-3-methoxybenzene (224 mg, 1.115 mmol). The reaction was stirred at rt for 16 h. The reaction mixture was slowly quenched with ice water (25 mL), then extracted with EtOAc (2×25 mL). The combined organic layer was washed with water and brine, dried over $Na_2SO_4$, filtered and concentrated. The crude product was purified by flash chromatography (12 g REDISEP® $SiO_2$ column, gradient elution; 100% Hex for 5 min; 0-100% EtOAc/Hex for 20 min.) to afford 1-(4-bromophenyl)-3-(3-methoxybenzyl)-4,4-dimethylimidazolidin-2-one (160 mg, 55% yield) as a white solid. MS(ESI) m/z: 391.0 $(M+H)^+$. $^1H$ NMR (300 MHz, DMSO-$d_6$) δ ppm 8.86-8.75 (m, 4H), 8.51 (t, J=8.3 Hz, 1H), 8.25-8.17 (m, 2H), 8.12-8.05 (m, 1H), 5.63 (s, 2H), 5.01 (s, 3H), 4.90 (s, 2H), 1.28 (s, 5H).

Example 137: Preparation of 1-(4-(1H-pyrazol-4-yl)phenyl)-3-(3-methoxybenzyl)-4,4-dimethylimidazolidin-2-one

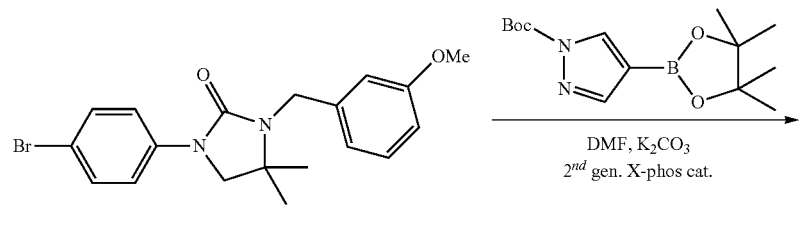

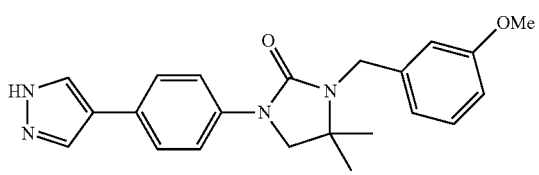

To a solution of 1-(4-bromophenyl)-3-(3-methoxybenzyl)-4,4-dimethylimidazolidin-2-one (160 mg, 0.411 mmol) in DMF (4 mL) were added tert-butyl 4-(4,4,5,5-tetramethyl-1,3,2-dioxaborolan-2-yl)-1H-pyrazole-1-carboxylate (169 mg, 0.575 mmol), $K_2CO_3$ (170 mg, 1.233 mmol) and water (0.4 mL). The reaction mixture was purged with nitrogen for 5 min and charged with 2nd generation XPhos precatalyst (19.4 mg, 0.025 mmol), reaction mixture was stirred at 90° C. for 16 h. Reaction mixture was cooled to rt, filtered through CELITE® pad, filtrate was concentrated. Crude product was purified by LC-MS based preparative HPLC to afford 1-(4-(1H-pyrazol-4-yl)phenyl)-3-(3-methoxybenzyl)-4,4-dimethylimidazolidin-2-one (63 mg, 40.5% yield) as a pale yellow solid. MS(ESI) m/z: 377.3 (M+H)+. 1H NMR (400 MHz, DMSO-d6) δ ppm 12.86 (br. s., 1H) 8.12 (br. s., 1H) 7.87 (br. s., 1H) 7.52-7.59 (m, 4H) 7.23 (t, J=8.03 Hz, 1H) 6.90-6.97 (m, 2H) 6.78-6.83 (m, 1H) 4.35 (s, 2H) 3.73 (s, 3H) 3.64 (s, 2H) 1.23 (s, 6H).

The following Examples in Table 8 were made by using the same procedure as shown in Example 137.

TABLE 8

| Ex. | R | Name | LCMS (M + H)+ | HPLC Method, RT (min.) and Purity | NMR |
|---|---|---|---|---|---|
| 138 | | 1-(4-(1H-pyrazol-4-yl)phenyl)-3-(3-fluoro-5-methoxybenzyl)-4,4-dimethylimidazolidin-2-one | 395.3 | E: 1.67, 94.2% F: 1.71, 99.3% | 1H NMR (400 MHz, DMSO-d6) d ppm 12.86 (br. s., 1H) 8.12 (br. s., 1H) 7.88 (br. s., 1H) 7.52-7.59 (m, 4H) 6.73-6.82 (m, 2 H) 6.69 (dt, J = 11.04, 2.26 Hz, 1H) 4.34 (s, 2H) 3.75 (s, 3H) 3.66 (s, 2H) 1.24 (s, 6H). 19F NMR (400 MHz, DMSO-d6) d ppm −111.972. |
| 139 | | 1-(4-(1H-pyrazol-4-yl)phenyl)-3-(3-fluoro-4-methoxybenzyl)-4,4-dimethylimidazolidin-2-one | 395.1 | E: 1.84, 100% F: 1.88, 100% | 1H NMR (400 MHz, DMSO-d6) d ppm 12.87 (br. s., 1H) 8.12 (br. s., 1H) 7.87 (br. s., 1H) 7.52-7.56 (m, 4H) 7.09-7.19 (m, 2H) 6.93 (td, J = 5.27, 2.01 Hz, 1H) 4.35 (s, 2H) 3.82 3H) 3.64 (s, 2H) 1.24 (s, 6H). |
| 140 | | 1-(4-(1H-pyrazol-4-yl)phenyl)-3-(4-fluoro-3-methoxybenzyl)-4,4-dimethylimidazolidin-2-one | 395.1 | E: 1.86, 100% F: 1.90, 99.7% | 1H NMR (400 MHz, DMSO-d6) d ppm 12.85 (br. s., 1H) 8.12 (br. s., 1H) 7.87 (br. s., 1H) 7.52-7.56 (m, 4H) 7.06-7.23 (m, 3H) 4.31 (s, 2H) 3.81 (s, 3H) 3.63 (s, 2H) 1.22 (s, 6H). |
| 141 | | 1-(4-(1H-pyrazol-4-yl)phenyl)-3-(3-fluorobenzyl)-4,4-dimethylimidazolidin-2-one | 365.2 | E: 1.88, 99.6% F: 1.92, 99.6% | 1H NMR (400 MHz, DMSO-d6) d ppm 12.87 (br. s., 1H) 8.09 (br. s., 1H) 7.89 (br. s., 1H) 7.52-7.60 (m, 4H) 7.36 (td, J = 8.03, 6.02 Hz, 1H) 7.15-7.24 (m, 2H) 7.06 (td, J = 8.53, 2.51 Hz, 1H) 4.39 (s, 2H) 3.66 (s, 2H) 1.24 (s, 6H). |
| 142 | | 1-(4-(1H-pyrazol-4-yl)phenyl)-3-(3-(difluoromethoxy)benzyl)-4,4-dimethylimidazolidin-2-one | 413.1 | E: 1.94, 100% F: 1.98, 99.6% | 1H NMR (400 MHz, DMSO-d6) d ppm 12.86 (br. s., 1H) 8.13 (s, 1H) 7.88 (s, 1H) 7.53-7.60 (m, 4H) 7.35-7.42 (m, 1H) 7.21-7.28 (m, 2H) 7.17 (s, 1H) 7.02-7.07 (m, 1H) 4.39 (s, 2H) 3.65 (s, 2H) 1.24 (s, 6H). |

TABLE 8-continued

| Ex. | R | Name | LCMS (M + H)+ | HPLC Method, RT (min.) and Purity | NMR |
|---|---|---|---|---|---|
| 143 | | 1-(4-(1H-pyrazol-4-yl)phenyl)-3-(2-fluoro-3-methoxybenzyl)-4,4-dimethylimidazolidin-2-one | 395.1 | E: 1.86, 100% F: 1.92, 99.4% | $^1$H NMR (400 MHz, DMSO-$d_6$) d ppm 8.01 (s, 2H) 7.52-7.60 (m, 4H) 7.02-7.12 (m, 2H) 6.93-7.01 (m, 1H) 4.41 (s, 2H) 3.84 (s, 3H) 3.66 (s, 2H) 1.25 (s, 6H). |
| 144 | | 1-(4-(1H-pyrazol-4-yl)phenyl)-3-(3-(cyclopropylmethoxy)benzyl)-4,4-dimethylimidazolidin-2-one | 417.2 | E: 2.21, 96.4% F: 2.16, 99.6% | $^1$H NMR (400 MHz, DMSO-$d_6$) d ppm 12.86 (br. s., 1H) 8.10 (br. s., 1H) 7.89 (br. s., 1H) 7.52-7.62 (m, 4H) 7.16-7.25 (m, 1H) 6.89-6.98 (m, 2H) 6.74-6.82 (m, 1H) 4.34 (s, 2H) 3.79 (d, J = 7.03 Hz, 2H) 3.64 (s, 2H) 1.13-1.29 (m, 7H) 0.50-0.60 (m, 2H) 0.27-0.35 (m, 2H). |
| 145 | | 1-(4-(1H-pyrazol-4-yl)phenyl)-3-(1-(3-methoxyphenyl)ethyl)-4,4-dimethylimidazolidin-2-one (Enantiomer 1) | 391.4 | A: 10.46, 99.1% B: 9.67, 99.1% | $^1$H NMR (400 MHz, methanol-$d_4$) d ppm 7.96 (br. s., 2H) 7.45-7.61 (m, 4H) 7.24 (t, J = 8.03 Hz, 1H) 7.05-7.15 (m, 2H) 6.81 (dd, J = 7.78, 2.26 Hz, 1H) 4.65 (q, J = 7.03 Hz, 1H) 3.80 (s, 3H) 3.69 (s, 2H) 1.85 (d, J = 7.53 Hz, 3H) 1.394 (s, 3H) 1.352 (s, 3H). |
| 146 | | 1-(4-(1H-pyrazol-4-yl)phenyl)-3-(1-(3-methoxyphenyl)ethyl)-4,4-dimethylimidazolidin-2-one (Enantiomer 2) | 391.4 | A: 10.45, 97.6% B: 9.68, 98.2% | $^1$H NMR (400 MHz, methanol-$d_4$) d ppm 7.92 (br. s., 2H) 7.54-7.59 (m, 2H) 7.48-7.53 (m, 2H) 7.21-7.28 (m, 1H) 7.05-7.14 (m, 2H) 6.81 (dd, J = 8.53, 2.01 Hz, 1H) 4.61-4.69 (m, 1H) 3.80 (s, 3H) 3.69 (s, 2H) 1.85 (d, J = 7.03 Hz, 3H) 1.404 (s, 3H) 1.362 (s, 3H). |
| 147 | | 1-(3-ethyl-4-(1H-pyrazol-4-yl)phenyl)-3-(3-fluoro-5-methoxybenzyl)-4,4-dimethylimidazolidin-2-one | 423.2 | E: 2.08, 99.27% F: 2.17, 100.0% | $^1$H NMR (400 MHz, DMSO-$d_6$) d 12.93 (br. s., 1H), 7.72 (br. s., 2H), 7.48 (d, J = 2.5 Hz, 1H), 7.42 (d, J = 2.5 Hz, 1H), 7.36-7.19 (m, 1H), 6.88-6.72 (m, 2H), 6.71-6.65 (m, 1H), 4.35 (s, 2H), 3.76 (s, 3H), 3.67 (s, 2H), 2.69 (q, 2H), 1.25 (s, 6H), 1.18-1.08 (t, J = 7.2 Hz, 3H). $^{19}$F NMR (400 MHz, methanol-$d_4$) d ppm −111.990. |

TABLE 8-continued

| Ex. | R | Name | LCMS (M + H)+ | HPLC Method, RT (min.) and Purity | NMR |
|---|---|---|---|---|---|
| 148 | | 1-(3-ethyl-4-(1H-pyrazol-4-yl)phenyl)-3-(3-methoxybenzyl)-4,4-dimethylimidazolidin-2-one | 405.2 | E: 2.03, 100.0% F: 1.98, 99.65% | 1H NMR (400 MHz, DMSO-d6) d ppm 12.89 (br. s., 1H) 7.83 (br. s., 1H) 7.61 (br. s, 1H) 7.49 (d, J = 2.45 Hz, 1H) 7.43 (dd, J = 8.31, 2.45 Hz, 1H) 7.19-7.30 (m, 2H) 6.90-6.97 (m, 2H) 6.76-6.84 (m, 1H) 4.35 (s, 2H) 3.74 (s, 3H) 3.65 (s, 2H) 3.18 (d, J = 5.14 Hz, 1H) 2.64-2.73 (q, J = 7.58 Hz, 2H) 1.24 (s, 6H) 1.14 (t, J = 7.58 Hz, 3H). |
| 151 | | 3-(3-fluoro-5-methoxybenzyl)-4,4-dimethyl-1-(6-methyl-5-(1H-pyrazol-4-yl)pyridin-2-yl)-imidazolidin-2-one | 410.2 | E: 1.49, 100.0% F: 2.05, 100.0% | 1H NMR (400 MHz, methanol-d4) d ppm 7.97 (br. s., 1H) 7.84 (s, 2H) 7.80 (br. s., 1H) 6.81 (s, 1 H) 6.74 (d, J = 9.04 Hz, 1H) 6.60 (dt, J = 10.79, 2.13 Hz, 1H) 4.48 (s, 2H) 3.93 (s, 2H) 3.81 (s, 3H) 2.59 (s, 3H) 1.33 (s, 6H). 19F NMR (400 MHz, methanol-d4) peaks at −77.028 and −113.801. |
| 152 | | 3-(4-fluoro-3-methoxybenzyl)-4,4-dimethyl-1-(6-methyl-5-(1H-pyrazol-4-yl)pyridin-2-yl)-imidazolidin-2-one | 410.2 | E: 1.43, 100.0% F: 2.03, 99.84% | 1H NMR (400 MHz, methanol-d4) d ppm 8.12 (d, J = 8.53 Hz, 1H) 7.92 (s, 2H) 7.63 (d, J = 9.04 Hz, 1H) 7.16 (dd, J = 8.03, 2.01 Hz, 1H) 7.01-7.09 (m, 1H) 6.94-7.00 (m, 1H) 4.53 (s, 2H) 3.92 (s, 2H) 3.88 (s, 3H) 2.70 (s, 3H) 1.37 (s, 6H). 19F NMR (400 MHz, methanol-d4) peaks at −77.344 and −139.066. |

Example 153

3-(4-(1H-Pyrazol-4-yl)phenyl)-5-(hydroxymethyl)-1-(3-methoxybenzyl)imidazolidine-2,4-dione

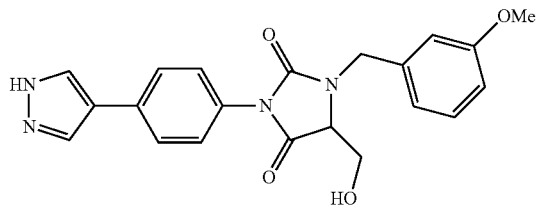 [SMILES: COc1cccc(CN2C(=O)N(c3ccc(-c4cn[nH]c4)cc3)C(=O)C2CO)c1]

Example 153A: Preparation of (S)-3-(4-bromophenyl)-5-(hydroxymethyl)imidazolidine-2,4-dione

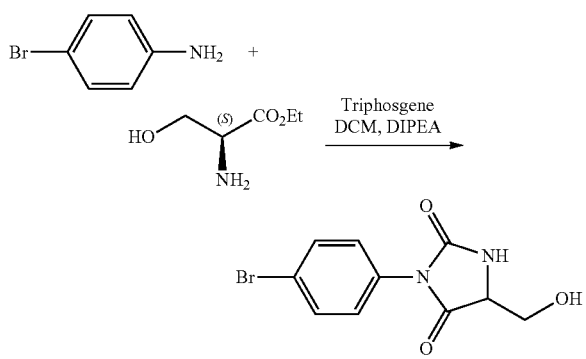

To the solution of 4-bromoaniline (500 mg, 2.91 mmol) in THF (10 mL) at 0° C., was added triphosgene (431 mg, 1.453 mmol) and TEA (1.215 mL, 8.72 mmol) dropwise. The mixture was stirred at rt for 30 min, then a solution of (S)-ethyl 2-amino-3-hydroxypropanoate (387 mg, 2.91 mmol) and TEA (1.22 mL, 8.72 mmol) in THF (10 mL) was added. The mixture was stirred at rt for 2.5 h. THF was evaporated and the residue was diluted with water. The resultant solid was filtered and dried under vacuum to afford the (S)-3-(4-bromophenyl)-5-(hydroxymethyl)imidazolidine-2,4-dione (300 mg, 20.5% yield) as a white solid. MS(ESI) m/z: 285.0 (M+H)$^+$. $^1$H NMR (300 MHz, DMSO-d$_6$) δ ppm 8.46 (s, 1H), 7.71-7.63 (m, 2H), 7.36-7.27 (m, 2H), 5.27-5.17 (m, 1H), 4.23 (t, J=2.8 Hz, 1H), 3.82-3.61 (m, 2H).

Example 153B: Preparation of (S)-3-(4-bromophenyl)-5-(hydroxymethyl)-1-(3-methoxybenzyl)imidazolidine-2,4-dione

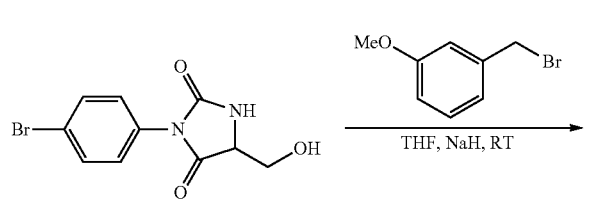

To the solution of (S)-3-(4-bromophenyl)-5-(hydroxymethyl)imidazolidine-2,4-dione (200 mg, 0.702 mmol) in DMF (5 mL) was added K$_2$CO$_3$ (145 mg, 1.052 mmol) and 1-(bromomethyl)-3-methoxybenzene (141 mg, 0.702 mmol). The reaction mixture was stirred at rt for 3 h. The reaction mixture was diluted with water (25 mL), then extracted with EtOAc (2×25 mL). The combined organic layer was washed with water and brine, dried over Na$_2$SO$_4$, filtered and concentrated. The crude product was purified by flash chromatography (12 g REDISEP® SiO$_2$ gradient elution; 100% Hex for 5 min; 0-100% EtOAc/Hex for 20 min) to afford the (S)-3-(4-bromophenyl)-5-(hydroxymethyl)-1-(3-methoxybenzyl)imidazolidine-2,4-dione (150 mg, 46% yield) as a white solid. MS(ESI) m/z: 407.1 (M+H)$^+$. $^1$H NMR (300 MHz, DMSO-d$_6$) δ ppm 7.72-7.66 (m, 2H), 7.40-7.33 (m, 2H), 7.31-7.23 (m, 1H), 6.98-6.92 (m, 2H), 6.87 (d, J=7.2 Hz, 1H), 5.28 (t, J=5.3 Hz, 1H), 4.88 (d, J=15.9 Hz, 1H), 4.31 (d, J=15.9 Hz, 1H), 4.10 (s, 1H), 3.85-3.79 (m, 2H), 3.76 (s, 3H).

Example 153: Preparation of 3-(4-(1H-pyrazol-4-yl)phenyl)-5-(hydroxymethyl)-1-(3-methoxybenzyl)imidazolidine-2,4-dione

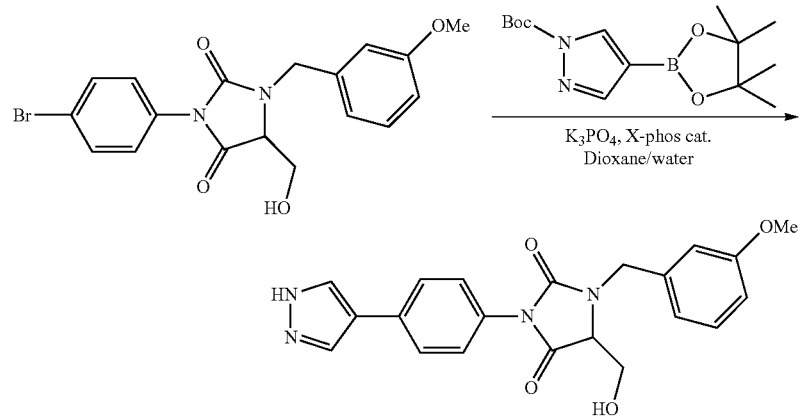

To the solution of 3-(4-bromophenyl)-5-(hydroxymethyl)-1-(3-methoxybenzyl) imidazolidine-2,4-dione (150 mg, 0.370 mmol) and 4-(4,4,5,5-tetramethyl-1,3,2-dioxaborolan-2-yl)-1H-pyrazole (108 mg, 0.555 mmol) in dioxane (5 mL), was added potassium phosphate tribasic (196 mg, 0.925 mmol) and water (0.5 mL). The reaction mixture was purged with nitrogen for 10 min, then was charged with 2nd generation XPhos precatalyst (17.47 mg, 0.022 mmol) and again purged with nitrogen for 10 min. The mixture was heated at 75° C. for 2.5 h. The reaction mixture was cooled, then diluted with ethyl acetate. The organic phase was washed with water and brine, dried over Na$_2$SO$_4$, and concentrated. The solid was dissolved in DCM (10 mL) and treated with TFA (0.198 mL, 2.57 mmol). The mixture was stirred at rt for 3 hr, then was concentrated. The residue was washed with hexanes and diethyl ether, then was purified by preparative HPLC to afford Example 153 (25 mg, 17%) MS(ESI) m/z: 393.0 (M+H)$^+$; $^1$H NMR (400 MHz, DMSO-d$_6$) δ ppm 12.92 (br. s., 1H) 8.25 (s, 1H) 7.97 (s, 1H)

7.69-7.74 (m, 2H) 7.34 (d, J=8.60 Hz, 2H) 7.29 (t, J=8.06 Hz, 1H) 6.94-6.98 (m, 2H) 6.85-6.89 (m, 1H) 5.29 (t, J=5.24 Hz, 1H) 4.89 (d, J=15.81 Hz, 1H) 4.31 (d, J=15.81 Hz, 1H) 4.09 (t, J=2.23 Hz, 1H) 3.79-3.89 (m, 2H) 3.76 (s, 3H). HPLC RT=7.46 min, 98.5% (Method A), HPLC RT=7.21 min, 96.3% (Method B).

Examples 154 and 155

1-(4-(1H-Pyrazol-4-yl)phenyl)-3-(2-hydroxy-1-(3-methoxyphenyl)ethyl)imidazolidin-2-one (Enantiomers 1 and 2)

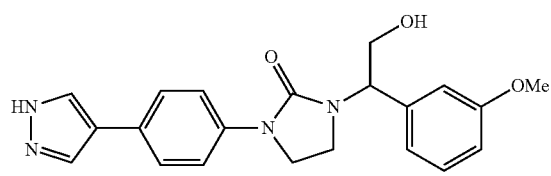 [SMILES: COc1cccc(C(CO)N2CCN(c3ccc(-c4cn[nH]c4)cc3)C2=O)c1]

Example 154A: Preparation of 2-(3-(4-bromophenyl)-2-oxoimidazolidin-1-yl)-2-(3-methoxyphenyl)acetic Acid

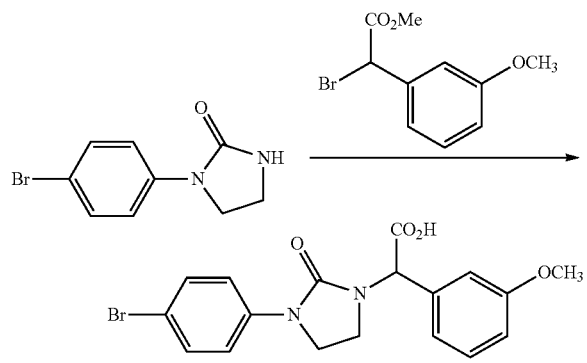

To the suspension of 1-(4-bromophenyl)imidazolidin-2-one (2.5 g, 10.37 mmol) in THF (10 mL) at 0° C., was added 60% NaH (1.25 g, 31.1 mmol). After 10 minutes, methyl 2-bromo-2-(3-methoxyphenyl)acetate (3.76 g, 14.52 mmol) was added and the mixture was warmed to rt and stirred for 16 h. The reaction was quenched with methanol, then concentrated. The residue was dissolved in sat. solution of NaHCO₃ and washed with diethyl ether. The aqueous phase was acidified to pH 2. The mixture was extracted with ethyl acetate. The combined organic layer was washed with brine, dried over Na₂SO₄, filtered and concentrated to afford 2-(3-(4-bromophenyl)-2-oxoimidazolidin-1-yl)-2-(3-methoxyphenyl)acetic acid (2.3 g, 54.7% yield) as a yellow solid. MS(ESI) m/z: 407.2 (M+H)+; ¹H NMR (400 MHz, DMSO-d₆) δ ppm 7.53-7.60 (m, 2H) 7.47-7.53 (m, 2H) 7.35 (t, J=7.78 Hz, 1H) 6.96 (d, J=8.03 Hz, 1H) 6.87-6.93 (m, 2H) 5.51 (s, 1H) 3.79-3.86 (m, 1H) 3.77 (s, 3H) 3.73-3.76 (m, 1H) 3.66-3.73 (m, 2H).

Examples 154B and 155A: Preparation of 1-(4-bromophenyl)-3-(2-hydroxy-1-(3-methoxyphenyl)ethyl)imidazolidin-2-one (Enantiomer 1 and Enantiomer 2)

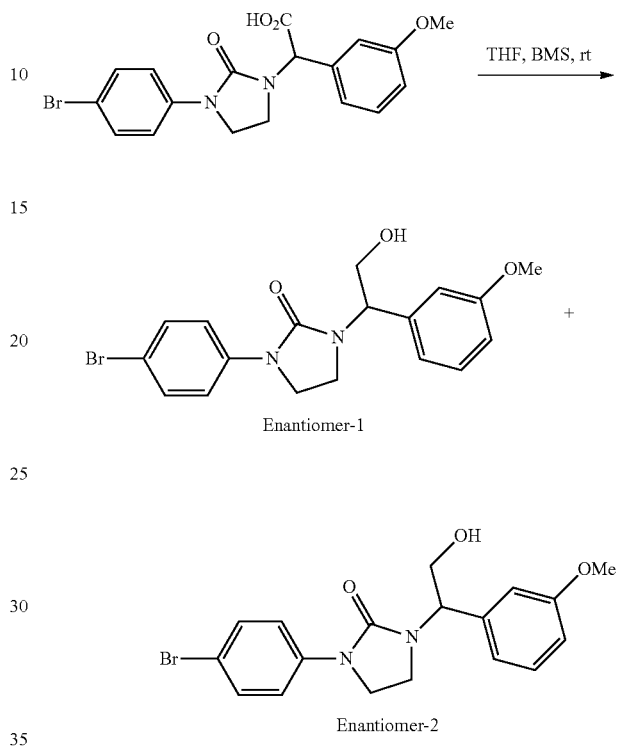

To a solution 2-(3-(4-bromophenyl)-2-oxoimidazolidin-1-yl)-2-(3-methoxyphenyl)acetic acid (700 mg, 1.73 mmol) in THF (10 mL) at 0° C., was added borane-methyl sulfide complex (0.984 mL, 10.4 mmol), After 10 minutes the mixture was warmed to rt and stirred at rt for 16 h. Reaction was carefully quenched with methanol, then was concentrated. The residue was purified by flash chromatography (loaded in DCM, gradient elution 0-100% EtOAc/Hex for 30 min.) to give a gummy solid (600 mg). The enantiomers were separated by Supercritical Fluid Chromatography (SFC) [Column: CHIRALCEL® OD-H (250×21 mm, 5μ), Co-solvent 20% (0.2% DEA in methanol) to afford faster eluting 1-(4-bromophenyl)-3-(2-hydroxy-1-(3-methoxyphenyl)ethyl) imidazolidin-2-one (Example 154B, Enantiomer 1, 0.170 g, 25.2% yield) as a yellow solid. MS(ESI) m/z: 393.0 (M+H)+; ¹H NMR (400 MHz, DMSO-d₆) δ ppm 7.51-7.58 (m, 2H) 7.44-7.51 (m, 2H) 7.24-7.31 (m, 1H) 6.90 (d, J=8.03 Hz, 1H) 6.83-6.88 (m, 2H) 4.91-5.02 (m, 2H) 3.87-3.92 (m, 1H) 3.82-3.87 (m, 1H) 3.79 (t, J=8.03 Hz, 2H) 3.73-3.76 (m, 3H) 3.56-3.66 (m, 1H); 100% ee (RT=7.45 min), $[\alpha]^{25.3}_D$=−102.400 (c 0.05, DMSO) and 1-(4-bromophenyl)-3-(2-hydroxy-1-(3-methoxyphenyl) ethyl)imidazolidin-2-one (slower eluting Example 155A, Enantiomer 2, 0.140 g, 20.7% yield) as a yellow solid. MS(ESI) m/z: 393.3 (M+H)+; ¹H NMR (400 MHz, DMSO-d₆) δ ppm 7.53-7.59 (m, 2H) 7.45-7.51 (m, 2H) 7.24-7.32 (m, 1H) 6.91 (d, J=7.53 Hz, 1H) 6.82-6.89 (m, 2H) 4.93-5.02 (m, 2H) 3.88-3.94 (m, 1H) 3.83-3.87 (m, 1H) 3.77-3.83 (m, 2H) 3.76 (s, 3H) 3.58-3.66 (m, 1H); 100% ee (RT 9.16 min), $[\alpha]^{25.3}_D$=+96 (c 0.05, DMSO).

Example 154: Preparation of 1-(4-(1H-pyrazol-4-yl)phenyl)-3-(2-hydroxy-1-(3-methoxyphenyl)ethyl)imidazolidin-2-one (Enantiomer 1)

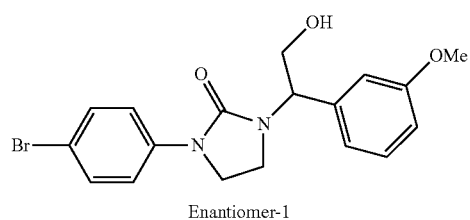

Enantiomer-1

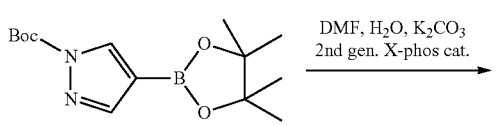

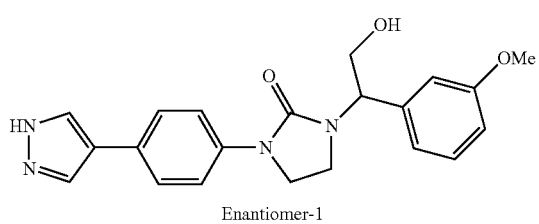

Enantiomer-1

To a solution of Example 154B (100 mg, 0.256 mmol) in DMF (5 mL), was added tert-butyl 4-(4,4,5,5-tetramethyl-1,3,2-dioxaborolan-2-yl)-1H-pyrazole-1-carboxylate (113 mg, 0.383 mmol), $K_2CO_3$ (106 mg, 0.767 mmol) and water (0.5 mL). The mixture was purged with nitrogen for 10 minutes, then was charged with 2nd generation XPhos precatalyst (12.1 mg, 0.015 mmol). The mixture was again purged with nitrogen for 10 minutes, then was heated at 90° C. for 16 h in a sealed tube. The reaction mixture was concentrated to give an off-white solid (250 mg), which was purified by reverse phase chromatography to afford of 1-(4-(1H-pyrazol-4-yl)phenyl)-3-(2-hydroxy-1-(3-methoxyphenyl)ethyl)imidazolidin-2-one (Enantiomer 1, 0.140 g, 20.7% yield) as a white solid. MS(ESI) m/z: 379.2 $(M+H)^+$; $^1H$ NMR (400 MHz, DMSO-$d_6$) δ ppm 12.85 (br. s., 1H) 8.11 (br. s., 1H) 7.87 (br. s., 1H) 7.51-7.60 (m, 4H) 7.25-7.32 (m, 1H) 6.92 (d, J=7.53 Hz, 1H) 6.84-6.90 (m, 2H) 4.94-5.03 (m, 2H) 3.80-3.95 (m, 4H) 3.76 (s, 3H) 3.57-3.67 (m, 1H). HPLC RT=6.22 min, 99.28% (Method I), 7.51 min, 97.64% (Method J), 100.0% ee (RT 9.83 min, VIII), $[α]^{25.3}_D$=−132.8 (c 0.05, DMSO).

Enantiomer 2, Example 155 was prepared as per the procedure shown in Example 154 starting from Example 155A. MS(ESI) m/z: 379.2 $(M+H)^+$; $^1H$ NMR (400 MHz, DMSO-$d_6$) δ ppm 12.85 (br. s., 1H) 8.11 (s, 1H) 7.87 (s, 1H) 7.50-7.60 (m, 4H) 7.25-7.34 (m, 1H) 6.92 (d, J=8.03 Hz, 1H) 6.83-6.90 (m, 2H) 4.93-5.03 (m, 2H) 3.79-3.95 (m, 4H) 3.76 (s, 3H) 3.56-3.67 (m, 1H). [α]25.3D=+100 (c 0.05, DMSO); HPLC RT=6.22 min, 98.82% (Method I), 7.51 min, 99.50% (Method J), 100.0% ee (RT 11 min, VIII).

Examples 156 and 157

1-(4-(1H-Pyrazol-4-yl)phenyl)-3-(2-methoxy-1-(3-methoxyphenyl)ethyl)imidazolidin-2-one (Enantiomers 1 and 2)

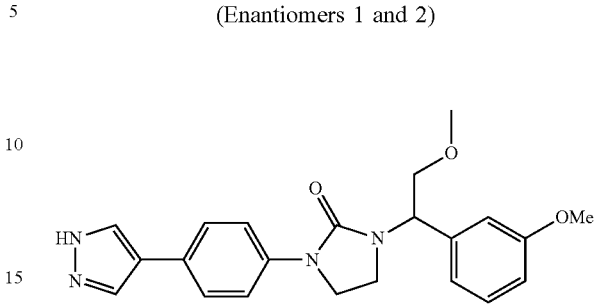

Examples 156A and 157A: Preparation of 1-(4-bromophenyl)-3-(2-methoxy-1-(3-methoxyphenyl)ethyl)imidazolidin-2-one (Enantiomers 1 and 2)

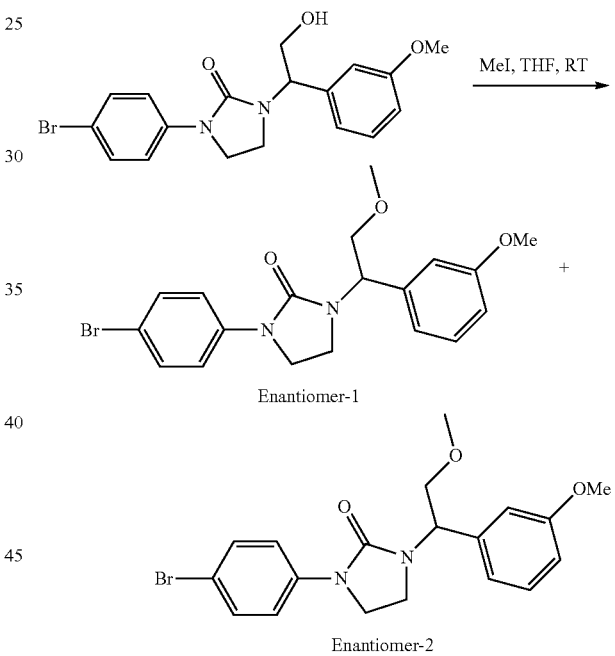

Enantiomer-1

Enantiomer-2

To 60% NaH (14.72 mg, 0.613 mmol), was added a solution of racemic 1-(4-bromophenyl)-3-(2-hydroxy-1-(3-methoxyphenyl)ethyl)imidazolidin-2-one (80 mg, 0.204 mmol) in THF (5 mL). The mixture was stirred at rt for 30 min., then methyl iodide (0.051 mL, 0.818 mmol) was added. The resulting mixture was stirred at rt for 16 h. The reaction was quenched with methanol, then concentrated. The residue was purified by flash chromatography (gradient elution; 0-100% EtOAc/hexanes) to afford the racemic product. The enantiomers were separated by SFC [Column: CHIRALCEL® OD-H (250×4.6 mm, 5μ), Co-solvent 20% methanol] to afford Enantiomer 1, Example 156A (0.035 g, 42.2% yield) as a yellow gummy solid. MS(ESI) m/z: 405.0 $(M+H)^+$; $^1H$ NMR (400 MHz, DMSO-$d_6$) δ ppm 7.51-7.57 (m, 2H) 7.45-7.51 (m, 2H) 7.24-7.32 (m, 1H) 6.92 (d, J=8.53 Hz, 1H) 6.85-6.90 (m, 2H) 5.13 (dd, J=9.04, 5.52 Hz, 1H) 3.86-3.94 (m, 1H) 3.77-3.84 (m, 2H) 3.74-3.76 (m, 4H)

3.49-3.58 (m, 1H) 3.34-3.38 (m, 1H) 3.33 (s, 3H), 100.0% ee (RT 6.58 min). Enantiomer 2, Example 157A (0.035 g, 42.2% yield) as a yellow gummy solid. MS(ESI) m/z: 405.2 (M+H)+; 1H NMR (400 MHz, DMSO-d6) δ ppm 7.51-7.56 (m, 2H) 7.45-7.51 (m, 2H) 7.24-7.32 (m, 1H) 6.92 (d, J=8.53 Hz, 1H) 6.85-6.90 (m, 2H) 5.13 (dd, J=9.04, 5.52 Hz, 1H) 3.85-3.93 (m, 1H) 3.77-3.84 (m, 2H) 3.72-3.77 (m, 4H) 3.50-3.59 3.34-3.38 (m, 1H) (m, 1H) 3.33 (s, 3H). 97.74% ee (RT=7.90 min).

Example 156: Preparation of 1-(4-(1H-pyrazol-4-yl)phenyl)-3-(2-methoxy-1-(3-methoxyphenyl)ethyl)imidazolidin-2-one

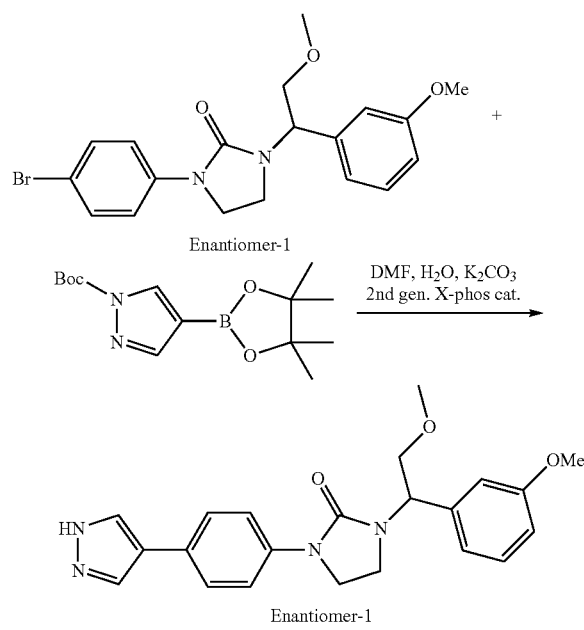

To a solution of Example 155A (35 mg, 0.086 mmol) in DMF (5 mL), was added tert-butyl 4-(4,4,5,5-tetramethyl-1,3,2-dioxaborolan-2-yl)-1H-pyrazole-1-carboxylate (30.5 mg, 0.104 mmol), K2CO3 (35.8 mg, 0.259 mmol) and water (0.5 mL). The mixture was purged with nitrogen for 10 minutes, then 2nd generation XPhos precatalyst (4.1 mg, 5.18 μmol) was added. The mixture was again purged with nitrogen for 10 minutes and then was heated at 90° C. for 16 h in a sealed tube. The reaction was cooled to rt and filtered. The filtrate was purified via preparative HPLC to afford 1-(4-(1H-pyrazol-4-yl)phenyl)-3-(2-methoxy-1-(3-methoxyphenyl)ethyl)imidazolidin-2-one (0.010 g, 30.5% yield) as a white solid. MS(ESI) m/z: 393.2 (M+H)+; 1H NMR (400 MHz, chloroform-d) δ ppm 7.83 (s, 2H) 7.56-7.63 (m, 2H) 7.43-7.50 (m, 2H) 7.28-7.32 (m, 1H) 6.93-6.99 (m, 2H) 6.85 (dd, J=8.26, 2.00 Hz, 1H) 5.37 (dd, J=7.88, 5.13 Hz, 1H) 4.00 (dd, J=10.38, 8.13 Hz, 1H) 3.73-3.89 (m, 6H) 3.59 (td, J=9.13, 6.50 Hz, 1H) 3.46 (s, 3H) 3.33 (td, J=9.01, 6.50 Hz, 1H); HPLC RT=1.63 min, 98.70% (Method E), 1.61 min, 98.47% (Method F), 100.0% ee (RT=28.418 min).

Example 157: Preparation of 1-(4-(1H-pyrazol-4-yl)phenyl)-3-(2-methoxy-1-(3-methoxyphenyl)ethyl)imidazolidin-2-one Example 157 (Enantiomer 2) was prepared using the similar procedure in example 156, starting with Example 157A: MS(ESI) m/z: 393.2 (M+H)+; 1H NMR (400 MHz, chloroform-d) δ ppm 7.83 (s, 2H) 7.60 (m, J=8.76 Hz, 2H) 7.48 (m, J=9.01 Hz, 2H) 7.28-7.33 (m, 1H) 6.92-7.04 (m, 2H) 6.82-6.88 (m, 1H) 5.37 (dd, J=7.88, 5.63 Hz, 1H) 4.00 (dd, J=10.51, 8.01 Hz, 1H) 3.74-3.88 (m, 6H) 3.55-3.65 (m, 1H) 3.45 (s, 3H) 3.26-3.39 (m, 1H). HPLC RT=1.62 min, 98.25% (Method E), 1.61 min, 99.62% (Method F), 100.0% ee (RT 23.16 min, X).

The following Examples in Table 9 were prepared in a similar fashion to Examples 154 and 155.

TABLE 9

| Ex. | R | Name | LCMS (M + H)+ | HPLC Method, RT (min.) and Purity | NMR |
|---|---|---|---|---|---|
| 158 | | 1-(6-ethyl-5-(1H-pyrazol-4-yl)pyridin-2-yl)-3-(2-hydroxy-1-(3-methoxyphenyl)ethyl)imidazolidin-2-one (Enantiomer 1) | 408.2 | M: 7.93, 96.04% N: 12.38, 95.78% VI: 11.47, 97.08% ee | 1H NMR (400 MHz, DMSO-d6) d ppm 12.96 (s, 1H) 8.00 (d, J = 8.53 Hz, 1H) 7.79 (br. s., 2H) 7.65 (d, J = 9.04 Hz, 1H) 7.24-7.32 (m, 1H) 6.92 (d, J = 7.53 Hz, 1H) 6.83-6.89 (m, 2H) 4.99 (dd, J = 8.78, 5.77 Hz, 2H) 4.00 (t, J = 8.78 Hz, 2H) 3.81-3.94 (m, 2H) 3.75 (s, 3H) 3.58-3.67 (m, 1H) 2.79 (q, J = 7.53 Hz, 2H) 1.20 (t, J = 7.28 Hz, 3H). |
| 159 | | 1-(6-ethyl-5-(1H-pyrazol-4-yl)pyridin-2-yl)-3-(2-hydroxy-1-(3-methoxyphenyl)ethyl)imidazolidin-2-one (Enantiomer 2) | 408.2 | M: 7.94, 94.96% N: 12.39, 96.58% VI: 14.72, 94.40% ee | 1H NMR (400 MHz, DMSO-d6) d ppm 12.99 (s, 1H) 8.14 (br. s., 1H) 8.00 (d, J = 8.53 Hz, 1H) 7.91 (br. s., 1H) 7.65 (d, J = 8.53 Hz, 1H) 7.25-7.32 (m, 1H) 6.92 (d, J = 7.53 Hz, 1H) 6.84-6.89 (m, 2H) 4.96-5.03 (m, 2H) 4.00 (t, J = 9.04 Hz, 2H) 3.80-3.95 (m, 2H) 3.75 (s, 3H) 3.58-3.66 (m, 1H) |

TABLE 9-continued

| Ex. | R | Name | LCMS (M + H)+ | HPLC Method, RT (min.) and Purity | NMR |
|---|---|---|---|---|---|
| | | | | | 2.79 (q, J = 7.36 Hz, 2H) 1.20 (t, J = 7.28 Hz, 3H). |
| 160 | | 1-(2-hydroxy-1-(3-methoxy-phenyl)ethyl)-3-(6-methyl-5-(1H-pyrazol-4-yl)pyridin-2-yl)imidazolidin-2-one (Enantiomer 1) | 394.2 | I: 10.53, 99.32% J: 11.32, 96.25% VII: 5.21, 96.86% ee | $^1$H NMR (400 MHz, methanol-d$_4$) d ppm 8.03 (d, J = 8.53 Hz, 1H) 7.80 (br. s., 2H) 7.68 (d, J = 8.53 Hz, 1H) 7.31 (t, J = 8.03 Hz, 1H) 6.94-6.99 (m, 2H) 6.87-6.92 (m, 1H) 5.14 (dd, J = 9.04, 5.52 Hz, 1H) 3.98-4.16 (m, 4H) 3.82 (s, 3H) 3.68 (td, J = 9.29, 6.53 Hz, 1H) 3.36-3.42 (m, 1H) 2.54 (s, 3H). [α]25.0D = −44 (c 0.10, DMSO). |
| 161 | | 1-(2-hydroxy-1-(3-methoxy-phenyl)ethyl)-3-(6-methyl-5-(1H-pyrazol-4-yl)pyridin-2-yl)imidazolidin-2-one (Enantiomer 2) | 394.2 | I: 10.55, 95.11% J: 11.31, 95.44% VII: 5.21, 96.82% ee | $^1$H NMR (400 MHz, methanol-d$_4$) d ppm 8.03 (d, J = 8.53 Hz, 1H) 7.80 (br. s., 2H) 7.68 (d, J = 8.53 Hz, 1H) 7.31 (t, J = 7.78 Hz, 1H) 6.94-7.01 (m, 2H) 6.87-6.92 (m, 1H) 5.14 (dd, J = 9.04, 5.52 Hz, 1H) 4.00- 4.16 (m, 4H) 3.80-3.85 (m, 3H) 3.68 (td, J = 9.29, 6.53 Hz, 1H) 3.36-3.42 (m, 3H) 2.54 (s, 3H). [α]25.1D = +54 (c 0.10, DMSO). |
| 162 | | 1-(4-(1H-pyrazol-4-yl)phenyl)-3-(2-hydroxy-1-phenylethyl)imidazolidin-2-one (Enantiomer 1) | 349.2 | E: 1.36, 98.51 J: 1.38, 98.46 IX: 9.92, 100% ee | $^1$H NMR (400 MHz, DMSO-d$_6$) δ ppm 12.85 (br. s., 1H) 8.11 (br. s., 1H) 7.86 (br. s., 1H) 7.55 (s, 4H) 7.32-7.39 (m, 4H) 7.26-7.31 (m, 1H) 4.97-5.05 (m, 2H) 3.78-3.95 (m, 4H) 3.56-3.68 (m, 1H) 3.27-3.30 (m, 1H). |
| 163 | | 1-(4-(1H-pyrazol-4-yl)phenyl)-3-(2-hydroxy-1-phenylethyl)imidazolidin-2-one (Enantiomer 2) | 349.2 | E: 1.36, 100.0% J: 1.38, 100.0% IX: 9.92, 100% ee | $^1$H NMR (400 MHz, DMSO-d$_6$) δ ppm 12.85 (br. s., 1H) 8.10 (br. s., 1H) 7.86 (br. s., 1H) 7.55 (s, 4H) 7.32-7.40 (m, 4H) 7.25-7.32 (m, 1H) 4.97-5.05 (m, 2H) 3.79-3.95 (m, 4H) 3.57-3.67 (m, 1H) 3.26-3.30 (m, 1H). |
| 164 | | 1-(2-hydroxy-1-(3-methoxy-phenyl)ethyl)-3-(3-methyl-4-(1H-pyrazol-4-yl)phenyl)imidazolidin-2-one (Enantiomer I) | 393.2 | O: 7.94, 99.76% J: 7.57, 99.61% VIII: 7.68, 100% ee | $^1$H NMR (400 MHz, DMSO-d$_6$) d ppm 12.87 (br., s, 1H) 779 (s, 2H) 7.41-7.46 (m, 2H) 7.25-7.34 (m, 2H) 6.92 (d, J = 7.78 Hz, 1H) 6.84-6.89 (m, 2H) 4.97 (dd, J = 8.66, 5.77 Hz, 2H) 3.79-3.95 (m, 4H) 3.74-3.77 (m, 3H) 3.56-3.66 (m, 1H) 2.36 (s, 3H); [α]25.3D = −92.00 (c 0.05, DMSO) |
| 165 | | 1-(2-hydroxy-1-(3-methoxy-phenyl)ethyl)-3-(3-methyl-4-(1H-pyrazol-4-yl)phenyl)imidazolidin-2-one (Enantiomer II) | 393.2 | O: 7.94, 99.79% J: 7.57, 99.63% VIII: 11.52, 98.56% ee | $^1$H NMR (400 MHz, DMSO-d$_6$) δ ppm 12.85 (br., s, 1H) 7.78 (s, 2H) 7.41-7.46 (m, 2H) 7.25-7.34 (m, 2H) 6.92 (d, J = 7.78 Hz, 1H) 6.84-6.89 (m, 2H) 4.97 (dd, J = 8.66, 5.77 Hz, 2H) 3.79-3.95 (m, 4H) 3.74-3.77 (m, 3H) 3.54-3.66 (m, 1H) 2.35 (s, 3H); $[α]^{25.3}{}_D$ = +84.00 (c 0.05, DMSO) |

TABLE 9-continued

| Ex. | R | Name | LCMS (M + H)+ | HPLC Method, RT (min.) and Purity | NMR |
|---|---|---|---|---|---|
| 166 | | 1-(3-ethyl-4-(1H-pyrazol-4-yl)phenyl)-3-(2-hydroxy-1-(3-methoxyphenyl)ethyl)imidazolidin-2-one (Enantiomer II) | 407.2 | I: 8.353, 99.3% J: 8.003, 99.7% | $^1$H NMR (400 MHz, DMSO-$d_6$) δ ppm = 12.90 (br. s., 1H), 7.83 (br. s., 1H), 7.60 (br. s., 1H), 7.51 (d, J = 2.5 Hz, 1H), 7.38 (dd, J = 8.5, 2.5 Hz, 1H), 7.32-7.21 (m, 2H), 6.94-6.83 (m, 3H), 5.03-4.93 (m, 2H), 3.94-3.79 (m, 4H), 3.75 (s, 3H), 3.67-3.57 (m, (1H), 3.32-3.27 (m, 1H), 2.71-2.63 (m, 2H), 1.12 (t, J = 7.3 Hz, 3H) |

The following Examples in Table 10 were prepared in a similar fashion to the Examples above.

TABLE 10

| Ex. | R | Name | LCMS (M + H)+ | HPLC Method, RT (min.) and Purity | NMR |
|---|---|---|---|---|---|
| 167 | | 1-(6-ethyl-5-(1H-pyrazol-4-yl)pyridin-2-yl)-3-(3-methoxybenzyl)imidazolidin-2-one, TFA | 378.2 | E: 1.38, 100.0% F: 1.97, 99.52% | $^1$H NMR (400 MHz, DMSO-$d_6$) d ppm 8.03 (d, J = 8.53 Hz, 1H) 7.81 (s, 2H) 7.68 (d, J = 8.53 Hz, 1H) 7.26-7.34 (m, 1H) 6.84-6.92 (m, 3H) 4.39 (s, 2H) 3.94-4.04 (m, 2H) 3.75 (s, 3H) 3.33-3.42 (m, 2H) 2.80 (q, J = 7.36 Hz, 2H) 1.20 (t, J = 7.6 Hz, 3H). $^{19}$F NMR (400 MHz, DMSO-$d_6$) d ppm −74.726. |
| 168 | | 1-(6-ethyl-5-(1H-pyrazol-4-yl)pyridin-2-yl)-3-(3-fluoro-5-methoxybenzyl)imidazolidin-2-one, TFA | 396.1 | E: 1.47, 100.0% F: 2.04, 99.52% | $^1$H NMR (400 MHz, DMSO-$d_6$) d ppm 8.03 (d, J = 8.53 Hz, 1H) 7.81 (s, 2H) 7.69 (d, J = 8.53 Hz, 1H) 6.68-6.82 (m, 3H) 4.39 (s, 2H) 4.02 (dd, J = 9.04, 7.03 Hz, 2H) 3.77 (s, 3H) 3.35-3.44 (m, 2H) 2.80 (q, J = 7.53 Hz, 2H) 1.21 (t, J = 7.53 Hz, 3H). $^{19}$F NMR (400 MHz, DMSO-$d_6$) d ppm −74.707 and −111.523. |
| 169 | | 1-(3-(cyclopropylmethoxy)benzyl)-3-(6-ethyl-5-(1H-pyrazol-4-yl)pyridin-2-yl)-imidazolidin-2-one | 418.2 | E: 1.67, 100.0% F: 2.25, 100.0% | $^1$H NMR (400 MHz, DMSO-$d_6$) d ppm 13.00 (br. s., 1H) 8.04 (d, J = 8.53 Hz, 1H) 7.92 (br. s., 1H) 7.67 (d, J = 8.53 Hz, 2H) 7.19-7.31 (m, 1H) 6.80-6.90 (m, 3H) 4.38 (s, 2H) 4.00 (dd, J = 9.29, 7.28 Hz, 2H) 3.81 (d, J = 7.03 Hz, 2H) 3.32-3.42 (m, 2H) 2.73-2.85 (m, 2H) 1.20 (m, 4H) 0.56 |

TABLE 10-continued

| Ex. | R | Name | LCMS (M + H)+ | HPLC Method, RT (min.) and Purity | NMR |
|---|---|---|---|---|---|
| | | | | | (dd, J = 8.03, 1.51 Hz, 2H) 0.32 (dd, J = 4.52, 1.51 Hz, 2H). |
| 170 | | 1-(6-ethyl-5-(1H-pyrazol-4-yl)pyridin-2-yl)-3-(4-fluoro-3-methoxybenzyl)imidazolidin-2-one, TFA | 396.1 | E: 1.42, 100.0% F: 1.99, 100.0% | ¹H NMR (400 MHz, DMSO-d₆) d ppm 8.29 (d, J = 8.62 Hz, 1H) 8.06 (s, 2H) 7.94 (d, J = 8.56 Hz, 1H) 7.41-7.50 (m, 1H) 7.37 (dd, J = 8.56, 1.77 Hz, 1H) 7.14 (ddd, J = 8.25, 4.34, 2.08 Hz, 1H) 4.65 (s, 2H) 4.21-4.30 (m, 2H) 4.10 (s, 3H) 3.59-3.67 (m, 2H) 3.06 (q, J = 7.42 Hz, 2H) 1.46 (t, J = 7.46 Hz, 3H). ¹⁹F NMR (400 MHz, DMSO-d₆) d ppm −74.784 and −137.405. |
| 171 | | 1-(6-ethyl-5-(1H-pyrazol-4-yl)pyridin-2-yl)-3-(4-fluoro-3-methoxybenzyl)-1H-imidazol-2(3H)-one | 394.2 | E: 1.73, 97.84% F: 1.78, 99.23% | ¹H NMR (400 MHz, DMSO-d₆) d ppm 13.33 (br. s., 1H) 8.44 (d, J = 8.56 Hz, 1H) 8.12 (d, J = 8.56 Hz, 2H) 7.86 (br. s., 1H) 7.65 (d, J = 3.18 Hz, 1H) 7.41-7.49 (m, 2H) 7.08-7.15 (m, 2H) 5.05 (s, 2H) 4.10 (s, 3H) 3.13 (q, J = 7.66 Hz, 2H) 1.49 (t, J = 7.46 Hz, 3H). ¹⁹F NMR (400 MHz, DMSO-d₆) d ppm −137.040. |
| 172 | | 1-(6-ethyl-5-(1H-pyrazol-4-yl)pyridin-2-yl)-3-(3-fluoro-5-methoxybenzyl)-1H-imidazol-2(3H)-one | 394.2 | E: 1.79, 99.92% F: 1.83, 99.69% | ¹H NMR (400 MHz, DMSO-d₆) d ppm 13.34 (br. s., 1H) 8.43 (d, J = 8.56 Hz, 1H) 8.25 (br. s., 1H) 8.12 (d, J = 8.31 Hz, 1H) 8.02 (br. s., 1H) 7.67 (d, J = 3.18 Hz, 1H) 7.12 (d, J = 3.18 Hz, 1H) 6.93-7.07 (m, 3H) 5.06 (s, 2H) 4.02 (s, 3H) 3.14 (q, J = 7.50 Hz, 2H) 1.50 (t, J = 7.46 Hz, 3H). ¹⁹F NMR (400 MHz, DMSO-d₆) d ppm −111.316. |
| 173 | | 1-(6-ethyl-5-(1H-pyrazol-4-yl)pyridin-2-yl)-3-(1-(3-methoxyphenyl)ethyl)imidazolidin-2-one (Enantiomer 1) | 392.2 | I: 7.08, 98.66% J: 7.54, 99.3% VII: 3.09, 100% ee | ¹H NMR (400 MHz, DMSO-d₆) d ppm 12.99 (br. s., 1H) 8.01 (d, J = 8.53 Hz, 1H) 7.92 (br. s., 1H) 7.66 (d, J = 8.53 Hz, 2H) 7.30 (t, J = 8.03 Hz, 1H) 6.83-6.98 (m, 3H) 5.15 (q, J = 7.36 Hz, 1H) 3.90-4.03 (m, 2H) 3.76 (s, 3H), 3.45-3.56 (m, 1H) 3.07-3.19 (m, 1H) 2.79 (q, J = 7.53 Hz, 2H) 1.52 (d, J = 7.03 |

TABLE 10-continued

| Ex. | R | Name | LCMS (M + H)+ | HPLC Method, RT (min.) and Purity | NMR |
|---|---|---|---|---|---|
| | | | | | Hz, 3H) 1.19 (t, J = 7.28 Hz, 3H). [α]25.0D = +80 (c 0.050, DMSO). |
| 174 | | 1-(6-ethyl-5-(1H-pyrazol-4-yl)pyridin-2-yl)-3-(1-(3-methoxyphenyl)ethyl)imidazolidin-2-one (Enantiomer 1) | 392.2 | I: 7.11, 96.95% J: 7.56, 99.08% VII: 4.48, 100% ee | $^1$H NMR (400 MHz, DMSO-$d_6$) d ppm 12.99 (br. s., 1H) 8.01 (d, J = 8.53 Hz, 1H) 7.92 (br. s., 1H) 7.66 (d, J = 8.53 Hz, 2H) 7.30 (t, J = 8.03 Hz, 1H) 6.83-6.98 (m, 3H) 5.15 (q, J = 7.03 Hz, 1H) 3.92-4.03 (m, 2H) 3.76 (s, 3H) 3.46-3.56 (m, 1H) 3.08-3.18 (m, 1H) 2.79 (q, J = 7.53 Hz, 2H) 1.52 (d, J = 7.03 Hz, 3H) 1.19 (t, J = 7.28 Hz, 3H). [α]24.8D = −88 (c 0.050, DMSO). |
| 175 | | 1-(4-(1H-pyrazol-4-yl)phenyl)-4-ethyl-3-(3-methoxybenzyl)imidazolidin-2-one | 377.2 | E: 1.42, 100.0% F: 1.99, 100.0% | $^1$H NMR (400 MHz, DMSO-$d_6$) d ppm 13.12 (br. s., 1H) 8.38 (br. s., 1H) 8.13 (br. s., 1H) 7.76-7.90 (m, 4H) 7.53 (t, J = 8.07 Hz, 1H) 7.04-7.21 (m, 3H) 4.86 (d, J = 15.41 Hz, 1H) 4.44 (d, J = 15.41 Hz, 1H) 4.13-4.25 (m, 1H) 4.00 (s, 3H) 3.67-3.83 (m, 2H) 1.91-2.06 (m, 1H) 1.73 (dt, J = 14.37, 7.12 Hz, 1H) 1.08 (t, J = 7.34 Hz, 3H). |
| 176 | | 1-(4-(1H-pyrazol-4-yl)phenyl)-4-ethyl-3-(3-fluoro-5-methoxybenzyl)imidazolidin-2-one | 395.1 | E: 1.98, 95.63% F: 2.02, 94.85% | $^1$H NMR (400 MHz, DMSO-$d_6$) d ppm 13.12 (br. s., 1H) 8.38 (br. s., 1H) 8.13 (br. s., 1H) 7.77-7.91 (m, 4H) 6.92-7.04 (m, 3H) 4.80 (d, J = 15.90 Hz, 1H) 4.49 (d, J = 15.65 Hz, 1H) 4.18-4.29 (m, 1H) 4.02 (s, 3H) 3.70-3.87 (m, 2H) 1.91-2.05 (m, 1H) 1.73 (dquin, J =14.26, 7.26, 7.26, 7.26, 7.26 Hz, 1H) 1.09 (t, J = 7.34 Hz, 3H). $^{19}$F NMR (400 MHz, DMSO-$d_6$) d ppm −11.591. |
| 177 | | 1-(4-(1H-pyrazol-4-yl)phenyl)-3-(3-(cyclopropylmethoxy)benzyl)-4-ethyl-imidazolidin-2-one | 417.2 | E: 2.17, 98.65% F: 2.20, 98.86% | $^1$H NMR (400 MHz, DMSO-$d_6$) d ppm 13.12 (br. s., 1H) 8.38 (s, 1H) 8.13 (s, 1H) 7.78-7.90 (m, 4H) 7.50 (t, J = 8.07 Hz, 1H) 7.05-7.17 (m, 3H) 4.85 (d, J = 15.41 Hz, 1H) 4.41 (d, J = 15.41 Hz, 1H) 4.16-4.25 (m, 1H) 4.05 (d, J = 6.85 Hz, 2H) 3.69-3.82 (m, |

TABLE 10-continued

| Ex. | R | Name | LCMS (M + H)+ | HPLC Method, RT (min.) and Purity | NMR |
|---|---|---|---|---|---|
| | | | | | 2H) 1.93-2.07 (m, 1H) 1.67-1.79 (m, 1H) 1.40-1.54 (m, 1H) 1.08 (t, J = 7.34 Hz, 3H) 0.77-0.86 (m, 2H) 0.52-0.60 (m, 2H). |
| 178 | | 1-(3-fluoro-5-methoxy-benzyl)-3-(6-methyl-5-(1H-pyrazol-4-yl)pyridin-2-yl)-imidazolidin-2-one | 382.1 | E: 1.36, 99.47% F: 1.88, 99.79% | $^1$H NMR (400 MHz, methanol-$d_4$) d ppm 8.31 (dd, J = 8.56, 0.49 Hz, 1H) 8.05 (br. s., 2H) 7.96 (d, J = 8.56 Hz, 1H) 7.01 (d, J = 1.47 Hz, 1H) 6.87-6.97 (m, 2H) 4.72 (s, 2H) 4.33-4.40 (m, 2H) 4.08 (s, 3H) 3.72 (dd, J = 8.80, 7.58 Hz, 2H) 2.81 (s, 3H). $^1$H NMR (400 MHz, methanol-$d_4$) d ppm −113.497. |
| 179 | | 1-(3-methoxy-benzyl)-3-(6-methyl-5-(1H-pyrazol-4-yl)pyridin-2-yl)-imidazolidin-2-one | 364.2 | E: 1.28, 99.64% F: 1.80, 99.56% | $^1$H NMR (400 MHz, methanol-$d_4$) d ppm 8.31 (dd, J = 8.56, 0.73 Hz, 1H) 8.11 (br. s., 1H) 8.01 (br. s., 1H) 7.96 (d, J = 8.56 Hz, 1H) 7.51-7.59 (m, 1H) 7.10-7.21 (m, 3H) 4.73 (s, 2H) 4.31-4.38 (m, 2H) 4.07 (s, 3H) 3.66-3.72 (m, 2H) 2.80 (s, 3H). |
| 180 | | 1-(6-ethyl-5-(1H-pyrazol-4-yl)pyridin-2-yl)-3-(3-methoxy-benzyl)-1H-imidazol-2(3H)-one | 376.2 | E: 1.82, 99.37% F: 1.87, 98.72% | $^1$H NMR (400 MHz, DMSO-$d_6$) d ppm 13.35 (br. s., 1H) 8.44 (d, J = 8.56 Hz, 1H) 8.11 (d, J = 8.56 Hz, 3H) 7.65 (s, 1H) 7.50-7.58 (m, 1H) 7.06-7.21 (m, 4H) 5.06 (s, 2H) 4.00 (s, 3H) 3.13 (q, J = 7.34 Hz, 2H) 1.23 (t, J = 7.20 Hz, 3H). |
| 181 | | 1-(1-(3-methoxy-phenyl)-ethyl)-3-(6-methyl-5-(1H-pyrazol-4-yl)pyridin-2-yl)-imidazolidin-2-one (Enantiomer 1) | 378.2 | I: 6.63, 99.16% J: 7.37, 99.90% IV: 3.62, 100% ee | $^1$H NMR (400 MHz, methanol-$d_4$) d ppm 8.03 (d, J = 8.53 Hz, 1H) 7.80 (br. s, 2H) 7.69 (d, J = 8.53 Hz, 1H) 7.31 (t, J = 8.03 Hz, 1H) 6.97-7.02 (m, 1H) 6.95 (t, J = 2.01 Hz, 1H) 6.88 (dd, J = 7.53, 2.51 Hz, 1H) 5.28 (q, J = 7.03 Hz, 1H) 3.97-4.12 (m, 2H) 3.81 (s, 3H) 3.57 (td, J = 9.29, 6.53 Hz, 1H) 3.13-3.23 (m, 1H) 2.54 (s, 3H) 1.62 (d, J = 7.03 Hz, 3H). [α]25.2D = +112 (c 0.050, DMSO). |

TABLE 10-continued

| Ex. | R | Name | LCMS (M + H)+ | HPLC Method, RT (min.) and Purity | NMR |
|---|---|---|---|---|---|
| 182 | | 1-(1-(3-methoxy-phenyl)-ethyl)-3-(6-methyl-5-(1H-pyrazol-4-yl)pyridin-2-yl)-imidazolidin-2-one (Enantiomer 2) | 378.2 | I: 6.60, 98.49% J: 7.36, 98.40% IV: 477, 99% ee | $^1$H NMR (400 MHz, methanol-d$_4$) d ppm 8.03 (d, J = 9.04 Hz, 1H) 7.80 (br. s., 2H) 7.69 (d, J = 8.53 Hz, 1H) 7.26-7.34 (m, 1H) 6.99 (dd, J = 7.28, 1.26 Hz, 1H) 6.95 (t, J = 2.26 Hz, 1H) 6.84-6.91 (m, 1H) 5.28 (q, J = 7.36 Hz, 1H) 3.96-4.13 (m, 2H) 3.81 (s, 3H) 3.57 (td, J = 9.54, 6.53 Hz, 1H) 3.12-3.23 (m, 1H) 2.54 (s, 3H) 1.62 (d, J = 7.53 Hz, 3H). [α]25.0D = −72 (c 0.050, DMSO). |
| 183 | | 1-(6-ethyl-5-(1H-pyrazol-4-yl)pyridin-2-yl)-3-(1-(3-methoxy-phenyl)-ethyl)-1H-imidazol-2(3H)-one (Enantiomer 1) | 390.2 | I: 10.54, 99.20% J: 9.37, 96.00% IV: 2.81, 100% ee | $^1$H NMR (400 MHz, methanol-d$_4$) d ppm 8.15 (d, J = 8.53 Hz, 1H) 7.80 (d, J = 8.53 Hz, 3H) 7.51 (d, J = 3.01 Hz, 1H) 7.27-7.34 (m, 1H) 6.91-6.99 (m, 2H) 6.85-6.90 (m, 1H) 6.76 (d, J = 3.51 Hz, 1H) 5.46 (q, J = 7.03 Hz, 1H) 3.81 (s, 3H) 2.93 (q, J = 7.53 Hz, 2H) 1.77 (d, J = 7.53 Hz, 3H) 1.31 (t, J = 7.53 Hz, 3H). [α]25.3D = +92 (c 0.050, DMSO). |
| 184 | | 1-(6-ethyl-5-(1H-pyrazol-4-yl)pyridin-2-yl)-3-(1-(3-methoxy-phenyl)-ethyl)-1H-imidazol-2(3H)-one (Enantiomer 2) | 390.2 | I: 10.54, 93.66% J: 9.36, 94.22% IV: 3.71, 98.66% ee | $^1$H NMR (400 MHz, methanol-d$_4$) d ppm 8.15 (d, J = 8.53 Hz, 1H) 7.68-7.90 (m, 3H) 7.51 (d, J = 3.01 Hz, 1H) 7.30 (t, J = 8.03 Hz, 1H) 6.91-6.99 (m, 2H) 6.85-6.90 (m, 1H) 6.76 (d, J = 3.51 Hz, 1H) 5.46 (q, J = 7.03 Hz, 1H) 3.81 (s, 3H) 2.93 (q, J = 7.53 Hz, 2H) 1.77 (d, J = 7.53 Hz, 3H) 1.31 (t, J = 7.53 Hz, 3H). [α]25.3D = −92 (c 0.050, DMSO). |
| 185 | | 1-(3-fluoro-5-methoxy-benzyl)-3-(6-methyl-5-(1H-pyrazol-4-yl)pyridin-2-yl)-1H-imidazol-2(3H)-one | 380.1 | E: 1.80, 100.0% F: 1.84, 99.81% | $^1$H NMR (400 MHz, methanol-d$_4$) d ppm 8.17 (d, J = 9.04 Hz, 1H) 7.77-7.98 (m, 3H) 7.48 (d, J = 3.01 Hz, 1H) 6.75 (d, J = 1.51 Hz, 1H) 6.61-6.70 (m, 3H) 4.87 (s, 2H) 3.81 (s, 3H) 2.63 (s, 3H). $^{19}$F NMR (400 MHz, methanol-d$_4$) d ppm −113.263. |

TABLE 10-continued

| Ex. | R | Name | LCMS (M + H)+ | HPLC Method, RT (min.) and Purity | NMR |
|---|---|---|---|---|---|
| 186 | | 1-(3-(cyclopropylmethoxy)benzyl)-3-(6-methyl-5-(1H-pyrazol-4-yl)pyridin-2-yl)imidazolidin-2-one | 404.2 | E: 1.54, 99.59% F: 2.08, 99.48% | ¹H NMR (400 MHz, methanol-d₄) d ppm 8.06 (d, J = 8.53 Hz, 1H) 7.87 (br. s., 1H) 7.75 (br. s., 1H) 7.70 (d, J = 8.53 Hz, 1H) 7.22-7.31 (m, 1H) 6.82-6.94 (m, 3H) 4.46 (s, 2H) 4.04-4.13 (m, 2H) 3.85 (s, 2H) 3.39-3.48 (m, 2H) 2.55 (s, 3H) 1.19-1.32 (m, 1H) 0.57-0.66 (m, 2H) 0.31-0.40 (m, 2H). |
| 187 | | 1-(3-methoxybenzyl)-3-(6-methyl-5-(1H-pyrazol-4-yl)pyridin-2-yl)-1H-imidazol-2(3H)-one | 362.1 | E: 1.72, 100.0% F: 1.77, 99.80% | ¹H NMR (400 MHz, methanol-d₄) d ppm 8.17 (d, J = 9.04 Hz, 1H) 7.87 (d, J = 8.53 Hz, 3H) 7.46 (d, J = 3.51 Hz, 1H) 7.27-7.32 (m, 1H) 6.86-6.94 (m, 3H) 6.64 (d, J = 3.01 Hz, 1H) 4.87 (s, 2H) 3.80 (s, 3H) 2.63 (s, 3H). |
| 188 | | 1-(1-(3-methoxyphenyl)ethyl)-3-(6-methyl-5-(1H-pyrazol-4-yl)pyridin-2-yl)-1H-imidazol-2(3H)-one (Enantiomer 1) | 376.2 | I: 9.61, 99.97% J: 8.54, 99.80% IV: 3.83, 100% ee | ¹H NMR (400 MHz, methanol-d₄) d ppm 8.15 (d, J = 9.04 Hz, 1H) 7.86 (d, J = 8.03 Hz, 3H) 7.47 (d, J = 3.51 Hz, 1H) 7.30 (t, J = 8.03 Hz, 1H) 6.91-6.99 (m, 2H) 6.88 (dd, J = 7.53, 2.51 Hz, 1H) 2.51 Hz, 1H) 6.76 (d, J = 3.01 Hz, 1H) 5.45 (q, J = 7.36 Hz, 1H) 3.81 (s, 3H) 2.63 (s, 3H) 1.76 (d, J = 7.03 Hz, 3H). [α]25.2D = +116 (c 0.05, DMSO). |
| 189 | | 1-(1-(3-methoxyphenyl)ethyl)-3-(6-methyl-5-(1H-pyrazol-4-yl)pyridin-2-yl)-1H-imidazol-2(3H)-one (Enantiomer 2) | 376.2 | I: 9.24, 99.18% J: 8.52, 99.15% IV: 5.22, 99.5% ee | ¹H NMR (400 MHz, methanol-d₄) d ppm 8.15 (d, J = 9.04 Hz, 1H) 7.86 (d, J = 8.03 Hz, 3H) 7.47 (d, J = 3.51 Hz, 1H) 7.25-7.34 (m, 1H) 6.91-6.99 (m, 2H) 6.88 (dd, J = 7.78, 2.26 Hz, 1H) 6.76 (d, J = 3.01 Hz, 1H) 5.45 (q, J = 7.53 Hz, 1H) 3.81 (s, 3H) 2.63 (s, 3H) 1.76 (d, J = 7.03 Hz, 3H). [α]25.2D = −120 (c 0.05, DMSO). |
| 190 | | 1-(4-ethyl-5-(1H-pyrazol-4-yl)pyridin-2-yl)-3-(3-methoxybenzyl)imidazolidin-2-one | 378.2 | E: 1.41, 99.35% F: 1.74, 99.53% | ¹H NMR (400 MHz, DMSO-d₆) d ppm 13.04 (br. s., 1H) 8.13-8.26 (m, 2H) 7.83 (br. s., 2H) 7.21-7.35 (m, 1H) 6.82-6.94 (m, 3H) 4.40 (s, 2H) 3.97 (dd, J = 9.04, 7.03 Hz, 2H) 3.76 (s, 3H) 3.29-3.43 (m, 2H) 2.71 (q, J = 7.53 Hz, |

TABLE 10-continued

| Ex. | R | Name | LCMS (M + H)+ | HPLC Method, RT (min.) and Purity | NMR |
|---|---|---|---|---|---|
| | | | | | 2H) 1.15 (t, J = 7.28 Hz, 3H). |
| 191 | | 1-(4-ethyl-5-(1H-pyrazol-4-yl)pyridin-2-yl)-3-(3-fluoro-5-methoxy-benzyl)imidazolidin-2-one | 396.2 | E: 1.43, 100% F: 1.83, 100% | ¹H NMR (400 MHz, DMSO-d₆) d ppm 13.04 (br. s., 1H) 8.21 (d, J = 10.04 Hz, 2H) 7.82 (br. s., 2H) 6.68-6.81 (m, 3H) 4.40 (s, 2H) 3.98 (dd, J = 9.29, 7.28 Hz, 2H) 3.78 (s, 3H) 3.36-3.45 (m, 2H) 2.71 (q, J = 7.53 Hz, 2H) 1.14 (t, J = 7.53 Hz, 3H). ¹⁹F NMR (400 MHz, methanol-d₄) d ppm −111.501. |
| 192 | | 1-(1-(3-methoxy-phenyl)-ethyl)-3-(3-methyl-4-(1H-pyrazol-4-yl)phenyl)imidazolidin-2-one (Enantiomer 1) | 377.2 | I: 9.80, 99.28% J: 9.21, 99.54% VI: 4.53, 98.94% ee | ¹H NMR (400 MHz, methanol-d₄) d ppm 7.74 (s, 2H) 7.46 (s, 1H) 7.42 (d, J = 2.51 Hz, 1H) 7.27-7.36 (m, 2H) 6.92-7.03 (m, 2H) 6.83-6.90 (m, 1H) 5.26 (q, J = 7.03 Hz, 1H) 3.74-3.97 (m, 5H) 3.50-3.65 (m, 1H) 3.11-3.24 (m, 1H) 2.41 (s, 3H) 1.61 (d, J = 7.03 Hz, 3H). [α]25.3D = −120 (c 0.05, DMSO). |
| 193 | | 1-(1-(3-methoxy-phenyl)-ethyl)-3-(3-methyl-4-(1H-pyrazol-4-yl)phenyl)imidazolidin-2-one (Enantiomer 2) | 377.2 | E: 1.82, 98.12% F: 1.86, 98.34% VI: 5.94, 97.96% ee | ¹H NMR (400 MHz, DMSO-d₆) d ppm 12.88 (br. s., 1H) 7.89 (br. s., 1H) 7.67 (br. s., 1H) 7.39-7.46 (m, 2H) 7.25-7.35 (m, 2H) 6.82-6.98 (m, 3H) 5.12 (q, J = 7.01 Hz, 1H) 3.71-3.82 (m, 5H) 3.45-3.55 (m, 1H) 3.06-3.15 (m, 1H) 2.33-2.37 (m, 3H) 1.51 (d, J = 7.34 Hz, 3H). [α]25.2D = +64 (c 0.05, DMSO). |
| 194 | | 1-(4-ethyl-5-(1H-pyrazol-4-yl)pyridin-2-yl)-3-(4-fluoro-3-methoxy-benzyl)imidazolidin-2-one | 396.2 | E: 1.41, 98.11% F: 1.68, 100% | ¹H NMR (400 MHz, DMSO-d₆) d ppm 8.20 (d, J = 6.11 Hz, 2H) 7.82 (br. s., 2H) 7.19 (dd, J = 11.62, 8.19 Hz, 1H) 7.11 (dd, J = 8.56, 1.96 Hz, 1H) 6.88 (ddd, J = 8.25, 4.34, 2.08 Hz, 1H) 4.40 (s, 2H) 3.96 (dd, J = 9.17, 6.97 Hz, 2H) 3.85 (s, 3H) 3.36-3.41 (m, 2H) 2.71 (q, J = 7.42 Hz, 2H) 1.14 (t, J = 7.58 Hz, 3H). ¹⁹F NMR (400 MHz, DMSO-d₆) d ppm −137.402. |

TABLE 10-continued

| Ex. | R | Name | LCMS (M + H)+ | HPLC Method, RT (min.) and Purity | NMR |
|---|---|---|---|---|---|
| 195 | | 1-(4-(1H-pyrazol-4-yl)-phenyl)-3-(1-(3-(cyclo-propyl-methoxy)-phenyl)-ethyl)-imidazolidin-2-one (Enantiomer 1) | 403.2 | K: 17.15, 97.90% L: 16.38, 99.81% IV: 4.27, 100% ee | $^1$H NMR (400 MHz, DMSO-d$_6$) d ppm 12.83 (br. s., 1H) 7.98 (br. s., 2H) 7.55 (s, 4H) 7.26 (t, J = 7.78 Hz, 1H) 6.81-6.94 (m, 3H) 5.11 (q, J = 7.19 Hz, 1H) 3.75-3.84 (m, 4H) 3.45-3.55 (m, 1H) 3.06-3.16 (m, 1H) 1.50 (d, J = 7.53 Hz, 3H) 1.21 (s, 1H) 0.52-0.60 (m, 2H) 0.28-0.35 (m, 2H). [α]25.0D = −104 (c 0.050, DMSO). |
| 196 | | 1-(4-(1H-pyrazol-4-yl)-phenyl)-3-(1-(3-(cyclo-propyl-methoxy)-phenyl)-ethyl)-imidazolidin-2-one (Enantiomer 2) | 403.2 | K: 17.44, 99.36% L: 15.82, 99.00% IV: 7.46, 97.96% ee | $^1$H NMR(400 MHz, DMSO-d$_6$)d ppm 12.87 (br. s., 1H) 8.11 (br. s., 1H) 7.88 (br. s., 1H) 7.55 (s, 4H) 7.27 (t, J = 7.78 Hz, 1H) 6.80-6.95 (m, 3H) 5.12(q, J = 7.19 Hz, 1H) 3.73-3.86 (m, 4H) 3.45-3.58 (m, 1H) 3.12 (q, J = 8.37 Hz, 1H) 1.51 (d, J = 7.03 Hz, 3H) 1.17-1.26 (m, 1H) 0.51-0.62 (m, 2H) 0.28-0.36 (m, 2H). [α]25.0D = +92 (c 0.050, DMSO). |
| 197 | | 1-(4-(1H-pyrazol-4-yl)-phenyl)-3-(1-(3-fluoro-5-methoxy-phenyl)ethyl)imidazolidin-2-one (Enantiomer 1) | 381.2 | I: 9.87, 99.84% J: 9.28, 99.81% IV: 5.22, 99.40% ee | $^1$H NMR (400 MHz, DMSO-d$_6$) d ppm 12.85 (br. s., 1H) 8.11 (br. s., 1H) 7.86 (br. s., 1H) 7.55 (s, 4H) 6.71-6.81 (m, 3H) 5.09 (q, J = 7.19 Hz, 1H) 3.81 (t, J = 8.03 Hz, 2H) 3.77 (s, 3H) 3.51 (q, J = 8.37 Hz, 1H) 3.17 (q, J = 8.20 Hz, 1H) 1.50 (d, J = 7.03 Hz, 3H). $^{19}$F NMR (400 MHz, DMSO-d$_6$) d ppm −114.423. [α]25.3D = +92 (c 0.10, DMSO). |
| 198 | | 1-(4-(1H-pyrazol-4-yl)-phenyl)-3-(1-(3-fluoro-5-methoxy-phenyl)ethyl)imidazolidin-2-one (Enantiomer 2) | 381.2 | I: 9.85, 99.80% J: 9.27, 99.57% IV: 6.50, 98.38% ee | $^1$H NMR (400 MHz, DMSO-d$_6$) d ppm 12.84 (br. s., 1H) 7.98 (br. s., 2H) 7.55 (s, 4H) 6.72-6.79 (m, 3H) 5.09 (q, J = 7.03 Hz, 1H) 3.81 (t, J = 8.28 Hz, 2H) 3.77 (s, 3H) 3.51 (q, J = 8.37 Hz, 1H) 3.12-3.22 (m, 1H) 1.50 (d, J = 7.03 Hz, 3H). $^{19}$F NMR (400 MHz, DMSO-d$_6$) d ppm −114.422. [α]25.2D = −114 (c 0.10, DMSO). |

| Ex. | R | Name | LCMS (M + H)+ | HPLC Method, RT (min.) and Purity | NMR |
|---|---|---|---|---|---|
| 199 | | 1-(4-fluoro-3-methoxy-benzyl)-3-(6-(methyl-amino)-5-(1H-pyrazol-4-yl)pyridin-2-yl)-imidazolidin-2-one | 397.1 | E: 1.30, 99.10% F: 1.94, 99.34% | ¹H NMR (400 MHz, DMSO-d₆) d ppm 12.94 (br. s., 1H) 7.91 (br. s., 1H) 7.69 (br. s., 1H) 7.33-7.43 (m, 2H) 7.19 (dd, J = 11.49, 8.31 Hz, 1H) 7.09 (dd, J = 8.31, 1.71 Hz, 1H) 6.86 (ddd, J=8.19, 4.40, 1.83 Hz, 1H) 5.66-5.75 (m, 1H) 4.36 (s, 2H) 4.00 (t, J = 8.07 Hz, 2H) 3.84 (s, 3H) 3.33-3.40 (m, 2H) 2.81 (d, J = 4.65 Hz, 3H). ¹⁹F NMR (400 MHz, methanol-d₄) peaks at −137.484. |
| 200 | | 1-(3-fluoro-5-methoxy-benzyl)-3-(6-(methyl-amino)-5-(1H-pyrazol-4-yl)pyridin-2-yl)-imidazolidin-2-one | 397.2 | E: 1.37, 97.02% F: 1.99, 99.56% | ¹H NMR (400 MHz, DMSO-d₆) d ppm 12.93 (s, 1H) 7.93 (br. s., 1H) 7.70 (br. s., 1H) 7.32-7.44 (m, 2H) 6.65-6.81 (m, 3H) 5.72 (d, J = 4.89 Hz, 1H) 4.37 (s, 2H) 4.02 (t, J = 8.19 Hz, 2H) 3.77 (s, 3H) 3.34-3.41 (m, 2H) 2.82 (d, J = 4.40 Hz, 3H). ¹⁹F NMR (400 MHz, methanol-d₄) peaks at −111.550. |
| 201 | | 1-(3-(cyclopropyl-methoxy)-benzyl)-3-(6-(methyl-amino)-5-(1H-pyrazol-4-yl)pyridin-2-yl)-imidazolidin-2-one | 419.2 | E: 1.51, 99.71% F: 2.18, 98.53% | ¹H NMR (400 MHz, DMSO-d₆) d ppm 12.94 (br. s., 1H) 7.92 (br. s., 1H) 7.68 (br. s., 1H) 7.34-7.41 (m, 2H) 7.20-7.31 (m, 1H) 6.78- 6.90 (m, 3H) 5.70 (d, J = 4.65 Hz, 1H) 4.34 (s, 2H) 3.99 (t, J = 8.07 Hz, 2H) 3.80 (d, J = 7.09 Hz, 2H) 3.34 (s, 1H) 2.81 (d, J = 4.65 Hz, 3H) 1.08-1.29 (m, 2H) 0.50-0.61 (m, 2H) 0.23-0.35 (m, 2H). |
| 202 | | 1-(3-methoxy-benzyl)-3-(6-(methyl-amino)-5-(1H-pyrazol-4-yl)pyridin-2-yl)-imidazolidin-2-one | 379.2 | E: 1.19, 99.88% F: 1.86, 100% | ¹H NMR (400 MHz, DMSO-d₆) d ppm 12.96 (br. s., 1H) 7.90 (br. s., 1H) 7.72 (br. s., 1H) 7.35-7.42 (m, 2H) 7.23-7.33 (m, 1H) 6.82-6.92 (m, 3H) 5.71 (d, J = 4.65 Hz, 1H) 4.37 (s, 2H) 4.00 (t, J = 8.07 Hz, 2H) 3.75 (s, 3 H) 3.17 (d, J = 5.14 Hz, 2H) 2.82 (d, J = 4.65 Hz, 3H). |

TABLE 10-continued

| Ex. | R | Name | LCMS (M + H)⁺ | HPLC Method, RT (min.) and Purity | NMR |
|---|---|---|---|---|---|
| 204 | | 1-(1-(3-(cyclopropyl-methoxy)-phenyl)-ethyl)-3-(6-methyl-5-(1H-pyrazol-4-yl)pyridin-2-yl)-imidazolidin-2-one (Enantiomer 2) | 418.2 | E: 1.63, 99.02% F: 1.89, 99.32% IV: 6.13, 99.8% ee | $^1$H NMR (400 MHz, methanol-d$_4$) d ppm 7.99-8.04 (m, 1H) 7.85 (br. s., 1H) 7.73 (br. s., 1H) 7.67 (d, J = 8.56 Hz, 1H) 7.27 (t, J = 7.95 Hz, 1H) 6.90-7.00 (m, 2H) 6.84 (dd, J = 7.95, 2.32 Hz, 1H) 5.25 (q, J = 7.09 Hz, 1H) 3.94-4.11 (m, 2H) 3.83 (d, J = 6.85 Hz, 2H) 3.55 (td, J = 9.35, 6.48 Hz, 1H) 3.16 (td, J = 9.35, 6.97 Hz, 1H) 2.52 (s, 3H) 1.60 (d, J = 7.09 Hz, 3H) 1.18-1.33 (m, 1H) 0.56-0.64 (m, 2H) 0.30-0.39 (m, 2H). [α]25.0D = +538.400 (c 0.05, DMSO). |
| 205 | | 1-(3'-fluoro-2-methyl-[3,4'-bipyridin]-6-yl)-3-(3-methoxy-benzyl)imidazolidin-2-one | 393.2 | E: 1.52, 95.32% F: 1.89, 95.73% | $^1$H NMR (400 MHz, methanol-d$_4$) d ppm 8.54 (d, J = 1.96 Hz, 1H) 8.46 (dd, J = 5.01, 0.86 Hz, 1H) 8.19 (d, J = 8.56 Hz, 1H) 7.60 (d, J = 8.56 Hz, 1H) 7.45 (dd, J = 6.48, 5.01 Hz, 1H) 7.22-7.32 (m, 1H) 6.82-6.95 (m, 3H) 4.46 (s, 2H) 4.05-4.13 (m, 2H) 3.79 (s, 3H) 3.44 (dd, J = 8.80, 7.58 Hz, 2H) 2.34 (d, J = 1.47 Hz, 3H). $^{19}$F NMR (400 MHz, methanol-d$_4$) peaks at −130.400. |
| 206 | | 1-(1-(3-fluoro-5-methoxy-phenyl)-ethyl)-3-(6-methyl-5-(1H-pyrazol-4-yl)pyridin-2-yl)-imidazolidin-2-one (Enantiomer 1) | 396.2 | E: 1.28, 99.83% F: 1.81, 100% IV: 3.7, 100% ee | $^1$H NMR (400 MHz, methanol-d$_4$) d ppm 7.97-8.04 (m, 1H) 7.82 (br. s., 1H) 7.73 (br. s., 1H) 7.66 (d, J = 8.56 Hz, 1H) 6.69-6.82 (m, 2H) 6.62 (dt, J = 10.76, 2.20 Hz, 1H) 5.22 (q, J = 7.25 Hz, 1H) 3.96-4.12 (m, 2H) 3.79 (s, 3H) 3.56 (td, J = 9.29, 6.60 Hz, 1H) 3.19 (td, J = 9.23, 6.97 Hz, 1H) 2.51 (s, 3H) 1.58 (d, J = 7.09 Hz, 3H). $^{19}$F NMR (400 MHz, methanol-d$_4$) d ppm −113.330. [α]25.3D = +105.600 (c 0.05, DMSO). |

TABLE 10-continued

| Ex. | R | Name | LCMS (M + H)+ | HPLC Method, RT (min.) and Purity | NMR |
|---|---|---|---|---|---|
| 207 | | 1-(1-(3-fluoro-5-methoxyphenyl)ethyl)-3-(6-methyl-5-(1H-pyrazol-4-yl)pyridin-2-yl)-imidazolidin-2-one (Enantiomer 2) | 396.2 | E: 1.26, 99.62% F: 1.81, 98.99% IV: 4.68, 99.21% ee | $^1$H NMR (400 MHz, methanol-$d_4$) d ppm 7.97-8.05 (m, 1H) 7.80 (br. s., 1H) 7.74 (br. s., 1H) 7.67 (d, J = 8.56 Hz, 1H) 6.68-6.80 (m, 2H) 6.63 (dt, J = 10.64, 2.38 Hz, 1H) 5.22 (q, J = 7.09 Hz, 1H) 3.96-4.13 (m, 2H) 3.80 (s, 3H) 3.56 (td, J = 9.41, 6.60 Hz, 1H) 3.19 (td, J = 9.29, 6.85 Hz, 1H) 2.52 (s, 3H) 1.58 (d, J = 7.09 Hz, 3H). $^{19}$F NMR (400 MHz, methanol-$d_4$) d ppm −113.328. [α]25.3D = −1.160 (c 5.0, DMSO). |
| 208 | | 1-(1-(4-fluoro-3-methoxyphenyl)ethyl)-3-(6-methyl-5-(1H-pyrazol-4-yl)pyridin-2-yl)-imidazolidin-2-one (Enantiomer 1) | 396.2 | E: 1.44, 98.81% F: 1.94, 97.17% XI: 30.22, 99.92% ee | $^1$H NMR (400 MHz, methanol-$d_4$) d ppm 8.01 (d, J = 8.56 Hz, 1H) 7.78 (br. s., 2H) 7.66 (d, J = 8.56 Hz, 1H) 7.04-7.14 (m, 2H) 6.96 (ddd, J = 8.31, 4.16, 2.20 Hz, 1H) 5.25 (q, J = 7.17 Hz, 1H) 3.94-4.11 (m, 2H) 3.87 (s, 3H) 3.56 (td, J = 9.35, 6.72 Hz, 1H) 3.16 (td, J = 9.29, 6.85 Hz, 1 H) 2.51 (s, 3H) 1.60 (d, J = 7.09 Hz, 3H). $^{19}$F NMR (400 MHz, methanol-$d_4$) d ppm −138.785. [α]25.2D = −100 (c 0.05, DMSO). |
| 209 | | 1-(1-(4-fluoro-3-methoxyphenyl)ethyl)-3-(6-methyl-5-(1H-pyrazol-4-yl)pyridin-2-yl)-imidazolidin-2-one (Enantiomer 2) | 396.2 | E: 1.44, 98.88% F: 1.95, 99.88% XI: 25.78, 100% ee | $^1$H NMR (400 MHz, methanol-$d_4$) d ppm 8.01 (d, J = 8.56 Hz, 1H) 7.82 (br. s., 1H) 7.74 (br. s., 1H) 7.67 (d, J = 8.56 Hz, 1H) 7.05-7.13 (m, 2H) 6.96 (ddd, J = 8.31, 4.16, 2.20 Hz, 1H) 5.26 (q, J = 7.01 Hz, 1H) 3.96-4.11 (m, 2H) 3.88 (s, 3H) 3.56 (td, J = 9.29, 6.36 Hz, 1H) 3.16 (td, J = 9.17, 6.85 Hz, 1H) 2.52 (s, 3H) 1.60 (d, J = 7.34 Hz, 3H). $^{19}$F NMR (400 MHz, methanol-$d_4$) d ppm −138.787. [α]25.3D = +84 (c 0.05, DMSO). |

TABLE 10-continued

| Ex. | R | Name | LCMS (M + H)⁺ | HPLC Method, RT (min.) and Purity | NMR |
|---|---|---|---|---|---|
| 210 | | 1-(3-(cyclopropyl methoxy)-4-fluoro-benzyl)-3-(6-methyl-5-(1H-pyrazol-4-yl)pyridin-2-yl)-imidazolidin-2-one | 422.2 | E: 1.54, 94.80% F: 1.97, 94.80% | $^1$H NMR (400 MHz, methanol-$d_4$) d ppm 8.04 (d, J = 8.56 Hz, 1H) 7.79 (br. s., 2H) 7.69 (d, J = 8.56 Hz, 1H) 7.02-7.12 (m, 2H) 6.89 (ddd, J = 8.25, 4.22, 1.96 Hz, 1H) 4.42 (s, 2H) 4.04-4.11 (m, 2H) 3.90 (d, J = 6.85 Hz, 2H) 3.38-3.44 (m, 2H) 2.53 (s, 3H) 1.20-1.32 (m, 1H) 0.56-0.65 (m, 2H) 0.31-0.39 (m, 2H). $^{19}$F NMR (400 MHz, methanol-$d_4$) d ppm −137.855. |
| 211 | | 1-(4-(1H-pyrazol-4-yl)phenyl)-3-(cyclohexyl-methyl)imidazolidin-2-one | 325.2 | E: 2.01, 100% F: 1.98, 100% | $^1$H NMR (400 MHz, DMSO-$d_6$) d ppm 12.85 (br. s., 1H) 8.10 (br. s., 1H) 7.86 (br. s., 1H) 7.54 (s, 4H) 3.81 (dd, J = 9.54, 6.53 Hz, 2H) 3.43-3.48 (m, 2H) 3.02 (d, J = 7.03 Hz, 2H) 1.52-1.74 (m, 6H) 1.13-1.29 (m, 3H) 0.84-0.99 (m, 2H). |
| 212 | | 1-(1-(3-(cyclopropyl-methoxy)-phenyl)-ethyl)-3-(6-methoxy-5-(1H-pyrazol-4-yl)pyridin-2-yl)-imidazolidin-2-one (Enantiomer 1) | 434.2 | K: 20.98, 95.3% L: 17.98, 97.5% | $^1$H NMR (400 MHz, DMSO-$d_6$) δ ppm 12.65 (br. s., 1H), 8.00 (s, 2H), 7.96 (d, J = 8.4 Hz, 1H), 7.74 (d, J = 8.0 Hz, 1H), 7.26 (t, J = 7.8 Hz, 1H), 6.95-6.77 (m, 3H), 5.17-5.05 (m, 1H), 4.02-3.95 (m, 2H), 3.94 (s, 3H), 3.80 (d, J = 7.0 Hz, 2H), 3.58-3.44 (m, 1H), 3.18-3.08 (m, 1H), 1.51 (d, J = 1.0 Hz, 3H), 1.29-1.09 (m, 1H), 0.62-0.48 (m, 2H), 0.38-0.23 (m, 2H) |
| 213 | | 1-(1-(3-(cyclopropyl-methoxy)-phenyl)-ethyl)-3-(6-methoxy-5-(1H-pyrazol-4-yl)pyridin-2-yl)-imidazolidin-2-one (Enantiomer 2) | 434.2 | K: 19.61, 97.3% L: 16.86, 96.8% | $^1$H NMR (400 MHz, DMSO-$d_6$) δ ppm 8.00 (s, 2H), 7.97 (d, J = 8.0 Hz, 1H), 7.74 (d, J = 8.5 Hz, 1H), 7.27 (t, J = 8.0 Hz, 1H), 6.95-6.80 (m, 3H), 5.18-5.06 (m, 1H), 4.02-3.96 (m, 2H), 3.94 (s, 3H), 3.81 (d, J = 7.0 Hz, 2H), 3.55-3.47 (m, 1H), 3.18-3.07 (m, 1H), 1.51 (d, J = 7.0 Hz, 3H), 1.27-1.12 (m, 1H), 0.60-0.51 (m, 2H), 0.35-0.27 (m, 2H) |

TABLE 10-continued

| Ex. | R | Name | LCMS (M + H)+ | HPLC Method, RT (min.) and Purity | NMR |
|---|---|---|---|---|---|
| 214 | | 1-(4-fluoro-3-methoxy-benzyl)-3-(6-methoxy-5-(1H-pyrazol-4-yl)pyridin-2-yl)-imidazolidin-2-one | 398.2 | I: 9.65, 99.1% J: 8.44, 99.6% | $^1$H NMR (400 MHz, DMSO-d$_6$) δ ppm 12.87 (br. s., 1H), 8.16-7.84 (m, 3H), 7.77 (d, J = 8.5 Hz, 1H), 7.20 (dd, J = 27.1, 24.1 Hz, 1H), 7.11 (dd, J = 8.5, 2.0 Hz, 1H), 6.92-6.83 (m, 1H), 4.38 (s, 2H), 4.07-3.99 (m, 2H), 3.95 (s, 3H), 3.84 (s, 3H), 3.43-3.36 (m, 2H) |
| 218 | | 1-(3-(cyclopropyl-methoxy)-4-fluoro-benzyl)-3-(6-methoxy-5-(1H-pyrazol-4-yl)pyridin-2-yl)-imidazolidin-2-one | 438.2 | E: 2.09, 98.4% F: 2.06, 98.2% | $^1$H NMR (400 MHz, DMSO-d$_6$) δ ppm 12.87 (br. s., 1H), 8.18-7.84 (m, 3H), 7.76 (d, J = 8.1 Hz, 1H), 7.18 (dd, J = 11.5, 8.3 Hz, 1H), 7.07 (d, J = 8.3 Hz, 1H), 6.92-6.83 (m, 1H), 4.36 (s, 2H), 4.01 (t, J = 7.9 Hz, 2H), 3.95 (s, 3H), 3.90 (d, J = 6.8 Hz, 2H), 3.40-3.33 (m, 2H), 1.28-1.18 (m, 1H), 0.62-0.53 (m, 2H), 0.38-0.27 (m, 2H) |
| 219 | | 1-(6-methoxy-5-(1H-pyrazol-4-yl)pyridin-2-yl)-3-(1-(3-methoxy-phenyl)-ethyl)-imidazolidin-2-one (Enantiomer 1) | 394.2 | K: 15.03, 99.5% L: 15.42, 99.0% | $^1$H NMR (400 MHz, DMSO-d$_6$) δ ppm 8.00 (s, 2H), 7.96 (d, J = 8.5 Hz, 1H), 7.75 (d, J = 8.0 Hz, 1H), 7.29 (t, J = 7.8 Hz, 1H), 6.94 (d, J = 7.5 Hz, 1H), 6.90-6.84 (m, 2H), 5.17-5.08 (m, 1H), 4.03-3.96 (m, 2H), 3.95 (s, 3H), 3.75 (s, 3H), 3.56-3.46 (m, 1H), 3.18-3.08 (m, 1H), 1.52 (d, J = 7.0 Hz, 3H) |
| 220 | | 1-(6-methoxy-5-(1H-pyrazol-4-yl)pyridin-2-yl)-3-(1-(3-methoxy-phenyl)-ethyl)-imidazolidin-2-one (Enantiomer 2) | 394.2 | K: 15.01, 97.9% L: 15.40, 97.4% | $^1$H NMR (400 MHz, DMSO-d$_6$) δ ppm 12.60 (br. s., 1H), 8.00 (s, 2H), 7.96 (d, J = 8.5 Hz, 1H), 7.75 (d, J = 8.5 Hz, 1H), 7.29 (t, J = 8.0 Hz, 1H), 6.94 (d, J = 7.5 Hz, 1H), 6.91-6.84 (m, 2H), 5.17-5.09 (m, 1H), 4.04-3.96 (m, 2H), 3.95 (s, 3H), 3.75 (s, 3H), 3.56-3.47 (m, 1H), 3.20-3.08 (m, 1H), 1.52 (d, J = 7.5 Hz, 3H) |

TABLE 10-continued

| Ex. | R | Name | LCMS (M + H)+ | HPLC Method, RT (min.) and Purity | NMR |
|---|---|---|---|---|---|
| 221 | | 1-(2-fluoro-5-methoxy-benzyl)-3-(6-methoxy-5-(1H-pyrazol-4-yl)pyridin-2-yl)-imidazolidin-2-one | 398.2 | E: 1.90, 100% F: 1.92, 98.8% | 1H NMR (400 MHz, DMSO-d6) δ ppm 12.87 (br. s., 1H), 8.08 (s, 1H), 7.98 (d, J = 8.4 Hz, 1H), 7.94 (s, 1H), 7.75 (d, J = 8.1 Hz, 1H), 7.21-7.10 (m, 1H), 6.95-6.84 (m, 2H), 4.43 (s, 2H), 4.02 (t, J = 8.1 Hz, 2H), 3.95 (s, 3H), 3.73 (s, 3H), 3.40 (t, J = 8.1 Hz, 2H) |
| 222 | | 1-(5-fluoro-2-methoxy-benzyl)-3-(6-methoxy-5-(1H-pyrazol-4-yl)pyridin-2-yl)-imidazolidin-2-one | 398.1 | E: 1.94, 100% F: 2.04, 99.4% | 1H NMR (400 MHz, DMSO-d6) δ ppm 12.87 (br. s., 1H), 8.08 (s, 1H), 7.98 (d, J = 8.4 Hz, 1H), 7.94 (br. s., 1H), 7.75 (d, J = 8.3 Hz, 1H), 7.14-7.00 (m, 3H), 4.37 (s, 2H), 4.08-4.01 (m, 2H), 3.96 (s, 3H), 3.81 (s, 3H), 3.43 (t, J = 8.1 Hz, 2H) |
| 223 | | 1-(2,3-difluoro-benzyl)-3-(6-methoxy-5-(1H-pyrazol-4-yl)-pyridin-2-yl)-imidazolidin-2-one | 386.1 | E: 1.94, 97.4% F: 1.94, 98.3% | 1H NMR (400 MHz, DMSO-d6) δ ppm 12.87 (br. s., 1H), 8.08 (br. s., 1H), 8.01-7.91 (m, 2H), 7.74 (d, J = 8.5 Hz, 1H), 7.45-7.34 (m, 1H), 7.27-7.19 (m, 2H), 4.52 (s, 2H), 4.07-3.99 (m, 2H), 3.96 (s, 3H), 3.46-3.39 (m, 2H) |
| 224 | | 1-(3-(cyclo-propyl-methoxy)-5-fluoro-benzyl)-3-(6-methoxy-5-(1H-pyrazol-4-yl)pyridin-2-yl)-imidazolidin-2-one | 438.2 | E: 2.28, 98.0% F: 2.27, 98.1% | 1H NMR (400 MHz, DMSO-d6) δ ppm 12.88 (br. s., 1H), 8.09 (s, 1H), 7.98 (d, J = 8.0 Hz, 1H), 7.94 (s, 1H), 7.76 (d, J = 8.3 Hz, 1H), 6.76-6.66 (m, 3H), 4.37 (s, 2H), 4.04 (dd, J = 8.9, 7.2 Hz, 2H), 3.96 (s, 3H), 3.82 (d, J = 7.1 Hz, 2H), 3.43-3.36 (m, 2H), 1.25-1.17 (m, 1H), 0.60-0.52 (m, 2H), 0.35-0.28 (m, 2H) |
| 225 | | 1-(3-fluoro-2-methoxy-benzyl)-3-(6-methoxy-5-(1H-pyrazol-4-yl)pyridin-2-yl)-imidazolidin-2-one | 398.2 | E: 1.98, 100% F: 1.92, 100% | 1H NMR (400 MHz, DMSO-d6) δ ppm 12.85 (br. s., 1H), 8.44-7.92 (m, 3H), 7.76 (d, J = 8.3 Hz, 1H), 7.27-7.18 (m, 1H), 7.14-7.07 (m, 2H), 4.45 (s, 2H), 4.02 (dd, J = 9.0, 7.1 Hz, 2H), 3.95 (s, 3H), 3.87 (d, J = 1.7 Hz, 3H), 3.44-3.37 (m, 2H) |

TABLE 10-continued

| Ex. | R | Name | LCMS (M + H)+ | HPLC Method, RT (min.) and Purity | NMR |
|---|---|---|---|---|---|
| 226 | | 1-(3-fluoro-benzyl)-3-(6-methoxy-5-(1H-pyrazol-4-yl)pyridin-2-yl)-imidazolidin-2-one | 368.1 | E: 1.88, 100% F: 1.96, 100% | $^1$H NMR (400 MHz, DMSO-$d_6$) δ ppm 12.87 (br. s., 1H), 8.09 (s, 1H), 7.99 (d, J = 8.0 Hz, 1H), 7.94 (s, 1H), 7.77 (d, J = 8.3 Hz, 1H), 7.46-7.38 (m, 1H), 7.20-7.09 (m, 3H), 4.44 (s, 2H), 4.04 (dd, J = 9.3, 7.1 Hz, 2H), 3.96 (s, 3H), 3.44-3.36 (m, 2H) |
| 227 | | 1-(cyclo-hexylmethyl)-3-(6-methoxy-5-(1H-pyrazol-4-yl)pyridin-2-yl)-imidazolidin-2-one | 356.2 | E: 2.19, 100% F: 2.26, 100% | $^1$H NMR (400 MHz, DMSO-$d_6$) δ ppm 12.87 (br. s., 1H), 8.08 (s, 1H), 7.97-7.91 (m, 2H), 7.72 (d, J = 8.3 Hz, 1H), 4.01 (t, J = 8.1 Hz, 2H), 3.96 (s, 3H), 3.46 (t, J = 8.1 Hz, 2H), 3.04 (d, J = 6.8 Hz, 2H), 1.74-1.56 (m, 6H), 1.29-1.11 (m, 3H), 0.98-0.85 (m, 2H |
| 228 | | 1-(1-(3-fluoro-5-methoxy-phenyl)-ethyl)-3-(6-methoxy-5-(1H-pyrazol-4-yl)-pyridin-2-yl)-imidazolidin-2-one (Enantiomer 1) | 412.2 | K: 15.92, 98.9% L: 15.25, 98.4% | $^1$H NMR (400 MHz, DMSO-$d_6$) δ ppm 12.87 (br. s., 1H), 8.11-7.90 (m, 3H), 7.73 (d, J = 8.4 Hz, 1H), 6.81-6.72 (m, 3H), 5.11 (q, J = 7.2 Hz, 1H), 4.01 (t, J = 8.3 Hz, 2H), 3.95 (s, 3H), 3.77 (s, 3H), 3.57-3.47 (m, 1H), 3.26-3.16 (m, 1H), 1.51 (d, J = 7.0 Hz, 3H) |
| 229 | | 1-(1-(3-fluoro-5-methoxy-phenyl)-ethyl)-3-(6-methoxy-5-(1H-pyrazol-4-yl)pyridin-2-yl)-imidazolidin-2-one (Enantiomer 2) | 412.2 | K: 15.99, 99.1% L: 15.73, 95.0% | $^1$H NMR (400 MHz, DMSO-$d_6$) δ ppm 12.83 (br. s., 1H), 8.04-7.94 (m, 3H), 7.74 (d, J = 8.3 Hz, 1H), 6.80-6.72 (m, 3H), 5.11 (q, J = 7.2 Hz, 1H), 4.01 (t, J = 8.2 Hz, 2H), 3.96 (s, 3H), 3.78 (s, 3H), 3.58-3.49 (m, 1H), 3.26-3.15 (m, 1H), 1.51 (d, J = 7.1 Hz, 3H) |
| 230 | | 1-(1-(4-fluoro-3-methoxy-phenyl)-ethyl)-3-(6-methoxy-5-(1H-pyrazol-4-yl)-pyridin-2-yl)-imidazolidin-2-one (Enantiomer 1) | 412.2 | I: 10.40, 97.9% J: 9.69, 98.9% | $^1$H NMR (400 MHz, DMSO-$d_6$) δ ppm 12.86 (br. s., 1H), 8.04-7.94 (m, 3H), 7.75 (d, J = 8.4 Hz, 1H), 7.19 (dd, J = 11.3, 8.3 Hz, 1H), 7.11 (dd, J = 8.5, 2.0 Hz, 1H), 6.98-6.89 (m, 1H), 5.14 (q, J = 7.2 Hz, 1H), 3.99 (dt, J = 9.3, 6.4 Hz, 2H), 3.95 (s, 3H), 3.85 (s, 3H), 3.58-3.48 (m, 1H), 3.19-3.11 (m, 1H), 1.53 (d, J = 7.0 Hz, 3H) |

TABLE 10-continued

| Ex. | R | Name | LCMS (M + H)+ | HPLC Method, RT (min.) and Purity | NMR |
|---|---|---|---|---|---|
| 231 | | 1-(1-(4-fluoro-3-methoxy-phenyl)-ethyl)-3-(6-methoxy-5-(1H-pyrazol-4-yl)-pyridin-2-yl)-imidazolidin-2-one (Enantiomer 2) | 412.2 | I: 10.39, 99.5% J: 9.69, 99.8% | ¹H NMR (400 MHz, DMSO-d₆) δ ppm 12.50 (br. s., 1H), 8.04-7.93 (m, 3H), 7.74 (d, J = 8.0 Hz, 1H), 7.18 (dd, J = 11.3, 8.3 Hz, 1H), 7.10 (dd, J = 8.0, 2.0 Hz, 1H), 6.97-6.89 (m, 1H), 5.14 (q, J = 7.2 Hz, 1H), 3.99 (dt, J = 9.3, 6.4 Hz, 2H), 3.94 (s, 3H), 3.85 (s, 3H), 3.58-3.48 (m, 1H), 3.19-3.10 (m, 1H), 1.52 (d, J = 7.5 Hz, 3H) |
| 233 | | 1-(3-(difluoro-methoxy)-benzyl)-3-(6-methoxy-5-(1H-pyrazol-4-yl)pyridin-2-yl)-imidazolidin-2-one | 416.1 | E: 2.01, 99.3% F: 1.95, 99.6% | ¹H NMR (400 MHz, DMSO-d₆) δ ppm 12.88 (br. s., 1H), 8.09 (br. s., 1H), 7.99 (d, J = 8.3 Hz, 1H), 7.94 (br. s., 1H), 7.77 (d, J = 8.3 Hz, 1H), 7.48-7.41 (m, 1H), 7.27-7.06 (m, 4H), 4.44 (s, 2H), 4.05 (dd, J = 9.2, 7.2 Hz, 2H), 3.96 (s, 3H), 3.45-3.36 (m, 2 H) |
| 234 | | 1-(5-(1H-pyrazol-4-yl)pyridin-2-yl)-3-(3-methyl-benzyl)imidazolidin-2-one | 334.1 | E: 1.77 F: 1.37 | ¹H NMR (400 MHz, DMSO-d₆) δ ppm 12.97 (br. s., 1H), 8.58 (d, J = 1.8 Hz, 1H), 8.24-8.18 (m, 2H), 7.99-7.91 (m, 2H), 7.29-7.23 (m, 1H), 7.14-7.08 (m, 3H), 4.39 (s, 2H), 4.00-3.92 (m, 2H), 3.40-3.35 (m, 2H), 2.31 (s, 3H) |
| 235 | | 3-((3-(5-(1H-pyrazol-4-yl)-pyridin-2-yl)-2-oxo-imidazolidin-1-yl)methyl)-benzonitrile | 345.1 | E: 1.48 F: 1.15 | ¹H NMR (400 MHz, DMSO-d₆) δ ppm 12.97 (br. s., 1H), 8.59 (d, J = 1.8 Hz, 1H), 8.21 (d, J = 8.8 Hz, 1H), 7.97 (dd, J = 8.8, 2.5 Hz, 1H), 7.83-7.75 (m, 1H), 7.71-7.65 (m, 1H), 7.63-7.56 (m, 1H), 4.49 (s, 2H), 4.00 ((t, J = 8.0 Hz, 2H), 3.42 (t, J = 8.0 Hz, 2H) |
| 236 | | 1-(5-(1H-pyrazol-4-yl)pyridin-2-yl)-3-(3,5-dimethyl-benzyl)imidazolidin-2-one | 348.2 | E: 1.92 F: 1.52 | ¹H NMR (400 MHz, DMSO-d₆) δ ppm 12.97 (br. s., 1H), 8.58 (d, J = 1.8 Hz, 1H), 8.22 (d, J = 8.8 Hz, 2H), 7.96 (dd, J = 8.8, 2.5 Hz, 2H), 6.95-6.89 (m, 3H), 4.34 (s, 2H), 3.96 (t, J = 8.0 Hz, 2H), 3.36 (t, J = 8.0 Hz, 2H), 2.27 (s, 6H) |

TABLE 10-continued

| Ex. | R | Name | LCMS (M + H)+ | HPLC Method, RT (min.) and Purity | NMR |
|---|---|---|---|---|---|
| 237 | (structure: pyrazole-pyridine-imidazolidinone-CH2-3-chlorophenyl) | 1-(5-(1H-pyrazol-4-yl)pyridin-2-yl)-3-(3-chlorobenzyl)-imidazolidin-2-one | 354 | E: 1.79<br>F: 1.41 | ¹H NMR (400 MHz, DMSO-d₆) δ ppm 12.97 (br. s., 1H), 8.58 (d, J = 1.8 Hz, 1H), 8.21 (d, J = 8.8 Hz, 2H), 7.97 (dd, J = 8.8, 2.3 Hz, 2H), 7.44-7.27 (m, 4H), 4.44 (s, 2H), 3.99 (t, J = 8.0 Hz, 2H), 3.41 (t, J = 8.0 Hz, 2H) |
| 238 | (structure: pyrazole-pyridine-imidazolidinone-CH2-3,4-difluorophenyl) | 1-(5-(1H-pyrazol-4-yl)pyridin-2-yl)-3-(3,4-difluorobenzyl) imidazolidin-2-one | 356.1 | E: 1.69<br>F: 1.34 | ¹H NMR (400 MHz, DMSO-d₆) δ ppm 12.97 (br. s., 1H), 8.58 (d, J = 1.8 Hz, 1H), 8.20 (d, J = 8.8 Hz, 1H), 7.97 (dd, J = 8.8, 2.5 Hz, 1H), 7.48-7.37 (m, 2H), 7.20 (br. s., 1H), 4.42 (s, 2H), 3.99 (t, J = 8.0 Hz, 2H), 3.40 (t, J = 8.0 Hz, 2H) |
| 239 | (structure: pyrazole-pyridine-imidazolidinone-CH2-3-carboxyphenyl) | 3-((3-(5-(1H-pyrazol-4-yl)pyridin-2-yl)-2-oxo-imidazolidin-1-yl)methyl)-benzoic acid | 364.1 | E: 0.98<br>F: 1.03 | ¹H NMR (400 MHz, DMSO-d₆) δ ppm 12.98 (br. s., 1H), 8.58 (d, J = 1.8 Hz, 1H), 8.22 (d, J = 8.8 Hz, 1H), 8.07 (br. s., 1H), 7.97 (dd, J = 8.8, 2.5 Hz, 1H), 7.90-7.86 (m, 2H), 7.60-7.48 (m, 2H), 4.50 (s, 2H), 3.98 (t, J = 8.0 Hz, 2H), 3.39 (t, J = 8.0 Hz, 2H) |
| 240 | (structure: pyrazole-pyridine-imidazolidinone-CH2-3-trifluoromethylphenyl) | 1-(5-(1H-pyrazol-4-yl)pyridin-2-yl)-3-(3-(trifluoromethyl)-benzyl)-imidazolidin-2-one | 388.1 | E: 1.87<br>F: 1.51 | ¹H NMR (400 MHz, DMSO-d₆) δ ppm 12.97 (br. s., 1H), 8.59 (d, J = 1.8 Hz, 1H), 8.23-8.19 (m, 2H), 7.99-7.93 (m, 2H), 7.70-7.61 (m, 4H), 4.53 (s, 2H), 3.99 (t, J = 8.0 Hz, 2H), 3.42 (t, J = 8.0 Hz, 2H |
| 241 | (structure: pyrazole-pyridine-imidazolidinone-CH2-3,4-dichlorophenyl) | 1-(5-(1H-pyrazol-4-yl)pyridin-2-yl)-3-(3,4-dichlorobenzyl) imidazolidin-2-one | 388 | E: 1.95<br>F: 1.60 | ¹H NMR (400 MHz, DMSO-d₆) δ ppm 12.97 (br. s., 1H), 8.59 (d, J = 1.8 Hz, 1H), 8.20 (d, J = 8.3 Hz, 2H), 7.97 (dd, J = 8.8, 2.5 Hz, 2H), 7.66-7.59 (m, 2H), 7.33 (dd, J = 8.3, 2.0 Hz, 1H), 4.44 (s, 2H), 3.98 (t, J = 8.0 Hz, 2H), 3.41 (t, J = 8.0 Hz, 2H) |
| 242 | (structure: pyrazole-pyridine-imidazolidinone-CH2-pyridin-3-yl) | 1-(5-(1H-pyrazol-4-yl)-pyridin-2-yl)-3-(pyridin-3-ylmethyl)-imidazolidin-2-one | 321.2 | E: 1.16<br>F: 0.41 | ¹H NMR (400 MHz, DMSO-d₆) δ ppm 12.98 (br. s., 1H), 8.57 (dd, J = 6.7, 1.9 Hz, 2H), 8.52 (dd, J = 4.8, 1.5 Hz, 1H), 8.21 (d, J = 8.8 Hz, 1H), 7.97 (dd, J = 8.8, 2.5 Hz, 1H), 7.78-7.73 (m, 1H), 7.41 |

TABLE 10-continued

| Ex. | R | Name | LCMS (M + H)+ | HPLC Method, RT (min.) and Purity | NMR |
|---|---|---|---|---|---|
| | | | | | (dd, J = 7.8, 4.8 Hz, 1H), 4.47 (s, 2H), 3.98 (t, J = 8.0 Hz, 2H), 3.41 (t, J = 8.0 Hz, 2H). |
| 243 | | 1-(5-(1H-pyrazol-4-yl)-pyridin-2-yl)-3-(pyridin-2-ylmethyl)-imidazolidin-2-one | 321.1 | E: 1.20 F: 0.56 | $^{1}$H NMR (400 MHz, DMSO-d$_{6}$) δ ppm 12.97 (br. s., 1H), 8.59 (d, J = 1.8 Hz, 1H), 8.55 (d, J = 4.0 Hz, 1H), 8.20 (d, J = 8.0 Hz, 2H), 7.98-7.92 (m, 2H), 7.80 (td, J = 7.7, 1.8 Hz, 1H), 7.37 (d, J = 7.8 Hz, 1H), 7.31 (dd, J = 7.0, 5.3 Hz, 1H), 4.53 (s, 2H), 4.01 (t, J = 8.0 Hz, 2H), 3.51 (t, J = 8.0 Hz, 2H) |
| 244 | | 1-(2-fluoro-benzyl)-3-(6-methoxy-5-(1H-pyrazol-4-yl)pyridin-2-yl)-imidazolidin-2-one | 368.1 | E: 1.85 F: 1.91 | $^{1}$H NMR (400 MHz, DMSO-d$_{6}$) δ ppm 12.87 (br. s., 1H), 7.98 (d, J = 8.5 Hz, 1H), 7.77-7.73 (m, 1H), 7.43-7.34 (m, 2H), 7.26-7.19 (m, 2H), 4.48 (s, 2H), 4.03 (dd, J = 9.0, 7.0 Hz, 2H), 3.95 (s, 3H), 3.44-3.38 (m, 3H) |
| 245 | | 1-(2,4-difluoro-benzyl)-3-(6-methoxy-5-(1H-pyrazol-4-yl)-pyridin-2-yl)-imidazolidin-2-one | 386.3 | E: 2.48 F: 2.33 | $^{1}$H NMR (400 MHz, DMSO-d$_{6}$) δ ppm 12.87 (br. s., 1H), 8.10-7.95 (m, 3H), 7.75 (d, J = 8.5 Hz, 1H), 7.46 (td, J = 8.5, 6.5 Hz, 1H), 7.31-7.23 (m, 1H), 7.10 (tt, J = 8.5, 1.8 Hz, 1H), 4.45 (s, 2H), 4.02 (dd, J = 9.0, 7.0 Hz, 2H), 3.95 (s, 3H), 3.41-3.37 (m, 2H) |
| 246 | | 1-(2,5-difluoro-benzyl)-3-(6-methoxy-5-(1H-pyrazol-4-yl)-pyridin-2-yl)-imidazolidin-2-one | 386.2 | E: 2.46 F: 2.30 | $^{1}$H NMR (400 MHz, DMSO-d$_{6}$) δ ppm 12.87 (br. s., 1H), 8.08 (br. s., 1H), 7.98 (d, J = 8.5 Hz, 1H), 7.94 (br. s., 1H), 7.75 (d, J = 8.0 Hz, 1H), 7.33-7.17 (m, 3H), 4.47 (s, 2H), 4.04 (dd, J = 9.0, 7.0 Hz, 2H), 3.96 (s, 3H), 3.46-3.42 (m, 2H) |
| 247 | | 1-(3,5-difluoro-benzyl)-3-(6-methoxy-5-(1H-pyrazol-4-yl)-pyridin-2-yl)-imidazolidin-2-one | 386.2 | E: 2.49 F: 2.33 | $^{1}$H NMR (400 MHz, DMSO-d$_{6}$) δ ppm 12.87 (br. s., 1H), 8.08 (br. s., 1H), 7.99 (d, J = 8.5 Hz, 1H), 7.97 (br. s., 1H), 7.78-7.74 (m, 1H), 7.16 (tt, J = 9.5, 2.3 Hz, 1H), 7.09-7.02 (m, 2H), 4.45 (s, 2H), 4.06 (dd, J = 9.3, 7.3 Hz, 2H), 3.96 (s, 3H), 3.42-3.38 (m, 2H)) |

TABLE 10-continued

| Ex. | R | Name | LCMS (M + H)+ | HPLC Method, RT (min.) and Purity | NMR |
|---|---|---|---|---|---|
| 248 | | 1-(3-fluoro-2-methyl-benzyl)-3-(6-methoxy-5-(1H-pyrazol-4-yl)pyridin-2-yl)-imidazolidin-2-one | 382.1 | E: 1.99<br>F: 2.05 | $^1$H NMR (400 MHz, DMSO-$d_6$) S δ ppm 12.87 (br. s., 1H), 8.08 (br. s., 1H), 7.98 (d, J = 8.0 Hz, 1H), 7.94 (br. s., 1H), 7.77 (d, J = 8.0 Hz, 1H), 7.27-7.20 (m, 1H), 7.14-7.08 (m, 2H), 4.46 (s, 2H), 4.03 (dd, J = 9.3, 7.3 Hz, 2H), 3.96 (s, 3H), 3.40-3.34 (m, 2H), 2.21 (d, J = 2.0 Hz, 3H) |
| 249 | | 1-(4-fluoro-2-methyl-benzyl)-3-(6-methoxy-5-(1H-pyrazol-4-yl)pyridin-2-yl)-imidazolidin-2-one | 382.3 | E: 2.58<br>F: 2.52 | $^1$H NMR (400 MHz, DMSO-$d_6$) δ ppm 12.87 (br. s., 1H), 8.07 (br. s., 1H), 7.98 (d, J = 8.0 Hz, 2H), 7.77 (d, J = 8.5 Hz, 1H), 7.28 (dd, J = 8.5, 6.0 Hz, 1H), 7.08 (dd, J = 10.0, 2.5 Hz, 1H), 7.01 (td, J = 8.5, 2.5 Hz, 1H), 4.40 (s, 2H), 4.02 (dd, J = 9.3, 7.3 Hz, 2H), 3.95 (s, 3H), 3.34-3.30 (m, 2H), 2.32 (s. 3H) |
| 250 | | 1-(5-fluoro-2-methyl-benzyl)-3-(6-methoxy-5-(1H-pyrazol-4-yl)pyridin-2-yl)-imidazolidin-2-one | 382.3 | E: 2.57<br>F: 2.41 | $^1$H NMR (400 MHz, DMSO-$d_6$) δ ppm 12.87 (br. s., 1H), 8.08 (br. s., 1H), 7.99 (d, J = 8.0 Hz, 1H), 7.95 (br. s., 1H), 7.77 (d, J = 8.5 Hz, 1H), 7.24 (dd, J = 8.5, 6.0 Hz, 1H), 7.09-7.00 (m, 2H), 4.41 (s, 2H), 4.05 (dd, J = 9.3, 7.3 Hz, 2H), 3.96 (s, 3H), 3.40-3.36 (m, 2H), 2.27 (s, 3H) |
| 251 | | 1-(4-fluoro-2-methoxy-benzyl)-3-(6-methoxy-5-(1H-pyrazol-4-yl)pyridin-2-yl)-imidazolidin-2-one | 398.2 | E: 2.51<br>F: 2.34 | $^1$H NMR (400 MHz, DMSO-$d_6$) δ ppm 12.87 (br. s., 1H), 7.97 (d, J = 8.5 Hz, 3H), 7.75 (d, J = 8.5 Hz, 1H), 7.29-7.21 (m, 1H), 6.94 (dd, J = 11.5, 2.5 Hz, 1H), 6.76 (td, J = 8.3, 2.5 Hz, 1H), 4.35 (s, 2H), 4.05-3.98 (dd, J = 9.3, 7.3 Hz, 2H), 3.95 (s, 2H), 3.83 (s, 3H), 3.40-3.36 (m, 2H) |
| 252 | | 1-(2-fluoro-3-methoxy-benzyl)-3-(6-methoxy-5-(1H-pyrazol-4-yl)pyridin-2-yl)-imidazolidin-2-one | 398.2 | E: 2.38<br>F: 2.22 | $^1$H NMR (400 MHz, DMSO-$d_6$) δ ppm 12.87 (br. s., 1H), 8.08 (br. s., 1H), 8.00-7.96 (m, 1H), 7.94 (br. s., 1H), 7.75 (d, J = 8.5 Hz, 1H), 7.15-7.10 (m, 2H), 6.95-6.90 (m, 1H), 4.47 (s, 2H), 4.05-3.99 (dd, J = 9.3, 7.3 Hz, 2H), 3.95 (s, 3H), 3.84 (s, 3H), 3.40-3.36 (m, 2H) |

TABLE 10-continued

| Ex. | R | Name | LCMS (M + H)+ | HPLC Method, RT (min.) and Purity | NMR |
|---|---|---|---|---|---|
| 253 | | 1-(6-methoxy-5-(1H-pyrazol-4-yl)pyridin-2-yl)-3-(pyridin-3-yl)methyl)-imidazolidin-2-one | 351.2 | E: 1.16 F: 1.06 | $^1$H NMR (400 MHz, DMSO-d$_6$) δ ppm 12.86 (br. s., 1H), 8.56 (d, J = 1.5 Hz, 1H), 8.52 (dd, J = 4.5, 1.5 Hz, 1H), 8.07 (br. s., 1H), 7.99 (d, J = 8.0 Hz, 1H), 779-7.72 (m, 2H), 7.40 (dd, J = 7.8, 4.8 Hz, 1H), 4.46 (s, 2H), 4.03 (dd, J = 9.3, 7.3 Hz, 2H), 3.95 (s, 3H), 3.42-3.38 (m, 2H) |
| 254 | | 1-(6-methoxy-5-(1H-pyrazol-4-yl)pyridin-2-yl)-3-((tetrahydrofuran-2-yl)methyl)-imidazolidin-2-one | 344.2 | E: 1.46 F: 1.40 | $^1$H NMR (400 MHz, DMSO-d$_6$) δ ppm 12.83 (br. s., 1H), 8.00 (s, 2H), 7.96 (d, J = 8.0 Hz, 1H), 7.72 (d, J = 8.0 Hz, 1H), 4.03-3.95 (m, 6H), 3.81-3.75 (m, 1H), 3.68-3.61 (m, 1H), 3.60-3.51 (m, 2H), 3.25-3.18 (m, 1H), 1.99-1.90 (m, 1H), 1.89-1.76 (m, 2H), 1.60-1.49 (m, 1H). |
| 255 | | 1-((6-methoxy-5-(1H-pyrazol-4-yl)pyridin-2-yl)-3-(5-methyl-1,2,4-oxadiazol-3-yl)methyl)-imidazolidin-2-one | 356.1 | E: 1.4, F: 1.34 | $^1$H NMR (400 MHz, DMSO-d$_6$) δ ppm 12.88 (br. s., 1H), 8.00-7.97 (m, 2H), 7.73-7.69 (m, 1H), 4.55 (s, 2H), 4.05 (dd, J = 8.8, 7.3 Hz, 2H), 3.97 (s, 3H), 3.57-3.52 (m, 2H), 2.59 (s, 3H) |
| 256 | | 1-(3-chlorobenzyl)-3-(6-methoxy-5-(1H-pyrazol-4-yl)pyridin-2-yl)-imidazolidin-2-one | 384.2 | E: 2.59 F: 2.43 | $^1$H NMR (400 MHz, DMSO-d$_6$) δ ppm 12.87 (br. s., 1H), 8.09 (br. s., 1H), 7.99 (d, J = 8.0 Hz, 1H), 7.94 (br. s., 1H), 7.78-7.75 (m, 1H), 7.44-7.35 (m, 3H), 7.31-7.28 (m, 1H), 4.43 (s, 2H), 4.04 (dd, J = 8.8, 7.3 Hz, 2H), 3.96 (s, 3H), 3.41-3.37 (m, 2H) |
| 257 | | 1-(6-methoxy-5-(1H-pyrazol-4-yl)pyridin-2-yl)-3-(3-methylbenzyl)imidazolidin-2-one | 364.3 | E: 2.57 F: 2.40 | $^1$H NMR (400 MHz, DMSO-d$_6$) δ ppm 12.87 (br. s., 1H), 8.08 (br. s., 1H), 7.98 (d, J = 8.5 Hz, 1H), 7.94 (br. s., 1H), 7.78 (d, J = 8.5 Hz, 1H), 7.28-7.23 (m, 1H), 7.13-7.08 (m, 3H), 4.38 (s, 2H), 4.02 (dd, J = 9.0, 7.0 Hz, 2H), 3.95 (s, 3H), 3.40-3.36 (m, 2H), 2.31 (s, 3H) |

TABLE 10-continued

| Ex. | R | Name | LCMS (M + H)+ | HPLC Method, RT (min.) and Purity | NMR |
|---|---|---|---|---|---|
| 258 | | 1-(4-(1H-pyrazol-4-yl)-phenyl)-3-(2-fluoro-3-methoxy-benzyl)imidazolidin-2-one | 367 | I: 8.870, 94.938% J: 8.643, 95.197% | 1H NMR (400 MHz, DMSO-$d_6$) δ = 12.86 (br. s., 1H), 8.12 (br. s., 1H), 7.87 (br. s., 1H), 7.56 (s, 4H), 7.17-7.08 (m, 2H), 6.92 (dd, J = 8.8, 4.8 Hz, 1H), 4.44 (s, 2H), 3.86-3.75 (m, 5H), 3.43-3.35 (m, 2H) |
| 259 | | 1-(4-(1H-pyrazol-4-yl)phenyl)-3-(3-fluoro-4-methoxy-benzyl)imidazolidin-2-one | 367 | I: 8.797, 96.776% J: 8.561, 96.714% | $^1$H NMR (400 MHz, DMSO-$d_6$) δ = 12.87 (br. s., 1H), 8.11 (br. s., 1H), 7.88 (br. s., 1H), 7.56 (s, 4H), 7.19-7.06 (m, 3H), 4.33 (s, 2H), 3.86-3.77 (m, 5H), 3.37 (s, 2H) |
| 260 | | 1-(4-(1H-pyrazol-4-yl)phenyl)-3-(3-fluoro-5-methoxy-benzyl)-imidazolidin-2-one | 367 | I: 9.335, 97.042% J: 9.001, 97.185% | $^1$H NMR (400 MHz, DMSO-$d_6$) δ = 12.86 (br. s., 1H), 8.12 (br. s., 1H), 7.87 (br. s., 1H), 7.61-7.53 (m, 4H), 6.79-6.67 (m, 3H), 4.37 (s, 2H), 3.88-3.81 (m, 2H), 3.77 (s, 3H), 3.40 (d, J = 8.0 Hz, 2H). |
| 261 | | 1-(4-(1H-pyrazol-4-yl)phenyl)-3-(5-fluoro-2-methoxy-benzyl)imidazolidin-2-one | 367 | I: 9.332, 96.704% J: 9.038, 98.168% | $^1$H NMR (400 MHz, DMSO-$d_6$) δ = 12.86 (br. s., 1H), 8.12 (br. s., 1H), 7.87 (br. s., 1H), 7.61-7.53 (m, 4H), 6.79-6.67 (m, 3H), 4.37 (s, 2H), 3.88-3.81 (m, 2H), 3.77 (s, 3H), 3.40 (d, J = 8.0 Hz, 2H). |
| 262 | | 1-(4-(1H-pyrazol-4-yl)phenyl)-3-(2-fluoro-5-methoxy-benzyl)imidazolidin-2-one | 367 | I: 9.079, 98.498% J: 8.757, 99.177% | $^1$H NMR (400 MHz, DMSO-$d_6$) δ = 12.87 (br. s., 1H), 8.12 (br. s., 1H), 7.87 (br. s., 1H), 7.56 (s, 4H), 7.20-7.10 (m, 1H), 6.94-6.86 (m, 2H), 4.41 (s, 2H), 3.83 (dd, J = 9.5, 6.5 Hz, 2H), 3.74 (s, 3H), 3.44-3.36 (m, 2H) |
| 263 | | 1-(4-(1H-pyrazol-4-yl)phenyl)-3-(4-fluoro-3-methoxy-benzyl)imidazolidin-2-one | 366.9 | I: 9.071, 98.604% J: 8.650, 98.116% | $^1$H NMR (400 MHz, DMSO-$d_6$) δ = 12.88 (br. s., 1H), 7.99 (br. s., 2H), 7.66-7.46 (m, 4H), 7.26-7.16 (m, 1H), 7.10 (dd, J = 8.3, 1.8 Hz, 1H), 6.93-6.83 (m, 1H), 4.36 (s, 2H), 3.97-3.69 (m, 5H), 3.37 (d, J = 8.5 Hz, 2H) |
| 264 | | 1-(4-(1H-pyrazol-4-yl)phenyl)-3-(3-fluoro-2-methoxy-benzyl)imidazolidin-2-one | 366.9 | I: 9.516, 98.730% J: 8.816, 98.030% | $^1$H NMR (400 MHz, DMSO-$d_6$) δ ppm = 12.86 (br. s., 1H), 8.17-8.05 (m, 1H), 7.94-7.80 (m, 1H), 7.56 (s, 4H), 7.27-7.16 (m, 1H), 7.14-7.06 (m, 2H), 4.44 (s, 2H), 3.87 (d, J = 2.0 |

TABLE 10-continued

| Ex. | R | Name | LCMS (M + H)+ | HPLC Method, RT (min.) and Purity | NMR |
|---|---|---|---|---|---|
| | | | | | Hz, 3H), 3.83 (dd, J = 9.0, 7.0 Hz, 2H), 3.43-3.35 (m, 2H) |
| 265 | | 1-(1-(3-(cyclopropyl-methoxy)-phenyl)-ethyl)-3-(6-ethyl-5-(1H-pyrazol-4-yl)-pyridin-2-yl)-imidazolidin-2-one (Enantiomer I) | 432.2 | I: 7.517, 98.376% J: 7.677, 99.376% | $^1$HNMR (400 MHz, DMSO-d$_6$) δ ppm = 12.98 (br. s., 1H), 8.01 (d, J = 8.5 Hz, 1H), 7.79 (br. s., 2H), 7.66 (d, J = 8.5 Hz, 1H), 7.29-7.23 (m, 1H), 6.94-6.82 (m, 3H), 5.13 (q, J = 7.4 Hz, 1H), 4.00-3.93 (m, 2H), 3.81 (d, J = 6.5 Hz, 2H), 3.55-3.47 (m, 1H), 3.17-3.08 (m, 1H), 2.78 (q, J = 7.5 Hz, 2H), 1.51 (d, J = 7.0 Hz, 3H), 1.26-1.14 (m, 4H), 0.59-0.52 (m, 2H), 0.34-0.29 (m, 2H) |
| 266 | | 1-(1-(3-ethoxy-phenyl)-ethyl)-3-(6-ethyl-5-(1H-pyrazol-4-yl)-pyridin-2-yl)-imidazolidin-2-one (Enantiomer I) | 406.4 | I: 7.386, 99.435% J: 8.323, 99.301% | $^1$H NMR (300 MHz, DMSO-d$_6$) δ ppm = 12.99 (br. s., 1H), 8.01 (d, J = 8.7 Hz, 1H), 7.89 (br. s., 2H), 7.66 (d, J = 8.7 Hz, 1H), 7.27 (t, J = 7.7 Hz, 1H), 6.95-6.81 (m, 3H), 5.13 (q, J = 6.9 Hz, 1H), 4.07-3.91 (m, 4H), 3.56-3.45 (m, 1H), 3.12 (q, J = 8.7 Hz, 1H), 2.78 (q, J = 7.4 Hz, 2H), 1.51 (d, J = 7.2 Hz, 3H), 1.32 (t, J = 7.0 Hz, 3H), 1.19 (t, J = 7.6 Hz, 3H). |
| 267 | | 1-(1-(3-ethoxy-phenyl)-ethyl)-3-(6-ethyl-5-(1H-pyrazol-4-yl)-pyridin-2-yl)-imidazolidin-2-one (Enantiomer II) | 406.4 | I: 7.345, 99.562% J: 8.326, 99.191% | $^1$H NMR (400 MHz, DMSO-d$_6$) δ ppm = 12.99 (br. s., 1H), 8.01 (d, J = 8.5 Hz, 1H), 7.79 (br. s., 2H), 7.66 (d, J = 8.5 Hz, 1H), 7.27 (t, J = 7.8 Hz, 1H), 6.95-6.82 (m, 3H), 5.14 (q, J = 7.0 Hz, 1H), 4.06-3.91 (m, 4H), 3.55-3.46 (m, 1H), 3.16-3.07 (m, 1H), 2.78 (q, J = 7.2 Hz, 2H), 1.51 (d, J = 7.5 Hz, 3H), 1.32 (t, J = 6.8 Hz, 3H), 1.19 (t, J = 7.5 Hz, 3H). |
| 268 | | 1-(6-ethyl-5-(1H-pyrazol-4-yl)pyridin-2-yl)-3-(1-(3-fluoro-5-methoxy-phenyl)-ethyl)-imidazolidin-2-one (Enantiomer I) | 410.2 | I: 7.263, 98.733% J: 8.115, 98.169% | 1H NMR (300 MHz, DMSO-d$_6$) δ ppm = 12.99 (br. s., 1H), 8.00 (d, J = 8.3 Hz, 1H), 7.79 (br. s., 2H), 7.66 (d, J = 8.7 Hz, 1H), 6.81-6.71 (m, 3H), 5.17-5.06 (m, 1H), 3.99 (t, J = 8.1 Hz, 2H), 3.77 (s, 3H), 3.57-3.45 (m, 1H), 3.24-3.12 (m, 1H), 2.79 (q, J = 7.6 Hz, |

TABLE 10-continued

| Ex. | R | Name | LCMS (M + H)+ | HPLC Method, RT (min.) and Purity | NMR |
|---|---|---|---|---|---|
| | | | | | 2H), 1.51 (d, J = 6.8 Hz, 3H), 1.19 (t, J = 7.4 Hz, 3H). |
| 269 | | 1-(6-ethyl-5-(1H-pyrazol-4-yl)pyridin-2-yl)-3-(1-(3-fluoro-5-methoxy-phenyl)-ethyl)-imidazolidin-2-one (Enantiomer II) | 410.2 | I: 9.746, 99.334% J: 12.023, 99.683% | ¹H NMR (400 MHz, DMSO-d₆) δ ppm = 13.02 (br. s., 1H), 8.00 (d, J = 8.5 Hz, 1H), 7.79 (br. s., 2H), 7.66 (d, J = 8.5 Hz, 1H), 6.81-6.71 (m, 3H), 5.11 (q, J = 7.0 Hz, 1H), 3.99 (t, J = 8.0 Hz, 2H), 3.77 (s, 3H), 3.57-3.48 (m, 1H), 3.18 (q, J = 8.5 Hz, 1H), 2.79 (q, J = 7.4 Hz, 2H), 1.51 (d, J = 7.0 Hz, 3H), 1.25-1.16 (m, 3H). |
| 270 | | 1-(6-ethyl-5-(1H-pyrazol-4-yl)pyridin-2-yl)-3-(1-(4-fluoro-3-methoxy-phenyl)-ethyl)-imidazolidin-2-one (Enantiomer I) | 410.2 | I: 5.872, 99.324% J: 7.605, 99.629% | ¹H NMR (400 MHz, DMSO-d₆) δ ppm = 13.00 (br. s., 1H), 8.02 (d, J = 9.0 Hz, 1H), 7.98-7.72 (m, 2H), 7.67 (d, J = 8.5 Hz, 1H), 7.20 (dd, J = 11.5, 8.0 Hz, 1H), 7.12 (dd, J = 8.5, 2.0 Hz, 1H), 6.94 (ddd, J = 8.5, 4.3, 1.8 Hz, 1H), 5.16 (q, J = 7.0 Hz, 1H), 4.05-3.92 (m, 2H), 3.86 (s, 3H), 3.56-3.47 (m, 1H), 3.20-3.11 (m, 1H), 2.79 (q, J = 7.2 Hz, 2H), 1.54 (d, J = 7.0 Hz, 3H), 1.20 (t, J = 7.5 Hz, 3H). |
| 271 | | 1-(6-ethyl-5-(1H-pyrazol-4-yl)pyridin-2-yl)-3-(1-(4-fluoro-3-methoxy-phenyl)-ethyl)-imidazolidin-2-one (Enantiomer II) | 410.2 | I: 5.943, 99.194% J: 7.722, 99.173% | ¹H NMR (400 MHz, DMSO-d₆) δ ppm = 8.02 (d, J = 8.5 Hz, 1H), 7.79 (s, 2H), 7.67 (d, J = 8.5 Hz, 1H), 7.20 (dd, J = 11.5, 8.5 Hz, 1H), 7.14-7.10 (m, 1H), 6.94 (d, J = 8.0 Hz, 1H), 5.16 (d, J = 7.0 Hz, 1H), 4.02-3.94 (m, 2H), 3.86 (s, 3H), 3.52 (d, J = 6.5 Hz, 1H), 3.15 (s, 1H), 2.79 (q, J = 7.4 Hz, 2H), 1.54 (d, J = 7.0 Hz, 3H), 1.20 (t, J = 7.5 Hz, 3H). |
| 272 | | (R)-1-(3-ethyl-4-(1H-pyrazol-4-yl)phenyl)-3-(1-(3-methoxy-phenyl)-ethyl)-imidazolidin-2-one | 391.2 | I: 10.13, 99.96% J: 9.67, 99.87% XIV: 23.71, 100% ee | ¹H NMR (400 MHz, DMSO-d₆) δ ppm 12.89 (br. s., 1H) 7.85 (br. s., 1H) 7.66 (br. s., 1H) 7.50 (d, J = 2.38 Hz, 1H) 7.39 (dd, J = 8.50, 2.42 Hz, 1H) 7.29 (t, J = 7.87 Hz, 1 H) 7.24 (d, J = 8.47 Hz, 1H) 6.94 (dd, J = 7.62, 0.72 Hz, 1H) 6.84-6.90 (m, 2H) 5.12 (q, J = 7.15 Hz, |

TABLE 10-continued

| Ex. | R | Name | LCMS (M + H)+ | HPLC Method, RT (min.) and Purity | NMR |
|---|---|---|---|---|---|
| | | | | | 1H) 3.77-3.83 (m, 2H) 3.75 (s, 3H) 3.46-3.55 (m, 1H) 3.11 (q, J = 8.51 Hz, 1H) 2.67 (q, J = 7.47 Hz, 2H) 1.51 (d, J = 7.22 Hz, 3H) 1.11 (t, J = 7.50 Hz, 3H) [α]$^{24.9}_D$ = +156.00 (c 0.1, MeOH). |
| 273 | | 1-(3-methoxy-benzyl)-3-(3-methyl-4-(1H-pyrazol-4-yl)phenyl)-imidazolidin-2-one | 363.3 | E: 1.48, 99.21% F: 1.53, 98.77% | $^1$H NMR (400 MHz, DMSO-d$_6$) δ ppm 12.91 (br. s., 1H) 7.91 (br. s., 1H) 7.69 (br. s., 1H) 7.45-7.48 (m, 2H) 7.26-7.35 (m, 2H) 6.84-6.90 (m, 3H) 4.36 (s, 2H) 3.81 (dd, J = 8.97, 7.03 Hz, 2H) 3.75 (s, 3 H) 3.33-3.40 (m, 2H) 2.36 (s, 3H) |
| 274 | | 1-(3-fluoro-5-methoxy-benzyl)-3-(3-methyl-4-(1H-pyrazol-4-yl)phenyl)-imidazolidin-2-one | 381.3 | E: 1.57, 96.83% F: 1.61, 95.22% | $^1$H NMR (400 MHz, DMSO-d$_6$) δ ppm 12.92 (br. s., 1H) 7.88 (br. s., 1H) 7.73 (br. s., 1H) 7.45-7.49 (m, 2H) 7.35 (d, J = 8.4 Hz, 1H) 6.69-6.78 (m, 3H) 4.36 (s, 2H) 3.83 (dd, J = 9.13, 6.81 Hz, 2H) 3.77 (s, 3H 3.36-3.41 (m, 2H) 2.36 (s, 3H); $^{19}$F NMR (400 MHz, DMSO-d$_6$) δ ppm −111.533 |
| 275 | | 1-(4-(1H-pyrazol-4-yl)-3-(trifluoro-methyl)-phenyl)-3-(3-methoxy-benzyl) imidazolidin-2-one | 417.1 | E: 1.93, 100% F: 1.95, 100% | $^1$H NMR (400 MHz, DMSO-d$_6$) δ ppm 12.98 (br. s., 1H) 8.22 (d, J = 2.32 Hz, 1H) 7.85 (s, 1H) 7.68 (dd, J = 8.56, 2.35 Hz, 1H) 7.59 (s, 1H) 7.48 (d, J = 8.53 Hz, 1H) 7.26-7.32 (m, 1H) 6.85-6.91 (m, 3H) 4.39 (s, 2H) 3.89 (dd, J = 9.07, 7.00 Hz, 2H) 3.75 (s, 3H) 3.38-3.44 (m, 2H); $^{19}$F NMR (400 MHz, DMSO-d$_6$,) δ ppm −57.223 |
| 276 | | 1-(4-(1H-pyrazol-4-yl)-3-(trifluoro-methyl)-phenyl)-3-(3-fluoro-5-methoxy-benzyl) imidazolidin-2-one | 435.1 | E: 1.99, 94.43% F: 2.02, 94.23% | $^1$H NMR (400 MHz, DMSO-d$_6$) δ ppm 12.97 (br. s., 1H) 8.22 (d, J = 2.32 Hz, 1H) 7.85 (br. s., 1H) 7.69 (dd, J = 8.60, 2.32 Hz, 1H) 7.59 (br. s., 1H) 7.47-7.51 (m, 1H) 6.70-6.79 (m, 3H) 4.39 (s, 2H) 3.91 (dd, J = 9.10, 6.96 Hz, 2H) 3.77 (s, 3H) 3.41-3.47 (m, 2H); $^{19}$F NMR (400 MHz, DMSO-d$_6$) δ ppm −57.223, −111.493 |

TABLE 10-continued

| Ex. | R | Name | LCMS (M + H)+ | HPLC Method, RT (min.) and Purity | NMR |
|---|---|---|---|---|---|
| 277 | | 5-(3-(3-methoxy-benzyl)-2-oxo-imidazolidin-1-yl)-2-(1H-pyrazol-4-yl)-benzonitrile | 374.1 | E: 1.74, 99.57% F: 1.75, 99.17% | $^1$H NMR (400 MHz, DMSO-$d_6$) δ ppm 13.18 (br. s., 1H) 8.24 (s, 1H) 8.02 (d, J = 2.51 Hz, 1H) 7.98 (s, 1H) 7.94 (dd, J = 8.78, 2.51 Hz, 1H) 7.72 (d, J = 9.03 Hz, 1H) 7.26-7.33 (m, 1H) 6.85-6.91 (m, 3H) 4.39 (s, 2H) 3.88 (dd, J = 9.03, 7.03 Hz, 2H) 3.76 (s, 3H) 3.37-3.45 (m, 2H) |
| 278 | | 5-(3-(3-fluoro-5-methoxy-benzyl)-2-oxo-imidazolidin-1-yl)-2-(1H-pyrazol-4-yl)-benzonitrile | 392.1 | E: 1.76, 98.01% F: 1.77, 99.76% | $^1$H NMR (400 MHz, DMSO-$d_6$) δ ppm 13.18 (br. s., 1H) 8.24 (s, 1H) 8.02 (d, J = 2.26 Hz, 1H) 7.98 (s, 1H) 7.94 (dd, J = 9.03, 2.51 Hz, 1H) 7.72 (d, J = 9.03 Hz, 1H) 6.70-6.79 (m, 3H) 4.39 (s, 2H) 3.90 (dd, J = 9.16, 6.90 Hz, 2H) 3.78 (s, 3H) 3.40-3.47 (m, 2H); $^{19}$F NMR (400 MHz, DMSO-$d_6$) δ ppm −111.499 |
| 279 | | 5-(3-(4-fluoro-3-methoxy-benzyl)-2-oxo-imidazolidin-1-yl)-2-(1H-pyrazol-4-yl)-benzonitrile | 392.1 | E: 1.81, 96.33% F: 1.83, 97.25% | $^1$H NMR (400 MHz, DMSO-$d_6$) δ ppm 13.18 (br. s., 1H) 8.24 (s, 1H) 8.03 (d, J = 2.51 Hz, 1H) 7.98 (s, 1H) 7.93 (dd, J = 9.03, 2.51 Hz, 1H) 7.71 (d, J = 8.78 Hz, 1H) 7.19 (dd, J = 11.54, 8.28 Hz, 1H) 7.11 (dd, J = 8.41, 1.88 Hz, 1H) 6.88 (ddd, J = 8.28, 4.27, 2.01 Hz, 1H) 4.39 (s, 2H) 3.86-3.91 (m, 2H) 3.85 (s, 3H) 3.38-3.45 (m, 2H); $^{19}$F NMR (400 MHz, DMSO-$d_6$) δ ppm −137.339 |
| 280 | | 1-(3-ethyl-4-(1H-pyrazol-4-yl)phenyl)-3-(3-fluoro-5-methoxy-benzyl)-imidazolidin-2-one | 395.2 | E: 1.92, 100% F: 1.95, 99.70% | $^1$H NMR (400 MHz, DMSO-$d_6$) δ ppm 12.92 (br. s., 1H) 7.72 (br. s., 2H) 7.52 (d, J = 2.38 Hz, 1H) 7.42 (dd, J = 8.47, 2.45 Hz, 1H) 7.26 (d, J = 8.47 Hz, 1H) 6.68-6.79 (m, 3H) 4.37 (s, 2H) 3.81-3.89 (m, 2H) 3.77 (s, 3H) 3.35-3.43 (m, 2H) 2.68 (q, J = 7.53 Hz, 2H) 1.13 (t, J = 7.50 Hz, 3H); $^{19}$F NMR (400 MHz, DMSO-$d_6$) δ ppm −111.565 |

TABLE 10-continued

| Ex. | R | Name | LCMS (M + H)+ | HPLC Method, RT (min.) and Purity | NMR |
|---|---|---|---|---|---|
| 281 | (structure) | 1-(3-ethyl-4-(1H-pyrazol-4-yl)phenyl)-3-(4-fluoro-3-methoxy-benzyl)imidazolidin-2-one | 395.2 | E: 1.86, 100% F: 1.90, 100% | $^1$H NMR (400 MHz, DMSO-d$_6$) δ ppm 12.89 (br. s., 1H) 7.75 (br. s., 1H) 7.65 (br. s., 1H) 7.51 (d, J = 2.38 Hz, 1H) 7.42 (dd, J = 8.47, 2.45 Hz, 1H) 7.25 (d, J = 8.47 Hz, 1H) 7.19 (dd, J = 11.58, 8.25 Hz, 1H) 7.10 (dd, J = 8.41, 2.01 Hz, 1H) 6.88 (ddd, J = 8.24, 4.38, 2.07 Hz, 1H) 4.37 (s, 2H) 3.77-3.92 (m, 5H) 3.32-3.41 (m, 2H) 2.62-2.78 (m, 2H) 1.12 (t, J = 7.53 Hz, 3H); $^{19}$F NMR (400 MHz, DMSO-d$_6$) δ ppm −137.474 |
| 282 | (structure) | 1-(4-fluoro-3-methoxy-benzyl)-3-(3-methyl-4-(1H-pyrazol-4-yl)-phenyl)-imidazolidin-2-one, TFA | 381.1 | E: 1.76, 100% F: 1.79, 99.63% | $^1$H NMR (400 MHz, DMSO-d$_6$) δ ppm 7.81 (br. s., 2H) 7.45-7.48 (m, 2H) 7.34 (d, J = 8.40, 1H) 7.17-7.24 (m, 1H) 7.11 (dd, J = 8.40, 2.01 Hz, 1H) 6.87 (ddd, J = 8.24, 4.38, 2.07 Hz, 1H) 4.36 (s, 2H) 3.80-3.84 (m, 5H)) 3.35-3.39 (m, 2H) 2.36 (s, 3H); $^{19}$F NMR (400 MHz, DMSO-d$_6$) δ ppm −74.68, −137.474 |
| 283 | (structure) | 1-(4-(1H-pyrazol-4-yl)-3-(trifluoro-methyl)-phenyl)-3-(4-fluoro-3-methoxy-benzyl)imidazolidin-2-one | 435.1 | E: 1.96, 100% F: 1.98, 100% | $^1$H NMR (400 MHz, DMSO-d$_6$) δ ppm 13.01 (br. s., 1H) 8.22 (d, J = 2.38 Hz, 1H) 7.86 (br. s., 1H) 7.69 (dd, J = 8.60, 2.38 Hz, 1H) 7.60 (br. s., 1H) 7.48 (d, J = 8.53 Hz, 1H) 7.19 (dd, J = 11.55, 8.22 Hz, 1H) 7.11 (dd, J = 8.38, 1.98 Hz, 1H) 6.88 (ddd, J = 8.25, 4.36, 2.07 Hz, 1H) 4.39 (s, 2H) 3.86-3.93 (m, 2H) 3.84 (s, 3H) 3.38-3.44 (m, 2H); $^{19}$F NMR (400 MHz, DMSO-d$_6$) δ ppm −57.225, −137.355. |
| 284 | (structure) | 1-(3-(cyclopropyl-methoxy)-benzyl)-3-(3-methyl-4-(1H-pyrazol-4-yl)-phenyl)-imidazolidin-2-one | 403.2 | E: 2.01, 96.03% F: 2.03, 96.06% | $^1$H NMR (400 MHz, DMSO-d$_6$) δ ppm 12.97 (br. s., 1H) 7.90 (br. s., 1H) 7.68 (br. s., 1H) 7.44-7.47 (m, 2H) 7.34 (d, J = 8.80 Hz, 1H) 7.23-7.27 (m, 1H) 6.83-6.86 (m, 3H) 4.34 (s, 2H) 3.79-3.83 (m, 4H) 3.31-3.37 (m, 2H) 2.33 (s, 3H) 1.17-123 (m, 1H) 0.54- |

TABLE 10-continued

| Ex. | R | Name | LCMS (M + H)+ | HPLC Method, RT (min.) and Purity | NMR |
|---|---|---|---|---|---|
| 285 | 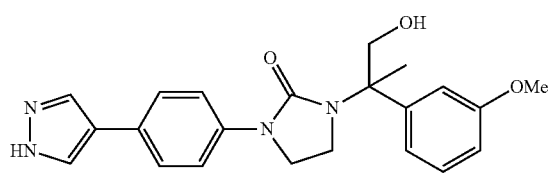 | 1-(3-(cyclopropyl-methoxy)-benzyl)-3-(3-ethyl-4-(1H-pyrazol-4-yl)phenyl)imidazolidin-2-one | 417.2 | E: 2.10, 100% F: 2.12, 99.67% | $^1$H NMR (400 MHz, DMSO-d$_6$) δ ppm 12.98 (br. s., 1H) 7.83 (br. s., 1H) 7.59 (br. s., 1H) 7.52 (d, J = 2.45 Hz, 1H) 7.42 (dd, J = 8.56, 2.45 Hz, 1H) 7.23-7.23 (m, 2H) 7.83-7.86 (m, 3H) 4.34 (s, 2H) 3.80-3.84 (m, 4H) 3.40-3.35 (m, 2H) 2.70-2.64 (m, 2H) 1.19-1.22 (m, 1H) 1.12 (t, J = 7.46 Hz, 3H) 0.53-0.58 (m, 2H) 0.29-0.33 (m, 2H). [previous row continued: 0.56 (m, 2H) 0.30-0.33 (m, 2H).] |

Examples 286 and 287

1-(4-(1H-Pyrazol-4-yl)phenyl)-3-(1-hydroxy-2-(3-methoxyphenyl)propan-2-yl)imidazolidin-2-one (Enantiomers 1 and 2)

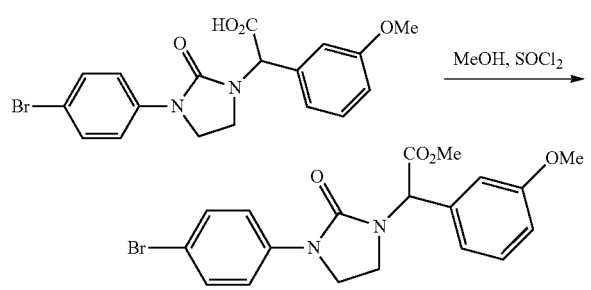

Example 286A: Preparation of methyl 2-(3-(4-bromophenyl)-2-oxoimidazolidin-1-yl)-2-(3-methoxyphenyl)acetate

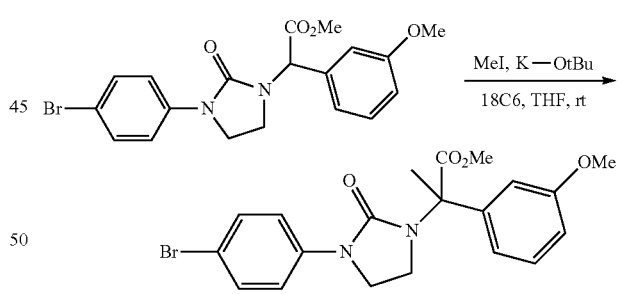

To a solution of 2-(3-(4-bromophenyl)-2-oxoimidazolidin-1-yl)-2-(3-methoxyphenyl)acetic acid (2.4 g, 5.92 mmol) in methanol (50 mL) at 0° C., was added thionyl chloride (1.297 mL, 17.77 mmol) dropwise. The reaction mixture was stirred at rt for 16 h. The reaction mixture was concentrated. The residue was partitioned between satd. solution of NaHCO$_3$ and ethyl acetate. The combined organic layers were washed with water and brine, dried over Na$_2$SO$_4$, and concentrated. The residue was purified by flash chromatography (gradient elution; 0-100% EtOAc/hexanes) to afford methyl 2-(3-(4-bromophenyl)-2-oxoimidazolidin-1-yl)-2-(3-methoxyphenyl)acetate (2.2 g, 89.0% yield) as a yellow solid. MS(ESI) m/z: 421.0 (M+H)+; $^1$H NMR (400 MHz, DMSO-d$_6$) δ ppm 7.52-7.56 (m, 2H) 7.46-7.52 (m, 2H) 7.31-7.39 (m, 1H) 6.94-7.01 (m, 1H) 6.85-6.91 (m, 2H) 5.62 (s, 1H) 3.79-3.88 (m, 1H) 3.75-3.78 (m, 3H) 3.68-3.75 (m, 4H) 3.57-3.67 (m, 1H) 3.04 (td, J=8.78, 5.52 Hz, 1H).

Example 286B: Preparation of methyl 2-(3-(4-bromophenyl)-2-oxoimidazolidin-1-yl)-2-(3-methoxyphenyl)propanoate To a sealed tube was added methyl 2-(3-(4-bromophenyl)-2-oxoimidazolidin-1-yl)-2-(3-methoxyphenyl)acetate (1.7 g, 4.05 mmol), potassium tert-butoxide (1.36 g, 12.2 mmol), methyl iodide (1.268 mL, 20.27 mmol) and 18-crown-6 (0.536 g, 2.03 mmol). The reaction mixture was stirred at rt for 16 h, then was filtered through CELITE®, rinsing with THF. The filtrate was concentrated. The residue was purified by flash chromatography (ethyl acetate/hexanes eluent) to give yellow solid, which was recrystallized from DCM/hexane to afford methyl 2-(3-(4-bromophenyl)-2-oxoimidazolidin-1-yl)-2-(3-methoxyphenyl)propanoate (1.2 g, 68.0% yield) as a white solid. MS(ESI) m/z: 435.0 (M+H)+; $^1$H NMR (400 MHz, DMSO-d$_6$) δ ppm 7.47-7.55 (m, 4H)

7.29-7.36 (m, 1H) 7.05-7.09 (m, 1H) 7.03 (t, J=2.01 Hz, 1H) 6.91-6.98 (m, 1H) 3.71-3.84 (m, 5H) 3.64 (s, 3H) 3.13-3.22 (m, 2H) 1.85 (s, 3H).

Example 286C: Preparation of 2-(3-(4-bromophenyl)-2-oxoimidazolidin-1-yl)-2-(3-methoxyphenyl)propanoic Acid

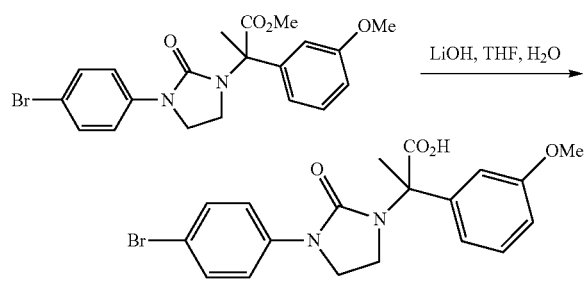

To a solution of methyl 2-(3-(4-bromophenyl)-2-oxoimidazolidin-1-yl)-2-(3-methoxyphenyl)propanoate (300 mg, 0.692 mmol) in THF (10 mL) and methanol (3 mL), was added LiOH (41.5 mg, 1.731 mmol) and water (3 mL). The reaction mixture was heated at 75° C. for 16 h, then was concentrated to afford. The resultant residue was acidified to pH 2. The precipitated solid was collected by filtration, washed with water and hexanes, and dried to afford 2-(3-(4-bromophenyl)-2-oxoimidazolidin-1-yl)-2-(3-methoxyphenyl)propanoic acid (0.250 g, 86.0% yield) as a white solid. MS(ESI) m/z: 419.0 (M+H)+; 1H NMR (400 MHz, DMSO-$d_6$) δ ppm 7.47-7.57 (m, 4H) 7.31-7.36 (m, 1H) 7.05-7.12 (m, 2H) 6.94 (dd, J=8.28, 2.26 Hz, 1H) 3.68-3.83 (m, 5H) 3.08-3.26 (m, 2H) 1.85 (s, 3H).

Examples 286D and 287A: Preparation of 1-(4-bromophenyl)-3-(1-hydroxy-2-(3-methoxyphenyl)propan-2-yl)imidazolidin-2-one (Enantiomer 1 and Enantiomer 2)

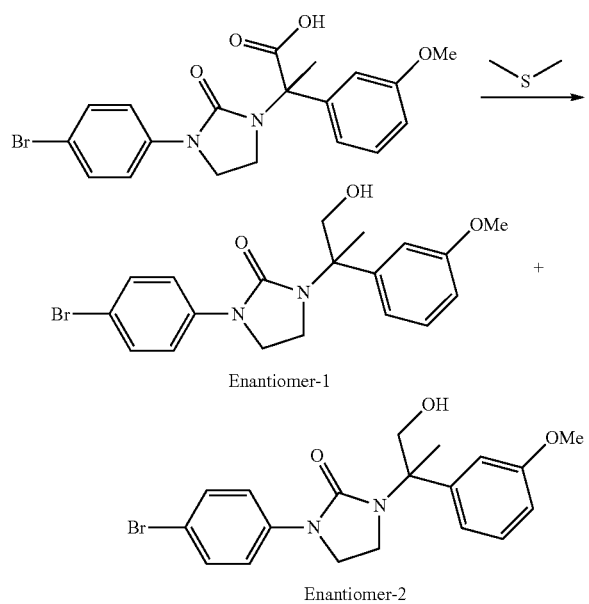

To a solution of 2-(3-(4-bromophenyl)-2-oxoimidazolidin-1-yl)-2-(3-methoxyphenyl)propanoic acid (250 mg, 0.596 mmol) in THF (10 mL) at 0° C., was added borane-methyl sulfide complex (0.566 mL, 5.96 mmol) dropwise. After 10 minutes, the reaction mixture was warmed to rt and stirred for 16 h. The reaction was carefully quenched with methanol and the mixture was concentrated in vacuo. The crude product was purified by flash chromatography (gradient elution; 0-100% EtOAc/hexanes) to afford the racemic product. The enantiomers were separated by SFC [Column: CHIRALPAK® AS-H (250×21) mm, 5µ, Co-solvent 30% 0.2% DEA in methanol] to afford Example 286D (Enantiomer 1, 0.090 g, 37.2% yield) as a yellow solid. MS(ESI) m/z: 405.0 (M+H)+; 1H NMR (300 MHz, DMSO-$d_6$) δ ppm 7.46 (d, J=3.40 Hz, 4H) 7.18-7.27 (m, 1H) 6.91 (d, J=7.93 Hz, 1H) 6.75-6.87 (m, 2H) 5.06 (s, 1H) 4.01 (s, 1H) 3.78 (d, J=9.44 Hz, 2H) 3.72 (s, 3H) 3.67 (d, J=9.07 Hz, 3H) 1.62 (s, 3H). 100.0% ee (rt-4.04 min), and to afford Example 287A (Enantiomer 2, 0.080 g, 33.1% yield) as a yellow solid. MS(ESI) m/z: 405.0 (M+H)+; 1H NMR (300 MHz, DMSO-$d_6$) δ ppm 7.46 (d, J=3.40 Hz, 4H) 7.17-7.28 (m, 1H) 6.91 (d, J=7.55 Hz, 1H) 6.75-6.87 (m, 2H) 5.06 (br. s., 1H) 3.99 (br. s., 1H) 3.78 (d, J=8.69 Hz, 2H) 3.72 (s, 3H) 3.68 (d, J=8.69 Hz, 3H) 1.62 (s, 3H). 99.216% ee (rt-7.17 min).

Example 286 (Enantiomer 1)

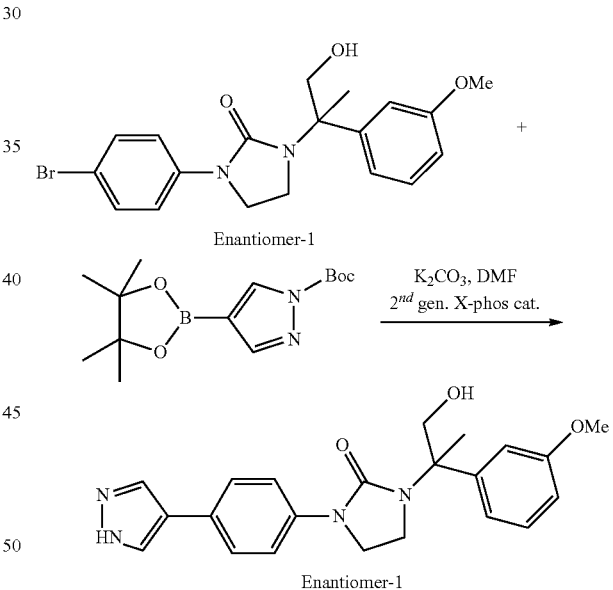

To a solution of Example 286D (90 mg, 0.222 mmol) in DMF (2 mL), were added tert-butyl 4-(4,4,5,5-tetramethyl-1,3,2-dioxaborolan-2-yl)-1H-pyrazole-1-carboxylate (91 mg, 0.311 mmol), $K_2CO_3$ (92 mg, 0.666 mmol) and water (0.4 mL). The reaction mixture was purged with nitrogen for 5 min and charged with 2nd generation XPhos precatalyst (10.5 mg, 0.013 mmol). The mixture was again purged with nitrogen for 3 min and heated at 90° C. for 16 h. The reaction mixture was cooled to rt, filtered and the filtrate was concentrated. The residue was purified by preparative HPLC to afford Example 286 (0.054 g, 61.3% yield) as a white solid. MS(ESI) m/z: 393.2 (M+H)+; 1H NMR (400 MHz, DMSO-$d_6$) δ ppm 12.84 (br. s., 1H) 8.09 (br. s., 1H) 7.85 (br. s., 1H) 7.42-7.57 (m, 4H) 7.23 (t, J=8.03 Hz, 1H) 6.93 (d, J=7.53 Hz, 1H) 6.87 (t, J=2.01 Hz, 1H) 6.80 (dd, J=8.28, 2.26 Hz, 1H) 5.07 (t, J=5.52 Hz, 1H) 4.09 (q, J=5.02 Hz, 1H) 4.02 (dd, J=11.04, 5.52 Hz, 1H) 3.78-3.86 (m, 2H) 3.73 (s, 3H) 3.57-3.71 (m, 2H) 1.63 (s, 3H). HPLC RT=1.53 min, 98.76% (Method E), 1.55 min, 99.35% (Method F). 100.0% ee (rt-12.618 min, XI), $[\alpha]^{24.9}_D$=+24 (c 0.05, DMSO).

Example 287 was prepared from Example 287A using a procedure similar to Example 286. m/z: 393.2 (M+H)+; $^1$H NMR (400 MHz, DMSO-d$_6$) δ ppm 12.84 (br. s., 1H) 8.09 (br. s., 1H) 7.86 (br. s., 1H) 7.41-7.58 (m, 4H) 7.23 (t, J=8.03 Hz, 1H) 6.90-6.98 (m, 1H) 6.84-6.90 (m, 1H) 6.80 (dd, J=8.28, 1.76 Hz, 1H) 5.07 (t, J=5.52 Hz, 1H) 4.02 (dd, J=11.04, 5.52 Hz, 1H) 3.78-3.87 (m, 2H) 3.73 (s, 3H) 3.59-3.72 (m, 3H) 1.63 (s, 3H); HPLC RT=1.52 min, 97.61% (Method E), 1.54 min, 98.38% (Method F). 100.0% ee (rt-15.85 min, XI), $[\alpha]^{24.9}_D$=−4 (c 0.05, DMSO).

Example 288

2-(3-(4-(1H-Pyrazol-4-yl)phenyl)-2-oxoimidazolidin-1-yl)-2-(3-methoxyphenyl)acetic Acid (Enantiomer 2)

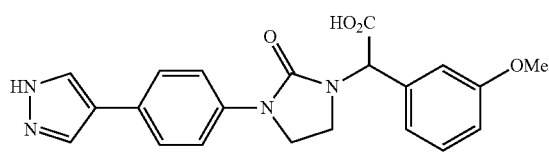 [SMILES: COc1cccc(C(C(=O)O)N2CCN(c3ccc(-c4cn[nH]c4)cc3)C2=O)c1]

Example 288A: 2-(3-(4-Bromophenyl)-2-oxoimidazolidin-1-yl)-2-(3-methoxyphenyl) acetic Acid

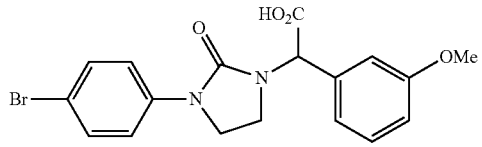 [SMILES: COc1cccc(C(C(=O)O)N2CCN(c3ccc(Br)cc3)C2=O)c1]

To a mixture of 1-(4-bromophenyl)imidazolidin-2-one (0.500 g, 2.074 mmol) in THF (10 mL) at 0° C., was added 58% NaH (0.257 g, 6.22 mmol). The mixture was stirred at rt for 10 min, then was cooled to 0° C. Methyl 2-bromo-2-(3-methoxyphenyl) acetate (0.806 g, 3.11 mmol) was added and the mixture was stirred at rt overnight. The reaction mixture was quenched with ice and acidified with 1.5N HCl. The mixture was extracted with EtOAc. The organic layer was washed with water and brine, dried over sodium sulfate and concentrated in vacuo. The crude product was purified by triturating with Et$_2$O (10 mL) and hexanes (20 mL), then was purified by flash chromatography (gradient elution 0-70% EtOAc/Hex) to afford 2-(3-(4-bromophenyl)-2-oxoimidazolidin-1-yl)-2-(3-methoxyphenyl)acetic acid (0.550 g, 1.357 mmol, 65.4% yield). m/z: 405 (M+H)+.

Example 288

To a solution of Example 288A (0.130 g, 0.321 mmol) in DMF (3 mL), water (0.3 mL) and tert-butyl 4-(4,4,5,5-tetramethyl-1,3,2-dioxaborolan-2-yl)-1H-pyrazole-1-carboxylate (142 mg, 0.48 mmol), was added K$_2$CO$_3$ (0.133 g, 0.962 mmol). The mixture was degassed using N$_2$ gas for 5 mins. 2nd generation XPhos precatalyst (0.025 g, 0.032 mmol) was added to the reaction, which was degassed again and then heated to 90° C. overnight. The mixture was purified by preparative HPLC, then the enantiomers were separated by chiral SFC. Concentration of the second peak afforded Example 288 (6.5 mg). $^1$H NMR (400 MHz, DMSO-d$_6$) δ ppm 12.93 (br. s., 1H) 8.00 (br. s., 1H) 7.51-7.63 (m, 4H) 7.32-7.42 (m, 1H) 6.85-7.01 (m, 3H) 5.54 (s, 1H) 3.83-3.94 (m, 2H) 3.78 (s, 3H) 3.61-3.74 (m, 2H). MS(ESI) 393.2 (M+H)+. HPLC RT=7.89 min (Method I), 7.64 min (Method J). Chiral purity: 96.26% ee (RT=9.1 min), determined by chiral SFC analysis column: CHIRALPAK® IC (250×4.6) mm, 5µ, Mobile Phase: 0.2% DEA in MeOH.

Examples 289 and 290

2-(3-(4-(1H-Pyrazol-4-yl)phenyl)-2-oxoimidazolidin-1-yl)-N-ethyl-2-(3-methoxyphenyl)acetamide (Enantiomers 1 and 2)

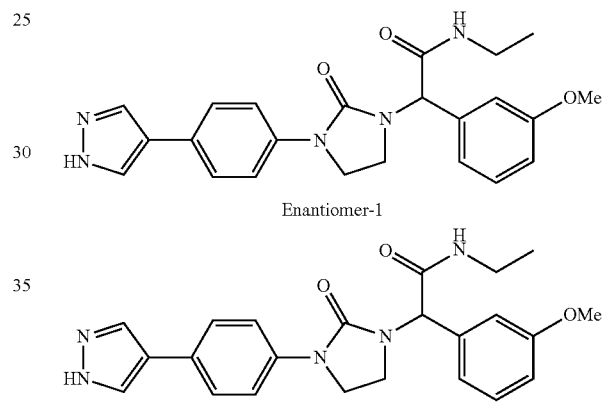

Example-289A: Preparation of 2-(3-(4-bromophenyl)-2-oxoimidazolidin-1-yl)-N-ethyl-2-(3-methoxyphenyl)acetamide

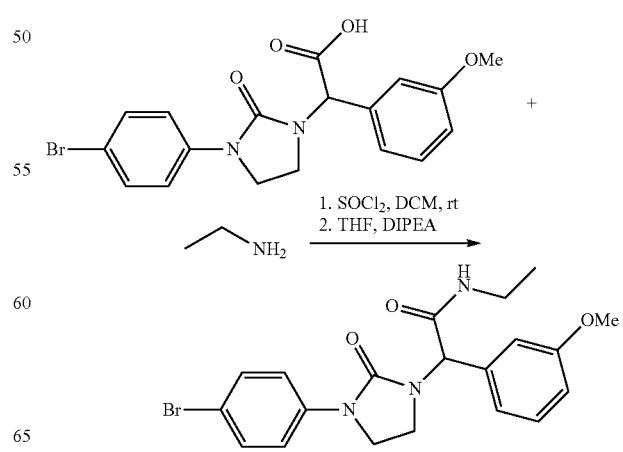

To a solution of 2-(3-(4-bromophenyl)-2-oxoimidazolidin-1-yl)-2-(3-methoxyphenyl)acetic acid (0.250 g, 0.47 mmol) in DCM (20 mL), was added thionyl chloride (0.360 mL, 4.94 mmol) and a drop of DMF. The reaction mixture was stirred at rt for 2 h. DCM and excess thionyl chloride were removed in vacuo. The residue obtained was dissolved in THF, added to a solution of ethanamine (2 M in THF) (1.180 mL, 2.360 mmol) and DIPEA (0.247 mL, 1.416 mmol) in DCM (10 mL), and the mixture was stirred at rt for 16 h. The reaction mixture was concentrated to give a yellow solid, which was purified by flash chromatography (gradient elution; 0-100% EtOAc/hexanes) to afford 2-(3-(4-bromophenyl)-2-oxoimidazolidin-1-yl)-N-ethyl-2-(3-methoxyphenyl) acetamide (0.120 g, 59.0% yield) as a white solid. MS(ESI) m/z: 434.2 (M+H)$^+$; $^1$H NMR (300 MHz, DMSO-d$_6$) δ ppm 8.30 (s, 1H) 7.44-7.60 (m, 4H) 7.28-7.37 (m, 1H) 6.93 (d, J=8.69 Hz, 1H) 6.79-6.90 (m, 2H) 5.52 (s, 1H) 3.65-3.86 (m, 6H) 3.13 (t, J=7.18 Hz, 2H) 2.99 (br. s., 1H) 1.03 (t, J=7.18 Hz, 3H).

Examples 289 and 290: 2-(3-(4-(1H-Pyrazol-4-yl)phenyl)-2-oxoimidazolidin-1-yl)-N-ethyl-2-(3-methoxyphenyl)acetamide (Enantiomer 1 and Enantiomer 2)

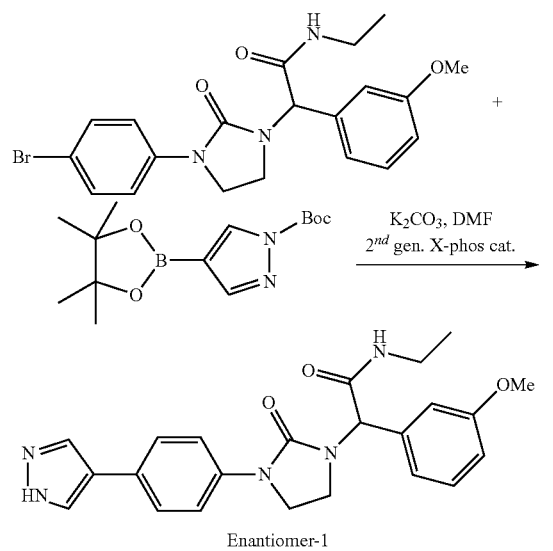

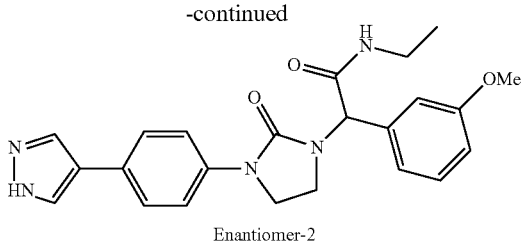

Enantiomer-2

To a solution of Example 289A (120 mg, 0.278 mmol) in DMF (6 mL), were added tert-butyl 4-(4,4,5,5-tetramethyl-1,3,2-dioxaborolan-2-yl)-1H-pyrazole-1-carboxylate (114 mg, 0.389 mmol), K$_2$CO$_3$ (115 mg, 0.833 mmol) and water (0.4 mL). The reaction mixture was purged with nitrogen for 5 min and charged with 2nd generation XPhos precatalyst (13.10 mg, 0.017 mmol), and again purged with nitrogen. The mixture was heated at 90° C. for 16 h, then was cooled, filtered. The filtrate was concentrated to give gummy solid (300 mg), which was purified by preparative HPLC. The enantiomers were separated by SFC [Column: CHIRALCEL® OJ-H (250×21) mm, 5µ, Co-solvent 30% DEA in methanol] to afford Example 289 (Enantiomer 1, 0.036 g, 30% yield) as a white solid. MS(ESI) m/z: 420.2 (M+H)$^+$; $^1$H NMR (400 MHz, DMSO-d$_6$) δ ppm 12.90 (br. s, 1H) 8.30 (t, J=5.52 Hz, 1H) 8.00 (s, 2H) 7.52-7.63 (m, 4H) 7.34 (t, J=7.78 Hz, 1H) 6.94 (dd, J=7.78, 2.26 Hz, 1H) 6.89 (d, J=7.53 Hz, 1H) 6.81-6.86 (m, 1H) 5.54 (s, 1H) 3.70-3.87 (m, 6H) 3.07-3.22 (m, 2H) 2.96-3.04 (m, 1H) 1.38 (t, J=7.53 Hz, 3H). HPLC RT=6.71 min, 97.02% (Method I), 7.82 min, 96.14% (Method J), 94.48% ee (rt-5.73 min), [α]$^{25.3}_D$=+17.2 (c 0.50, DMSO) and to afford Example 290 (Enantiomer 2, 0.034 g, 29% yield) as a white solid. MS(ESI) m/z: 420.2 (M+H)$^+$; $^1$H NMR (400 MHz, DMSO-d$_6$) δ ppm 8.30 (t, J=5.52 Hz, 1H) 8.00 (s, 2H) 7.52-7.61 (m, 4H) 7.31-7.38 (m, 1H) 6.92-6.98 (m, 1H) 6.89 (d, J=7.53 Hz, 1H) 6.82-6.86 (m, 1H) 5.54 (s, 1H) 3.70-3.87 (m, 6H) 3.10-3.21 (m, 2H) 2.95-3.04 (m, 1H) 1.38 (t, J=7.53 Hz, 3H). HPLC RT=6.71 min, 98.02% (Method I), 7.82 min, 98.41% (Method J). 94.86% ee (rt-8.03 min), [α]$^{25.1}_D$=−16 (c 0.50, DMSO).

The following Examples in Table 11 were prepared in a similar fashion to Examples 289 and 290.

TABLE 11

| Ex. | R | Name | LCMS (M + H)$^+$ | HPLC Method, RT (min.) and Purity | NMR |
|---|---|---|---|---|---|
| 291 | | 2-(3-(4-(1H-pyrazol-4-yl)phenyl)-2-oxoimidazolidin-1-yl)-2-(3-methoxyphenyl)-N-methylacetamide (Enantiomer 1) | 406.2 | I: 9.72, 99.56% J: 8.63, 98.81% IV: 4.05, 100% ee | $^1$H NMR (400 MHz, DMSO-d$_6$) d ppm 12.85 (br. s., 1 H) 8.20 (d, J = 4.52 Hz, 1 H) 8.00 (br. s., 2 H) 7.55 (s, 4 H) 7.33 (t, J = 8.03 Hz, 1 H) 6.91-6.99 (m, 1 H) 6.79-6.90 (m, 2 H) 5.53 (s, 1 H) 3.68-3.86 (m, 6 H) 2.92-3.05 (m, 1 H) 2.61-2.72 (m, 3 H). [α]24.9D = −148 (c 0.05, DMSO). |

TABLE 11-continued

| Ex. | R | Name | LCMS (M + H)+ | HPLC Method, RT (min.) and Purity | NMR |
|---|---|---|---|---|---|
| 292 | | 2-(3-(4-(1H-pyrazol-4-yl)phenyl)-2-oxoimidazolidin-1-yl)-2-(3-methoxyphenyl)-N-methylacetamide (Enantiomer 2) | 406.2 | I: 9.67, 99.20% J: 8.63, 98.38% IV: 5.73, 100% ee | ¹H NMR (400 MHz, DMSO-d₆) d ppm 12.79 (br. s., 1 H) 8.20 (d, J = 4.02 Hz, 1H) 7.99 (s, 2 H) 7.55 (s, 4 H) 7.28-7.37 (m, 1 H) 6.94 (dd, J = 8.03, 2.01 Hz, 1 H) 6.79-6.90 (m, 2 H) 5.53 (s, 1 H) 3.69-3.87 (m, 6 H) 2.94-3.06 (m, 1 H) 2.61-2.69 (m, 3 H). [α]24.9D = +196 (c 0.05, DMSO). |
| 293 | | 2-(3-(4-(1H-pyrazol-4-yl)phenyl)-2-oxoimidazolidin-1-yl)-N-isobutyl-2-(3-methoxyphenyl)acetamide (Enantiomer 1) | 448.2 | I: 8.87, 98.86% J: 8.61, 97.88% II: 5.62, 97.78% ee | ¹H NMR (400 MHz, DMSO-d₆) d ppm 12.50 (br.s, 1 H) 8.28 (t, J = 5.77 Hz, 1 H) 7.99 (s, 2 H) 7.50-7.60 (m, 4 H) 7.33 (t, J = 8.03 Hz, 1 H) 6.93 (dd, J = 8.78, 2.26 Hz, 1 H) 6.89 (d, J = 8.03 Hz, 1 H) 6.85 (d, J = 2.01 Hz, 1 H) 5.59 (s, 1 H) 3.78-3.86 (m, 2 H) 3.75 (s, 3 H) 3.68-3.74 (m, 1 H) 2.96-3.05 (m, 2 H) 2.84-2.94 (m, 1 H) 1.72 (dt, J = 13.43, 6.59 Hz, 1 H) 0.83 (dd, J = 7.03, 2.01 Hz, 6 H). [α]25.2D = −168 (c 0.05, DMSO). |
| 294 | | 2-(3-(4-(1H-pyrazol-4-yl)phenyl)-2-oxoimidazolidin-1-yl)-N-isobutyl-2-(3-methoxyphenyl)acetamide (Enantiomer 2) | 448.4 | I: 11.78, 99.30% J: 9.11, 98.39% II: 7.38, 100% ee | ¹H NMR (400 MHz, DMSO-d₆) d ppm 8.28 (t, J = 5.77 Hz, 1 H) 7.99 (s, 2 H) 7.51-7.59 (m, 4 H) 7.33 (t, J = 8.03 Hz, 1 H) 6.93 (dd, J = 8.53, 2.51 Hz, 1 H) 6.89 (d, J = 8.03 Hz, 1 H) 6.83-6.86 (m, 1 H) 5.59 (s, 1 H) 3.77-3.85 (m, 2 H) 3.75 (s, 3 H) 3.70-3.74 (m, 1 H) 2.96-3.05 (m, 2 H) 2.84-2.95 (m, 1 H) 1.66-1.78 (m, 1 H) 0.83 (dd, J = 7.03, 2.01 Hz, 6 H). [α]25.1D = +164 (c 0.05, DMSO). |
| 295 | | 2-(3-(4-(1H-pyrazol-4-yl)phenyl)-2-oxoimidazolidin-1-yl)-2-(3-methoxyphenyl)acetamide (Enantiomer 1) | 392.2 | I: 5.78, 93.30% J: 6.92, 93.00% II: 10.36, 93.2 1% ee | ¹H NMR (400 MHz, DMSO-d₆) d ppm 12.83 (br. s., 1 H) 7.97 (br. s., 2 H) 7.65 (br. s., 1 H) 7.56 (s, 4 H) 7.34 (t, J = 7.78 Hz, 1 H) 7.22 (br. s., 1 H) 6.91-6.98 (m, 2 H) 6.89 (d, J = 2.01 Hz, 1 H) 5.54 (s, 1 H) 3.80-3.87 (m, 2 H) 3.78 (s, 3 H) 3.69-3.76 (m, 1 H) 2.94-3.04 (m, 1 H). [α]25.0D = −76 (c 0.05, DMSO). |
| 296 | | 2-(3-(4-(1H-pyrazol-4-yl)phenyl)-2-oxoimidazolidin-1-yl)-N-(cyclopropylmethyl)-2-(3-methoxyphenyl)acetamide (Enantiomer 1) | 446.4 | I: 7.34, 97.35% J: 7.30, 97.30% V: 6.55, 86.83% ee | ¹H NMR (400 MHz, DMSO-d₆) d ppm 8.40 (t, J = 5.77 Hz, 1 H) 7.99 (s, 2 H) 7.49-7.60 (m, 4 H) 7.33 (t, J = 8.03 Hz, 1 H) 6.87-6.99 (m, 2 H) 6.82-6.87 (m, 1 H) 5.59 (s, 1 H) 3.70-3.87 (m, 6 H) 3.32-3.39 (m, 1 H) 2.94-3.08 (m, 2 H) 0.84-0.98 (m, 1 H) 0.34-0.46 (m, 2 H) 0.10-0.23 (m, 2 H). [α]25.0D = +11.600 (c 0.50, DMSO). |
| 297 | | 2-(3-(4-(1H-pyrazol-4-yl)phenyl)-2-oxoimidazolidin-1-yl)-N-(cyclopropylmethyl)-2-(3-methoxyphenyl)acetamide (Enantiomer 2) | 446.4 | I: 7.54, 97.94% J: 8.60, 98.19% V: 10.24, 96.30% ee | ¹H NMR (400 MHz, DMSO-d₆) d ppm 8.38-8.43 (m, 1 H) 8.00 (s, 2 H) 7.56 (s, 4 H) 7.34 (t, J = 8.03 Hz, 1 H) 6.89-6.98 (m, 2 H) 6.86 (s, 1 H) 5.60 (s, 1 H) 3.78-3.87 (m, 3 H) 3.76 (s, 3 H) 3.38-3.47 (m, 1 H) 2.97-3.10 (m, 2 H) 0.93 (s, 1 H) 0.41 (dd, J = 8.28, 1.76 Hz, 2 H) 0.14-0.22 (m, 2 H). [α]25.0D = −13.600 (c 0.50, DMSO). |

TABLE 11-continued

| Ex. | R | Name | LCMS (M + H)+ | HPLC Method, RT (min.) and Purity | NMR |
|---|---|---|---|---|---|
| 299 | | 2-(3-(4-(1H-pyrazol-4-yl)phenyl)-2-oxoimidazolidin-1-yl)-N-methyl-2-phenylacetamide (Enantiomer 2) | 376.2 | I: 7.15, 99.64% J: 7.20, 99.89% V: 7.71, 98.42% ee | ¹H NMR (400 MHz, DMSO-d₆) d ppm 12.68 (s, 1 H) 8.24 (d, J = 4.52 Hz, 1 H) 8.00 (s, 2 H) 7.52-7.60 (m, 4 H) 7.39-7.46 (m, 2 H) 7.34-7.39 (m, 1 H) 7.27-7.34 (m, 2 H) 5.58 (s, 1 H) 3.70-3.86 (m, 3 H) 2.92-3.02 (m, 1 H) 2.66 (d, J = 4.8 Hz, 3 H). [α]25.1D = −16 (c 0.50, DMSO). |
| 300 | | 2-(3-(4-(1H-pyrazol-4-yl)phenyl)-2-oxoimidazolidin-1-yl)-N-cyclopropyl-2-(3-methoxyphenyl)acetamide (Enantiomer 1) | 432.2 | I: 8.15, 99.77% J: 9.13, 99.89% IV: 6.51, 93.59% ee | ¹H NMR (400 MHz, DMSO-d₆) d ppm 8.37 (d, J = 4.52 Hz, 1 H) 8.00 (s, 2 H) 7.49-7.62 (m, 4 H) 7.34 (t, J = 8.03 Hz, 1 H) 6.94 (dd, J = 8.53, 2.01 Hz, 1 H) 6.87 (d, J = 7.53 Hz, 1 H) 6.79-6.84 (m, 1 H) 5.50 (s, 1 H) 3.68-3.87 (m, 5 H) 2.69-2.76 (m, 1 H) 0.85 (d, J = 8.53 Hz, 1 H) 0.55-0.69 (m, 2 H) 0.36-0.48 (m, 2 H). [α]25.1D = −120 (c 0.05, DMSO). |
| 301 | | 2-(3-(4-(1H-pyrazol-4-yl)phenyl)-2-oxoimidazolidin-1-yl)-N-cyclopropyl-2-(3-methoxyphenyl)acetamide (Enantiomer 2) | 432.2 | I: 8.16, 99.86% J: 9.12, 99.75% IV: 6.51, 94.84% ee | ¹H NMR (400 MHz, DMSO-d₆) d ppm 12.83 (br. s., 1 H) 8.37 (d, J = 4.52 Hz, 1 H) 8.00 (s, 2 H) 7.51-7.62 (m, 4 H) 7.34 (t, J = 8.03 Hz, 1 H) 6.91-6.98 (m, 1 H) 6.87 (d, J = 7.53 Hz, 1 H) 6.79-6.84 (m, 1 H) 5.50 (s, 1 H) 3.69-3.87 (m, 5 H) 2.96-3.05 (m, 1 H) 2.68-2.76 (m, 1 H) 0.58-0.71 (m, 2 H) 0.34-0.49 (m, 2 H). [α]25.2D = +148 (c 0.05, DMSO). |
| 302 | | 2-(3-(4-(1H-pyrazol-4-yl)phenyl)-2-oxoimidazolidin-1-yl)-N-(2-hydroxy-2-methylpropyl)-2-(3-methoxyphenyl)acetamide (Enantiomer 1) | 464.2 | I: 9.42, 99.37% J: 7.49, 99.80% V: 4.31, 53.78% ee | ¹H NMR (400 MHz, DMSO-d₆) d ppm 12.81 (br. s., 1 H) 8.14 (t, J = 6.36 Hz, 1 H) 7.99 (br. s., 2 H) 7.51-7.60 (m, 4 H) 7.32 (t, J = 7.95 Hz, 1 H) 6.90-6.96 (m, 2 H) 6.86-6.90 (m, 1 H) 5.68 (s, 1 H) 4.42 (s, 1 H) 3.69-3.83 (m, 6 H) 3.10-3.20 (m, 1 H) 2.96-3.08 (m, 2 H) 1.03 (s, 3 H) 1.06 (s, 3 H). |
| 303 | | 2-(3-(4-(1H-pyrazol-4-yl)phenyl)-2-oxoimidazolidin-1-yl)-N-(2-hydroxy-2-methylpropyl)-2-(3-methoxyphenyl)acetamide (Enantiomer 2) | 464.2 | I: 9.42, 99.64% J: 7.49, 99.35% V: 5.88, 57.38% ee | ¹H NMR (400 MHz, DMSO-d₆) d ppm 8.15 (t, J = 5.99 Hz, 1 H) 7.98 (s, 2 H) 7.49-7.59 (m, 4 H) 7.32 (t, J = 7.83 Hz, 1 H) 6.89-6.96 (m, 2 H) 6.88 (d, J = 1.96 Hz, 1 H) 5.67 (s, 1 H) 4.42 (br. s., 1 H) 3.67-3.85 (m, 6 H) 3.10-3.18 (m, 1 H) 2.95-3.08 (m, 2 H) 1.03 (s, 3 H) 1.06 (s, 3 H). |

Example 304

2-(3-(4-(1H-Pyrazol-4-yl)phenyl)-2-oxoimidazolidin-1-yl)-2-(3-methoxyphenyl)-N-methylpropanamide (Enantiomer 1)

Example 304A: Preparation of 2-(3-(4-bromophenyl)-2-oxoimidazolidin-1-yl)-2-(3-methoxyphenyl)propanoic Acid (Enantiomer 1)

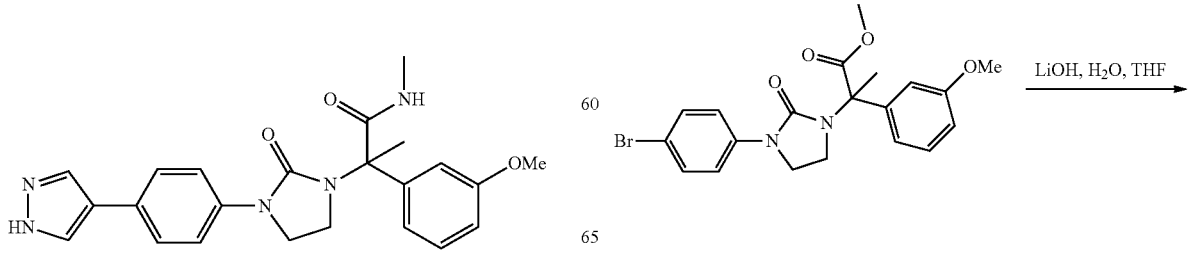

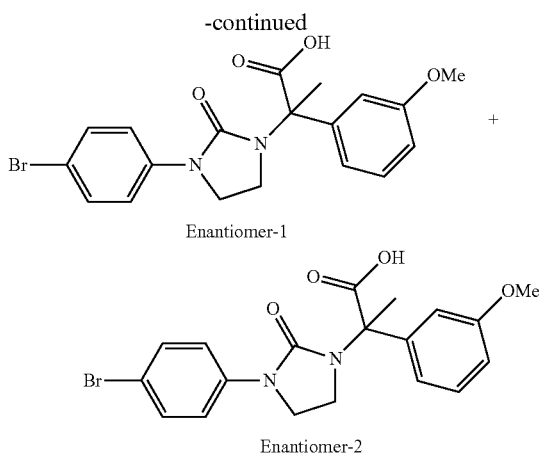

Enantiomer-1

Enantiomer-2

To a solution of methyl 2-(3-(4-bromophenyl)-2-oxoimidazolidin-1-yl)-2-(3-methoxyphenyl)propanoate (900 mg, 2.08 mmol) in a mixture of THF (20 mL) and methanol (10 mL), was added LiOH (249 mg, 10.39 mmol) and water (5 mL). The reaction mixture was heated at 75° C. for 16 h, then was concentrated. The residue was acidified to pH 2 with HCl solution and the precipitated solid was filtered, washed with water and hexanes and dried to give white gummy solid. The residue was coevaporated with toluene to give a white solid (700 mg). The enantiomers were separated by SFC [Column: CHIRALPAK® AS-H (250×21) mm, 5 t, Co-solvent 10% (0.2% DEA in methanol)] to afford Example 304A (Enantiomer 1, 0.240 g, 27.5% yield) as a white solid. MS(ESI) m/z: 421.0 (M+H)$^+$; $^1$H NMR (300 MHz, DMSO-d$_6$) δ ppm 7.41-7.53 (m, 4H) 7.17-7.26 (m, 1H) 7.06-7.18 (m, 2H) 6.81 (d, J=6.42 Hz, 1H) 3.73 (s, 3H) 3.60-3.68 (m, 2H) 310-3.24 (m, 2H) 1.80 (s, 3H) 100.0% ee (RT 7.93 min), [α]$^{25.1}_D$=-12 (c 0.05, DMSO).

Example 304B: Preparation of 2-(3-(4-bromophenyl)-2-oxoimidazolidin-1-yl)-2-(3-methoxyphenyl)-N-methylpropanamide (Enantiomer 1)

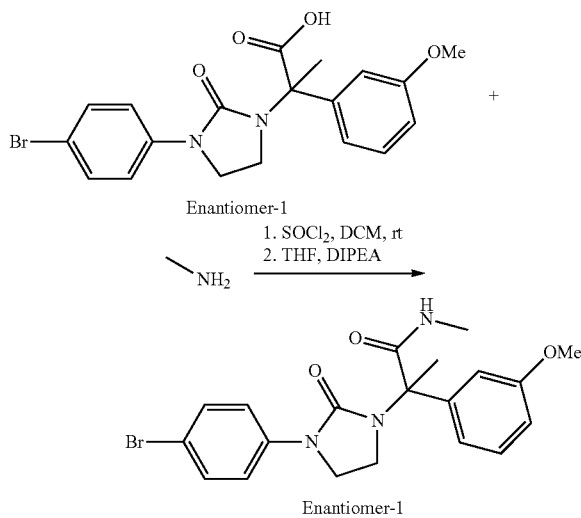

Enantiomer-1

Enantiomer-1

To a solution of Example 304A (0.240 g, 0.572 mmol) in DCM (8 mL) was added SOCl$_2$ and a drop of DMF. The reaction mixture was stirred at rt for 2 h, then was concentrated. The residue obtained was dissolved in THF and the resulting solution was added to a solution of methylamine (2 M in THF) (0.021 g, 0.685 mmol) and DIPEA (0.072 mL, 0.411 mmol) in THF (5 mL). The reaction mixture was stirred at rt for 16 h, and then concentrated to give yellow solid. The residue was purified by flash chromatography (gradient elution; 0-100% EtOAc/hexanes) to afford of Example 304B (0.045 g, 76.0% yield) as a white solid. MS(ESI) m/z: 434.1 (M+H)$^+$; $^1$H NMR (400 MHz, DMSO-d$_6$) δ ppm 7.87 (d, J=4.02 Hz, 1H) 7.45-7.56 (m, 4H) 7.26-7.33 (m, 1H) 7.00-7.07 (m, 2H) 6.90 (dd, J=8.03, 2.51 Hz, 1H) 3.75 (s, 3H) 3.65-3.74 (m, 2H) 3.16-3.24 (m, 1H) 3.02-3.11 (m, 1H) 2.59 (d, J=4.52 Hz, 3H) 1.82 (s, 3H). 100.0% ee (RT 5.399 min, Method XII).

Example 304: Preparation of 2-(3-(4-(1H-pyrazol-4-yl)phenyl)-2-oxoimidazolidin-1-yl)-2-(3-methoxyphenyl)-N-methylpropanamide (Enantiomer 1)

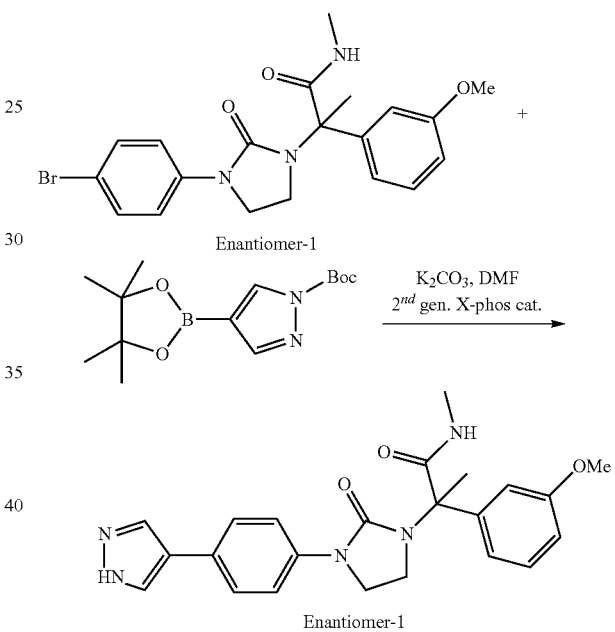

Enantiomer-1

Enantiomer-1

To a solution of 2-(3-(4-bromophenyl)-2-oxoimidazolidin-1-yl)-2-(3-methoxyphenyl)-N-methylpropanamide (45 mg, 0.104 mmol) in DMF (2 mL), were added tert-butyl 4-(4,4,5,5-tetramethyl-1,3,2-dioxaborolan-2-yl)-1H-pyrazole-1-carboxylate (42.9 mg, 0.146 mmol), K$_2$CO$_3$ (43.2 mg, 0.312 mmol) and water (0.4 mL). The reaction mixture was purged with nitrogen for 5 min and charged with 2nd generation XPhos precatalyst (4.91 mg, 6.25 µmol). The mixture was again purged with nitrogen for 3 min, then heated at 90° C. for 16 h. The reaction was cooled to rt and filtered. The filtrate was purified by preparative HPLC to afford Example 304 (Enantiomer 1, 0.015 g, 34.5% yield) as an off-white solid. MS(ESI) m/z: 420.2 (M+H)$^+$; $^1$H NMR (400 MHz, DMSO-d$_6$) δ ppm 12.82 (br. s., 1H) 8.10 (br. s., 1H) 7.86 (br. s., 1H) 7.81 (d, J=4.52 Hz, 1H) 7.50-7.59 (m, 4H) 7.26-7.34 (m, 1H) 7.02-7.11 (m, 2H) 6.87-6.94 (m, 1H) 3.68-3.82 (m, 5H) 3.19-3.24 (m, 1H) 3.10 (q, J=8.53 Hz, 1H) 2.62 (d, J=4.52 Hz, 3H) 1.84 (s, 3H). HPLC RT=1.39 min, 100.0% (Method E), 1.30 min, 99.54% (Method F). 99.536% ee (RT 6.97 min, Method V), [α]$^{25.1}_D$=-40 (c 0.05, DMSO).

The following Examples in Table 12 were prepared in a similar fashion to Example 304.

TABLE 12

| Ex. | R | Name | LCMS (M + H)+ | HPLC Method, RT (min.) and Purity | NMR |
|---|---|---|---|---|---|
| 306 | (structure) | 2-(3-(4-(1H-pyrazol-4-yl)phenyl)-2-oxoimidazolidin-1-yl)-2-(3-methoxyphenyl)propanamide (Enantiomer I) | 406.2 | E: 1.33, 100% F: 1.24, 100% XIV: 18.89, 100% ee | $^1$H NMR (400 MHz, DMSO-$d_6$) δ ppm 12.81 (br. s., 1 H) 8.10 (br. s., 1 H) 7.86 (br. s., 1 H) 7.55 (s, 4 H) 7.38 (br. s., 1 H) 7.31 (t, J = 8.28 Hz, 1 H) 7.09-7.15 (m, 2 H) 7.01 (br. s., 1 H) 6.88-6.93 (m, 1 H) 3.78 (s, 3 H) 3.74 (dd, J = 9.04, 5.52 Hz, 2 H) 3.152-3.179 (m, 1 H) 3.11 (d, J = 7.53 Hz, 1 H) 1.84 (s, 3 H). |

Examples 309 and 310

1-(4-(1H-Pyrazol-4-yl)phenyl)-3-(1-(3-methoxyphenyl)-2-(methylamino)ethyl)imidazolidin-2-one (Enantiomer 1 and Enantiomer 2)

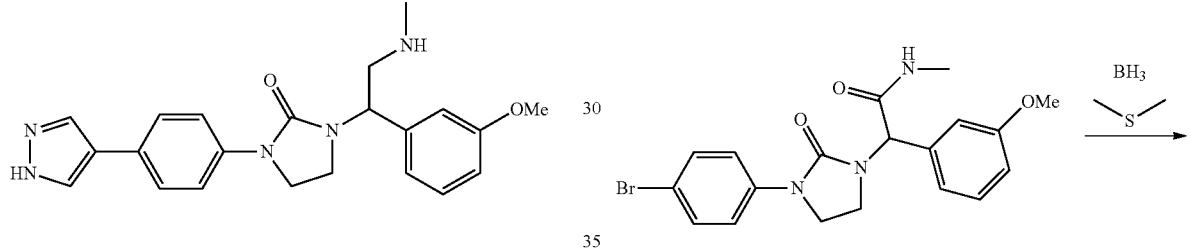

Example 309A: Preparation of 2-(3-(4-bromophenyl)-2-oxoimidazolidin-1-yl)-2-(3-methoxyphenyl)-N-methylacetamide

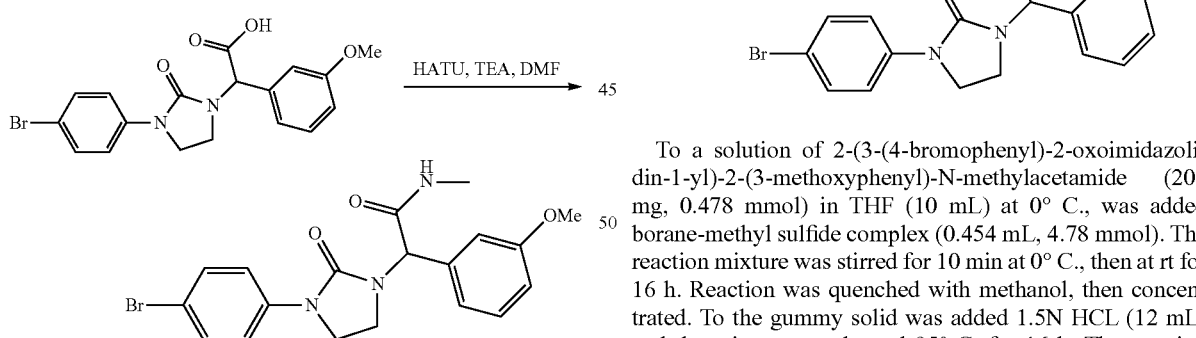

To a solution of 2-(3-(4-bromophenyl)-2-oxoimidazolidin-1-yl)-2-(3-methoxyphenyl)acetic acid (500 mg, 1.24 mmol) in DMF (3 mL), were added methylamine hydrochloride (167 mg, 2.468 mmol), TEA (0.860 mL, 6.17 mmol) and HATU (704 mg, 1.851 mmol). The reaction mixture was stirred at rt for 16 h, then was diluted with water, stirred for 30 min. The precipitated solid was collected by filtration, and was washed with water and hexanes to afford 2-(3-(4-bromophenyl)-2-oxoimidazolidin-1-yl)-2-(3-methoxyphenyl)-N-methylacetamide (0.200 g, 39% yield) as a yellow solid. MS(ESI) m/z: 418.0 (M+H)+; $^1$H NMR (400 MHz, DMSO-$d_6$) δ ppm 8.21 (d, J=4.52 Hz, 1H) 7.55 (d, J=9.04 Hz, 2H) 7.50 (d, J=9.04 Hz, 2H) 7.33 (t, J=8.03 Hz, 1H) 6.94 (dd, J=8.03, 2.01 Hz, 1H) 6.80-6.90 (m, 2H) 5.53 (s, 1H) 3.68-3.85 (m, 6H) 2.93-3.06 (m, 1H) 2.65 (d, J=4.52 Hz, 3H).

Example 309B: Preparation of 1-(4-bromophenyl)-3-(1-(3-methoxyphenyl)-2-(methylamino)ethyl)imidazolidin-2-one To a solution of 2-(3-(4-bromophenyl)-2-oxoimidazolidin-1-yl)-2-(3-methoxyphenyl)-N-methylacetamide (200 mg, 0.478 mmol) in THF (10 mL) at 0° C., was added borane-methyl sulfide complex (0.454 mL, 4.78 mmol). The reaction mixture was stirred for 10 min at 0° C., then at rt for 16 h. Reaction was quenched with methanol, then concentrated. To the gummy solid was added 1.5N HCL (12 mL) and the mixture was heated 95° C. for 16 h. The reaction mixture was cooled to rt, neutralized with sat. NaHCO$_3$ solution, extracted with ethyl acetate. The combined ethyl acetate layers were washed with water and brine, dried over Na$_2$SO$_4$, and concentrated to afford 1-(4-bromophenyl)-3-(1-(3-methoxyphenyl)-2-(methylamino)ethyl)imidazolidin-2-one (0.080 g, 41% yield) as a yellow gummy solid. MS(ESI) m/z: 406.2 (M+H)+; $^1$H NMR (300 MHz, DMSO-$d_6$) δ ppm 7.55 (d, J=9.44 Hz, 2H) 7.47 (d, J=9.44 Hz, 2H) 7.24-7.32 (m, 1H) 6.83-6.95 (m, 3H) 5.04 (dd, J=9.63, 5.48 Hz, 1H) 3.72-3.83 (m, 5H) 3.49-3.60 (m, 1H) 3.16-3.26 (m, 2H) 3.06 (d, J=10.58 Hz, 1H) 2.91 (d, J=4.91 Hz, 1H) 2.34 (s, 3H).

Preparation of Examples 309 and 310 (Enantiomer 1 and Enantiomer 2)

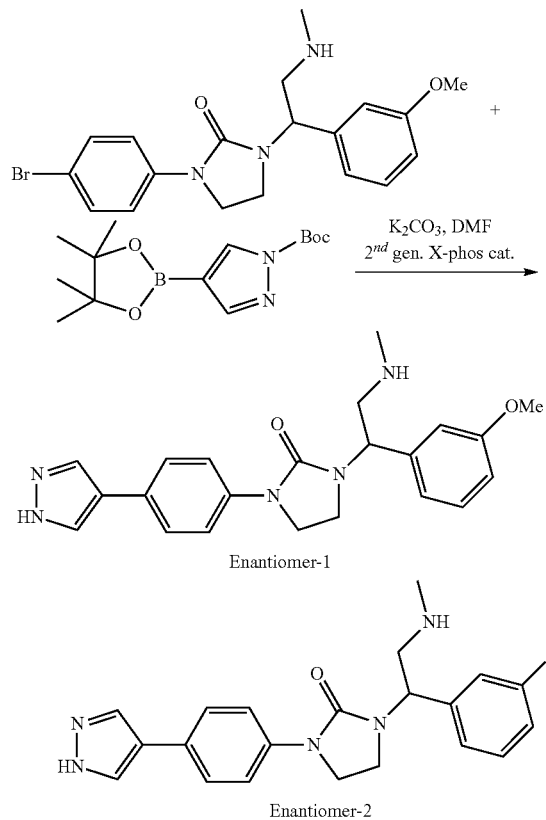

Enantiomer-1

Enantiomer-2

To a solution of 1-(4-bromophenyl)-3-(1-(3-methoxyphenyl)-2-(methylamino)ethyl)imidazolidin-2-one (80 mg, 0.198 mmol) in DMF (4 mL), were added tert-butyl 4-(4,4,5,5-tetramethyl-1,3,2-dioxaborolan-2-yl)-1H-pyrazole-1-carboxylate (81 mg, 0.277 mmol), $K_2CO_3$ (82 mg, 0.594 mmol) and water (0.4 mL). The reaction mixture was purged with nitrogen for 5 min and charged with 2nd generation XPhos precatalyst (9.34 mg, 0.012 mmol). The mixture was again purged with nitrogen for 3 min, then heated at 90° C. for 16 h. The reaction mixture was cooled, filtered and the filtrate was concentrated. The residue obtained was purified by prep HPLC to give the racemic product (140 mg). The enantiomers were separated by SFC [Column: CHIRALPAK® AS-H (250×21) mm, 5μ, Co-solvent 30% (0.2% DEA in methanol)] to afford Example 309 (Enantiomer 1, 0.013 g, 16% yield) as an off-white solid. MS(ESI) m/z: 392.2 $(M+H)^+$; $^1H$ NMR (400 MHz, DMSO-$d_6$) δ ppm 12.85 (br. s., 1H) 7.98 (br. s., 2H) 7.51-7.59 (m, 4H) 7.24-7.31 (m, 1H) 6.83-6.97 (m, 3H) 5.05 (dd, J=9.79, 5.27 Hz, 1H) 3.77-3.86 (m, 2H) 3.75 (s, 3H) 3.47-3.62 (m, 1H) 3.16-3.26 (m, 1H) 3.07 (dd, J=12.30, 10.29 Hz, 1H) 2.90 (dd, J=12.30, 5.27 Hz, 1H) 2.33-2.39 (m, 3H). HPLC RT=10.50 min, 99.06% (Method M), 10.85 min, 98.00% (Method N). 96.5% ee (rt-7.87 min), $[α]^{25.2}_D$=−46.400 (c 0.05, DMSO) and afford Example 310 (Enantiomer 2, 0.008 g, 10% yield) as a pale yellow solid. MS(ESI) m/z: 392.2 $(M+H)^+$; $^1H$ NMR (400 MHz, DMSO-$d_6$) δ ppm 7.97 (br. s., 2H) 7.53 (s, 4H) 7.22-7.34 (m, 1H) 6.92 (d, J=7.83 Hz, 1H) 6.80-6.89 (m, 2H) 5.05 (dd, J=9.90, 5.26 Hz, 1H) 3.77-3.85 (m, 2H) 3.54 (dd, J=14.92, 8.80 Hz, 3H) 3.01-3.13 (m, 2H) 2.90 (dd, J=12.47, 5.38 Hz, 1H) 2.34 (s, 3H). HPLC RT=1.33 min, 99.74% (Method E), 1.34 min, 100.0% (Method F). 90.74% ee (rt-15.07 min).

Example 311

(S)-1-(5-(1H-Pyrazol-4-yl)pyridin-2-yl)-3-(4-fluoro-3-methoxybenzyl)-4-(hydroxymethyl)imidazolidin-2-one

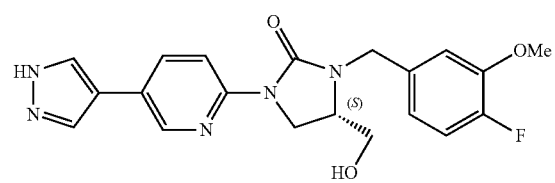

Example 311A: Phenyl (5-bromopyridin-2-yl)carbamate

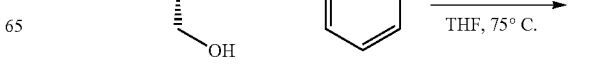

To a solution of 5-bromopyridin-2-amine (1.5 g, 8.67 mmol) in THF (30 mL) was added pyridine (0.686 g, 8.67 mmol). The mixture was cooled to 0° C., then phenyl chloroformate (1.561 g, 9.97 mmol) was added dropwise. The reaction mixture was stirred at rt for 1 h. The precipitate was collected by filtration and was washed with water and dried under suction to give phenyl (5-bromopyridin-2-yl) carbamate (2.52 g, 8.56 mmol, 99% yield) as an off-white solid. MS(ESI) m/z: 293.0 $(M+H)^+$. $^1H$ NMR (400 MHz, DMSO-$d_6$) δ ppm 10.93 (s, 1H), 8.45 (d, J=2.0 Hz, 1H), 8.03 (dd, J=8.5, 2.5 Hz, 1H), 7.79 (d, J=9.0 Hz, 1H), 7.47-7.39 (m, 2H), 7.31-7.19 (m, 3H).

Example 311B: (S)-1-(1-(Benzyloxy)-3-hydroxypropan-2-yl)-3-(5-bromopyridin-2-yl)urea

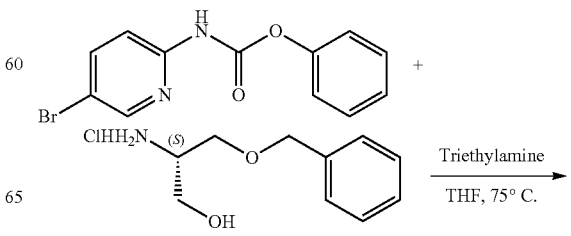

-continued

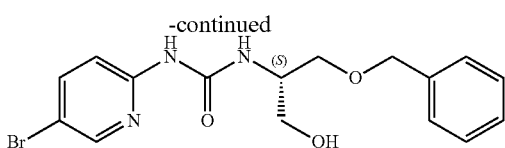

A mixture of phenyl (5-bromopyridin-2-yl)carbamate (0.25 g, 0.853 mmol), (S)-2-amino-3-(benzyloxy)propan-1-ol hydrochloride (0.186 g, 0.853 mmol) and triethylamine (0.594 mL, 4.26 mmol) in THF (10 mL) were stirred at 75° C. for 15 h. The solvent was evaporated, then the resultant residue was suspended in water and stirred for 30 min. The precipitate was collected by filtration and dried to give (S)-1-(1-(benzyloxy)-3-hydroxypropan-2-yl)-3-(5-bromopyridin-2-yl)urea (0.32 g, 98% yield) as an off-white solid. MS(ESI) m/z: 380.2 (M+H)$^+$. $^1$H NMR (400 MHz, DMSO-d$_6$) δ ppm 9.33 (s, 1H), 8.21 (d, J=2.0 Hz, 1H), 7.87 (dd, J=8.8, 2.8 Hz, 1H), 7.65 (d, J=7.0 Hz, 1H), 7.53 (d, J=9.0 Hz, 1H), 7.34 (d, J=4.5 Hz, 4H), 7.32-7.26 (m, 1H), 4.84 (t, J=5.3 Hz, 1H), 4.52 (s, 2H), 3.85 (br. s., 1H), 3.59-3.42 (m, 4H).

Example 311C: (S)-4-((Benzyloxy)methyl)-1-(5-bromopyridin-2-yl)imidazolidin-2-one

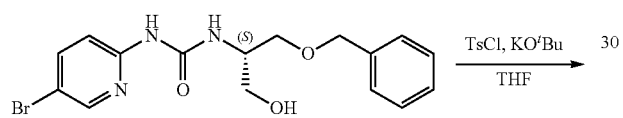

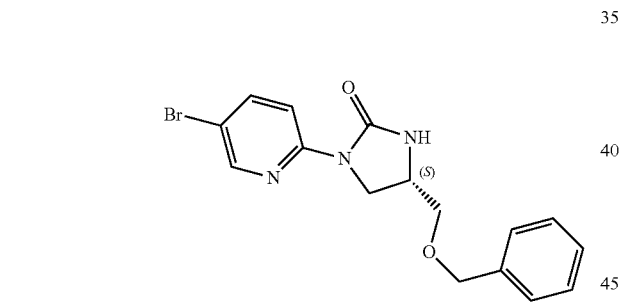

To a mixture of (S)-1-(1-(benzyloxy)-3-hydroxypropan-2-yl)-3-(5-bromopyridin-2-yl)urea (0.32 g, 0.842 mmol) and potassium tert-butoxide (0.236 g, 2.104 mmol) in THF (10 mL) at 0° C., was added a solution of p-toluenesulfonyl chloride (0.152 g, 0.800 mmol) in THF (2.5 mL) dropwise. The reaction mixture was stirred at 0° C. for 90 min, then was quenched with saturated aqueous NH$_4$Cl solution (10 mL). The mixture was diluted with water (20 mL) and extracted with EtOAc (2×20 mL). Combined organic extracts were washed with water and brine, dried over Na$_2$SO$_4$ and concentrated. The crude product was purified by flash chromatography (eluting with 30-40% EtOAc in hexane) to give (S)-4-((benzyloxy)methyl)-1-(5-bromopyridin-2-yl)imidazolidin-2-one (0.1 g, 27% yield) as an off-white solid. MS(ESI) m/z: 362.0 (M+H)$^+$. $^1$H NMR (400 MHz, DMSO-d$_6$) δ ppm 8.36 (d, J=2.5 Hz, 1H), 8.16 (d, J=9.5 Hz, 1H), 7.88 (dd, J=9.0, 2.5 Hz, 1H), 7.53 (s, 1H), 7.36-7.25 (m, 5H), 4.54 (s, 2H), 4.07-3.99 (m, 1H), 3.94-3.86 (m, 1H), 3.75 (dd, J=10.5, 5.0 Hz, 1H), 3.47 (d, J=5.0 Hz, 2H).

Example 311D: (S)-4-((Benzyloxy)methyl)-1-(5-bromopyridin-2-yl)-3-(4-fluoro-3-methoxybenzyl) imidazolidin-2-one

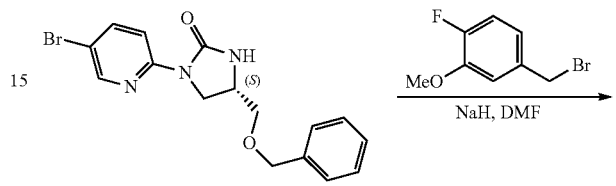

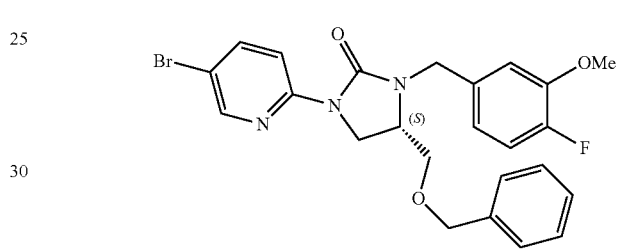

To a solution of (S)-4-((benzyloxy)methyl)-1-(5-bromopyridin-2-yl)imidazolidin-2-one (125 mg, 0.345 mmol) in DMF (4 mL) at 0° C., was added sodium hydride (60% suspension in mineral oil) (48.3 mg, 1.208 mmol). The reaction mixture was stirred at 10° C. for 30 min, then 4-(bromomethyl)-1-fluoro-2-methoxybenzene (151 mg, 0.690 mmol) was added dropwise. The reaction mixture was stirred at rt for 3 h, then was quenched with saturated aqueous NH$_4$Cl solution (10 mL). The mixture was diluted with water (40 mL) and extracted with EtOAc (2×50 mL). Combined organic extracts were washed with water and brine, dried over Na$_2$SO$_4$ and concentrated to give crude product which was purified by flash chromatography (eluting with 10-20% EtOAc in hexane) to give (S)-4-((benzyloxy)methyl)-1-(5-bromopyridin-2-yl)-3-(4-fluoro-3-methoxybenzyl) imidazolidin-2-one (135 mg, 59% yield) as a colorless oil. MS(ESI) m/z: 500.0 (M+H)$^+$. $^1$H NMR (400 MHz, DMSO-d$_6$) δ ppm 8.40 (d, J=2.0 Hz, 1H), 8.22 (d, J=9.0 Hz, 1H), 7.94 (dd, J=9.0, 2.7 Hz, 1H), 7.36-7.21 (m, 5H), 7.17-7.10 (m, 1H), 7.05 (dd, J=8.4, 2.1 Hz, 1H), 6.89-6.81 (m., 1H), 4.60 (d, J=15.4 Hz, 1H), 4.43 (s, 2H), 4.31-4.24 (m, 2H), 4.08-4.00 (m, 1H), 3.85-3.72 (m, 4H), 3.64-3.51 (m, 2H).

Example 311E: Preparation of (S)-1-(5-(1H-pyrazol-4-yl)pyridin-2-yl)-4-((benzyloxy)methyl)-3-(4-fluoro-3-methoxybenzyl)imidazolidin-2-one

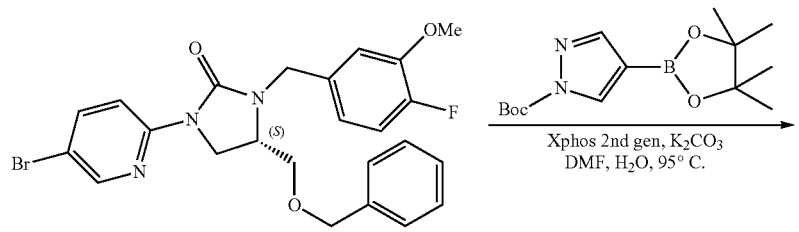

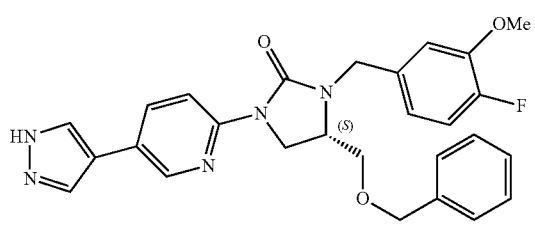

(S)-4-((Benzyloxy)methyl)-1-(5-bromopyridin-2-yl)-3-(4-fluoro-3-methoxybenzyl)imidazolidin-2-one (180 mg, 0.360 mmol), tert-butyl 4-(4,4,5,5-tetramethyl-1,3,2-dioxaborolan-2-yl)-1H-pyrazole-1-carboxylate (169 mg, 0.576 mmol) and potassium carbonate (149 mg, 1.079 mmol) in DMF (10 mL) and water (5 mL) were mixed in a sealed tube. Reaction mixture was degassed with nitrogen, then 2nd generation XPhos precatalyst (28.3 mg, 0.036 mmol) was added and the mixture was stirred at 95° C. for 6 h. Reaction mixture was cooled to rt and filtered. The filtrate was concentrated and the residue was purified by preparative HPLC to give Example 311E (52 mg, 30% yield) as an off-white solid. MS(ESI) m/z: 488.2 (M+H)+. 1H NMR (400 MHz, DMSO-$d_6$) δ ppm 12.93 (br. s., 1H), 8.57 (dd, J=2.5, 1.0 Hz, 1H), 8.23-8.18 (m, 2H), 7.98-7.94 (m, 2H), 7.37-7.23 (m, 5H), 7.14 (dd, J=11.5, 8.5 Hz, 1H), 7.05 (dd, J=8.5, 2.0 Hz, 1H), 6.86 (ddd, J=6.3, 4.3, 2.0 Hz, 1H), 4.61 (d, J=15.1 Hz, 1H), 4.44 (s, 2H), 4.29 (d, J=15.6 Hz, 1H), 4.11-4.00 (m, 1H), 3.85-3.75 (m, 2H), 3.74 (s, 3H), 3.65-3.53 (m, 2H).

Preparation of Example 311

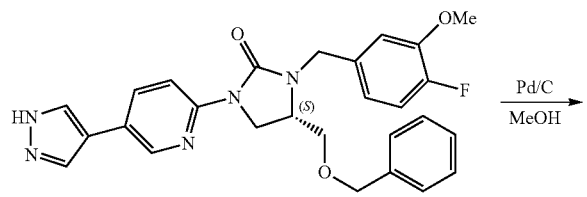

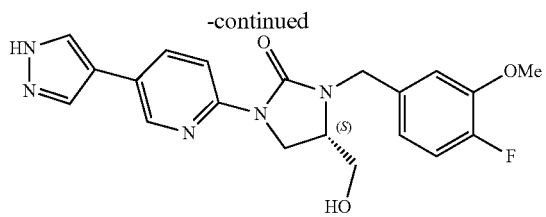

To a solution of (S)-1-(5-(1H-pyrazol-4-yl)pyridin-2-yl)-4-((benzyloxy)methyl)-3-(4-fluoro-3-methoxybenzyl)imidazolidin-2-one (25 mg, 0.051 mmol) in methanol (15 mL) was added Pd—C (60 mg, 0.056 mmol) and the reaction mixture was hydrogenated in a autoclave under 3.5 kg pressure for 15 h. The reaction mixture was degassed with nitrogen, filtered over CELITE® and the filtrate was concentrated. The residue was purified by preparative HPLC to give (S)-1-(5-(1H-pyrazol-4-yl)pyridin-2-yl)-3-(4-fluoro-3-methoxybenzyl)-4-(hydroxymethyl)imidazolidin-2-one (1.7 mg, 8% yield) MS(ESI) m/z: 398.2 (M+H)+. 1H NMR (400 MHz, DMSO-$d_6$) δ ppm 12.96 (br. s., 1H), 8.57 (s, 1H), 8.25-8.16 (m, 2H), 7.99-7.90 (m, 2H), 7.20-7.10 (m, 2H), 6.96-6.85 (m, 1H), 5.02-4.96 (m, 1H), 4.67 (d, J=15.2 Hz, 1H), 4.24 (d, J=15.7 Hz, 1H), 4.02 (t, J=10.1 Hz, 1H), 3.86-3.77 (m, 4H), 3.66-3.56 (m, 2H), 3.53-3.46 (m, 1H)). HPLC RT=1.16 min, 94.3% (Method E) and RT=1.32 min, 94.2% (Method F) and Chiral HPLC RT=10.53 min, 100% ee.

The following Examples in Table 13 were prepared in a similar fashion to Example 311.

TABLE 13

| Ex. | R | Name | LCMS (M + H)+ | HPLC Method, RT (min.) and Purity | NMR |
|---|---|---|---|---|---|
| 312 | Chiral | (S)-1-(5-(1H-pyrazol-4-yl)pyridin-2-yl)-3-(3-fluoro-5-methoxybenzyl)-4-(hydroxymethyl)imidazolidin-2-one | 398.2 | E: 1.18, 98.6% F: 1.48, 100% | $^1$H NMR (400 MHz, DMSO-$d_6$) δ ppm 12.97 (br. s., 1 H), 8.61-8.55 (m, 1 H), 8.24-7.92 (m, 4 H), 6.81-6.68 (m, 3 H), 5.03-4.97 (m, 1 H), 4.65 (d, J = 15.9 Hz, 1 H), 4.26 (d, J = 15.7 Hz, 1 H), 4.09-4.00 (m, 1 H), 3.87-3.79 (m, 1 H), 3.76 (s, 3 H), 3.68-3.56 (m, 2 H), 3.55-3.47 (m, 1 H) |
| 313 | Chiral | (R)-1-(5-(1H-pyrazol-4-yl)pyridin-2-yl)-3-(3-fluoro-5-methoxybenzyl)-4-(hydroxymethyl)imidazolidin-2-one | 398.2 | E: 1.22, 100% F: 1.48, 98.1% | $^1$H NMR (400 MHz, DMSO-$d_6$) δ ppm 12.96 (br. s., 1 H), 8.57 (d, J = 2.5 Hz, 1 H), 8.25-8.12 (m, 2 H), 8.04-7.92 (m, 2 H), 6.82-6.66 (m, 3 H), 5.04-4.93 (m, 1 H), 4.65 (d, J = 16.1 Hz, 1 H), 4.26 (d, J = 15.6 Hz, 1 H), 4.10-4.00 (m, 1 H), 3.86-3.78 (m, 1 H), 3.76 (s, 3 H), 3.68-3.58 (m, 2 H), 3.54-3.47 (m, 1 H) |
| 314 | Chiral | (S)-1-(5-(1H-pyrazol-4-yl)pyridin-2-yl)-4-(hydroxymethyl)-3-(3-methoxybenzyl)imidazolidin-2-one, TFA | 380.2 | E: 1.08, 99.5% F: 1.39, 100% | $^1$H NMR (400 MHz, DMSO-$d_6$) δ ppm 8.57 (dd, J = 2.5, 1.0 Hz, 1 H), 8.25-8.18 (m, 1 H), 8.07 (br. s., 2 H), 7.95 (dd, J = 9.0, 2.5 Hz, 1 H), 7.32-7.23 (m, 1 H), 6.94-6.80 (m, 3 H), 5.07-4.90 (m, 1 H), 4.70 (d, J = 15.6 Hz, 1 H), 4.21 (d, J = 15.6 Hz, 1 H), 4.07-3.96 (m, 1 H), 3.85-3.77 (m, 1 H), 3.74 (s, 3 H), 3.64-3.51 (m, 3 H) |

Example 316

1-(3'-Fluoro-2-methoxy-[3,4'-bipyridin]-6-yl)-3-(3-methoxybenzyl)imidazolidin-2-one

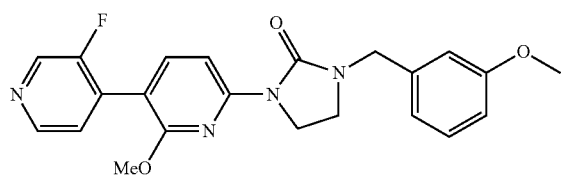 [SMILES: COc1cccc(CN2CCN(c3ccc(-c4ccncc4F)c(OC)n3)C2=O)c1]

Example 316A: 1-(5-Bromo-6-methoxypyridin-2-yl)-3-(3-methoxybenzyl)imidazolidin-2-one

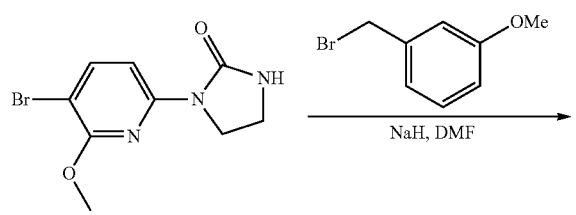

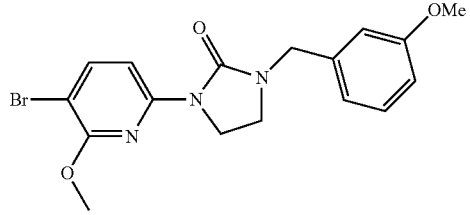

To a solution of 1-(5-bromo-6-methoxypyridin-2-yl)imidazolidin-2-one (0.2 g, 0.735 mmol) in DMF (6 mL) at 0° C., was added sodium hydride (60% suspension in mineral oil) (0.103 g, 2.57 mmol). The reaction mixture was stirred at 10° C. for 30 min. 1-(Bromomethyl)-3-methoxybenzene (0.369 g, 1.838 mmol) was added dropwise and the reaction mixture was stirred at RT for 3 h. The reaction mixture was quenched with saturated aqueous NH$_4$Cl solution (10 mL), diluted with water (40 mL) and extracted with EtOAc (2×50 mL). The combined organic extracts were washed with water and brine, dried over Na$_2$SO$_4$ and concentrated to give crude product. The crude product was purified by flash chromatography (eluting with 10-20% EtOAc in hexane) to give 1-(5-bromo-6-methoxypyridin-2-yl)-3-(3-methoxybenzyl)imidazolidin-2-one (0.255 g, 82% yield) as an off-white solid. MS(ESI) m/z: 392.2 (M+H)+. $^1$H NMR (400 MHz, DMSO-$d_6$) δ ppm 7.89 (d, J=8.5 Hz, 1H), 7.73 (d, J=13.1 Hz, 1H), 7.31-7.25 (m, 1H), 6.92-6.81 (m, 3H), 4.38 (s, 2H), 3.99 (dd, J=8.8, 7.3 Hz, 2H), 3.90 (s, 3H), 3.75 (s, 3H), 3.40-3.34 (m, 2H).

Preparation of Example 316

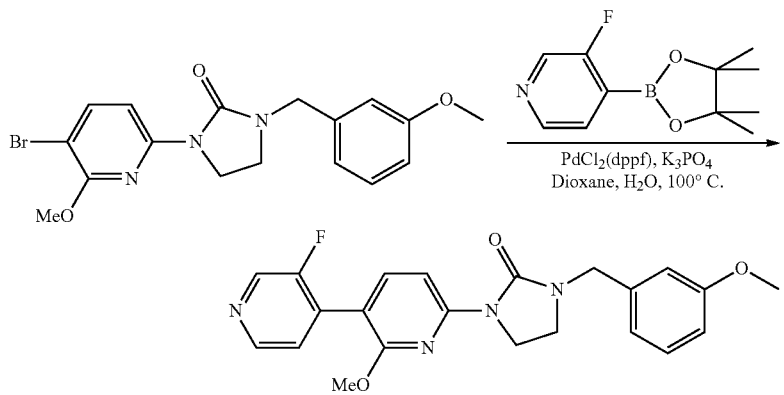

In a sealed tube, 1-(5-bromo-6-methoxypyridin-2-yl)-3-(3-methoxybenzyl) imidazolidin-2-one (50 mg, 0.127 mmol), 3-fluoropyridine-4-boronic acid pinacol ester (34.1 mg, 0.153 mmol) and potassium phosphate tribasic (67.6 mg, 0.319 mmol) were combined in 1,4-dioxane (4 mL) and water (1.2 mL). The reaction tube was degassed with nitrogen, then $PdCl_2$(dppf)-DCM adduct (12.5 mg, 0.015 mmol) was added and the mixture was stirred at 100° C. for 5 h. The reaction mixture was cooled to rt, diluted with water (20 mL) and extracted with EtOAc (2×20 mL). The combined organic extracts were washed with water and brine, dried over $Na_2SO_4$ and concentrated. The residue was purified by preparative HPLC to give 1-(3'-fluoro-2-methoxy-[3,4'-bipyridin]-6-yl)-3-(3-methoxybenzyl)imidazolidin-2-one (34 mg, 65% yield). MS(ESI) m/z: 409.2 (M+H)+. 1H NMR (400 MHz, DMSO-d6) δ ppm 8.60 (d, J=2.0 Hz, 1H), 8.46 (dd, J=4.9, 1.0 Hz, 1H), 7.91 (d, J=8.3 Hz, 1H), 7.77 (dd, J=8.3, 0.7 Hz, 1H), 7.52 (dd, J=6.6, 4.9 Hz, 1H), 7.34-7.24 (m, 1H), 6.92-6.84 (m, 3H), 4.41 (s, 2H), 4.06 (dd, J=9.0, 7.1 Hz, 2H), 3.88 (s, 3H), 3.76 (s, 3H), 3.47-3.39 (m, 2H). HPLC: RT=1.73 min, 99.8% (Method E) and RT=1.96 min, 99.8% (Method F).

The following Examples in Table 14 were prepared in a similar fashion to Example 316.

TABLE 14

| Ex. | R | Name | LCMS (M + H)+ | HPLC Method, RT (min.) and Purity | NMR |
|---|---|---|---|---|---|
| 318 | | 1-(6-methoxy-5-(1H-pyrrolo[2,3-b]pyridin-4-yl)pyridin-2-yl)-3-(3-methoxybenzyl)imidazolidin-2-one | 430.2 | E: 1.52, 99.9%<br>F: 1.92, 98.8% | 1H NMR (400 MHz, DMSO-d6) δ ppm 11.69 (br, s., 1 H), 8.23 (d, J = 5.1 Hz, 1 H), 7.92 (d, J = 8.0 Hz, 1 H), 7.86 (d, J = 8.4 Hz, 1 H), 7.49-7.45 (m, 1 H), 7.36-7.25 (m, 1 H), 7.14 (d, J = 4.9 Hz, 1 H), 6.93-6.84 (m, 3 H), 6.33 (dd, J = 3.4, 2.0 Hz, 1 H), 4.42 (s, 2 H), 4.13-4.05 (m, 2 H), 3.88 (s, 3 H), 3.76 (s, 3 H), 3.45-3.37 (m, 2 H) |
| 319 | | 1-(2'-fluoro-2-methoxy-[3,4'-bipyridin]-6-yl)-3-(3-methoxybenzyl)imidazolidin-2-one | 409.2 | E: 2.41, 94.5%<br>F: 2.32, 100% | 1H NMR (400 MHz, DMSO-d6) δ ppm 8.24 (d, J = 5.4 Hz, 1 H), 8.02 (d, J = 8.4 Hz, 1 H), 7.92 (d, J = 8.3 Hz, 1 H), 7.62 (d, J = 5.4 Hz, 1 H), 7.42 (s, 1 H), 7.29 (dd, J = 8.9, 7.5 Hz, 1 H), 6.92-6.85 (m, 3 H), 4.41 (s, 2 H), 3.41 (t, J = 7.8 Hz, 2 H), 3.95 (s, 3 H), 3.76 (s, 3 H), 3.41 (t, J = 7.9 Hz, 2 H) |

TABLE 14-continued

| Ex. | R | Name | LCMS (M + H)+ | HPLC Method, RT (min.) and Purity | NMR |
|---|---|---|---|---|---|
| 320 | | 1-(6-methoxy-5-(5-methyl-1H-pyrazol-4-yl)pyridin-2-yl)-3-(3-methoxybenzyl)imidazolidin-2-one | 394.2 | E: 1.86, 100% F: 1.83, 97.5% | 1H NMR (400 MHz, DMSO-d6) δ ppm 7.78 (d, J = 8.3 Hz, 1 H), 7.63-7.59 (m, 2 H), 7.32-7.25 (m, 1 H), 6.92-6.84 (m, 3 H), 4.39 (s, 2 H), 4.06-3.99 (m, 2 H), 3.86 (s, 3 H), 3.75 (s, 3 H), 3.41-3.33 (m, 2 H), 2.21 (s, 3 H) |

Example 321

1-(4-Bromophenyl)-3-(3-fluorobenzyl)-1H-imidazol-2(3H)-one

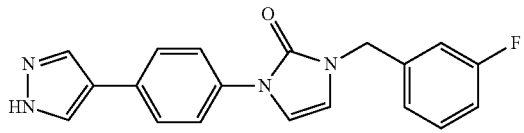 [SMILES: O=c1n(Cc2cccc(F)c2)ccn1-c1ccc(-c2cn[nH]c2)cc1]

Example 321A: Preparation of 1-(4-bromophenyl)-3-(3-fluorobenzyl)-1H-imidazol-2(3H)-one

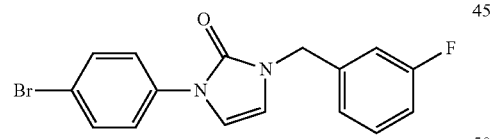

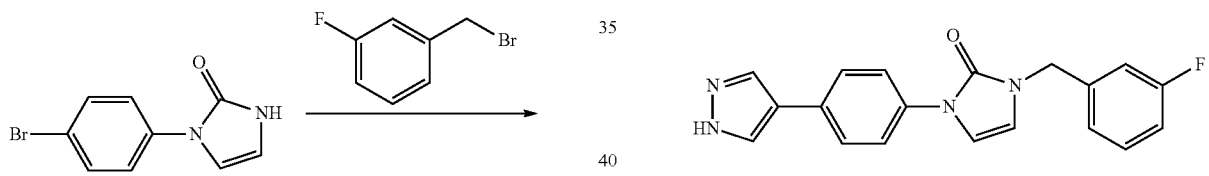

To a mixture of 1-(4-bromophenyl)-1H-imidazol-2(3H)-one (0.3 g, 1.255 mmol) and K2CO3 (0.347 g, 2.510 mmol) in DMF (5 mL), was added 1-(bromomethyl)-3-fluorobenzene (0.231 mL, 1.882 mmol). The reaction mixture was heated at 80° C. for 8 h. The reaction mixture was quenched with ice and diluted with ethyl acetate. The organic layer was separated and washed with water and brine, dried over sodium sulfate and concentrated. The crude product was purified using flash instrument (2% MeOH in CHCl3) to afford 1-(4-bromophenyl)-3-(3-fluorobenzyl)-1H-imidazol-2(3H)-one (0.38 g, 1.073 mmol, 85% yield) as an off-white solid. MS(ESI) m/z: 345.3 (M+H)+. 1H NMR (400 MHz, DMSO-d6) δ=7.78-7.70 (m, 2H), 7.66-7.59 (m, 2H), 7.45-7.36 (m, 1H), 7.17-7.09 (m, 3H), 6.88 (d, J=3.5 Hz, 1H), 4.82 (s, 2H).

Preparation of 1-(4-bromophenyl)-3-(3-fluorobenzyl)-1H-imidazol-2(3H)-one

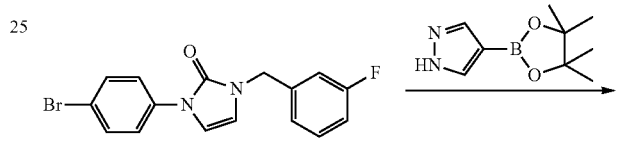

The mixture of 1-(4-bromophenyl)-3-(3-fluorobenzyl)-1H-imidazol-2(3H)-one (0.15 g, 0.432 mmol), 4-(4,4,5,5-tetramethyl-1,3,2-dioxaborolan-2-yl)-1H-pyrazole (0.252 g, 1.296 mmol) and K2CO3 (0.18 g, 1.3 mmol) in DMF (3 mL) and water (1 mL) was degassed by bubbling N2 gas into it for 10 minutes. To the reaction mixture was added 2nd generation XPhos precatalyst (0.017 g, 0.022 mmol), and the reaction mixture was heated at 90° C. for 4 h. The reaction mixture was cooled to rt, filtered through CELITE®, and the filtrate was diluted with ethyl acetate. The organic phase was washed with water followed by brine and concentrated in vacuo. This crude solid was purified by preparative HPLC to afford Example 321 (68 mg, 0.200 mmol, 46% yield) as an off-white solid. MS(ESI) m/z: 335.2, 99.857%; 1H NMR (400 MHz, DMSO-d6) δ=12.95 (br. s., 1H), 8.20 (br. s., 1H), 7.95 (br. s., 1H), 7.74-7.64 (m, 4H), 7.46-7.37 (m, 1H), 7.17-7.07 (m, 4H), 6.85 (d, J=3.0 Hz, 1H), 4.83 (s, 2H); 19F NMR (400 MHz, DMSO-d6): δ ppm −113.027 HPLC: RT=8.429 min, 98.528% (Method G); RT=8.139 min, 99.387% (Method H).

Example 322

Preparation of 1-(4-(1H-pyrrolo[2,3-b]pyridin-4-yl)phenyl)-3-(3-methoxybenzyl)-1H-imidazol-2(3H)-one

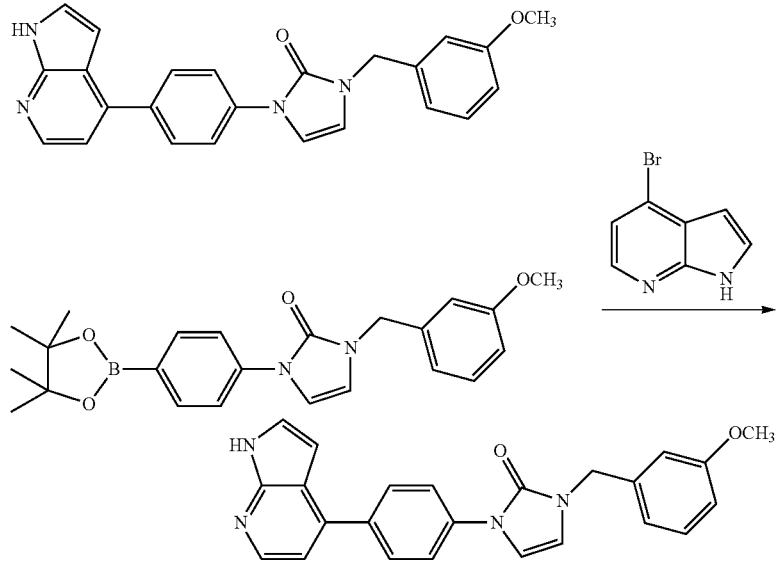

The mixture of 1-(3-methoxybenzyl)-3-(4-(4,4,5,5-tetramethyl-1,3,2-dioxaborolan-2-yl)phenyl)-1H-imidazol-2(3H)-one (0.1 g, 0.246 mmol), 4-bromo-1H-pyrrolo[2,3-b]pyridine (0.097 g, 0.492 mmol) and K$_2$CO$_3$ (0.102 g, 0.738 mmol) in 1,4-dioxane (5 mL) and water (1 mL) was degassed by purging N$_2$ gas. To the reaction mixture, was added 1,1'-bis(diphenylphosphino)ferrocene-palladium(II) dichloride dichloromethane complex (0.020 g, 0.025 mmol), and the reaction mixture was heated at 90° C. for 16 h. The reaction mixture was cooled to rt, filtered through CELITE®, and the filtrate was diluted with ethyl acetate. The organic phase was washed with water followed by brine, dried over sodium sulfate and concentrated. The product was purified by preparative HPLC to afford 1-(4-(1H-pyrrolo[2,3-b]pyridin-4-yl)phenyl)-3-(3-methoxybenzyl)-1H-imidazol-2(3H)-one (11.5 mg, 11% yield) as an off-white solid. m/z: 397.2; $^1$H NMR (400 MHz, DMSO-d$_6$) δ=11.81 (br. s., 1H), 8.33-8.26 (m, 1H), 7.98-7.92 (m, 2H), 7.89-7.82 (m, 2H), 7.60-7.51 (m, 1H), 7.29 (t, J=8.0 Hz, 1H), 7.23-7.15 (m, 2H), 6.93-6.84 (m, 4H), 6.64 (dd, J=3.5, 2.0 Hz, 1H), 4.80 (s, 2H), 3.75 (s, 3H); HPLC: RT: 6.886 min, 96.232% (Method G); RT: 7.616 min, 96.274 (Method H).

Examples 323 and 324

1-(4-(1H-Pyrazol-4-yl)phenyl)-3-(2-hydroxy-1-(3-methoxyphenyl)ethyl)-1H-imidazol-2(3H)-one (Enantiomers 1 and 2)

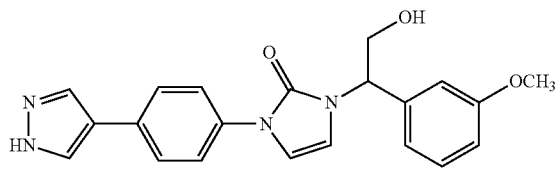 [SMILES: COc1cccc(C(CO)n2ccn(-c3ccc(-c4cn[nH]c4)cc3)c2=O)c1]

Example 323A: Preparation of methyl 2-(3-(4-bromophenyl)-2-oxo-2,3-dihydro-1H-imidazol-1-yl)-2-(3-methoxyphenyl)acetate

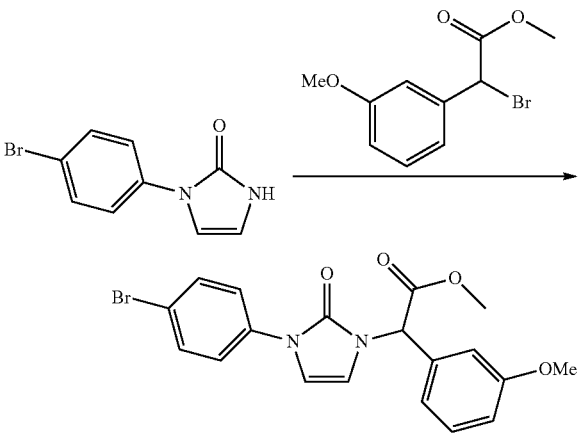

To a mixture of 1-(4-bromophenyl)-1H-imidazol-2(3H)-one (2.5 g, 10.46 mmol) and K$_2$CO$_3$ (3.61 g, 26.1 mmol) in acetonitrile (50 mL), was added methyl 2-bromo-2-(3-methoxyphenyl)acetate (3.25 g, 12.55 mmol) and the reaction mixture was heated at 70° C. for 16 h. The reaction mixture was filtered through CELITE®, and the filtrate was concentrated in vacuo. The residue obtained was extracted with ethyl acetate, washed with water followed by brine, dried over anhydrous sodium sulfate and concentrated. The crude product was purified using flash instrument (18% ethyl acetate in petroleum ether) to afford methyl 2-(3-(4-bromophenyl)-2-oxo-2,3-dihydro-1H-imidazol-1-yl)-2-(3- methoxyphenyl)acetate (1.9 g, 39% yield) as a brown pasty mass. MS(ESI) m/z: 417.0 (M+H)⁺.

Example 323B: Preparation of 1-(4-bromophenyl)-3-(2-hydroxy-1-(3-methoxyphenyl) ethyl)-1H-imidazol-2(3H)-one

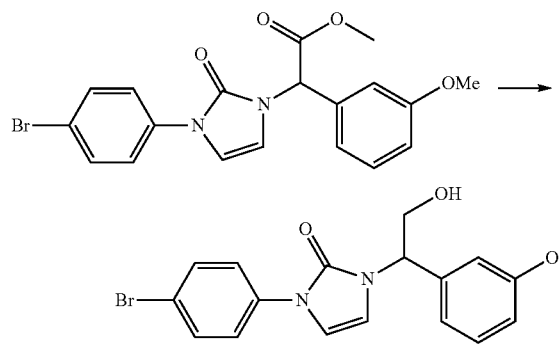

To a mixture of methyl 2-(3-(4-bromophenyl)-2-oxo-2,3-dihydro-1H-imidazol-1-yl)-2-(3-methoxyphenyl)acetate (750 mg, 1.797 mmol) in THF (5 mL) at −10° C., was added LAH (1.797 mL, 1.797 mmol) very slowly. The reaction mixture was allowed to warm to rt and was stirred for 16 h. The reaction mixture was cooled to 0° C. and quenched with aq. 10% NaOH solution. The reaction mixture was extracted with ethyl acetate. The combined organic layers were washed with water followed by brine, dried over sodium sulfate, and concentrated. The crude product was purified using flash chromatography (16% ethyl acetate in petroleum ether) to afford 1-(4-bromophenyl)-3-(2-hydroxy-1-(3-methoxyphenyl)ethyl)-1H-imidazol-2(3H)-one (560 mg, 80% yield) as an off-white semi-solid. MS(ESI) m/z: 391.0 (M+H)2⁺; ¹H NMR (400 MHz, DMSO-d₆) δ=7.79-7.70 (m, 2H), 7.66-7.58 (m, 2H), 7.26 (t, J=8.1 Hz, 1H), 7.10 (dd, J=17.9, 3.2 Hz, 2H), 6.92-6.82 (m, 3H), 5.21-5.09 (m, 2H), 4.09-3.97 (m, 1H), 3.93-3.82 (m, 1H), 3.74 (s, 3H).

Examples 323 and 324 (Enantiomer 1 and Enantiomer 2)

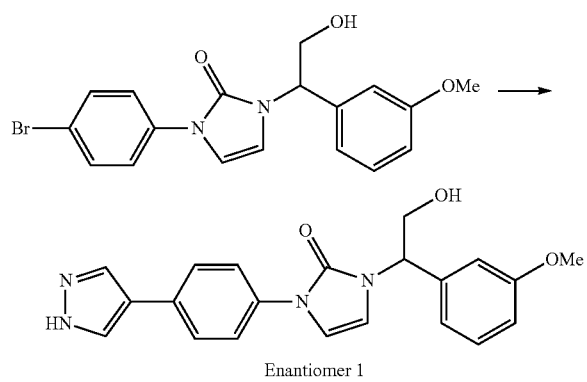

Enantiomer 1

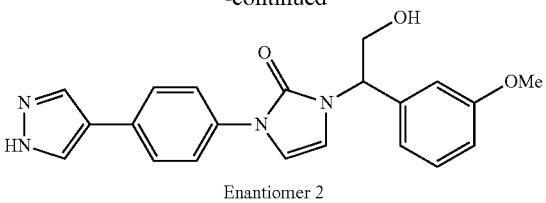

Enantiomer 2

The mixture of 1-(4-bromophenyl)-3-(2-hydroxy-1-(3-methoxyphenyl)ethyl)-1H-imidazol-2(3H)-one (100 mg, 0.257 mmol), tert-butyl 4-(4,4,5,5-tetramethyl-1,3,2-dioxaborolan-2-yl)-1H-pyrazole-1-carboxylate (91 mg, 0.308 mmol) and potassium phosphate tribasic (164 mg, 0.771 mmol) in 1,4-dioxane (5 mL) and water (0.5 mL) was degassed by purging with N₂ gas for 10 min. 2nd generation XPhos precatalyst (10.11 mg, 0.013 mmol) was added, and the reaction mixture was heated at 70° C. for 2 h. The reaction mixture was cooled to rt, filtered through CELITE®, and the filtrate was diluted with ethyl acetate. The organic phase was washed with water followed by brine and concentrated. The product was dissolved in DCM (5 mL), cooled to 0° C., and treated with trifluoroacetic acid (1 mL). The mixture was stirred well at rt temperature for 3 h. The reaction mixture was concentrated to give the crude product, which was purified by preparative HPLC to afford the racemic product. The enantiomers were separated by SFC [Column: WHELK-O® 1 (R,R) (250×4.6) mm, 5 Co-solvent is 40% (0.2% DEA in methanol) to afford Example 323 (Enantiomer 1; 12 mg, 0.031 mmol, 12% yield) as an off-white solid and Example 324 (Enantiomer 2; 15 mg, 0.040 mmol, 15% yield) as an off-white solid. MS(ESI) m/z: 377.2; ¹H NMR (400 MHz, DMSO-d₆) δ ppm=12.93 (br. s., 1H), 8.20 (br. s., 1H), 7.93 (br. s., 1H), 7.74-7.63 (m, 4H), 7.28 (t, J=8.0 Hz, 1H), 7.14-7.08 (m, 1H), 7.07-7.02 (m, 1H), 6.93-6.84 (m, 3H), 5.23-5.11 (m, 2H), 4.10-3.99 (m, 1H), 3.96-3.86 (m, 1H), 3.75 (s, 3H); HPLC: RT: 6.803 min, 96.495% (Method G); RT: 7.001 min, 95.867% (Method H); Chiral purity: 100% ee (RT 5.87), determined by chiral SFC analysis column: WHELK-O® 1 (R,R) (250×4.6) mm, 5μ, Mobile Phase: 40% (0.2% DEA in methanol); SOR: [α]²⁵·¹_D=−92 (c 0.05, DMSO.

Examples 325 and 326

1-(4-(1H-Pyrrolo[2,3-b]pyridin-4-yl)phenyl)-3-(1-(3-methoxyphenyl)ethyl)-1H-imidazol-2(3H)-one (Enantiomers 1 and 2)

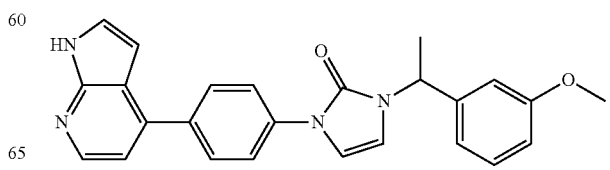

Example 325A: Preparation of 1-(4-bromophenyl)-3-(1-(3-methoxyphenyl)ethyl)-1H-imidazol-2(3H)-one

Example 325B: Preparation of 1-(1-(3-methoxyphenyl)ethyl)-3-(4-(4,4,5,5-tetramethyl-1,3,2-dioxaborolan-2-yl)phenyl)-1H-imidazol-2(3H)-one

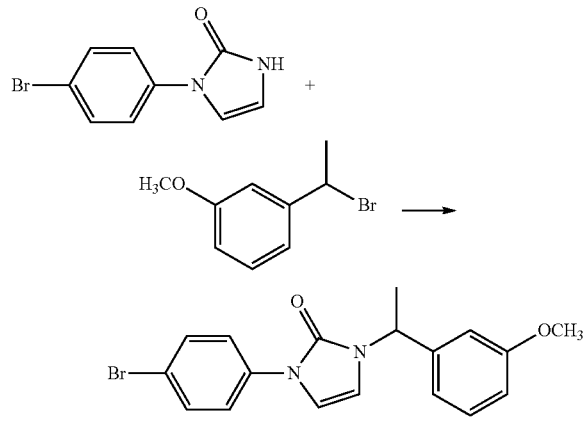

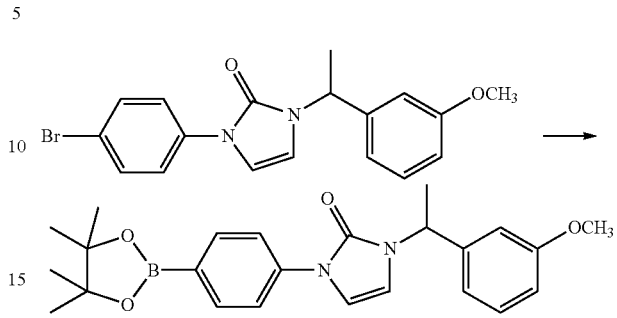

To a mixture of 1-(4-bromophenyl)-1H-imidazol-2(3H)-one (1.25 g, 5.23 mmol) in DMF (30 mL) at 0° C., was added sodium hydride (0.376 g, 15.69 mmol). The mixture was stirred at rt for 10 min, then was cooled to 0° C. 1-(1-Bromoethyl)-3-methoxybenzene (2.249 g, 10.46 mmol) was added to the mixture, which was then heated at 60° C. for 16 h. The reaction mixture was cooled to rt and quenched with ice and diluted with ethyl acetate. The organic layer was separated and washed with water followed by brine, dried over anhydrous sodium sulfate and concentrated in vacuo to get the crude product, which was purified by flash chromatography (2% MeOH in CHCl$_3$) to afford 1-(4-bromophenyl)-3-(1-(3-methoxyphenyl)ethyl)-1H-imidazol-2(3H)-one (1.3 g, 3.48 mmol, 66.6% yield) as an off-white semi-solid. MS(ESI) m/z: 375.0; $^1$H NMR (400 MHz, DMSO-d$_6$) δ ppm=7.77-7.71 (m, 2H), 7.65-7.59 (m, 2H), 7.30-7.25 (m, 1H), 7.13 (d, J=3.5 Hz, 1H), 7.01 (d, J=3.5 Hz, 1H), 6.93-6.84 (m, 3H), 5.32 (q, J=7.2 Hz, 1H), 3.77-3.72 (m, 3H), 1.67 (d, J=7.5 Hz, 3H).

A mixture of 1-(4-bromophenyl)-3-(1-(3-methoxyphenyl)ethyl)-1H-imidazol-2(3H)-one (150 mg, 0.402 mmol), bis(pinacolato)diboron (204 mg, 0.804 mmol) and potassium acetate (118 mg, 1.21 mmol) in 1,4-dioxane (5 mL) was degassed well by purging with N$_2$ gas. 1,1'-Bis(diphenylphosphino)ferrocene-palladium(II)dichloride dichloromethane complex (32.8 mg, 0.040 mmol) was added and the mixture was heated at 100° C. for 16 h. The reaction mixture was cooled to rt, filtered through CELITE®, diluted with ethyl acetate and washed with water followed by brine and concentrated. The crude product was purified flash chromatography (20% ethyl acetate in petroleum ether) to afford 1-(1-(3-methoxyphenyl)ethyl)-3-(4-(4,4,5,5-tetramethyl-1,3,2-dioxaborolan-2-yl)phenyl)-1H-imidazol-2(3H)-one (180 mg, 0.377 mmol, 94% yield) as an off-white semi-solid. MS(ESI) m/z: 421.2 (M+H)$^+$.

Examples 325 and 326

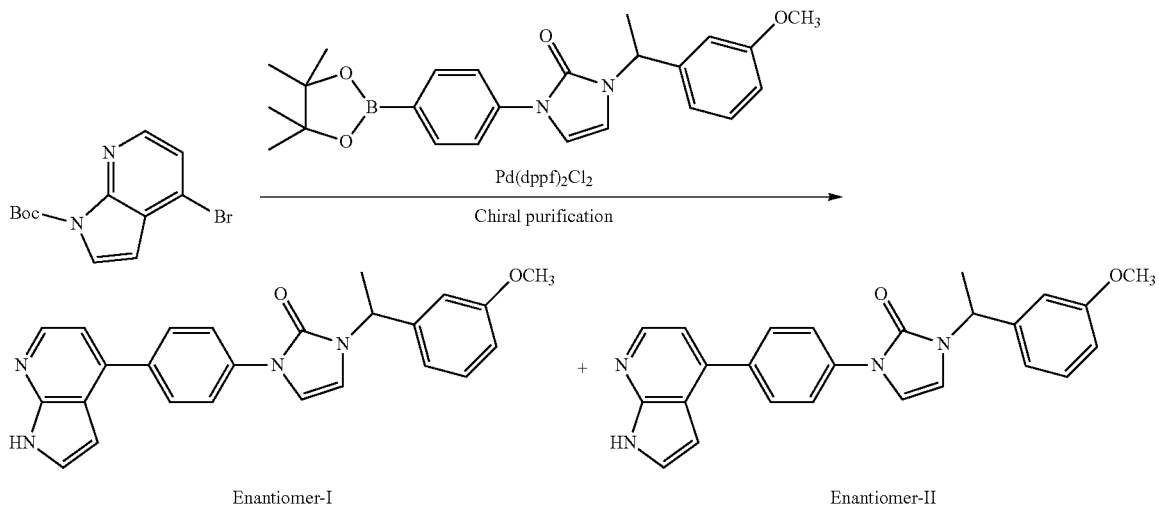

Enantiomer-I + Enantiomer-II

The mixture of tert-butyl 4-bromo-1H-pyrrolo[2,3-b]pyridine-1-carboxylate (100 mg, 0.337 mmol) and 1-(1-(3-methoxyphenyl)ethyl)-3-(4-(4,4,5,5-tetramethyl-1,3,2-dioxaborolan-2-yl)phenyl)-1H-imidazol-2(3H)-one (170 mg, 0.404 mmol) and K$_2$CO$_3$ (140 mg, 1.010 mmol) in 1,4-dioxane (5 mL) and water (0.5 mL) was degassed by purging N$_2$ gas. 1,1'-Bis(diphenylphosphino)ferrocene-palladium(II) dichloride dichloromethane complex (13.74 mg, 0.017 mmol) was added and the mixture was heated at 90° C. for 16 h. The reaction mixture was filtered through CELITE®, and the filtrate was diluted with ethyl acetate. The organic phase was washed with water followed by brine and concentrated. The crude product was purified by preparative HPLC to afford the racemate compound as an off-white solid. This enantiomers were separated by SFC using column CHIRALPAK® AS-H (250×21) mm, 5 Co-solvent in 20% methanol to afford Example 325 (Enantiomer 1, 17 mg, 0.041 mmol, 12.25% yield) as an off-white solid. MS(ESI) m/z: 411.2; $^1$H NMR (400 MHz, DMSO-d$_6$) δ ppm=11.80 (br. s., 1H), 8.29 (d, J=5.0 Hz, 1H), 8.00-7.91 (m, 2H), 7.89-7.81 (m, 2H), 7.60-7.51 (m, 1H), 7.29 (t, J=8.0 Hz, 1H), 7.21 (t, J=4.3 Hz, 2H), 7.04 (d, J=3.0 Hz, 1H), 6.97-6.83 (m, 3H), 6.64 (dd, J=3.5, 1.5 Hz, 1H), 5.36 (q, J=7.4 Hz, 1H), 3.76 (s, 3H), 1.70 (d, J=7.0 Hz, 3H); HPLC: RT: 7.236 min, 99.887% (Method G); RT: 8.408 min, 99.526% (Method H); Chiral purity: 100% ee (RT 11.88 min), determined by chiral SFC analysis column: CHIRALPAK® OJ-H (250×4.6) mm, 5 t, Mobile Phase: 20% (0.2% DEA in methanol); SOR: $[α]^{25.1}_D$=−164 (c 0.05, MeOH), and to afford Example 326 (Enantiomer 2, 10 mg, 0.024 mmol, 7.15% yield) as an off-white solid. MS(ESI) m/z: 411.2; $^1$H NMR (400 MHz, DMSO-d$_6$) δ ppm 11.85 (s, 1H), 8.29 (d, J=5.0 Hz, 1H), 7.97-7.92 (m, 2H), 7.88-7.83 (m, 2H), 7.56 (d, J=3.5 Hz, 1H), 7.30 (t, J=8.0 Hz, 1H), 7.23-7.19 (m, 2H), 7.04 (d, J=3.0 Hz, 1H), 6.95-6.90 (m, 2H), 6.87 (d, J=9.0 Hz, 1H), 6.64 (d, J=3.5 Hz, 1H), 5.41-5.31 (m, 1H), 3.76 (s, 3H), 1.70 (d, J=7.5 Hz, 3H); HPLC: RT: 7.224 min, 99.390% (Method G); RT: 7.893 min, 98.767% (Method H); Chiral purity: 98.1366% ee (RT 13.27 min), determined by chiral SFC analysis column: CHIRALPAK® OJ-H (250×4.6) mm, 5μ, Mobile Phase: 20% (0.2% DEA in methanol); SOR; $[α]^{25.3}_D$=+152 (c 0.05, MeOH).

Example 327

Preparation of 1-(4-(2-fluoropyridin-4-yl)phenyl)-3-(1-(3-methoxyphenyl)ethyl)-1H-imidazol-2(3H)-one (Enantiomer 1)

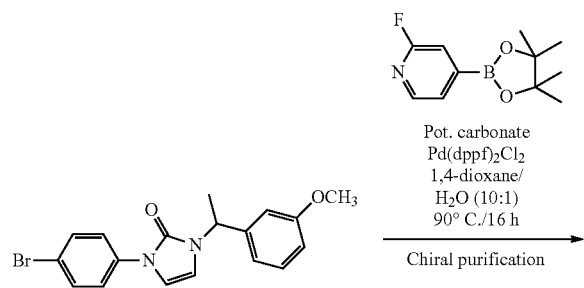

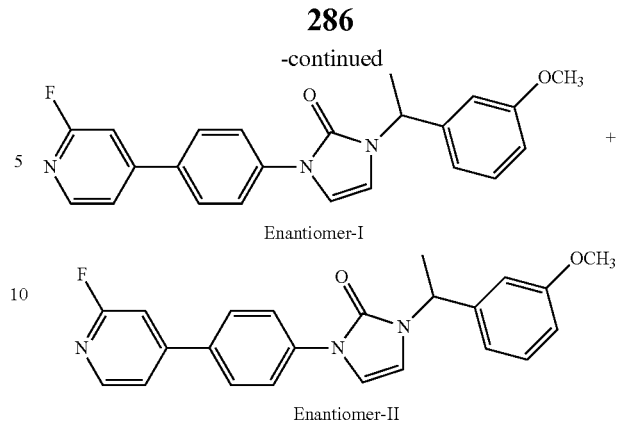

A mixture of 2-fluoro-4-(4,4,5,5-tetramethyl-1,3,2-dioxaborolan-2-yl)pyridine (134 mg, 0.603 mmol), 1-(4-bromophenyl)-3-(1-(3-methoxyphenyl)ethyl)-1H-imidazol-2 (3H)-one (150 mg, 0.402 mmol) and K$_2$CO$_3$ (167 mg, 1.206 mmol) in 1,4-dioxane (5 mL) and water (0.5 mL) was degassed well by purging with N$_2$ gas. 1,1′-Bis(diphenylphosphino)ferrocene-palladium(II)dichloride dichloromethane complex (16.41 mg, 0.020 mmol) was added and the mixture was heated at 90° C. for 16 h. The reaction mixture was cooled, filtered through CELITE®, and the filtrate was diluted with ethyl acetate. The organic phase was washed with water followed by brine and concentrated in vacuo. The crude product was purified by preparative HPLC to afford the racemic product as an off-white solid. The enantiomers were separated by SFC purification [Column CHIRALPAK® AS-H (250×21) mm, 5 Co-solvent is 20% methanol] to afford Example 327 (Enantiomer I) (14 mg, 0.035 mmol, 9% yield) as a pale brown gummy solid. MS(ESI) m/z: 390.2; $^1$H NMR (400 MHz, DMSO-d$_6$) δ ppm=8.30 (d, J=5.5 Hz, 1H), 8.01-7.93 (m, 4H), 7.75 (d, J=5.5 Hz, 1H), 7.58 (s, 1H), 7.32-7.23 (m, 2H), 7.06 (d, J=3.0 Hz, 1H), 6.94-6.90 (m, 2H), 6.89-6.84 (m, 1H), 5.35 (q, J=7.0 Hz, 1H), 3.76 (s, 3H), 1.69 (d, J=7.0 Hz, 3H); $^{19}$F NMR (400 MHz, DMSO-d$_6$): δ ppm −68.776; HPLC: RT: 16.330 min, 98.275% (Method G); RT: 16.435 min, 98.394% (Method H); Chiral purity: 100% ee (rt=4.34 min), determined by chiral SFC analysis column: CHIRALPAK® AS-H (250× 4.6) mm, 5 t, Mobile Phase: 20% (0.2% DEA in methanol); SOR: $[α]^{25.1}_D$=+176.800 (c 0.05, MeOH).

The following Examples in Table 15 were made by using the same procedure as shown in Examples 321 to 327.

TABLE 15

| Ex. | R | Name | LCMS (M + H)$^+$ | HPLC Method, RT (min.) and Purity | NMR |
|---|---|---|---|---|---|
| 330 | ![pyrazolyl-phenyl-fluorophenyl R group] | 1-(4-(1H-pyrazol-4-yl)phenyl)-3-(2-fluorophenethyl)-1H-imidazol-2(3H)-one | 349.2 | I: 8.689, 98.837% J: 8.320, 96.684% | $^1$H NMR (400 MHz, DMSO-d$_6$) δ = 13.03-12.88 (m, 1H), 8.19 (br. s., 1H), 7.95 (br. s., 1H), 7.70-7.62 (m, 4H), 7.35-7.24 (m, 2H), 7.20-7.09 (m, 2H), 7.00 (d, J = 3.5 Hz, 1H), 6.68 (d, J = 3.0 Hz, 1H), 3.84 (t, J = 7.3 Hz, 2H), 3.00 (t, J = 7.0 Hz, 2H). |

TABLE 15-continued

| Ex. | R | Name | LCMS (M + H)+ | HPLC Method, RT (min.) and Purity | NMR |
|---|---|---|---|---|---|
| 331 | | 1-(4-(1H-pyrazol-4-yl)phenyl)-3-(1-phenylethyl)-1H-imidazol-2(3H)-one | 331.2 | A: 5.941, 99.839% B: 8.468, 99.874% | $^1$H NMR (400 MHz, DMSO-$d_6$) δ = 12.90 (br. s., 1H), 8.07 (s, 2H), 7.73-7.61 (m, 4H), 7.40-7.24 (m, 5H), 7.11 (d, J = 3.0 Hz, 1H), 6.97 (d, J = 3.0 Hz, 1H), 5.36 (q, J = 7.4 Hz, 1H), 1.68 (d, J = 7.0 Hz, 3H). |
| 332 | | 1-(4-(1H-pyrazol-4-yl)phenyl)-3-(1-phenylethyl)-1H-imidazol-2(3H)-one | 333.2 | A: 5.929, 99.916% B: 8.470, 98.637% | $^1$H NMR (400 MHz, DMSO-$d_6$) δ = 12.95 (br. s., 1H), 8.18 (br. s., 1H), 7.94 (br. s., 1H), 7.72-7.62 (m, 4H), 7.41-7.31 (m, 3H), 7.31-7.24 (m, 2H), 7.11 (d, J = 3.5 Hz, 1H), 6.97 (d, J = 3.0 Hz, 1H), 5.36 (q, J = 7.4 Hz, 1H), 1.68 (d, J = 7.0 Hz, 3H). |
| 333 | | 1-(4-(1H-pyrazol-4-yl)phenyl)-3-(3-(difluoromethoxy)benzyl)-1H-imidazol-2(3H)-one | 383.2 | I: 8.863, 99.613% J: 8.584, 99.795% | $^1$H NMR (400 MHz, DMSO-$d_6$) δ = 12.94 (br. s., 1H), 8.21 (br. s., 1H), 7.94 (br. s., 1H), 7.74-7.64 (m, 4H), 7.46-7.38 (m, 1H), 7.25-7.03 (m, 5H), 6.84 (d, J = 3.0 Hz, 1H), 4.83 (s, 2H) |
| 334 | | 1-(4-(1H-pyrazol-4-yl)phenyl)-3-(3-methoxybenzyl)-1H-imidazol-2(3H)-one | 347.2 | I: 8.258, 99.060% J: 7.994, 98.801% | $^1$H NMR (400 MHz, DMSO-$d_6$) δ = 12.94 (br. s., 1H), 8.21 (br. s., 1H), 7.94 (br. s., 1H), 7.69 (q, J = 8.5 Hz, 4H), 7.28 (t, J = 7.8 Hz, 1H), 7.08 (d, J = 3.0 Hz, 1H), 6.93-6.84 (m, 3H), 6.81 (d, J = 3.0 Hz, 1H), 4.77 (s, 2H), 3.74 (s, 3H). |
| 335 | | 1-(4-(1H-pyrazol-4-yl)phenyl)-3-phenethyl-1H-imidazol-2(3H)-one | 331.2 | I: 13.121, 98.106% J: 12.254, 98.071% | $^1$H NMR (400 MHz, DMSO-$d_6$) δ = 13.02 (s, 1H), 8.06 (br. s., 2H), 7.72-7.60 (m, 4H), 7.35-7.18 (m, 5H), 7.01 (d, J = 3.4 Hz, 1H), 6.71 (d, J = 3.0 Hz, 1H), 3.90-3.70 (m, 2H), 2.96 (t, J = 7.4 Hz, 2H). |
| 336 | | 1-(4-(1H-pyrazol-4-yl)phenyl)-3-(3-fluoro-5-methoxybenzyl)-1H-imidazol-2(3H)-one | 365.2 | A: 8.684, 95.691% B: 8.379, 97.645% | $^1$H NMR (400 MHz, DMSO-$d_6$) δ = 12.95 (br. s., 1H), 8.21 (br. s., 1H), 7.94 (br. s., 1H), 7.75-7.62 (m, 4H), 7.09 (br. s., 1H), 6.84 (br. s., 1H), 6.80-6.65 (m, 3H), 4.77 (s, 2H), 3.76 (s, 3H). |

TABLE 15-continued

| Ex. | R | Name | LCMS (M + H)+ | HPLC Method, RT (min.) and Purity | NMR |
|---|---|---|---|---|---|
| 337 | 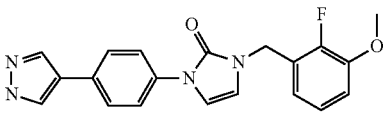 | 1-(4-(1H-pyrazol-4-yl)phenyl)-3-(2-fluoro-3-methoxybenzyl)-1H-imidazol-2(3H)-one | 365.2 | A: 12.629, 97.171% B: 11.809, 97.244% | 1H NMR (400 MHz, DMSO-d6) δ = 12.94 (br. s., 1H), 8.21 (br. s., 1H), 7.94 (br. s., 1H), 7.77-7.60 (m, 4H), 7.18-7.05 (m, 3H), 6.84-6.77 (m, 1H), 6.75 (d, J = 3.0 Hz, 1H), 4.85 (s, 2H), 3.84 (s, 3H). |
| 338 | 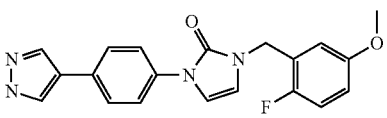 | 1-(4-(1H-pyrazol-4-yl)phenyl)-3-(2-fluoro-5-methoxybenzyl)-1H-imidazol-2(3H)-one | 365.2 | A: 13.186, 96.057% B: 12.317, 96.233% | 1H NMR (400 MHz, DMSO-d6): δ = 12.98 (br. s., 1H), 8.07 (br. s., 2H), 7.73-7.61 (m, 4H), 7.17 (t, J = 9.3 Hz, 1H), 7.09 (d, J = 3.0 Hz, 1H), 6.95-6.87 (m, 1H), 6.82 (dd, J = 3.0, 6.0 Hz, 1H), 6.76 (d, J = 3.0 Hz, 1H), 4.82 (s, 2H), 3.72 (s, 3H). |
| 339 | 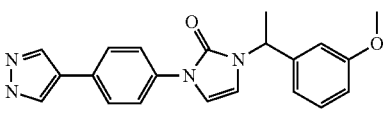 | 1-(4-(1H-pyrazol-4-yl)phenyl)-3-(1-(3-methoxyphenyl)ethyl)-1H-imidazol-2(3H)-one (Enantiomer I) | 361 | I: 8.695, 99.750% J: 8.348, 99.071% | 1H NMR (400 MHz, DMSO-d6) δ = 12.94 (br. s., 1H), 8.20 (br. s., 1H), 7.94 (br. s., 1H), 7.73-7.61 (m, 4H), 7.28 (t, J = 8.0 Hz, 1H), 7.10 (d, J = 3.0 Hz, 1H), 6.99 (d, J = 3.5 Hz, 1H), 6.94-6.82 (m, 3H), 5.32 (q, J = 7.0 Hz, 1H), 3.81-3.67 (m, 3H), 1.67 (d, J = 7.5 Hz, 3H). |
| 340 | 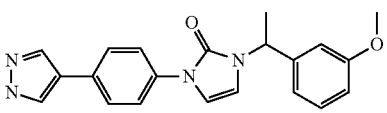 | 1-(4-(1H-pyrazol-4-yl)phenyl)-3-(l-(3-methoxyphenyl)ethyl)-1H-imidazol-2(3H)-one (Enantiomer II) | 361.2 | I: 8.693, 97.855% J: 8.337, 97.478% | 1H NMR (400 MHz, DMSO-d6) δ = 12.94 (br. s., 1H), 8.09 (br. s., 2H), 7.74-7.60 (m, 4H), 7.28 (t, J = 8.0 Hz, 1H), 7.10 (d, J = 3.0 Hz, 1H), 6.99 (d, J = 3.5 Hz, 1H), 6.94-6.82 (m, 3H), 5.32 (q, J = 7.0 Hz, 1H), 3.79-3.71 (m, 3H), 1.67 (d, J = 7.5 Hz, 3H). |
| 342 | 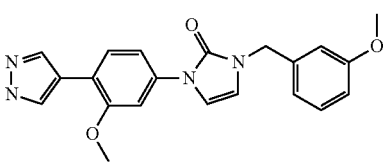 | 1-(3-methoxy-4-(1H-pyrazol-4-yl)phenyl)-3-(3-methoxybenzyl)-1H-imidazol-2(3H)-one | 376.9 | I: 8.368, 99.413% J: 7.765, 97.795% | 1H NMR (400 MHz, DMSO-d6) δ ppm = 12.87 (br. s., 1H), 8.12 (br. s., 1H), 7.96 (br. s., 1H), 7.66 (d, J = 8.3 Hz, 1H), 7.51 (d, J = 2.0 Hz, 1H), 7.34-7.23 (m, 2H), 7.14 (d, J = 3.0 Hz, 1H), 6.92-6.84 (m, 3H), 6.82 (d, J = 3.0 Hz, 1H), 4.77 (s, 2H), 3.90 (s, 3H), 3.75 (s, 3H) |

TABLE 15-continued

| Ex. | R | Name | LCMS (M + H)+ | HPLC Method, RT (min.) and Purity | NMR |
|---|---|---|---|---|---|
| 343 | | 1-(3-fluoro-5-methoxybenzyl)-3-(3-methoxy-4-(1H-pyrazol-4-yl)phenyl)-1H-imidazol-2(3H)-one | 394.9 | I: 8.759, 98.819% J: 8.723, 99.150% | $^1$H NMR (400 MHz, DMSO-$d_6$) δ ppm = 12.86 (br. s., 1H), 8.11 (br. s., 1H), 7.97 (br. s., 1H), 7.66 (d, J = 8.3 Hz, 1H), 7.50 (d, J = 2.0 Hz, 1H), 7.31 (dd, J = 8.5, 2.0 Hz, 1H), 7.16 (d, J = 3.3 Hz, 1H), 6.85 (d, J = 3.0 Hz, 1H), 6.81-6.64 (m, 3H), 4.78 (s, 2H), 3.96-3.85 (m, 3H), 3.83-3.68 (m, 3H) |
| 344 | | 1-(5-(1H-pyrazol-4-yl)pyridin-2-yl)-3-(3-methoxybenzyl)-1H-imidazol-2(3H)-one | 348.1 | F: 1.575, 98.974% E: 1.524, 99.001% | $^1$H NMR (400 MHz, DMSO-$d_6$) δ ppm = 13.31 (br. s., 1H), 8.97 (dd, J = 2.4, 0.7 Hz, 1H), 8.63-8.52 (m, 2H), 8.39 (dd, J = 8.6, 2.4 Hz, 1H), 8.27 (s, 1H), 7.60 (d, J = 3.2 Hz, 1H), 7.57-7.50 (m, 1H), 7.19-7.07 (m, 4H), 5.05 (s, 2H), 4.01 (s, 3H) |
| 345 | | 1-(5-(1H-pyrazol-4-yl)pyridin-2-yl)-3-(3-fluoro-5-methoxybenzyl)-1H-imidazol-2(3H)-one | 366.1 | F: 1.658, 98.753% E: 1.607, 99.528% | $^1$H NMR (400 MHz, DMSO-$d_6$) δ ppm = 13.31 (br. s., 1H), 8.98 (dd, J = 2.3, 0.9 Hz, 1H), 8.62-8.52 (m, 2H), 8.39 (dd, J = 8.6, 2.4 Hz, 1H), 8.28 (br. s., 1H), 7.61 (d, J = 3.2 Hz, 1H), 7.13 (d, J = 3.2 Hz, 1H), 7.07-6.93 (m, 3H), 5.06 (s, 2H), 4.06-3.97 (m, 3H) |
| 346 | | 1-(5-(1H-pyrazol-4-yl)pyridin-2-yl)-3-(4-fluoro-3-methoxybenzyl)-1H-imidazol-2(3H)-one | 366.1 | F: 1.594, 97.968% E: 1.544, 99.392% | $^1$H NMR (400 MHz, DMSO-$d_6$) δ ppm = 13.32 (br. s., 1H), 8.97 (dd, J = 2.4, 0.7 Hz, 1H), 8.60 (dd, J = 8.6, 0.7 Hz, 3H), 8.39 (dd, J = 8.6, 2.4 Hz, 1H), 7.60 (d, J = 3.2 Hz, 1H), 7.49-7.40 (m, 2H), 7.17-7.03 (m, 2H), 5.05 (s, 2H), 4.15-4.04 (m, 3H). |

TABLE 15-continued

| Ex. | R | Name | LCMS (M + H)+ | HPLC Method, RT (min.) and Purity | NMR |
|---|---|---|---|---|---|
| 347 | | 1-(5-(1H-pyrazol-4-yl)pyridin-2-yl)-3-(3-(cyclopropylmethoxy)benzyl)-1H-imidazol-2(3H)-one | 388.1 | F: 1.931, 95.954% E: 1.883, 95.288% | $^1$H NMR (400 MHz, DMSO-d$_6$) δ ppm = 13.31 (br. s., 1H), 8.98 (dd, J = 2.4, 0.7 Hz, 1H), 8.62-8.53 (m, 2H), 8.40 (dd, J = 8.8, 2.4 Hz, 1H), 8.28 (br. s., 1H), 7.60 d, J = 3.2 Hz, 1H), 7.56-7.48 (m, 1H), 7.18-7.05 (m, 4H), 5.04 (s, 2H), 4.10-4.01 (m, 2H), 1.53-1.38 (m, 1H), 0.86-0.71 (m, 2H), 0.63-0.51 (m, 2H) |
| 348 | | 1-(3-ethyl-4-(1H-pyrazol-4-yl)phenyl)-3-(4-fluoro-3-methoxybenzyl)-1H-imidazol-2(3H)-one | 393.2 | F: 1.787, 99.896% E: 1.840, 99.639% | $^1$H NMR (400 MHz, DMSO-d$_6$) δ ppm = 12.97 (br. s., 1H), 7.78 (br. s., 2H), 7.63 (d, J = 2.4 Hz, 1H), 7.55 (dd, J = 8.6, 2.4 Hz, 1H), 7.36 (d, J = 8.3 Hz, 1H), 7.22-7.15 (m, 2H), 7.07 (d, J = 3.2 Hz, 1H), 6.90-6.78 (m, 2H), 4.76 (s, 2H), 3.83 (s, 3H), 2.72 (q, J = 7.6 Hz, 2H), 1.14 (t, J = 7.6 Hz, 3H) |
| 351 | | 2-(3-(5-(1H-pyrazol-4-yl)pyridin-2-yl)-2-oxo-2,3-dihydro-1H-imidazol-1-yl)-2-(3-methoxyphenyl)acetic acid | 392.2 | I: 7.785, 93.799% J: 6.976, 93.888% | $^1$H NMR (400 MHz, DMSO-d$_6$) δ ppm = 13.28 (br. s., 1H), 8.73 (d, J = 2.5 Hz, 1H), 8.32 (s, 1H), 8.26-8.08 (m, 3H), 7.44-7.34 (m, 1H), 7.30 (d, J = 3.0 Hz, 1H), 7.09-6.93 (m, 3H), 6.59 (d, J = 3.5 Hz, 1H), 5.87 (s, 1H), 3.78 (s, 3H) |
| 352 | | 2-(3-(3-methoxy-4-(1H-pyrazol-4-yl)phenyl)-2-oxo-2,3-dihydro-1H-imidazol-1-yl)-2-(3-methoxyphenyl)acetic acid | 397.1 | I: 8.742, 96.204% J: 9.635, 98.965% | $^1$H NMR (400 MHz, DMSO-d$_6$) δ ppm = 8.05 (s, 2H), 7.67 (d, J = 8.0 Hz, 1H), 7.50 (d, J = 2.5 Hz, 1H), 7.42-7.35 (m, 1H), 7.31 (dd, J = 8.3, 2.3 Hz, 1H), 7.12 (d, J = 3.5 Hz, 1H), 7.04-6.97 (m, 3H), 6.60 (d, J = 3.5 Hz, 1H), 5.86 (s, 1H), 3.91 (s, 3H), 3.79 (s, 3H) |

TABLE 15-continued

| Ex. | R | Name | LCMS (M + H)+ | HPLC Method, RT (min.) and Purity | NMR |
|---|---|---|---|---|---|
| 353 | | 1-(3-ethyl-4-(1H-pyrazol-4-yl)phenyl)-3-(1-(3-methoxyphenyl)ethyl)-1H-imidazol-2(3H)-one (Enantiomer I) | 389.2 | I: 9.250, 98.784% J: 9.042, 98.080% | $^1$H NMR (400 MHz, DMSO-$d_6$) δ ppm = 12.95 (br. s., 1H), 7.90 (br. s., 1H), 7.64 (d, J = 2.0 Hz, 2H), 7.54 (dd, J = 8.3, 2.3 Hz, 1H), 7.35 (d, J = 8.0 Hz, 1H), 7.30-7.24 (m, 1H), 7.10 (d, J = 3.5 Hz, 1H), 6.98 (d, J = 3.0 Hz, 1H), 6.93-6.88 (m, 2H), 6.88-6.83 (m, 1H), 5.32 (q, J = 7.2 Hz, 1H), 3.75 (s, 3H), 2.75-2.65 (m, 2H), 1.67 (d, J = 7.0 Hz, 3H), 1.14 (t, J = 7.5 Hz, 3H) |
| 354 | | 1-(5-(1H-pyrazol-4-yl)pyridin-2-yl)-3-(1-(3-methoxyphenyl)ethyl)-1H-imidazol-2(3H)-one (Enantiomer I) | 362.2 | I: 8.737, 99.772% J: 8.163, 99.648% | $^1$H NMR (400 MHz, DMSO-$d_6$) δ ppm = 13.06 (br. s., 1H), 8.72 (d, J = 1.5 Hz, 1H), 8.35-8.27 (m, 2H), 8.13 (dd, J = 8.5, 2.5 Hz, 1H), 8.02 (s, 1H), 7.36 (d, J = 3.0 Hz, 1H), 7.29 (t, J = 8.3 Hz, 1H), 7.01 (d, J = 3.5 Hz, 1H), 6.94-6.90 (m, 2H), 6.87 (d, J = 9.5 Hz, 1H), 5.38-5.31 (m, 1H), 3.76 (s, 3H), 1.69 (d, J = 7.0 Hz, 3H) |
| 355 | | 1-(5-(1H-pyrazol-4-yl)pyridin-2-yl)-3-(1-(3-methoxyphenyl)ethyl)-1H-imidazol-2(3H)-one (Enantiomer II) | 362.2 | I: 8.902, 96.677% J: 8.171, 97.782% | 13.05 (br. s., 1H), 8.71 (d, J = 2.5 Hz, 1H), 8.32 (d, J = 9.0 Hz, 2H), 8.13 (dd, J = 8.5, 2.5 Hz, 1H), 8.02 (br. s., 1H), 7.36 (s, 1H), 7.29 (t, J = 8.0 Hz, 1H), 7.01 (d, J = 3.5 Hz, 1H), 6.94-6.90 (m, 2H), 6.87 (d, J = 9.5 Hz, 1H), 5.35 (d, J = 7.5 Hz, 1H), 3.76 (s, 3H), 1.69 (d, J = 7.0 Hz, 3H) |

TABLE 15-continued

| Ex. | R | Name | LCMS (M + H)+ | HPLC Method, RT (min.) and Purity | NMR |
|---|---|---|---|---|---|
| 356 | 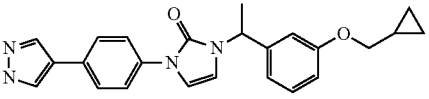 | 1-(4-(1H-pyrazol-4-yl)phenyl)-3-(1-(3-(cyclopropylmethoxy)phenyl)ethyl)-1H-imidazol-2(3H)-one (Enantiomer I) | 401.2 | I: 9.794, 99.726% J: 8.634, 99.213% | $^1$H NMR (400 MHz, DMSO-$d_6$) δ ppm = 12.93 (br. s., 1H), 8.20 (s, 1H), 7.94 (s, 1H), 7.68 (q, J = 9.0 Hz, 4H), 7.26 (t, J = 8.0 Hz, 1H), 7.10 (d, J = 3.0 Hz, 1H), 6.99 (d, J = 3.5 Hz, 1H), 6.91-6.86 (m, 2H), 6.86-6.80 (m, 1H), 5.31 (d, J = 7.0 Hz, 1H), 3.81 (d, J = 7.0 Hz, 2H), 1.67 (d, J = 7.0 Hz, 3H), 1.21 (s, 1H), 0.60-0.53 (m, 2H), 0.35- 0.29 (m, 2H) |
| 357 | 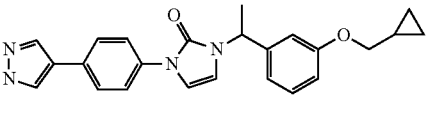 | 1-(4-(1H-pyrazol-4-yl)phenyl)-3-(1-(3-(cyclopropylmethoxy)phenyl)ethyl)-1H-imidazol-2(3H)-one (Enantiomer II) | 401.2 | I: 9.791, 99.635% J: 8.633, 98.979% | $^1$H NMR (400 MHz, DMSO-$d_6$) δ ppm = 12.93 (br. s., 1H), 8.21 (s, 1H), 7.94 (s, 1H), 7.73-7.62 (m, 4H), 7.26 (t, J = 8.0 Hz, 1H), 7.10 (d, J = 3.0 Hz, 1H), 6.99 (d, J = 3.5 Hz, 1H), 6.92-6.86 (m, 2H), 6.86-6.81 (m, 1H), 5.35-5.27 (m, 1H), 3.81 (d, J = 6.5 Hz, 2H), 1.67 (d, J = 7.0 Hz, 3H), 1.24-1.19 (m, 1H), 0.60-0.53 (m, 2H), 0.35-0.28 (m, 2H) |
| 358 | 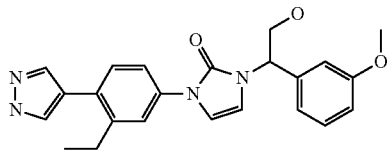 | 1-(3-ethyl-4-(1H-pyrazol-4-yl)phenyl)-3-(2-hydroxy-1-(3-methoxyphenyl)ethyl)-1H-imidazol-2(3H)-one (Enantiomer I) | 405.3 | I: 8.412, 98.314% J: 7.423, 99.039% | $^1$H NMR (400 MHz, DMSO-$d_6$) δ ppm = 12.97 (br. s., 1H), 7.90 (s, 1H), 7.65 (d, J = 2.0 Hz, 2H), 7.57-7.52 (m, 1H), 7.35 (d, J = 8.5 Hz, 1H), 7.31-7.24 (m, 1H), 7.11 (d, J = 3.5 Hz, 1H), 7.05 (d, J = 3.0 Hz, 1H), 6.92-6.84 (m, 3H), 5.22-5.11 (m, 2H), 4.04 (ddd, J = 11.5, 9.0, 6.0 Hz, 1H), 3.89 (dt, J = 11.4, 5.1 Hz, 1H), 3.75 (s, 3H), 2.75-2.66 (m, 2H), 1.14 (t, J = 7.5 Hz, 3H). |

TABLE 15-continued

| Ex. | R | Name | LCMS (M + H)+ | HPLC Method, RT (min.) and Purity | NMR |
|---|---|---|---|---|---|
| 359 | | 1-(3-ethyl-4-(1H-pyrazol-4-yl)phenyl)-3-(2-hydroxy-1-(3-methoxyphenyl)ethyl)-1H-imidazol-2(3H)-one (Enantiomer II) | 405.3 | I: 7.576, 98.298% J: 6.811, 98.270% | 1H NMR (400 MHz, DMSO-d6) δ ppm = 13.02-12.91 (m, 1H), 7.90 (br. s., 1H), 7.65 (d, J = 2.0 Hz, 2H), 7.55 (dd, J = 8.5, 2.5 Hz, 1H), 7.36 (d, J = 8.5 Hz, 1H), 7.32-7.25 (m, 1H), 7.11 (d, J = 3.0 Hz, 1H), 7.05 (d, J = 3.0 Hz, 1H), 6.94-6.84 (m, 3H), 5.19 (dd, J = 8.8, 5.3 Hz, 1H), 5.14 (t, J = 5.5 Hz, 1H), 4.05 (ddd, J = 11.5, 9.0, 6.0 Hz, 1H), 3.95-3.87 (m, 1H), 3.75 (s, 3H), 2.76-2.67 (m, 2H), 1.20-1.12 (m, 3H). |
| 360 | | 1-(2-hydroxy-1-(3-methoxyphenyl)ethyl)-3-(3-methoxy-4-(1H-pyrazol-4-yl)phenyl)-1H-imidazol-2(3H)-one (Enantiomer I) | 407.2 | I: 6.968, 99.605% J: 6.311, 99.543% | 1H NMR (400 MHz, DMSO-d6) δ ppm = 12.88 (br. s., 1H), 8.12 (s, 1H), 7.96 (s, 1H), 7.65 (d, J = 8.5 Hz, 1H), 7.51 (d, J = 2.0 Hz, 1H), 7.32-7.24 (m, 2H), 7.17 (d, J = 3.5 Hz, 1H), 7.07 (d, J = 3.5 Hz, 1H), 6.92-6.84 (m, 3H), 5.19 (dd, J = 9.0, 5.0 Hz, 1H), 5.16-5.10 (m, 1H), 4.04 (ddd, J = 11.5, 9.0, 6.0 Hz, 1H), 3.93-3.85 (m, 4H), 3.75 (s, 3H) |
| 361 | | 1-(2-hydroxy-1-(3-methoxyphenyl)ethyl)-3-(3-methoxy-4-(1H-pyrazol-4-yl)phenyl)-1H-imidazol-2(3H)-one (Enantiomer I) | 407.2 | I: 7.401, 97.346% J: 7.156, 98.081% | 1H NMR (400 MHz, DMSO-d6) δ ppm = 12.88 (br. s., 1H), 8.12 (br. s., 1H), 7.96 (br. s., 1H), 7.65 (d, J = 8.0 Hz, 1H), 7.51 (d, J = 2.0 Hz, 1H), 7.33-7.24 (m, 2H), 7.17 (d, J = 3.0 Hz, 1H), 7.09-7.05 (m, 1H), 6.93-6.84 (m, 3H), 5.19 (dd, J = 9.0, 5.0 Hz, 1H), 5.14 (t, J = 5.5 Hz, 1H), 4.04 (ddd, J = 11.4, 8.9, 5.8 Hz, 1H), 3.93-3.84 (m, 4H), 3.77-3.72 (m, 3H). |

TABLE 15-continued

| Ex. | R | Name | LCMS (M + H)+ | HPLC Method, RT (min.) and Purity | NMR |
|---|---|---|---|---|---|
| 362 | | 1-(6-ethyl-5-(1H-pyrazol-4-yl)pyridin-2-yl)-3-(1-(3-fluoro-5-methoxyphenyl)ethyl)-1H-imidazol-2(3H)-one (Enantiomer I) | 408.2 | I: 15.405, 99.440% J: 15.575, 99.607% | $^1$H NMR (400 MHz, DMSO-d$_6$) δ ppm = 13.07 (br. s., 1H), 8.15 (d, J = 8.0 Hz, 1H), 7.85 (d, J = 8.5 Hz, 3H), 7.43 (d, J = 3.5 Hz, 1H), 7.04 (d, J = 3.5 Hz, 1H), 6.81-6.72 (m, 3H), 5.35 (q, J = 7.0 Hz, 1H), 3.77 (s, 3H), 2.88 (q, J = 7.5 Hz, 2H), 1.69 (d, J = 7.0 Hz, 3H), 1.29-1.21 (m, 3H) |
| 363 | | 1-(6-ethyl-5-(1H-pyrazol-4-yl)pyridin-2-yl)-3-(1-(3-fluoro-5-methoxyphenyl)ethyl)-1H-imidazol-2(3H)-one (Enantiomer II) | 408.2 | I: 15.395, 99.658% J: 15.577, 99.478% | $^1$H NMR (400 MHz, DMSO-d$_6$) δ ppm = 13.07 (br. s., 1H), 8.14 (d, J = 8.5 Hz, 1H), 7.93-7.81 (m, 3H), 7.42 (d, J = 3.0 Hz, 1H), 7.03 (d, J = 3.5 Hz, 1H), 6.80-6.71 (m, 3H), 5.34 (q, J = 7.4 Hz, 1H), 3.76 (s, 3H), 2.87 (q, J = 7.5 Hz, 2H), 1.68 (d, J = 7.5 Hz, 3H), 1.24 (t, J = 7.5 Hz, 3H). |
| 364 | | 1-(1-(3-ethoxyphenyl)ethyl)-3-(6-ethyl-5-(1H-pyrazol-4-yl)pyridin-2-yl)-1H-imidazol-2(3H)-one (Enantiomer I) | 404.2 | I: 16.977, 98.509% J: 16.019, 98.299% | $^1$H NMR (400 MHz, DMSO-d$_6$) δ ppm = 13.07 (br. s., 1H), 8.16 (d, J = 8.5 Hz, 1H), 8.00 (br. s., 1H), 7.85 (d, J = 8.0 Hz, 1H), 7.75 (br. s., 1H), 7.41 (d, J = 3.5 Hz, 1H), 7.30-7.22 (m, 1H), 6.99 (d, J = 3.0 Hz, 1H), 6.93-6.81 (m, 3H), 5.40-5.28 (m, 1H), 4.06-3.96 (m, 2H), 2.88 (q, J = 7.5 Hz, 2H), 1.69 (d, J = 7.0 Hz, 3H), 1.32 (t, J = 7.0 Hz, 3H), 1.24 (t, J = 7.3 Hz, 3H). |
| 365 | | 1-(1-(3-ethoxyphenyl)ethyl)-3-(6-ethyl-5-(1H-pyrazol-4-yl)pyridin-2-yl)-1H-imidazol-2(3H)-one (Enantiomer II) | 404.2 | I: 10.871, 99.114% J: 7.177, 99.348% | $^1$H NMR (400 MHz, DMSO-d$_6$) δ ppm = 13.07 (br. s., 1H), 8.16 (d, J = 8.5 Hz, 1H), 8.00 (br. s., 1H), 7.85 (d, J = 8.5 Hz, 1H), 7.74 (br. s., 1H), 7.41 (d, J = 3.0 Hz, 1H), 7.31-7.22 (m, 1H), 6.99 (d, J = 3.0 Hz, 1H), 6.93-6.81 (m, 3H), 5.34 (q, J = 7.4 Hz, 1H), 4.02 (q, J = 7.0 Hz, 2H), 2.88 (q, J = 7.5 Hz, 2H), 1.74-1.62 (m, 3H), 1.32 (t, J = 6.8 Hz, 3H), 1.28-1.19 (m, 3H). |

TABLE 15-continued

| Ex. | R | Name | LCMS (M + H)+ | HPLC Method, RT (min.) and Purity | NMR |
|---|---|---|---|---|---|
| 366 | | 1-(4-(1H-pyrazol-4-yl)phenyl)-3-(1-(3-fluoro-5-methoxyphenyl)ethyl)-1H-imidazol-2(3H)-one (Enantiomer I) | 379.2 | I: 9.537, 97.567% J: 8.809, 99.061% | ¹H NMR (400 MHz, DMSO-d₆) δ ppm = 12.94 (br. s., 1H), 8.21 (s, 1H), 7.94 (br. s., 1H), 7.74-7.62 (m, 4H), 7.12 (d, J = 3.0 Hz, 1H), 7.02 (d, J = 3.5 Hz, 1H), 6.79-6.70 (m, 3H), 5.37-5.24 (m, 1H), 3.77 (s, 3H), 1.67 (d, J = 7.0 Hz, 3H). |
| 367 | | 1-(4-(1H-pyrazol-4-yl)phenyl)-3-(1-(3-fluoro-5-methoxyphenyl)ethyl)-1H-imidazol-2(3H)-one (Enantiomer II) | 379.2 | I: 8.957, 97.715% J: 8.629, 97.344% | ¹H NMR (400 MHz, DMSO-d₆) δ ppm = 12.94 (br. s., 1H), 8.20 (br. s., 1H), 7.95 (br. s., 1H), 7.76-7.62 (m, 4H), 7.12 (d, J = 3.0 Hz, 1H), 7.02 (d, J = 3.0 Hz, 1H), 6.81-6.70 (m, 3H), 5.32 (q, J = 7.4 Hz, 1H), 3.77 (s, 3H), 1.67 (d, J = 7.5 Hz, 3H). |
| 368 | | 1-(4-(1H-pyrazol-4-yl)phenyl)-3-(1-(3-ethoxyphenyl)ethyl)-1H-imidazol-2(3H)-one (Enantiomer I) | 375.2 | I: 8.416, 98.643% J: 9.176, 99.101% | ¹H NMR (400 MHz, DMSO-d₆) δ ppm = 12.93 (br. s., 1H), 8.21 (br. s., 1H), 7.94 (br. s., 1H), 7.73-7.64 (m, 4H), 7.27 (t, J = 8.0 Hz, 1H), 7.10 (d, J = 3.0 Hz, 1H), 6.98 (d, J = 3.0 Hz, 1H), 6.92-6.82 (m, 3H), 5.32 (q, J = 7.0 Hz, 1H), 4.02 (q, J = 7.0 Hz, 2H), 1.67 (d, J = 7.0 Hz, 3H), 1.32 (t, J = 7.0 Hz, 3H). |
| 369 | | 1-(4-(1H-pyrazol-4-yl)phenyl)-3-(1-(3-ethoxyphenyl)ethyl)-1H-imidazol-2(3H)-one (Enantiomer II) | 375.2 | I: 9.490, 99.430% J: 9.178, 99.694% | ¹H NMR (400 MHz, DMSO-d₆) δ ppm = 12.93 (br. s., 1H), 8.20 (br. s., 1H), 7.93 (br. s., 1H), 7.72-7.62 (m, 4H), 7.29-7.22 (m, 1H), 7.09 (d, J = 3.0 Hz, 1H), 6.98 (d, J = 3.0 Hz, 1H), 6.91-6.81 (m, 3H), 5.31 (q, J = 7.2 Hz, 1H), 4.01 (q, J = 7.0 Hz, 2H), 1.67 (d, J = 7.5 Hz, 3H), 1.31 (t, J = 6.8 Hz, 3H). |

TABLE 15-continued

| Ex. | R | Name | LCMS (M + H)+ | HPLC Method, RT (min.) and Purity | NMR |
|---|---|---|---|---|---|
| 370 | | 1-(5-(1H-pyrazol-4-yl)pyridin-2-yl)-3-(1-(3-ethoxyphenyl)ethyl)-1H-imidazol-2(3H)-one (Enantiomer I) | 376.2 | I: 9.962, 99.563% J: 8.929, 99.232% | $^1$H NMR (400 MHz, DMSO-$d_6$) δ ppm = 13.05 (br. s., 1H), 8.71 (dd, J = 2.5, 1.0 Hz, 1H), 8.33-8.28 (m, 2H), 8.12 (dd, J = 8.5, 2.5 Hz, 1H), 8.01 (br. s., 1H), 7.35245 (d, J = 3.5 Hz, 1H), 7.29-7.23 (m, 1H), 7.00 (d, J = 3.0 Hz, 1H), 6.92-6.82 (m, 3H), 5.33 (d, J = 7.0 Hz, 1H), 4.04-3.97 (m, 2H), 1.68 (d, J = 7.5 Hz, 3H), 1.31 (t, J = 7.0 Hz, 3H). |
| 371 | | 1-(5-(1H-pyrazol-4-yl)pyridin-2-yl)-3-(1-(3-ethoxyphenyl)ethyl)-1H-imidazol-2(3H)-one (Enantiomer II) | 376.2 | I: 9.642, 99.644% J: 8.931, 99.725% | $^1$H NMR (400 MHz, DMSO-$d_6$) δ ppm = 13.06 (br. s., 1H), 8.73-8.69 (m, 1H), 8.34-8.08 (m, 4H), 7.36 (d, J = 3.0 Hz, 1H), 7.30-7.23 (m, 1H), 7.01 (d, J = 3.0 Hz, 1H), 6.94-6.81 (m, 3H), 5.34 (q, J = 7.0 Hz, 1H), 4.02 (q, J = 7.0 Hz, 2H), 1.69 (d, J = 7.0 Hz, 3H), 1.32 (t, J = 7.0 Hz, 3H) |
| 372 | | 1-(1-(3-(cyclopropylmethoxy)phenyl)ethyl)-3-(6-ethyl-5-(1H-pyrazol-4-yl)pyridin-2-yl)-1H-imidazol-2(3H)-one (Enantiomer I) | 430.2 | I: 11.337, 98.214% J: 10.258, 98.557% | $^1$H NMR (400 MHz, DMSO-$d_6$) δ ppm = 13.07 (s, 1H), 8.16 (d, J = 8.5 Hz, 1H), 8.01 (br. s., 1H), 7.85 (d, J = 8.5 Hz, 1H), 7.74 (br. s., 1H), 7.41 (d, J = 3.0 Hz, 1H), 7.29-7.22 (m, 1H), 7.00 (d, J = 3.5 Hz, 1H), 6.92-6.87 (m, 2H), 6.86-6.81 (m, 1H), 5.34 (q, J = 7.4 Hz, 1H), 3.81 (d, J = 7.0 Hz, 2H), 2.88 (q, J = 7.4 Hz, 2H), 1.68 (d, J = 7.0 Hz, 3H), 1.27-1.16 (m, 4H), 0.59-0.52 (m, 2H), 0.34-0.28 (m, 2H). |

TABLE 15-continued

| Ex. | R | Name | LCMS (M + H)+ | HPLC Method, RT (min.) and Purity | NMR |
|---|---|---|---|---|---|
| 373 | | 1-(2-fluoro-5-methoxybenzyl)-3-(6-methoxy-5-(1H-pyrazol-4-yl)pyridin-2-yl)-1H-imidazol-2(3H)-one | 396.1 | E: 1.805, 99.465% F: 1.762, 99.622% | ¹H NMR (400 MHz, DMSO-d₆) δ ppm = 12.95 (br. s., 1H), 8.14 (d, J = 8.1 Hz, 2H), 8.01 (br. s., 1H), 7.91 (d, J = 7.8 Hz, 1H), 7.40 (d, J = 2.9 Hz, 1H), 7.17 (t, J = 9.2 Hz, 1H), 6.96-6.88 (m, 1H), 6.84 (dd, J = 6.0, 3.1 Hz, 1H), 6.79 (d, J = 2.9 Hz, 1H), 4.84 (s, 2H), 4.02 (s, 3H), 3.72 (s, 3H). |
| 374 | | 1-(5-fluoro-2-methoxybenzyl)-3-(6-methoxy-5-(1H-pyrazol-4-yl)pyridin-2-yl)-1H-imidazol-2(3H)-one | 396.1 | E: 1.819, 97.573% F: 1.790, 97.666% | ¹H NMR (400 MHz, DMSO-d₆) δ ppm = 12.97 (br. s., 1H), 8.14 (d, J = 8.1 Hz, 2H), 8.11-7.98 (m, 1H), 7.91 (d, J = 8.1 Hz, 1H), 7.40 (d, J = 2.9 Hz, 1H), 7.13 (td, J = 8.7, 2.9 Hz, 1H), 7.09-7.02 (m, 1H), 6.86 (dd, J = 8.7, 2.8 Hz, 1H), 6.77 (d, J = 2.9 Hz, 1H), 4.77 (s, 2H), 4.02 (s, 3H), 3.83 (s, 3H). |
| 375 | | 1-(2,3-difluorobenzyl)-3-(6-methoxy-5-(1H-pyrazol-4-yl)pyridin-2-yl)-1H-imidazol-2(3H)-one | 384.1 | E: 1.819, 99.723% F: 1.774, 99.678% | ¹H NMR (400 MHz, DMSO-d₆) δ ppm = 12.97 (br. s., 1H), 8.22-8.11 (m, 2H), 8.00 (br. s., 1H), 7.90 (d, J = 7.8 Hz, 1H), 7.47-7.35 (m, 2H), 7.28-7.18 (m, 1H), 7.17-7.07 (m, 1H), 6.84 (d, J = 3.2 Hz, 1H), 4.94 (s, 2H), 4.02 (s, 3H). |
| 376 | | 1-(6-methoxy-5-(1H-pyrazol-4-yl)pyridin-2-yl)-3-(3-methoxybenzyl)-1H-imidazol-2(3H)-one | 378.2 | E: 1.490, 99.628% F: 1.546, 98.624% | ¹H NMR (400 MHz, DMSO-d₆) δ ppm = 12.97 (br. s., 1H), 8.17-7.97 (m, 3H), 7.93 (d, J = 8.1 Hz, 1H), 7.39 (d, J = 2.9 Hz, 1H), 7.28 (t, J = 7.8 Hz, 1H), 6.91-6.81 (m, 4H), 4.79 (s, 2H), 4.02 (s, 3H), 3.74 (s, 3H). |

TABLE 15-continued

| Ex. | R | Name | LCMS (M + H)+ | HPLC Method, RT (min.) and Purity | NMR |
|---|---|---|---|---|---|
| 377 | | 1-(3-(cyclopropylmethoxy)-4-fluorobenzyl)-3-(6-methoxy-5-(1H-pyrazol-4-yl)pyridin-2-yl)-1H-imidazol-2(3H)-one | 436.1 | E: 2.046, 99.629% F: 2.022, 99.515% | $^1$H NMR (400 MHz, DMSO-$d_6$) δ ppm = 12.97 (br. s., 1H), 8.14 (d, J = 8.1 Hz, 2H), 8.01 (br. s.,1 H), 7.92 (d, J = 8.1 Hz, 1H), 7.38 (d, J = 2.9 Hz, 1H), 7.22-7.13 (m, 2H), 6.88-6.82 (m, 2H), 4.76 (s, 2H), 4.01 (s, 3H), 3.89 (d, J = 7.1 Hz, 2H), 1.29-1.17 (m, 1H), 0.61-0.53 (m, 2H), 0.36-0.29 (m, 2H). |
| 378 | | 1-(3-(cyclopropylmethoxy)benzyl)-3-(6-methoxy-5-(1H-pyrazol-4-yl)pyridin-2-yl)-1H-imidazol-2(3H)-one | 418.1 | E: 2.048, 99.632% F: 2.013, 100% | $^1$H NMR (400 MHz, DMSO-$d_6$) δ ppm = 12.97 (br. s., 1H), 8.20-8.08 (m, 2H), 8.01 (br. s., 1H), 7.93 (d, J = 8.1 Hz, 1H), 7.39 (d, J = 3.2 Hz, 1H), 7.26 (t, J = 7.8 Hz, 1H), 6.92-6.79 (m, 4H), 4.77 (s, 2H), 4.02 (s, 3H), 3.87-3.73 (m, 2H), 1.28-1.12 (m, 1H), 0.61-0.46 (m, 2H), 0.38-0.19 (m, 2H). |
| 380 | | 1-(3-fluoro-2-methylbenzyl)-3-(6-methoxy-5-(1H-pyrazol-4-yl)pyridin-2-yl)-1H-imidazol-2(3H)-one | 380.1 | E: 1.939, 95.974% F: 1.985, 96.663% | $^1$H NMR (400 MHz, DMSO-$d_6$) δ ppm = = 12.97 (br. s., 1H), 8.20-8.12 (m, 2H), 8.00 (s, 1H), 7.93 (d, J = 8.1 Hz, 1H), 7.42 (d, J = 3.2 Hz, 1H), 7.27-7.19 (m, 1H), 7.10 (s, 1H), 6.96 (d, J = 7.6 Hz, 1H), 6.73 (d, J = 3.2 Hz, 1H), 4.86 (s, 2H), 4.02 (s, 3H), 2.24 (d, J = 1.7 Hz, 3H). |
| 381 | | 1-(4-fluoro-2-methylbenzyl)-3-(6-methoxy-5-(1H-pyrazol-4-yl)pyridin-2-yl)-1H-imidazol-2(3H)-one | 380.2 | E: 1.931, 99.650% F: 1.977, 98.993% | $^1$H NMR (400 MHz, DMSO-$d_6$) δ ppm = = 13.14-12.80 (m, 1H), 8.15 (d, J = 8.1 Hz, 1H), 8.09 (br. s., 2H), 7.93 (d, J = 8.1 Hz, 1H), 7.45-7.37 (m, 1H), 7.17 (dd, J = 8.4, 6.0 Hz, 1H), 7.09 (dd, J = 9.8, 2.7 Hz, 1H), 7.05-6.98 (m, 1H), 6.70 (d, J = 3.2 Hz, 1H), 4.84-4.75 (m, 2H), 4.06-3.99 (m, 3H), 2.34 (s, 3H). |

TABLE 15-continued

| Ex. | R | Name | LCMS (M + H)+ | HPLC Method, RT (min.) and Purity | NMR |
|---|---|---|---|---|---|
| 382 | | 1-(5-fluoro-2-methylbenzyl)-3-(6-methoxy-5-(1H-pyrazol-4-yl)pyridin-2-yl)-1H-imidazol-2(3H)-one | 380.1 | E: 1.925, 100% F: 1.972, 99.791% | ¹H NMR (400 MHz, DMSO-d₆) δ ppm = = 13.11-12.76 (m, 1H), 8.15 (d, J = 8.1 Hz, 2H), 8.01 (br. s., 1H), 7.93 (d, J = 8.1 Hz, 1H), 7.44 (d, J = 3.2 Hz, 1H), 7.26 (dd, J = 8.3, 6.1 Hz, 1H), 7.05 (td, J = 8.5, 2.8 Hz, 1H), 6.89 (dd, J = 9.9, 2.6 Hz, 1H), 6.77 (d, J = 3.2 Hz, 1H), 4.85-4.79 (m, 2H), 4.03 (s, 3H), 2.30 (s, 3H). |
| 383 | | 1-(4-fluoro-2-methoxybenzyl)-3-(6-methoxy-5-(1H-pyrazol-4-yl)pyridin-2-yl)-1H-imidazol-2(3H)-one | 396.1 | E: 1.882, 100% F: 1.933, 99.374% | ¹H NMR (400 MHz, DMSO-d₆) δ ppm = = 12.96 (br. s., 1H), 8.16 (s, 1H), 8.13 (d, J = 8.1 Hz, 1H), 8.00 (br. s., 1H), 7.91 (d, J = 8.3 Hz, 1H), 7.37 (d, J = 3.2 Hz, 1H), 7.12 (dd, J = 8.3, 6.8 Hz, 1H), 6.96 (dd, J = 11.4, 2.6 Hz, 1H), 6.79-6.69 (m, 2H), 4.73 (s, 2H), 4.02 (s, 3H), 3.86 (s, 3H). |
| 387 | | 1-(4-(3-fluoropyridin-4-yl)phenyl)-3-(1-(3-methoxyphenyl)ethyl)-1H-imidazol-2(3H)-one (Enantiomer I) | 390.2 | I: 8.451, 99.624% J: 9.247, 99.749% | ¹H NMR (400 MHz, DMSO-d₆) δ ppm = 8.67 (d, J = 3.0 Hz, 1H), 8.51 (d, J = 4.5 Hz, 1H), 7.95 (d, J = 9.0 Hz, 2H), 7.77 (d, J = 7.5 Hz, 2H), 7.68 (dd, J = 7.0, 5.0 Hz, 1H), 7.29 (t, J = 8.0 Hz, 1H), 7.22 (d, J = 3.5 Hz, 1H), 7.05 (d, J = 3.5 Hz, 1H), 6.95-6.89 (m, 2H), 6.89-6.84 (m, 1H), 5.35 (q, J = 7.2 Hz, 1H), 3.76 (s, 3H), 1.69 (d, J = 7.0 Hz, 3H). |
| 388 | | 1-(6-ethyl-5-(1H-pyrazol-4-yl)pyridin-2-yl)-3-(1-(4-fluoro-3-methoxyphenyl)ethyl)-1H-imidazol-2(3H)-one (Enantiomer 1) | 408.2 | I: 8.943, 99.480% J: 9.526, 99.846% | ¹H NMR (400 MHz, DMSO-d₆) δ ppm = 13.07 (s, 1H), 8.15 (d, J = 8.5 Hz, 1H), 7.84 (d, J = 8.5 Hz, 3H), 7.40 (d, J = 3.5 Hz, 1H), 7.22-7.15 (m, 2H), 7.01 (d, J = 3.5 Hz, 1H), 6.89 (br. s., 1H), 5.36 (d, J = 7.0 Hz, 1H), 3.85 (s, 3H), 2.87 (q, J = 7.5 Hz, 2H), 1.69 (d, J = 7.0 Hz, 3H), 1.23 (t, J = 7.3 Hz, 3H). |

TABLE 15-continued

| Ex. | R | Name | LCMS (M + H)+ | HPLC Method, RT (min.) and Purity | NMR |
|---|---|---|---|---|---|
| 389 | | 1-(1-(4-fluoro-3-methoxyphenyl)ethyl)-3-(6-methoxy-5-(1H-pyrazol-4-yl)pyridin-2-yl)-1H-imidazol-2(3H)-one (Enantiomer I) | 410.2 | I: 8.769, 99.197% J: 9.272, 99.741% | $^1$H NMR (400 MHz, DMSO-d$_6$) δ ppm = 12.96 (br. s., 1H), 8.13 (d, J = 8.0 Hz, 1H), 8.08 (s, 2H), 7.90 (d, J = 8.0 Hz, 1H), 7.40 (d, J = 3.5 Hz, 1H), 7.22-7.15 (m, 2H) 7.02 (d, J = 3.0 Hz, 1H), 6.88 (ddd, J = 8.3, 4.3, 2.0 Hz, 1H), 5.36 (q, J = 7.2 Hz, 1H), 4.02 (s, 3H), 3.85 (s, 3H), 1.69 (d, J = 7.5 Hz, 3H). |
| 390 | | 1-(1-(4-fluoro-3-methoxyphenyl)ethyl)-3-(6-methoxy-5-(1H-pyrazol-4-yl)pyridin-2-yl)-1H-imidazol-2(3H)-one (Enantiomer II) | 410.2 | I: 8.765, 99.872% J: 9.243, 99.780% | $^1$H NMR (400 MHz, DMSO-d$_6$) δ ppm = 12.80 (s, 1H), 8.13 (d, J = 7.9 Hz, 1H), 8.08 (s, 2H), 7.90 (d, J = 8.3 Hz, 1H), 7.40 (d, J = 3.0 Hz, 1H), 7.23-7.13 (m, 2H), 7.02 (d, J = 3.4 Hz, 1H), 6.89 (br. s., 1H), 5.36 (d, J = 6.8 Hz, 1H), 4.02 (s, 3H), 3.85 (s, 3H), 1.69 (d, J = 7.2 Hz, 3H). |
| 391 | | 1-(4-(1H-pyrazol-4-yl)phenyl)-3-(1-(4-fluoro-3-methoxyphenyl)ethyl)-1H-imidazol-2(3H)-one (Enantiomer I) | 379.2 | I: 8.646, 97.517% J: 8.580, 97.712% | $^1$H NMR (400 MHz, DMSO-d$_6$) δ ppm = 12.99 (s, 1H) 8.07 (s, 2H), 7.72-7.63 (m, 4H), 7.21-7.15 (m, 2H), 7.10 (d, J = 3.5 Hz, 1H), 7.00 (d, J = 3.0 Hz, 1H), 6.88 (ddd, J = 8.4, 4.1, 2.5 Hz, 1H), 5.33 (q, J = 7.0 Hz, 1H), 3.85 (s, 3H), 1.68 (d, J = 7.5 Hz, 3H). |
| 392 | | 1-(4-(1H-pyrazol-4-yl)phenyl)-3-(1-(4-fluoro-3-methoxyphenyl)ethyl)-1H-imidazol-2(3H)-one (Enantiomer II) | 379.2 | I: 8.647, 99.803% J: 8.584, 99.810% | $^1$H NMR (400 MHz, DMSO-d$_6$) δ ppm = 12.94 (br. s., 1H), 8.20 (br. s., 1H), 7.93 (br. s., 1H), 7.71-7.61 (m, 4H), 7.22-7.14 (m, 2H), 7.10 (d, J = 3.5 Hz, 1H), 7.00 (d, J = 3.0 Hz, 1H), 6.90-6.84 (m, 1H), 5.37-5.29 (m, 1H), 3.85 (s, 3H), 1.68 (d, J = 7.5 Hz, 3H). |

TABLE 15-continued

| Ex. | R | Name | LCMS (M + H)+ | HPLC Method, RT (min.) and Purity | NMR |
|---|---|---|---|---|---|
| 393 | | 1-(5-(1H-pyrazol-4-yl)pyridin-2-yl)-3-(1-(3-fluoro-5-methoxyphenyl)ethyl)-1H-imidazol-2(3H)-one (Enantiomer I) | 380.2 | I: 9.032, 99.883% J: 8.701, 99.960% | $^1$H NMR (400 MHz, DMSO-d$_6$) δ ppm = 13.06 (br. s., 1H), 8.71 (s, 1H), 8.33-8.26 (m, 2H), 8.12 (d, J = 11.0 Hz, 1H), 8.01 (br. s., 1H), 7.37 (d, J = 3.0 Hz, 1H), 7.04 (d, J = 3.4 Hz, 1H), 6.80-6.72 (m, 3H), 5.33 (d, J = 7.2 Hz, 1H), 3.76 (s, 3H), 1.68 (d, J = 7.2 Hz, 3H). |
| 394 | | 1-(5-(1H-pyrazol-4-yl)pyridin-2-yl)-3-(1-(3-fluoro-5-methoxyphenyl)ethyl)-1H-imidazol-2(3H)-one (Enantiomer II) | 380.2 | I: 9.030, 99.460% J: 8.701, 99.848% | $^1$H NMR (400 MHz, DMSO-d$_6$) δ ppm = 13.00 (s, 1H), 8.71 (d, J = 1.5 Hz, 1H), 8.30 (d, J = 8.5 Hz, 1H), 8.18-8.09 (m, 3H), 7.37 (d, J = 3.5 Hz, 1H), 7.05 (d, J = 3.0 Hz, 1H), 6.79-6.72 (m, 3H), 5.33 (d, J = 7.0 Hz, 1H), 3.76 (s, 3H), 1.68 (d, J = 7.0 Hz, 3H). |
| 395 | | 1-(3-(cyclopropylmethoxy)-5-fluorobenzyl)-3-(6-methoxy-5-(1H-pyrazol-4-yl)pyridin-2-yl)-1H-imidazol-2(3H)-one | 436.2 | E: 1.969, 98.925% F: 2.062, 97.947% | $^1$H NMR (400 MHz, DMSO-d$_6$) δ ppm = 12.97 (br. s., 1H), 8.20-8.11 (m, 2H), 8.01 (s, 1H), 7.92 (d, J = 8.1 Hz, 1H), 7.41 (d, J = 3.2 Hz, 1H), 6.88 (d, J = 3.2 Hz, 1H), 6.77-6.65 (m, 3H), 4.78 (s, 2H), 4.02 (s, 3H), 3.81 (d, J = 7.1 Hz, 2H), 1.26-1.14 (m, 1H), 0.59-0.52 (m, 2H), 0.33-0.27 (m, 2H). |
| 396 | | 1-(4-(1H-pyrazol-4-yl)phenyl)-3-(3-(cyclopropylmethoxy)-5-fluorobenzyl-1H-imidazol-2(3H)-one | 405.2 | E: 1.735, 100% F: 1.801, 99.838% | $^1$H NMR (400 MHz, DMSO-d$_6$) δ ppm = 12.93 (br. s., 1H), 8.21 (br. s., 1H), 7.94 (br. s., 1H), 7.73-7.64 (m, 4H), 7.09 (d, J = 3.2 Hz, 1H), 6.84 (d, J = 3.2 Hz, 1H), 6.76-6.65 (m, 3H), 4.76 (s, 2H), 3.81 (d, J = 7.1 Hz, 2H), 1.26-1.14 (m, 1H), 0.59-0.52 (m, 2H), 0.34-0.28 (m, 2H). |

TABLE 15-continued

| Ex. | R | Name | LCMS (M + H)+ | HPLC Method, RT (min.) and Purity | NMR |
|---|---|---|---|---|---|
| 397 | | 1-(1-(3-fluoro-5-methoxyphenyl)ethyl)-3-(6-methoxy-5-(1H-pyrazol-4-yl)pyridin-2-yl)-1H-imidazol-2(3H)-one (Enantiomer I) | 410.2 | I: 10.268, 99.596% J: 9.501, 99.593% | $^1$H NMR (400 MHz, DMSO-$d_6$) δ ppm = 12.85 (s, 1H), 8.14 (d, J = 8.0 Hz, 1H), 8.09 (s, 2H), 7.90 (d, J = 8.0 Hz, 1H), 7.43 (d, J = 3.0 Hz, 1H), 7.05 (d, J = 3.5 Hz, 1H), 6.80-6.72 (m, 3H), 5.34 (q, J = 7.2 Hz, 1H), 4.03 (s, 3H), 3.77 (s, 3H), 1.68 (d, J = 7.0 Hz, 3H). |
| 398 | | 1-(1-(3-fluoro-5-methoxyphenyl)ethyl)-3-(6-methoxy-5-(1H-pyrazol-4-yl)pyridin-2-yl)-1H-imidazol-2(3H)-one (Enantiomer II) | 410.2 | I: 10.292, 97.917% J: 9.485, 99.281% | $^1$H NMR (400 MHz, DMSO-$d_6$) δ ppm = 12.99 (br. s., 1H), 8.14 (d, J = 8.5 Hz, 1H), 8.09 (br. s., 2H), 7.90 (d, J = 8.0 Hz, 1H), 7.43 (d, J = 3.0 Hz, 1H), 7.05 (d, J = 3.5 Hz, 1H), 6.80-6.73 (m, 3H), 5.34 (q, J = 7.2 Hz, 1H), 4.03 (s, 3H), 3.77 (s, 3H), 1.68 (d, J = 7.0 Hz, 3H). |
| 399 | | 1-(4-(2-aminopyrimidin-4-yl)phenyl)-3-(1-(3-methoxyphenyl)ethyl)-1H-imidazol-2(3H)-one (Enantiomer I) | 388.2 | I: 5.415, 99.474% J: 7.232, 99.531% | $^1$H NMR (400 MHz, DMSO-$d_6$) δ ppm = 8.31 (d, J = 5.0 Hz, 1H), 8.18-8.12 (m, 2H), 7.94-7.88 (m, 2H), 7.32-7.25 (m, 1H), 7.21 (d, J = 3.5 Hz, 1H), 7.15 (d, J = 5.0 Hz, 1H), 7.04 (d, J = 3.0 Hz, 1H), 6.94-6.89 (m, 2H), 6.89-6.84 (m, 1H), 6.65 (s, 2H), 5.34 (q, J = 7.2 Hz, 1H), 3.76 (s, 3H), 1.69 (d, J = 7.5 Hz, 3H). |
| 400 | | 1-(6-methoxy-5-(1H-pyrazol-4-yl)pyridin-2-yl)-3-(1-(3-methoxyphenyl)ethyl)-1H-imidazol-2(3H)-one (Enantiomer I) | 392.2 | I: 13.968, 99.914% J: 14.297, 99.876% | $^1$H NMR (400 MHz, DMSO-$d_6$) δ ppm = 12.97 (br. s., 1H), 8.16-8.02 (m, 3H), 7.90 (d, J = 7.9 Hz, 1H), 7.40 (d, J = 3.4 Hz, 1H), 7.28 (t, J = 8.1 Hz, 1H), 7.01 (d, J = 3.4 Hz, 1H), 6.93-6.82 (m, 3H), 5.34 (q, J = 6.9 Hz, 1H), 4.02 (s, 3H), 3.74 (s, 3H), 1.68 (d, J = 7.2 Hz, 3H). |

TABLE 15-continued

| Ex. | R | Name | LCMS (M + H)+ | HPLC Method, RT (min.) and Purity | NMR |
|---|---|---|---|---|---|
| 401 | | 1-(6-methoxy-5-(1H-pyrazol-4-yl)pyridin-2-yl)-3-(1-(3-methoxyphenyl)ethyl)-1H-imidazol-2(3H)-one (Enantiomer II) | 392.2 | I: 13.972, 99.005% J: 14.290, 99.802% | $^1$H NMR (400 MHz, DMSO-d$_6$) δ ppm = 12.97 (br. s., 1H), 8.14 (d, J = 8.0 Hz, 3H), 7.91 (d, J = 8.5 Hz, 1H), 7.41 (d, J = 3.5 Hz, 1H), 7.32-7.25 (m, 1H), 7.01 (d, J = 3.5 Hz, 1H), 6.94-6.83 (m, 3H), 5.35 (q, J = 7.2 Hz, 1H), 4.03 (s, 3H), 3.75 (s, 3H), 1.69 (d, J = 7.0 Hz, 3H). |
| 402 | | 1-(4-(1H-pyrazol-4-yl)phenyl)-3-(3-fluoro-2-methylbenzyl)-1H-imidazol-2(3H)-one | 349.1 | E: 1.75 F: 1.66 | $^1$H NMR (400 MHz, DMSO-d$_6$) δ ppm 12.94 (br. s., 1H), 8.21 (s, 1H), 7.94 (s, 1H), 7.74-7.65 (m, 4H), 7.27-7.20 (m, 1H), 7.15-7.08 (m, 2H), 6.96 (d, J = 7.5 Hz, 1H), 6.69 (d, J = 3.0 Hz, 1H), 4.84 (s, 2H), 2.24 (d, J = 2.0 Hz, 3H) |
| 403 | | 1-(4-(1H-pyrazol-4-yl)phenyl)-3-(4-fluoro-2-methylbenzyl)-1H-imidazol-2(3H)-one | 349.1 | E: 1.75 F: 1.65 | $^1$H NMR (400 MHz, DMSO-d$_6$) δ ppm 12.93 (br. s., 1H), 8.20 (br. s., 1H), 7.94 (br. s., 1H), 7.73-7.65 (m, 4H), 7.17 (dd, J = 8.5, 6.0 Hz, 1H), 7.09 (d, J = 3.5 Hz, 2H), 7.07 (d, J = 2.5 Hz, 1H), 7.05-6.99 (m, 1H), 6.67 (d, J = 3.5 Hz, 1H), 4.77 (s, 2H), 2.34 (s, 3H) |
| 404 | | 1-(4-(1H-pyrazol-4-yl)phenyl)-3-(5-fluoro-2-methylbenzyl)-1H-imidazol-2(3H)-one | 349.1 | E: 1.74 F: 1.64 | $^1$H NMR (400 MHz, DMSO-d$_6$) δ ppm 12.94 (br. s., 1H), 8.21 (s, 1H), 7.94 (s, 1H), 7.74-7.66 (m, 4H), 7.25 (dd, J = 8.5, 6.0 Hz, 1H), 7.13-7.11 (m, 1H), 7.04 (td, J = 8.5, 3.0 Hz, 1H), 6.88 (dd, J = 10.0, 3.0 Hz, 1H), 6.74 (d, J = 3.0 Hz, 1H), 4.80 (s, 2H), 2.30 (s, 3H) |
| 405 | | 1-(4-(1H-pyrazol-4-yl)phenyl)-3-(3-fluoro-2-methoxybenzyl)-1H-imidazol-2(3H)-one | 365.1 | E: 1.69 F: 1.59 | $^1$H NMR (400 MHz, DMSO-d$_6$) δ ppm 12.93 (br. s., 1H), 8.20 (s, 1H), 7.93 (s, 1H), 7.73-7.64 (m, 4H), 7.27-7.19 (m, 1H), 7.13-7.06 (m, 2H), 6.98 (d, J = 7.5 Hz, 1H), 6.74 (d, J = 3.0 Hz, 1H), 4.83 (s, 2H), 3.90 (d, J = 2.0 Hz, 3H) |

TABLE 15-continued

| Ex. | R | Name | LCMS (M + H)+ | HPLC Method, RT (min.) and Purity | NMR |
|---|---|---|---|---|---|
| 406 | | 1-(4-(1H-pyrazol-4-yl)phenyl)-3-(2,3-difluorobenzyl)-1H-imidazol-2(3H)-one | 353.1 | E: 1.66 F: 1.56 | ¹H NMR (400 MHz, DMSO-d₆) δ ppm 12.93 (br. s., 1H), 8.20 (br. s., 1H), 7.94 (br. s., 1H), 7.72-7.64 (m, 5H), 7.44-7.35 (m, 1H), 7.26-7.19 (m, 1H), 7.14-7.08 (m, 2H), 6.80 (d, J = 3.0 Hz, 1H), 4.92 (s, 2H) |
| 407 | | 1-(4-(1H-pyrazol-4-yl)phenyl)-3-(4-fluoro-3-methoxybenzyl)-1H-imidazol-2(3H)-one | 365.1 | E: 1.61 F: 1.51 | ¹H NMR (400 MHz, DMSO-d₆) δ ppm 12.93 (br. s., 1H), 8.20 (br. s., 1H), 7.94 (br. s., 1H), 7.73-7.65 (m, 5H), 7.22-7.16 (m, 3H), 7.07 (d, J = 3.5 Hz, 1H), 6.85 (ddd, J = 8.5, 4.5, 2.0 Hz, 1H), 6.82 (d, J = 3.0 Hz, 1H), 4.76 (s, 2H), 3.84 (s, 3H) |
| 408 | | 1-(4-(1H-pyrazol-4-yl)phenyl)-3-(2,5-difluorobenzyl)-1H-imidazol-2(3H)-one | 353.1 | E: 1.63 F: 1.53 | ¹H NMR (400 MHz, DMSO-d₆) δ ppm 12.94 (br. s., 1H), 8.21 (s, 1H), 7.94 (br. s., 1H), 7.72-7.64 (m, 5H), 7.35-7.28 (m, 1H), 7.26-7.19 (m, 1H), 7.15-7.08 (m, 2H), 6.80 (d, J = 3.0 Hz, 1H), 4.86 (s, 2H) |
| 409 | | 1-(4-(1H-pyrazol-4-yl)phenyl)-3-(2,4-difluorobenzyl)-1H-imidazol-2(3H)-one | 353.2 | E: 1.66 F: 1.56 | ¹H NMR (400 MHz, DMSO-d₆) δ ppm 12.93 (br. s., 1H), 8.20 (s, 1H), 7.93 (s, 1H), 7.72-7.64 (m, 5H), 7.37 (td, J = 8.7, 6.8 Hz, 1H), 7.29 (ddd, J = 10.4, 9.2, 2.5 Hz, 1H), 7.14-7.07 (m, 2H), 6.76 (d, J = 3.0 Hz, 1H), 4.84 (s, 2H) |
| 410 | | 1-(4-(1H-pyrazol-4-yl)phenyl)-3-(pyridin-3-ylmethyl)-1H-imidazol-2(3H)-one | 318.1 | E: 1.14 F: 0.41 | ¹H NMR (400 MHz, DMSO-d₆) δ ppm 12.94 (br. s., 1H), 8.58 (d, J = 1.5 Hz, 1H), 8.52 (dd, J = 4.8, 1.8 Hz, 1H), 8.20 (s, 1H), 7.94 (s, 1H), 7.75-7.64 (m, 6H), 7.42-7.37 (m, 1H), 7.09 (d, J = 3.5 Hz, 1H), 6.87 (d, J = 3.0 Hz, 1H), 4.85 (s, 2H) |

TABLE 15-continued

| Ex. | R | Name | LCMS (M + H)+ | HPLC Method, RT (min.) and Purity | NMR |
|---|---|---|---|---|---|
| 412 | | 1-(4-(1H-pyrazol-4-yl)phenyl)-3-(4-fluoro-2-methoxybenzyl)-1H-imidazol-2(3H)-one | 365.1 | E: 1.68<br>F: 1.70 | $^1$H NMR (400 MHz, DMSO-$d_6$) δ ppm 12.94 (br. s., 1H), 8.21 (s, 1H), 7.94 (s, 1H), 7.73-7.64 (m, 5H), 7.13-7.06 (m, 3H), 6.97 (dd, J = 11.0, 2.5 Hz, 1H), 6.77 (td, J = 8.5, 2.5 Hz, 1H), 6.69 (d, J = 3.0 Hz, 1H), 4.72 (s, 2H), 3.87 (s, 3H) |
| 413 | | 1-(3-fluorobenzyl)-3-(6-methoxy-5-(1H-pyrazol-4-yl)pyridin-2-yl)-1H-imidazol-2(3H)-one | 366.1 | E: 1.82<br>F: 1.83 | $^1$H NMR (400 MHz, DMSO-$d_6$) δ ppm 12.96 (br. s., 1H), 8.17 (br. s., 1H), 8.15-8.12 (m, 1H), 8.00 (br. s., 1H), 7.92 (d, J = 8.0 Hz, 1H), 7.46-7.37 (m, 2H), 7.18-7.13 (m, 3H), 6.90-6.86 (m, 1H), 4.85 (s, 2H), 4.02 (s, 3H) |
| 414 | | 1-(2,4-difluorobenzyl)-3-(6-methoxy-5-(1H-pyrazol-4-yl)pyridin-2-yl)-1H-imidazol-2(3H)-one | 384.1 | E: 1.9<br>F: 1.89 | $^1$H NMR (400 MHz, DMSO-$d_6$) δ ppm 12.96 (br. s., 1H), 8.17 (s, 1H), 8.14 (d, J = 8.0 Hz, 2H), 8.00 (br. s., 1H), 7.90 (d, J = 8.5 Hz, 1H), 7.42-7.35 (m, 2H), 7.29 (ddd, J = 10.5, 9.5, 2.5 Hz, 1H), 7.11 (tdd, J = 8.5, 2.5, 1.0 Hz, 1H), 6.79 (d, J = 3.0 Hz, 1H), 4.86 (s, 2H), 4.02 (s, 3H) |
| 415 | | 1-(2,5-difluorobenzyl)-3-(6-methoxy-5-(1H-pyrazol-4-yl)pyridin-2-yl)-1H-imidazol-2(3H)-one | 384.1 | E: 1.85<br>F: 1.86 | $^1$H NMR (400 MHz, DMSO-$d_6$) δ ppm 12.97 (br. s., 1H), 8.18-8.12 (m, 2H), 8.01 (br. s., 1H), 7.90 (d, J = 8.0 Hz, 1H), 7.43-7.39 (m, 1H), 7.35-7.27 (m, 1H), 7.26-7.19 (m, 1H), 7.14 (ddd, J = 8.8, 5.8, 3.5 Hz, 1H), 6.83 (d, J = 3.0 Hz, 1H), 4.88 (s, 2H), 4.02 (s, 3H) |

TABLE 15-continued

| Ex. | R | Name | LCMS (M + H)+ | HPLC Method, RT (min.) and Purity | NMR |
|---|---|---|---|---|---|
| 416 | | 1-(3-fluoro-2-methoxybenzyl)-3-(6-methoxy-5-(1H-pyrazol-4-yl)pyridin-2-yl)-1H-imidazol-2(3H)-one | 396.2 | E: 1.91 F: 1.91 | ¹H NMR (400 MHz, DMSO-d₆) δ ppm 12.96 (br. s., 1H), 8.17 (s, 1H), 8.14 (d, J = 8.0 Hz, 1H), 8.00 (s, 1H), 7.92 (d, J = 8.0 Hz, 1H), 7.42-7.38 (m, 1H), 7.23 (ddd, J = 11.8, 8.3, 1.5 Hz, 1H), 7.10 (td, J = 7.9, 5.3 Hz, 1H), 6.98 (d, J = 7.5 Hz, 1H), 6.77 (d, J = 3.0 Hz, 1H), 4.85 (s, 2H), 4.02 (s, 3H), 3.90 (d, J = 1.5 Hz, 3H) |
| 417 | | 1-(6-methoxy-5-(1H-pyrazol-4-yl)pyridin-2-yl)-3-(pyridin-3-ylmethyl)-1H-imidazol-2(3H)-one | 349.1 | E: 1.3 F: 1.00 | ¹H NMR (400 MHz, DMSO-d₆) δ ppm 12.96 (br. s., 1H), 8.59 (d, J = 1.5 Hz, 1H), 8.53-8.50 (m, 1H), 8.16 (br. s., 1H), 8.14 (d, J = 8.0 Hz, 1H), 8.00 (br. s., 1H), 7.91 (d, J = 8.5 Hz, 1H), 7.76-7.71 (m, 1H), 7.43-7.37 (m, 2H), 6.92-6.89 (m, 1H), 4.88 (s, 2H), 4.02 (s, 3H) |
| 418 | | 1-(6-methoxy-5-(1H-pyrazol-4-yl)pyridin-2-yl)-3-((tetrahydrofuran-2-yl)methyl)-1H-imidazol-2(3H)-one | 342.2 | E: 1.47 F: 1.47 | ¹H NMR (400 MHz, DMSO-d₆) δ ppm 12.96 (br. s., 1H), 8.16 (br. s., 1H), 8.13 (d, J = 8.0 Hz, 1H), 8.00 (br. s., 1H), 7.92 (d, J = 8.0 Hz, 1H), 7.34 (d, J = 3.0 Hz, 1H), 6.76 (d, J = 3.0 Hz, 1H), 4.12-4.04 (m, 1H), 4.02 (s, 3H), 3.81-3.75 (m, 1H), 3.69-3.61 (m, 3H), 1.98-1.89 (m, 1H), 1.86-1.77 (m, 2H), 1.64-1.53 (m, 1H) |
| 419 | | 1-(3-(difluoromethoxy)benzyl)-3-(6-methoxy-5-(1H-pyrazol-4-yl)pyridin-2-yl)-1H-imidazol-2(3H)-one | 414.1 | E: 1.89 F: 1.90 | ¹H NMR (400 MHz, DMSO-d₆) δ ppm 12.96 (br. s., 1H), 8.17 (s, 1H), 8.14 (d, J = 8.0 Hz, 2H), 8.00 (s, 1H), 7.94-7.90 (m, 1H), 7.45-7.39 (m, 2H), 7.32 (t, J = 76.0 Hz, 1H), 7.20-7.09 (m, 3H), 6.88 (d, J = 3.5 Hz, 1H), 4.85 (s, 2H), 4.02 (s, 3H) |

TABLE 15-continued

| Ex. | R | Name | LCMS (M + H)+ | HPLC Method, RT (min.) and Purity | NMR |
|---|---|---|---|---|---|
| 420 | 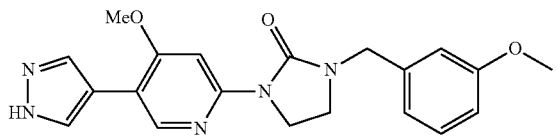 | 1-(cyclohexylmethyl)-3-(6-methoxy-5-(1H-pyrazol-4-yl)pyridin-2-yl)-1H-imidazol-2(3H)-one | 354.2 | E: 2.11<br>F: 2.11 | $^1$H NMR (400 MHz, DMSO-$d_6$) δ ppm 12.96 (br. s., 1H), 8.16 (br. s., 1H), 8.13 (d, J = 8.5 Hz, 1H), 8.00 (br. s., 1H), 7.92 (d, J = 8.0 Hz, 1H), 7.35 (d, J = 3.0 Hz, 1H), 6.77 (d, J = 3.0 Hz, 1H), 4.02 (s, 3H), 3.44 (d, J = 7.0 Hz, 2H), 1.74-1.57 (m, 6H), 1.25-1.11 (m, 3H), 1.02-0.89 (m, 2H) |

Example 423

1-(4-Methoxy-5-(1H-pyrazol-4-yl)pyridin-2-yl)-3-(3-methoxybenzyl)imidazolidin-2-one

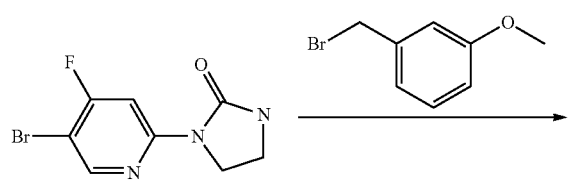

Example 423A: 1-(5-Bromo-4-methoxypyridin-2-yl)-3-(3-methoxybenzyl)imidazolidin-2-one

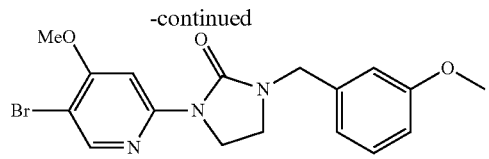

To a solution of 1-(5-bromo-4-fluoropyridin-2-yl)imidazolidin-2-one (100 mg, 0.385 mmol) in THF (5 mL) at 0° C., was added NaH (9.23 mg, 0.385 mmol). The mixture was stirred for 30 min at 0° C. To it was added 1-(bromomethyl)-3-methoxybenzene (77 mg, 0.385 mmol) over period of 10 min. The reaction mixture was allowed to warm to rt and stirred overnight. The reaction mixture was quenched with methanol (5 mL) and solvents were evaporated. The solid was dissolved in ethyl acetate and washed with water (50 mL) and brine (20 mL). The organic layer was dried over Na$_2$SO$_4$, filtered and concentrated at reduced pressure to give crude. The crude compound was purified by flash chromatography (2%-20% ethyl acetate/pet ether gradient elution) to give 1-(5-bromo-4-methoxypyridin-2-yl)-3-(3-methoxybenzyl)imidazolidin-2-one as a white solid (110 mg, 73%).

Preparation of 1-(4-methoxy-5-(1H-pyrazol-4-yl)pyridin-2-yl)-3-(3-methoxybenzyl) imidazolidin-2-one

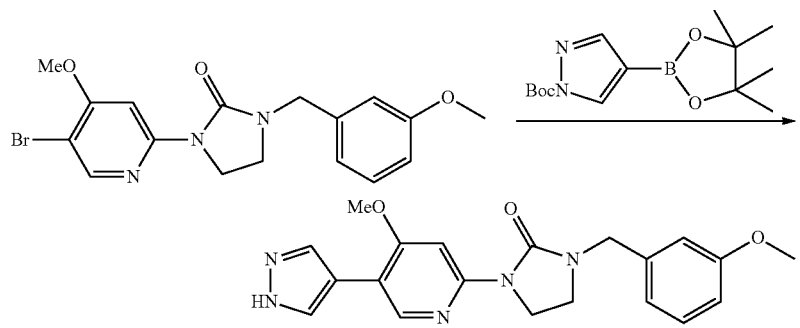

To a solution of 1-(5-bromo-4-methoxypyridin-2-yl)-3-(3-methoxybenzyl) imidazolidin-2-one (100 mg, 0.246 mmol) in DMF (5 mL), were added tert-butyl 4-(4,4,5,5-tetramethyl-1,3,2-dioxaborolan-2-yl)-1H-pyrazole-1-carboxylate (87 mg, 0.295 mmol), $K_2CO_3$ (102 mg, 0.738 mmol) and water (0.2 mL). The reaction mixture was purged with nitrogen for 5 min and charged with 2nd generation XPhos precatalyst (5.81 mg, 7.38 μmol). The mixture was again purged with nitrogen for 3 min, then heated at 90° C. for 16 h. The reaction was cooled to rt and filtered, and the filtrate was concentrated. The residue was purified by preparative HPLC to afford 1-(4-methoxy-5-(1H-pyrazol-4-yl)pyridin-2-yl)-3-(3-methoxybenzyl)imidazolidin-2-one (0.0164 g, 16% yield) as an off-white solid. MS(ESI) m/z: 380.2 $(M+H)^+$; $^1$H NMR (400 MHz, DMSO-$d_6$) δ ppm 8.45 (s, 1H), 8.04 (s, 2H), 7.89 (s, 1H), 7.38-7.23 (m, 1H), 6.97-6.81 (m, 3H), 4.40 (s, 2H), 4.20 (q, J=7.0 Hz, 2H), 4.03-3.89 (m, 2H), 3.76 (s, 3H) 1.46 (t, J=6.9 Hz, 3H).

The following Examples in Table 16 were prepared following similar routes to the Examples above.

TABLE 16

| Ex. | R | Name | LCMS (M + H)+ | HPLC Method, RT (min.) and Purity | NMR |
|---|---|---|---|---|---|
| 424 | (structure) | 1-(5-fluoro-2-methoxybenzyl)-3-(3-fluoro-4-(1H-pyrazol-4-yl)phenyl)imidazolidin-2-one | 385.2 | E: 1.560, 98.88% F: 1.550, 97.64% | ¹H NMR (400 MHz, DMSO-d₆) δ ppm 13.00 (s, 1H), 8.09 (s, 1H), 7.89 (s, 1H), 7.72-7.57 (m, 2H), 7.33 (dd, J = 2.2, 8.6 Hz, 1H), 7.15-6.97 (m, 3H), 4.36 (s, 2H), 3.86 (dd, J = 6.9, 9.2 Hz, 2H), 3.81 (s, 3H), 3.50-3.41 (m, 2H); ¹⁹F NMR (400 MHz, DMSO-d₆) δ ppm −113.984, −123.783 |
| 425 | (structure) | 1-(3-fluoro-4-(1H-pyrazol-4-yl)phenyl)-3-(3-fluoro-5-methoxybenzyl)imidazolidin-2-one | 385.2 | E: 1.556, 96.66% F: 1.560, 96.23% | ¹H NMR (400 MHz, DMSO-d₆) δ ppm 13.01 (s, 1H), 8.09 (br. s., 1H), 7.89 (br. s., 1H), 7.72-7.57 (m, 2H), 7.34 (dd, J = 2.2, 8.6 Hz, 1H), 7.19 (dd, J = 8.2, 11.5 Hz, 1H), 7.10 (dd, J = 1.9, 8.4 Hz, 1H), 6.87 (ddd, J = 2.0, 4.4, 8.3 Hz, 1H), 4.36 (s, 2H), 3.87-3.79 (m, 5H), 3.42-3.35 (m, 2H); ¹⁹F NMR (400 MHz, DMSO-d₆) δ ppm −111.519 and −113.946 |

TABLE 16-continued

| Ex. | R | Name | LCMS (M + H)+ | HPLC Method, RT (min.) and Purity | NMR |
|---|---|---|---|---|---|
| 426 | | 1-(3-fluoro-4-(1H-pyrazol-4-yl)phenyl)-3-(2-fluoro-5-methoxybenzyl)imidazolidin-2-one | 385.2 | E: 1.530, 93.90% F: 1.534, 94.65% | $^1$H NMR (400 MHz, DMSO-d$_6$) δ ppm 13.01 (s, 1H), 8.09 (d, J = 4.8 Hz, 1H), 7.88 (br. s., 1H), 7.71-7.60 (m, 2H), 7.33 (dd, J = 2.3, 8.7 Hz, 1H), 7.19-7.12 (m, 1H), 6.93-6.87 (m, 2H), 4.42 (s, 2H), 3.87-3.82 (m, 2H), 3.74 (s, 3H), 3.45-3.39 (m, 2H); $^{19}$F NMR (400 MHz, DMSO-d$_6$) δ ppm −112.189, −129.596 |
| 427 | | 1-(5-(1H-pyrazol-4-yl)pyridin-2-yl)-3-(2-fluoro-3-methoxybenzyl)imidazolidin-2-one | 368.2 | E: 1.358, 95.22% F: 1.00, 96.4% | $^1$H NMR (400 MHz, DMSO-d$_6$) δ ppm 12.98 (br. s., 1H), 8.58 (s, 1H), 8.21 (d, J = 1.0 Hz, 2H), 8.03-7.87 (m, 2H), 7.22-7.07 (m, 2H), 6.99-6.81 (m, 1H), 4.48 (m, 2H), 3.98 (m, 2H), 3.87 (s, 3H), 3.48-3.37 (m, 2H); $^{19}$F NMR (400 MHz, DMSO-d$_6$) δ ppm −141.500 |

TABLE 16-continued

| Ex. | R | Name | LCMS (M + H)+ | HPLC Method, RT (min.) and Purity | NMR |
|---|---|---|---|---|---|
| 428 | | 1-(5-(1H-pyrazol-4-yl)pyridin-2-yl)-3-(3-fluoro-5-methoxybenzyl)imidazolidin-2-one | 368.2 | E: 1.448, 95.62%<br>F: 1.106, 95.6% | $^1$H NMR (400 MHz, DMSO-d$_6$) δ ppm 12.98 (br. s., 1H), 8.58 (m, 1H), 8.22 (m, 2H), 8.00-7.89 (m, 2H), 6.83-6.60 (m, 3H), 4.39 (s, 2H), 3.98 (m, 2H), 3.77 (s, 3H), 3.48-3.36 (m, 2H); $^{19}$F NMR (400 MHz, DMSO-d$_6$) δ ppm -111.509 |
| 429 | | 1-(5-(1H-pyrazol-4-yl)pyridin-2-yl)-3-(4-fluoro-3-methoxybenzyl)imidazolidin-2-one | 368.2 | E: 1.383, 99.20%<br>F: 1.042, 99.34% | $^1$H NMR (400 MHz, DMSO) δ ppm 12.98 (br. s., 1H), 8.58 (m, 1H), 8.22 (m, 2H), 8.00-7.89 (m, 2H), 7.23-7.15 (m, 1H), 7.11 (dd, J = 8.5, 2.0 Hz, 1H), 6.88 (ddd, J = 8.5, 4.5, 2.0 Hz, 1H), 4.39 (s, 2H), 4.01-3.91 (m, 2H), 3.84 (s, 3H), 3.42-3.34 (m, 2H); $^{19}$F NMR (400 MHz, DMSO-d$_6$) δ ppm -137.416 |

TABLE 16-continued

| Ex. | R | Name | LCMS (M + H)+ | HPLC Method, RT (min.) and Purity | NMR |
|---|---|---|---|---|---|
| 430 | (structure) | 1-(3-fluoro-4-(1H-pyrazol-4-yl)phenyl)-3-(3-methoxybenzyl)imidazolidin-2-one | 367.3 | E: 1.544, 95.15%<br>F: 1.520, 96.95% | $^1$H NMR (400 MHz, DMSO-d$_6$) δ ppm 13.01 (s, 1H), 8.09 (s, 1H), 7.89 (br. s., 1H), 7.71-7.60 (m, 2H), 7.37-7.25 (m, 2H), 6.91-6.83 (m, 3H), 4.37 (s, 2H), 3.87-3.80 (m, 2H), 3.75 (s, 3H), 3.41-3.35 (m, 2H); $^{19}$F NMR (400 MHz, DMSO-d$_6$) δ ppm −113.964 |
| 431 | (structure) | 1-(3-fluoro-4-(1H-pyrazol-4-yl)phenyl)-3-(2-fluoro-6-methoxybenzyl)imidazolidin-2-one | 385.2 | I: 1.608 93.404%<br>J: 1.582, 93.23% | $^1$H NMR (400 MHz, DMSO-d$_6$) δ ppm 13.01 (s, 1H), 8.09 (d, J = 4.8 Hz, 1H), 7.88 (br. s., 1H), 7.70-7.57 (m, 2H), 7.40-7.26 (m, 2H), 6.93 (s, 1H), 6.84 (t, J = 8.6 Hz, 1H), 4.45 (s, 2H), 3.84 (s, 3H), 3.79-3.71 (m, 2H), 3.31-3.25 (m, 2H); $^{19}$F NMR (400 MHz, DMSO-d$_6$) δ ppm −114.017, −116.111 |

TABLE 16-continued

| Ex. | R | Name | LCMS (M + H)+ | HPLC Method, RT (min.) and Purity | NMR |
|---|---|---|---|---|---|
| 432 | | 1-(3-fluoro-4-(1H-pyrazol-4-yl)phenyl)-3-(3-fluoro-4-methoxybenzyl)imidazolidin-2-one | 385.2 | E: 1.535, 94.59% F: 1.510, 97.00% | ¹H NMR (400 MHz, DMSO-d₆) δ ppm 13.01 (s, 1H), 8.10 (br. s., 1H), 7.89 (br. s., 1H), 7.71-7.60 (m, 2H), 7.35-7.29 (m, 1H), 7.19-7.07 (m, 3H), 4.34 (s, 2H), 3.86-3.77 (m, 5H), 3.40-3.34 (m, 2H); ¹⁹F NMR (400 MHz, DMSO-d₆) δ ppm -113.960, -135.202 |
| 433 | | 1-(2-fluoro-3-methoxybenzyl)-3-(3-fluoro-4-(1H-pyrazol-4-yl)phenyl)imidazolidin-2-one | 385.2 | E: 1.538, 95.04% F: 1.514, 94.66% | ¹H NMR (400 MHz, DMSO-d₆) δ ppm 13.01 (s, 1H), 8.09 (br. s., 1H), 7.89 (br. s., 1H), 7.72-7.56 (m, 2H), 7.32 (dd, J = 2.3, 8.7 Hz, 1H), 7.19-7.07 (m, 2H), 6.96-6.87 (m, 1H), 4.45 (s, 2H), 3.87-3.80 (m, 5H), 3.44-3.37 (m, 2H); ¹⁹F NMR (400 MHz, DMSO-d₆) δ ppm -113.945, 141.498 |

TABLE 16-continued

| Ex. | R | Name | LCMS (M + H)+ | HPLC Method, RT (min.) and Purity | NMR |
|---|---|---|---|---|---|
| 434 | | 1-(4-fluoro-3-methoxybenzyl)-3-(3-fluoro-4-(1H-pyrazol-4-yl)phenyl)imidazolidin-2-one | 385.1 | I: 1.803, 100% J: 1.772, 97.56% | ¹H NMR (400 MHz, DMSO-d₆) δ ppm 13.01 (s, 1H), 8.09 (br. s., 1H), 7.89 (br. s., 1H), 7.72-7.57 (m, 2H), 7.34 (dd, J = 2.2, 8.6 Hz, 1H), 7.19 (dd, J = 8.2, 11.5 Hz, 1H), 7.10 (dd, J = 1.9, 8.4 Hz, 1H), 6.87 (ddd, J = 2.0, 4.4, 8.3 Hz, 1H), 4.36 (s, 2H), 3.87-3.79 (m, 5H), 3.42-3.35 (m, 2H); ¹⁹F NMR (400 MHz, DMSO-d₆) δ ppm -113.954, -137.416 |
| 437 | | 1-(6-(1H-pyrazol-4-yl)pyridin-3-yl)-3-(3-fluoro-5-methoxybenzyl)imidazolidin-2-one | 368.1 | I: 1.555, 100% J: 1.288, 100% | ¹H NMR (400 MHz, DMSO-d₆) δ ppm 12.97 (br. s., 1 H) 8.702-8.708 (d, = 2.4 Hz, 1 H) 8.11 (s, 2H) 8.01-8.04 (dd, J = 2.8 Hz, 1 H) 7.64-7.67 (m, 1 H) 6.71-6.78 (m, 3 H) 4.38 (s, 2 H) 3.87-3.91 (m, 2 H) 3.77 (s, 3H) 3.41-3.45 (m, 2 H); ¹⁹F NMR (400 MHz, DMSO-d₆) δ ppm -111.519 |

TABLE 16-continued

| Ex. | R | Name | LCMS (M + H)+ | HPLC Method, RT (min.) and Purity | NMR |
|---|---|---|---|---|---|
| 438 | | 1-(5-(1H-pyrazol-4-yl)pyridin-2-yl)-3-(3-(cyclopropylmethoxy)benzyl)imidazolidin-2-one | 390.2 | E: 1.884, 96.93% F: 1.557, 100% | 1H NMR (400 MHz, DMSO-d6) δ ppm 12.98 (br. s., 1 H) 8.57-8.58 (m, 1 H) 8.20-8.22 (q, J = 0.8 Hz, 1 H) 7.95-7.97 (m, 3 H) 7.24-7.28 (m, 1 H) 6.83-6.87 (m, 3 H) 4.38 (s, 2 H) 3.94-3.98 (m, 2 H) 3.80-3.81 (d, J = 6.8 Hz, 2H) 3.31-3.39 (m, 2 H) 1.18-1.21 (m, 1 H) 0.53-0.58 (m, 2H) 0.29-0.33 (m, 2H). |
| 439 | | 1-(6-(1H-pyrazol-4-yl)pyridin-3-yl)-3-(3-methoxybenzyl)imidazolidin-2-one | 350.2 | E: 1.484, 100% F: 1.222, 100% | 1H NMR (400 MHz, DMSO-d6) δ ppm 12.97 (br. s., 1 H) 8.702-8.708 (d. = 2.4 Hz, 1 H) 8.22 (s, 2H) 8.02-8.04 (dd, J = 2.8 Hz, 1 H) 7.64-7.67 (m, 1 H) 7.27-7.31 (m, 1H) 6.86-6.90 (m, 3 H) 4.38 (s, 2 H) 3.85-3.89 (m, 2 H) 3.76 (s, 3H) 3.39-3.43 (m, 2 H). |

TABLE 16-continued

| Ex. | R | Name | LCMS (M + H)+ | HPLC Method, RT (min.) and Purity | NMR |
|---|---|---|---|---|---|
| 440 | 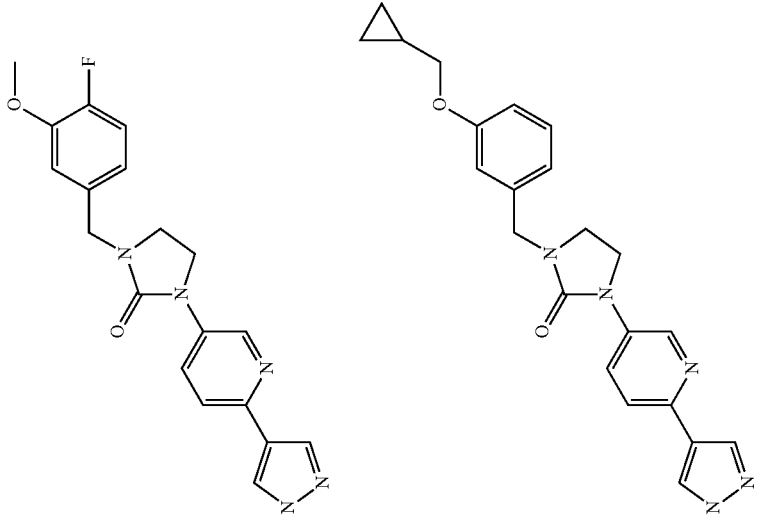 | 1-(6-(1H-pyrazol-4-yl)pyridin-3-yl)-3-(4-fluoro-3-methoxybenzyl)imidazolidin-2-one | 368.1 | E: 1.498, 100% F: 1.243, 100% | $^1$H NMR (400 MHz, DMSO-d$_6$) δ ppm 12.97 (br. s., 1 H) 8.70-8.71 (d, = 2.4 Hz, 1 H) 8.11 (s, 2H) 8.01-8.04 (dd, J = 2.8 Hz, 1 H) 7.64-7.67 (m, 1 H) 7.17-7.22 (m, 1H) 7.09-7.12 (m, 1H) 6.86-6.90 (m, 1 H) 4.38 (s, 2 H) 3.84-3.89 (m, 5 H) 3.41-3.45 (m, 2 H); $^{19}$F NMR (400 MHz, DMSO-d$_6$) δ ppm −137.411 |
| 441 | | 1-(6-(1H-pyrazol-4-yl)pyridin-3-yl)-3-(3-(cyclopropylmethoxy)benzyl)imidazolidin-2-one | 390.2 | E: 1.758, 98.29% F: 1.478, 100% | $^1$H NMR (400 MHz, DMSO-d$_6$) δ ppm 12.98 (br. s., 1 H) 8.69-8.70 (m, 1 H) 8.19 (s, 2H) 8.01-8.04 (q, J = 0.8 Hz, 1 H) 7.64-7.66 (m, 1 H) 7.24-7.28 (m, 1 H) 6.83-6.87 (m, 3 H) 4.38 (s, 2 H) 3.94-3.98 (m, 2 H) 3.80-3.81 (d, J = 6.8 Hz, 2H) 3.31-3.39 (m, 2 H) 1.18-1.21 (m, 1 H) 0.53-0.58 (m, 2H) 0.29-0.33 (m, 2H). |

TABLE 16-continued

| Ex. | R | Name | LCMS (M + H)+ | HPLC Method, RT (min.) and Purity | NMR |
|---|---|---|---|---|---|
| 442 | | 1-(5-(1H-pyrazol-4-yl)pyridin-2-yl)-3-(2-hydroxy-1-(3-methoxyphenyl)ethyl)imidazolidin-2-one | 380 | I: 1.377, 100%<br>J: 1.107, 100% | $^1$H NMR (400 MHz, DMSO-d$_6$) δ ppm 12.95 (br. s., 1 H) 8.52-8.568 (m, 1H) 8.14-8.16 (dd, J = 0.4 Hz, 1 H) 8.06 (s, 2H) 7.92-7.95 (dd, J = 2.8 Hz, 1 H) 7.24-7.28 (m, 1 H) 6.95-6.97 (m, 2 H) 6.82-6.84 (m, 1H) 5.53 (s, 1 H) 4.78(s, 1 H) 3.89-3.94 (m, 2H) 3.76(s, 3 H) 3.60-3.62 (m, 1H) 3.32-3.37 (m, 1H) 3.32-3.37 (m, 2H). |
| 443 | | 1-(3-fluoro-4-(1H-pyrazol-4-yl)phenyl)-3-(3-isobutoxybenzyl)imidazolidin-2-one | 409.2 | E: 2.989, 100%<br>F: 2.263, 100% | $^1$H NMR (400 MHz, DMSO-d$_6$) δ ppm 13.03 (s, 1H) 7.89 (s, 2H) 7.81-7.56 (m, 2H), 7.50-7.06 (m, 2H), 7.01-6.53 (m, 3H), 4.36 (s, 2H), 3.81-3.86 (m, 2H), 3.74 (d, J = 6.5 Hz, 2H), 3.52-3.34 (m, 2H), 2.00 (dt, J = 13.3, 6.7 Hz, 1H), 0.97-0.98 (d, J = 4 Hz, 6H); $^{19}$F NMR (400 MHz, DMSO-d$_6$) δ ppm -113.975 |
| 444 | | 1-(5-(1H-pyrazol-4-yl)pyridin-2-yl)-3-(3-isobutoxybenzyl)imidazolidin-2-one | 392.2 | E: 2.839, 100%<br>F: 1.748, 100% | $^1$H NMR (400 MHz, DMSO-d$_6$) δ ppm 13.01 (s, 1H) 8.58 (dd, J = 2.4, 0.8 Hz, 1H), 8.21 (dd, J = 8.8, 0.8 Hz, 1H), 8.06 (s, 2H) 7.96 (dd, J = 8.8, 2.4 Hz, 1H), 7.31-7.22 (m, 1H), 6.91-6.82 (m, 3H), 4.38 (s, 2H), 3.97 (dd, J = 9.1, 7.1 Hz, 2H), 3.74 (d, J = 6.5 Hz, 2H), 3.42-3.35 (m, 2H), 2.00 (dt, J = 13.3, 6.7 Hz, 1H), 0.97 (d, J = 6.7 Hz, 6H) |

TABLE 16-continued

| Ex. | R | Name | LCMS (M + H)+ | HPLC Method, RT (min.) and Purity | NMR |
|---|---|---|---|---|---|
| 446 | | 1-(5-(1H-pyrazol-4-yl)pyridin-2-yl)-3-(3-methoxybenzyl)imidazolidin-2-one | 350.1 | I: 1.667, 98.25% J: 1.329, 98.70% | $^1$H NMR (400 MHz, DMSO-d$_6$) δ ppm 3.34-3.41 (m, 3 H) 3.75 (s, 3 H) 3.90-4.06 (m, 2 H) 4.39 (s, 2 H) 6.95 (s, 3 H) 7.22-7.38 (m, 1H) 7.96 (dd, J = 8.68, 2.32 Hz, 2 H) 8.21 (d, J = 8.80 Hz, 2 H) 8.57 (d, J = 2.45 Hz, 1 H) 12.87-13.11 (m, 1 H). |
| 447 | | 1-(2,5-difluoro-4-(1H-pyrazol-4-yl)phenyl)-3-(3-methoxybenzyl)imidazolidin-2-one | 385.2 | E: 1.649, 99.6% F: 1.660, 98.59% | $^1$H NMR (400 MHz, DMSO-d$_6$) δ ppm 13.16 (s, 1H) 8.09 (s, 2 H) 7.74 (dd, J = 7.2, 5.2 Hz, 1H), 7.55 (dd, J = 7.2, 5.2 Hz, 1H), 7.32-7.28 (m, 1H), 6.89-6.87 (m, 3H), 4.36 (s, 2H), 3.85-3.3.83 (m, 5H), 3.40-3.33(m, 2H); $^{19}$F NMR (400 MHz, DMSO-d$_6$) δ ppm -119.208, -126.086 |
| 448 | | 1-(2,5-difluoro-4-(1H-pyrazol-4-yl)phenyl)-3-(3-fluoro-5-methoxybenzyl)imidazolidin-2-one | 403.2 | E: 1.723, 96.80% F: 1.726, 94.02% | $^1$H NMR (400 MHz, DMSO-d$_6$) δ ppm 13.16 (s, 1H) 8.10 (s, 2 H) 7.74 (dd, J = 7.2, 5.2 Hz, 1H), 7.55 (dd, J = 7.2, 5.2 Hz, 1H), 6.79-6.73 (m, 3H), 4.36 (s, 2H), 3.87-3.78 (m, 2H), 3.71 (s, 3 H) 3.40-3.33(m, 2H); $^{19}$F NMR (400 MHz, DMSO-d$_6$) δ ppm -111.520, -119.218, -126.085. |
| 449 | | 1-(2,5-difluoro-4-(1H-pyrazol-4-yl)phenyl)-3-(4-fluoro-3-methobenzyl)imidazolidin-2-one | 403.2 | E: 1.675, 96.90% F: 1.670, 99.53% | $^1$H NMR (400 MHz, DMSO-d$_6$)δ ppm 13.17 (s, 1H) 8.10 (s, 2 H) 7.74 (dd, J = 7.2, 5.2 Hz, 1H), 7.55 (dd, J = 7.2, 5.2 Hz, 1H), 7.23-7.18 (m, 1H) 7.11 (dd, J = 6.4, 2.0 Hz, 1H), 6.89-6.87 (m, 1H), 4.36 (s, 2H), 3.85-3.3.83 (m, 5H), 3.40-3.33(m, 2H); $^{19}$F NMR (400 MHz, DMSO-d$_6$) δ ppm -119.207, -126.097 -137.403 |

TABLE 16-continued

| Ex. | R | Name | LCMS (M + H)+ | HPLC Method, RT (min.) and Purity | NMR |
|---|---|---|---|---|---|
| 450 | | 1-(5-(1H-pyrazol-4-yl)pyridin-2-yl)-3-(4-fluoro-3-methoxybenzyl)-4,4-dimethylimidazolidin-2-one | 396.2 | E: 1.835, 99.64% F: 1.507, 99.67% | $^1$H NMR (400 MHz, DMSO-d$_6$) δ ppm 12.97 (s, 1H) 8.83 (dd, J = 2.4, 0.8 Hz, 1H), 8.52-8.40 (dd, J = 8.8, 2.4 Hz, 2H), 8.22 (dd, J = 8.8, 2.4 Hz, 2H), 7.52-7.31 (m, 2H), 7.20 (ddd, J = 8.3, 4.4, 2.0 Hz, 1H), 4.64 (s, 2H), 3.82 (s, 3H) 3.79(s, 2H), 1.51 (s, 6H); $^{19}$F NMR (400 MHz, DMSO-d$_6$) δ ppm −138.149 |
| 451 | | 1-(5-(1H-pyrazol-4-yl)pyridin-2-yl)-3-(3-methoxybenzyl)-4,4-dimethylimidazolidin-2-one | 378.1 | E: 1.817, 99.46% F: 1.473, 99.69% | $^1$H NMR (400 MHz, DMSO-d$_6$) δ ppm 12.97 (s, 1H) 8.83 (dd, J = 2.4, 0.8 Hz, 1H), 8.46 (dd, J = 8.7, 0.8 Hz, 2H), 8.22 (dd, J = 8.8, 2.4 Hz, 2H), 7.50 (t, J = 8.1 Hz, 1H), 7.26-7.16 (m, 2H), 7.12-7.01 (m, 1H), 4.64 (s, 2H), 4.05 (s, 2H), 4.00 (s, 3H), 1.50 (s, 6H) |
| 452 | | 1-(5-(1H-pyrazol-4-yl)pyridin-2-yl)-3-(3-(cyclopropylmethoxy)benzyl)-4,4-dimethylimidazolidin-2-one | 418.2 | E: 2.088, 95.43% F: 1.752, 95.35% | $^1$H NMR (400 MHz, DMSO-d$_6$) δ ppm 13.01 (s, 1H) 8.83 (dd, J = 2.4, 0.8 Hz, 1H), 8.46 (dd, J = 8.8, 0.8 Hz, 2H), 8.22 (dd, J = 8.8, 2.4 Hz, 2H), 7.47 (t, J = 8.1 Hz, 1H), 7.24-7.13 (m, 2H), 7.04 (dd, J = 7.7, 2.0 Hz, 1H), 4.62 (s, 2H), 4.05 (t, J = 3.5 Hz, 4H), 1.54-1.42 (m, 7H), 0.88-0.75 (m, 2H), 0.63-0.49 (m, 2H) |
| 453 | | 1-(3-ethyl-4-(1H-pyrazol-4-yl)phenyl)-3-(3-methoxybenzyl)-1H-imidazol-2(3H)-one | 375.1 | E: 1.784, 98.43% F: 1.743, 99.522% | $^1$H NMR (400 MHz, DMSO-d$_6$) δ ppm 13.24 (br. s., 1H), 8.16 (br. s., 1H), 7.90 (d, J = 2.4 Hz, 2H), 7.81 (dd, J = 8.4, 2.3 Hz, 1H), 7.62 (d, J = 8.3 Hz, 1H), 7.58-7.50 (m, 1H), 7.34 (d, J = 3.2 Hz, 1H), 7.17-7.11 (m, 3H), 7.07 (d, J = 3.2 Hz, 1H), 5.03 (s, 2H), 4.01 (s, 3H), 2.98 (q, J = 7.6 Hz, 2H), 1.46-1.37 (m, 3H) |

TABLE 16-continued

| Ex. | R | Name | LCMS (M + H)+ | HPLC Method, RT (min.) and Purity | NMR |
|---|---|---|---|---|---|
| 454 | | 1-(3-ethyl-4-(1H-pyrazol-4-yl)phenyl)-3-(3-fluoro-5-methoxybenzyl)-1H-imidazol-2(3H)-one | 393.1 | E: 1.849, 98.205% F: 1.814, 97.675% | 1H NMR (400 MHz, DMSO-d6) δ ppm 13.24 (br. s., 1H), 8.17 (br. s., 1H), 7.90 (d, J = 2.2 Hz, 2H), 7.81 (dd, J = 8.3, 2.4 Hz, 1H), 7.62 (d, J = 8.6 Hz, 1H), 7.36 (d, J = 3.2 Hz, 1H), 7.10 (d, J = 2.9 Hz, 1H), 7.07-6.92 (m, 3H), 5.03 (s, 2H), 4.06-3.98 (m, 3H), 2.98 (q, J = 7.5 Hz, 2H), 1.41 (t, J = 7.5 Hz, 3H); 19F NMR (400 MHz, DMSO-d6) δ ppm -111.350. |
| 455 | | 1-(3-(cyclopropylmethoxy)benzyl)-3-(3-ethyl-4-(1H-pyrazol-4-yl)phenyl)-1H-imidazol-2(3H)-one | 415.2 | E: 2.031, 94.962% F: 2.005, 94.761% | 1H NMR (400 MHz, DMSO-d6) δ ppm 13.24 (br. s., 1H), 8.17 (br. s., 1H), 7.91 (d, J = 2.2 Hz, 2H), 7.81 (dd, J = 8.6, 2.4 Hz, 1H), 7.66-7.59 (m, 1H), 7.55-7.47 (m, 1H), 7.38-7.31 (m, 1H), 7.15-7.05 (m, 4H), 5.01 (s, 2H), 4.06 (d, J = 6.8 Hz, 2H), 2.98 (q, J = 7.6 Hz, 2H), 1.52-1.44 (m, 1H), 1.41 (t, J = 7.5 Hz, 3H), 0.87-0.77 (m, 2H), 0.60-0.53 (m, 2H) |
| 456 | | (S)-1-(4-(1H-pyrazol-4-yl)phenyl)-3-(1-(3-methoxyphenyl)ethyl)imidazolidin-2-one | 418.2 | A: 9.437, 99.49% B: 8.949, 99.45% I: 26.99, 98.91% ee | 1H NMR (400 MHz, DMSO-d6) δ ppm 12.86 (br. s., 1 H) 8.11 (s, 1 H) 7.89 (s, 1 H) 7.55 (s, 4 H) 7.27-7.37 (m, 1 H) 7.63-7.69 (m, 1 H) 6.85-6.89 (m, 2 H) 5.10 (q, J = 7.2 Hz, 1 H) 3.76-3.79 (m, 5 H) 3.48-3.54 (m, 1 H) 3.08-3.14 (m, 1 H) 1.50 (d, J = 7.2 Hz, 3 H); SOR: [α]25 D = -137.2 (c 0.1, MeOH) |
| 459 | | 1-(5-(1H-pyrazol-4-yl)pyridin-2-yl)-3-(1-(3-methoxyphenyl)ethyl)imidazolidin-2-one (Enantiomer I) | 364.2 | A: 7.029, 98.94% B: 7.204, 99.01% II: 7.12, 99.17%, 98.34% ee | 1H NMR (400 MHz, DMSO-d6) δ ppm 12.96 (br, s, 1H) 8.56 (dd, J = 2.4, 0.8 Hz, 1H), 8.20 (d, J = 0.8 Hz, 2H), 7.94 (dd, J = 8.7, 2.4 Hz, 2 H), 7.29 (t, J = 7.9 Hz, 1H), 7.02-6.76 (m, 3H), 5.14 (q, J = 7.1 Hz, 1H), 4.04-3.85 (m, 2H), 3.76 (s, 3H), 3.52 (td, J = 9.0, 6.8 Hz, 1H), 3.21-3.00 (m, 1H), 1.52 (d, J = 7.2 Hz, 3H); SOR: [α]25.1 D = -124 (c 0.1, MeOH) |

TABLE 16-continued

| Ex. | R | Name | LCMS (M + H)+ | HPLC Method, RT (min.) and Purity | NMR |
|---|---|---|---|---|---|
| 460 | | 1-(5-(1H-pyrazol-4-yl)pyridin-2-yl)-3-(1-(3-methoxyphenyl)ethyl)imidazolidin-2-one (Enantiomer II) | 364.2 | A: 7.016, 99.32% B: 7.217, 98.99% II: 9.92, 98.62% ee | $^1$H NMR (400 MHz, DMSO-$d_6$) δ ppm 12.96 (br, s, 1 H) 8.56 (dd, J = 2.4, 0.8 Hz, 1H), 8.20 (d, J = 0.8 Hz, 1H), 8.05 (br, s, 2 H) 7.94 (dd, J = 8.7, 2.4 Hz, 1 H ) 7.29 (t, J = 7.9 Hz, 1H), 7.02-6.76 (m, 3H), 5.14 (q, J = 7.1 Hz, 1H), 4.04-3.85 (m, 2H), 3.76 (s, 3H), 3.52 (td, J = 9.0, 6.8 Hz, 1H), 3.21-3.00 (m, 1H), 1.52 (d, J = 7.2 Hz, 3H); SOR: [α]25.1 D = +128 (c 0.1, MeOH) |
| 461 | | 1-(5-(1H-pyrazol-4-yl)pyridin-2-yl)-3-(2-hydroxy-1-(3-methoxyphenyl)ethyl)imidazolidin-2-one (Enantiomer I) | 380.2 | A: 10.649, 98.06% B: 11.088, 98.30% III: 3.36, 99.48% ee | $^1$H NMR (400 MHz, chloroform-d) δ ppm 12.95 (s, 1 H) 8.60-8.51 (m, 1H), 8.21-8.14 (m, 2H), 7.94 (dd, J = 8.8, 2.4 Hz, 2H), 7.35-7.23 (m, 1H), 6.92 (d, J = 7.8 Hz, 1H), 6.89-6.82 (m, 2H), 5.05-4.92 (m, 2H), 4.03-3.93 (m, 2H), 3.93-3.88 (m, 1H), 3.88-3.79 (m, 1H), 3.75 (s, 3H), 3.67-3.58 (m, 1H), 3.34-3.30 (m, 1 H); SOR: [α]24.8 D = +40 (c 0.1, MeOH) |
| 462 | | 1-(5-(1H-pyrazol-4-yl)pyridin-2-yl)-3-(2-hydroxy-1-(3-methoxyphenyl)ethyl)imidazolidin-2-one (Enantiomer II) | 380.2 | A: 10.644, 98.18% B: 11.068, 98.71% III: 4.36, 96.76%, 93.52% ee | $^1$H NMR (400 MHz, chloroform-d) δ ppm 12.95 (s, 1 H) 8.60-8.51 (m, 1H), 8.21-8.14 (m, 2H), 7.94 (dd, J = 8.8, 2.4 Hz, 2H), 7.35-7.23 (m, 1H), 6.92 (d, J = 7.8 Hz, 1H), 6.89-6.82 (m, 2H), 5.05-4.92 (m, 2H), 4.03-3.93 (m, 2H), 3.93-3.88 (m, 1H), 3.88-3.79 (m, 1H), 3.75 (s, 3H), 3.67-3.58 (m, 1H), 3.34-3.30 (m, 1 H); SOR: [α]24.8 D = −74 (c 0.1, MeOH) |

TABLE 16-continued

| Ex. | R | Name | LCMS (M + H)+ | HPLC Method, RT (min.) and Purity | NMR |
|---|---|---|---|---|---|
| 463 | | 1-(3-fluoro-4-(1H-pyrazol-4-yl)phenyl)-3-(2-hydroxy-1-(3-methoxyphenyl)ethyl)imidazolidin-2-one | 397.2 | E: 1.664, 99.68% F: 1.642, 99.73% | 1H NMR (400 MHz, DMSO-d6) δ ppm 13.00 (s, 1H) 8.24 (br. s., 2H), 8.01-7.79 (m, 2H), 7.64-7.46 (m, 2H), 7.23-7.05 (m, 3H), 5.23 (dd, J = 8.8, 5.6 Hz, 2H), 4.25-4.05 (m, 4H), 4.01 (s, 3H), 3.96-3.85 (m, 1H), 3.43 (s, 1H); 19F NMR (400 MHz, DMSO-d6) δ ppm −114.00 |
| 458 | | 1-(5-(1H-pyrazol-4-yl)pyridin-2-yl)-3-(3-fluoro-5-methoxybenzyl)-4,4-dimethylimidazolidin-2-one | 396.1 | E: 2.015, 98.45% F: 1.988, 99.15% | 1H NMR (400 MHz, DMSO-d6) δ ppm 12.94 (s, 1H) 8.84 (dd, J = 2.4, 0.8 Hz, 1H), 8.45 (dd, J = 8.8, 0.8 Hz, 2H), 8.23 (dd, J = 8.8, 2.4 Hz, 2H), 7.15-6.85 (m, 3H), 4.37 (s, 2H), 3.81(s, 2H), 3.76 (s, 3H) 1.25 (s, 6H); 19F NMR (400 MHz, DMSO-d6) δ ppm −111.909 |
| 464 | | 1-(3-fluoro-5-methoxybenzyl)-3-(4-methyl-5-(1H-pyrazol-4-yl)pyridin-2-yl)imidazolidin-2-one | 382.2 | E: 1.737, 97.22% F: 1.758, 98.34% | 1H NMR (400 MHz, DMSO-d6) δ ppm 13.03 (br, s, 1H) 8.28 (s, 1H), 8.12 (s, 1H), 7.88 (br, s, 2H) 6.83-6.60 (m, 3H), 4.39 (s, 2H), 3.97 (dd, J = 9.1, 7.1 Hz, 2H), 3.40 (s, 3H), 3.55-3.34 (m, 2H), 2.37 (s, 3H); 19F NMR (400 MHz, DMSO-d6) δ ppm −111.505 |
| 465 | | 1-(3-methoxybenzyl)-3-(4-methyl-5-(1H-pyrazol-4-yl)pyridin-2-yl)imidazolidin-2-one | 364.1 | E: 1.646, 99.28% F: 1.6678, 99.40% | 1H NMR (400 MHz, DMSO-d6) δ ppm 13.06 (br, s, 1H) 8.27 (s, 1H), 8.12 (s, 1H), 7.87 (br, s, 2H) 7.30-7.26 (m, 1H) 6.89-6.86 (m, 3H), 4.39 (s, 2H), 3.97 (dd, J = 9.1, 7.1 Hz, 2H), 3.39 (s, 3H), 3.37-3.31 (m, 2H), 2.37 (s, 3H) |

TABLE 16-continued

| Ex. | R | Name | LCMS (M + H)+ | HPLC Method, RT (min.) and Purity | NMR |
|---|---|---|---|---|---|
| 466 | | 1-(6-methoxy-5-(1H-pyrazol-4-yl)pyridin-2-yl)-3-(3-methoxybenzyl)imidazolidin-2-one | 380.2 | E: 1.819, 99.82% F: 1.854, 99.64% | $^1$H NMR (400 MHz, DMSO-$d_6$) δ ppm 12.87 (br. s., 1H), 8.08 (br. s., 1H), 8.01-7.89 (m, 2H), 7.77 (d, J = 8.3 Hz, 1H), 7.35-7.23 (m, 1H), 6.95-6.77 (m, 3H), 4.39 (s, 2H), 4.08-3.99 (m, 2H), 3.96 (s, 3H), 3.75 (s, 3H), 3.45-3.34 (m, 2H) |
| 467 | | 1-(3-fluoro-5-methoxybenzyl)-3-(6-methoxy-5-(1H-pyrazol-4-yl)pyridin-2-yl)imidazolidin-2-one | 398.1 | E: 1.896, 99.57% F: 1.932, 100% | $^1$H NMR (400 MHz, DMSO-$d_6$) δ ppm 12.87 (br. s., 1H), 8.09 (br. s., 1H), 8.00 (d, J = 8.3 Hz, 1H), 7.94 (br. s., 1H), 7.76 (d, J = 8.3 Hz, 1H), 6.83-6.67 (m, 3H), 4.39 (s, 2H), 4.15-4.01 (m, 3H), 3.96 (s, 3H), 3.77 (s, 3H), 3.47-3.35 (m, 2H); $^{19}$F NMR (400 MHz, DMSO-$d_6$) δ ppm −111.520 |
| 468 | | 1-(3-cyclopropyl-4-(1H-pyrazol-4-yl)phenyl)-3-(3-methoxybenzyl)imidazolidin-2-one | 389.2 | E: 2.06, 99.52% F: 2.032, 99.52% | $^1$H NMR (400 MHz, DMSO-$d_6$) δ ppm 12.90 (bs, 1 H) 7.75-8.00 (bs, 2 H) 7.25-7.40 (m, 4 H) 6.83-6.90 (m, 3 H) 4.35 (s, 2 H) 3.81 (dd, J = 9.05, 6.97 Hz, 2 H) 3.75 (s, 3 H) 3.35 (d, J = 8.13 Hz, 2 H) 3.17 (s, 1 H) 1.99-2.10 (m, 1 H) 0.93 (dd, J = 8.41, 1.99 Hz, 2 H) 0.65 (dd, J = 5.41, 1.80 Hz, 2 H) |

TABLE 16-continued

| Ex. | R | Name | LCMS (M + H)+ | HPLC Method, RT (min.) and Purity | NMR |
|---|---|---|---|---|---|
| 469 | (structure) | 1-(3-cyclopropyl-4-(1H-pyrazol-4-yl)phenyl)-3-(3-fluoro-5-methoxybenzyl)imidazolidin-2-one | 407.1 | E: 1.969, 98.447% F: 1.970, 98.62% | $^1$H NMR (400 MHz, DMSO-d$_6$) δ ppm 12.90 (bs, 1 H) 7.75-8.00 (bs, 2 H) 7.31-7.39 (m, 2 H) 7.28 (d, J = 2.20 Hz, 1 H) 6.67-6.78 (m, 3 H) 4.36 (s, 2 H) 4.05-4.11 (m, 1 H) 3.83 (dd, J = 9.05, 6.97 Hz, 3 H) 3.77 (s, 3 H) 3.34-3.40 (m, 2H) 3.17 (d, J = 5.01 Hz, 2 H) 2.01-2.11 (m, 1 H) 0.93 (dd, J = 8.41, 1.99 Hz, 2 H) 0.64 (dd, J = 5.44, 1.90 Hz, 2 H); $^{19}$F NMR (400 MHz, DMSO-d$_6$) δ ppm -111.563 |
| 470 | (structure) | 1-(1-(3-methoxyphenyl)ethyl)-3-(4-methyl-5-(1H-pyrazol-4-yl)pyridin-2-yl)imidazolidin-2-one (Enantiomer I) | 378.2 | A: 6.4415, 98.43% B: 7.248, 96.97% III: 2.54, 100% ee | $^1$H NMR (400 MHz, DMSO-d$_6$) 13.01 (br, s, 1H) 8.26 (s, 1H), 8.10 (s, 1H), 7.89 (br, s, 2H) 7.29 (t, J = 7.9 Hz, 1H), 7.01-6.75 (m, 3H), 5.13 (q, J = 7.1 Hz, 1H), 4.00-3.86 (m, 2H), 3.75 (s, 3H), 3.52 (td, J = 9.0, 6.8 Hz, 1H), 3.21-3.04 (m, 1H), 2.42-2.27 (s, 3H), 1.52 (d, J = 7.2 Hz, 3H); SOR: [α]24.8 D = +84 (c 0.1, MeOH) |
| 471 | (structure) | 1-(1-(3-methoxyphenyl)ethyl)-3-(4-methyl-5-(1H-pyrazol-4-yl)pyridin-2-yl)imidazolidin-2-one (Enantiomer II) | 378.2 | A: 6.4416, 96.314% B: 7.249, 95.38% III: 4.11, 100% ee | $^1$H NMR (400 MHz, DMSO-d$_6$) δ ppm 13.01 (br, s, 1H) 8.26 (s, 1H), 8.10 (s, 1H), 7.89 (br, s, 2H) 7.29 (t, J = 7.9 Hz, 1H), 7.01-6.75 (m, 3H), 5.13 (q, J = 7.1 Hz, 1H), 4.00-3.86 (m, 2H), 3.75 (s, 3H), 3.52 (td, J = 9.0, 6.8 Hz, 1H), 3.21-3.04 (m, 1H), 2.42-2.27 (s, 3H), 1.52 (d, J = 7.2 Hz, 3H); SOR: [α]24.8 D = -64 (c 0.1, MeOH) |

TABLE 16-continued

| Ex. | R | Name | LCMS (M + H)+ | HPLC Method, RT (min.) and Purity | NMR |
|---|---|---|---|---|---|
| 472 | 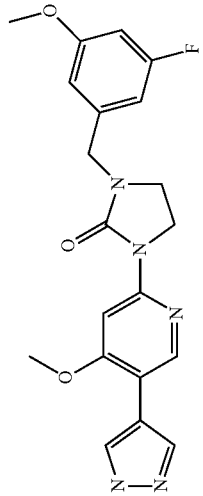 | 1-(3-fluoro-5-methoxybenzyl)-3-(4-methoxy-5-(1H-pyrazol-4-yl)pyridin-2-yl)imidazolidin-2-one | 398.1 | E: 1.735, 99.96% F: 1.373, 99.80% | $^1$H NMR (400 MHz, DMSO-$d_6$) δ ppm 12.93 (br. s., 1H), 8.45 (s, 1H), 8.03 (br. s., 2H), 8.00 (s, 1H), 6.82-6.63 (m, 3H), 4.40 (s, 2H), 3.99 (dd, J = 9.1, 7.2 Hz, 2H), 3.92 (s, 3H), 3.78 (s, 3H), 3.52-3.38 (m, 2H); $^{19}$F NMR (400 MHz, DMSO-$d_6$) δ ppm −111.485 |
| 473 | 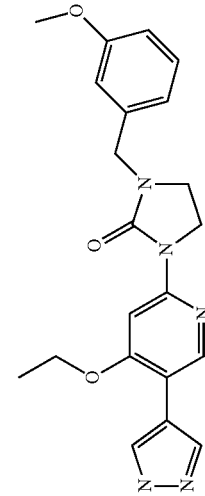 | 1-(4-ethoxy-5-(1H-pyrazol-4-yl)pyridin-2-yl)-3-(3-methoxybenzyl)imidazolidin-2-one | 394.2 | E: 1.769, 96.95% F: 1.413, 96.06% | $^1$H NMR (400 MHz, DMSO-$d_6$) δ ppm 8.45 (s, 1H), 8.04 (s, 2H), 7.89 (s, 1H), 7.38-7.23 (m, 1H), 6.97-6.81 (m, 3H), 4.40 (s, 2H), 4.20 (q, J = 7.0 Hz, 2H), 4.03-3.89 (m, 2H), 3.76 (s, 3H) 1.46 (t, J = 6.9 Hz, 3H) |
| 474 | 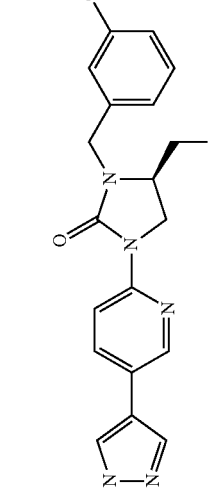 | (R)-1-(5-(1H-pyrazol-4-yl)pyridin-2-yl)-4-(hydroxymethyl)-3-(3-methoxybenzyl)imidazolidin-2-one | 380.2 | E: 1.36, 100% F: 1.113, 100% | $^1$H NMR (400 MHz, DMSO-$d_6$) δ ppm 12.96 (br. s., 1 H), 8.57 (d, J = 1.7 Hz, 1 H), 8.24-8.18 (m, 2 H), 7.97-7.92 (m, 2 H), 7.27 (t, J = 8.2 Hz, 1 H), 6.92-6.82 (m, 3 H), 4.98 (t, J = 5.3 Hz, 1 H), 4.70 (d, J = 15.4 Hz, 1 H), 4.21 (d, J = 15.4 Hz, 1 H), 4.05-3.97 (m, 1 H), 3.86-3.77 (m, 1 H) 3.74 (s, 3 H), 3.63-3.46 (m, 3 H) |
| 475 | 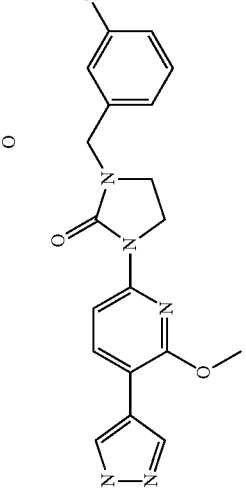 | 1-(3-(cyclopropylmethoxy)benzyl)-3-(6-methoxy-5-(1H-pyrazol-4-yl)pyridin-2-yl)imidazolidin-2-one | 420.2 | E: 2.19, 99.14% F: 2.15, 98.60% | $^1$H NMR (400 MHz, DMSO-$d_6$) δ ppm 12.86 (br. s., 1 H), 8.08 (br. s., 1 H), 7.98 (d, J = 8.3 Hz, 1 H), 7.94 (br. s., 1 H), 7.77 (d, J = 8.3 Hz, 1 H), 7.29-7.23 (m, 1 H), 6.89-6.82 (m, 3 H), 4.37 (s, 2 H), 4.02 (dd, J = 9.0, 7.1 Hz, 2 H), 3.96 (s, 3 H), 3.81 (d, J = 7.1 Hz, 2 H), 3.41-3.34 (m, 2 H), 1.66-1.15 (m, 1 H), 0.60-0.50 (m, 2 H), 0.35-0.28 (m, 2 H) |

TABLE 16-continued

| Ex. | R | Name | LCMS (M + H)+ | HPLC Method, RT (min.) and Purity | NMR |
|---|---|---|---|---|---|
| 476 | Chiral structure | (S)-1-(4-(1H-pyrazol-4-yl)phenyl)-3-(3-(cyclopropylmethoxy)benzyl)-4-(hydroxymethyl)imidazolidin-2-one | 419.2 | E: 1.676, 98.347% F: 1.735, 98.731% II: 13.26, 99.48% ee | 1H NMR (400 MHz, DMSO-d6) δ ppm 12.84 (br. s., 1 H) 8.10 (br. s., 1 H) 7.86 (br. s., 1 H) 7.52-7.61 (m, 4 H) 7.23 (t, J = 8.07 Hz, 1 H) 6.79-6.89 (m, 3 H) 4.96 (t, J = 5.26 Hz, 1 H) 4.66 (d, J = 15.41 Hz, 1 H) 4.16 (d, J = 15.65 Hz, 1 H) 3.86-3.93 (m, 1 H) 3.78 (d, J = 7.09 Hz, 2 H) 3.45-3.64 (m, 4 H) 1.21 (d, J = 14.67 Hz, 1 H) 0.51-0.58 (m, 2 H) 0.27-0.33 (m, 2 H); SOR: [α]25.3D = +76.000 (c 0.050, DMSO). |
| 477 | structure | 1-(4-fluoro-3-methoxybenzyl)-3-(6-methoxy-5-(1H-pyrazol-4-yl)pyridin-2-yl)-1H-imidazol-2(3H)-one | 396.2 | E: 1.502, 98.74% F: 1.557, 99.424% | 1H NMR (400 MHz, DMSO-d6) δ ppm 12.96 (br. s, 1H), 8.18-8.11 (m, 2H), 8.00 (s, 1H), 7.93 (d, J = 8.3 Hz, 1H), 7.39 (d, J = 2.9 Hz, 1H), 7.23-7.15 (m, 2H), 6.86 (d, J = 2.7 Hz, 2H), 4.79 (s, 2H), 4.02 (s, 3H), 3.86-3.80 (m, 3H); 19F NMR (400 MHz, DMSO-d6) δ ppm −137.017 |
| 478 | structure | 1-(3-fluoro-5-methoxybenzyl)-3-(6-methoxy-5-(1H-pyrazol-4-yl)pyridin-2-yl)-1H-imidazol-2(3H)-one | 396.2 | E: 1.566, 98.662% F: 1.621, 99.582% | 1H NMR (400 MHz, DMSO-d6) δ ppm 12.97 (br. s, 1H), 8.14 (d, J = 8.3 Hz, 2H), 8.03 (br. s., 1H), 7.92 (d, J = 8.1 Hz, 1H), 7.40 (d, J = 3.2 Hz, 1H), 6.87 (d, J = 3.2 Hz, 1H), 6.80-6.67 (m, 3H), 4.79 (s, 2H), 4.02 (s, 3H), 3.76 (s, 3H); 19F NMR (400 MHz, DMSO-d6) δ ppm −111.322 |

What is claimed is:

1. A compound according to Formula (I):

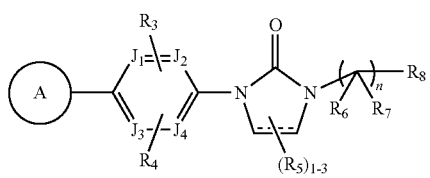

or an enantiomer, a diastereomer, a stereoisomer, a tautomer, a pharmaceutically acceptable salt thereof, wherein --- is an optional bond;

Ring A is independently selected from

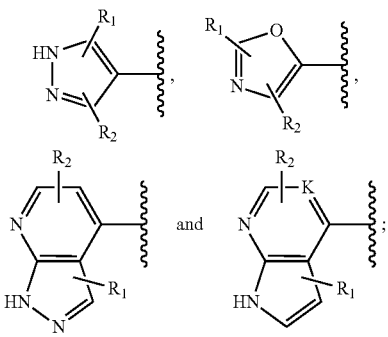

$J_1$, $J_2$, $J_3$, and $J_4$ are independently selected from N and $CR_3$; provided one of $J_1$, $J_2$, $J_3$, and $J_4$ is N and no more than two of $J_1$, $J_2$, $J_3$, and $J_4$ are N;

K is independently selected from N and $CR_1$;

$R_1$ is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$ is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from H, =O, $C_{1-4}$ alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_6$ and $R_7$ are independently selected from H, $C_{1-4}$ alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from $C_{3-6}$ cycloalkyl, heterocyclyl, aryl and heteroaryl, each substituted with 0-5 $R_9$;

$R_9$ is independently selected from F, Cl, Br, $C_{1-4}$ alkyl, $C_{2-4}$ alkenyl, $C_{2-4}$ alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $C_{3-6}$ carbocyclyl, and heterocyclyl;

$R_d$, at each occurrence, is independently selected from H and $C_{1-4}$ alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$ and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$ alkyl;

n is independently selected from 1, 2, and 3;

p, at each occurrence, is independently selected from zero, 1, and 2; and r, at each occurrence, is independently selected from zero, 1, 2, 3, and 4.

2. The compound of claim 1 or an enantiomer, a diastereomer, a stereoisomer, a tautomer, a pharmaceutically acceptable salt thereof, wherein
$R_1$ is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;
$R_2$ is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rNR_aC(=O)OR_b$, —$(CH_2)_rOC(=O)NR_aR_a$, —$(CH_2)_rC(=O)OR_b$, —$(CH_2)_rNR_aS(O)_pNR_aR_a$, and —$(CH_2)_rNR_aS(O)_pR_c$;
$R_3$ is independently selected from H, F, Cl, Br, CN, $C_{1-4}$ alkyl substituted with 0-3 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;
$R_4$ is independently selected from H, F, Cl, Br, OH, CN, and $C_{1-4}$ alkyl substituted with 0-3 $R_e$;
$R_5$ is independently selected from H, =O, $C_{1-4}$alkyl substituted with 0-4 $R_e$, —$(CH_2)_r$ $OR_b$, $C(=O)R_b$, and —$C(=O)OR_b$;
$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rC(=O)OR_b$, $(CH_2)_r$—$C_{3-6}$ carbocyclyl substituted with 0-3 $R_e$, and —$(CH_2)_r$-heterocyclyl substituted with 0-3 $R_e$;
$R_8$ is independently selected from

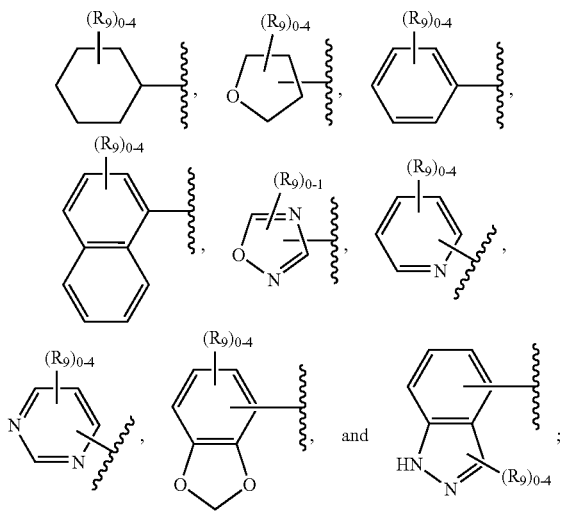

$R_9$ is independently selected from F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$.

3. A compound according to Formula (IIa):

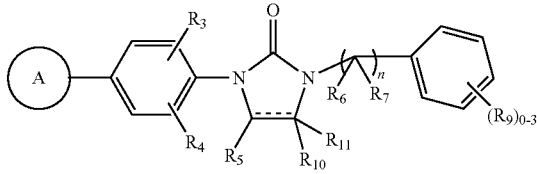

(IIa)

or an enantiomer, a diastereomer, a stereoisomer, a tautomer, a pharmaceutically acceptable salt thereof, wherein
--- is an optional bond;
Ring A is independently selected from

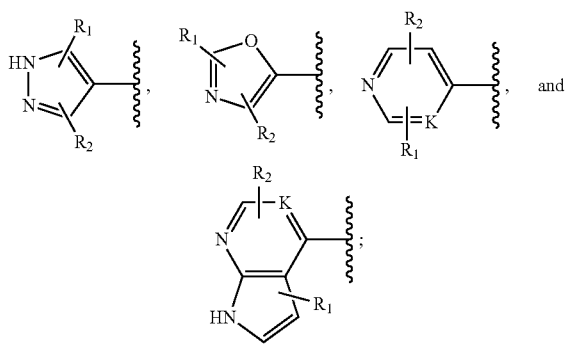

$R_1$ is independently selected from H, F, Cl, Br, CN, $NR_aR_a$, and $C_{1-4}$alkyl substituted with 0-4 $R_e$;
$R_2$ is independently selected from H, F, Cl, Br, OH, CN, $NR_aR_a$, and $C_{1-4}$alkyl substituted with 0-4 $R_e$;
$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;
$R_4$ is independently selected from H, F, Cl, Br, OH, CN, $OC_{1-4}$ alkyl substituted with 0-3 $R_e$, and $C_{1-4}$ alkyl substituted with 0-3 $R_e$;
$R_5$, $R_{10}$, and $R_{11}$ are independently selected from H, =O, and $C_{1-4}$alkyl substituted with 0-4 $R_e$;
provided $R_5$, $R_{10}$, and $R_{11}$ are not all H;
$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aR_a$, —$(CH_2)_rC(=O)NR_aR_a$, —$(CH_2)_rNR_aC(=O)R_b$, —$(CH_2)_rC(=O)OR_b$, $(CH_2)_r$—$C_{3-6}$ carbocyclyl substituted with 0-3 $R_e$, and —$(CH_2)_r$-heterocyclyl substituted with 0-3 $R_e$;
$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$; $R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$- heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4; and provided (1) $R_9$ is not a substituted piperazine;

(2) when n is 3, $R_8$ is not

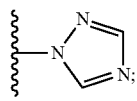

and (3) when A

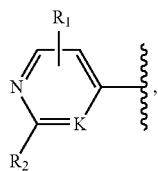

$R_2$ is not —C(=O)$NR_aR_a$, —$NR_aC(=O)R_b$, and —$NR_aC(=O)NR_aR_a$.

4. The compound of claim 3, having Formula (IIIa):

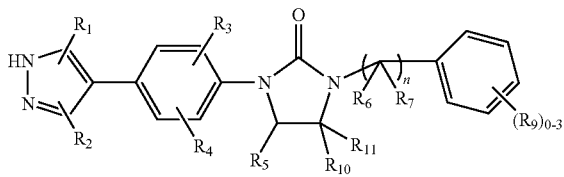

(IIIa)

or an enantiomer, a diastereomer, a stereoisomer, a tautomer, a pharmaceutically acceptable salt thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, —$(CH_2)_rOR_b$, and —$C_{3-6}$ cycloalkyl;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$, $R_{10}$, and $R_{11}$ are independently selected from H, =O, and $C_{1-4}$alkyl substituted with 0-4 $R_e$;

provided $R_5$, $R_{10}$, and $R_{11}$ are not all H;

$R_6$ is independently selected from H, $C_{1-4}$alkyl substituted with 0-4 $R_e$, —$CH_2OR_b$, —C(=O)$R_b$, $NR_aC(=O)R_b$, —$CH_2NR_aR_a$, —C(=O)$NR_aR_a$, —$_rC(=O)OR_b$, and heterocyclyl substituted with 0-3 $R_e$;

$R_7$ is independently selected from H and $C_{1-4}$alkyl;

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rN$-$R_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

5. The compound of claim 4, having Formula (IVa):

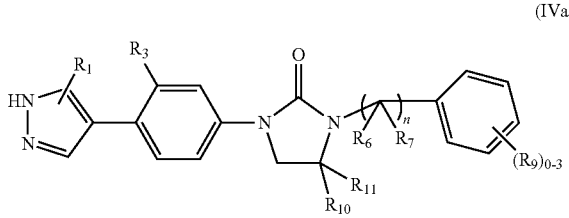

(IVa)

or enantiomer, a diastereomer, a stereoisomer, a tautomer, a pharmaceutically acceptable salt thereof, wherein
$R_1$ is independently selected from H and $CF_3$;
$R_3$ is independently selected from H, CN, $C_{1-4}$ alkyl, $—OC_{1-3}$ alkyl, and $—C_{3-6}$ cycloalkyl;
$R_5$ is independently selected from H, =O, $C_{1-4}$alkyl substituted with 0-4 $R_e$, $—CH_2OR_b$, $C(=O)R_b$, and $—C(=O)OR_b$;
$R_6$ is independently selected from H, $C_{1-4}$alkyl substituted with 0-3 $R_e$, $—(CH_2)_rOR_b$, $—CH_2NR_aR_a$, $—C(=O)NR_aR_a$ and $—(CH_2)_rC(=O)OR_b$;
$R_7$ is independently selected from H and $C_{1-4}$alkyl;
$R_9$ is independently selected from F, Cl, $C_{1-4}$ alkyl substituted with 0-3 $R_e$, $—OR_b$, and heterocyclyl substituted with 0-3 $R_e$;
$R_{10}$, and $R_{11}$ are independently selected from H, $C_{1-4}$alkyl substituted with 0-4 $R_e$; provided $R_{10}$ and $R_{11}$ are not all H;
$R_a$, at each occurrence, is independently selected from H, $C_{1-6}$ alkyl substituted with 0-5 $R_e$, $—(CH_2)_r—C_{3-6}$ cycloalkyl substituted with 0-5 $R_e$, $—(CH_2)_r$-aryl substituted with 0-5 $R_e$, and $—(CH_2)_r$-heterocyclyl substituted with 0-5 $R_e$;
$R_b$, at each occurrence, is independently selected from H, $C_{1-6}$ alkyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
n is independently selected from 1 and 2; and
r, at each occurrence, is independently selected from zero, 1, 2, and 3.

6. A compound according to Formula (Va):

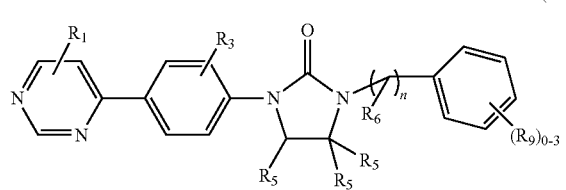

(Va)

or an enantiomer, a diastereomer, a stereoisomer, a tautomer, a pharmaceutically acceptable salt thereof, wherein
$R_1$ is independently selected from H, F, Cl, Br, CN, $NR_aR_a$, and $C_{1-4}$alkyl substituted with 0-4 $R_e$;
$R_3$ is independently selected from H, CN, $C_{1-4}$ alkyl substituted with 0-3 $R_e$, and $—OR_b$;

$R_5$ is independently selected from H, =O, $C_{1-4}$alkyl substituted with 0-4 $R_e$, $—(CH_2)_rOR_b$, $C(=O)R_b$, and $—C(=O)OR_b$;
$R_6$ is independently selected from H, $C_{1-4}$alkyl substituted with 0-4 $R_e$, $—(CH_2)_rOR_b$, $—(CH_2)_rC(=O)R_b$, $—(CH_2)_rNR_aC(=O)R_b$, $—(CH_2)_rC(=O)OR_b$, and heterocyclyl substituted with 0-3 $R_e$;
$R_9$ is independently selected from F, Cl, Br, $C_{1-4}$ alkyl, nitro, $—S(O)_pR_c$, $—S(O)_pNR_aR_a$, $—OR_b$, $—NR_aR_a$, $—C(=O)OR_b$, $—(CH_2)_rC(=O)R_b$, $—(CH_2)_r$-cycloalkyl, $—(CH_2)_r$-heterocyclyl, $—(CH_2)_r$-aryl, and $—(CH_2)_r$-heteroaryl, wherein said alkyl, cycloalkyl, heterocyclyl, aryl, or heteroaryl is substituted with 0-4 $R_e$;
$R_a$, at each occurrence, is independently selected from H, $C_{1-6}$ alkyl substituted with 0-5 $R_e$, $—(CH_2)_r—C_{3-6}$cycloalkyl substituted with 0-5 $R_e$, $—(CH_2)_r$-aryl substituted with 0-5 $R_e$, and $—(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_e$, at each occurrence, is independently selected from $C_{1-6}$ alkyl substituted with 0-5 $R_f$, $C_{2-6}$ alkenyl, $C_{2-6}$ alkynyl, $—(CH_2)_r—C_{3-6}$ cycloalkyl, $—(CH_2)_r—C_{4-6}$ heterocyclyl, F, Cl, Br, CN, $NO_2$, =O, $CO_2H$, $—(CH_2)_rOR_f$, $S(O)_pR_f$, $S(O)_pNR_fR_f$, and $—(CH_2)_rNR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
n is independently selected from 1 and 2;
p, at each occurrence, is independently selected from zero, 1, and 2; and
r, at each occurrence, is independently selected from zero, 1, 2, 3, and 4.

7. A compound according to Formula (VIa):

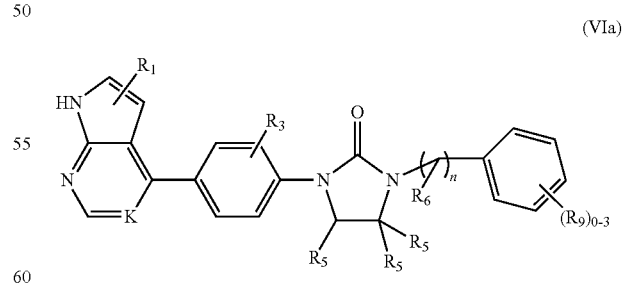

(VIa)

or an enantiomer, a diastereomer, a stereoisomer, a tautomer, a pharmaceutically acceptable salt thereof, wherein
K is independently selected from N and CH;
$R_1$ is independently selected from H, F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and —$OR_b$;

$R_5$ is independently selected from H, =O, $C_{1-4}$alkyl substituted with 0-4 $R_e$, —$(CH_2)_r OR_b$, $C(=O)R_b$, and —$C(=O)OR_b$;

$R_6$ is independently selected from H, $C_{1-4}$alkyl substituted with 0-4 $R_e$, —$(CH_2)_r OR_b$, —$(CH_2)_r C(=O)R_b$, —$(CH_2)_r NR_a C(=O)R_b$, —$(CH_2)_r C(=O)OR_b$, and heterocyclyl substituted with 0-3 $R_e$;

$R_9$ is independently selected from F, Cl, Br, $C_{1-4}$ alkyl, nitro, —$S(O)_p R_c$, —$S(O)_p NR_a R_a$, —$OR_b$, —$NR_a R_a$, —$C(=O)OR_b$, —$(CH_2)_r C(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_r OR_f$, $S(O)_p R_f$, $S(O)_p NR_f R_f$, and —$(CH_2)_r NR_f R_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, and 2;

p, at each occurrence, is independently selected from zero, 1, and 2; and r, at each occurrence, is independently selected from zero, 1, 2, 3, and 4.

8. The compound of claim 1, having Formula (VII):

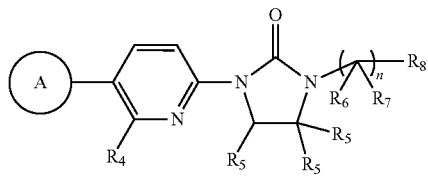

(VII)

or an enantiomer, a diastereomer, a stereoisomer, a tautomer, a pharmaceutically acceptable salt thereof, wherein Ring A is independently selected from

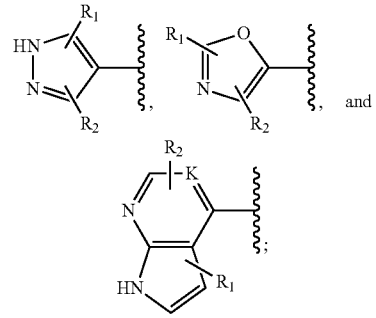

, and $R_1$ is independently selected from H, F, Cl, Br, CN, $NR_a R_a$, and $C_{1-4}$alkyl substituted with 0-4 $R_e$;

$R_2$ is independently selected from H, F, Cl, Br, OH, CN, $NR_a R_a$, and $C_{1-4}$alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_r OR_b$, $C(=O)R_b$, and —$C(=O)OR_b$;

$R_6$ and $R_7$ are independently selected from H, $C_{1-4}$alkyl substituted with 0-4 $R_e$, —$(CH_2)_r OR_b$, —$(CH_2)_r C(=O)R_b$, —$(CH_2)_r NR_a C(=O)R_b$, —$(CH_2)_r C(=O)OR_b$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from

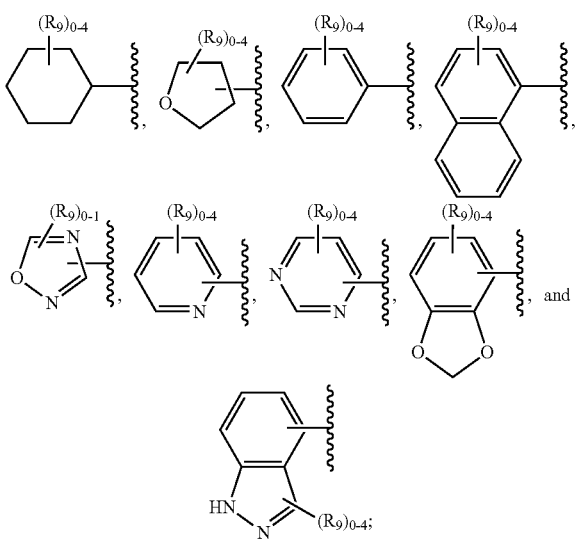

$R_9$ is independently selected from F, Cl, Br, $C_{1-4}$ alkyl, nitro, —$(CH_2)_r S(O)_p R_c$, —$(CH_2)_r S(O)_p NR_a R_a$, —$(CH_2)_r NR_a S(O)_p R_c$, —$(CH_2)_r OR_b$, —$(CH_2)_r CN$, —$(CH_2)_r NR_a R_a$, —$(CH_2)_r NR_a C(=O)R_b$, —$(CH_2)_r N-R_a C(=O)NR_a R_a$, —$(CH_2)_r C(=O)OR_b$, —$(CH_2)_r C(=O)R_b$, —$(CH_2)_r OC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

9. The compound of claim 1, having Formula (VIII):

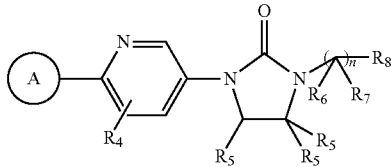

(VIII)

or an enantiomer, a diastereomer, a stereoisomer, a tautomer, a pharmaceutically acceptable salt thereof, wherein Ring A is independently selected from

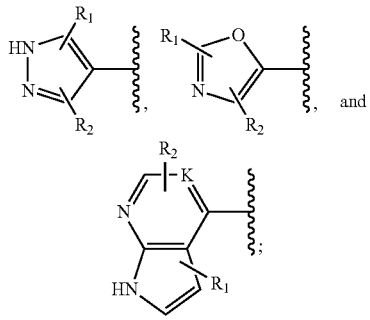

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_r$ $OR_b$, $C(=O)R_b$, and —$C(=O)OR_b$;

$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aC(=O)R_b$, —$(CH_2)_rC(=O)OR_b$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from

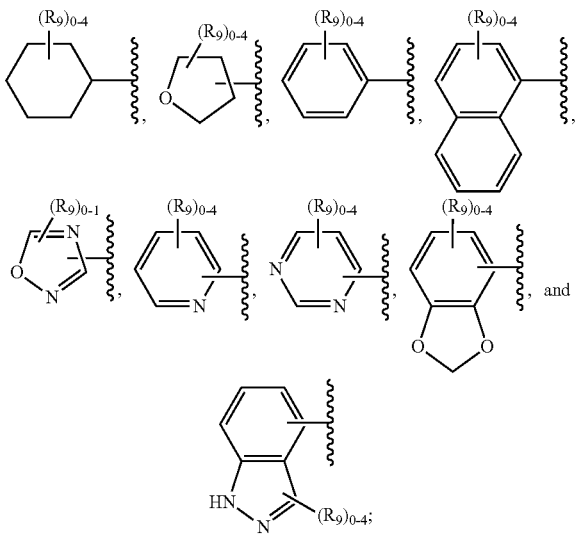

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

10. The compound of claim 1, having Formula (IX):

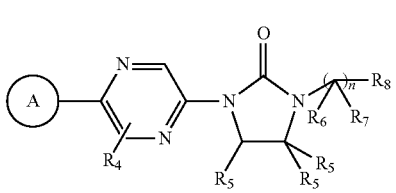

(IX)

or an enantiomer, a diastereomer, a stereoisomer, a tautomer, a pharmaceutically acceptable salt thereof, wherein Ring A is independently selected from

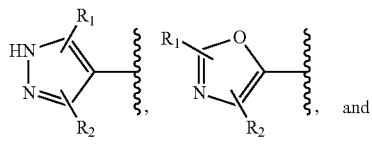

, and

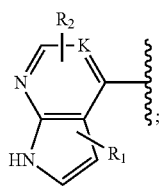

;

$R_1$ is independently selected from H, F, Cl, Br, CN, $NR_aR_a$, and $C_{1-4}$alkyl substituted with 0-4 $R_e$;

$R_2$ is independently selected from H, F, Cl, Br, OH, CN, $NR_aR_a$, and $C_{1-4}$alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, —$(CH_2)_r$ $OR_b$, $C(=O)R_b$, and —$C(=O)OR_b$;

$R_6$ and $R_7$ are independently selected from H, $C_{1-4}$alkyl substituted with 0-4 $R_e$, —$(CH_2)_rOR_b$, —$(CH_2)_rC(=O)R_b$, —$(CH_2)_rNR_aC(=O)R_b$, —$(CH_2)_rC(=O)$ $OR_b$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from

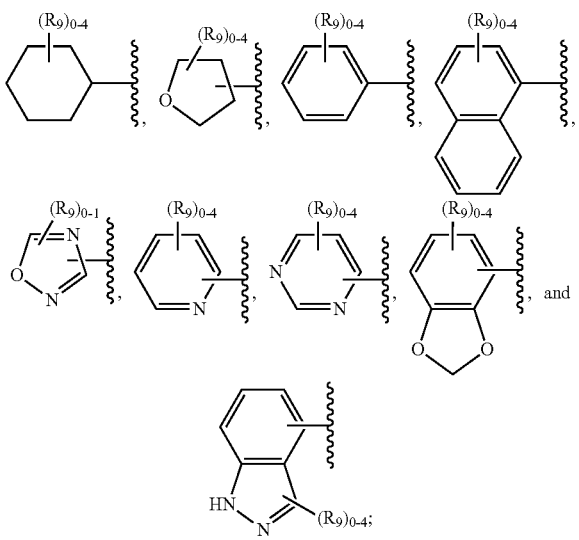

$R_9$ is independently selected from F, Cl, Br, $C_{1-4}$ alkyl, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_rCN$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_r$-cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, F, Cl, Br, CN, $NO_2$, =O, $CO_2H$, —$(CH_2)_rOR_f$, $S(O)_pR_f$, $S(O)_pNR_fR_f$, and —$(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

11. The compound of claim 1, having Formula (X):

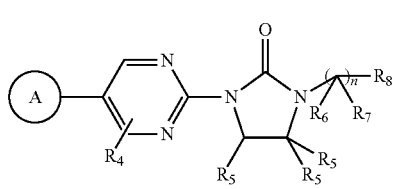

or an enantiomer, a diastereomer, a stereoisomer, a tautomer, a pharmaceutically acceptable salt thereof, wherein Ring A is independently selected from

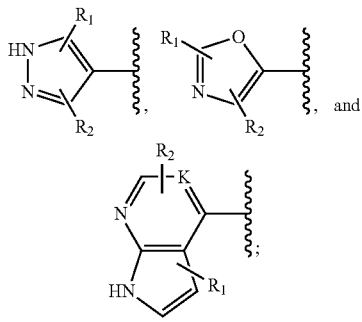

$R_1$ is independently selected from H, F, Cl, Br, CN, $NR_aR_a$, and $C_{1-4}$ alkyl substituted with 0-4 $R_e$;

$R_2$ is independently selected from H, F, Cl, Br, OH, CN, $NR_aR_a$, and $C_{1-4}$ alkyl substituted with 0-4 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H, =O, $C_{1-4}$alkyl substituted with 0-4 $R_e$, $-(CH_2)_r$ $OR_b$, $C(=O)R_b$, and $-C(=O)OR_b$;

$R_6$ and $R_7$ are independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, $(CH_2)_r-C_{3-6}$ carbocyclyl substituted with 0-3 $R_e$, and $-(CH_2)_r$-heterocyclyl substituted with 0-3 $R_e$;

$R_8$ is independently selected from

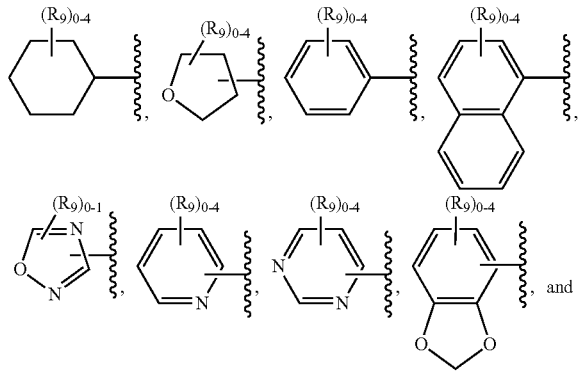

-continued

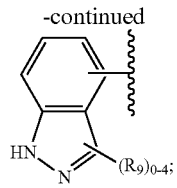

$R_9$ is independently selected from F, Cl, Br, $C_{1-4}$ alkyl, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rN-R_aC(=O)NR_aR_a$, $-(CH_2)_rC(=O)OR_b$, $-(CH_2)_rC(=O)R_b$, $-(CH_2)_rOC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, =O, $CO_2H$, $-(CH_2)_rOR_f$, $S(O)_pR_f$, $S(O)_pNR_fR_f$, and $-(CH_2)_rN-R_fR_f$;

$R_f$ at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4.

12. A compound according to Formula (XI):

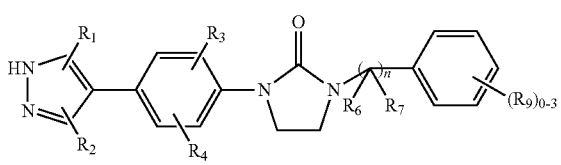

or an enantiomer, a diastereomer, a stereoisomer, a tautomer, a pharmaceutically acceptable salt thereof, wherein $R_1$ is independently selected from H, F, Cl, Br, CN, $NR_aR_a$, and $C_{1-4}$alkyl substituted with 0-4 $R_e$;

$R_2$ is independently selected from H and $C_{1-4}$alkyl substituted with 0-4 $R_e$;

$R_3$ is independently selected from H, F, Cl, Br, CN, $C_{1-4}$ alkyl substituted with 0-3 $R_e$, $-(CH_2)_rOR_b$, and $-C_{3-6}$ cycloalkyl;

$R_3$ is independently selected from H, F, Cl, Br, CN, $C_{1-4}$ alkyl substituted with 0-3 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rNR_aC(=O)R_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_r-C_{3-6}$ carbocyclyl substituted with 0-3 $R_e$, and $-(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_6$ is independently selected from H, $C_{1-4}$alkyl substituted with OH, $-CH_2OR_b$, $-C(=O)R_b$, $NR_aC(=O)R_b$, $-CH_2NR_aR_a$, $-C(=O)NR_aR_a$, $-,C(=O)OR_b$, and heterocyclyl substituted with 0-3 $R_e$;

$R_7$ is independently selected from H and $C_{1-4}$alkyl; provided $R_6$ and $R_7$ are not both H; when $R_7$ is $C_{1-4}$alkyl, $R_6$ is not H;

$R_9$ is independently selected from F, Cl, Br, $C_{1-4}$ alkyl, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-(CH_2)_rOC(=O)R_b$, $-(CH_2)_rC(=O)NR_aR_a$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

13. A compound according to Formula (XII):

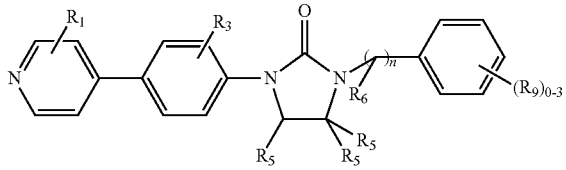

(XII)

or an enantiomer, a diastereomer, a stereoisomer, a tautomer, a pharmaceutically acceptable salt thereof, wherein $R_1$ is independently selected from F, Cl, Br, CN, $NR_aR_a$, and $C_{1-4}$alkyl substituted with 0-4 $R_e$;

$R_3$ is independently selected from H, CN, $C_{1-4}$ alkyl substituted with 0-3 $R_e$, and $-OR_b$;

$R_5$ is independently selected from H, $=O$, $C_{1-4}$alkyl substituted with 0-4 $R_e$, $-(CH_2)_r$ $OR_b$, $C(=O)R_b$, and $-C(=O)OR_b$;

$R_6$ is independently selected from H, $C_{1-4}$alkyl substituted with 0-4 $R_e$, $-(CH_2)_rOR_b$, $-(CH_2)_rC(=O)R_b$, $-(CH_2)_rNR_aC(=O)R_b$, $-(CH_2)_rC(=O)OR_b$, and heterocyclyl substituted with 0-3 $R_e$;

$R_9$ is independently selected from F, Cl, Br, $C_{1-4}$ alkyl, nitro, $-S(O)_pR_c$, $-S(O)_pNR_aR_a$, $-OR_b$, $-NR_aR_a$, $-C(=O)OR_b$, $-(CH_2)_rC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $-(CH_2)_r-C_{3-6}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r-C_{4-6}$ heterocyclyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1 and 2;

p, at each occurrence, is independently selected from zero, 1, and 2; and r, at each occurrence, is independently selected from zero, 1, 2, 3, and 4.

14. A compound according to Formula (XIII):

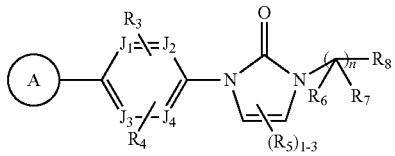
(XIII)

or an enantiomer, a diastereomer, a stereoisomer, a tautomer, a pharmaceutically acceptable salt thereof, wherein Ring A is independently selected from

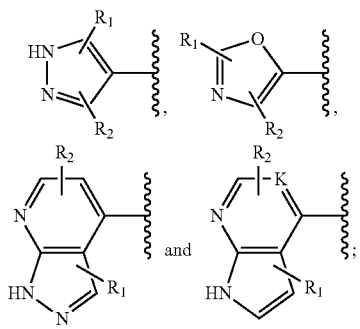

and ;

$J_1$, $J_2$, $J_3$, and $J_4$ are independently selected from N and $CR_3$;

K is independently selected from N and $CR_1$;

$R_1$ is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$ is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from H, =O, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_8$ is independently selected from $C_{3-6}$ cycloalkyl, heterocyclyl, aryl and heteroaryl, each substituted with 0-5 $R_9$;

$R_9$ is independently selected from F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$OC(=O)$R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$—$C_{4-6}$ heterocyclyl, —$(CH_2)_r$-aryl, —$(CH_2)_r$-heteroaryl, F, Cl, Br, CN, $NO_2$, =O, $CO_2H$, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$, and —$(CH_2)_rNR_fR_f$;

$R_f$, at each occurrence, is independently selected from H, F, Cl, Br, CN, OH, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n is independently selected from 1, 2, and 3;

p, at each occurrence, is independently selected from zero, 1, and 2; and r, at each occurrence, is independently selected from zero, 1, 2, 3, and 4; and provided $R_9$ is not a substituted piperazine.

15. A pharmaceutical composition comprising one or more compounds according to claim 1 and a pharmaceutically acceptable carrier or diluent.

16. A method for treatment of a disorder associated with aberrant Rho kinase activity, comprising administrating to a patient in need thereof a therapeutically effective amount of the compound of claim 1.

17. The method of claim 16, wherein said disorder is selected from the group consisting of a cardiovascular disorder, a smooth muscle related disorder, a fibrotic disease, an inflammatory disease, a neuropathic disorder, an oncologic disorder, and an autoimmune disorder.

18. The method of claim 17, wherein said cardiovascular disorder is selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension.

* * * * *